US010730930B2

(12) United States Patent
Bradley et al.

(10) Patent No.: US 10,730,930 B2
(45) Date of Patent: Aug. 4, 2020

(54) ANTIBODIES, VARIABLE DOMAINS AND CHAINS TAILORED FOR HUMAN USE

(71) Applicant: Kymab Limited, Cambridge (GB)

(72) Inventors: Allan Bradley, Cambridge (GB); Glenn Friedrich, Cambridge (GB); E-Chiang Lee, Cambridge (GB); Mark Strivens, Cambridge (GB); Nicholas England, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 15/656,897

(22) Filed: Jul. 21, 2017

(65) Prior Publication Data

US 2017/0320936 A1 Nov. 9, 2017

Related U.S. Application Data

(62) Division of application No. 13/875,892, filed on May 2, 2013, now Pat. No. 9,783,593.

(51) Int. Cl.

| | |
|---|---|
| ***A01K 67/027*** | (2006.01) |
| ***C12N 5/071*** | (2010.01) |
| ***C12N 15/63*** | (2006.01) |
| ***A61K 39/395*** | (2006.01) |
| ***A01N 63/00*** | (2020.01) |
| ***C07H 21/04*** | (2006.01) |
| ***C07K 16/00*** | (2006.01) |
| *C07K 16/46* | (2006.01) |
| *C12N 15/85* | (2006.01) |

(52) U.S. Cl.

CPC .......... *C07K 16/00* (2013.01); *A01K 67/0278* (2013.01); *A01K 2207/15* (2013.01); *A01K 2217/072* (2013.01); *A01K 2217/075* (2013.01); *A01K 2227/105* (2013.01); *C07H 21/04* (2013.01); *C07K 16/46* (2013.01); *C07K 16/462* (2013.01); *C12N 15/63* (2013.01); *C12N 15/8509* (2013.01)

(58) Field of Classification Search

CPC ............ A01K 67/0278; A01K 2207/15; A01K 2217/072; A01K 2217/15; A01K 2227/105; C07K 16/18; C07K 15/462; C12N 15/63; C12N 15/8509; C07H 21/04

USPC ........ 800/18; 435/326, 328, 455; 424/93.21, 424/133.1; 536/23.5

See application file for complete search history.

(56) References Cited

U.S. PATENT DOCUMENTS

| | | | |
|---|---|---|---|
| 4,720,449 | A | 1/1988 | Borror et al. |
| 5,169,939 | A | 12/1992 | Gefter et al. |
| 5,545,806 | A | 8/1996 | Lonberg et al. |
| 5,545,807 | A | 8/1996 | Surani et al. |
| 5,565,321 | A | 10/1996 | Spriggs et al. |
| 5,633,425 | A | 5/1997 | Lonberg et al. |
| 5,770,429 | A | 6/1998 | Lonberg et al. |
| 5,789,215 | A | 8/1998 | Berns et al. |
| 5,807,715 | A | 9/1998 | Morrison et al. |
| 5,939,598 | A | 8/1999 | Kucherlapati et al. |
| 5,948,600 | A | 9/1999 | Roschger et al. |
| 6,130,364 | A | 10/2000 | Jakobovits et al. |
| 6,162,963 | A | 12/2000 | Kucherlapati et al. |
| 6,319,906 | B1 | 11/2001 | Bennett et al. |
| 6,395,487 | B1 | 5/2002 | Bradley et al. |
| 6,461,818 | B1 | 10/2002 | Bradley et al. |
| 6,596,541 | B2 | 7/2003 | Murphy et al. |
| 6,673,986 | B1 | 1/2004 | Kucherlapati et al. |
| 6,713,610 | B1 | 3/2004 | Kucherlapati et al. |
| 6,833,268 | B1 | 12/2004 | Green et al. |
| 6,914,128 | B1 | 7/2005 | Salfeld et al. |
| 6,992,235 | B2 | 1/2006 | Bode et al. |
| 6,998,514 | B2 | 2/2006 | Bruggemann |
| 7,105,348 | B2 | 9/2006 | Murphy et al. |
| 7,119,248 | B1 | 10/2006 | Rajewsky et al. |
| 7,205,140 | B2 | 4/2007 | Gottschalk et al. |
| 7,205,148 | B2 † | 4/2007 | Economides |
| 7,294,754 | B2 | 11/2007 | Poueymirou et al. |
| 7,435,871 | B2 | 10/2008 | Green et al. |
| 7,501,552 | B2 | 3/2009 | Lonberg et al. |
| 7,605,237 | B2 † | 10/2009 | Stevens |
| 7,605,238 | B2 | 10/2009 | Korman et al. |
| 7,910,798 | B2 | 3/2011 | Tanamachi et al. |
| 7,932,431 | B2 | 4/2011 | Bruggemann |

(Continued)

FOREIGN PATENT DOCUMENTS

| | | | |
|---|---|---|---|
| CA | 230750386 | A1 | 11/2001 |
| DE | 10251918 | A1 | 5/2004 |

(Continued)

OTHER PUBLICATIONS

McWhirter et al., 2013, US 20130247235 A1.*

(Continued)

*Primary Examiner* — Shin Lin Chen

(74) *Attorney, Agent, or Firm* — Nutter McClennen & Fish LLP

(57) ABSTRACT

The invention relates to the provision of antibody therapeutics and prophylactics that are tailored specifically for human use. The present invention provides libraries, vertebrates and cells, such as transgenic mice or rats or transgenic mouse or rat cells. Furthermore, the invention relates to methods of using the vertebrates to isolate antibodies or nucleotide sequences encoding antibodies. Antibodies, heavy chains, polypeptides, nucleotide sequences, pharmaceutical compositions and uses are also provided by the invention.

15 Claims, 13 Drawing Sheets

Specification includes a Sequence Listing.

(56) References Cited

U.S. PATENT DOCUMENTS

| | | | |
|---|---|---|---|
| 8,158,419 | B2 | 4/2012 | Lonberg et al. |
| 8,502,018 | B2 | 8/2013 | Murphy et al. |
| 8,592,644 | B2 | 11/2013 | Harriman et al. |
| 8,642,835 | B2 | 2/2014 | MacDonald et al. |
| 8,697,940 | B2 | 4/2014 | MacDonald et al. |
| 8,754,287 | B2 | 6/2014 | MacDonald et al. |
| 8,791,323 | B2 | 7/2014 | Murphy et al. |
| 8,877,901 | B2 | 11/2014 | Govindan |
| 9,253,965 | B2 | 2/2016 | Liang et al. |
| 9,434,782 | B2 | 9/2016 | Bradley et al. |
| 9,445,581 | B2 | 9/2016 | Bradley et al. |
| 9,447,177 | B2 | 9/2016 | Bradley et al. |
| 9,504,236 | B2 | 11/2016 | Bradley et al. |
| 9,505,827 | B2 | 11/2016 | Bradley et al. |
| 9,783,593 | B2 | 10/2017 | Bradley et al. |
| 9,783,618 | B2 | 10/2017 | Friedrich et al. |
| 9,788,534 | B2 | 10/2017 | Bradley et al. |
| 2002/0088016 | A1 | 7/2002 | Bruggemann |
| 2002/0183275 | A1 | 12/2002 | Murphy et al. |
| 2003/0108925 | A1 | 6/2003 | Dix et al. |
| 2003/0217373 | A1 | 11/2003 | Green et al. |
| 2004/0128703 | A1 | 7/2004 | Shizuya |
| 2004/0231012 | A1 | 11/2004 | Bruggemann |
| 2005/0048621 | A1 | 3/2005 | Grasso et al. |
| 2006/0015949 | A1 | 1/2006 | Lonberg et al. |
| 2006/0015957 | A1 | 1/2006 | Lonberg et al. |
| 2006/0021074 | A1 | 1/2006 | Kellermann et al. |
| 2006/0199204 | A1 | 9/2006 | Dix et al. |
| 2007/0280945 | A1 | 12/2007 | Stevens et al. |
| 2008/0098490 | A1 | 4/2008 | Jakobovits et al. |
| 2009/0083870 | A1 | 3/2009 | Horn et al. |
| 2009/0083879 | A1 | 3/2009 | Dhugga |
| 2009/0093059 | A1 | 4/2009 | Baszczynski et al. |
| 2009/0209036 | A1 | 8/2009 | Reynaud et al. |
| 2009/0307787 | A1 | 12/2009 | Grosveld et al. |
| 2010/0011450 | A1 | 1/2010 | Garcia et al. |
| 2010/0069614 | A1 | 3/2010 | Houtzager et al. |
| 2010/0146647 | A1 | 6/2010 | Logtenberg et al. |
| 2010/0196367 | A1 | 8/2010 | Day |
| 2010/0330676 | A1 | 12/2010 | Horowitz et al. |
| 2011/0119779 | A1 | 5/2011 | Shizuya et al. |
| 2011/0138489 | A1 | 6/2011 | Tanamachi et al. |
| 2011/0145937 | A1 | 6/2011 | MacDonald et al. |
| 2011/0195454 | A1 † | 8/2011 | McWhirter |
| 2011/0236378 | A1 | 9/2011 | Green et al. |
| 2011/0283376 | A1 | 11/2011 | Murphy et al. |
| 2012/0070861 | A1 | 3/2012 | MacDonald et al. |
| 2012/0073004 | A1 | 3/2012 | MacDonald et al. |
| 2012/0096572 | A1 | 4/2012 | MacDonald et al. |
| 2012/0195910 | A1 | 8/2012 | Wu et al. |
| 2012/0204278 | A1 † | 8/2012 | Bradley |
| 2012/0233715 | A1 | 9/2012 | Kuroiwa et al. |
| 2012/0322108 | A1 | 12/2012 | MacDonald et al. |
| 2013/0039850 | A1 | 2/2013 | Lonberg et al. |
| 2013/0096287 | A1 | 4/2013 | MacDonald et al. |
| 2013/0102031 | A1 | 4/2013 | King et al. |
| 2013/0160153 | A1 | 6/2013 | MacDonald et al. |
| 2013/0198879 | A1 | 8/2013 | McWhirter et al. |
| 2013/0212719 | A1 | 8/2013 | MacDonald et al. |
| 2013/0247235 | A1 | 9/2013 | McWhirter et al. |
| 2013/0254911 | A1 | 9/2013 | MacDonald et al. |
| 2013/0323790 | A1 | 12/2013 | MacDonald et al. |
| 2013/0323791 | A1 | 12/2013 | MacDonald et al. |
| 2013/0326647 | A1 | 12/2013 | MacDonald et al. |
| 2013/0333057 | A1 | 12/2013 | MacDonald et al. |
| 2014/0017228 | A1 | 1/2014 | MacDonald et al. |
| 2014/0041067 | A1 | 2/2014 | Bradley et al. |
| 2014/0120582 | A1 | 5/2014 | Bradley et al. |
| 2014/0130193 | A1 | 5/2014 | MacDonald et al. |
| 2014/0130194 | A1 | 5/2014 | MacDonald et al. |
| 2014/0137275 | A1 | 5/2014 | MacDonald et al. |
| 2014/0150125 | A1 | 5/2014 | Bradley et al. |
| 2014/0150126 | A1 | 5/2014 | Bradley et al. |
| 2014/0182003 | A1 | 6/2014 | Bradley et al. |
| 2014/0201854 | A1 | 7/2014 | Bradley et al. |
| 2014/0201856 | A1 | 7/2014 | Bradley et al. |
| 2014/0212416 | A1 | 7/2014 | Friedrich et al. |
| 2014/0213773 | A1 | 7/2014 | MacDonald et al. |
| 2014/0323327 | A1 | 10/2014 | Bradley et al. |
| 2014/0325690 | A1 | 10/2014 | Bradley et al. |
| 2014/0331339 | A1 | 11/2014 | Bradley et al. |
| 2014/0331344 | A1 | 11/2014 | Friedrich et al. |
| 2014/0359797 | A1 | 12/2014 | Bradley et al. |
| 2015/0033369 | A1 | 1/2015 | Bradley et al. |
| 2015/0033372 | A1 | 1/2015 | Bradley et al. |
| 2015/0040250 | A1 | 2/2015 | Bradley et al. |
| 2015/0082466 | A1 | 3/2015 | Clube |
| 2015/0113669 | A1 | 4/2015 | Bradley et al. |
| 2015/0133641 | A1 | 5/2015 | Germaschewski et al. |
| 2015/0196015 | A1 | 7/2015 | MacDonald et al. |
| 2015/0334998 | A1 | 11/2015 | Bradley et al. |
| 2016/0044900 | A1 | 2/2016 | Bradley et al. |
| 2016/0150768 | A1 | 6/2016 | Bradley et al. |
| 2016/0219846 | A1 | 8/2016 | Liang |
| 2016/0249592 | A1 | 9/2016 | Bradley et al. |
| 2016/0345551 | A1 | 12/2016 | Bradley et al. |
| 2016/0345552 | A1 | 12/2016 | Bradley et al. |
| 2016/0353719 | A1 | 12/2016 | Friedrich et al. |
| 2017/0051045 | A1 | 2/2017 | Bradley et al. |
| 2017/0071174 | A1 | 3/2017 | Bradley et al. |
| 2017/0081423 | A1 | 3/2017 | Bradley et al. |
| 2017/0094956 | A1 | 4/2017 | Bradley et al. |
| 2017/0096498 | A1 | 4/2017 | Bradley et al. |
| 2017/0099815 | A1 | 4/2017 | Bradley et al. |
| 2017/0099816 | A1 | 4/2017 | Bradley et al. |
| 2017/0099817 | A1 | 4/2017 | Bradley et al. |
| 2017/0101482 | A1 | 4/2017 | Bradley et al. |
| 2017/0101483 | A1 | 4/2017 | Bradley et al. |
| 2017/0105396 | A1 | 4/2017 | Bradley et al. |
| 2017/0135327 | A1 | 5/2017 | Lee |
| 2017/0320936 | A1 | 11/2017 | Bradley et al. |
| 2018/0030121 | A1 | 2/2018 | Bradley et al. |

FOREIGN PATENT DOCUMENTS

| | | | |
|---|---|---|---|
| EP | 1780272 | A1 | 5/2007 |
| GB | 2398784 | A | 9/2004 |
| GB | 2403475 | A | 1/2005 |
| KR | 20050042792 | A | 5/2005 |
| WO | WO-9004036 | A1 | 4/1990 |
| WO | WO-9100906 | A1 | 1/1991 |
| WO | WO-9110741 | A1 | 7/1991 |
| WO | WO-92/03918 | A1 | 3/1992 |
| WO | WO-9312227 | A1 | 6/1993 |
| WO | WO-9402602 | A1 | 2/1994 |
| WO | WO-9404667 | A1 | 3/1994 |
| WO | WO-9425585 | A1 | 11/1994 |
| WO | WO-9630498 | A1 | 10/1996 |
| WO | WO-9824884 | A1 | 6/1998 |
| WO | WO-9824893 | A2 | 6/1998 |
| WO | WO-9945962 | A1 | 9/1999 |
| WO | WO-00/71585 | | 11/2000 |
| WO | WO-0208409 | A2 | 1/2002 |
| WO | WO-0236789 | A2 | 5/2002 |
| WO | WO-0243478 | A2 | 6/2002 |
| WO | WO-02053596 | A2 | 7/2002 |
| WO | WO-02059263 | A2 | 8/2002 |
| WO | WO-02066630 | A1 | 8/2002 |
| WO | WO-02070648 | A2 | 9/2002 |
| WO | WO 03006639 | A1 | 1/2003 |
| WO | WO-03047336 | A2 | 6/2003 |
| WO | WO-03061363 | A2 | 7/2003 |
| WO | WO-2004050838 | A2 | 6/2004 |
| WO | WO-2005003364 | A2 | 1/2005 |
| WO | WO-2005004592 | A2 | 1/2005 |
| WO | WO-2005019463 | A1 | 3/2005 |
| WO | WO-2005058815 | A2 | 6/2005 |
| WO | WO-2005092926 | A2 | 10/2005 |
| WO | WO-2006008548 | A2 | 1/2006 |
| WO | WO-2006/029459 | A1 | 3/2006 |
| WO | WO-2006044492 | A2 | 4/2006 |
| WO | WO-2006055704 | A2 | 5/2006 |
| WO | WO-2006068953 | A2 | 6/2006 |
| WO | WO-2006122442 | A1 | 11/2006 |

(56) References Cited

FOREIGN PATENT DOCUMENTS

| | | | | |
|---|---|---|---|---|
| WO | WO-2007085837 | A1 | | 8/2007 |
| WO | WO-2007096779 | A2 | | 8/2007 |
| WO | WO-2007117410 | A2 | | 10/2007 |
| WO | WO-2007143168 | A2 | | 12/2007 |
| WO | WO-2008022391 | A1 | | 2/2008 |
| WO | WO-2008054606 | A2 | | 5/2008 |
| WO | WO-2008070367 | A2 | | 6/2008 |
| WO | WO-2008076379 | A2 | | 6/2008 |
| WO | WO-2008081197 | A1 | | 7/2008 |
| WO | WO-2008094178 | A2 | | 8/2008 |
| WO | WO-2008103474 | A1 | | 8/2008 |
| WO | WO-2008/108918 | | | 9/2008 |
| WO | WO-2008118970 | A2 | | 10/2008 |
| WO | WO-2008122886 | A2 | | 10/2008 |
| WO | WO-2008151081 | A1 | | 12/2008 |
| WO | WO-2009013620 | A2 | | 1/2009 |
| WO | WO-2009018411 | A1 | | 2/2009 |
| WO | WO-2009023540 | A1 | | 2/2009 |
| WO | WO-2009076464 | A2 | | 6/2009 |
| WO | WO-2009080254 | A1 | | 7/2009 |
| WO | WO-2009097006 | A2 | | 8/2009 |
| WO | WO-2009118524 | A2 | | 10/2009 |
| WO | WO-2009129247 | A2 | | 10/2009 |
| WO | WO-2009143472 | A2 | | 11/2009 |
| WO | WO-2009157771 | A2 | | 12/2009 |
| WO | WO-2010039900 | A2 | | 4/2010 |
| WO | WO-2010070263 | A1 | | 6/2010 |
| WO | 2010/077854 | A1 | † | 7/2010 |
| WO | WO-2010077854 | A1 | | 7/2010 |
| WO | WO-2010097385 | A1 | | 9/2010 |
| WO | WO-2010109165 | A2 | | 9/2010 |
| WO | WO-2010113039 | A1 | | 10/2010 |
| WO | WO-2011004192 | A1 | | 1/2011 |
| WO | WO-2011008093 | A1 | | 1/2011 |
| WO | WO-2011056864 | A1 | | 5/2011 |
| WO | WO-2011062206 | A1 | | 5/2011 |
| WO | WO-2011062207 | A1 | | 5/2011 |
| WO | WO-2011071957 | A1 | | 6/2011 |
| WO | WO-2011072204 | A1 | | 6/2011 |
| WO | WO-2011097603 | A1 | | 8/2011 |
| WO | WO-2011146121 | A1 | | 11/2011 |
| WO | WO-2011158009 | A1 | | 12/2011 |
| WO | WO-2011163311 | A1 | | 12/2011 |
| WO | WO-2011163314 | A1 | | 12/2011 |
| WO | WO-2012018764 | A1 | | 2/2012 |
| WO | WO-2012023053 | A2 | | 2/2012 |
| WO | WO-2012141798 | A1 | | 10/2012 |
| WO | WO-2012148873 | A2 | | 11/2012 |
| WO | WO-2013022782 | A1 | | 2/2013 |
| WO | 2013041846 | A2 | † | 3/2013 |
| WO | WO-2013041844 | A2 | | 3/2013 |
| WO | WO-2013041845 | A2 | | 3/2013 |
| WO | WO-2013059230 | A1 | | 4/2013 |
| WO | WO-2013061098 | A2 | | 5/2013 |
| WO | WO-2013096142 | A1 | | 6/2013 |
| WO | WO-2013116609 | A1 | | 8/2013 |
| WO | WO-2013/130981 | A1 | | 9/2013 |
| WO | WO-2013134263 | A1 | | 9/2013 |
| WO | WO-2013176772 | A1 | | 11/2013 |
| WO | WO-2014093622 | A2 | | 6/2014 |

OTHER PUBLICATIONS

Carstea et al., 2009, World Journals of Stem Cells, vol. 1, No. 1, p. 22-29.*

Patil et al., 2011, Indian Journal of Public Health research & Development, vol. 2, No. 1, p. 106-109.*

Khodarovich et al., 2013, Applied Biochemistry and Microbiology, vol. 49, No. 9, pp. 711-722.*

Selsby et al., 2015, ILAR Journal, vol. 56, No. 1, p. 116-126.*

Maksimenko et al., 2013, Acta Naturae, vol. 5, No. 1, p. 33-46.*

Yang et al., 2016, PNAS, 113(41), E6209-E6218, p. 1-10.*

U.S. Appl. No. 13/310,431, filed Dec. 2, 2011.

U.S. Appl. No. 13/846,672, filed Mar. 18, 2013, issued Oct. 17, 2017 as U.S. Pat. No. 9,788,534.

U.S. Appl. No. 13/886,511, filed May 3, 2013.

U.S. Appl. No. 14/040,405, filed Sep. 27, 2013.

U.S. Appl. No. 14/040,427, filed Sep. 27, 2013.

U.S. Appl. No. 14/052,259, filed Oct. 11, 2013.

U.S. Appl. No. 14/056,434, filed Oct. 17, 2013.

U.S. Appl. No. 14/056,700, filed Oct. 17, 2013.

U.S. Appl. No. 14/056,707, filed Oct. 17, 2013.

U.S. Appl. No. 14/080,630, filed Nov. 14, 2013.

U.S. Appl. No. 14/220,080, filed Mar. 19, 2014.

U.S. Appl. No. 14/220,099, filed Mar. 19, 2014.

U.S. Appl. No. 14/226,698, filed Mar. 26, 2014.

U.S. Appl. No. 14/226,706, filed Mar. 26, 2014.

U.S. Appl. No. 14/263,158, filed Apr. 28, 2014.

U.S. Appl. No. 14/263,176, filed Apr. 28, 2014.

U.S. Appl. No. 14/497,054, filed Sep. 25, 2014.

U.S. Appl. No. 14/498,685, filed Sep. 26, 2014.

U.S. Appl. No. 14/516,461, filed Oct. 16, 2014.

U.S. Appl. No. 15/088,805, filed Apr. 1, 2016.

U.S. Appl. No. 15/369,595, filed Dec. 5, 2016.

U.S. Appl. No. 15/690,183, filed Aug. 29, 2017; and.

U.S. Appl. No. 15/786,281, filed Oct. 17, 2017.

Adekar S.P., et al., "A Natural Human IgM Antibody that Neutralizes Botulinum Neurotoxin in vivo," *Hybridoma*, 2008, vol. 27 (2), pp. 65-69.

Aizenshtein E., et al., "Immunological complex for enhancement of innate immune response in passive vaccination," *Vaccine*, Jan. 2013, vol. 31 (4), pp. 626-631 [abstract only—1 page].

Australian IP Office, Notification of material filed by a third-party for Application No. 2012311288 in the name of Kymab Ltd., Applicant, dated Nov. 20, 2017, 14 pages.

Boyd S.D., et al., "Individual Variation in the Germline Ig Gene Repertoire Inferred from Variable Region Gene Rearrangements," *The Journal of Immunology*, Jun. 2010, vol. 184 (12), pp. 6986-6992.

Bradley A., Declarations of Allan Bradley (Tanamachi/Grosveld), as submitted in U.S. Appl. No. 13/416,684, 5 pages.

Bradley A., Declaration of Allan Bradley (commercial success), with exhibits, as submitted in U.S. Appl. No. 13/416,684, dated Feb. 12, 2015, 15 pages.

Bradley A., Declaration of Allan Bradley (mouse strain), with exhibits, as submitted in U.S. Appl. No. 13/416,684, dated Feb. 12, 2015, 68 pages.

Bradshaw, et al., "*Handbook of Cell Signalling*," 2010, Chapter 5, p. 33 (excerpt).

Brüggemann M., et al., "Selection Strategies III: Transgenic Mice," in *Handbook of Therapeutic Antibodies—Technologies, Emerging Developments and Approved Therapeutics*, 2010, Chapter 4, pp. 69-91.

Burton D.R., et al., "Antibody vs. HIB in a clash of evolutionary titans," *Proceedings of the National Academy of Sciences of the U.S.A*, Oct. 2005, vol. 102 (42), pp. 14943-14948.

Camboni M., et al., "Active and passive immunization strategies based on the SDPM1 peptide demonstrate pre-clinical efficacy in the APPswePSEN1dE9 mouse model for Alzheimer's disease," *Neurobiology of Disease*, Feb. 2014, vol. 52, pp. 31-43 [abstract only—2 pages].

Collis A.V.J., et al., "Analysis of the Antigen Combining Site: Correlations Between Length and Sequence Composition of the Hypervariable Loops and the Nature of the Antigen," *Journal of Molecular Biology*, 2003, vol. 325, pp. 337-354.

Davis C.G., et al., "Production of Human Antibodies from Transgenic Mice," *Antibody Engineering, Methods and Protocols, Methods in Mol. Biol.*, Chapter 10, 2004, pp. 191-200.

Delves P.J., et al., "Antibodies," Chapter 3, *Roitt's Essential Immunology*, Eleventh edition, 2006, pp. 37-60.

Dörner T., et al., "Delineation of Selective Influences Shaping the Mutated Expressed Human Ig Heavy Chain Repertoire," *The Journal of Immunology*, Mar. 1998, vol. 160 (6), pp. 2831-2841.

Dörner T., et al., "Analysis of the targeting of the hypermutational machinery and the impact of subsequent selection on the distribu-

(56) References Cited

OTHER PUBLICATIONS tion of nucleotide changes in human $V_HDJ_H$ rearrangements," *Immunologic Reviews*, Apr. 1998, vol. 162 (1), pp. 161-171.
Dörner T., et al., "Somatic hypermutation of human immunoglobulin heavy chain genes: targeting of RGYW motifs on both DNA strands," *European Journal of Immunology*, 1998, vol. 28, pp. 3384-3396.
Dübel S., "Therapeutic Antibodies—From Past to Future," in *Handbook of Therapeutic Antibodies—Technologies, Emerging Developments and Approved Therapeutics*, 2010, Chapter 1 (excerpt: pp. 3-5).
European Patent Office, Examination Report for Application No. 13723933.1, dated Jan. 17, 2018, 6 pages.
European Patent Office, Extended European Search Report for Application No. 17196214.5, dated Jan. 2, 2018, 13 pages.
European Patent Office, Opposition against EP2798950 Animal Models and Therapeutic Molecules in the name of Kymab Limited pertaining to Application No. 14170196.1, dated Jan. 18, 2018, 33 pages.
Frigerio B., et al., "Antibody Engineering as Opportunity for Selection and Organization of Anti-HIV Therapeutic Agents," *The Open Autoimmunity Journal*, 2010, vol. 2, pp. 127-138.
Genbank, "*Homo sapiens* partial IGHJ6 gene for immunoglobulin heavy joining 6, exon 1, allele 4," AJ879487.1, dated Jul. 26, 2016, 1 page.
Giudicelli V., et al., "IMGT/GENE-DB: a comprehensive database for human and mouse immunoglobulin and T cell receptor genes," Nucleic Acids Research, 2005, vol. 33, pp. D256-D261.
He Y., et al., "Efficient Isolation of Novel Human Monoclonal Antibodies with Neutralizing Activity Against HIV-1 from Transgenic Mice Expressing Human Ig Loci," *The Journal of Immunology*, 2002, vol. 169, pp. 595-605.
HGNC (HUGO Gene Nomenclature Committee), "Gene Family: Immunoglobulin Heavy Locus at 14q32.33 (IGH)," 4 pages. [retrieved on Jul. 31, 2017 at http://www.genenames.org/cgi-bin/genefamilies/set/349].
Hülseweh B., et al, "Human-like antibodies neutralizing Western equine encephalitis virus," *mAbs*, May/Jun. 2014, vol. 6 (3), pp. 718-727.
Imbimbo B.P., et al., "Solanezumab for the treatment of mild-to-moderate Alzheimer's disease," *Expert Review of Clinical Immunology*, Feb. 2012, vol. 8 (2), pp. 135-149 [abstract only—1 page].
IMGT, *the International ImMunoGeneTics Information system database*, "IMGT/GENE-DB entry for *Homo sapiens* IGHD3-9," 2007, 2 pages.
IMGT, *the International ImMunoGeneTics Information system database*, "Alignment of alleles: Human IGHJ6," dated Jun. 29, 2011, 1 page.
IMGT, *the International ImMunoGeneTics Information system database*, "IMGT/GENE-DB entry for *Homo sapiens* IGHJ6," dated Jul. 26, 2017, version 3.1.17, 4 pages.
IMGT, *the International ImMunoGeneTics Information system database*, "IMGT/GENE-DB reference sequences," Nucleotide sequences of the four human IGHJ6 alleles, dated Jul. 26, 2017, version 3.1.17, 1 page.
IMGT, *the International ImMunoGeneTics Information system database*, "IMGT/GENE-DB reference sequences," Amino acid sequences of the four human IGHJ6 alleles, dated Jul. 26, 2017, version 3.1.17, 7 pages.
Jackson S.M., et al., "Human B Cell Subsets," *Advances in Immunology*, Chapter 5, 2008, vol. 98, pp. 151-224.
Kim S.J., et al., "Antibody Engineering for the Development of Therapeutic Antibodies," *Mol. Cells*, 2005, vol. 20 (1), pp. 17-29.
Kriangkum J., et al., "Molecular Characterization of Waldenstrom's Macroglobulinemia Reveals Frequent Occurrence of Two B-Cell Clones Having Distinct IgH VDJ Sequences," *Clinical Cancer Research*, Apr. 2007, vol. 13 (7), pp. 2005-2013.
Lee E., et al., "Use of IGHJ and IGHD gene mutations in analysis of immunoglobulin sequences for the prognosis of chronic lymphocytic leukemia," *Leukemia Research*, 2007, vol. 31, pp. 1247-1252.
Lonberg N., et al., "Human Antibodies from Transgenic Mice," *Intern. Rev. Immunol.*, 1995, vol. 13, pp. 65-93.
Lonberg N., "Human Monoclonal Antibodies from Transgenic Mice," *Therapeutic Antibodies. Handbook of Experimental Pharmacology*, 2008, pp. 69-97.
Potter K.N., et al., "Features of the overexpressed V1-69 genes in the unmutated subset of chronic lymphocytic leukemia are distinct from those in the healthy elderly repertoire," *Blood*, Apr. 2003, vol. 101 (8), pp. 3082-3084.
Prak E.T.L, et al., "B cell receptor editing in tolerance and autoimmunity," *Annals of the New York Academy of Sciences*, Jan. 2011, vol. 1217, pp. 96-121.
Raaphorst F.M., et al., "Human Ig heavy chain CDR3 regions in adult bone marrow pre-B cells display an adult phenotype of diversity: evidence for structural selection of $D_H$ amino acid sequences," *International Immunology*, Oct. 1997, vol. 9 (10), pp. 1503-1515.
Ren L., et al., "Silencing of the immunoglobulin heavy chain locus by removal of all eight constant-region genes in a 200-kb region," *Genomics*, Aug. 2004, vol. 84, pp. 686-695.
Rudolf M.P., et al., "Molecular basis for nonanaphylactogenicity of a monoclonal anti-IgE antibody," *Journal of Immunology*, Jul. 2010, vol. 165 (2), pp. 813-819.
Ruiz M., et al, "The Human Immunoglobulin Heavy Diversity (IGHD) and Joining (IGHJ) Segments," *Experimental and Clinical Immunogenetics*, 1999, vol. 16, pp. 173-184.
Russell N.D., et al., "Production of Protective Human Antipneumococcal Antibodies by Transgenic Mice with Human Immunoglobulin Loci," *Infection and Immunity*, Apr. 2000, vol. 68 (4), pp. 1820-1826.
Shore D.E., Attorney for Applicant, Third-Party Pre-Issuance Submission Under 37 CFR Sec. 1.290 in U.S. Appl. No. 15/088,805, filed Nov. 17, 2017, 44 pages.
Shore D.E., Attorney for Applicant, Third-Party Pre-Issuance Submission Under 37 CFR Sec. 1.290 in U.S. Appl. No. 15/690,183, filed Feb. 28, 2018, 60 pages.
Siman-Tov D.D., et al., "Differentiation of a passive vaccine and the humoral immune response toward infection: Analysis of phage displayed peptides," *Vaccine*, Jan. 2006, vol. 24, pp. 607-612.
Table S1 (from Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857-1-e16857-11.), 60 pages.
Table S2 (from Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857-1-e16857-11.), 14 pages.
Taylor L.D., et al., "A transgenic mouse that expresses a diversity of human sequence heavy and light chain immunoglobulins," *Nucleic Acids Research*, 1992, vol. 20 (23), pp. 6287-6295.
Zwick M.B., et al., "The Long Third Complementarity-Determining Region of the Heavy Chain Is Important in the Activity of the Broadly Neutralizing Anti-Human Immunodeficiency Virus Type 1 Antibody 2F5," *Journal of Virology*, Mar. 2004, vol. 78 (6), pp. 3155-3161.
1st International MUGEN Conference on Animal Models for Human Immunological Disease, Sep. 10-13, 2006—Athens Greece (Abstracts 1-52), 52 pages.
Adams D.J., et al., "A Genome-Wide, End-Sequenced 129Sv BAC Library Resource for Targeting Vector Construction," *Genomics*, 2005, vol. 86 (6), pp. 753-758.
Adams D.J., et al., "Contemporary approaches for modifying the mouse genome," *Physiological Genomics*, vol. 34, 2008, pp. 225-238.
Adams D.J., et al., "Mutagenic Insertion and Chromosome Engineering Resource (MICER)," *Nature Genetics*, vol. 36 (8), Aug. 2004, pp. 867-871.
Affidavits Evidencing Murphy Slides as Printed Publication, dated Jun. 20, 2016, 84 pages.
Aguilera R.J., et al., "Characterization of immunoglobulin enhancer deletions in murine plasmacytomas," *The EMBO Journal*, 1985, vol. 4 (13B), pp. 3689-3693.

(56) References Cited

OTHER PUBLICATIONS

Ahmed T., "Sanofi-aventis and Regeneron Extend Therapeutic Antibody Agreement," *PharmaDeals Review*, Nov. 2009, vol. 11, p. 115.
Arnaout R., et al., "High-Resolution Description of Antibody Heavy-Chain Repertoires in Humans," *PLoS One*, Aug. 2011, vol. 6 (8), pp. e22365-1-e22365-8.
Arthur J.S.C., et al., "Gene-Targeting Vectors," *Transgenesis Techniques, Principles and Protocols*, Third edition, Chapter 9, 2009 (24 pages, including cover sheet, copyright and preface pages and table of contents), pp. 127-144.
Asenbauer H., et al., "The immunoglobulin lambda light chain enhancer consists of three modules which synergize in activation of transcription," *European Journal of Immunology*, 1999, vol. 29, pp. 713-724.
Askew G.R., et al., "Site-Directed Point Mutations in Embryonic Stem Cells: A Gene-Targeting Tag-and-Exchange Strategy," *Molecular and Cellular Biology*, Jul. 1993, vol. 13 (7), pp. 4115-4124.
Atlas of Genetics and Cytogenetics in Oncology and Haematology, VPREB1 (pre-B lymphocyte 1), 5 pages. [Retrieved online at http://atlasgeneticsoncolgy.org/Genes/GC_VPREB1.html on May 25, 2015].
Auerbach W., et al., "Establishment and Chimera Analysis of 129/SvEv- and C57BL/6-Derived Mouse Embryonic Stem Cell Lines," BioTechniques, 2000, vol. 29 (5), pp. 1024-1032.
Australian IP Office, Examination Report No. 1 for Standard Patent Application for Application No. 2016244295, dated Aug. 18, 2017, 4 pages.
Avery S., Attorney for Applicant, Third-Party Pre-Issuance Submission Under 37 CFR Section 1.290 in U.S. Appl. No. 14/517,755, dated Jun. 26, 2015, 16 pages.
Baer A., et al., "Coping with kinetic and thermodynamic barriers: RMCE, an efficient strategy for the targeted integration of transgenes," *Current Opinions in Biotechnology*, Oct. 2001, vol. 12 (5), pp. 473-480.
Baker A.M., et al., "Adaptation of TCR Expression Vectors for the Construction of Mouse-Human Chimeric MBP-Specific TCR Transgenes," *Journal of Neuroscience Research*, 1996, vol. 45 (4), pp. 487-491.
Baker M.D., et al., "Homologous Recombination Between Transferred and Chromosomal Immunoglobulin Kappa Genes," *Molecular and Cellular Biology*, Oct. 1988, vol. 8 (10), pp. 4041-4047.
Barreto V.M., et al., "AID from bony fish catalyzes class switch recombination," *Journal of Experimental Medicine*, 2005, vol. 202 (6), pp. 733-738.
Bates J.G., et al., "Chromosomal Position of a $V_H$ Gene Segment Determines its Activation and Inactivation as a Substrate for V(D)J Recombination," *Journal of Experimental Medicine*, 2007, vol. 204 (13), pp. 3247-3256.
Baxendale H.E., et al., "Natural human antibodies to pneumococcus have distinctive molecular characteristics and protect against pneumococcal disease," *Clinical and Experimental Immunology*, 2007, vol. 151, pp. 51-60.
Beard C., et al., "Efficient Method to Generate Single-Copy Transgenic Mice by Site-Specific Integration in Embryonic Stem Cells," *Genesis*, 2006, vol. 44 (1), pp. 23-28.
Beck E., et al., "Nucleotide Sequence and Exact Localization of the Neomycin Phosphotransferase Gene From Transposon Tn5," *Genesis*, 1982, vol. 19 (3), pp. 327-336.
Beck J.A., et al., "Genealogies of mouse inbred strains," *Nature Genetics*, 2000, vol. 24, pp. 23-25 (with supporting table and chart).
Beerli R.R., et al., "Mining Human Antibody Repertoires," *mAbs*, Jul./Aug. 2010, vol. 2 (4), pp. 365-378.
Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.
Berg D.E., et al., "Inverted Repeats of Tn5 are Transposable Elements," *Proceedings of the National Academy of Sciences U.S.A*, 1982, vol. 79 (8), pp. 2632-2635.
Bethke B., et al., "Segmental Genomic Replacement by Cre-Mediated Recombination: Genotoxic Stress Activation of the p53 Promoter in Single-Copy Transformants," *Nucleic Acids Research*, 1997, vol. 25 (14), pp. 2828-2834.
Bhattacharya P., et al., "Switch Region Identity Plays an Important Role in Ig Class Switch Recombination," *Journal of Immunology*, 2010, vol. 184 (11), pp. 6242-6248.
Billiard F., et al., "Ongoing DII4-Notch Signaling is Required for T-Cell Homeostasis in the Adult Thymus," *European Journal of Immunology*, 2011, vol. 41 (8), pp. 2207-2216.
Birling M.C., et al., "Site-Specific Recombinases for Manipulation of the Mouse Genome," *Transgenesis Techniques, Principles and Protocols*, Third edition, Chapter 16, 2009 (25 pages, including cover sheet, copyright and preface pages and table of contents), pp. 245-263.
Blankenstein T., et al., "Immunoglobulin $V_H$ Region Genes of the Mouse are Organized in Overlapping Clusters," *European Journal of Immunology*, 1987, vol. 17 (9), pp. 1351-1357.
Board of Appeal of the European Patent Office, Datasheet for the Decision of Nov. 9, 2015 for Application No. 02709544.7, Case T 2220/14-3.3.08, 83 pages.
Bode J., et al., "The Transgeneticist's Toolbox: Novel Methods for the Targeted Modification of Eukaryotic Genomes," *Biological Chemistry*, Sep./Oct. 2000, vol. 381 (9-10), pp. 801-813.
Bogen B., et al., "A Rearranged $\lambda_2$ Light Gene Chain Retards but does not Exclude $\kappa$ and $\lambda_1$ Expression," *European Journal of Immunology*, 1991, vol. 21 (10), pp. 2391-2395.
Bolland D.J., et al., "Antisense Intergenic Transcription Precedes Igh D-To-J Recombination and is Controlled by the Intronic Enhancer Eμ," *Molecular and Cellular Biology*, 2007, vol. 27 (15), pp. 5523-5533.
Bonin A., et al., "Isolation, Microinjection, and Transfer of Mouse Blastocysts," *Methods in Molecular Biology*, Chapter 9, 2001, vol. 158, pp. 121-134.
Bornstein G.G. et al., "Development of a new fully human anti-CD20 monoclonal antibody for the treatment of B-cell malignancies", *Investigational New Drugs*, 2010, vol. 28, pp. 561-574.
Bottaro A., et al., "Deletion of the IgH Intronic Enhancer and Associated Matrix-Attachment Regions Decreases, but does not Abolish, Class Switching at the μ Locus," *International Immunology*, 1998, vol. 10 (6), pp. 799-806.
Bradley A., et al., "Formation of Germ-Line Chimaeras from Embryo-Derived Teratocarcinoma Cell Lines," *Nature*, 1984, vol. 309 (5965), pp. 255-256.
Bransteitter R., et al., "Activation-Induced Cytidine Deaminase Deaminates Deoxycytidine on Single-Stranded DNA but Requires the Action of RNase," *Proceedings of the National Academy of Sciences of the U.S.A.*, Apr. 2003, vol. 100 (7), pp. 4102-4107.
Brault V., et al., "Modeling Chromosomes in Mouse to Explore the Function of Genes, Genomic Disorders, and Chromosonal Organization," *PLoS Genetics*, Jul. 2006, vol. 2 (7), pp. e86-1-e86-9.
Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857.
Brezinschek H.P., et al., "Analysis of the Human $V_H$ Gene Repertoire," *Journal of Clinical Investigation*, 1997, vol. 99 (10), pp. 2488-2501.
Brüggemann M., et al., "A Repertoire of Monoclonal Antibodies with Human Heavy Chains from Transgenic Mice," *Proceedings of the National Academy of Sciences U.S.A*, 1989, vol. 86 (17), pp. 6709-6713.
Brüggemann M., "Human Antibody Expression in Transgenic Mice," *Archivum Immunologiae et Therapia Experimentalis*, 2001, vol. 49 (3), pp. 203-208.
Brüggemann M., et al., "Human Antibody Production in Transgenic Mice: Expression from 100 Kb of the Human IgH Locus," *European Journal of Immunology*, May 1991, vol. 21 (5), pp. 1323-1326.
Brüggemann M., et al., "Immunoglobulin Heavy Chain Locus of the Rat: Striking Homology to Mouse Antibody Genes," *Proceedings of the National Academy of Sciences U.S.A*, 1986, vol. 83 (16), pp. 6075-6079.

(56) References Cited

OTHER PUBLICATIONS

Brüggemann M., et al., "The Immunogenicity of Chimeric Antibodies," *The Journal of Experimental Medicine*, Dec. 1989, vol. 170 (6), pp. 2153-2157.
Brüggemann M., et al., "Strategies for Expressing Human Antibody Repertoires in Transgenic Mice," *Immunology Today*, Aug. 1996, vol. 17 (8), pp. 391-397.
Briney B.S., et al., "Human Peripheral Blood Antibodies with Long HCDR3s are Established Primarily at Original Recombination using a Limited Subset of Germline Genes," *PLoS One*, 2012, vol. 7 (5), pp. e36750-1-e36750-13.
Brocker C.N., et al., "Evolutionary Divergence and Functions of the ADAM and ADAMTS Gene Families," Human Genomics, 2009, vol. 4 (1), pp. 43-55.
Büggemann M., "Human Monoclonal Antibodies from Translocus Mice," Molecular Biology of B Cells, Chapter 34, 2003, pp. 547-561.
Buehr M., et al., "Capture of Authentic Embryonic Stem Cells from Rat Blastocysts," *Cell*, 2008, vol. 135 (7), pp. 1287-1298.
Butler J.E., "Immunoglobulin Diversity, B-Cell and Antibody Repertoire Development in Large Farm Animals," *Revue scientifique et technique* (*International Office of Epizootics*), 1998, vol. 17 (7), pp. 43-70.
Cadiñanos J., et al., "Generation of an Inducible and Optimized PiggyBac Transposon System," *Nucleic Acids Research*, 2007, vol. 35 (12), pp. e87.
Call L.M., et al., "A Cre-lox recombination system for the targeted integration of circular yeast artificial chromosomes into embryonic stem cells," *Human Molecular Genetics*, 2000, vol. 9 (12), pp. 1745-1751.
Carstea A.C., et al., "Germline Competence of Mouse ES and iPS Cell Lines: Chimera Technologies and Genetic Background," *World Journal of Stem Cells*, 2009, vol. 1 (1), pp. 22-29.
Carter T.C., et al., "Standardized Nomenclature for Inbred Strains of Mice," *Cancer Research*, 1952, vol. 12 (8), pp. 602-613.
Casrouge A., et al., "Size Estimate of the αβ TCR Repertoire of Naive Mouse Splenocytes," *The Journal of Immunology*, 2000, vol. 164 (11), pp. 5782-5787.
Chan A.C., et al., "Therapeutic Antibodies for Autoimmunity and Inflammation," *Nature Reviews Immunology*, 2010, vol. 10 (5), pp. 301-316.
Chen C., et al., "Immunoglobulin Heavy Chain Gene Replacement: A Mechanism of Receptor Editing," *Immunity*, 1995, vol. 3 (6), pp. 747-755.
Chen J., et al., "B Cell Development in Mice that Lack One or Both Immunoglobulin κ Light Chain Genes," *The EMBO Journal*, 1993, vol. 12 (3), pp. 821-830.
Chen Y., "PiggyBac Transposon-Mediated, Reversible Gene Transfer in Human Embryonic Stem Cells," *Stem Cells and Development*, Nov. 2010, vol. 19 (6), 9 pages.
Chia R., et al., "The origins and uses of mouse outbred stocks," *Nature Genetics*, 2005, vol. 37 (11), pp. 1181-1186.
Chinese Patent Office, First Office Action (English Translation) for Chinese Application No. 201180039668.1, dated Jan. 3, 2014, 6 pages.
Chinese Patent Office, First Office Action for Chinese Patent Application No. 201180039668.1, dated Jan. 3, 2014, 6 pages.
Chinese Patent Office, Office Action (English Translation) for Chinese Patent Application No. 201380029744.1, dated Nov. 10, 2016, 2 pages.
Chinese Patent Office, Office Action for Chinese Patent Application No. 201380027944.1, dated Nov. 10, 2016, 5 pages.
Chinese Patent Office, Search Report (English Translation), Chinese Patent Application No. 201180039668.1, dated Jan. 3, 2014, 2 pages.
Chinese Patent Office, Search Report, Chinese Patent Application No. 201180039668.1, dated Jan. 3, 2014, 1 page.
Cho C., "Testicular and Epididymal ADAMs: Expression and Function During Fertilization," *Nature Reviews Urology*, 2012, vol. 9 (10), pp. 550-560.
Choi I., et al., "Characterization and Comparative Genomic Analysis of Intronless Adams with Testicular Gene Expression," *Genomics*, 2004, vol. 83 (4), pp. 636-646.
Clark J ., et al., "A Future for Transgenic Livestock," *Nature Reviews Genetics*, 2003, vol. 4 (10), pp. 825-833.
Clark L.A., et al., "Trends in Antibody Sequence Changes During the Somatic Hypermutation Process," *The Journal of Immunology*, 2006, vol. 177 (1), pp. 333-340.
Clark M.R., "IgG Effector Mechanisms," *Chemical Immunology*, 1997, vol. 65, pp. 88-110.
Colbère-Garapin F., et al., "A New Dominant Hybrid Selective Marker for Higher Eukaryotic Cells," *Journal of Molecular Biology*, 1981, vol. 150 (1), pp. 1-14.
Collins F.S., et al., "A Mouse for All Reasons," *Cell*, 2007, vol. 128 (1), pp. 9-13.
Collins A.M., et al., "The reported germline repertoire of human immunoglobulin kappa chain genes is relatively complete and accurate," *Immunogenetics*, 2008, vol. 60, pp. 669-676.
Combriato G., et al., "Regulation of Human Igλ Light Chain Gene Expression by NF-κB1," *The Journal of Immunology*, 2002, vol. 168 (3), pp. 1259-1266.
Conrath K.E., et al., "Camel Single-domain Antibodies as Modular Building Units in Bispecific and Bivalent Antibody Constructs," *The Journal of Biological Chemistry*, 2001, vol. 276 (10), pp. 7346-7350.
Copeland N.G., et al., "Recombineering: A Powerful New Tool for Mouse Functional Genomics," *Nature Reviews Genetics*, 2001, vol. 2 (10), pp. 769-779.
Corbett S.J., et al., "Sequence of the Human Immunoglobulin Diversity (D) Segment Locus: a Systematic Analysis Provides No Evidence for the Use of DIR Segments, Inverted D Segments, "Minor" D Segments or D-D Recombination," Journal of Molecular Biology, 1997, vol. 270 (4), pp. 587-597.
Corti D., et al., "A Neutralizing Antibody Selected from Plasma Cells that Binds to Group 1 and Group 2 Influenza A Hemagglutinins," *Science*, 2011, vol. 333 (6044), pp. 850-856.
Crouch E.E., et al., "Regulation of AID expression in the Immune Response," *Journal of Experimental Medicine*, May 2007, vol. 204 (5), pp. 1145-1156.
Cuesta A.M., et al., "Multivalent Antibodies: When Design Surpasses Evolution," *Trends in Biotechnology*, 2010, vol. 28 (7), pp. 355-362.
Davies N.P., et al., "Creation of Mice Expressing Human Antibody Light Chains by Introduction of a Yeast Artificial Chromosome Containing the Core Region of the Human Immunoglobulin κ Locus," *Nature Biotechnology*, Aug. 1993, vol. 11 (8), pp. 911-914.
D'Eustachio P., et al., "Mouse Chromosome 12," *Mammalian Genome*, 1998, vol. 8, pp. S241-257.
De Bono B., et al., "$V_H$ Gene Segments in the Mouse and Human Genomes," *Journal of Molecular Biology*, 2004, vol. 342 (1), pp. 131-143.
De Kruif J., et al., "Human Immunoglobulin Repertoires Against Tetanus Toxoid Contain a Large and Diverse Fraction of High-Affinity Promiscuous $V_H$ Genes," *Journal of Molecular Biology*, 2009, vol. 387 (3), pp. 548-558.
De Saint Vincent B.R., et al., "Homologous Recombination in Mammalian Cells Mediates Formation of a Functional Gene from Two Overlapping Gene Fragments," *Proceedings of the National Academy of Sciences of the U.S.A*, 1983, vol. 80 (7), pp. 2002-2006.
De Wildt R.M.T., et al., "Analysis of Heavy and Light Chain Pairings Indicates that Receptor Editing Shapes the Human Antibody Repertoire," *Journal of Molecular Biology*, 1999, vol. 285, pp. 895-901.
Dechiara T.M., et al., "Producing Fully ES Cell-Derived Mice from Eight-Cell Stage Embryo Injections," *Methods in Enzymology*, Chapter 16, 2010, vol. 476, pp. 285-294.
Dechiara T.M., et al., "VelociMouse: Fully ES Cell-Derived F0-Generation Mice Obtained from the Injection of EA Cells into Eight-Cell-Stage Embryos," *Methods in Molecular Biology*, Chapter 16, 2009, vol. 530, pp. 311-324.
Declerck P.J., et al., "Generation of Monoclonal Antibodies against autologous Proteins in Gene-inactivated Mice," *The Journal of Biological Chemistry*, Apr. 1995, vol. 270 (15), pp. 8397-8400.

(56) References Cited

OTHER PUBLICATIONS

Deftos, M., et al., "Defining the Genetic Origins of Three Rheumatoid Synovium-derived IgG Rheumatoid Factors," *Journal of Clinical Investigations*, Jun. 1994, vol. 93, pp. 2545-2553.
Deng C., et al., "Reexamination of Gene Targeting Frequency as a Function of the Extent of Homology Between the Targeting Vector and the Target Locus," *Molecular and Cellular Biology*, Aug. 1992, vol. 12 (8), pp. 3365-3371.
Denome R.M., et al., "Patterns of Polyadenylation Site Selection in Gene Constructs Containing Multiple Polyadenylation Signals," *Molecular and Cellular Biology*, 1988, vol. 8 (11), pp. 4829-4839.
Di Noia, J.M., et al., "Molecular Mechanisms of Antibody Somatic Hypermutation," *Annual Review of Biochemistry*, 2007, vol. 76, pp. 1-22.
Diez-Roux G., et al., "A High-Resolution Anatomical Atlas of the Transcriptome in the Mouse Embryo," *PLoS Biology*, 2011, vol. 9 (1), pp. 1-13.
Ding L., et al., "Generation of High-Affinity Fully Human Anti-Interleukin-8 Antibodies from its cDNA by Two-Hybrid Screening and Affinity Maturation in Yeast," *Protein Science*, 2010, vol. 19 (10), pp. 1957-1966.
Doetschman T., et al., "Establishment of Hamster Blastocyst-Derived Embryonic Stem (ES) Cells," *Developmental Biology*, 1988, vol. 127 (1), pp. 224-227.
Doetschman T., et al., "Targeted Mutation of the *Hprt* Gene in Mouse Embryonic Stem Cells," *Proceedings of the National Academy of Sciences of the U.S.A*, 1988, vol. 85 (22), pp. 8583-8587.
Donohoe M.E., et al., "Transgenic Human λ5 Rescues the Murine λ5 Nullizygous Phenotype," *Journal of Immunology*, 2000, vol. 164, pp. 5269-5276.
Doyle A., et al., "The Construction of Transgenic and Gene Knockout/Knockin Mouse Models of Human Disease," *Transgenic Research*, 2012, vol. 21 (2), pp. 327-349.
Durbin R., "A Map of Human Genome Variation from Population-Scale Sequencing," *Nature*, 1000 Genomes Project Consortium, 2010, vol. 467 (7319), pp. 1061-1073.
Durdik J., et al., "Isotype Switching by a Microinjected μ Immunoglobulin Heavy Chain Gene in Transgenic Mice," *Proceedings of the National Academy of Sciences of the U.S.A*, 1989, vol. 86 (7), pp. 2346-2350.
Ebert A., et al., "The Distal $V_H$ Gene Cluster of the lgh Locus Contains Distinct Regulatory Elements with Pax5 Transcription Factor-Dependent Activity in Pro-B Cells," *Immunity*, Feb. 2011, vol. 34 (2), pp. 175-187.
Edwards D.R., et al., "The ADAM Metalloproteinases," *Molecular Aspects of Medicine*, 2008, vol. 29 (5), pp. 258-289.
Eisener-Dorman A.F., et al., "Cautionary Insights on Knockout Mouse Studies: The Gene or not the Gene?," *Brain, Behavior, and Immunity*, 2009, vol. 23 (3), pp. 318-324.
Ekiert D.C., et al., "A Highly Conserved Neutralizing Epitope on Group 2 Influenza A Viruses," *Science*, 2011, vol. 333 (6044), pp. 843-850.
Engel H., et al., "Expression level of a transgenic λ2 chain results in isotype exclusion and commitment to B1 cells," *European Journal of Immunology*, 1998, vol. 28, pp. 2289-2299.
European Patent Office, Examination Report for Application No. 12194970.5, dated Sep. 23, 2013, 6 pages.
European Patent Office, Examination Report for Application No. 12762378.3, dated Jun. 8, 2016, 5 pages.
European Patent Office, Examination Report for Application No. 12778780.2, dated Oct. 14, 2016, 3 pages.
European Patent Office, Examination Report for Application No. 12795841.1, dated Feb. 12, 2016, 5 pages.
European Patent Office, Examination Report for Application No. 13711119.1, dated Dec. 17, 2015, 6 pages.
European Patent Office, Examination Report for Application No. 13711119.1, dated Jul. 13, 2016, 6 pages.
European Patent Office, Examination Report for Application No. 14176740.0, dated Jun. 6, 2016, 5 pages.
European Patent Office, Examination Report for Application No. 14176740.0, dated Oct. 23, 2015, 5 pages.
European Patent Office, Examination Report for Application No. 15188522.5, dated Aug. 11, 2017, 6 pages.
European Patent Office, Communication pursuant to Rule 114(2) EPC regarding 14772198.9, dated Mar. 30, 2016, 16 pages.
European Patent Office, Extended European Search Report for Application No. 16189625.3, dated Nov. 23, 2016, 8 pages.
European Patent Office, European Search Report for Application No. 12194977.0, dated Jul. 5, 2013, 4 pages.
European Patent Office, Extended European Search Report for Application No. 12171791.2, dated Jun. 18, 2013, 5 pages.
European Patent Office, Extended European Search Report for Application No. 12171793.8 dated Jun. 21, 2013, 8 pages.
European Patent Office, Extended European Search Report for Application No. 12194970.5, dated Jan. 23, 2013, 9 pages.
European Patent Office, Extended European Search Report for Application No. 12194977.0, dated Jul. 17, 2013, 8 pages.
European Patent Office, Extended European Search Report for Application No. 12195041.4, dated Nov. 18, 2013, 8 pages.
European Patent Office, Extended European Search Report for Application No. 14170196.1, dated Oct. 8, 2014, 8 pages.
European Patent Office, Extended European Search Report for Application No. 14176740.0, dated Oct. 15, 2014, 7 pages.
European Patent Office, Extended European Search Report for Application No. 14196645.7, dated Jun. 26, 2015, 12 pages.
European Patent Office, Extended European Search Report for Application No. 15188522.5 dated Feb. 2, 2016, 15 pages.
European Patent Office, Extended European Search Report for Application No. 16151215.7, dated Mar. 16, 2016, 11 pages.
European Patent Office, Extended European Search Report for Application No. 17174426.1, dated Sep. 14, 2017, 10 pages.
European Patent Office, International Searching Authority, Examiners Report on Allowable Claims for Application No. PCT/GB2010/051122, dated Jan. 2004, 1 page.
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized officer, International Search Report for Application No. PCT/GB2010/051122, dated Sep. 29, 2010, 9 pages, together with the Written Opinion of the International Searching Authority.
European Patent Office, Laurent Deleu, Authorized officer, International Search Report for Application No. PCT/GB2011/050019, dated May 16, 2011, 12 pages, together with the Written Opinion of the International Searching Authority.
European Patent Office, Invitation to Pay Additional Fees and, Where Applicable, Protest Fee, Application No. PCT/GB2012/052296, dated Jan. 24, 2013, 9 pages.
European Patent Office, Alessandro Brero, Authorized officer, International Search Report for Application No. PCT/GB2012/052296, dated May 17, 2013, 30 pages, together with the Written Opinion of the International Searching Authority.
European Patent Office, Alessandro Brero, Authorized officer, International Search Report for Application No. PCT/GB2012/052297, dated Jun. 19, 2013, 24 pages, together with the Written Opinion of the International Searching Authority.
European Patent Office, Alessandro Brero, Authorized Officer, International Search Report for Application No. PCT/GB2012/052298, dated Jun. 13, 2013, 21 pages, together with the Written Opinion of the International Searching Authority.
European Patent Office, F. Chambonnet, Authorized officer, International Search Report for Application No. PCT/GB2012/052380, dated Jan. 3, 2013, 17 pages, together with the Written Opinion of the International Searching Authority.
European Patent Office, Julien Landre, Authorized officer, International Search Report for Application No. PCT/GB2012/052670, dated Feb. 14, 2013, 12 pages, together with the Written Opinion of the International Searching Authority.
European Patent Office, Gaby Brouns, Authorized officer, International Search Report for Application No. PCT/GB2012/052956,

(56) References Cited

OTHER PUBLICATIONS dated Mar. 1, 2013, 14 pages, together with the Written Opinion of the International Searching Authority.

European Patent Office, Gaby Brouns, Authorized officer, International Search Report for Application No. PCT/GB2012/052960, dated Apr. 29, 2013, 19 pages, together with the Written Opinion of the International Searching Authority.

European Patent Office, Gaby Brouns, Authorized officer, International Search Report for Application No. PCT/GB2013/050682, dated Sep. 25, 2013, 16 pages, together with the Written Opinion of the International Searching Authority.

European Patent Office, Gaby Brouns, Authorized officer, International Search Report for Application No. PCT/GB2013/050683, dated Jul. 9, 2013, 11 pages, together with the Written Opinion of the International Searching Authority.

European Patent Office, Gaby Brouns, Authorized officer, International Search Report for Application No. PCT/GB2013/051280, dated Nov. 15, 2013, 19 pages, together with the Written Opinion of the International Searching Authority.

European Patent Office, Opposition against EP2421357 Animal Models and Therapeutic Molecules in the name of Kymab Limited pertaining to Application No. 10734546.4, dated Jan. 23, 2013, 41 pages.

European Patent Office, Opposition against EP2421357 Animal Models and Therapeutic Molecules in the name of Kymab Limited pertaining to Application No. 10734546.4, dated Oct. 22, 2013, 41 pages.

European Patent Office, Opposition against EP2421357 Animal Models and Therapeutic Molecules in the name of Kymab Limited pertaining to Application No. 10734546.4, dated Oct. 23, 2013, 44 pages.

European Patent Office, Opposition against EP2517557 Animal Models and Therapeutic Molecules in the name of Kymab Limited pertaining to Application No. 12171793.8, dated Jan. 17, 2017, 39 pages.

European Patent Office, Opposition against EP2604110 Animal Models and Therapeutic Molecules in the name of Kymab Limited pertaining to Application No. 12194777.0, dated Aug. 28, 2017, 73 pages.

European Patent Office, Opposition against EP2758535 Antibodies, Variable Domains and Chains Tailored for Human Use in the name of Kymab Limited pertaining to Application No. 12772122.3, dated Aug. 9, 2017, 75 pages.

Evans J.P., "Fertilin β and Other ADAMs as Integrin Ligands: Insights into Cell Adhesion and Fertilization," *Bioessays*, 2001, vol. 23 (7), pp. 628-639.

Featherstone K., et al., "The Mouse Immunoglobulin Heavy Chain V-D Intergenic Sequence Contains Insulators that May Regulate Ordered V(D)J Recombination," *Journal of Biological Chemistry*, 2010, vol. 285 (13), pp. 9327-9338.

Feeney A.J., "Genetic and Epigenetic Control of V Gene Rearrangement Frequency," *Advances in Experimental Medicine and Biology*, Chapter 6, 2009, vol. 650, pp. 73-81.

Fell H.P. et al., "Homologous Recombination in Hybridoma Cells: Heavy Chain Chimeric Antibody Produced by Gene Targeting," *Proceedings of the National Academy of Sciences of the U.S.A*, 1989, vol. 86 (21), pp. 8507-8511.

Feng Y.Q., et al., "Site-Specific Chromosomal Integration in Mammalian Cells: Highly Efficient CRE Recombinase-Mediated Cassette Exchange," *Journal of Molecular Biology*, 1999, vol. 292 (4), pp. 779-785.

Feschotte C., et al., "DNA Transposons and the Evolution of Eukaryotic Genomes," *Annual Review of Genetics*, 2007, vol. 41, pp. 331-368.

Festing, M.F.W., et al., "Revised nomenclature for strain 129 mice," *Mammalian Genome*, 1999, vol. 10, p. 836.

Fleischer B., et al., "Reactivity of Mouse T-Cell Hybridomas Expressing Human Vβ Gene Segments With Staphylococcal and Streptococcal Superantigens," *Infection and Immunity*, Mar. 1996, vol. 64 (3), pp. 987-994.

Folger K.R., et al., "Patterns of Integration of DNA Microinjected into Cultured Mammalian Cells: Evidence for Homologous Recombination Between Injected Plasmid DNA Molecules," *Molecular and Cellular Biology*, 1982, vol. 2 (11), pp. 1372-1387.

Forconi F., et al., "The Normal IGHV1-69-Derived B-Cell Repertoire Contains Stereotypic Patterns Characteristic of Unmutated CLL," *Blood*, 2010, vol. 115 (1), pp. 71-77.

Forsman A., et al., "Llama Antibody Fragments with Cross-Subtype Human Immunodeficiency Virus Type I (HIV-1)-Neutralizing Properties and High Affinity for HIV-1 gp120," *Journal of Virology*, Dec. 2008, vol. 82 (24), pp. 12069-12081.

French Patent Office, INPI, Laurent Deleu, Authorized officer, International Search Report for Patent Application No. 1359518, dated Aug. 20, 2014, 3 pages.

Friedrich G., Statement of Dr. Glenn Friedrich, dated Mar. 3, 2016, 4 pages.

Fujieda S., et al., "Multiple Types of Chimeric Germ-Line Ig Heavy Chain Transcripts in Human B Cells: Evidence for Trans-Splicing of Human Ig RNA," *Journal of Immunology*, 1996, vol. 157 (8), pp. 3450-3459.

Fukita Y., et al., "Somatic Hypermutation in the Heavy Chain Locus Correlates with Transcription," *Immunity*, 1998, vol. 9 (1), pp. 105-114.

Gallo M.L., et al., "The Human Immunoglobulin Loci Introduced into Mice: V (D) and J Gene Segment Usage Similar to that of Adult Humans," *European Journal of Immunology*, 2000, vol. 30 (2), pp. 534-540.

Gama Sosa M.A., et al., "Animal Transgenesis: An Overview," *Brain Structure and Function*, 2010, vol. 214 (2-3), pp. 91-109.

Gavilondo J.V., et al., "Antibody Engineering at the Millennium," *BioTechniques*, Jul. 2000, vol. 29 (1), pp. 128-145.

Genbank (D. Muzny et al.), "Rattus norvegicus clone CH230-30N12, * Sequencing in Progress *, 6 unordered pieces," Accession No. AC111740, Nov. 9, 2002, 42 pages. [Retrieved from the Internet: http://www.ncbi.nlm.nih.gov/nuccore/AC111740 on Feb. 28, 2013].

Genbank, "DNA Sequence of the Human Immunoglobulin D Segment Locus," Accession No. x97051.1 S64822, Aug. 6, 2014, 29 pages. [Retrieved from the Internet: http://www.ncbi.nlm.nih.gov/nuccore/X97051].

Genbank, "DNA Sequence of the Human Immunoglobulin D Segment Locus," Accession No. x97051.1 S64822, updated Mar. 3, 2015, 26 pages.

Genbank, "*Homo sapiens* immunoglobulin heavy-chain (IGHV2-5) gene, IGHV2-5*10 allele, partial sequence," Accession No. KF698731.1, dated Nov. 18, 2013, 1 page.

Genbank, "Mus musculus strain 129S1/SvImJ chromosome 12 genomic sca locus group 129S1/SvImJ 129S1/SVIMJ_MMCHR12_CTG1," NCBI Reference Sequence No. NT_114985.3, dated May 5, 2014, 1 page.

Gerdes T., et al., "Physical Map of the Mouse λ Light Chain and Related Loci," *Immunogenetics*, 2002, vol. 54 (1), pp. 62-65.

Gerstein R.M., et al., "Isotype Switching of an Immunoglobulin Heavy Chain Transgene Occurs by DNA Recombination Between Different Chromosomes," *Cell*, 1990, vol. 63 (3), pp. 537-548.

Geurts A.M., et al., "Knockout Rats Via Embryo Microinjection of Zinc-Finger Nucleases," *Science*, 2009, vol. 325 (5939), p. 433.

Giallourakis C.C., et al., "Elements Between the IgH Variable (V) and Diversity (D) Clusters Influence Antisense Transcription and Lineage-Specific V(D)J Recombination," *Proceedings of the National Academy of Sciences of the U.S.A.*, 2010, vol. 107 (51), pp. 22207-22212.

Giraldo P., et al., "Size Matters: Use of YACs, BACs and PACs in Transgenic Animals," *Transgenic Research*, 2001, vol. 10 (2), pp. 83-103.

Giusti A.M., et al., "Hypermutation is Observed only in Antibody H Chain V Region Transgenes that have Recombined with Endogenous Immunoglobulin H DNA: Implications for the Location of cis-acting Elements Required for Somatic Mutation," *The Journal of Experimental Medicine*, Mar. 1993, vol. 177 (3), pp. 797-809.

Glanville J., et al., "Naive Antibody Gene-Segment Frequencies are Heritable and Unaltered by Chronic Lymphocyte Ablation," *Pro-*

(56) References Cited

OTHER PUBLICATIONS

*ceedings of the National Academy of Sciences of the U.S.A*, Dec. 2011, vol. 108 (50), pp. 20066-20071.
Glaser S. et al., "Current issues in mouse genome engineering," *Nature Genetics*, Nov. 2005, Vo. 37 (11), pp. 1187-1193.
Gluzman Y., "SV40-Transformed Simian Cells Support the Replication of Early SV40 Mutants," *Cell*, 1981, vol. 23 (1), pp. 175-182.
Goldman I.L., et al., "Transgenic Animals in Medicine: Integration and Expression of Foreign Genes, Theoretical and Applied Aspects," *Medical Science Monitor*, 2004, vol. 10 (11), pp. RA274-RA285.
Goodhardt M., et al., "Rearrangement and Expression of Rabbit Immunoglobulin κ Light Chain Gene in Transgenic Mice," *Proceedings of the National Academy of Sciences of the U.S.A.*, 1987, vol. 84 (12), pp. 4229-4233.
Gorman J.R., et al., "The Igκ 3' Enhancer Influences the Ratio of Igκ Versus Igλ B Lymphocytes," *Immunity*, 1996, vol. 5 (3), pp. 241-252.
Gorny M.K., et al., "Human Anti-V3 HIV-1 Monoclonal Antibodies Encoded by the VH5-51/VL Lambda Genes Define a Conserved Antigenic Structure," *PLoS One*, 2011, vol. 6 (12), pp. e27780-1-e27780-10.
Goyenechea B., et al., "Cells Strongly Expressing IgK Transgenes Show Clonal Recruitment of Hypermutation: A Role for Both MAR and the Enhancers," *EMBO Journal*, 1997, vol. 16 (13), pp. 3987-3994.
Grandea A.G., III., et al., "Human antibodies reveal a protective epitope that is highly conserved among human and nonhuman influenza A viruses," *Proceedings of the National Academy of Sciences of the U.S.A.*, Jul. 2010, vol. 107 (28), pp. 12658-12663.
Gratz S. et al., "Genome Engineering of *Drosophila* with the CRISPR RNA-Guided Cas9 Nuclease," *Genetics*, Aug. 2013, vol. 194, pp. 1029-1035.
Green L.L., "Antibody Engineering via Genetic Engineering of the Mouse: XenoMouse Strains are a Vehicle for the Facile Generation of Therapeutic Human Monoclonal Antibodies," *Journal of Immunological Methods*, Dec. 1999, vol. 231 (1-2), pp. 11-23.
Green L.L., et al., "Human Ig Heavy and Light Chain YACs," *Nature Genetics*, May 1994, vol. 7 (1), pp. 13-21.
Green L.L., et al., "Regulation of B Cell Development by Variable Gene Complexity in Mice Reconstituted with Human Immunoglobulin Yeast Artificial Chromosomes," *The Journal of Experimental Medicine*, Aug. 1998, vol. 188 (3), pp. 483-495.
Grippo V., et al., "The Heavy Chain Variable Segment Gene Repertoire in Chronic Chagas' Heart Disease," *The Journal of Immunology*, Dec. 2009, vol. 182 (12), pp. 8015-8025.
Grund M., European Patent Attorney, Grund Intellectual Property Group, Third-Party Observations according to Article 115 EPC regarding 11705964.2, dated Apr. 30, 2014, 4 pages.
Grund M., European Patent Attorney, Grund Intellectual Property Group, Third-Party Observations according to Article 115 EPC regarding 11705964.2, dated Oct. 9, 2013, 8 pages.
Grund M., European Patent Attorney, Grund Intellectual Property Group, Third-Party Observations according to Article 115 EPC regarding 11705964.2, dated Feb. 26, 2015, 5 pages.
Grund M., European Patent Attorney, Grund Intellectual Property Group, Third-Party Observations according to Article 115 EPC regarding 11705964.2, dated Aug. 5, 2016, 11 pages.
Grund M., European Patent Attorney, Grund Intellectual Property Group, Third-Party Observations according to Article 115 EPC regarding 12171791.2, dated Aug. 4, 2014, 6 pages.
Grund M., European Patent Attorney, Grund Intellectual Property Group, Third-Party Observations according to Article 115 EPC regarding 12171791.2, dated Dec. 19, 2014, 7 pages.
Grund M., European Patent Attorney, Grund Intellectual Property Group, Third-Party Observations according to Article 115 EPC regarding 12171791.2, dated Feb. 26, 2014, 9 pages.
Grund M., European Patent Attorney, Grund Intellectual Property Group, Third-Party Observations according to Article 115 EPC regarding 12171793.8, dated Jun. 25, 2014, 7 pages.
Grund M., European Patent Attorney, Grund Intellectual Property Group, Third-Party Observations according to Article 115 EPC regarding 12194970.5, dated Apr. 25, 2014, 6 pages.
Grund M., European Patent Attorney, Grund Intellectual Property Group, Third-Party Observations according to Article 115 EPC regarding 12194970.5, dated Aug. 12, 2014, 5 pages.
Grund M., European Patent Attorney, Grund Intellectual Property Group, Third-Party Observations according to Article 115 EPC regarding 12194970.5, dated Mar. 5, 2014, 9 pages.
Grund M., European Patent Attorney, Grund Intellectual Property Group, Third-Party Observations according to Article 115 EPC regarding 12194970.5, dated Nov. 15, 2013, 6 pages.
Grund M., European Patent Attorney, Grund Intellectual Property Group, Third-Party Observations according to Article 115 EPC regarding 12194970.5, dated Sep. 9, 2013, 11 pages.
Grund M., European Patent Attorney, Grund Intellectual Property Group, Third-Party Observations according to Article 115 EPC regarding 12194977.0, dated Mar. 26, 2014, 4 pages.
Grund M., European Patent Attorney, Grund Intellectual Property Group, Third-Party Observations according to Article 115 EPC regarding 12194977.0, dated May 12, 2015, 5 pages.
Grund M., European Patent Attorney, Grund Intellectual Property Group, Third-Party Observations according to Article 115 EPC regarding 12195041.4, dated Jul. 30, 2014, 5 pages.
Grund M., European Patent Attorney, Grund Intellectual Property Group, Third-Party Observations according to Article 115 EPC regarding 12762377.5, dated Jun. 20, 2017, 4 pages.
Grund M., European Patent Attorney, Grund Intellectual Property Group, Third-Party Observations according to Article 115 EPC regarding 12762377.5, dated Feb. 12, 2016, 8 pages.
Grund M., European Patent Attorney, Grund Intellectual Property Group, Third-Party Observations according to Article 115 EPC regarding 12762377.5, dated May 22, 2015, 7 pages.
Grund M., European Patent Attorney, Grund Intellectual Property Group, Third-Party Observations according to Article 115 EPC regarding 12762378.3, dated Feb. 15, 2017, 6 pages.
Grund M., European Patent Attorney, Grund Intellectual Property Group, Third-Party Observations according to Article 115 EPC regarding 12772122.3, dated Mar. 12, 2015, 5 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 12795606.8, dated Feb. 26, 2014, 6 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 12795606.8, dated Mar. 26, 2015, 4 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding 14176740.0, dated Nov. 2, 2016, 4 pages.
Grund M., European Patent Attorney, Grund Intellectual Property Group, Third-Party Observations according to Article 115 EPC regarding 16151215.7, dated Mar. 1, 2017, 4 pages.
Grund M., European Patent Attorney, Grund Intellectual Property Group, Third-Party Observations according to Article 115 EPC regarding 16189625.3, dated Mar. 23, 2017, 5 pages.

(56) References Cited

OTHER PUBLICATIONS

Grund M., European Patent Attorney, Grund Intellectual Property Group, Third-Party Observations regarding Application No. PCT/GB2012/052297, dated Jan. 17, 2014, 3 pages.
Grund M., European Patent Attorney, Grund Intellectual Property Group, Third-Party Observations regarding Application No. PCT/GB2012/052298, dated Jan. 17, 2014, 4 pages.
Grund M., European Patent Attorney, Grund Intellectual Property Group, Third-Party Observations regarding Application No. PCT/GB2012/052380, dated Jan. 24, 2014, 4 pages.
Grund M., European Patent Attorney, Grund Intellectual Property Group, Third-Party Observations regarding Application No. PCT/GB2012/052956, dated Mar. 26, 2014, 2 pages.
Grund M., European Patent Attorney, Grund Intellectual Property Group, Third-Party Observations regarding Application No. PCT/GB2012/052960, dated Apr. 2, 2014, 3 pages.
Grund M., European Patent Attorney, Grund Intellectual Property Group, Third-Party Observations regarding Application No. PCT/GB2013/050682, dated Jul. 28, 2014, 3 pages.
Grund M., European Patent Attorney, Grund Intellectual Property Group, Third-Party Observations regarding Application No. PCT/GB2013/050683, dated Jul. 28, 2014, 2 pages.
Grund M., European Patent Attorney, Grund Intellectual Property Group, Third-Party Observations regarding Application No. PCT/US2012/026416, dated Jun. 6, 2013, 2 pages.
Gu H., et al., "Independent Control of Immunoglobulin Switch Recombination at Individual Switch Regions Evidenced Through Cre-loxP-Mediated Gene Targeting," *Cell*, 1993, vol. 73 (6), pp. 1155-1164.
Guan C., et al., "A Review of Current Large-Scale Mouse Knockout Efforts," *Genesis*, vol. 48, 2010, pp. 73-85.
Guerrero C., et al., "The Bleomycin Resistance Gene of Transposon Tn5 is an Excellent Marker for Transformation of Corynebacteria," *Applied Microbiology and Biotechnology*, 1992, vol. 36 (6), pp. 759-762.
Guirouilh-Barbat J., et al., "Is homologous recombination really an error-free process?", *Frontiers in Genetics*, Jun. 2014, vol. 5 (175), 15 pages.
Guntaka R.V., "Transcription Termination and Polyadenylation in Retroviruses," *Microbiological Reviews*, 1993, vol. 57 (3), pp. 511-521.
Guo Y., et al., "A Preliminary Analysis of the Immunoglobulin Genes in the African Elephant (*Loxodonta africana*)," *PLoS ONE*, Feb. 2011, vol. 6 (2), pp. e16889-1-e16889-14.
Hagiwara S., "Transgenic Expression of VpreB-3 Under the Control of the Immunoglobulin Heavy Chain Enhancer and SV40 Promoter," *Kobe Journal of Medical Sciences*, 1996, vol. 42 (1), pp. 43-59 (abstract only).
Hamers-Caterman C., et al., "Naturally occurring antibodies devoid of light chains," *Nature*, Jun. 1993, vol. 363, pp. 446-448.
Han C., et al., "Comprehensive Analysis of Reproductive ADAMs: Relationship of ADAM4 and ADAM6 with an ADAM Complex Required for Fertilization in Mice," *Biology of Reproduction*, 2009, vol. 80 (5), pp. 1001-1008.
Harding F.A., et al., "Class Switching in Human Immunoglobulin Transgenic Mice," *Annals of the New York Academy of Sciences*, 1995, vol. 764, pp. 536-546.
Hasty P., et al., "Target Frequency and Integration Pattern for Insertion and Replacement Vectors in Embryonic Stem Cells," *Molecular and Cellular Biology*, 1991, vol. 11 (9), pp. 4509-4517.
Hendricks J., et al., "Organization of the Variable Region of the Immunoglobulin Heavy-Chain Gene Locus of the Rat," *Immunogenetics*, 2010, vol. 62 (7), pp. 479-486.
Herschbach Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association between the lgk and lgh immunoglobulin loci mediated by the 3' lgk enhancer Induces 'decontraction' of the lgh locus in pre-B cells," *Nature Immunology*, Apr. 2008, vol. 9 (4), pp. 396-404.
Hong J., et al., "Derivation and Characterization of Embryonic Stem Cells Lines Derived from Transgenic Fischer 344 and Dark Agouti Rats," *Stem Cells and Development*, 2012, vol. 21 (6), pp. 1571-1586.
Houdebine L.M., "The Methods to Generate Transgenic Animals and to Control Transgene Expression," *Journal of Biotechnology*, 2002, vol. 98 (2-3), pp. 145-160.
Houdebine L.M., "Transgenic Animal Models in Biomedical Research," *Methods in Molecular Biology*, Chapter 10, 2007, vol. 360, pp. 163-202.
Houldsworth J., et al., "Comparative Genomic Hybridization: An Overview," *The American Journal of Pathology*, Dec. 1994, vol. 145 (6), pp. 1253-1260.
Hsu E., et al., "The plasticity of immunoglobulin gene systems in evolution," *Immunology Reviews*, vol. 210, Apr. 2006, pp. 8-26.
Huang C., et al., "Structural Basis of Tyrosine Sulfation and $V_H$-Gene Usage in Antibodies that Recognize the HIV Type 1 Coreceptor-Binding Site on gp120," *Proceedings of the National Academy of Sciences of the U.S.A.*, 2004, vol. 101 (9), pp. 2706-2711.
Huang D., et al., "Sequence Analyses of Three Immunoglobulin G Anti-virus Antibodies Reveal Their Utilization of Autoantibody-related Immunoglobulin Vh Genes, but Not Vλ Genes," *Journal of Clinical Investigations*, Dec. 1992, vol. 90, pp. 2197-2208.
Huber V.C., et al., "Distinct Contributions of Vaccine-Induced Immunoglobulin G1 (IgG1) and IgG2a Antibodies to Protective Immunity Against Influenza," *Clinical and Vaccine Immunology*, 2006, vol. 13 (9), pp. 981-990.
Hudziak R.M., et al., "Establishment of Mammalian Cell Lines Containing Multiple Nonsense Mutations and Functional Suppressor tRNA Genes," *Cell*, 1982, vol. 31 (1), pp. 137-146.
Huovila A.J., et al., "Shedding Light on ADAM Metalloproteinases," *Trends in Biochemical Sciences*, 2005, vol. 30 (7), pp. 413-422.
Iglesias-Ussel M.D., et al., "Forced Expression of AID Facilitates the Isolation of Class Switch Variants from Hybridoma Cells," *Journal of Immunological Methods*, 2006, vol. 316 (1-2), pp. 59-66.
Ivics Z., et al., "The Expanding Universe of Transposon Technologies for Gene and Cell Engineering," *Mobile DNA*, 2010, vol. 1 (1), 15 pages.
Ivics Z., et al., "The Sleeping Beauty Transposable Element: Evolution, Regulation and Genetic Applications," *Current Issues in Molecular Biology*, 2004, vol. 6 (1), pp. 43-55.
Izsvák Z., et al., "Sleeping Beauty Transposition: Biology and Applications for Molecular Therapy," *Molecular Therapy*, 2004, vol. 9 (2), pp. 147-156.
Jacob H.J., et al., "Gene Targeting in the Rat: Advances and Opportunities," *Trends in Genetics*, 2010, vol. 26 (12), pp. 510-518.
Jakobovits A., et al., "From XenoMouse Technology to Panitumumab, the First Fully Human Antibody Product from Transgenic Mice," *Nature Biotechnology*, 2007, vol. 25 (10), pp. 1134-1143.
Jakobovits A., "Production of Fully Human Antibodies by Transgenic Mice," *Current Opinion in Biotechnology*, 1995, vol. 6 (5), pp. 561-566.
Jakobovits A., "The Long-Awaited Magic Bullets: Therapeutic Human Monoclonal Antibodies from Transgenic Mice," *Expert Opinion Investigational Drugs*, 1998, vol. 7 (4), pp. 607-614.
Janeway C.A. et al., "The rearrangement of antigen-receptor gene segments controls lymphocyte development," Immunobiology: The Immune System in Health and Disease, 5th Edition, Aug. 2015, 13 pages. [Retrieved from the Internet: http://www.ncbi.nlm.nih.gov/books/NBK27113/].
Janeway et al., "Structural Variation in Immunoglobulin Constant Regions," *Immunobiology: The Immune System in Health and Disease*, 5th Edition, 2001, 5 pages.
Janssens R., et al., "Generation of Heavy-Chain-only Antibodies in Mice," *Proceedings of the National Academy of Sciences of the U.S.A.*, 2006, vol. 103 (41), pp. 15130-15135.
Jasper, P.J., et al., "B lymphocyte deficiency in IgH-transgenic rabbits," *European Journal of Immunology*, 2007, vol. 37, pp. 2290-2299.

(56) References Cited

OTHER PUBLICATIONS

Jendreyko N., et al., "Intradiabodies, Bispecific, Tetravalent Antibodies for the Simultaneous Functional Knockout of Two Cell Surface Receptors," *The Journal of Biological Chemistry*, 2003, vol. 278 (48), pp. 47812-47819.
Jessen K.A., et al., "Molecular Analysis of Metastasis in a Polyomavirus Middle T Mouse Model: the Role of Osteopontin," *Breast Cancer Research*, 2004, vol. 6 (3), pp. R157-R169.
Johnston C.M., et al., "Complete Sequence Assembly and Characterization of the C57BL/6 Mouse Ig Heavy Chain V Region," *The Journal of Immunology*, 2006, vol. 176 (7), pp. 4221-4234.
Jones B.T. Attorney for Applicant, Third-Party Pre-Issuance Submission Under 37 CFR Sec. 1.290 in U.S. Appl. No. 15/016,211, filed Oct. 4, 2016, 59 pages.
Jones B.T. Attorney for Applicant, Third-Party Pre-Issuance Submission Under 37 CFR Sec. 1.290 in U.S. Appl. No. 15/018,670, filed Aug. 12, 2016, 26 pages.
Jones B.T. Attorney for Applicant, Third-Party Pre-Issuance Submission Under 37 CFR Sec. 1.290 in U.S. Appl. No. 15/095,315, filed Sep. 16, 2016, 26 pages.
Jones B.T. Attorney for Applicant, Third-Party Pre-Issuance Submission Under 37 CFR Sec. 1.290 in U.S. Appl. No. 15/214,963, filed Mar. 2, 2017, 42 pages.
Jones B.T. Attorney for Applicant, Third-Party Pre-Issuance Submission Under 37 CFR Sec. 1.290 in U.S. Appl. No. 15/232,122, filed Mar. 13, 2017, 32 pages.
Jones B.T. Attorney for Applicant, Third-Party Pre-Issuance Submission Under 37 CFR Sec. 1.290 in U.S. Appl. No. 15/251,969, filed May 4, 2017, 22 pages.
Jones B.T. Attorney for Applicant, Third-Party Pre-Issuance Submission Under 37 CFR Sec. 1.290 in U.S. Appl. No. 15/360,502, filed May 8, 2017, 40 pages.
Jones B.T. Attorney for Applicant, Third-Party Pre-Issuance Submission Under 37 CFR Sec. 1.290 in U.S. Appl. No. 15/383,101, filed May 30, 2017, 32 pages.
Jones B.T. Attorney for Applicant, Third-Party Pre-Issuance Submission Under 37 CFR Sec. 1.290 in U.S. Appl. No. 15/383,188, filed May 30, 2017, 33 pages.
Jones B.T. Attorney for Applicant, Third-Party Pre-Issuance Submission Under 37 CFR Sec. 1.290 in U.S. Appl. No. 15/383,196, filed May 8, 2017, 25 pages.
Jones B.T., Attorney for Applicant, Third-Party Pre-Issuance Submission Under 37 CFR Sec. 1.290 in U.S. Appl. 15/383,202, filed May 3, 2017, 23 pages.
Jung D., et al., "Mechanism and Control of V(D)J Recombination at the Immunoglobulin Heavy Chain Locus," *Annual Review of Immunology*, 2006, vol. 24, pp. 541-570.
Kaminski D.A., et al., "Antibody Class Switching differs among SJL, C57BL/6 and 129 Mice," *International Immunology*, 2007, vol. 19 (4), pp. 545-556.
Karu A.E., et al., "Recombinant Antibody Technology," *ILAR Journal / National Research Council, Institute of Laboratory Animal Resources*, 1995, vol. 37 (3), pp. 132-141.
Kaushik A., et al., "Novel Insight into Antibody Diversification from Cattle," *Veterinary Immunology and Immunopathology*, 2002, vol. 87 (3-4), pp. 347-350.
Kawasaki K., et al., "One-Megabase Sequence Analysis of the Human Immunoglobulin λ Gene Locus," *Genome Research*, 1997, vol. 7, pp. 250-261.
Kellermann S., et al., "Developing the XENOMOUSE® Technology for Evaluating Immunogenicity," AntibOZ 2: An International Forum to Predict the Next Wave of Protein-based Therapies and Immuno Diagnostics, 2004, *AntibOZ 2 Conference*, Australia, 1 page (abstract only).
Kenter A.L., et al., "Three-Dimensional Architecture of the IgH Locus Facilitates Class Switch Recombination," *Annals of the New York Academy of Sciences*, 2012, vol. 1267, pp. 86-94.
Köhrer C., et al., "Import of Amber and Ochre Suppressor tRNAs into Mammalian Cells: a General Approach to Site-Specific Insertion of Amino Acid Analogues into Proteins," *Proceedings of the National Academy of Sciences of the U.S.A.*, 2001, vol. 98 (25), pp. 14310-14315.
Kim J.Y., et al., "CHO Cells in Biotechnology for Production of Recombinant Proteins: Current State and Further Potential," *Applied Microbiology Biotechnology*, 2012, vol. 93 (3), pp. 917-930.
Kim T., et al., "Expression and Relationship of Male Reproductive ADAMs in Mouse," *Biology of Reproduction*, 2006, vol. 74 (4), pp. 744-750.
Kindt T.J. et al., "Organization and Expression of Immunoglobulin Genes," *Immunology*, Sixth edition, Chapter 5, 2007 (36 pages, including cover sheet and copyright page), pp. 111-144.
Kingzette M., et al., "Trans-Chromosomal Recombination within the Ig Heavy Chain Switch Region in B Lymphocytes," *Proceedings of the National Academy of Sciences of the U.S.A.*, 1998, vol. 95 (20), pp. 11840-11845.
Kitamura D., et al., "A B Cell-Deficient Mouse by Targeted Disruption of the Membrane Exon of the Immunoglobulin μ Chain Gene," Nature, 1991, vol. 350 (6317), pp. 423-426.
Kondo S., et al., "Highly improved Gene Targeting by Germline-Specific Cas9 Expression in *Drosophila," Genetics*, vol. 195, Nov. 2013, pp. 715-721 (Abstract).
Kondo S., et al., "Highly improved Gene Targeting by Germline-Specific Cas9 Expression in *Drosophila," Genetics*, vol. 195, Nov. 2013, pp. 715-721.
Kostenuik P.J., et al., "Denosumab, a Fully Human Monoclonal Antibody to RANKL, Inhibits Bone Resorption and Increases BMD in Knock-in Mice that Express Chimeric (Murine/Human) RANKL," *Journal of Bone and Mineral Research*, 2009, vol. 24 (2), pp. 182-195.
Kotzamanis G., et al., "Recombining Overlapping BACs into a Single Larger BAC," *BMC Biotechnology*, 2004, vol. 4 (1), 10 pages.
Kouskoff V., et al., "Cassette Vectors Directing Expression of T Cell Receptor Genes in Transgenic Mice," *Journal of Immunological Methods*, 1995, vol. 180 (2), pp. 273-280.
Krause J.C., et al., "Epitope-Specific Human Influenza Antibody Repertoires Diversify by B Cell Intraclonal Sequence Divergence and Interclonal Convergence," *Journal of Immunology*, 2011, vol. 187 (7), pp. 3704-3711.
Krutskikh A., et al., "Epididymal Protein Rnase10 is Required for Post-Testicular Sperm Maturation and Male Fertility," *The FASEB Journal*, 2012, vol. 26 (10), pp. 4198-4209.
Kucherlapati R.S., et al., "Homologous Recombination Between Plasmids in Mammalian Cells can be Enhanced by Treatment of Input DNA," *Proceedings of the National Academy of Sciences of the U.S.A.*, 1984, vol. 81 (10), pp. 3153-3157.
Kuraoka M., et al., "AID Expression During B-Cell Development: Searching for Answers," *Immunologic Research*, 2011, vol. 49 (1-3), pp. 3-13.
Kuroiwa Y., et al., "Sequential Targeting of the Genes Encoding Immunoglobulin-μ and Prion Protein in Cattle," *Nature Genetics*, 2004, vol. 36 (7), pp. 775-780.
Kuzin I.I., et al, "Requirement for enhancer specificity in immunoglobulin heavy chain locus regulation," *Journal of Immunology*, Jun. 2008, vol. 180 (11), pp. 7443-7450.
Laffleur B., et al., "Production of Human or Humanized Antibodies in Mice," *Methods in Molecular Biology*, Chapter 9, 2012, vol. 901, pp. 149-159.
Largaespada D.A., "Transposon Mutagenesis in Mice," *Methods in Molecular Biology*, vol. 530, 2009, pp. 379-390.
Laventie B., et al., "Heavy Chain-Only Antibodies and Tetravalent Bispecific Antibody Neutralizing *Staphylococcus aureus* Leukotoxins," *Proceedings of the National Academy of Sciences of the U.S.A.*, 2011, vol. 108 (39), pp. 16404-16409.
Le Mouellic H., et al., "Pattern of Transcription of the Homeo Gene Hox-3.1 in the Mouse Embryo," *Genes & Development*, 1988, vol. 2 (1), pp. 125-135.
Lee E., et al., "Complete Humanization of the Mouse Immunoglobulin Loci Enables Efficient Therapeutic Antibody Discovery," *Nature Biotechnology*, 2014, vol. 32 (4), pp. 356-363.

(56) References Cited

OTHER PUBLICATIONS

Lee E., et al., "The Application of Transgenic Mice for Therapeutic Antibody Discovery," *Methods in Molecular Biology*, Chapter 8, 2012, vol. 901, pp. 137-148.
Lee H., et al., "Human C5aR Knock-in Mice Facilitate the Production and Assessment of Anti-Inflammatory Monoclonal Antibodies," *Nature Biotechnology*, 2006, vol. 24 (10), pp. 1279-1284.
Lefranc M., Appendix 1P, Abbreviations and Useful Data, "Nomenclature of the Human Immunoglobulin Genes,"*Current Protocols in Immunology*, 2000, Supp. 40, pp. A.1P.1-A.1P.37.
Lefranc M.P., et al., " IGHJ group," The Immunoglobulin FactsBook, *IMGR*, the international ImMunoGeneTics database, May 2001, 4 pages (including cover sheet and copyright pages).
Lefranc M.P., et al., Excerpts from "The Immunoglobulin FactsBook," *IMGT*, the international ImMunoGeneTics database, May 2001, 455 pages.
Lefranc M.P., et al., "Immunoglobulin Lambda (IGL) Genes of Human and Mouse," *Molecular Biology of B Cells*, Chapter 4, p. 47, 2004 (Edtrs. Honjo et al.).
Lefranc M.P., "Nomenclature of the Human Immunoglobulin Heavy (IGH) Genes," *Experimental and Clinical Immunogenetics*, 2001, vol. 18 (2), pp. 100-116.
Lefranc M.P., "Nomenclature of the Human Immunoglobulin Kappa (IGK) Genes," *Experimental and Clinical Immunogenetics*, 2001, vol. 18 (3), pp. 161-174.
Lefranc M.P., "Nomenclature of the Human Immunoglobulin Lambda (IGL) Genes," *Experimental and Clinical Immunogenetics*, 2001, vol. 18 (4), pp. 242-254.
Levin A.M., et al., "Optimizing the affinity and specificity of proteins with molecular display," *Molecular Biosystems*, 2006, vol. 2, pp. 49-57.
Li H., et al., "Genetic Diversity of the Human Immunoglobulin Heavy Chain $V_H$ Region," *Immunological Reviews*, Dec. 2002, vol. 190, pp. 53-68.
Li L., et al., "Transgenic Mice with a Diverse Human T Cell Antigen Receptor Repertoire," *Nature Medicine*, 2010, vol. 16 (9), pp. 1029-1034.
Li M., Second Declaration of Dr. Meng (Amy) Li, dated Sep. 5, 2016, 2 pages.
Li M.A., et al., "Crafting Rat Genomes with Zinc Fingers," *Nature Biotechnology*, 2011, vol. 29 (1), pp. 39-41.
Li P., et al., "Germline Competent Embryonic Stem Cells Derived from Rat Blastocysts," *Cell*, 2008, vol. 135 (7), pp. 1299-1310.
Li X., et al., "The Minimum Internal and External Sequence Requirements for Transposition of the Eukaryotic Transformation Vector PiggyBac," *Molecular Genetics & Genomics*, 2001, vol. 266 (2), pp. 190-198.
Liang Q., et al., "Extensive genomic copy number variation in embryonic stem cells," *Proceedings of the National Academy of Sciences of the U.S.A.*, Nov. 2008, vol. 105 (45), pp. 17453-17456.
Liao J., et al., "Generation of Induced Pluripotent Stem Cell Lines from Adult Rat Cells," *Cell Stem Cell*, 2009, vol. 4 (1), pp. 11-15.
Little M., et al., "Generation of a Large Complex Antibody Library from Multiple Donors," *Journal of Immunological Methods*, 1999, vol. 231 (1-2), pp. 3-9.
Liu L., et al., "Potent and Broad Anti-HIV-1 Activity Exhibited by a Glycosyl-Phosphatidylinositol-Anchored Peptide derived from the CDR H3 of Broadly Neutralizing Antibody PG16," *Journal of Virology*, 2011, vol. 85 (17), pp. 8467-8476.
Lonberg N., "Human Antibodies from Transgenic Animals," *Nature Biotechnology*, 2005, vol. 23 (9), pp. 1117-1125.
Lonberg N., "Fully Human Antibodies from Transgenic Mouse and Phage Display Platforms," *Current Opinion in Immunology*, 2008, vol. 20 (4), pp. 450-459.
Loveslati B.Y., et al., "A Study of Gm Allotypes and Immunoglobulin Heavy Gamma IGHG Genes in Berbers, Arabs and Sub-Saharan Africans from Jerba Island, Tunisia," *European Journal of Immunogenetics*, 2001, vol. 28 (5), pp. 531-538.
Luby T.M., et al., "The μ Switch Region Tandem Repeats are Important, but not Required, for Antibody Class Switch Recombination," *The Journal of Experimental Medicine*, 2001, vol. 193 (2), pp. 159-168.
Luciw P.A., et al., "Location and Function of Retroviral and SV40 Sequences that Enhance Biochemical TRransformarion afrer Microinjection of DNA," *Cell*, vol. 33 (3), pp. 705-716.
Luo G., et al., "Chromosomal Transposition of a Tc1/Mariner-like Element in Mouse Embryonic Stem Cells," *Proceedings of the National Academy of Sciences of the U.S.A.*, 1998, vol. 95 (18), pp. 10769-10773.
Lyon C., Attorney for Applicant, Third-Party Pre-Issuance Submission Under 37 CFR Sec. 1.290 in U.S. Appl. No. 13/846,672, dated Mar. 17, 2015, 32 pages.
Lyon C., Attorney for Applicant, Third-Party Pre-Issuance Submission Under 37 CFR Sec. 1.290 in U.S. Appl. No. 13/875,892, dated May 5, 2015, 49 pages.
Lyon C., Attorney for Applicant, Third-Party Pre-Issuance Submission Under 37 CFR Sec. 1.290 in U.S. Appl. No. 13/886,511, dated May 5, 2015, 18 pages.
Lyon C., Attorney for Applicant, Third-Party Pre-Issuance Submission Under 37 CFR Sec. 1.290 in U.S. Appl. No. 14/040,405, dated Jan. 16, 2015, 18 pages.
Lyon C., Attorney for Applicant, Third-Party Pre-Issuance Submission Under 37 CFR Sec. 1.290 in U.S. Appl. No. 14/040,427, dated Jan. 16, 2015, 20 pages.
Lyon C., Attorney for Applicant, Third-Party Pre-Issuance Submission Under 37 CFR Sec. 1.290 in U.S. Appl. No. 14/056,434, dated Dec. 15, 2014, 6 pages.
Lyon C., Attorney for Applicant, Third-Party Pre-Issuance Submission Under 37 CFR Sec. 1.290 in U.S. Appl. No. 14/056,700, dated Nov. 28, 2014, 6 pages.
Lyon C., Attorney for Applicant, Third-Party Pre-Issuance Submission Under 37 CFR Sec. 1.290 in U.S. Appl. No. 14/056,707, dated Nov. 28, 2014, 10 pages.
Lyon C., Attorney for Applicant, Third-Party Pre-Issuance Submission Under 37 CFR Sec. 1.290 in U.S. Appl. No. 14/080,630, dated Oct. 31, 2014, 8 pages.
Lyon C., Attorney for Applicant, Third-Party Pre-Issuance Submission Under 37 CFR Sec. 1.290 in U.S. Appl. No. 14/137,902, dated Nov. 13, 2014, 9 pages.
Lyon C., Attorney for Applicant, Third-Party Pre-Issuance Submission Under 37 CFR Sec. 1.290 in U.S. Appl. No. 14/220,080, dated Jul. 28, 2015, 28 pages.
Lyon C., Attorney for Applicant, Third-Party Pre-Issuance Submission Under 37 CFR Sec. 1.290 in U.S. Appl. No. 14/220,095, dated Aug. 4, 2015, 19 pages.
Lyon C., Attorney for Applicant, Third-Party Pre-Issuance Submission Under 37 CFR Sec. 1.290 in U.S. Appl. No. 14/220,099, dated April 29, 2015, 43 pages.
Lyon C., Attorney for Applicant, Third-Party Pre-Issuance Submission Under 37 CFR Sec. 1.290 in U.S. Appl. No. 14/226,698, dated Jun. 3, 2015, 53 pages.
Lyon C., Attorney for Applicant, Third-Party Pre-Issuance Submission Under 37 CFR Sec. 1.290 in U.S. Appl. No. 14/226,706, dated Jul. 28, 2015, 53 pages.
Lyon C., Attorney for Applicant, Third-Party Pre-Issuance Submission Under 37 CFR Sec. 1.290 in U.S. Appl. No. 14/263,158, dated Apr. 29, 2015, 16 pages.
Lyon C., Attorney for Applicant, Third-Party Pre-Issuance Submission Under 37 CFR Sec. 1.290 in U.S. Appl. No. 14/263,176, dated Apr. 29, 2015, 16 pages.
Lyon C., Attorney for Applicant, Third-Party Pre-Issuance Submission Under 37 CFR Sec. 1.290 in U.S. Appl. No. 14/497,054, dated Oct. 21, 2015, 81 pages.
Lyon C., Attorney for Applicant, Third-Party Pre-Issuance Submission Under 37 CFR Sec. 1.290 in U.S. Appl. No. 14/498,685, dated Sep. 18, 2015, 37 pages.
Lyon C., Attorney for Applicant, Third-Party Pre-Issuance Submission Under 37 CFR Sec. 1.290 in U.S. Appl. No. 14/516,461, dated Aug. 4, 2015, 27 pages.

(56) References Cited

OTHER PUBLICATIONS

Lyon C., Attorney for Applicant, Third-Party Pre-Issuance Submission Under 37 CFR Sec. 1.290 in U.S. Appl. No. 14/543,359, dated Nov. 13, 2015, 36 pages.
Ma B., et al., "Human Antibody Expression in Transgenic Rats: Comparison of Chimeric IgH Loci with Human $V_H$, D and $J_H$ but Bearing Different Rat C-Gene Regions," *Journal of Immunological Methods*, 2013, vols. 400-401, pp. 78-86.
MacDonald L., Curriculum Vitae of Lynn E. MacDonald, Ph.D., 3 pages.
MacDonald L., Declaration of Lynn E. MacDonald with Exhibits, dated Feb. 3, 2015, relating to International Application No. PCT/US02/04500 (Published as WO02/066630 A1), 13 pages.
MacDonald L., Declaration of Lynne E. Macdonald, dated Jun. 29, 2016, 4 pages.
MacDonald L., et al., Expanded Poster: "Velocigene® Technology Extended to Humanization of Several Megabases of Complex Gene Loci," Sep. 2006, 6 pages.
MacDonald L., et al., Poster (Exhibit IJR-47): "Velocigene® Technology Extended to Humanization of Several Megabases of Complex Gene Loci," and evidence of unavailability, Sep. 2006, 42 pages.
MacDonald L., et al., "Velocigene® Technology Extended to Humanization of Several Megabases of Complex Gene Loci," (Abstract-21) 1st International MUGEN Conference on Animal Models for Human Immunological Disease, Athens Greece, Sep. 10-13, 2006, 1 page.
MacDonald L.E., et al., "Precise and in Situ Genetic Humanization of 6 Mb of Mouse Immunoglobulin Genes," *Proceedings of the National Academy of Sciences of the U.S.A.*, 2014, vol. 111 (14), pp. 5147-5152.
Mack M., et al., "A Small Bispecific Antibody Construct Expressed as a Functional Single-Chain Molecule with High Tumor Cell Cytotoxicity," *Proceedings of the National Academy of Sciences of the U.S.A.*, 1995, vol. 92 (15), pp. 7021-7025.
Magadán S., et al., "Production of Antigen-Specific Human Monoclonal Antibodies: Comparison of Mice Carrying IgH/κ or IgH/κ/λ transloci," *Biotechniques*, 2002, vol. 33 (3), pp. 680, 682, 684 passim.
Magdelaine-Beuzelin C., et al., "Structure-function relationships of the variable domains of monoclonal antibodies approved for cancer treatment," *Critical Reviews in Oncology/Hematology*, 2007, vol. 64, pp. 210-225.
Maitta R.W., et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," *Infection and Immunity*, 2004, vol. 72 (1), pp. 196-208.
Makris J.C., et al., "Mutational Analysis of Insertion Sequence 50 (IS50) and Transposon 5 (Tn5) Ends," *Proceedings of the National Academy of Sciences of the U.S.A.*, 1988, vol. 85 (7), pp. 2224-2228.
Mallender W.D., et al., "Construction, Expression, and Activity of a Bivalent Bispecific Single-Chain Antibody," *The Journal of Biological Chemistry*, 1994, vol. 269 (1), pp. 199-206.
Manis J.P., et al., "Mechanism and Control of Class-Switch Recombination," *Trends in Immunology*, 2002, vol. 23 (1), pp. 31-39.
Marcello M.R., et al., "Lack of Tyrosylprotein Sulfotransferase-2 Activity Results in Altered Sperm-Egg Interactions and Loss of ADAM3 and ADAM6 in Epididymal Sperm," *The Journal of Biological Chemistry*, 2011, vol. 286 (15), pp. 13060-13070.
Marchalonis J.J., et al., "Emergence of the immunoglobulin family: conservation in protein sequence and plasticity in gene organization," *Glycobiology*, vol. 6, 1996, pp. 657-663.
Mårtensson I.L., et al., "Role of the Surrogate Light Chain and the Pre-B-Cell Receptor in Mouse B-Cell Development," *Immunology*, 2000, vol. 101 (4), pp. 435-441.
Mårtensson I.L., et al., "The pre-B-cell receptor," *Current Opinion in Immunology*, 2007, vol. 19, pp. 137-142.
Martinez C., et al., "The Mouse (*Mus musculus*) Immunoglobulin Kappa Variable (IGKV) Genes and Joining (IGKJ) Segments," *Experimental and Clinical Immunogenetics*, Jul. 1998, vol. 15, pp. 184-193.
Martínez P., et al., "Antibody Synthesis in Vitro," Encyclopedia of Life Sciences, 2005, pp. 1-8.
Martinez-Jean C., et al., "Nomenclature and Overview of the Mouse (*Mus musculus* and *Mus* sp.) Immunoglobulin Kappa (IGK) Genes," *Experimental and Clinical Immunogenetics*, 2001, vol. 18 (4), pp. 255-279.
Matthews V.B., et al., "A Locus Affecting Immunoglobulin Isotype Selection (Igis1) Maps to the MHC Region in C57BL, Balb/c and NOD Mice," *Immunology and Cell Biology*, 2001, vol. 79 (6), pp. 576-582.
Mattila P.S., et al., "Extensive Allelic Sequence Variation in the J Region of the Human Immunoglobulin Heavy Chain Gene Locus," *European Journal of Immunology*, 1995, vol. 25 (9), pp. 2578-2582.
Maul R.W., et al., "AID and Somatic Hypermutation," *Advances in Immunology*, Chapter 6, 2010, vol. 105, pp. 159-191.
McCreath K.J., et al., "Production of Gene-Targeted Sheep by Nuclear Transfer from Cultured Somatic Cells," *Nature*, 2000, vol. 405 (6790), pp. 1066-1069.
McMurry M.T., et al., "Enhancer Control of Local Accessibility to V(D)J Recombinase," *Molecular and Cellular Biology*, Aug. 1997, vol. 17 (8), pp. 4553-4561.
Mejía J.E., et al., "The Assembly of Large BACs by in Vivo Recombination," *Genomics*, 2000, vol. 70 (2), pp. 165-170.
Mendez M.J., et al., "Functional Transplant of Megabase Human Immunoglobulin Loci Recapitulates Human Antibody Response in Mice," *Nature Genetics*, Feb. 1997, vol. 15 (2), pp. 146-156.
Mester G., European Patent Attorney, Grund Intellectual Property Group, Third-Party Observations according to Article 115 EPC regarding 12778780.2, dated Sep. 30, 2016, 5 pages.
MGI, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages [printed: Mar. 6, 2012—http://www.informatics.jax.org/mgihome/nomen/strains.shtml].
Mills F.C., et al., "Enhancer Complexes Located Downstream of Both Human Immunoglobulin Cα Genes," *The Journal of Experimental Medicine*, Sep. 1997, vol. 186 (6), pp. 845-858.
Milner E.C., et al., "Polymorphism and Utilization of Human $V_H$ Genes," *Annals of the New York Academy of Sciences*, 1995, vol. 764, pp. 50-61.
Minaee S., et al., "Mapping and Functional Analysis of Regulatory Sequences in the Mouse λ5-VpreB1 Domain," *Molecular Immunology*, 2005, vol. 42 (11), pp. 1283-1292.
Mir K.U., "Sequencing Genomes: From Individuals to Populations," *Briefings in Functional Genomics & Proteomics*, 2009, vol. 8 (5), pp. 367-378.
Müller U., "Ten Years of Gene Targeting: Targeted Mouse Mutants, from Vector Design to Phenotype Analysis," *Mechanisms of Development*, 1999, vol. 82 (1-2), pp. 3-21.
Moffatt S., et al., "PEGylated J591 mAb loaded in PLGA-PEG-PLGA tri-block copolymer for targeted delivery: In vitro evaluation in human prostate cancer cells," *International Journal of Pharmaceutics*, 2006, vol. 317, pp. 10-13.
Monaco A.P., et al., "YACs, BACs, PACs and MACs: Artificial Chromosomes as Research Tools," *Trends in Biotechnology*, Jul. 1994, vol. 12 (7), pp. 280-286.
Moran N., "Mouse Platforms Jostle for Slice of Humanized Antibody Market," *Nature Biotechnology*, Apr. 2013, vol. 31 (4), pp. 267-268.
Moreau P., et al., "The SV40 72 Base Repair Repeat has a Striking Effect on Gene Expression Both in SV40 and Other Chimeric Recombinants," *Nucleic Acids Research*, 1981, vol. 9 (22), pp. 6047-6068.
Moreno R.D., et al., "The Emerging Role of Matrix Metalloproteases of the ADAM Family in Male Germ Cell Apoptosis," *Spermatogenesis*, 2011, vol. 1 (3), pp. 195-208.
Mortuza F.Y., et al., "Immunoglobulin Heavy-Chain Gene Rearrangement in Adult Acute Lymphoblastic Leukemia Reveals Pref-

(56) References Cited

OTHER PUBLICATIONS erential Usage of $J_H$-Proximal Variable Gene Segments," *Blood*, 2001, vol. 97 (9), pp. 2716-2726.
Mullins L.J., et al., "Transgenesis in the Rat and Larger Mammals," Perspective Series: Molecular Medicine in Genetically Engineered Animals, *Journal of Clinical Investigation*, Apr. 1996, vol. 97 (7), pp. 1557-1560.
Muñoz M., et al., "Constraints to Progress in Embryonic Stem Cells from Domestic Species," *Stem Cell Review and Reports*, 2009, vol. 5, pp. 6-9.
Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., dated Oct. 6, 2014, 62 pages.
Murphy A., "Veloclmmune: Immunoglobulin Variable Region Humanized Mice,"*Recombinant Antibodies for Immunotherapy*, 1st Edition, Chapter 8, 2009, pp. 100-108.
Murphy A.J., et al., "Mice with megabase humanization of their Immunoglobulin Genes Generate Antibodies as Efficiently as Normal Mice," *Proceedings of the National Academy of Sciences of the U.S.A.*, 2014, vol. 111 (14), pp. 5153-5158.
Murphy D., "BAC-based Modifications of the Mouse Genome: The Big and the Backward," The Advanced Course: Genetic Manipulation of ES Cells, dated Nov. 3, 2009, VP Target Discovery, Regeneron Pharmaceuticals, 58 pages.
Murphy K., et al., The Generation of Lymphocyte Antigen Receptors, excerpt from *Janeway's Immunobiology*, Seventh edition, Chapter 4, 2008, p. 158.
Muyrers J.P.P., et al., "Rapid Modification of Bacterial Artificial Chromosomes by ET-Recombination," *Nucleic Acids Research*, 1999, vol. 27 (6), pp. 1555-1557.
Nadel B., et al., "Sequence of the Spacer in the Recombination Signal Sequence Affects V(D)J Rearrangement Frequency and Correlates with Nonrandom Vκ Usage in Vivo," *The Journal of Experimental Medicine*, 1998, vol. 187 (9), pp. 1495-1503.
Nagle M., "Regeneron Helps Make Sanofi Velocimmune to its 'Weak' Pipeline," 2007, 2 pages.
Nandi A.K., et al., "Regulated Expression of Genes Inserted at the Human Chromosomal β-globin Locus by Homologous Recombination," *Proceedings of the National Academy of Sciences of the U.S.A.*, 1988, vol. 85 (11), pp. 3845-3849.
Narayanan K., et al., "Bacterial Artificial Chromosome Mutagenesis Using Recombineering, Article ID: 971296," Journal of Biomedicine and Biotechnology, 2010, vol. 2011, Article ID No. 971296, 10 pages.
Narayanan K., et al., "Efficient and Precise Engineering of a 200 kb β-Globin Human/Bacterial Artificial Chromosome in *E. coli* DH10B using an Inducible Homologous Recombination System," *Gene Therapy*, 1999, vol. 6 (3), pp. 442-447.
Nelson A.L., et al., "Development Trends for Human Monoclonal Antibody Therapeutics," *Nature Reviews Drug Discovery*, 2010, vol. 9 (10), pp. 767-774.
Neuberger M.S., et al., "Isotype Exclusion and Transgene Down-Regulation in Immunoglobulin-λ Transgenic Mice," *Nature*, Mar. 1989, vol. 338 (6213), pp. 350-352.
Neuberger M.S., et al., "Somatic Hypermutation," *Current Opinion in Immunology*, 1995, vol. 7 (2), pp. 248-254.
Neuberger M.S., "Expression and regulation of immunoglobulin heavy chain gene transfected into lymphoid cells," *The EMBO Journal*, 1983, vol. 2 (8), pp. 1373-1378.
New Zealand Patent Office, Simon Maguire, Authorized Officer, Further Examination Report for Patent No. 623756, dated Sep. 9, 2015, 3 pages.
Nicholson I.C., et al., "Antibody Repertoires of Four- and Five-Feature Translocus Mice Carrying Human Immunoglobulin Heavy Chain and κ and λ Light Chain Yeast Artificial Chromosomes," *Journal of Immunology*, 1999, vol. 163 (12), pp. 6898-6906.
Niemann H., et al., "Transgenic Farm Animals: Present and Future," *Revue scientifique et technique* (*International Office of Epizootics*), 2005, vol. 24 (1), pp. 285-298.
Nucleotide Sequence RID Y55HBK1W114, accessed Aug. 6, 2014, 2 pages.
Oancea A.E., et al., "Expression of the (recombinant) Endogenous Immunoglobulin Heavy-Chain Locus Requires the Intronic Matrix Attachment Regions," *Molecular and Cellular Biology*, 1997, vol. 17 (5), pp. 2658-2668.
Oberdoerffer P., et al., "Unidirectional Cre-Mediated Genetic Inversion in Mice using the Mutant loxP Pair lox66/lox71," *Nucleic Acids Research*, 2003, vol. 31 (22), pp. e140-1-e140-7.
O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.
O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.
O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.
Ohlin M., et al., "The Human Antibody Repertoire to Infectious Agents: Implications for Disease Pathogenesis," Molecular Immunology, 2003, vol. 40 (1), pp. 1-11.
Ohm-Laursen L., et al., "Identification of Two New Alleles, IGHV3-23*04 and IGHJ6*04, and the Complete Sequence of the IGHV3-h Pseudogene in the Human Immunoglobulin Locus and their Prevalences in Danish Caucasians," *Immunogenetics*, 2005, vol. 57 (9), pp. 621-627.
Osborn M.J., et al., "High-Affinity IgG Antibodies Develop Naturally in Ig-Knockout Rats Carrying Germline Human IgH/Igκ/Igλ Loci Bearing the Rat $C_H$ Region," *Journal of Immunology*, 2013, vol. 190 (4), pp. 1481-1490.
Osoegawa K., et al., "Bacterial Artificial Chromosome Libraries for Mouse Sequencing and Functional Analysis," *Genome Research*, 2000, vol. 10 (1), pp. 116-128.
Oumard A., et al., "Recommended method for chromosome exploitation: RMCE-based cassette-exchange systems in animal cell biotechnology," *Cytotechnology*, 2006, vol. 50, pp. 93-108.
Parng C.L., et al., "Gene Conversion Contributes to Ig Light Chain Diversity in Cattle," Journal of Immunology, 1996, vol. 157 (12), pp. 5478-5486.
Pavlicek A., et al., "Ancient Transposable Elements, Processed Pseudogenes, and Endogenous Retroviruses," *Genomic Disorders*, Chapter 4, 2006, pp. 57-72.
Pear W.S., et al., "Localization of the Rat Immunoglobulin Heavy Chain Locus to Chromosome 6," *Immunogenetics*, 1986, vol. 23 (6), pp. 393-395.
Pelham H., et al., "Expression of a *Drosophila* Heat Shock Protein in Mammalian Cells: Transient Association with Nucleoli After Heat Shock," *Philosophical Transactions of the Royal Society B: Biological Sciences*, 1984, vol. 307 (1132), pp. 301-307.
Pera M.F., et al., "Human embryonic stem cells," *Journal of Cell Science*, 2000, vol. 113, pp. 5-10.
Pérez-Luz S., et al., "Factor VIII mRNA expression from a BAC carrying the intact locus made by homologous recombination," *Genomics*. 2007, vol. 90, pp. 610-619.
Perlot T., et al., "Antisense Transcripts from Immunoglobulin Heavy-Chain Locus V(D)J and Switch Regions," *Proceedings of the National Academy of Sciences of the U.S.A.*, 2008, vol. 105 (10), pp. 3843-3848.
Perlot T., et al., "Cis-Regulatory Elements and Epigenetic Changes control genomic rearrangements of the IgH locus," *Advances in Immunology*, Chapter 1, 2008, vol. 99, pp. 1-32.
Pettersson S., et al., "A second B cell-specific enhancer 3' of the immunoglobulin heavy-chain locus," *Nature*, Mar. 1990, vol. 344, pp. 165-168.
Pettitt S.J., et al., "Agouti C57BL/6N Embryonic Stem Cells for Mmouse Genetic Resources," *Nature Methods*, 2009, vol. 6 (7), pp. 493-495.
Plasterk R.H., et al., "Resident Aliens: the Tc1/Mariner Superfamily of Transposable Elements," *Trends Genetics*, 1999, vol. 15(8), pp. 326-332.

(56) References Cited

OTHER PUBLICATIONS

Pobursky K., Third-Party Pre-Issuance Submission Under 37 CFR 1.290 in U.S. Appl. No. 13/843,528, dated Mar. 18, 2014, 14 pages.
Pobursky K., Third-Party Pre-Issuance Submission Under 37 CFR 1.290 in U.S. Appl. No. 13/433,084, dated Apr. 1, 2014, 15 pages.
Pobursky K., Third-Party Pre-Issuance Submission Under 37 CFR 1.290 in U.S. Appl. No. 13/434,361, dated Apr. 1, 2014, 15 pages.
Pobursky K., Third-Party Pre-Issuance Submission Under 37 CFR 1.290 in U.S. Appl. No. 13/740,727, dated May 27, 2014, 25 pages.
Ponsel D., et al., "High Affinity, Developability and Functional Size: the Holy Grail of Combinatorial Antibody by Library Generation," *Molecules*, 2011, vol. 16 (5), pp. 3675-3700.
Popov A.V., et al., "A Human Immunoglobulin λ Locus is Similarly Well Expressed in Mice and Humans," *The Journal of Experimental Medicine*, 1999, vol. 189 (10), pp. 1611-1620.
Pramanik S., et al., "Segmental Duplication as One of the Driving Forces Underlying the Diversity of the Human Immunoglobulin Heavy Chain Variable Gene Region," *BMC Genomics*, Jan. 2011, vol. 12 (1), p. 78.
Presta L., "Molecular engineering and design of therapeutic antibodies," *Current Opinion in Immunology*, 2008, vol. 20, pp. 460-470.
Primakoff P., et al., "Penetration, Adhesion, and Fusion in Mammalian Sperm-Egg Interaction," *Science*, 2002, vol. 296 (5576), pp. 2183-2185.
Primakoff P., et al., "The *ADAM* Gene Family: Surface Proteins with Adhesion and Protease Activity," *Trends Genetics*, 2000, vol. 16 (2), pp. 83-87.
Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
Prosser H.M., et al., "A Resource of Vectors and ES Cells for Targeted Deletion of MicroRNAs in Mice," *Nature Biotechnology*, 2011, vol. 29 (9), pp. 840-845.
Prosser H.M., et al., "Mosaic Complementation Demonstrates a Regulatory Role for Myosin Vlla in Actin Dynamics of Stereocilia," *Molecular and Cellular Biology*, 2008, vol. 28 (5), pp. 1702-1712.
Pruzina S., et al., "Human Monoclonal Antibodies to HIVC-1 gp140 from Mice Bearing YAC-Based Human Immunoglobulin Transloci," *Protein Engineering, Design & Selection*, 2011, vol. 24 (10), pp. 791-799.
Puente X.S., et al., "Comparative Genomic Analysis of Human and Chimpanzee Proteases," *Genomics*, 2005, vol. 86 (6), pp. 638-647.
Qi N.R., et al., "A New Transgenic Rat Model of Hepatic Steatosis and the Metabolic Syndrome," *Hypertension*, 2005, vol. 45 (5), pp. 1004-1011.
Qu S., et al., "Gene Targeting of ErbB3 Using a Cre-Mediated Unidirectional DNA Inversion Strategy," *Genesis*, 2006, vol. 44 (10), pp. 477-486.
Ramírez-Solis R., et al., "Chromosome Engineering in Mice," *Nature*, 1995, vol. 378 (6558), pp. 720-724.
Ramsden D.A., et al., "Conservation of Sequence in Recombination Signal Sequence Spacers," *Nucleic Acids Research*, 1994, vol. 22 (10), pp. 1785-1796.
Ray P., et al., "Ectopic Expression of a c-kit$^{W42}$ Minigene in Transgenic Mice: Recapitulation of W Phenotypes and Evidence for c-kit Function in Melanoblast Progenitors," *Genes & Development*, 1991, vol. 5 (12A), pp. 2265-2273.
Raynard S.J., et al., "Cis-Acting Regulatory Sequences Promote High-Frequency Gene Conversion between Repeated Sequences in Mammalian Ccells," *Nucleic Acids Research*, 2004, vol. 32 (19), pp. 5916-5927.
Reddy S.T., et al., "Monoclonal Antibiotics Isolated without Screening by Analysing the Variable-Gene Repertoire of Plasma Cells," *Nature Biotechnology*, 2010, vol. 28 (9), pp. 965-971.
Regeneron Pharmaceuticals, Inc., et al., "Big Pharma Vies for Mice," *Nature Biotechnology*, 2007, vol. 25 (6), pp. 613.
Regeneron Pharmaceuticals, Inc., Press Release—"Astellas Licenses Regeneron's Veloclmmune® Technology for Discovering Human Monoclonal Antibodies," dated Mar. 30, 2007, 2 pages.
Regeneron Pharmaceuticals, Inc., Press Release—"AstraZeneca Licenses Regeneron's Veloclmmune® Technology for Discovering Human Monoclonal Antibodies—AstraZeneca Is First Licensee of Novel VelocImmune Rechnology License Fees Total up to $120 Million Over Six Years.," dated Feb. 5, 2007, 2 pages.
Regeneron Pharmaceuticals, Inc., Press Release—"Regeneron Initiates Major Global Collaboration with Sanofi-aventis of Develop and Commercialize Fully-Human Therapeutic Antibodies," dated Nov. 29, 2007, 2 pages.
Ren S.Y., et al., "Targeted Insertion Results in a Rhombomere 2-Specific Hoxa2 Knockdown and Ectopic Activation of Hoxal Expression," *Developmental Dynamics*, 2002, vol. 225 (3), pp. 305-315.
Renaut L., et al., "Affinity Maturation of Antibodies: Optimized Methods to Generate High-Quality ScFv Libraries and Isolate IgG Candidates by High-Throughput Screening," *Antibody Engineering: Methods and Protocols*, Second Edition, Chapter 26, 2012, vol. 907, pp. 451-461.
Retter I., et al., "Sequence and Characterization of the Ig Heavy Chain Constant and Partial Variable Region of the Mouse Strain 129S1," *The Journal of Immunology*, 2007, vol. 179 (4), pp. 2419-2427.
Ricker M., European Patent Attorney, Opposition against EP2421357B1 in the name of Kymab Limited Statement of Facts and Arguments pertaining to Application No. 10734546.4, dated Oct. 23, 2013, 29 pages.
Ricker M., European Patent Attorney, Opposition against EP2758535 in the name of Kymab Limited Statement of Facts and Arguments pertaining to Application No. 12772122.3, dated Aug. 9, 2017, 42 pages.
Ristevski S., "Making Better Transgenic Models: Conditional, Temporal, and Spatial Approaches," *Molecular Biotechnology*, 2005, vol. 29 (2), pp. 153-163.
Rivera J., et al., "Genetic Background and the Dilemma of Translating Mouse Studies to Humans," *Immunity*, 2008, vol. 28 (1), pp. 1-4.
Rock E.P., et al., "CDR3 Length in Antigen-specific Immune Receptors", *Journal of Experimental Medicine*, Jan. 1994, vol. 179, pp. 323-328.
Rodríguez C.I., et al., "High-Efficiency Deleter Mice Show that FLPe is an Alternative to Cre-loxP," *Nature Genetics*, 2000, vol. 25 (2), pp. 139-140.
Rogozin I.B., et al., "Cutting edge: DGYW/WRCH is a Better Predictor of Mmutability at G:C bases in Lg Hypermutation than the Widely Accepted RGYW/WRCY Motif and Probably Reflects a Two-Step Activation-Induced Cytidine Deaminase-Triggered Process," *The Journal of Immunology*, 2004, vol. 172 (6), pp. 3382-3384.
Rosner K., et al., "Third Complementarity-Determining Region of Mutated $V_H$ Immunoglobulin Genes Contains Shorter V, D, J, P, and N Components than Non-Mutated Genes," *Immunology*, 2001, vol. 103 (2), pp. 179-187.
Rourke J., Declaration of Jeffrey Rourke, Registered Patent Attorney for Regeneron Pharmaceuticals, Inc.—In the matter of Patent Acceptance 2011266843 in the Name of Kymab Limited and in the Matter of Opposition thereto by Regeneron Pharmaceuticals, Inc., dated Jan. 29, 2016, 5 pages.
Rusk N., "Making Mice at High Speed," *Nature Methods*, Mar. 2007, vol. 4 (3), pp. 196-197.
Sabbattini P., et al., "Analysis of Mice with Single and Multiple Copies of Transgenes Reveals a Novel Arrangement for the λ5-$V_{preB1}$ Locus Control Region," *Molecular and Cellular Biology*, Jan. 1999, vol. 19 (1), pp. 671-679.
Sakai E., et al., "Recombination and Transcription of the Endogenous Ig Heavy Chain Locus is Effected by the Ig Heavy Chain Intronic Enhancer Core Region in the Absence of the Matrix Attachment Regions," *Proceedings of the National Academy of Sciences of the U.S.A.*, 1999, vol. 96 (4), pp. 1526-1531.

(56) References Cited

OTHER PUBLICATIONS

Sarkar A., et al., "Molecular Evolutionary Analysis of the Widespread PiggyBac Transposon Family and Related "Domesticated" Sequences," *Molecular Genetics & Genomics*, 2003, vol. 270 (2), pp. 173-180.
Sasso E.H., et al., "Ethnic Differences of Polymorphism of an Immunoglobulin $V_H3$ Gene," *Journal of Clinical Investigation*, 1995, vol. 96 (3), pp. 1591-1600.
Sasso E.H., et al., "Expression of the Immunoglobulin $V_H$ Gene 51p1 is Proportional to its Germline Gene Copy Number," *Journal of Clinical Investigation*, 1996, vol. 97 (9), pp. 2074-2080.
Sauer B., et al., "Cre-Stimulated Recombination at loxP-Containing DNA Sequences Placed into the Mammalian Genome," *Nucleic Acids Research*, 1989, vol. 17 (1), pp. 147-161.
Sauer B., et al., "Site-Specific DNA Recombination in Mammalian Cells by the Cre Recombinase of Bacteriophage P1," *Proceedings of the National Academy of Sciences of the U.S.A.*, 1988, vol. 85 (14), pp. 5166-5170.
Sauer B., "Functional Expression of the cre-lox Site-Specific Recombination System in the Yeast *Saccharomyces cerevisiae," Molecular and Cellular Biology*, 1987, vol. 7 (6), pp. 2087-2096.
Scapini P., et al., "Myeloid Cells, BAFF, and IFN-γ Establish an Inflammatory Loop that Exacerbates Autoimmunity in Lyn-Deficient Mice," *The Journal of Experimental Medicine*, Jul. 2010, vol. 207 (8), pp. 1757-1773
Schlake T., et al., "Use of Mutated Flp Recognition Target (FRT) Sites for the Exchange of Expression Cassettes at Defined Chromosomal Loci," *Biochemistry*, 1994, vol. 33 (43), pp. 12746-12751.
Schnütgen F., et al., "A Directional Strategy for Monitoring Cre-Mediated Recombination at the Cellular Level in the Mouse," Nature Biotechnology, 2003, vol. 21 (5), pp. 562-565.
Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.
Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.
Schonewald, S.L., Attorney for Applicant, Third-Party Pre-Issuance Submission Under 37 CFR Sec. 1.290 in U.S. Appl. No. 14/818,162, dated May 24, 2016, 47 pages.
Schonewald S.L., Attorney for Applicant, Third-Party Pre-Issuance Submission Under 37 CFR Sec. 1.290 in U.S. Appl. No. 14/935,010, dated Aug. 19, 2016, 27 pages.
Schroeder Jr. H.W, et al., "Preferential Utilization of Conserved Immunoglobulin Heavy Chain Variable Gene Segments During Human Fetal Life," *Proceedings of the National Academy of Sciences of the U.S.A.*, 1990, vol. 87 (16), pp. 6146-6150.
Schroeder, Jr. H.W., "Similarity and divergence in the development and expression of the mouse and human antibody repertoires," *Developmental and Comparative Immunology*, vol. 30, 2006, pp. 119-135.
Schröck E., et al., "Comparative Genomic Hybridization (CGH)—Detection of Unbalanced Genetic Aberrations Using Conventional and Micro-Array Techniques," *Current Protocols in Cytometry*, Chapter 8, 2001, Unit 8.12.1, Supplement 18, 30 pages.
Schweinfest C.W., et al., "A Heat-Shock-Inducible Eukaryotic Expression Vector," *Gene*, 1988, vol. 71 (1), pp. 207-210.
Scott C.T., "Mice with a Human Touch," *Nature Biotechnology*, 2007, vol. 25 (10), pp. 1075-1077.
Seals D.F., et al., "The ADAMs Family of Metalloproteases: Multidomain Proteins with Multiple Functions," *Genes & Development*, 2003, vol. 17 (1), pp. 7-30.
Seed B., "Purification of Genomic Sequences from Bacteriophage Libraries by Recombination and Selection in Vivo," *Nucleic Acids Research*, 1983, vol. 11 (8), pp. 2427-2445.
Seidl K.J., et al., "An Expressed $neo^r$ Cassette Provides Required Functions of the 1γ2b Exon for Class Switching,"*International Immunology*, 1998, vol. 10 (11), pp. 1683-1692.
Seidl K.J., et al., "Position-Dependent Inhibition of Class-Switch Recombination by PGK-$neo^r$ Cassettes Inserted into the Immunoglobulin Heavy Chain Constant Region Locus," *Proceedings of the National Academy of Sciences of the U.S.A.*, Mar. 1999, vol. 96 (6), pp. 3000-3005.
Sekiguchi J., et al., "The Mechanism of V(D)J Recombination," *Molecular Biology of B Cells*, Chapter 5, 2004, pp. 61-82.
Sen R., et al., "Multiple Nuclear Factors Interact with the Immunoglobulin Enhancer Sequences," *Cell*, 1986, vol. 46 (5), pp. 705-716.
Seong E., et al., "To Knockout in 129 or in C57BL/6: That is the Question," *Trends in Genetics*, 2004, vol. 20 (2), pp. 59-62.
Sequence Listing to WO2008054606A2, 163 pages.
Serwe M., et al., "V(D)J Recombination in B Cells is Impaired but not Blocked by Targeted Deletion of the Immunoglobulin Heavy Chain Intron Enhancer," *The EMBO Journal*, 1993, vol. 12 (6), pp. 2321-2327.
Sharon J., et al., "Expression of a VHC Kappa Chimaeric Protein in Mouse Myeloma Cells," *Nature*, 1984, vol. 309 (5966), pp. 364-367.
Shaul Y., et al., "Homologous Recombination Between a Defective Virus and a Chromosomal Sequence in Mammalian Cells," *Proceedings of the National Academy of Sciences of the U.S.A.*, 1985, vol. 82 (11), pp. 3781-3784.
Shi B., et al., "Comparative Analysis of Human and Mouse Immunoglobulin Variable Heavy Regions from IMGT/LIGM-DB with IMGT/HighV-QUEST," *Theoretical Biology and Medical Modelling*, 2014, vol. 11, pp. 1-11.
Shi Y.P., et al., "The Mapping of Transgenes by Fluorescence in Situ Hybridization on G-Banded Mouse Chromosomes," *Mammalian Genome*, 1994, vol. 5 (6), pp. 337-341.
Shin H.H., "Discovery Process for Antibody-Based Therapeutics," *Development of Antibody-Based Therapeutics*, Chapter 2, 2012, pp. 9-32.
Shimizu A., et al., "Immunoglobulin Double-Isotype Expression by Trans-mRNA in a Human Immunoglobulin Transgenic Mouse," *Proceedings of the National Academy of Sciences of the U.S.A.*, 1989, vol. 86 (20), pp. 8020-8023.
Shore, D.E., Attorney for Applicant, Third-Party Pre-Issuance Submission Under 37 CFR Sec. 1.290 in U.S. Appl. No. 14/543,359, filed Mar. 3, 2017, 16 pages.
Shore D.E., Attorney for Applicant, Third-Party Pre-Issuance Submission Under 37 CFR Sec. 1.290 in U.S. Appl. No. 15/199,575, filed May 31, 2017, 37 pages.
Shultz L.D., et al., "Humanized Mice in Translational Biomedical Research," *Nature Reviews / Immunology*, 2007, vol. 7 (2), pp. 118-130.
Sigmund C.D., "Viewpoint: Are Studies in Genetically Altered Mice Out of Control?," *Arteriosclerosis, Thrombosis, and Vascular Biology*, Jun. 2000, vol. 20 (6), pp. 1425-1429.
Simpson E.M., et al., "Genetic Variation Among 129 Substrains and its Importance for Targeted Mutagenesis in Mice," *Nature Genetics*, 1997, vol. 16 (1), pp. 19-27.
Sirac C., et al., "Role of the Monoclonal κ Chain ν Domain and Reversibility of Renal Damage in a Transgenic Model of Acquired Fanconi Syndrome," *Blood*, 2006, vol. 108 (2), pp. 536-543.
Skarnes W.C., et al., "A Conditional Knockout Resource for the Genome-Wide Study of Mouse Gene Function," *Nature*, 2011, vol. 474 (7351), pp. 337-342.
Skoultchi A.I., et al., "Expression of Genes Inserted at the Human β-Globin Locus by Homologous Recombination," *Progress in Clinical and Biological Research*, 1987, vol. 251, pp. 581-594.
Smith K.R., "Gene Transfer in Higher Animals: Theoretical Considerations and Key Concepts," *Journal of Biotechnology*, 2002, vol. 99 (1), pp. 1-22.
Smithies O., "Direct Alteration of a Gene in the Human Genome," *Journal of Inherited Metabolic Disease*, 1986, vol. 9 (Suppl. 1), pp. 92-97.
Smithies O., et al., "Insertion of DNA Sequences into the Human Chromosomal β-Globin Locus by Homologous Recombination," *Nature*, 1985, vol. 317 (6034), pp. 230-234.
Sohn J., et al., "Somatic Hypermutation of an Immunoglobulin μ Heavy Chain Transgene," *The Journal of Experimental Medicine*, 1993, vol. 177 (2), pp. 493-504.

(56) References Cited

OTHER PUBLICATIONS

Song K., et al., "Accurate Modification of a Chromosomal Plasmid by Homologous Recombination in Human Cells," *Proceedings of the National Academy of Sciences of the U.S.A.*, 1987, vol. 84 (19), pp. 6820-6824.
Sonoda E., et al., "B Cell Development Under the Condition of Allelic Inclusion," *Immunity*, 1997, vol. 6 (3), pp. 225-233.
Sopher B., . et al, "Efficient recombination-based methods for bacterial artificial chromosome fusion and mutagenesis," *Gene*, 2006, vol. 371, pp. 136-143.
Sorrell D.A., et al., "Targeted modification of mammalian genomes," *Biotechnology Advances*, vol. 23, 2005, pp. 431-469.
Soukharev S., et al., "Segmental Genomic Replacement in Embryonic Stem Cells by Double Lox Targeting," Nucleic Acids Research, 1999, vol. 27 (18), pp. e21.
Spanopoulou E., et al., "Functional Immunoglobulin Transgenes Guide Ordered B-Cell Differentiation in Rag-1-Deficient Mice," *Genes & Development*, 1994, vol. 8 (9), pp. 1030-1042.
Stavnezer J., et al., "Mechanism and Regulation of Class Switch Recombination," *Annual Review of Immunology*, 2008, vol. 26, pp. 261-292.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Stephen R., Kymab Limited Statement of Facts and Evidence in opposition to EP2550363, Olswang LLP, dated Sep. 10, 2015, 22 pages.
Stephen R., Olswang, Response to Examination Report dated Jun. 6, 2016 for Application No. 14176740.0, as filed with the European Patent Office on Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.
Stevens S., et al., Expanded Poster: "VelocImmune$^{IM}$: Humanization of immunoglobulin loci using VelociGene® technology," Sep. 2006, 6 pages.
Stevens S., et al., Poster (Exhibit IJR-46): "VelocImmune$^{IM}$: Humanization of immunoglobulin loci using VelociGene® technology," and evidence of unavailability, Sep. 2006, 42 pages.
Stevens S. et al., "VelocImmune$^{IM}$: Humanization of immunoglobulin loci using VelociGene® technology," (Abstract-4) Presented at 1st International MUGEN Conference on Animal Models for Human Immunological Disease, Athens, Greece, Sep. 10-13, 2006, 1 page.
Stevens S., "Human Antibody Discovery, VelocImmune—A Novel Platform," *Pharma Focus Asia*, 2008, vol. 8, pp. 72-74.
Storb U., et al., "Physical Linkage of Mouse λ Genes by Pulsed-Field Gel Electrophoresis Suggests that the Rearrangement Process Favors Proximate Target Sequences," *Molecular and Cellular Biology*, 1989, vol. 9 (2), pp. 711-718.
Sun Y., et al., "Repertoire of Human Antibodies against the Polysaccharide Capsule of *Streptococcus pneumoniae* Serotype 6B," *Infection and Immunity*, Mar. 1999, vol. 67 (3), pp. 1172-1179.
Suárez E., et al., "Human monoclonal antibodies produced in transgenic BABκ,λ mice recognising idiotypic immunoglobulins of human lymphoma cells," *Molecular Immunology*, 2004, vol. 41, pp. 519-526.
Suárez E., et al., "Rearrangement of Only One Human IGHV Gene is Sufficient to Generate a Wide Repertoire of Antigen Specific Antibody Responses in Transgenic Mice," *Molecular Immunology*, 2006, vol. 43 (11), pp. 1827-1835.
Takeda S., et al., "Construction of Chimaeric Processed Immunoglobulin Genes Containing Mouse Variable and Human Constant Region Sequences," *Nature*, Apr. 1985, vol. 314 (6010), pp. 452-454.
Taki S., et al., "Targeted Insertion of a Variable Region Gene into the Immunoglobulin Heavy Chain Locus," *Science*, 1993, vol. 262 (5137), pp. 1268-1271.
Talbot P., et al., "Cell Adhesion and Fertilization: Steps in Oocyte Transport, Sperm-Zona Pellucida Interactions, and Sperm-Egg Fusion," *Biology of Reproduction*, 2003, vol. 68 (1), pp. 1-9.
Tan L.K., et al., "A Human-Mouse Chimeric Immunoglobulin Gene with a Human Variable Region is Expressed in Mouse Myeloma Cells," *Journal of Immunology*, Nov. 1985, vol. 135 (5), pp. 3564-3567.
Tanimoto Y., et al., "Embryonic Stem Cells Derived from C57BL/6J and C57BL/6N Mice," *Comparative Medicine*, Aug. 2008, vol. 58 (4), pp. 347-352.
Taylor L.D., et al., "Human Immunoglobulin Transgenes Undergo Rearrangement, Somatic Mutation and Class Switching in Mice that Lack Endogenous IgM," *International Immunology*, 1994, vol. 6 (4), pp. 579-591.
Te Riele H., et al., "Highly Efficient Gene Targeting in Embryonic Stem Cells through Homologous Recombination with Isogenic DNA Constructs," *Proceedings of the National Academy of Sciences of the U.S.A.*, 1992, vol. 89 (11), pp. 5128-5132.
The Jackson Laboratory, "Breeding Strategies for Maintaining Colonies of Laboratory Mice," A *Jackson Laboratory Resource Manual*, 2007, pp. 1-29.
Thomas K.R., et al., "High Frequency Targeting of Genes to Specific Sites in the Mammalian Genome," *Cell*, 1986, vol. 44 (3), pp. 419-428.
Thomas K.R., et al., "Introduction of Homologous DNA Sequences into Mammalian Cells Induces Mutations in the Cognate Gene," *Nature*, 1986, vol. 324 (6092), pp. 34-38.
Thomas K.R., et al., "Site-Directed Mutagenesis by Gene Targeting in Mouse Embryo-Derived Stem Cells," *Cell*, 1987, vol. 51 (3), pp. 503-512.
Thykjaer T., et al., "Gene Targeting Approaches Using Positive-Negative Selection and Large Flanking Regions," *Plant Molecular Biology*, 1997, vol. 35 (4), pp. 523-530.
Tomizuka K., et al., "Double Trans-Chromosomic Mice: Maintenance of Two Individual Human Chromosome Fragments Containing Ig Heavy and κ Loci and Expression of Fully Human Antibodies," *Proceedings of the National Academy of Sciences of the U.S.A.*, Jan. 2000, vol. 97 (2), pp. 722-727.
Tonegawa S., "Somatic Generation of Antibody Diversity," *Nature*, Apr. 1983, vol. 302 (5909), pp. 575-581.
Tong C., et al., "Production of *p53* gene knockout rats by homologous recombination in embryonic stem cells," *Nature*, Sep. 2010, vol. 467 (7312), pp. 211-213.
Torres R., et al., "Laboratory Protocols for Conditional Gene Targeting", *Institute for Genetics*, University of Cologne, 1997, pp. 37-40.
Tuaillon N., et al., "Human immunoglobulin heavy-chain minilocus recombination in transgenic mice: Gene-segment use in μ and β transcripts," *Proceedings of the National Academy of Sciences of the U.S.A.*, Apr. 1993, vol. 90, pp. 3720-3724.
Tucker P.W., et al., "Mouse IgA Heavy Chain Gene Sequence: Implications for Evolution of Immunoglobulin Hinge Axons," *Proceedings of the National Academy of Sciences of the U.S.A.*, Dec. 1981, vol. 78 (12), pp. 7684-7688.
Ungrin M.D., et al., "Strict Control of Telomerase Activation Using Cre-Mediated Inversion," *BMC Biotechnology*, 2006, vol. 6, pp. 1-9, 2006.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Combined Search and Examination Report under Sections 17 and 18(3) for Application No. GB1317447.9, dated Jan. 14, 2014, 7 pages.
United Kingdom Intellectual Property Office, Corrected Search Report Under Section 17 for Application No. GB1122047.2, dated Apr. 20, 2012, 5 pages.
United Kingdom Intellectual Property Office, Search Report under Section 17 for Application No. GB1116122.1, dated Feb. 2, 2012, 1 page.

(56) References Cited

OTHER PUBLICATIONS

Urquhart-Dykes & Lord LLP, Third-Party Observation for Application No. EP20140772198, dated Dec. 14, 2015, 8 pages.
USPTO, Excerpts from U.S. Appl. No. 14/682,859, filed Apr. 9, 2015, including Applicant-initiated Interview Summary; Amendments to the Claims and Information Disclosure Statement, 14 pages.
Valenzuela D.M., et al., "High-Throughput Engineering of the Mouse Genome Coupled with High-Resolution Expression Analysis," *Nature Biotechnology*, 2003, vol. 21 (6), pp. 652-659 and vol. 21 (7), p. 822.
Van Der Weyden L., et al., "Mouse Chromosome Engineering for Modeling Human Disease," *Europe PMC Funders Group*, Author Manuscript, Dec. 2008, 32 pages.
Van Dijk M., Declaration of Marcus Van Dijk with exhibits, Apr. 30, 2016, 139 pages.
Van Loo, P.F., et al., "Surrogate-Light-Chain Silencing Is Not Critical for the Limitation of Pre-B Cell Expansion but Is for the Termination of Constitutive Signaling," *Immunity*, Sep. 2007, vol. 27, pp. 468-480.
Van Snick J.L., et al., "Genetic Control of Rheumatoid Factor Production in the Mouse. Role of Genes Linked to the Immunoglobulin Heavy Chain Locus and to the Major Histocompatibility Complex," *Arthritis and Rheumatism*, Sep. 1983, vol. 26 (9), pp. 1085-1090.
Van Spriel A.B., et al., "Immunotherapeutic Perspective for Bispecific Antibodies," *Immunology Today*, 2000, vol. 21 (8), pp. 391-397.
Vasicek T.J., et al., "Structure and Expression of the Human Immunoglobulin λ Genes," *The Journal of Experimental Medicine*, 1990, vol. 172 (2), pp. 609-620.
Vassilieva S., et al., "Establishment of SSEA-1- and Oct-4-Expressing Rat Embryonic Stem-Like Cell Lines and Effects of Cytokines of the IL-6 Family on Clonal Growth," *Experimental Cell Research*, 2000, vol. 258 (2), pp. 361-373.
Venken K.J.T., et al., "P[acman]: a BAC Transgenic Platform for Targeted Insertion of Large DNA Fragments in *D. melanogaster*," *Science*, 2006, vol. 314 (5806), pp. 1747-1751.
Vieira P., et al., "The half-lives of serum immunoglobulins in adult mice," *European Journal of Immunology*, 1988, vol. 18, pp. 313-316.
Vollmer J., et al., "Antigen Contacts by Ni-Reactive TCR: Typical αβ Chain Cooperation Versus α Chain-Dominated Specificity," *International Immunology*, 2000, vol. 12 (12), pp. 1723-1731.
Vora K.A., et al., "Altering the Antibody Repertoire via Transgene Homologous Recombination: Evidence for Global and Clone-Autonomous Regulation of Antigen-Driven B Cell Differentiation," *The Journal of Experimental Medicine*, 1995, vol. 181 (1), pp. 271-281.
Wagner S.D., et al., "Antibodies Generated from Human Immunoglobulin Miniloci in Transgenic Mice," *Nucleic Acids Research*, 1994, vol. 22 (8), pp. 1389-1393.
Wallace H.A.C., et al., "Manipulating the Mouse Genome to Engineer Precise Functional Syntenic Replacements with Human Sequence," *Cell*, 2007, vol. 128 (1), pp. 197-209.
Wang M., et al., "AID Upmutants Isolated Using a High-Throughput Screen Highlight the Immunity/Cancer Balance Limiting DNA Deaminase Activity," *Nature Structural & Molecular Biology*, 2009, vol. 16 (7), pp. 769-776.
Wang M., et al., "Altering the Spectrum of Immunoglobulin V Gene Somatic Hypermutation by Modifying the Active Site of AID," *The Journal of Experimental Medicine*, 2010, vol. 207 (1), pp. 141-153.
Wang T.T., et al., "Catching a Moving Target," Science, 2011, vol. 333 (6044), pp. 834-835.
Wang W., et al., "Chromosomal Transposition of PiggyBac in Mouse Embryonic Stem Cells," *Proceedings of the National Academy of Sciences of the U.S.A.*, 2008, vol. 105 (27), pp. 9290-9295.
Wang X., et al., "Recombination, transcription, and diversity of a partially germline-joined VH in a mammal," *Immunogenetics*, 2012, vol. 64, pp. 713-717.
Wang Y., et al., "Many Human Immunoglobulin Heavy-Chain IGHV Gene Polymorphisms have been Reported in Error," *Immunology and Cell Biology*, 2008, vol. 86 (2), pp. 111-115.
Wasserman R., et al., "The Pattern of Joining ($J_H$) Gene Usage in the Human IgH Chain Is Established Predominantly at the B PreCursor Cell Stage," *The Journal of Immunology*, Jul. 1992, vol. 149 (2), pp. 511-516.
Waterhouse P., et al., "Combinatorial Infection and in Vivo Recombination: a Strategy for Making Large Phage Antibody Repertoires," *Nucleic Acids Research*, 1993, vol. 21 (9), pp. 2265-2266.
Waterston R.H., et al., "Initial Sequencing and Comparative Analysis of the Mouse Genome," *Nature*, Dec. 2002, vol. 420 (6915), pp. 520-562.
Webpage corroborating non-confidential nature of 2006 MUGEN Conference, Athens (www.mugen.noe.org), accessed Aug. 9, 2016, 4 pages.
Weichhold G.M., et al., "Megabase Inversions in the Human Genome as Physiological Events," *Nature*, Sep. 1990, vol. 347 (6288), pp. 90-92.
Weichhold G.M., et al., "The Human Immunoglobulin κ Locus Consists of Two Copies that are Organized in Opposite Polarity," *Genomics*, 1993, vol. 16 (2), pp. 503-511.
Weiner L.M., "Fully Human Therapeutic Monoclonal Antibodies," *Journal of Immunology*, Jan./Feb. 2006, vol. 29 (1), pp. 1-9.
White J.K., et al., "Genome-Wide Generation and Systematic Phenotyping of Knockout Mice Reveals New Roles for Many Genes," *Cell*, 2013, vol. 154 (2), pp. 452-464.
Wikipedia, "Monoclonal antibody," 2008, 8 pages.
Wikipedia, "Polyclonal antibodies," 2008, 5 pages.
Wilke K., et al., "Diagnosis of Haploidy and Triploidy Based on Measurement of Gene Copy Number by Real-Time PCR," *Human Mutation*, 2000, vol. 16 (5), pp. 431-436.
Wilkie T.M., et al., "Analysis of the Integrant in MyK-103 Transgenic Mice in which Males Fail to Transmit the Integrant," *Molecular and Cellular Biology*, 1987, vol. 7 (5), pp. 1646-1655.
Williams G.S., et al., "Unequal $V_H$ Gene Rearrangement Frequency within the Large $V_H$7183 Gene Family is not due to Recombination Signal Sequence Variation, and Mapping of the Genes Shows a Bias of Rearrangement Based on Chromosomal Location," *Journal of Immunology*, 2001, vol. 167 (1), pp. 257-263.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Wuerffel R., et al., "S-S Synapsis During Class Switch Recombination is Promoted by Distantly Located Transcriptional Elements and Activation-Induced Deaminase," *Immunity*, Nov. 2007, vol. 27 (5), pp. 711-722.
Xiao X., et al., "Germline-like predecessors of broadly neutralizing antibodies lack measurable binding to HIC-1 envelope glycoproteins: Implications for evasion of immune responses and design of vaccine immunogens," *Biochemical and Biophysical Communications*, 2009, vol. 390, pp. 404-409.
Xu L., et al., "Combinatorial Surrobody Libraries," *Proceedings of the National Academy of Sciences of the U.S.A.*, 2008, vol. 105 (31), pp. 10756-10761.
Xu Y., et al., "Deletion of the Igκ Light Chain Intronic Enhancer/Matrix Attachment Region Impairs but does not Abolish VκJκ Rearrangement," *Immunity*, Apr. 1996, vol. 4 (4), pp. 377-385.
Yamada M., et al., "Preferential Utilization of Specific Immunoglobulin Heavy Chain Diversity and Joining Segments in Adult Human Peripheral Blood B Lymphocytes," *Journal of Experimental Medicine*, Feb. 1991, vol. 173, pp. 395-407.
Yancopoulos G.D., et al., "Preferential Utilization of the Most $J_H$-Proximal $V_H$ Gene Segments in Pre-B-Cell Lines," *Nature*, 1984, vol. 311 (5988), pp. 727-733.
Yang X.W., et al., "Homologous Recombination Based Modification in *Escherichia coli* and Germline Transmission in Transgenic Mice of a Bacterial Artificial Chromosome," *Nature Biotechnology*, Sep. 1997, vol. 15 (9), pp. 859-865.

(56) References Cited

OTHER PUBLICATIONS

Yu C.C.K., et al., "Differential Usage of $V_H$ Gene Segments is Mediated by cis Elements," *Journal of Immunology*, 1998, vol. 161 (7), pp. 3444-3454.
Yu Y., et al., "Engineering Chromosomal Rearrangements in Mice," *Nature Reviews Genetics*, 2001, vol. 2 (10), pp. 780-790.
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, 2003, vol. 334 (4), pp. 733-749.
Zhang X., et al., "Combination of overlapping bacterial artificial chromosones by a two-step recombinogenic engineering method," *Nucleic Acids Research*, 2003, vol. 31 (15), pp. e81-1-e81-6.
Zhang Y., et al., "A New Logic for DNA Engineering Using Recombination in *Escherichia coli," Nature Genetics*, 1998, vol. 20 (2), pp. 123-128.
Zhao S., "A Comprehensive BAC Resource," *Nucleic Acids Research*, 2001, vol. 29 (1), pp. 141-143.
Zhao Y., et al., "Physical Mapping of the Bovine Immunoglobulin Heavy Chain Constant Region Gene Locus," *Journal of Biological Chemistry*, Sep. 2003, vol. 278 (37), pp. 35024-35032.
Zheng B., et al., "Engineering Mouse Chromosomes with Cre-loxP: Range, Efficiency, and Somatic Applications," *Molecular and Cellular Biology*, 2000, vol. 20 (2), pp. 648-655.
Zheng J., et al., "Immunoglobulin Gene Transcripts Have distinctive $V_HDJ_H$ Recombination Characteristics in Human Epithelial Cancer Cells", *Journal of Biological Chemistry*, Mar. 2009, vol. 284 (20), pp. 13610-13619.
Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.
Zou X., et al., "Removal of the BiP-Retention Domain in Cμ Permits Surface Deposition and Developmental Progression Without L-Chain," *Molecular Immunology*, 2008, vol. 45 (13), pp. 3573-3579.
Zou X., et al., "Subtle differences in antibody responses and hypermutation of lambda λ chains in mice with a disrupted κ contant region," *European Journal of Immunology*, 1995, vol. 25, pp. 2154-2162.
Zou Y., et al., "Cre-loxP-Mediated Gene Replacement: a Mouse Strain Producing Humanized Antibodies," *Current Biology*, 1994, vol. 4 (12), pp. 1099-1103.
Canadian Intellectual Property Office; Office Action for Application No. 2,857,569, dated Jan. 14, 2019, 6 pages.
Genbank "Immunoglobulin Heavy Chain Variable Region (*Homo sapiens*)," Accession No. BAA75060, dated Jul. 2, 2008, 1 page.
Grund M., European Patent Attorney, Grund Intellectual Property Group, Third-Party Observations according to Article 115 EPC regarding 15188522.5, dated Mar. 13, 2019, 4 pages.
Grund M., European Patent Attorney, Grund Intellectual Property Group, Third-Party Observations according to Article 115 EPC regarding 17196235.0, dated Dec. 4, 2018, 23 pages.
Grund M., European Patent Attorney, Grund Intellectual Property Group, Third-Party Observations according to Article 115 EPC regarding 17174426.1, dated Feb. 18, 2019, 6 pages.
Japanese Patent Office, Application No. 2016-548441, Notice of Reasons for Rejection, dated Aug. 5, 2019, together with English translation, 12 pages.
Japanese Patent Office, Application No. 2017-017360, Notice of Reasons for Rejection, dated Mar. 19, 2018, together with English translation, 7 pages.
Japanese Patent Office, Application No. 2017-021028, Notice of Reasons for Rejection, dated Dec. 21, 2018, together with English translation, 11 pages.
Japanese Patent Office, Application No. 2017-021028, Decision of Rejection, dated Sep. 9, 2019, 9 pages.
Japanese Patent Office, Application No. 2018-088749, Notice of Reasons for Rejection, dated May 27, 2019, together with English translation, 11 pages.
Morrison S.L., et al. "Vectors and Approaches for the Eukaryotic Expression of Antibodies and Antibody Fusion Proteins" Antibody Engineering, 2nd Edition, Chapter 9, Edited by Carl A. K., Borrebaeck NY Oxford; Oxford University Press, 1995, 31 pages.
Oberdoerffer, et al., Unidirectional Cre-mediated Genetic Inversion in Mice using the Mutant loxP pair lox66/lox71, Nuc. Acids. Res., 31(22): e140, 2003.†
Zheng, et al., Engineering Mouse Chromosomes with Cre-loxP: Range, Efficiency, and Somatic Applications, Mol. Cell. Biol., 20(2): 648-655, 2000.†
U.S. Pat. No. 6,596,541 and supporting Exhibits 1-3, Methods of Modifying Eukaryotic Cells, Priority to Oct. 31, 2000, filed Feb. 16, 2001, Issued Jul. 22, 2003.†
International PCT Publication WO 02_066630 and supporting Exhibits 1-3, Methods of Modifying Eukaryotic Cells, filed Feb. 15, 2002, published Aug. 29, 2002, Priority to Feb. 16, 2001.†
Boyd et al., Individual Variation in the Germline Ig Gene Repertoire Inferred from Variable Region Gene Rearrangements, J. Immunol., 184(12): 6986-6992, 2010.†
Briney et al., Human Peripheral Blood Antibodies with Long HCDR3s Are Established Primarily at Original Recombination using a Limited Subset of Germline Genes, PlosONE 7(5): e36750, 2012.†
Declaration of Lynn E. Macdonald, including Annexes 1-4, as together made publicly available at least upon submission to and online publication by the European Patent Office on Mar. 12, 2015.†
Raaphorst et al., Human Ig Heavy Chain CDR3 Regions in Adult Bone Marrow Pre-B Cells Display an Adult Phenotype of Diversity: Evidence for Structural Selection of DH Amino Acid Sequences, Int. Immunol., 9(10): 1503-1515, 1997.†
Lefranc, Marie-Paule, and Gérard Lefranc., Immunoglobulin Facts Book, London: Academic Press, 2001, 457 pages.†
Rosner et al., Third Complementarity-Determining Region of Mutated VH Immunoglobulin Genes Contains Shorter V, D, J, P, and N Components Than Non-Mutated Genes, Immunology, 103:179-187, 2001.†
Zemlin et al., Expressed Murine and Human CDR-H3 Intervals of Equal Length Exhibit Distinct Repertoires that Differ in their Amino Acid Composition and Predicted Range of Structures, JMB, 334:733-749, 2003.†
Weyden and Bradley, Mouse Chromosome Engineering for Modeling Human Disease, Annu. Rev. Genomics Hum. Genet., 7:247-276, 2006.†
Valenzuela, et al., High-Throughput Engineering of the Mouse Genome Coupled with High-Resolution Expression Analysis, Nat. Biotech., 21(6): 652-659, 2003.†
Stevens, S., et al., Sep. 10-13, 2006, Velocimmune: Humanization of Immunoglobulin Loci Using Velocigene Technology, Abstract of poster presented at 1st International MUGEN Conference on Animal Models for Human Immunological Disease, Athens, Greece.†
Response to Oppositions in the name of Kymab Limited, Submitted in European Patent No. 2758535 and entered into public record on Mar. 22, 2018.†
Macdonald, et al., Sep. 10-13, 2006, Velocigene Technology Extended to Humanization of Several Megabases of Complex Gene Loci, Presented at 1st International MUGEN Conference on Animal Models for Human Immunological Disease, Athens, Greece.†
Adams et al., A Genome-Wide, End-Sequenced 129Sv BAC Library Resource for Targeting Vector Construction, Genomics, 86(6): 753-758, 2005.†
Murphy, A., VelocImmune: Immunoglobulin Variable Region Humanized Mice, In M. Little (ed.), Recombinant Antibodies for Immunotherapy, pp. 100-107, New York, NY: Cambridge University Press, Published Jul. 27, 2009.†

* cited by examiner
† cited by third party

Recombineered BAC Vectors to add Polymorphic V-regions to the Mouse Genome

Adding Polymorphic V-regions to the Genome using SRMCE of Modified BACs

1. Insertion at a 'Landing Pad' site during SRMCE

```
                                             1   2   3   4   5   6   7   8   9  10  11  12  13  14  15  16  17  18  19  20  21  22  23  24  25  26
                                             Q   V   Q   L   V   Q   S   G   A       E   V   K   K   P   G   S   S   V   K   V   S   C   K   A   S
L22582  ,IGHV1-69*01, hv1051               CAG GTG CAG CTG GTG CAG TCT GGG GCT ... GAG GTG AAG AAG CCT GGG TCC TCG GTG AAG GTC TCC TGC AAG GCT TCT
Z27506  ,IGHV1-69*02, yIGH6(YAC7)          --- --C --- --- --- --A --- --- --- ... --- --- --- --- --- --- --- --- --- --- --- --- --- --- --- ---
X92340  ,IGHV1-69*03, 57GTA8               --- --- --- --- --- --- --- --- --- ... --- --- --- --- --- --- --- --- --- --- --- --- --- --- --- ---
M83132  ,IGHV1-69*04, hv1263               --- --C --- --- --- --- --- --- --- ... --- --- --- --- --- --- --- --- --- --- --- --- --- --- --- ---
X67905  ,IGHV1-69*05, RR.VH1.2             --- --C --- --- --- --- --- --- --- ... --- --- --- --- --- --- --- --- --- --- --- --- --- --- --- ---
L22583  ,IGHV1-69*06, hv1051K              --- --- --- --- --- --- --- --- --- ... --- --- --- --- --- --- --- --- --- --- --- --- --- --- --- ---
Z29978  ,IGHV1-69*07, DA-2                                                                  -- --- --- --- --- --- --- --- --- --- --- --- --- ---
Z14309  ,IGHV1-69*08                       --- --C --- --- --- --A --- --- --- ... --- --- --- --- --- --- --- --- --- --- --- --- --- --- --- ---
Z14307  ,IGHV1-69*09                       --- --- --- --- --- --- --- --- --- ... --- --- --- --- --- --- --- --- --- --- --- --- --- --- --- ---
Z14300  ,IGHV1-69*10                       --- --C --- --- --- --- --- --- --- ... --- --- --- --- --- --- --- --A --- --- --- --- --- --- --- ---
Z14296  ,IGHV1-69*11                       --- --C --- --- --- --- --- --- --- ... --- --- --- --- --- --- --- --- --- --- --- --- --- --- --- ---
Z14301  ,IGHV1-69*12                       --- --C --- --- --- --- --- --- --- ... --- --- --- --- --- --- --- --- --- --- --- --- --- --- --- ---
Z14214  ,IGHV1-69*13                       --- --C --- --- --- --- --- --- --- ... --- --- --- --- --- --- --- --A --- --- --- --- --- --- --- ---
```

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Figure 5A

| | | CDR1 | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 |
| | | G | G | T | F | S | S | Y | A | | | | | I | S | W | V | R | Q | A | P | G | Q | G | L | E | W | M |
| L22582 | ,IGHV1-69*01, hv1051 | GGA | GGC | ACC | TTC | AGC | AGC | TAT | GCT | ... | ... | ... | ... | ATC | AGC | TGG | GTG | CGA | CAG | GCC | CCT | GGA | CAA | GGG | CTT | GAG | TGG | ATG |
| | | | | | | | | | T | | | | | | | | | | | | | | | | | | | |
| Z27506 | ,IGHV1-69*02, yIGH6(YAC7) | --- | --- | --- | --- | --- | --- | --- | A-- | ... | ... | ... | ... | --- | --- | --- | --- | --- | --- | --- | --- | --- | --- | --- | --- | --- | --- | --- |
| X92340 | ,IGHV1-69*03, 57GTA8 | --- | --- | --- | --- | --- | --- | --- | --- | ... | ... | ... | ... | --- | --- | --- | --- | --- | --- | --- | --- | --- | --- | --- | --- | --- | --- | --- |
| M83132 | ,IGHV1-69*04, hv1263 | --- | --- | --- | --- | --- | --- | --- | --- | ... | ... | ... | ... | --- | --- | --- | --- | --- | --- | --- | --- | --- | --- | --- | --- | --- | --- | --- |
| X67905 | ,IGHV1-69*05, RR.VH1.2 | --- | --- | --- | --- | --- | --- | --- | --- | ... | ... | ... | ... | --- | --- | --- | --- | --- | --- | --- | --- | --- | --- | --- | --- | --- | --- | --- |
| L22583 | ,IGHV1-69*06, hv1051K | --- | --- | --- | --- | --- | --- | --- | --- | ... | ... | ... | ... | --- | --- | --- | --- | --- | --- | --- | --- | --- | --- | --- | --- | --- | --- | --- |
| Z29978 | ,IGHV1-69*07, DA-2 | --- | --- | --- | --- | --- | --- | --- | --- | ... | ... | ... | ... | --- | --- | --- | --- | --- | --- | --- | --- | --- | --- | --- | --- | --- | --- | --- |
| | | | | | | | | | T | | | | | | | | | | | | | | | | | | | |
| Z14309 | ,IGHV1-69*08 | --- | --- | --- | --- | --- | --- | --- | A-- | ... | ... | ... | ... | --- | --- | --- | --- | --- | --- | --- | --- | --- | --- | --- | --- | --- | --- | --- |
| Z14307 | ,IGHV1-69*09 | --- | --- | --- | --- | --- | --- | --- | --- | ... | ... | ... | ... | --- | --- | --- | --- | --- | --- | --- | --- | --- | --- | --- | --- | --- | --- | --- |
| Z14300 | ,IGHV1-69*10 | --- | --- | --- | --- | --- | --- | --- | --- | ... | ... | ... | ... | --- | --- | --- | --- | --- | --- | --- | --- | --- | --- | --- | --- | --- | --- | --- |
| Z14296 | ,IGHV1-69*11 | --- | --- | --- | --- | --- | --- | --- | --- | ... | ... | ... | ... | --- | --- | --- | --- | --- | --- | --- | --- | --- | --- | --- | --- | --- | --- | --- |
| Z14301 | ,IGHV1-69*12 | --- | --- | --- | --- | --- | --- | --- | --- | ... | ... | ... | ... | --- | --- | --- | --- | --- | --- | --- | --- | --- | --- | --- | --- | --- | --- | --- |
| Z14214 | ,IGHV1-69*13 | --- | --- | --- | --- | --- | --- | --- | --- | ... | ... | ... | ... | --- | --- | --- | --- | --- | --- | --- | --- | --- | --- | --- | --- | --- | --- | --- |

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Figure 5B

```
                                                              CDR2
                                    54  55  56  57  58  59  60  61  62  63  64  65  66  67  68  69  70  71  72  73  74  75  76  77  78  79  80
                                    G   G   I   I   P   I   F   G   T   A           N   Y   A   Q   K   F   Q       G   R   V   T   I   T   A
L22582  ,IGHV1-69*01, hv1051        GGA GGG ATC ATC CCT ATC TTT GGT ACA GCA ... ... AAC TAC GCA CAG AAG TTC CAG ... GGC AGA GTC ACG ATT ACC GCG
                                        R                   L       I
Z27506  ,IGHV1-69*02, yIGH6(YAC7    --- A-- --- --- --- --- C-- --- -T- --- ... ... --- --- --- --- --- --- --- ... --- --- --- --- --- --- ---

X92340  ,IGHV1-69*03, 57GTA8        --- --- --- --- --- --- --- --- --- --- ... ... --- --- --- --- --- --- --- ... --- --- --- --- --- --- ---
                                        R                   L       I
M83132  ,IGHV1-69*04, hv1263        --- A-- --- --- --- --- C-- --- -T- --- ... ... --- --- --- --- --- --- --- ... --- --- --- --- --- --- ---
                                                                                                                                            T
X67905  ,IGHV1-69*05, RR.VH1.2      --- --- --- --- --- --- --- --- --- --- ... ... --- --- --- --- --- --- --- ... --- --- --- --- --- --- A--

L22583  ,IGHV1-69*06, hv1051K       --- --- --- --- --- --- --- --- --- --- ... ... --- --- --- --- --- --- --- ... --- --- --- --- --- --- ---
                                        R
Z29978  ,IGHV1-69*07, DA-2          --- A-- --- --- --- --- --- --- --- --- ... ... --- --- --- --- --- --- --- ... --- --- --- --- --- --- ---
                                        R                   L
Z14309  ,IGHV1-69*08                --- A-- --- --- --- --- C-- --- --- --- ... ... --- --- --- --- --- --- --- ... --- --- --- --- --- --- ---
                                        R                   L       I
Z14307  ,IGHV1-69*09                --- A-- --- --- --- --- C-- --- -T- --- ... ... --- --- --- --- --- --- --- ... --- --- --- --- --- --- ---
                                                            L       I
Z14300  ,IGHV1-69*10                --- --- --- --- --- --- C-- --- -T- --- ... ... --- --- --- --- --- --- --- ... --- --- --- --- --- --- ---
                                        R                   L
Z14296  ,IGHV1-69*11                --- A-- --- --- --- --- C-- --- --- --- ... ... --- --- --- --- --- --- --- ... --- --- --- --- --- --- ---

Z14301  ,IGHV1-69*12                --- --- --- --- --- --- --- --- --- --- ... ... --- --- --- --- --- --- --- ... --- --- --- --- --- --- ---

Z14214  ,IGHV1-69*13                --- --- --- --- --- --- --- --- --- --- ... ... --- --- --- --- --- --- --- ... --- --- --- --- --- --- ---
```

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Figure 5C

```
                                                                                                                    __CDR3___
                                   81  82  83  84  85  86  87  88  89  90  91  92  93  94  95  96  97  98  99  100 101 102 103 104 105 106
                                   D   E   S   T   S   T   A   Y   M   E   L   S   S   L   R   S   E   D   T   A   V   Y   Y   C   A   R
L22582  ,IGHV1-69*01, hv1051       GAC GAA TCC ACG AGC ACA GCC TAC ATG GAG CTG AGC AGC CTG AGA TCT GAG GAC ACG GCC GTG TAT TAC TGT GCG AGA GA
                                       K
Z27506  ,IGHV1-69*02, yIGH6(YAC7)--- A-- --- --- --- --- --- --- --- --- --- --- --- --- --- --- --- --- --- --- --- --- --- --- --- --- --
                                                                                       D
X92340  ,IGHV1-69*03, 57GTA8       --- --- --- --- --- --- --- --- --- --- --- --- --- --- --- --- --T --- --- -
                                       K
M83132  ,IGHV1-69*04, hv1263       --- A-- --- --- --- --- --- --- --- --- --- --- --- --- --- --- --- --- --- --- --- --- --- --- --- --- --

X67905  ,IGHV1-69*05, RR.VH1.2     --- --- --- --- --- --- --- --- --- --- --- --- --- --- --- --- --- --- --- --- --- --- --- --- --- ---
                                       K
L22583  ,IGHV1-69*06, hv1051K      --- A-- --- --- --- --- --- --- --- --- --- --- --- --- --- --- --- --- --- --- --- --- --- --- --- --- --

Z29978  ,IGHV1-69*07, DA-2         --- --- --- --- --- --- --- --- --- --- --- --- --- --- --- --- ---
                                       K
Z14309  ,IGHV1-69*08               --- A-- --- --- --- --- --- --- --- --- --- --- --- --- --- --- --- --- --- --- --- --- --- --- --- --- --
                                       K
Z14307  ,IGHV1-69*09               --- A-- --- --- --- --- --- --- --- --- --- --- --- --- --- --- --- --- --- --- --- --- --- --- --- --- --
                                       K
Z14300  ,IGHV1-69*10               --- A-- --- --- --- --- --- --- --- --- --- --- --- --- --- --- --- --- --- --- --- --- --- --- --- --- --

Z14296  ,IGHV1-69*11               --- --- --- --- --- --- --- --- --- --- --- --- --- --- --- --- --- --- --- --- --- --- --- --- --- --- --

Z14301  ,IGHV1-69*12               --- --- --- --- --- --- --- --- --- --- --- --- --- --- --- --- --- --- --- --- --- --- --- --- --- --- --

Z14214  ,IGHV1-69*13               --- --- --- --- --- --- --- --- --- --- --- --- --- --- --- --- --- --- --- --- --- --- --- --- --- --- --
```

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

| | | 1 | 2 | 3 | 4 | 5 | 6 | 7 | 8 | 9 | 10 | 11 | 12 | 13 | 14 | 15 | 16 | 17 | 18 | 19 | 20 | |
|---|---|---|---|---|---|---|---|---|---|---|---|---|---|---|---|---|---|---|---|---|---|---|
| | | Y | Y | Y | Y | Y | G | M | D | V | W | G | Q | G | T | T | V | T | V | S | S | |
| J00256,IGHJ6*01 | AT | TAC | TAC | TAC | TAC | TAC | GGT | ATG | GAC | GTC | TGG | GGG | CAA | GGG | ACC | ACG | GTC | ACC | GTC | TCC | TCA | G |
| X86355,IGHJ6*02 | -- | --- | --- | --- | --- | --- | --- | --- | --- | --- | --- | --**C** | --- | --- | --- | --- | --- | --- | --- | --- | --- | |
| X86357,IGHJ6*02 | -- | --- | --- | --- | --- | --- | --- | --- | --- | --- | --- | --**C** | --- | --- | --- | --- | --- | --- | --- | --- | --- | |
| X86358,IGHJ6*02 | -- | --- | --- | --- | --- | --- | --- | --- | --- | --- | --- | --**C** | --- | --- | --- | --- | --- | --- | --- | --- | --- | |
| M63031,IGHJ6*02 | -- | --- | --- | --- | --- | --- | --- | --- | --- | --- | --- | --**C** | --- | --- | --- | --- | --- | --- | --- | --- | --- | - |
| X97051,IGHJ6*02 | -- | --- | --- | --- | --- | --- | --- | --- | --- | --- | --- | --**C** | --- | --- | --- | --- | --- | --- | --- | --- | --- | - |
| M25625,IGHJ6*02 | -- | --- | --- | --- | --- | --- | --- | --- | --- | --- | --- | --**C** | --- | --- | --- | --- | --- | --- | --- | --- | --- | - |
| X86356,IGHJ6*03 | -- | --- | --- | --- | --- | --- | **TAC** (**Y**) | --- | --- | --- | --- | --**C** | **A**-- (**K**) | --- | --- | --- | --- | --- | --- | --- | --- | |
| X86359,IGHJ6*03 | -- | --- | --- | --- | --- | --- | **TAC** (**Y**) | --- | --- | --- | --- | --**C** | **A**-- (**K**) | --- | --- | --- | --- | --- | --- | --- | --- | |
| M63030,IGHJ6*03 | -- | --- | --- | --- | --- | --- | **TAC** (**Y**) | --- | --- | --- | --- | --**C** | **A**-- (**K**) | --- | --- | --- | --- | --- | --- | --- | --- | - |
| AJ879487,IGHJ6*04 | -- | --- | --- | --- | --- | --- | --- | --- | --- | --- | --- | --**C** | **A**-- (**K**) | --- | --- | --- | --- | --- | --- | --- | --- | - |

FIGURE 8

```
                                         Y   Y   G   M   D   L
Rabbit JH6                           at tac tac ggc atg gac ctc

                                         Y   Y   G   V   D   V
Sheep  JH6                           at tac tac ggt gta gat gtc

                                         Y   Y   G   V   D   V
Bovine JH6                           at tac tac ggt gta gat gtc

                                         Y   Y   G   M   D   Y
Dog    JH3                           at tac tat ggt atg gac tac

                             Y   Y   Y   Y   Y   G   M   D   V
Human  JH6*02            at tac tac tac tac tac ggt atg gac gtc
```

FIGURE 9

| | T | | | C | | | A | | | G | | |
|---|---|---|---|---|---|---|---|---|---|---|---|---|
| T | TTT | Phe | F | TCT | Ser | S | TAT | Tyr | Y | TGT | Cys | C |
| | TTC | Phe | F | TCC | Ser | S | TAC | Tyr | Y | TGC | Cys | C |
| | TTA | Leu | L | TCA | Ser | S | TAA | stop | * | TGA | stop | * |
| | TTG | Leu | L | TCG | Ser | S | TAG | stop | * | TGG | Trp | W |
| C | CTT | Leu | L | CCT | Pro | P | CAT | His | H | CGT | Arg | R |
| | CTC | Leu | L | CCC | Pro | P | CAC | His | H | CGC | Arg | R |
| | CTA | Leu | L | CCA | Pro | P | CAA | Gln | Q | CGA | Arg | R |
| | CTG | Leu | L | CCG | Pro | P | CAG | Gln | Q | CGG | Arg | R |
| A | ATT | Ile | I | ACT | Thr | T | AAT | Asn | N | AGT | Ser | S |
| | ATC | Ile | I | ACC | Thr | T | AAC | Asn | N | AGC | Ser | S |
| | ATA | Ile | I | ACA | Thr | T | AAA | Lys | K | AGA | Arg | R |
| | ATG | Met | M | ACG | Thr | T | AAG | Lys | K | AGG | Arg | R |
| G | GTT | Val | V | GCT | Ala | A | GAT | Asp | D | GGT | Gly | G |
| | GTC | Val | V | GCC | Ala | A | GAC | Asp | D | GGC | Gly | G |
| | GTA | Val | V | GCA | Ala | A | GAA | Glu | E | GGA | Gly | G |
| | GTG | Val | V | GCG | Ala | A | GAG | Glu | E | GGG | Gly | G |

SEQUENCE LISTING

```
<160> NUMBER OF SEQ ID NOS: 481

<210> SEQ ID NO 1
<211> LENGTH: 49
<212> TYPE: DNA
<213> ORGANISM: homo sapiens;
```

<400> SEQUENCE: 1
ttgaccaagc tggggacccc ggtcccttgg gaccagtggc agaggagtc 49

<210> SEQ ID NO 2
<211> LENGTH: 61
<212> TYPE: DNA
<213> ORGANISM: homo sapiens;

<400> SEQUENCE: 2
atgatgatga tgatgatgta cctgcagacc ccgtttccct ggtgccagtg gcagaggagt 60
c 61

<210> SEQ ID NO 3
<211> LENGTH: 52
<212> TYPE: DNA
<213> ORGANISM: homo sapiens;

<400> SEQUENCE: 3
atgaccatga agctagagac cccggcaccg tgggaccagt gacagaggag tc 52

<210> SEQ ID NO 4
<211> LENGTH: 61
<212> TYPE: DNA
<213> ORGANISM: homo sapiens;

<400> SEQUENCE: 4
atgatgatga tgatgccata cctgcagacc ccggttccct ggtgccagtg gcagaggagt 60
c 61

<210> SEQ ID NO 5
<211> LENGTH: 49
<212> TYPE: DNA
<213> ORGANISM: homo sapiens;

<400> SEQUENCE: 5
aactggttcg acccctgggg ccagggaacc ctggtcaccg tctcctcag 49

<210> SEQ ID NO 6
<211> LENGTH: 16
<212> TYPE: PRT
<213> ORGANISM: homo sapiens;

<400> SEQUENCE: 6

Asn Trp Phe Asp Pro Trp Gly Gln Gly Thr Leu Val Thr Val Ser Ser
1 5 10 15

<210> SEQ ID NO 7
<211> LENGTH: 61
<212> TYPE: DNA
<213> ORGANISM: homo sapiens;

<400> SEQUENCE: 7
tactactact actactacat ggacgtctgg ggcaaaggga ccacggtcac cgtctcctca 60
g 61

<210> SEQ ID NO 8
<211> LENGTH: 20
<212> TYPE: PRT
<213> ORGANISM: homo sapiens;

<400> SEQUENCE: 8

-continued

```
Tyr Tyr Tyr Tyr Tyr Tyr Met Asp Val Trp Gly Lys Gly Thr Thr Val
1               5                   10                  15

Thr Val Ser Ser
            20


<210> SEQ ID NO 9
<211> LENGTH: 52
<212> TYPE: DNA
<213> ORGANISM: homo sapiens;

<400> SEQUENCE: 9

tactggtact tcgatctctg gggccgtggc accctggtca ctgtctcctc ag             52


<210> SEQ ID NO 10
<211> LENGTH: 17
<212> TYPE: PRT
<213> ORGANISM: homo sapiens;

<400> SEQUENCE: 10

Tyr Trp Tyr Phe Asp Leu Trp Gly Arg Gly Thr Leu Val Thr Val Ser
1               5                   10                  15

Ser


<210> SEQ ID NO 11
<211> LENGTH: 296
<212> TYPE: DNA
<213> ORGANISM: homo sapiens;

<400> SEQUENCE: 11

caggtgcagc tggtgcagtc tggggctgag gtgaagaagc ctggggcctc agtgaaggtc     60

tcctgcaagg cttctggata caccttcacc ggctactata tgcactgggt gcgacaggcc    120

cctggacaag ggcttgagtg gatgggacgg atcaacccta acagtggtgg cacaaactat    180

gcacagaagt ttcagggcag ggtcaccagt accagggaca cgtccatcag cacagcctac    240

atggagctga gcaggctgag atctgacgac acggtcgtgt attactgtgc gagaga        296


<210> SEQ ID NO 12
<211> LENGTH: 296
<212> TYPE: DNA
<213> ORGANISM: homo sapiens;

<400> SEQUENCE: 12

caggtccagc ttgtgcagtc tggggctgag gtgaagaagc ctggggcctc agtgaaggtt     60

tcctgcaagg cttctggata caccttcact agctatgcta tgcattgggt gcgccaggcc    120

cccggacaaa ggcttgagtg gatgggatgg atcaacgctg gcaatggtaa cacaaaatat    180

tcacagaagt tccagggcag agtcaccatt accagggaca catccgcgag cacagcctac    240

atggagctga gcagcctgag atctgaagac acggctgtgt attactgtgc gagaga        296


<210> SEQ ID NO 13
<211> LENGTH: 296
<212> TYPE: DNA
<213> ORGANISM: homo sapiens;

<400> SEQUENCE: 13

caggtgcagc tggtgcagtc tggggctgag gtgaagaagc ctggggcctc agtgaaggtc     60

tcctgcaagg cttctggata caccttcacc agttatgata tcaactgggt gcgacaggcc    120

actggacaag ggcttgagtg gatgggatgg atgaacccta acagtggtaa cacaggctat    180
```

```
gcacagaagt tccagggcag agtcaccatg accaggaaca cctccataag cacagcctac    240

atggagctga gcagcctgag atctgaggac acggccgtgt attactgtgc gagagg       296


<210> SEQ ID NO 14
<211> LENGTH: 296
<212> TYPE: DNA
<213> ORGANISM: homo sapiens;

<400> SEQUENCE: 14

caggtccagc tggtacagtc tggggctgag gtgaagaagc ctggggcctc agtgaaggtc     60

tcctgcaagg tttccggata caccctcact gaattatcca tgcactgggt gcgacaggct    120

cctggaaaag ggcttgagtg gatgggaggt tttgatcctg aagatggtga aacaatctac    180

gcacagaagt tccagggcag agtcaccatg accgaggaca catctacaga cacagcctac    240

atggagctga gcagcctgag atctgaggac acggccgtgt attactgtgc aacaga       296


<210> SEQ ID NO 15
<211> LENGTH: 296
<212> TYPE: DNA
<213> ORGANISM: homo sapiens;
<220> FEATURE:
<221> NAME/KEY: misc_feature
<222> LOCATION: (295)..(295)
<223> OTHER INFORMATION: n is a, c, g, or t

<400> SEQUENCE: 15

cagatgcagc tggtgcagtc tggggctgag gtgaagaaga ctgggtcctc agtgaaggtt     60

tcctgcaagg cttccggata caccttcacc taccgctacc tgcactgggt gcgacaggcc    120

cccggacaag cgcttgagtg gatgggatgg atcacacctt tcaatggtaa caccaactac    180

gcacagaaat tccaggacag agtcaccatt actagggaca ggtctatgag cacagcctac    240

atggagctga gcagcctgag atctgaggac acagccatgt attactgtgc aagana       296


<210> SEQ ID NO 16
<211> LENGTH: 296
<212> TYPE: DNA
<213> ORGANISM: homo sapiens;

<400> SEQUENCE: 16

caggtgcagc tggtgcagtc tggggctgag gtgaagaagc ctggggcctc agtgaaggtt     60

tcctgcaagg catctggata caccttcacc agctactata tgcactgggt gcgacaggcc    120

cctggacaag ggcttgagtg gatgggaata atcaacccta gtggtggtag cacaagctac    180

gcacagaagt tccagggcag agtcaccatg accagggaca cgtccacgag cacagtctac    240

atggagctga gcagcctgag atctgaggac acggccgtgt attactgtgc gagaga       296


<210> SEQ ID NO 17
<211> LENGTH: 296
<212> TYPE: DNA
<213> ORGANISM: homo sapiens;

<400> SEQUENCE: 17

caaatgcagc tggtgcagtc tgggcctgag gtgaagaagc ctgggacctc agtgaaggtc     60

tcctgcaagg cttctggatt cacctttact agctctgctg tgcagtgggt gcgacaggct    120

cgtggacaac gccttgagtg gataggatgg atcgtcgttg gcagtggtaa cacaaactac    180

gcacagaagt tccaggaaag agtcaccatt accagggaca tgtccacaag cacagcctac    240

atggagctga gcagcctgag atccgaggac acggccgtgt attactgtgc ggcaga       296
```

<210> SEQ ID NO 18
<211> LENGTH: 296
<212> TYPE: DNA
<213> ORGANISM: homo sapiens;

<400> SEQUENCE: 18
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 19
<211> LENGTH: 294
<212> TYPE: DNA
<213> ORGANISM: homo sapiens;

<400> SEQUENCE: 19
caggtccagc tggtgcagtc ttgggctgag gtgaggaagt ctggggcctc agtgaaagtc 60
tcctgtagtt tttctgggtt taccatcacc agctacggta tacattgggt gcaacagtcc 120
cctggacaag ggcttgagtg gatgggatgg atcaaccctg gcaatggtag cccaagctat 180
gccaagaagt ttcagggcag attcaccatg accagggaca tgtccacaac cacagcctac 240
acagacctga gcagcctgac atctgaggac atggctgtgt attactatgc aaga 294

<210> SEQ ID NO 20
<211> LENGTH: 294
<212> TYPE: DNA
<213> ORGANISM: homo sapiens;

<400> SEQUENCE: 20
gaggtccagc tggtacagtc tggggctgag gtgaagaagc ctggggctac agtgaaaatc 60
tcctgcaagg tttctggata caccttcacc gactactaca tgcactgggt gcaacaggcc 120
cctggaaaag ggcttgagtg gatgggactt gttgatcctg aagatggtga aacaatatac 180
gcagagaagt tccagggcag agtcaccata accgcggaca cgtctacaga cacagcctac 240
atggagctga gcagcctgag atctgaggac acggccgtgt attactgtgc aaca 294

<210> SEQ ID NO 21
<211> LENGTH: 302
<212> TYPE: DNA
<213> ORGANISM: homo sapiens;

<400> SEQUENCE: 21
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaatga tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacaga 300
cc 302

<210> SEQ ID NO 22
<211> LENGTH: 301
<212> TYPE: DNA

<213> ORGANISM: homo sapiens;

<400> SEQUENCE: 22
caggtcacct tgaaggagtc tggtcctgtg ctggtgaaac ccacagagac cctcacgctg 60
acctgcaccg tctctgggtt ctcactcagc aatgctagaa tgggtgtgag ctggatccgt 120
cagcccccag ggaaggccct ggagtggctt gcacacattt tttcgaatga cgaaaaatcc 180
tacagcacat ctctgaagag caggctcacc atctccaagg acacctccaa aagccaggtg 240
gtccttacca tgaccaacat ggaccctgtg gacacagcca catattactg tgcacggata 300
c 301

<210> SEQ ID NO 23
<211> LENGTH: 301
<212> TYPE: DNA
<213> ORGANISM: homo sapiens;

<400> SEQUENCE: 23
caggtcacct tgagggagtc tggtcctgcg ctggtgaaac ccacacagac cctcacactg 60
acctgcacct tctctgggtt ctcactcagc actagtggaa tgtgtgtgag ctggatccgt 120
cagcccccag ggaaggccct ggagtggctt gcactcattg attgggatga tgataaatac 180
tacagcacat ctctgaagac caggctcacc atctccaagg acacctccaa aaaccaggtg 240
gtccttacaa tgaccaacat ggaccctgtg gacacagcca cgtattactg tgcacggata 300
c 301

<210> SEQ ID NO 24
<211> LENGTH: 296
<212> TYPE: DNA
<213> ORGANISM: homo sapiens;

<400> SEQUENCE: 24
gaggtgcagc tggtggagtc tgggggaggc ttggtccagc ctggggggtc cctgagactc 60
tcctgtgcag cctctggatt cacctttagt agctattgga tgagctgggt ccgccaggct 120
ccagggaagg ggctggagtg ggtggccaac ataaagcaag atggaagtga gaaatactat 180
gtggactctg tgaagggccg attcaccatc tccagagaca acgccaagaa ctcactgtat 240
ctgcaaatga acagcctgag agccgaggac acggctgtgt attactgtgc gagaga 296

<210> SEQ ID NO 25
<211> LENGTH: 298
<212> TYPE: DNA
<213> ORGANISM: homo sapiens;

<400> SEQUENCE: 25
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attagttgga atagtggtag cataggctat 180
gcggactctg tgaagggccg attcaccatc tccagagaca acgccaagaa ctccctgtat 240
ctgcaaatga acagtctgag agctgaggac acggccttgt attactgtgc aaaagata 298

<210> SEQ ID NO 26
<211> LENGTH: 296
<212> TYPE: DNA
<213> ORGANISM: homo sapiens;

<400> SEQUENCE: 26

```
caggtgcagc tggtggagtc tgggggaggc ttggtcaagc ctggagggtc cctgagactc     60

tcctgtgcag cctctggatt caccttcagt gactactaca tgagctggat ccgccaggct    120

ccagggaagg ggctggagtg ggtttcatac attagtagta gtggtagtac catatactac    180

gcagactctg tgaagggccg attcaccatc tccagggaca acgccaagaa ctcactgtat    240

ctgcaaatga acagcctgag agccgaggac acggccgtgt attactgtgc gagaga        296
```

<210> SEQ ID NO 27
<211> LENGTH: 293
<212> TYPE: DNA
<213> ORGANISM: homo sapiens;

<400> SEQUENCE: 27

```
gaggtgcagc tggtggagtc tgggggaggc ttggtacagc ctggggggtc cctgagactc     60

tcctgtgcag cctctggatt caccttcagt agctacgaca tgcactgggt ccgccaagct    120

acaggaaaag gtctggagtg ggtctcagct attggtactg ctggtgacac atactatcca    180

ggctccgtga agggccgatt caccatctcc agagaaaatg ccaagaactc cttgtatctt    240

caaatgaaca gcctgagagc cggggacacg gctgtgtatt actgtgcaag aga           293
```

<210> SEQ ID NO 28
<211> LENGTH: 302
<212> TYPE: DNA
<213> ORGANISM: homo sapiens;

<400> SEQUENCE: 28

```
gaggtgcagc tggtggagtc tgggggaggc ttggtaaagc ctggggggtc ccttagactc     60

tcctgtgcag cctctggatt cactttcagt aacgcctgga tgagctgggt ccgccaggct    120

ccagggaagg ggctggagtg ggttggccgt attaaaagca aaactgatgg tgggacaaca    180

gactacgctg cacccgtgaa aggcagattc accatctcaa gagatgattc aaaaaacacg    240

ctgtatctgc aaatgaacag cctgaaaacc gaggacacag ccgtgtatta ctgtaccaca    300

ga                                                                   302
```

<210> SEQ ID NO 29
<211> LENGTH: 296
<212> TYPE: DNA
<213> ORGANISM: homo sapiens;

<400> SEQUENCE: 29

```
gaggtacaac tggtggagtc tgggggaggc ttggtacagc ctggggggtc cctgagactc     60

tcctgtgcag cctctggatt caccttcagt aacagtgaca tgaactgggc ccgcaaggct    120

ccaggaaagg ggctggagtg ggtatcgggt gttagttgga atggcagtag gacgcactat    180

gtggactccg tgaagcgccg attcatcatc tccagagaca attccaggaa ctccctgtat    240

ctgcaaaaga acagacggag agccgaggac atggctgtgt attactgtgt gagaaa        296
```

<210> SEQ ID NO 30
<211> LENGTH: 296
<212> TYPE: DNA
<213> ORGANISM: homo sapiens;

<400> SEQUENCE: 30

```
acagtgcagc tggtggagtc tgggggaggc ttggtagagc ctggggggtc cctgagactc     60

tcctgtgcag cctctggatt caccttcagt aacagtgaca tgaactgggt ccgccaggct    120
```

ccaggaaagg ggctggagtg ggtatcgggt gttagttgga atggcagtag gacgcactat 180
gcagactctg tgaagggccg attcatcatc tccagagaca attccaggaa cttcctgtat 240
cagcaaatga acagcctgag gcccgaggac atggctgtgt attactgtgt gagaaa 296

<210> SEQ ID NO 31
<211> LENGTH: 296
<212> TYPE: DNA
<213> ORGANISM: homo sapiens;

<400> SEQUENCE: 31
gaggtgcagc tggtggagtc tgggggaggt gtggtacggc ctgggggggtc cctgagactc 60 tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttgt atcactgtgc gagaga 296

<210> SEQ ID NO 32
<211> LENGTH: 296
<212> TYPE: DNA
<213> ORGANISM: homo sapiens;

<400> SEQUENCE: 32
gaggtgcagc tggtggagtc tgggggaggc ctggtcaagc ctgggggggtc cctgagactc 60 tcctgtgcag cctctggatt caccttcagt agctatagca tgaactgggt ccgccaggct 120
ccagggaagg ggctggagtg ggtctcatcc attagtagta gtagtagtta catatactac 180
gcagactcag tgaagggccg attcaccatc tccagagaca acgccaagaa ctcactgtat 240
ctgcaaatga acagcctgag agccgaggac acggctgtgt attactgtgc gagaga 296

<210> SEQ ID NO 33
<211> LENGTH: 296
<212> TYPE: DNA
<213> ORGANISM: homo sapiens;

<400> SEQUENCE: 33
gaggtgcagc tgttggagtc tgggggaggc ttggtacagc ctgggggggtc cctgagactc 60 tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaaga 296

<210> SEQ ID NO 34
<211> LENGTH: 296
<212> TYPE: DNA
<213> ORGANISM: homo sapiens;

<400> SEQUENCE: 34
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 35
<211> LENGTH: 294
<212> TYPE: DNA
<213> ORGANISM: homo sapiens;

<400> SEQUENCE: 35
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gaga 294

<210> SEQ ID NO 36
<211> LENGTH: 296
<212> TYPE: DNA
<213> ORGANISM: homo sapiens;

<400> SEQUENCE: 36
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatactat 180
gcagactccg tgaagggccg attcaccatc tccagagaca attccaagaa cacgctgtat 240
ctgcaaatga acagcctgag agccgaggac acggctgtgt attactgtgc gagaga 296

<210> SEQ ID NO 37
<211> LENGTH: 296
<212> TYPE: DNA
<213> ORGANISM: homo sapiens;

<400> SEQUENCE: 37
gaggtgcagc tggtggagtc tgggggaggc ttggtacagc ctgggggatc cctgagactc 60
tcctgtgcag cctctggatt caccttcagt aacagtgaca tgaactgggt ccatcaggct 120
ccaggaaagg ggctggagtg ggtatcgggt gttagttgga atggcagtag gacgcactat 180
gcagactctg tgaagggccg attcatcatc tccagagaca attccaggaa caccctgtat 240
ctgcaaacga atagcctgag ggccgaggac acggctgtgt attactgtgt gagaaa 296

<210> SEQ ID NO 38
<211> LENGTH: 292
<212> TYPE: DNA
<213> ORGANISM: homo sapiens;

<400> SEQUENCE: 38
gaggtgcagc tggtggagtc tgggggaggc ttggtacagc ctagggggtc cctgagactc 60
tcctgtgcag cctctggatt caccgtcagt agcaatgaga tgagctggat ccgccaggct 120
ccagggaagg ggctggagtg ggtctcatcc attagtggtg gtagcacata ctacgcagac 180
tccaggaagg gcagattcac catctccaga gacaattcca agaacacgct gtatcttcaa 240
atgaacaacc tgagagctga gggcacggcc gcgtattact gtgccagata ta 292

<210> SEQ ID NO 39
<211> LENGTH: 298
<212> TYPE: DNA
<213> ORGANISM: homo sapiens;

<400> SEQUENCE: 39
gaagtgcagc tggtggagtc tgggggagtc gtggtacagc ctgggggtc cctgagactc 60 tcctgtgcag cctctggatt cacctttgat gattatacca tgcactgggt ccgtcaagct 120
ccggggaagg gtctggagtg ggtctctctt attagttggg atggtggtag cacatactat 180
gcagactctg tgaagggccg attcaccatc tccagagaca acagcaaaaa ctccctgtat 240
ctgcaaatga acagtctgag aactgaggac accgccttgt attactgtgc aaaagata 298

<210> SEQ ID NO 40
<211> LENGTH: 291
<212> TYPE: DNA
<213> ORGANISM: homo sapiens;

<400> SEQUENCE: 40
gaggatcagc tggtggagtc tgggggaggc ttggtacagc ctgggggtc cctgcgaccc 60 tcctgtgcag cctctggatt cgccttcagt agctatgctc tgcactgggt tcgccgggct 120
ccagggaagg gtctggagtg ggtatcagct attggtactg gtggtgatac atactatgca 180
gactccgtga tgggccgatt caccatctcc agagacaacg ccaagaagtc cttgtatctt 240
catatgaaca gcctgatagc tgaggacatg gctgtgtatt attgtgcaag a 291

<210> SEQ ID NO 41
<211> LENGTH: 296
<212> TYPE: DNA
<213> ORGANISM: homo sapiens;

<400> SEQUENCE: 41
gaggtgcagc tggtggagtc tgggggaggc ttggtacagc ctgggggtc cctgagactc 60 tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagagaca atgccaagaa ctcactgtat 240
ctgcaaatga acagcctgag agccgaggac acggctgtgt attactgtgc gagaga 296

<210> SEQ ID NO 42
<211> LENGTH: 302
<212> TYPE: DNA
<213> ORGANISM: homo sapiens;

<400> SEQUENCE: 42
gaggtgcagc tggtggagtc tgggggaggc ttggtacagc cagggcggtc cctgagactc 60
tcctgtacag cttctggatt cacctttggt gattatgcta tgagctggtt ccgccaggct 120
ccagggaagg ggctggagtg ggtaggtttc attagaagca aagcttatgg tgggacaaca 180
gaatacaccg cgtctgtgaa aggcagattc accatctcaa gagatggttc caaaagcatc 240
gcctatctgc aaatgaacag cctgaaaacc gaggacacag ccgtgtatta ctgtactaga 300
ga 302

<210> SEQ ID NO 43
<211> LENGTH: 293
<212> TYPE: DNA
<213> ORGANISM: homo sapiens;

<400> SEQUENCE: 43
gaggtgcagc tggtggagtc tggaggaggc ttgatccagc ctgggggtc cctgagactc 60 tcctgtgcag cctctgggtt caccgtcagt agcaactaca tgagctgggt ccgccaggct 120
ccagggaagg ggctggagtg ggtctcagtt atttatagcg gtggtagcac atactacgca 180
gactccgtga agggccgatt caccatctcc agagacaatt ccaagaacac gctgtatctt 240
caaatgaaca gcctgagagc cgaggacacg gccgtgtatt actgtgcgag aga 293

<210> SEQ ID NO 44
<211> LENGTH: 296
<212> TYPE: DNA
<213> ORGANISM: homo sapiens;

<400> SEQUENCE: 44
gaggtgcagc tggtggagtc tgggggaggc ttggtccagc ctgggggggtc cctgagactc 60 tcctgtgcag cctctggatt caccttcagt agctatgcta tgcactgggt ccgccaggct 120
ccagggaagg gactggaata tgtttcagct attagtagta atgggggtag cacatattat 180
gcaaactctg tgaagggcag attcaccatc tccagagaca attccaagaa cacgctgtat 240
cttcaaatgg gcagcctgag agctgaggac atggctgtgt attactgtgc gagaga 296

<210> SEQ ID NO 45
<211> LENGTH: 293
<212> TYPE: DNA
<213> ORGANISM: homo sapiens;

<400> SEQUENCE: 45
gaggtgcagc tggtggagtc tgggggaggc ttggtccagc ctgggggggtc cctgagactc 60 tcctgtgcag cctctggatt caccgtcagt agcaactaca tgagctgggt ccgccaggct 120
ccagggaagg ggctggagtg ggtctcagtt atttatagcg gtggtagcac atactacgca 180
gactccgtga agggcagatt caccatctcc agagacaatt ccaagaacac gctgtatctt 240
caaatgaaca gcctgagagc cgaggacacg gctgtgtatt actgtgcgag aga 293

<210> SEQ ID NO 46
<211> LENGTH: 302
<212> TYPE: DNA
<213> ORGANISM: homo sapiens;

<400> SEQUENCE: 46
gaggtgcagc tggtggagtc tgggggaggc ttggtccagc ctggagggtc cctgagactc 60
tcctgtgcag cctctggatt caccttcagt gaccactaca tggactgggt ccgccaggct 120
ccagggaagg ggctggagtg ggttggccgt actagaaaca aagctaacag ttacaccaca 180
gaatacgccg cgtctgtgaa aggcagattc accatctcaa gagatgattc aaagaactca 240
ctgtatctgc aaatgaacag cctgaaaacc gaggacacgg ccgtgtatta ctgtgctaga 300
ga 302

<210> SEQ ID NO 47
<211> LENGTH: 302
<212> TYPE: DNA
<213> ORGANISM: homo sapiens;

<400> SEQUENCE: 47
gaggtgcagc tggtggagtc tgggggaggc ttggtccagc ctgggggggtc cctgaaactc 60 tcctgtgcag cctctgggtt caccttcagt ggctctgcta tgcactgggt ccgccaggct 120
tccgggaaag ggctggagtg ggttggccgt attagaagca aagctaacag ttacgcgaca 180
gcatatgctg cgtcggtgaa aggcaggttc accatctcca gagatgattc aaagaacacg 240
gcgtatctgc aaatgaacag cctgaaaacc gaggacacgg ccgtgtatta ctgtactaga 300

-continued

```
ca                                                                 302


<210> SEQ ID NO 48
<211> LENGTH: 296
<212> TYPE: DNA
<213> ORGANISM: homo sapiens;

<400> SEQUENCE: 48

gaggtgcagc tggtggagtc cgggggaggc ttagttcagc ctggggggtc cctgagactc   60

tcctgtgcag cctctggatt caccttcagt agctactgga tgcactgggt ccgccaagct  120

ccagggaagg ggctggtgtg ggtctcacgt attaatagtg atgggagtag cacaagctac  180

gcggactccg tgaagggccg attcaccatc tccagagaca acgccaagaa cacgctgtat  240

ctgcaaatga acagtctgag agccgaggac acggctgtgt attactgtgc aagaga       296


<210> SEQ ID NO 49
<211> LENGTH: 288
<212> TYPE: DNA
<213> ORGANISM: homo sapiens;

<400> SEQUENCE: 49

gaggtgcagc tggtggagtc tcggggagtc ttggtacagc ctggggggtc cctgagactc   60

tcctgtgcag cctctggatt caccgtcagt agcaatgaga tgagctgggt ccgccaggct  120

ccagggaagg gtctggagtg ggtctcatcc attagtggtg gtagcacata ctacgcagac  180

tccaggaagg gcagattcac catctccaga gacaattcca agaacacgct gcatcttcaa  240

atgaacagcc tgagagctga ggacacggct gtgtattact gtaagaaa               288


<210> SEQ ID NO 50
<211> LENGTH: 293
<212> TYPE: DNA
<213> ORGANISM: homo sapiens;

<400> SEQUENCE: 50

gaggtgcagc tggtggagtc tgggggaggc ttggtaaagc ctggggggtc cctgagactc   60

tcctgtgcag cctctggatt caccttcagt gactactaca tgaactgggt ccgccaggct  120

ccagggaagg ggctggagtg ggtctcatcc attagtagta gtagtaccat atactacgca  180

gactctgtga agggccgatt caccatctcc agagacaacg ccaagaactc actgtatctg  240

caaatgaaca gcctgagagc cgaggacacg gctgtgtatt actgtgcgag aga          293


<210> SEQ ID NO 51
<211> LENGTH: 296
<212> TYPE: DNA
<213> ORGANISM: homo sapiens;

<400> SEQUENCE: 51

caggtgcagc tgcaggagtc gggcccagga ctggtgaagc ctccggggac cctgtccctc   60

acctgcgctg tctctggtgg ctccatcagc agtagtaact ggtggagttg ggtccgccag  120

cccccaggga aggggctgga gtggattggg gaaatctatc atagtgggag caccaactac  180

aacccgtccc tcaagagtcg agtcaccata tcagtagaca agtccaagaa ccagttctcc  240

ctgaagctga gctctgtgac cgccgcggac acggccgtgt attgctgtgc gagaga       296


<210> SEQ ID NO 52
<211> LENGTH: 296
<212> TYPE: DNA
<213> ORGANISM: homo sapiens;
```

<400> SEQUENCE: 52
caggtgcagc tgcaggagtc gggcccagga ctggtgaagc cttcggacac cctgtccctc 60
acctgcgctg tctctggtta ctccatcagc agtagtaact ggtggggctg gatccggcag 120
cccccaggga agggactgga gtggattggg tacatctatt atagtgggag cacctactac 180
aacccgtccc tcaagagtcg agtcaccatg tcagtagaca cgtccaagaa ccagttctcc 240
ctgaagctga gctctgtgac cgccgtggac acggccgtgt attactgtgc gagaaa 296

<210> SEQ ID NO 53
<211> LENGTH: 299
<212> TYPE: DNA
<213> ORGANISM: homo sapiens;

<400> SEQUENCE: 53
cagctgcagc tgcaggagtc cggctcagga ctggtgaagc cttcacagac cctgtccctc 60
acctgcgctg tctctggtgg ctccatcagc agtggtggtt actcctggag ctggatccgg 120
cagccaccag ggaagggcct ggagtggatt gggtacatct atcatagtgg gagcacctac 180
tacaacccgt ccctcaagag tcgagtcacc atatcagtag acaggtccaa gaaccagttc 240
tccctgaagc tgagctctgt gaccgccgcg gacacggccg tgtattactg tgccagaga 299

<210> SEQ ID NO 54
<211> LENGTH: 299
<212> TYPE: DNA
<213> ORGANISM: homo sapiens;

<400> SEQUENCE: 54
caggtgcagc tgcaggagtc gggcccagga ctggtgaagc cttcacagac cctgtccctc 60
acctgcactg tctctggtgg ctccatcagc agtggtgatt actactggag ttggatccgc 120
cagcccccag ggaagggcct ggagtggatt gggtacatct attacagtgg gagcacctac 180
tacaacccgt ccctcaagag tcgagttacc atatcagtag acacgtccaa gaaccagttc 240
tccctgaagc tgagctctgt gactgccgca gacacggccg tgtattactg tgccagaga 299

<210> SEQ ID NO 55
<211> LENGTH: 299
<212> TYPE: DNA
<213> ORGANISM: homo sapiens;

<400> SEQUENCE: 55
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tctagttacc atatcagtag acacgtctaa gaaccagttc 240
tccctgaagc tgagctctgt gactgccgcg gacacggccg tgtattactg tgcgagaga 299

<210> SEQ ID NO 56
<211> LENGTH: 293
<212> TYPE: DNA
<213> ORGANISM: homo sapiens;

<400> SEQUENCE: 56
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag agg 293

<210> SEQ ID NO 57
<211> LENGTH: 299
<212> TYPE: DNA
<213> ORGANISM: homo sapiens;

<400> SEQUENCE: 57
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccagttc 240
tccctgaagc tgagctctgt gaccgccgca gacacggctg tgtattactg tgcgagaca 299

<210> SEQ ID NO 58
<211> LENGTH: 296
<212> TYPE: DNA
<213> ORGANISM: homo sapiens;

<400> SEQUENCE: 58
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tccgtagaca cgtccaagaa ccagttctac 240
ctgaagctga gctctgtgac cgccgcggac acggccgtgt attactgtgc gagata 296

<210> SEQ ID NO 59
<211> LENGTH: 293
<212> TYPE: DNA
<213> ORGANISM: homo sapiens;

<400> SEQUENCE: 59
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag aga 293

<210> SEQ ID NO 60
<211> LENGTH: 299
<212> TYPE: DNA
<213> ORGANISM: homo sapiens;

<400> SEQUENCE: 60
caggtgcagc tgcaggagtc gggcccagga ctggtgaagc cttcggagac cctgtccctc 60
acctgcactg tctctggtgg ctccgtcagc agtggtagtt actactggag ctggatccgg 120
cagcccccag ggaagggact ggagtggatt gggtatatct attacagtgg gagcaccaac 180
tacaacccct ccctcaagag tcgagtcacc atatcagtag acacgtccaa gaaccagttc 240
tccctgaagc tgagctctgt gaccgctgcg gacacggccg tgtattactg tgcgagaga 299

<210> SEQ ID NO 61
<211> LENGTH: 294
<212> TYPE: DNA
<213> ORGANISM: homo sapiens;

<400> SEQUENCE: 61
caggtgcagc tgcaggagtc gggcccagga ctggtgaagc cttcggagac cctgtccctc 60
acctgcgctg tctctggtta ctccatcagc agtggttact actggggctg gatccggcag 120
cccccaggga aggggctgga gtggattggg agtatctatc atagtgggag cacctactac 180
aacccgtccc tcaagagtcg agtcaccata tcagtagaca cgtccaagaa ccagttctcc 240
ctgaagctga gctctgtgac cgccgcagac acggccgtgt attactgtgc gaga 294

<210> SEQ ID NO 62
<211> LENGTH: 296
<212> TYPE: DNA
<213> ORGANISM: homo sapiens;

<400> SEQUENCE: 62
gaggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gagaca 296

<210> SEQ ID NO 63
<211> LENGTH: 294
<212> TYPE: DNA
<213> ORGANISM: homo sapiens;

<400> SEQUENCE: 63
gaagtgcagc tggtgcagtc tggagcagag gtgaaaaagc ccggggagtc tctgaggatc 60
tcctgtaagg gttctggata cagctttacc agctactgga tcagctgggt gcgccagatg 120
cccgggaaag gcctggagtg gatggggagg attgatccta gtgactctta taccaactac 180
agcccgtcct tccaaggcca cgtcaccatc tcagctgaca agtccatcag cactgcctac 240
ctgcagtgga gcagcctgaa ggcctcggac accgccatgt attactgtgc gaga 294

<210> SEQ ID NO 64
<211> LENGTH: 305
<212> TYPE: DNA
<213> ORGANISM: homo sapiens;

<400> SEQUENCE: 64
caggtacagc tgcagcagtc aggtccagga ctggtgaagc cctcgcagac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatctgt gaaaagtcga ataaccatca acccagacac atccaagaac 240
cagttctccc tgcagctgaa ctctgtgact cccgaggaca cggctgtgta ttactgtgca 300
agaga 305

<210> SEQ ID NO 65
<211> LENGTH: 294
<212> TYPE: DNA
<213> ORGANISM: homo sapiens;

<400> SEQUENCE: 65
caggtgcagc tggtgcaatc tgggtctgag ttgaagaagc ctggggcctc agtgaaggtt 60
tcctgcaagg cttctggata caccttcact agctatgcta tgaattgggt gcgacaggcc 120
cctggacaag ggcttgagtg gatgggatgg atcaacacca acactgggaa cccaacgtat 180
gcccagggct tcacaggacg gtttgtcttc tccttggaca cctctgtcag cacggcatat 240
ctgcagatct gcagcctaaa ggctgaggac actgccgtgt attactgtgc gaga 294

<210> SEQ ID NO 66
<211> LENGTH: 296
<212> TYPE: DNA
<213> ORGANISM: homo sapiens;

<400> SEQUENCE: 66
caggtgcagc tggtgcagtc tggccatgag gtgaagcagc ctggggcctc agtgaaggtc 60
tcctgcaagg cttctggtta cagtttcacc acctatggta tgaattgggt gccacaggcc 120
cctggacaag ggcttgagtg gatgggatgg ttcaacacct acactgggaa cccaacatat 180
gcccagggct tcacaggacg gtttgtcttc tccatggaca cctctgccag cacagcatac 240
ctgcagatca gcagcctaaa ggctgaggac atggccatgt attactgtgc gagata 296

<210> SEQ ID NO 67
<211> LENGTH: 17
<212> TYPE: DNA
<213> ORGANISM: homo sapiens;

<400> SEQUENCE: 67
ggtacaactg gaacgac 17

<210> SEQ ID NO 68
<211> LENGTH: 17
<212> TYPE: DNA
<213> ORGANISM: homo sapiens;

<400> SEQUENCE: 68
ggtataactg gaactac 17

<210> SEQ ID NO 69
<211> LENGTH: 17
<212> TYPE: DNA
<213> ORGANISM: homo sapiens;

<400> SEQUENCE: 69
ggtataaccg gaaccac 17

<210> SEQ ID NO 70
<211> LENGTH: 17
<212> TYPE: DNA
<213> ORGANISM: homo sapiens;

<400> SEQUENCE: 70
ggtataactg gaacgac 17

<210> SEQ ID NO 71
<211> LENGTH: 20
<212> TYPE: DNA
<213> ORGANISM: homo sapiens;

<400> SEQUENCE: 71
ggtatagtgg gagctactac 20

```
<210> SEQ ID NO 72
<211> LENGTH: 31
<212> TYPE: DNA
<213> ORGANISM: homo sapiens;

<400> SEQUENCE: 72

aggatattgt agtagtacca gctgctatgc c                               31

<210> SEQ ID NO 73
<211> LENGTH: 31
<212> TYPE: DNA
<213> ORGANISM: homo sapiens;

<400> SEQUENCE: 73

aggatattgt actaatggtg tatgctatac c                               31

<210> SEQ ID NO 74
<211> LENGTH: 31
<212> TYPE: DNA
<213> ORGANISM: homo sapiens;

<400> SEQUENCE: 74

aggatattgt agtggtggta gctgctactc c                               31

<210> SEQ ID NO 75
<211> LENGTH: 28
<212> TYPE: DNA
<213> ORGANISM: homo sapiens;

<400> SEQUENCE: 75

agcatattgt ggtggtgatt gctattcc                                   28

<210> SEQ ID NO 76
<211> LENGTH: 31
<212> TYPE: DNA
<213> ORGANISM: homo sapiens;

<400> SEQUENCE: 76

gtattacgat ttttggagtg gttattatac c                               31

<210> SEQ ID NO 77
<211> LENGTH: 31
<212> TYPE: DNA
<213> ORGANISM: homo sapiens;

<400> SEQUENCE: 77

gtattacgat attttgactg gttattataa c                               31

<210> SEQ ID NO 78
<211> LENGTH: 31
<212> TYPE: DNA
<213> ORGANISM: homo sapiens;

<400> SEQUENCE: 78

gtattactat ggttcgggga gttattataa c                               31

<210> SEQ ID NO 79
<211> LENGTH: 37
<212> TYPE: DNA
<213> ORGANISM: homo sapiens;

<400> SEQUENCE: 79
```

gtattatgat tacgtttggg ggagttatgc ttatacc 37

<210> SEQ ID NO 80
<211> LENGTH: 31
<212> TYPE: DNA
<213> ORGANISM: homo sapiens;

<400> SEQUENCE: 80
gtattactat gatagtagtg gttattacta c 31

<210> SEQ ID NO 81
<211> LENGTH: 16
<212> TYPE: DNA
<213> ORGANISM: homo sapiens;

<400> SEQUENCE: 81
tgactacagt aactac 16

<210> SEQ ID NO 82
<211> LENGTH: 16
<212> TYPE: DNA
<213> ORGANISM: homo sapiens;

<400> SEQUENCE: 82
tgactacagt aactac 16

<210> SEQ ID NO 83
<211> LENGTH: 16
<212> TYPE: DNA
<213> ORGANISM: homo sapiens;

<400> SEQUENCE: 83
tgactacggt gactac 16

<210> SEQ ID NO 84
<211> LENGTH: 19
<212> TYPE: DNA
<213> ORGANISM: homo sapiens;

<400> SEQUENCE: 84
tgactacggt ggtaactcc 19

<210> SEQ ID NO 85
<211> LENGTH: 20
<212> TYPE: DNA
<213> ORGANISM: homo sapiens;

<400> SEQUENCE: 85
gtggatacag ctatggttac 20

<210> SEQ ID NO 86
<211> LENGTH: 23
<212> TYPE: DNA
<213> ORGANISM: homo sapiens;

<400> SEQUENCE: 86
gtggatatag tggctacgat tac 23

<210> SEQ ID NO 87
<211> LENGTH: 20
<212> TYPE: DNA
<213> ORGANISM: homo sapiens;

<400> SEQUENCE: 87
gtggatacag ctatggttac 20

<210> SEQ ID NO 88
<211> LENGTH: 20
<212> TYPE: DNA
<213> ORGANISM: homo sapiens;

<400> SEQUENCE: 88
gtagagatgg ctacaattac 20

<210> SEQ ID NO 89
<211> LENGTH: 18
<212> TYPE: DNA
<213> ORGANISM: homo sapiens;

<400> SEQUENCE: 89
gagtatagca gctcgtcc 18

<210> SEQ ID NO 90
<211> LENGTH: 21
<212> TYPE: DNA
<213> ORGANISM: homo sapiens;

<400> SEQUENCE: 90
gggtatagca gcagctggta c 21

<210> SEQ ID NO 91
<211> LENGTH: 21
<212> TYPE: DNA
<213> ORGANISM: homo sapiens;

<400> SEQUENCE: 91
gggtatagca gtggctggta c 21

<210> SEQ ID NO 92
<211> LENGTH: 18
<212> TYPE: DNA
<213> ORGANISM: homo sapiens;

<400> SEQUENCE: 92
gggtatagca gcggctac 18

<210> SEQ ID NO 93
<211> LENGTH: 11
<212> TYPE: DNA
<213> ORGANISM: homo sapiens;

<400> SEQUENCE: 93
ctaactgggg a 11

<210> SEQ ID NO 94
<211> LENGTH: 52
<212> TYPE: DNA
<213> ORGANISM: homo sapiens;

<400> SEQUENCE: 94
gctgaatact tccagcactg gggccagggc accctggtca ccgtctcctc ag 52

<210> SEQ ID NO 95
<211> LENGTH: 53
<212> TYPE: DNA
<213> ORGANISM: homo sapiens;

<400> SEQUENCE: 95
ctactggtac ttcgatctct ggggccgtgg caccctggtc actgtctcct cag 53

<210> SEQ ID NO 96
<211> LENGTH: 50
<212> TYPE: DNA
<213> ORGANISM: homo sapiens;

<400> SEQUENCE: 96
tgatgctttt gatgtctggg gccaagggac aatggtcacc gtctcttcag 50

<210> SEQ ID NO 97
<211> LENGTH: 48
<212> TYPE: DNA
<213> ORGANISM: homo sapiens;

<400> SEQUENCE: 97
actactttga ctactggggc caaggaaccc tggtcaccgt ctcctcag 48

<210> SEQ ID NO 98
<211> LENGTH: 51
<212> TYPE: DNA
<213> ORGANISM: homo sapiens;

<400> SEQUENCE: 98
acaactggtt cgactcctgg ggccaaggaa ccctggtcac cgtctcctca g 51

<210> SEQ ID NO 99
<211> LENGTH: 63
<212> TYPE: DNA
<213> ORGANISM: homo sapiens;

<400> SEQUENCE: 99
attactacta ctactacggt atggacgtct gggggcaagg gaccacggtc accgtctcct 60
cag 63

<210> SEQ ID NO 100
<211> LENGTH: 287
<212> TYPE: DNA
<213> ORGANISM: homo sapiens;

<400> SEQUENCE: 100
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctatgat gcctccagtt tggaaagtgg ggtcccatca 180
aggttcagcg gcagtggatc tgggacagaa ttcactctca ccatcagcag cctgcagcct 240
gatgattttg caacttatta ctgccaacag tataatagtt attctcc 287

<210> SEQ ID NO 101
<211> LENGTH: 287
<212> TYPE: DNA
<213> ORGANISM: homo sapiens;

<400> SEQUENCE: 101
gccatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagctcct gatctatgct gcatccagtt tacaaagtgg ggtcccatca 180
aggttcagcg gcagtggatc tggcacagat ttcactctca ccatcagcag cctgcagcct 240
gaagattttg caacttatta ctgtctacaa gattacaatt accctcc 287

<210> SEQ ID NO 102
<211> LENGTH: 287
<212> TYPE: DNA
<213> ORGANISM: homo sapiens;

<400> SEQUENCE: 102
gccatccgga tgacccagtc tccatcctca ttctctgcat ctacaggaga cagagtcacc 60
atcacttgtc gggcgagtca gggtattagc agttatttag cctggtatca gcaaaaacca 120
gggaaagccc ctaagctcct gatctatgct gcatccactt tgcaaagtgg ggtcccatca 180
aggttcagcg gcagtggatc tgggacagat ttcactctca ccatcagctg cctgcagtct 240
gaagattttg caacttatta ctgtcaacag tattatagtt accctcc 287

<210> SEQ ID NO 103
<211> LENGTH: 287
<212> TYPE: DNA
<213> ORGANISM: homo sapiens;

<400> SEQUENCE: 103
gtcatctgga tgacccagtc tccatcctta ctctctgcat ctacaggaga cagagtcacc 60
atcagttgtc ggatgagtca gggcattagc agttatttag cctggtatca gcaaaaacca 120
gggaaagccc ctgagctcct gatctatgct gcatccactt tgcaaagtgg ggtcccatca 180
aggttcagtg gcagtggatc tgggacagat ttcactctca ccatcagttg cctgcagtct 240
gaagattttg caacttatta ctgtcaacag tattatagtt tccctcc 287

<210> SEQ ID NO 104
<211> LENGTH: 287
<212> TYPE: DNA
<213> ORGANISM: homo sapiens;

<400> SEQUENCE: 104
gacatccagt tgacccagtc tccatccttc ctgtctgcat ctgtaggaga cagagtcacc 60
atcacttgcc gggccagtca gggcattagc agttatttag cctggtatca gcaaaaacca 120
gggaaagccc ctaagctcct gatctatgct gcatccactt tgcaaagtgg ggtcccatca 180
aggttcagcg gcagtggatc tgggacagaa ttcactctca caatcagcag cctgcagcct 240
gaagattttg caacttatta ctgtcaacag cttaatagtt accctcc 287

<210> SEQ ID NO 105
<211> LENGTH: 287
<212> TYPE: DNA
<213> ORGANISM: homo sapiens;

<400> SEQUENCE: 105
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacagtt tccctcc 287

<210> SEQ ID NO 106
<211> LENGTH: 287
<212> TYPE: DNA

<213> ORGANISM: homo sapiens;

<400> SEQUENCE: 106
gccatccagt tgacccagtc tccatcctcc ctgtctgcat ctgtaggaga cagagtcacc 60
atcacttgcc gggcaagtca gggcattagc agtgctttag cctgatatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaataatt accctca 287

<210> SEQ ID NO 107
<211> LENGTH: 287
<212> TYPE: DNA
<213> ORGANISM: homo sapiens;

<400> SEQUENCE: 107
gacatccaga tgacccagtc tccatcctca ctgtctgcat ctgtaggaga cagagtcacc 60
atcacttgtc gggcgagtca gggcattagc aattatttag cctggtttca gcagaaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctcc 287

<210> SEQ ID NO 108
<211> LENGTH: 287
<212> TYPE: DNA
<213> ORGANISM: homo sapiens;

<400> SEQUENCE: 108
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctcc 287

<210> SEQ ID NO 109
<211> LENGTH: 287
<212> TYPE: DNA
<213> ORGANISM: homo sapiens;

<400> SEQUENCE: 109
gacatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag cataatagtt accctcc 287

<210> SEQ ID NO 110
<211> LENGTH: 287
<212> TYPE: DNA
<213> ORGANISM: homo sapiens;

<400> SEQUENCE: 110
aacatccaga tgacccagtc tccatctgcc atgtctgcat ctgtaggaga cagagtcacc 60
atcacttgtc gggcgaggca gggcattagc aattatttag cctggtttca gcagaaacca 120
gggaaagtcc ctaagcacct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag cataatagtt accctcc 287

<210> SEQ ID NO 111
<211> LENGTH: 287
<212> TYPE: DNA
<213> ORGANISM: homo sapiens;

<400> SEQUENCE: 111
gacatccaga tgacccagtc tccatcctcc ctgtctgcat ctgtaggaga cagagtcacc 60
atcacttgcc gggcgagtca gggcattagc aattatttag cctggtatca gcagaaacca 120
gggaaagttc ctaagctcct gatctatgct gcatccactt tgcaatcagg ggtcccatct 180
cggttcagtg gcagtggatc tgggacagat ttcactctca ccatcagcag cctgcagcct 240
gaagatgttg caacttatta ctgtcaaaag tataacagtg cccctcc 287

<210> SEQ ID NO 112
<211> LENGTH: 287
<212> TYPE: DNA
<213> ORGANISM: homo sapiens;

<400> SEQUENCE: 112
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaatt tggaaacagg ggtcccatca 180
aggttcagtg gaagtggatc tgggacagat tttactttca ccatcagcag cctgcagcct 240
gaagatattg caacatatta ctgtcaacag tatgataatc tccctcc 287

<210> SEQ ID NO 113
<211> LENGTH: 287
<212> TYPE: DNA
<213> ORGANISM: homo sapiens;

<400> SEQUENCE: 113
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaatt tggaaacagg ggtcccatca 180
aggttcagtg gaagtggatc tgggacagat tttactttca ccatcagcag cctgcagcct 240
gaagatattg caacatatta ctgtcaacag tatgataatc tccctcc 287

<210> SEQ ID NO 114
<211> LENGTH: 287
<212> TYPE: DNA
<213> ORGANISM: homo sapiens;

<400> SEQUENCE: 114
gacatccagt tgacccagtc tccatcctcc ctgtctgcat ctgtaggaga cagagtcacc 60
atcacttgcc gggtgagtca gggcattagc agttatttaa attggtatcg gcagaaacca 120
gggaaagttc ctaagctcct gatctatagt gcatccaatt tgcaatctgg agtcccatct 180
cggttcagtg gcagtggatc tgggacagat ttcactctca ctatcagcag cctgcagcct 240
gaagatgttg caacttatta cggtcaacgg acttacaatg cccctcc 287

<210> SEQ ID NO 115
<211> LENGTH: 287
<212> TYPE: DNA
<213> ORGANISM: homo sapiens;

<400> SEQUENCE: 115
gacatccagt tgacccagtc tccatcctcc ctgtctgcat ctgtaggaga cagagtcacc 60
atcacttgcc gggtgagtca gggcattagc agttatttaa attggtatcg gcagaaacca 120
gggaaagttc ctaagctcct gatctatagt gcatccaatt tgcaatctgg agtcccatct 180
cggttcagtg gcagtggatc tgggacagat ttcactctca ctatcagcag cctgcagcct 240
gaagatgttg caacttatta cggtcaacgg acttacaatg cccctcc 287

<210> SEQ ID NO 116
<211> LENGTH: 287
<212> TYPE: DNA
<213> ORGANISM: homo sapiens;

<400> SEQUENCE: 116
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctcc 287

<210> SEQ ID NO 117
<211> LENGTH: 287
<212> TYPE: DNA
<213> ORGANISM: homo sapiens;

<400> SEQUENCE: 117
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctcc 287

<210> SEQ ID NO 118
<211> LENGTH: 287
<212> TYPE: DNA
<213> ORGANISM: homo sapiens;

<400> SEQUENCE: 118
gacatccaga tgatccagtc tccatctttc ctgtctgcat ctgtaggaga cagagtcagt 60
atcatttgct gggcaagtga gggcattagc agtaatttag cctggtatct gcagaaacca 120
gggaaatccc ctaagctctt cctctatgat gcaaaagatt tgcaccctgg ggtctcatcg 180
aggttcagtg gcaggggatc tgggacggat ttcactctca ccatcatcag cctgaagcct 240
gaagattttg cagcttatta ctgtaaacag gacttcagtt accctcc 287

<210> SEQ ID NO 119
<211> LENGTH: 287
<212> TYPE: DNA
<213> ORGANISM: homo sapiens;

<400> SEQUENCE: 119
gccatccgga tgacccagtc tccattctcc ctgtctgcat ctgtaggaga cagagtcacc 60
atcacttgct gggccagtca gggcattagc agttatttag cctggtatca gcaaaaacca 120
gcaaaagccc ctaagctctt catctattat gcatccagtt tgcaaagtgg ggtcccatca 180
aggttcagcg gcagtggatc tgggacggat tacactctca ccatcagcag cctgcagcct 240
gaagattttg caacttatta ctgtcaacag tattatagta cccctcc 287

<210> SEQ ID NO 120
<211> LENGTH: 302
<212> TYPE: DNA
<213> ORGANISM: homo sapiens;

<400> SEQUENCE: 120
gatattgtga tgacccagac tccactctcc tcacctgtca cccttggaca gccggcctcc 60
atctcctgca ggtctagtca aagcctcgta cacagtgatg gaaacaccta cttgagttgg 120
cttcagcaga ggccaggcca gcctccaaga ctcctaattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagctac acaatttcct 300
ca 302

<210> SEQ ID NO 121
<211> LENGTH: 302
<212> TYPE: DNA
<213> ORGANISM: homo sapiens;

<400> SEQUENCE: 121
gatattgtga tgacccagac tccactctcc tcgcctgtca cccttggaca gccggcctcc 60
atctccttca ggtctagtca aagcctcgta cacagtgatg gaaacaccta cttgagttgg 120
cttcagcaga ggccaggcca gcctccaaga ctcctaattt ataaggtttc taaccggttc 180
tctggggtcc cagacagatt cagtggcagt ggggcaggga cagatttcac actgaaaatc 240
agcagggtgg aagctgagga tgtcggggtt tattactgca cgcaagctac acaatttcct 300
ca 302

<210> SEQ ID NO 122
<211> LENGTH: 302
<212> TYPE: DNA
<213> ORGANISM: homo sapiens;

<400> SEQUENCE: 122
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
cc 302

<210> SEQ ID NO 123
<211> LENGTH: 302
<212> TYPE: DNA
<213> ORGANISM: homo sapiens;

<400> SEQUENCE: 123

-continued gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
cc 302

<210> SEQ ID NO 124
<211> LENGTH: 302
<212> TYPE: DNA
<213> ORGANISM: homo sapiens;

<400> SEQUENCE: 124
gatattgtga tgacccagac tccactctct ctgtccgtca cccctggaca gccggcctcc 60
atctcctgca agtctagtca gagcctcctg catagtgatg gaaagaccta tttgtattgg 120
tacctgcaga agccaggcca gtctccacag ctcctgatct atgaagtttc cagccggttc 180
tctggagtgc cagataggtt cagtggcagc gggtcaggga cagatttcac actgaaaatc 240
agccgggtgg aggctgagga tgttggggtt tattactgaa tgcaaggtat acaccttcct 300
cc 302

<210> SEQ ID NO 125
<211> LENGTH: 302
<212> TYPE: DNA
<213> ORGANISM: homo sapiens;

<400> SEQUENCE: 125
gatattgtga tgacccagac tccactctct ctgtccgtca cccctggaca gccggcctcc 60
atctcctgca agtctagtca gagcctcctg catagtgatg gaaagaccta tttgtattgg 120
tacctgcaga agccaggcca gcctccacag ctcctgatct atgaagtttc caaccggttc 180
tctggagtgc cagataggtt cagtggcagc gggtcaggga cagatttcac actgaaaatc 240
agccgggtgg aggctgagga tgttggggtt tattactgca tgcaaagtat acagcttcct 300
cc 302

<210> SEQ ID NO 126
<211> LENGTH: 302
<212> TYPE: DNA
<213> ORGANISM: homo sapiens;

<400> SEQUENCE: 126
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
cc 302

<210> SEQ ID NO 127
<211> LENGTH: 302
<212> TYPE: DNA
<213> ORGANISM: homo sapiens;

<400> SEQUENCE: 127

-continued gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taactgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
cc 302

<210> SEQ ID NO 128
<211> LENGTH: 305
<212> TYPE: DNA
<213> ORGANISM: homo sapiens;

<400> SEQUENCE: 128
gatattgtga tgacccagac tccactctcc ctgcccgtca cccctggaga gccggcctcc 60
atctcctgca ggtctagtca gagcctcttg gatagtgatg atggaaacac ctatttggac 120
tggtacctgc agaagccagg gcagtctcca cagctcctga tctatacgct ttcctatcgg 180
gcctctggag tcccagacag gttcagtggc agtgggtcag gcactgattt cacactgaaa 240
atcagcaggg tggaggctga ggatgttgga gtttattact gcatgcaacg tatagagttt 300
ccttc 305

<210> SEQ ID NO 129
<211> LENGTH: 305
<212> TYPE: DNA
<213> ORGANISM: homo sapiens;

<400> SEQUENCE: 129
gatattgtga tgacccagac tccactctcc ctgcccgtca cccctggaga gccggcctcc 60
atctcctgca ggtctagtca gagcctcttg gatagtgatg atggaaacac ctatttggac 120
tggtacctgc agaagccagg gcagtctcca cagctcctga tctatacgct ttcctatcgg 180
gcctctggag tcccagacag gttcagtggc agtgggtcag gcactgattt cacactgaaa 240
atcagcaggg tggaggctga ggatgttgga gtttattact gcatgcaacg tatagagttt 300
ccttc 305

<210> SEQ ID NO 130
<211> LENGTH: 290
<212> TYPE: DNA
<213> ORGANISM: homo sapiens;

<400> SEQUENCE: 130
gaaattgtaa tgacacagtc tccacccacc ctgtctttgt ctccagggga aagagtcacc 60
ctctcctgca gggccagtca gagtgttagc agcagctact taacctggta tcagcagaaa 120
cctggccagg cgcccaggct cctcatctat ggtgcatcca ccagggccac tagcatccca 180
gccaggttca gtggcagtgg gtctgggaca gacttcactc tcaccatcag cagcctgcag 240
cctgaagatt ttgcagttta ttactgtcag caggatcata acttacctcc 290

<210> SEQ ID NO 131
<211> LENGTH: 290
<212> TYPE: DNA
<213> ORGANISM: homo sapiens;

<400> SEQUENCE: 131
gaaattgtaa tgacacagtc tccacccacc ctgtctttgt ctccagggga aagagtcacc 60
ctctcctgca gggccagtca gagtgttagc agcagctact taacctggta tcagcagaaa 120
cctggccagg cgcccaggct cctcatctat ggtgcatcca ccagggccac tagcatccca 180
gccaggttca gtggcagtgg gtctgggaga gacttcactc tcaccatcag cagcctgcag 240
cctgaagatt ttgcagttta ttactgtcag caggatcata acttacctcc 290

<210> SEQ ID NO 132
<211> LENGTH: 290
<212> TYPE: DNA
<213> ORGANISM: homo sapiens;

<400> SEQUENCE: 132
gaaattgtaa tgacacagtc tccagccacc ctgtctttgt ctccagggga aagagccacc 60
ctctcctgca gggccagtca gagtgttagc agcagctact tatcctggta ccagcagaaa 120
cctgggcagg ctcccaggct cctcatctat ggtgcatcca ccagggccac tggcatccca 180
gccaggttca gtggcagtgg gtctgggaca gacttcactc tcaccatcag cagcctgcag 240
cctgaagatt ttgcagttta ttactgtcag caggattata acttacctcc 290

<210> SEQ ID NO 133
<211> LENGTH: 287
<212> TYPE: DNA
<213> ORGANISM: homo sapiens;

<400> SEQUENCE: 133
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag cgtagcaact ggcctcc 287

<210> SEQ ID NO 134
<211> LENGTH: 287
<212> TYPE: DNA
<213> ORGANISM: homo sapiens;

<400> SEQUENCE: 134
gaaattgtgt tgacacagtc tccagccacc ctgtctttgt ctccagggga aagagccacc 60
ctctcctgca gggccagtca gggtgttagc agctacttag cctggtacca gcagaaacct 120
ggccaggctc ccaggctcct catctatgat gcatccaaca gggccactgg catcccagcc 180
aggttcagtg gcagtgggcc tgggacagac ttcactctca ccatcagcag cctagagcct 240
gaagattttg cagtttatta ctgtcagcag cgtagcaact ggcatcc 287

<210> SEQ ID NO 135
<211> LENGTH: 287
<212> TYPE: DNA
<213> ORGANISM: homo sapiens;

<400> SEQUENCE: 135
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataataact ggcctcc 287

<210> SEQ ID NO 136
<211> LENGTH: 287
<212> TYPE: DNA
<213> ORGANISM: homo sapiens;

<400> SEQUENCE: 136
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg catcccagcc 180
aggttcagtg gcagtgggtc tgggacagag ttcactctca ccatcagcag cctgcagtct 240
gaagattttg cagtttatta ctgtcagcag tataataact ggcctcc 287

<210> SEQ ID NO 137
<211> LENGTH: 290
<212> TYPE: DNA
<213> ORGANISM: homo sapiens;

<400> SEQUENCE: 137
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctcc 290

<210> SEQ ID NO 138
<211> LENGTH: 290
<212> TYPE: DNA
<213> ORGANISM: homo sapiens;

<400> SEQUENCE: 138
gaaattgtgt tgacgcagtc tccagccacc ctgtctttgt ctccagggga aagagccacc 60
ctctcctgcg gggccagtca gagtgttagc agcagctact tagcctggta ccagcagaaa 120
cctggcctgg cgcccaggct cctcatctat gatgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctcc 290

<210> SEQ ID NO 139
<211> LENGTH: 305
<212> TYPE: DNA
<213> ORGANISM: homo sapiens;

<400> SEQUENCE: 139
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
cctcc 305

<210> SEQ ID NO 140

<211> LENGTH: 287
<212> TYPE: DNA
<213> ORGANISM: homo sapiens;

<400> SEQUENCE: 140
gaaacgacac tcacgcagtc tccagcattc atgtcagcga ctccaggaga caaagtcaac 60
atctcctgca aagccagcca agacattgat gatgatatga actggtacca acagaaacca 120
ggagaagctg ctattttcat tattcaagaa gctactactc tcgttcctgg aatcccacct 180
cgattcagtg gcagcgggta tggaacagat tttaccctca caattaataa catagaatct 240
gaggatgctg catattactt ctgtctacaa catgataatt tccctct 287

<210> SEQ ID NO 141
<211> LENGTH: 287
<212> TYPE: DNA
<213> ORGANISM: homo sapiens;

<400> SEQUENCE: 141
gaaattgtgc tgactcagtc tccagacttt cagtctgtga ctccaaagga gaaagtcacc 60
atcacctgcc gggccagtca gagcattggt agtagcttac actggtacca gcagaaacca 120
gatcagtctc caaagctcct catcaagtat gcttcccagt ccttctcagg ggtcccctcg 180
aggttcagtg gcagtggatc tgggacagat ttcaccctca ccatcaatag cctggaagct 240
gaagatgctg caacgtatta ctgtcatcag agtagtagtt tacctca 287

<210> SEQ ID NO 142
<211> LENGTH: 287
<212> TYPE: DNA
<213> ORGANISM: homo sapiens;

<400> SEQUENCE: 142
gaaattgtgc tgactcagtc tccagacttt cagtctgtga ctccaaagga gaaagtcacc 60
atcacctgcc gggccagtca gagcattggt agtagcttac actggtacca gcagaaacca 120
gatcagtctc caaagctcct catcaagtat gcttcccagt ccttctcagg ggtcccctcg 180
aggttcagtg gcagtggatc tgggacagat ttcaccctca ccatcaatag cctggaagct 240
gaagatgctg caacgtatta ctgtcatcag agtagtagtt tacctca 287

<210> SEQ ID NO 143
<211> LENGTH: 287
<212> TYPE: DNA
<213> ORGANISM: homo sapiens;

<400> SEQUENCE: 143
gatgttgtga tgacacagtc tccagctttc ctctctgtga ctccagggga gaaagtcacc 60
atcacctgcc aggccagtga aggcattggc aactacttat actggtacca gcagaaacca 120
gatcaagccc caaagctcct catcaagtat gcttcccagt ccatctcagg ggtcccctcg 180
aggttcagtg gcagtggatc tgggacagat ttcaccttta ccatcagtag cctggaagct 240
gaagatgctg caacatatta ctgtcagcag ggcaataagc accctca 287

<210> SEQ ID NO 144
<211> LENGTH: 296
<212> TYPE: DNA
<213> ORGANISM: homo sapiens;

<400> SEQUENCE: 144
cagtctgtgc tgactcagcc accctcggtg tctgaagccc ccaggcagag ggtcaccatc 60
tcctgttctg gaagcagctc caacatcgga aataatgctg taaactggta ccagcagctc 120
ccaggaaagg ctcccaaact cctcatctat tatgatgatc tgctgccctc aggggtctct 180
gaccgattct ctggctccaa gtctggcacc tcagcctccc tggccatcag tgggctccag 240
tctgaggatg aggctgatta ttactgtgca gcatgggatg acagcctgaa tggtcc 296

<210> SEQ ID NO 145
<211> LENGTH: 299
<212> TYPE: DNA
<213> ORGANISM: homo sapiens;

<400> SEQUENCE: 145
cagtctgtgc tgacgcagcc gccctcagtg tctggggccc cagggcagag ggtcaccatc 60
tcctgcactg ggagcagctc caacatcggg gcaggttatg atgtacactg gtaccagcag 120
cttccaggaa cagcccccaa actcctcatc tatggtaaca gcaatcggcc ctcaggggtc 180
cctgaccgat tctctggctc caagtctggc acctcagcct ccctggccat cactgggctc 240
caggctgagg atgaggctga ttattactgc cagtcctatg acagcagcct gagtggttc 299

<210> SEQ ID NO 146
<211> LENGTH: 296
<212> TYPE: DNA
<213> ORGANISM: homo sapiens;

<400> SEQUENCE: 146
cagtctgtgt tgacgcagcc gccttcagtg tctgcggccc caggacagaa ggtcaccatc 60
tcctgctctg gaagcagctc cgacatgggg aattatgcgg tatcctggta ccagcagctc 120
ccaggaacag cccccaaact cctcatctat gaaaataata agcgaccctc agggattcct 180
gaccgattct ctggctccaa gtctggcacc tcagccaccc tgggcatcac tggcctctgg 240
cctgaggacg aggccgatta ttactgctta gcatgggata ccagcccgag agcttg 296

<210> SEQ ID NO 147
<211> LENGTH: 296
<212> TYPE: DNA
<213> ORGANISM: homo sapiens;

<400> SEQUENCE: 147
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtcc 296

<210> SEQ ID NO 148
<211> LENGTH: 296
<212> TYPE: DNA
<213> ORGANISM: homo sapiens;

<400> SEQUENCE: 148
cagtctgtgc tgactcagcc accctcagcg tctgggaccc ccgggcagag ggtcaccatc 60
tcttgttctg gaagcagctc caacatcgga agtaattatg tatactggta ccagcagctc 120
ccaggaacgg cccccaaact cctcatctat aggaataatc agcggccctc aggggtccct 180
gaccgattct ctggctccaa gtctggcacc tcagcctccc tggccatcag tgggctccgg 240

-continued tccgaggatg aggctgatta ttactgtgca gcatgggatg acagcctgag tggtcc 296

<210> SEQ ID NO 149
<211> LENGTH: 299
<212> TYPE: DNA
<213> ORGANISM: homo sapiens;

<400> SEQUENCE: 149
cagtctgtgc tgacgcagcc gccctcagtg tctggggccc cagggcagag ggtcaccatc 60
tcctgcactg ggagcagctc caacattggg gcgggttatg ttgtacattg gtaccagcag 120
cttccaggaa cagcccccaa actcctcatc tatggtaaca gcaatcggcc ctcaggggtc 180
cctgaccaat tctctggctc caagtctggc acctcagcct ccctggccat cactggactc 240
cagtctgagg atgaggctga ttattactgc aaagcatggg ataacagcct gaatgctca 299

<210> SEQ ID NO 150
<211> LENGTH: 296
<212> TYPE: DNA
<213> ORGANISM: homo sapiens;

<400> SEQUENCE: 150
cagtctgtgt tgacgcagcc gccctcagtg tctgcggccc caggacagaa ggtcaccatc 60
tcctgctctg gaagcagctc caacattggg aataattatg tatcctggta ccagcagctc 120
ccaggaacag cccccaaact cctcatttat gacaataata agcgaccctc agggattcct 180
gaccgattct ctggctccaa gtctggcacg tcagccaccc tgggcatcac cggactccag 240
actggggacg aggccgatta ttactgcgga acatgggata gcagcctgag tgctgg 296

<210> SEQ ID NO 151
<211> LENGTH: 297
<212> TYPE: DNA
<213> ORGANISM: homo sapiens;

<400> SEQUENCE: 151
cagtctgccc tgactcagcc tccctccgcg tccgggtctc ctggacagtc agtcaccatc 60
tcctgcactg gaaccagcag tgacgttggt ggttataact atgtctcctg gtaccaacag 120
cacccaggca aagcccccaa actcatgatt tatgaggtca gtaagcggcc ctcaggggtc 180
cctgatcgct tctctggctc caagtctggc aacacggcct ccctgaccgt ctctgggctc 240
caggctgagg atgaggctga ttattactgc agctcatatg caggcagcaa caatttc 297

<210> SEQ ID NO 152
<211> LENGTH: 297
<212> TYPE: DNA
<213> ORGANISM: homo sapiens;

<400> SEQUENCE: 152
cagtctgccc tgactcagcc tcgctcagtg tccgggtctc ctggacagtc agtcaccatc 60
tcctgcactg gaaccagcag tgatgttggt ggttataact atgtctcctg gtaccaacag 120
cacccaggca aagcccccaa actcatgatt tatgatgtca gtaagcggcc ctcaggggtc 180
cctgatcgct tctctggctc caagtctggc aacacggcct ccctgaccat ctctgggctc 240
caggctgagg atgaggctga ttattactgc tgctcatatg caggcagcta cactttc 297

<210> SEQ ID NO 153
<211> LENGTH: 297
<212> TYPE: DNA
<213> ORGANISM: homo sapiens;

<400> SEQUENCE: 153
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgaggtca gtaatcggcc ctcaggggtt 180
tctaatcgct tctctggctc caagtctggc aacacggcct ccctgaccat ctctgggctc 240
caggctgagg acgaggctga ttattactgc agctcatata caagcagcag cactctc 297

<210> SEQ ID NO 154
<211> LENGTH: 297
<212> TYPE: DNA
<213> ORGANISM: homo sapiens;

<400> SEQUENCE: 154
cagtctgccc tgactcagcc tccctccgtg tccgggtctc ctggacagtc agtcaccatc 60
tcctgcactg gaaccagcag tgacgttggt agttataacc gtgtctcctg gtaccagcag 120
cccccaggca cagcccccaa actcatgatt tatgaggtca gtaatcggcc ctcaggggtc 180
cctgatcgct tctctgggtc caagtctggc aacacggcct ccctgaccat ctctgggctc 240
caggctgagg acgaggctga ttattactgc agcttatata caagcagcag cactttc 297

<210> SEQ ID NO 155
<211> LENGTH: 298
<212> TYPE: DNA
<213> ORGANISM: homo sapiens;

<400> SEQUENCE: 155
cagtctgccc tgactcagcc tgcctccgtg tctgggtctc ctggacagtc gatcaccatc 60
tcctgcactg gaaccagcag tgatgttggg agttataacc ttgtctcctg gtaccaacag 120
cacccaggca aagcccccaa actcatgatt tatgagggca gtaagcggcc ctcaggggtt 180
tctaatcgct tctctggctc caagtctggc aacacggcct ccctgacaat ctctgggctc 240
caggctgagg acgaggctga ttattactgc tgctcatatg caggtagtag cactttac 298

<210> SEQ ID NO 156
<211> LENGTH: 297
<212> TYPE: DNA
<213> ORGANISM: homo sapiens;

<400> SEQUENCE: 156
caatctgccc tgactcagcc tccttttgtg tccggggctc ctggacagtc ggtcaccatc 60
tcctgcactg gaaccagcag tgacgttggg gattatgatc atgtcttctg gtaccaaaag 120
cgtctcagca ctacctccag actcctgatt tacaatgtca atactcggcc ttcagggatc 180
tctgacctct tctcaggctc caagtctggc aacatggctt ccctgaccat ctctgggctc 240
aagtccgagg ttgaggctaa ttatcactgc agcttatatt caagtagtta cactttc 297

<210> SEQ ID NO 157
<211> LENGTH: 285
<212> TYPE: DNA
<213> ORGANISM: homo sapiens;

<400> SEQUENCE: 157
tcctatgagc tgactcagcc accctcagtg tccgtgtccc caggacagac agccagcatc 60
acctgctctg gagataaatt gggggataaa tatgcttgct ggtatcagca gaagccaggc 120

```
cagtcccctg tgctggtcat ctatcaagat agcaagcggc cctcagggat ccctgagcga    180

ttctctggct ccaactctgg gaacacagcc actctgacca tcagcgggac ccaggctatg    240

gatgaggctg actattactg tcaggcgtgg gacagcagca ctgca                    285


<210> SEQ ID NO 158
<211> LENGTH: 290
<212> TYPE: DNA
<213> ORGANISM: homo sapiens;

<400> SEQUENCE: 158

tcctatgagc tgacacagcc accctcggtg tcagtgtccc caggacaaac ggccaggatc     60

acctgctctg gagatgcatt gccaaaaaaa tatgcttatt ggtaccagca gaagtcaggc    120

caggcccctg tgctggtcat ctatgaggac agcaaacgac cctccgggat ccctgagaga    180

ttctctggct ccagctcagg gacaatggcc accttgacta tcagtggggc ccaggtggag    240

gatgaagctg actactactg ttactcaaca gacagcagtg gtaatcatag              290


<210> SEQ ID NO 159
<211> LENGTH: 290
<212> TYPE: DNA
<213> ORGANISM: homo sapiens;

<400> SEQUENCE: 159

tcctatgagc tgactcagcc acactcagtg tcagtggcca cagcacagat ggccaggatc     60

acctgtgggg gaaacaacat tggaagtaaa gctgtgcact ggtaccagca aaagccaggc    120

caggaccctg tgctggtcat ctatagcgat agcaaccggc cctcagggat ccctgagcga    180

ttctctggct ccaacccagg gaacaccacc accctaacca tcagcaggat cgaggctggg    240

gatgaggctg actattactg tcaggtgtgg gacagtagta gtgatcatcc              290


<210> SEQ ID NO 160
<211> LENGTH: 290
<212> TYPE: DNA
<213> ORGANISM: homo sapiens;

<400> SEQUENCE: 160

tcctatgagc tgacacagcc accctcggtg tcagtgtccc taggacagat ggccaggatc     60

acctgctctg gagaagcatt gccaaaaaaa tatgcttatt ggtaccagca gaagccaggc    120

cagttccctg tgctggtgat atataaagac agcgagaggc cctcagggat ccctgagcga    180

ttctctggct ccagctcagg gacaatagtc acattgacca tcagtggagt ccaggcagaa    240

gacgaggctg actattactg tctatcagca gacagcagtg gtacttatcc              290


<210> SEQ ID NO 161
<211> LENGTH: 290
<212> TYPE: DNA
<213> ORGANISM: homo sapiens;

<400> SEQUENCE: 161

tcttctgagc tgactcagga ccctgctgtg tctgtggcct tgggacagac agtcaggatc     60

acatgccaag gagacagcct cagaagctat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgg gacagcagtg gtaaccatct              290
```

<210> SEQ ID NO 162
<211> LENGTH: 290
<212> TYPE: DNA
<213> ORGANISM: homo sapiens;

<400> SEQUENCE: 162
tcctatgtgc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gacagtagta gtgatcatcc 290

<210> SEQ ID NO 163
<211> LENGTH: 284
<212> TYPE: DNA
<213> ORGANISM: homo sapiens;

<400> SEQUENCE: 163
tcctatgagc tgacacagct accctcggtg tcagtgtccc caggacagac agccaggatc 60
acctgctctg gagatgtact gggggaaaat tatgctgact ggtaccagca gaagccaggc 120
caggcccctg agttggtgat atacgaagat agtgagcggt accctggaat ccctgaacga 180
ttctctgggt ccacctcagg gaacacgacc accctgacca tcagcagggt cctgaccgaa 240
gacgaggctg actattactg tttgtctggg gatgaggaca atcc 284

<210> SEQ ID NO 164
<211> LENGTH: 290
<212> TYPE: DNA
<213> ORGANISM: homo sapiens;

<400> SEQUENCE: 164
tcctatgagc tgatgcagcc accctcggtg tcagtgtccc caggacagac ggccaggatc 60
acctgctctg gagatgcatt gccaaagcaa tatgcttatt ggtaccagca gaagccaggc 120
caggcccctg tgctggtgat atataaagac agtgagaggc cctcagggat ccctgagcga 180
ttctctggct ccagctcagg gacaacagtc acgttgacca tcagtggagt ccaggcagaa 240
gatgaggctg actattactg tcaatcagca gacagcagtg gtacttatcc 290

<210> SEQ ID NO 165
<211> LENGTH: 284
<212> TYPE: DNA
<213> ORGANISM: homo sapiens;

<400> SEQUENCE: 165
tcctatgagc tgacacagcc atcctcagtg tcagtgtctc cgggacagac agccaggatc 60
acctgctcag gagatgtact ggcaaaaaaa tatgctcggt ggttccagca gaagccaggc 120
caggcccctg tgctggtgat ttataaagac agtgagcggc cctcagggat ccctgagcga 180
ttctccggct ccagctcagg gaccacagtc accttgacca tcagcggggc ccaggttgag 240
gatgaggctg actattactg ttactctgcg gctgacaaca atct 284

<210> SEQ ID NO 166
<211> LENGTH: 284
<212> TYPE: DNA
<213> ORGANISM: homo sapiens;

<400> SEQUENCE: 166
tcctctgggc caactcaggt gcctgcagtg tctgtggcct tgggacaaat ggccaggatc 60
acctgccagg gagacagcat ggaaggctct tatgaacact ggtaccagca gaagccaggc 120
caggcccccg tgctggtcat ctatgatagc agtgaccggc cctcaaggat ccctgagcga 180
ttctctggct ccaaatcagg caacacaacc accctgacca tcactggggc ccaggctgag 240
gatgaggctg attattacta tcagttgata gacaaccatg ctac 284

<210> SEQ ID NO 167
<211> LENGTH: 314
<212> TYPE: DNA
<213> ORGANISM: homo sapiens;

<400> SEQUENCE: 167
ctgcctgtgc tgactcagcc cccgtctgca tctgccttgc tgggagcctc gatcaagctc 60
acctgcaccc taagcagtga gcacagcacc tacaccatcg aatggtatca acagagacca 120
gggaggtccc cccagtatat aatgaaggtt aagagtgatg gcagccacag caagggggac 180
gggatccccg atcgcttcat gggctccagt tctggggctg accgctacct caccttctcc 240
aacctccagt ctgacgatga ggctgagtat cactgtggag agagccacac gattgatggc 300
caagtcggtt gagc 314

<210> SEQ ID NO 168
<211> LENGTH: 297
<212> TYPE: DNA
<213> ORGANISM: homo sapiens;

<400> SEQUENCE: 168
cagcctgtgc tgactcaatc atcctctgcc tctgcttccc tgggatcctc ggtcaagctc 60
acctgcactc tgagcagtgg gcacagtagc tacatcatcg catggcatca gcagcagcca 120
gggaaggccc ctcggtactt gatgaagctt gaaggtagtg gaagctacaa caaggggagc 180
ggagttcctg atcgcttctc aggctccagc tctggggctg accgctacct caccatctcc 240
aacctccagt tagaggatga ggctgattat tactgtgaga cctgggacag taacact 297

<210> SEQ ID NO 169
<211> LENGTH: 299
<212> TYPE: DNA
<213> ORGANISM: homo sapiens;

<400> SEQUENCE: 169
cagcttgtgc tgactcaatc gccctctgcc tctgcctccc tgggagcctc ggtcaagctc 60
acctgcactc tgagcagtgg gcacagcagc tacgccatcg catggcatca gcagcagcca 120
gagaagggcc ctcggtactt gatgaagctt aacagtgatg gcagccacag caagggggac 180
gggatccctg atcgcttctc aggctccagc tctggggctg agcgctacct caccatctcc 240
agcctccagt ctgaggatga ggctgactat tactgtcaga cctggggcac tggcattca 299

<210> SEQ ID NO 170
<211> LENGTH: 312
<212> TYPE: DNA
<213> ORGANISM: homo sapiens;

<400> SEQUENCE: 170
cagcctgtgc tgactcagcc accttcctcc tccgcatctc ctggagaatc cgccagactc 60
acctgcacct tgcccagtga catcaatgtt ggtagctaca acatatactg gtaccagcag 120
aagccaggga gccctcccag gtatctcctg tactactact cagactcaga taagggccag 180
ggctctggag tccccagccg cttctctgga tccaaagatg cttcagccaa tacagggatt 240
ttactcatct ccgggctcca gtctgaggat gaggctgact attactgtat gatttggcca 300
agcaatgctt ct 312

<210> SEQ ID NO 171
<211> LENGTH: 312
<212> TYPE: DNA
<213> ORGANISM: homo sapiens;

<400> SEQUENCE: 171
caggctgtgc tgactcagcc ggcttccctc tctgcatctc ctggagcatc agccagtctc 60
acctgcacct tgcgcagtgg catcaatgtt ggtacctaca ggatatactg gtaccagcag 120
aagccaggga gtcctcccca gtatctcctg aggtacaaat cagactcaga taagcagcag 180
ggctctggag tccccagccg cttctctgga tccaaagatg cttcggccaa tgcagggatt 240
ttactcatct ctgggctcca gtctgaggat gaggctgact attactgtat gatttggcac 300
agcagcgctt ct 312

<210> SEQ ID NO 172
<211> LENGTH: 312
<212> TYPE: DNA
<213> ORGANISM: homo sapiens;

<400> SEQUENCE: 172
cagcctgtgc tgactcagcc aacttccctc tcagcatctc ctggagcatc agccagactc 60
acctgcacct tgcgcagtgg catcaatctt ggtagctaca ggatattctg gtaccagcag 120
aagccagaga gccctccccg gtatctcctg agctactact cagactcaag taagcatcag 180
ggctctggag tccccagccg cttctctgga tccaaagatg cttcgagcaa tgcagggatt 240
ttagtcatct ctgggctcca gtctgaggat gaggctgact attactgtat gatttggcac 300
agcagtgctt ct 312

<210> SEQ ID NO 173
<211> LENGTH: 317
<212> TYPE: DNA
<213> ORGANISM: homo sapiens;

<400> SEQUENCE: 173
cagcctgtgc tgactcagcc atcttcccat tctgcatctt ctggagcatc agtcagactc 60
acctgcatgc tgagcagtgg cttcagtgtt ggggacttct ggataaggtg gtaccaacaa 120
aagccaggga accctccccg gtatctcctg tactaccact cagactccaa taagggccaa 180
ggctctggag ttcccagccg cttctctgga tccaacgatg catcagccaa tgcagggatt 240
ctgcgtatct ctgggctcca gcctgaggat gaggctgact attactgtgg tacatggcac 300
agcaactcta agactca 317

<210> SEQ ID NO 174
<211> LENGTH: 296
<212> TYPE: DNA
<213> ORGANISM: homo sapiens;

<400> SEQUENCE: 174
aattttatgc tgactcagcc ccactctgtg tcggagtctc cggggaagac ggtaaccatc 60
tcctgcaccc gcagcagtgg cagcattgcc agcaactatg tgcagtggta ccagcagcgc 120
ccgggcagtt cccccaccac tgtgatctat gaggataacc aaagaccctc tggggtccct 180
gatcggttct ctggctccat cgacagctcc tccaactctg cctccctcac catctctgga 240
ctgaagactg aggacgaggc tgactactac tgtcagtctt atgatagcag caatca 296

<210> SEQ ID NO 175
<211> LENGTH: 294
<212> TYPE: DNA
<213> ORGANISM: homo sapiens;

<400> SEQUENCE: 175
cagactgtgg tgactcagga gccctcactg actgtgtccc caggagggac agtcactctc 60
acctgtgctt ccagcactgg agcagtcacc agtggttact atccaaactg gttccagcag 120
aaacctggac aagcacccag ggcactgatt tatagtacaa gcaacaaaca ctcctggacc 180
cctgcccggt tctcaggctc cctccttggg ggcaaagctg ccctgacact gtcaggtgtg 240
cagcctgagg acgaggctga gtattactgc ctgctctact atggtggtgc tcag 294

<210> SEQ ID NO 176
<211> LENGTH: 294
<212> TYPE: DNA
<213> ORGANISM: homo sapiens;

<400> SEQUENCE: 176
caggctgtgg tgactcagga gccctcactg actgtgtccc caggagggac agtcactctc 60
acctgtggct ccagcactgg agctgtcacc agtggtcatt atccctactg gttccagcag 120
aagcctggcc aagcccccag gacactgatt tatgatacaa gcaacaaaca ctcctggaca 180
cctgcccggt tctcaggctc cctccttggg ggcaaagctg ccctgaccct ttcgggtgcg 240
cagcctgagg atgaggctga gtattactgc ttgctctcct atagtggtgc tcgg 294

<210> SEQ ID NO 177
<211> LENGTH: 296
<212> TYPE: DNA
<213> ORGANISM: homo sapiens;

<400> SEQUENCE: 177
cagactgtgg tgacccagga gccatcgttc tcagtgtccc ctggagggac agtcacactc 60
acttgtggct tgagctctgg ctcagtctct actagttact accccagctg gtaccagcag 120
accccaggcc aggctccacg cacgctcatc tacagcacaa acactcgctc ttctggggtc 180
cctgatcgct tctctggctc catccttggg aacaaagctg ccctcaccat cacgggggcc 240
caggcagatg atgaatctga ttattactgt gtgctgtata tgggtagtgg catttc 296

<210> SEQ ID NO 178
<211> LENGTH: 317
<212> TYPE: DNA
<213> ORGANISM: homo sapiens;

<400> SEQUENCE: 178
cagcctgtgc tgactcagcc accttctgca tcagcctccc tgggagcctc ggtcacactc 60
acctgcaccc tgagcagcgg ctacagtaat tataaagtgg actggtacca gcagagacca 120
gggaagggcc cccggtttgt gatgcgagtg ggcactggtg ggattgtggg atccaagggg 180
gatggcatcc ctgatcgctt ctcagtcttg ggctcaggcc tgaatcggta cctgaccatc 240
aagaacatcc aggaagagga tgagagtgac taccactgtg gggcagacca tggcagtggg 300
agcaacttcg tgtaacc 317

<210> SEQ ID NO 179
<211> LENGTH: 296
<212> TYPE: DNA
<213> ORGANISM: homo sapiens;

<400> SEQUENCE: 179
caggcagggc tgactcagcc accctcggtg tccaagggct tgagacagac cgccacactc 60
acctgcactg ggaacagcaa caatgttggc aaccaaggag cagcttggct gcagcagcac 120
cagggccacc ctcccaaact cctatcctac aggaataaca accggccctc agggatctca 180
gagagattat ctgcatccag gtcaggaaac acagcctccc tgaccattac tggactccag 240
cctgaggacg aggctgacta ttactgctca gcatgggaca gcagcctcag tgctca 296

<210> SEQ ID NO 180
<211> LENGTH: 312
<212> TYPE: DNA
<213> ORGANISM: homo sapiens;

<400> SEQUENCE: 180
cggcccgtgc tgactcagcc gccctctctg tctgcatccc cgggagcaac agccagactc 60
ccctgcaccc tgagcagtga cctcagtgtt ggtggtaaaa acatgttctg gtaccagcag 120
aagccaggga gctctcccag gttattcctg tatcactact cagactcaga caagcagctg 180
ggacctgggg tccccagtcg agtctctggc tccaaggaga cctcaagtaa cacagcgttt 240
ttgctcatct ctgggctcca gcctgaggac gaggccgatt attactgcca ggtgtacgaa 300
agtagtgcta at 312

<210> SEQ ID NO 181
<211> LENGTH: 38
<212> TYPE: DNA
<213> ORGANISM: homo sapiens;

<400> SEQUENCE: 181
gtggacgttc ggccaaggga ccaaggtgga aatcaaac 38

<210> SEQ ID NO 182
<211> LENGTH: 39
<212> TYPE: DNA
<213> ORGANISM: homo sapiens;

<400> SEQUENCE: 182
tgtacacttt tggccagggg accaagctgg agatcaaac 39

<210> SEQ ID NO 183
<211> LENGTH: 38
<212> TYPE: DNA
<213> ORGANISM: homo sapiens;

<400> SEQUENCE: 183
attcactttc ggccctggga ccaaagtgga tatcaaac 38

<210> SEQ ID NO 184
<211> LENGTH: 38
<212> TYPE: DNA
<213> ORGANISM: homo sapiens;

<400> SEQUENCE: 184
gctcactttc ggcggaggga ccaaggtgga gatcaaac 38

<210> SEQ ID NO 185
<211> LENGTH: 38
<212> TYPE: DNA
<213> ORGANISM: homo sapiens;

<400> SEQUENCE: 185
gatcaccttc ggccaaggga cacgactgga gattaaac 38

<210> SEQ ID NO 186
<211> LENGTH: 38
<212> TYPE: DNA
<213> ORGANISM: homo sapiens;

<400> SEQUENCE: 186
ttatgtcttc ggaactggga ccaaggtcac cgtcctag 38

<210> SEQ ID NO 187
<211> LENGTH: 38
<212> TYPE: DNA
<213> ORGANISM: homo sapiens;

<400> SEQUENCE: 187
tgtggtattc ggcggaggga ccaagctgac cgtcctag 38

<210> SEQ ID NO 188
<211> LENGTH: 38
<212> TYPE: DNA
<213> ORGANISM: homo sapiens;

<400> SEQUENCE: 188
tgtggtattc ggcggaggga ccaagctgac cgtcctag 38

<210> SEQ ID NO 189
<211> LENGTH: 38
<212> TYPE: DNA
<213> ORGANISM: homo sapiens;

<400> SEQUENCE: 189
ttttgtattt ggtggaggaa cccagctgat cattttag 38

<210> SEQ ID NO 190
<211> LENGTH: 38
<212> TYPE: DNA
<213> ORGANISM: homo sapiens;

<400> SEQUENCE: 190
ctgggtgttt ggtgagggga ccgagctgac cgtcctag 38

<210> SEQ ID NO 191
<211> LENGTH: 38
<212> TYPE: DNA
<213> ORGANISM: homo sapiens;

<400> SEQUENCE: 191
taatgtgttc ggcagtggca ccaaggtgac cgtcctcg 38

<210> SEQ ID NO 192
<211> LENGTH: 38
<212> TYPE: DNA
<213> ORGANISM: homo sapiens;

<400> SEQUENCE: 192
tgctgtgttc ggaggaggca cccagctgac cgtcctcg 38

<210> SEQ ID NO 193
<211> LENGTH: 302
<212> TYPE: DNA
<213> ORGANISM: homo sapiens;

<400> SEQUENCE: 193
gagattgtga tgacccagac tccactctcc ttgtctatca cccctggaga gcaggcctcc 60
atctcctgca ggtctagtca gagcctcctg catagtgatg gatacaccta tttgtattgg 120
tttctgcaga aagccaggcc agtctccaca ctcctgatct atgaagtttc caaccggttc 180
tctggagtgc cagataggtt cagtggcagc gggtcaggga cagatttcac actgaaaatc 240
agccgggtgg aggctgagga ttttggagtt tattactgca tgcaagatgc acaagatcct 300
cc 302

<210> SEQ ID NO 194
<211> LENGTH: 296
<212> TYPE: DNA
<213> ORGANISM: homo sapiens;

<400> SEQUENCE: 194
cagtctgtgc tgactcagcc accctcggtg tctgaagccc ccaggcagag ggtcaccatc 60
tcctgttctg gaagcagctc caacatcgga aataatgctg taaactggta ccagcagctc 120
ccaggaaagg ctcccaaact cctcatctat tatgatgatc tgctgccctc aggggtctct 180
gaccgattct ctggctccaa gtctggcacc tcagcctccc tggccatcag tgggctccag 240
tctgaggatg aggctgatta ttactgtgca gcatgggatg acagcctgaa tggtcc 296

<210> SEQ ID NO 195
<211> LENGTH: 296
<212> TYPE: DNA
<213> ORGANISM: homo sapiens;

<400> SEQUENCE: 195
cagtctgtgc tgactcagcc accctcagcg tctgggaccc ccgggcagag ggtcaccatc 60
tcttgttctg gaagcagctc caacatcgga agtaattatg tatactggta ccagcagctc 120
ccaggaacgg cccccaaact cctcatctat aggaataatc agcggccctc aggggtccct 180
gaccgattct ctggctccaa gtctggcacc tcagcctccc tggccatcag tgggctccgg 240
tccgaggatg aggctgatta ttactgtgca gcatgggatg acagcctgag tggtcc 296

<210> SEQ ID NO 196
<211> LENGTH: 299
<212> TYPE: DNA
<213> ORGANISM: homo sapiens;

<400> SEQUENCE: 196
cagtctgtgc tgacgcagcc gccctcagtg tctggggccc cagggcagag ggtcaccatc 60
tcctgcactg ggagcagctc caacattggg gcgggttatg ttgtacattg gtaccagcag 120
cttccaggaa cagcccccaa actcctcatc tatggtaaca gcaatcggcc ctcaggggtc 180
cctgaccaat tctctggctc caagtctggc acctcagcct ccctggccat cactggactc 240
cagtctgagg atgaggctga ttattactgc aaagcatggg ataacagcct gaatgctca 299

<210> SEQ ID NO 197
<211> LENGTH: 296
<212> TYPE: DNA

<213> ORGANISM: homo sapiens;

<400> SEQUENCE: 197
cagtctgtgt tgacgcagcc gccctcagtg tctgcggccc caggacagaa ggtcaccatc 60
tcctgctctg gaagcagctc caacattggg aataattatg tatcctggta ccagcagctc 120
ccaggaacag cccccaaact cctcatttat gacaataata agcgaccctc agggattcct 180
gaccgattct ctggctccaa gtctggcacg tcagccaccc tgggcatcac cggactccag 240
actggggacg aggccgatta ttactgcgga acatgggata gcagcctgag tgctgg 296

<210> SEQ ID NO 198
<211> LENGTH: 296
<212> TYPE: DNA
<213> ORGANISM: homo sapiens;

<400> SEQUENCE: 198
caggcagggc tgactcagcc accctcggtg tccaagggct tgagacagac cgccacactc 60
acctgcactg ggaacagcaa caatgttggc aaccaaggag cagcttggct gcagcagcac 120
cagggccacc ctcccaaact cctatcctac aggaataaca accggccctc agggatctca 180
gagagattat ctgcatccag gtcaggaaac acagcctccc tgaccattac tggactccag 240
cctgaggacg aggctgacta ttactgctca gcatgggaca gcagcctcag tgctca 296

<210> SEQ ID NO 199
<211> LENGTH: 312
<212> TYPE: DNA
<213> ORGANISM: homo sapiens;

<400> SEQUENCE: 199
cggcccgtgc tgactcagcc gccctctctg tctgcatccc cgggagcaac agccagactc 60
ccctgcaccc tgagcagtga cctcagtgtt ggtggtaaaa acatgttctg gtaccagcag 120
aagccaggga gctctcccag gttattcctg tatcactact cagactcaga caagcagctg 180
ggacctgggg tccccagtcg agtctctggc tccaaggaga cctcaagtaa cacagcgttt 240
ttgctcatct ctgggctcca gcctgaggac gaggccgatt attactgcca ggtgtacgaa 300
agtagtgcta at 312

<210> SEQ ID NO 200
<211> LENGTH: 297
<212> TYPE: DNA
<213> ORGANISM: homo sapiens;

<400> SEQUENCE: 200
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgaggtca gtaatcggcc ctcaggggtt 180
tctaatcgct tctctggctc caagtctggc aacacggcct ccctgaccat ctctgggctc 240
caggctgagg acgaggctga ttattactgc agctcatata caagcagcag cactctc 297

<210> SEQ ID NO 201
<211> LENGTH: 297
<212> TYPE: DNA
<213> ORGANISM: homo sapiens;

<400> SEQUENCE: 201
cagtctgccc tgactcagcc tccctccgtg tccgggtctc ctggacagtc agtcaccatc 60
tcctgcactg gaaccagcag tgacgttggt agttataacc gtgtctcctg gtaccagcag 120
cccccaggca cagcccccaa actcatgatt tatgaggtca gtaatcggcc ctcaggggtc 180
cctgatcgct tctctgggtc caagtctggc aacacggcct ccctgaccat ctctgggctc 240
caggctgagg acgaggctga ttattactgc agcttatata caagcagcag cactttc 297

<210> SEQ ID NO 202
<211> LENGTH: 298
<212> TYPE: DNA
<213> ORGANISM: homo sapiens;

<400> SEQUENCE: 202
cagtctgccc tgactcagcc tgcctccgtg tctgggtctc ctggacagtc gatcaccatc 60
tcctgcactg gaaccagcag tgatgttggg agttataacc ttgtctcctg gtaccaacag 120
cacccaggca aagcccccaa actcatgatt tatgagggca gtaagcggcc ctcaggggtt 180
tctaatcgct tctctggctc caagtctggc aacacggcct ccctgacaat ctctgggctc 240
caggctgagg acgaggctga ttattactgc tgctcatatg caggtagtag cactttac 298

<210> SEQ ID NO 203
<211> LENGTH: 297
<212> TYPE: DNA
<213> ORGANISM: homo sapiens;

<400> SEQUENCE: 203
cagtctgccc tgactcagcc tccctccgcg tccgggtctc ctggacagtc agtcaccatc 60
tcctgcactg gaaccagcag tgacgttggt ggttataact atgtctcctg gtaccaacag 120
cacccaggca aagcccccaa actcatgatt tatgaggtca gtaagcggcc ctcaggggtc 180
cctgatcgct tctctggctc caagtctggc aacacggcct ccctgaccgt ctctgggctc 240
caggctgagg atgaggctga ttattactgc agctcatatg caggcagcaa caatttc 297

<210> SEQ ID NO 204
<211> LENGTH: 285
<212> TYPE: DNA
<213> ORGANISM: homo sapiens;

<400> SEQUENCE: 204
tcctatgagc tgactcagcc accctcagtg tccgtgtccc caggacagac agccagcatc 60
acctgctctg gagataaatt gggggataaa tatgcttgct ggtatcagca gaagccaggc 120
cagtcccctg tgctggtcat ctatcaagat agcaagcggc cctcagggat ccctgagcga 180
ttctctggct ccaactctgg gaacacagcc actctgacca tcagcgggac ccaggctatg 240
gatgaggctg actattactg tcaggcgtgg gacagcagca ctgca 285

<210> SEQ ID NO 205
<211> LENGTH: 290
<212> TYPE: DNA
<213> ORGANISM: homo sapiens;

<400> SEQUENCE: 205
tcctatgagc tgactcagcc acactcagtg tcagtggcca cagcacagat ggccaggatc 60
acctgtgggg gaaacaacat tggaagtaaa gctgtgcact ggtaccagca aaagccaggc 120
caggaccctg tgctggtcat ctatagcgat agcaaccggc cctcagggat ccctgagcga 180
ttctctggct ccaacccagg gaacaccacc accctaacca tcagcaggat cgaggctggg 240

-continued gatgaggctg actattactg tcaggtgtgg gacagtagta gtgatcatcc 290

<210> SEQ ID NO 206
<211> LENGTH: 290
<212> TYPE: DNA
<213> ORGANISM: homo sapiens;

<400> SEQUENCE: 206
tcttctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgg gacagcagtg gtaaccatct 290

<210> SEQ ID NO 207
<211> LENGTH: 290
<212> TYPE: DNA
<213> ORGANISM: homo sapiens;

<400> SEQUENCE: 207
tcctatgtgc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gacagtagta gtgatcatcc 290

<210> SEQ ID NO 208
<211> LENGTH: 284
<212> TYPE: DNA
<213> ORGANISM: homo sapiens;

<400> SEQUENCE: 208
tcctatgagc tgacacagct accctcggtg tcagtgtccc caggacagac agccaggatc 60
acctgctctg gagatgtact gggggaaaat tatgctgact ggtaccagca gaagccaggc 120
caggcccctg agttggtgat atacgaagat agtgagcggt accctggaat ccctgaacga 180
ttctctgggt ccacctcagg gaacacgacc accctgacca tcagcagggt cctgaccgaa 240
gacgaggctg actattactg tttgtctggg gatgaggaca atcc 284

<210> SEQ ID NO 209
<211> LENGTH: 290
<212> TYPE: DNA
<213> ORGANISM: homo sapiens;

<400> SEQUENCE: 209
tcctatgagc tgatgcagcc accctcggtg tcagtgtccc caggacagac ggccaggatc 60
acctgctctg gagatgcatt gccaaagcaa tatgcttatt ggtaccagca gaagccaggc 120
caggcccctg tgctggtgat atataaagac agtgagaggc cctcagggat ccctgagcga 180
ttctctggct ccagctcagg gacaacagtc acgttgacca tcagtggagt ccaggcagaa 240
gatgaggctg actattactg tcaatcagca gacagcagtg gtacttatcc 290

<210> SEQ ID NO 210
<211> LENGTH: 297
<212> TYPE: DNA
<213> ORGANISM: homo sapiens;

<400> SEQUENCE: 210
cagcctgtgc tgactcaatc atcctctgcc tctgcttccc tgggatcctc ggtcaagctc 60
acctgcactc tgagcagtgg gcacagtagc tacatcatcg catggcatca gcagcagcca 120
gggaaggccc ctcggtactt gatgaagctt gaaggtagtg gaagctacaa caaggggagc 180
ggagttcctg atcgcttctc aggctccagc tctggggctg accgctacct caccatctcc 240
aacctccagt tagaggatga ggctgattat tactgtgaga cctgggacag taacact 297

<210> SEQ ID NO 211
<211> LENGTH: 312
<212> TYPE: DNA
<213> ORGANISM: homo sapiens;

<400> SEQUENCE: 211
cagcctgtgc tgactcagcc accttcctcc tccgcatctc ctggagaatc cgccagactc 60
acctgcacct tgcccagtga catcaatgtt ggtagctaca acatatactg gtaccagcag 120
aagccaggga gccctcccag gtatctcctg tactactact cagactcaga taagggccag 180
ggctctggag tccccagccg cttctctgga tccaaagatg cttcagccaa tacagggatt 240
ttactcatct ccgggctcca gtctgaggat gaggctgact attactgtat gatttggcca 300
agcaatgctt ct 312

<210> SEQ ID NO 212
<211> LENGTH: 312
<212> TYPE: DNA
<213> ORGANISM: homo sapiens;

<400> SEQUENCE: 212
caggctgtgc tgactcagcc ggcttccctc tctgcatctc ctggagcatc agccagtctc 60
acctgcacct tgcgcagtgg catcaatgtt ggtacctaca ggatatactg gtaccagcag 120
aagccaggga gtcctcccca gtatctcctg aggtacaaat cagactcaga taagcagcag 180
ggctctggag tccccagccg cttctctgga tccaaagatg cttcggccaa tgcagggatt 240
ttactcatct ctgggctcca gtctgaggat gaggctgact attactgtat gatttggcac 300
agcagcgctt ct 312

<210> SEQ ID NO 213
<211> LENGTH: 312
<212> TYPE: DNA
<213> ORGANISM: homo sapiens;

<400> SEQUENCE: 213
cagcctgtgc tgactcagcc aacttccctc tcagcatctc ctggagcatc agccagactc 60
acctgcacct tgcgcagtgg catcaatctt ggtagctaca ggatattctg gtaccagcag 120
aagccagaga gccctccccg gtatctcctg agctactact cagactcaag taagcatcag 180
ggctctggag tccccagccg cttctctgga tccaaagatg cttcgagcaa tgcagggatt 240
ttagtcatct ctgggctcca gtctgaggat gaggctgact attactgtat gatttggcac 300
agcagtgctt ct 312

<210> SEQ ID NO 214
<211> LENGTH: 296
<212> TYPE: DNA
<213> ORGANISM: homo sapiens;

<400> SEQUENCE: 214
aattttatgc tgactcagcc ccactctgtg tcggagtctc cggggaagac ggtaaccatc 60
tcctgcaccc gcagcagtgg cagcattgcc agcaactatg tgcagtggta ccagcagcgc 120
ccgggcagtt cccccaccac tgtgatctat gaggataacc aaagaccctc tggggtccct 180
gatcggttct ctggctccat cgacagctcc tccaactctg cctccctcac catctctgga 240
ctgaagactg aggacgaggc tgactactac tgtcagtctt atgatagcag caatca 296

<210> SEQ ID NO 215
<211> LENGTH: 294
<212> TYPE: DNA
<213> ORGANISM: homo sapiens;

<400> SEQUENCE: 215
caggctgtgg tgactcagga gccctcactg actgtgtccc caggagggac agtcactctc 60
acctgtggct ccagcactgg agctgtcacc agtggtcatt atccctactg gttccagcag 120
aagcctggcc aagcccccag gacactgatt tatgatacaa gcaacaaaca ctcctggaca 180
cctgcccggt tctcaggctc cctccttggg ggcaaagctg ccctgaccct ttcgggtgcg 240
cagcctgagg atgaggctga gtattactgc ttgctctcct atagtggtgc tcgg 294

<210> SEQ ID NO 216
<211> LENGTH: 296
<212> TYPE: DNA
<213> ORGANISM: homo sapiens;

<400> SEQUENCE: 216
cagactgtgg tgacccagga gccatcgttc tcagtgtccc ctggagggac agtcacactc 60
acttgtggct tgagctctgg ctcagtctct actagttact accccagctg gtaccagcag 120
accccaggcc aggctccacg cacgctcatc tacagcacaa acactcgctc ttctggggtc 180
cctgatcgct tctctggctc catccttggg aacaaagctg ccctcaccat cacgggggcc 240
caggcagatg atgaatctga ttattactgt gtgctgtata tgggtagtgg catttc 296

<210> SEQ ID NO 217
<211> LENGTH: 1134
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 217
ncttccacca agggcccatc ggtcttcccc ctggcgccct gctccaggag cacctctggg 60
ggcacagcgg ccctgggctg cctggtcaag gactacttcc cagaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacacctgca acgtgaatca caagcccagc aacaccaagg tggacaagag agttgagctc 300
aaaaccccac ttggtgacac aactcacaca tgcccacggt gcccagagcc caaatcttgt 360
gacacacctc ccccgtgccc acggtgccca gagcccaaat cttgtgacac acctccccca 420
tgcccacggt gcccagagcc caaatcttgt gacacacctc ccccgtgccc aaggtgccca 480
gcacctgaac tcctgggagg accgtcagtc ttcctcttcc ccccaaaacc caaggatacc 540
cttatgattt cccggacccc tgaggtcacg tgcgtggtgg tggacgtgag ccacgaagac 600

```
cccgaggtcc agttcaagtg gtacgtggac ggcgtggagg tgcataatgc caagacaaag    660

ccgcgggagg agcagtacaa cagcacgttc cgtgtggtca gcgtcctcac cgtcctgcac    720

caggactggc tgaacggcaa ggagtacaag tgcaaggtct ccaacaaagc cctcccagcc    780

cccatcgaga aaaccatctc caaaaccaaa ggacagcccc gagaaccaca ggtgtacacc    840

ctgcccccat cccgggagga gatgaccaag aaccaggtca gcctgacctg cctggtcaaa    900

ggcttctacc ccagcgacat cgccgtggag tgggagagca gcgggcagcc ggagaacaac    960

tacaacacca cgcctcccat gctggactcc gacggctcct tcttcctcta cagcaagctc   1020

accgtggaca agagcaggtg gcagcagggg aacatcttct catgctccgt gatgcatgag   1080

gctctgcaca accgcttcac gcagaagagc ctctccctgt ctccgggtaa atga         1134
```

<210> SEQ ID NO 218
<211> LENGTH: 1023
<212> TYPE: DNA
<213> ORGANISM: homo sapiens;

<400> SEQUENCE: 218

```
gcatccccga ccagccccaa ggtcttcccg ctgagcctcg acagcacccc ccaagatggg     60

aacgtggtcg tcgcatgcct ggtccagggc ttcttccccc aggagccact cagtgtgacc    120

tggagcgaaa gcggacagaa cgtgaccgcc agaaacttcc cacctagcca ggatgcctcc    180

ggggacctgt acaccacgag cagccagctg accctgccgg ccacacagtg cccagacggc    240

aagtccgtga catgccacgt gaagcactac acgaattcca gccaggatgt gactgtgccc    300

tgccgagttc ccccacctcc cccatgctgc cacccccgac tgtcgctgca ccgaccggcc    360

ctcgaggacc tgctcttagg ttcagaagcg aacctcacgt gcacactgac cggcctgaga    420

gatgcctctg gtgccacctt cacctggacg ccctcaagtg ggaagagcgc tgttcaagga    480

ccacctgagc gtgacctctg tggctgctac agcgtgtcca gtgtcctgcc tggctgtgcc    540

cagccatgga accatgggga gaccttcacc tgcactgctg cccaccccga gttgaagacc    600

ccactaaccg ccaacatcac aaaatccgga aacacattcc ggcccgaggt ccacctgctg    660

ccgccgccgt cggaggagct ggccctgaac gagctggtga cgctgacgtg cctggcacgt    720

ggcttcagcc ccaaggatgt gctggttcgc tggctgcagg ggtcacagga gctgccccgc    780

gagaagtacc tgacttgggc atcccggcag gagcccagcc agggcaccac cacctacgct    840

gtaaccagca tactgcgcgt ggcagctgag gactggaaga agggggagac cttctcctgc    900

atggtgggcc acgaggccct gccgctggcc ttcacacaga agaccatcga ccgcatggcg    960

ggtaaaccca cccacatcaa tgtgtctgtt gtcatggcgg aggcggatgg cacctgctac   1020

tga                                                                 1023
```

<210> SEQ ID NO 219
<211> LENGTH: 981
<212> TYPE: DNA
<213> ORGANISM: homo sapiens;

<400> SEQUENCE: 219

```
gcctccacca agggcccatc ggtcttcccc ctggcgccct gctccaggag cacctccgag     60

agcacagcgg ccctgggctg cctggtcaag gactacttcc ccgaaccggt gacggtgtcg    120

tggaactcag gcgctctgac cagcggcgtg cacaccttcc cggctgtcct acagtcctca    180

ggactctact ccctcagcag cgtggtgacc gtgccctcca gcaacttcgg cacccagacc    240
```

```
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt cgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatctc cgtggagtgg    780
gagagcaatg ggcagccgga gaacaactac aagaccacac ctcccatgct ggactccgac    840
ggctccttct tcctctacag caagctcacc gtggacaaga gcaggtggca gcaggggaac    900
gtcttctcat gctccgtgat gcatgaggct ctgcacaacc actacacaca gaagagcctc    960
tccctgtctc cgggtaaatg a                                              981
```

<210> SEQ ID NO 220
<211> LENGTH: 1287
<212> TYPE: DNA
<213> ORGANISM: homo sapiens;

<400> SEQUENCE: 220

```
gcctccacac agagcccatc cgtcttcccc ttgacccgct gctgcaaaaa cattccctcc     60
aatgccacct ccgtgactct gggctgcctg gccacgggct acttcccgga gccggtgatg    120
gtgacctggg acacaggctc cctcaacggg acaactatga ccttaccagc caccaccctc    180
acgctctctg gtcactatgc caccatcagc ttgctgaccg tctcgggtgc gtgggccaag    240
cagatgttca cctgccgtgt ggcacacact ccatcgtcca cagactgggt cgacaacaaa    300
accttcagcg tctgctccag ggacttcacc ccgcccaccg tgaagatctt acagtcgtcc    360
tgcgacggcg gcgggcactt ccccccgacc atccagctcc tgtgcctcgt ctctgggtac    420
accccaggga ctatcaacat cacctggctg gaggacgggc aggtcatgga cgtggacttg    480
tccaccgcct ctaccacgca ggagggtgag ctggcctcca cacaaagcga gctcaccctc    540
agccagaagc actggctgtc agaccgcacc tacacctgcc aggtcaccta tcaaggtcac    600
acctttgagg acagcaccaa gaagtgtgca gattccaacc cgagaggggt gagcgcctac    660
ctaagccggc ccagcccgtt cgacctgttc atccgcaagt cgcccacgat cacctgtctg    720
gtggtggacc tggcacccag caaggggacc gtgaacctga cctggtcccg ggccagtggg    780
aagcctgtga accactccac cagaaaggag gagaagcagc gcaatggcac gttaaccgtc    840
acgtccaccc tgccggtggg cacccgagac tggatcgagg gggagaccta ccagtgcagg    900
gtgacccacc cccacctgcc cagggccctc atgcggtcca cgaccaagac cagcggcccg    960
cgtgctgccc cggaagtcta tgcgtttgcg acgccggagt ggccggggag ccgggacaag   1020
cgcaccctcg cctgcctgat ccagaacttc atgcctgagg acatctcggt gcagtggctg   1080
cacaacgagg tgcagctccc ggacgcccgg cacagcacga cgcagccccg caagaccaag   1140
ggctccggct tcttcgtctt cagccgcctg gaggtgacca gggccgaatg ggagcagaaa   1200
gatgagttca tctgccgtgc agtccatgag gcagcaagcc cctcacagac cgtccagcga   1260
gcggtgtctg taaatcccgg taaatga                                       1287
```

<210> SEQ ID NO 221
<211> LENGTH: 30
<212> TYPE: DNA
<213> ORGANISM: homo sapiens;

<400> SEQUENCE: 221
tccggcttct tcgtcttcag ccgcctggag 30

<210> SEQ ID NO 222
<211> LENGTH: 1062
<212> TYPE: DNA
<213> ORGANISM: homo sapiens;

<400> SEQUENCE: 222
gcatccccga ccagccccaa ggtcttcccg ctgagcctct gcagcaccca gccagatggg 60
aacgtggtca tcgcctgcct ggtccagggc ttcttccccc aggagccact cagtgtgacc 120
tggagcgaaa gcggacaggg cgtgaccgcc agaaacttcc cacccagcca ggatgcctcc 180
ggggacctgt acaccacgag cagccagctg accctgccgg ccacacagtg cctagccggc 240
aagtccgtga catgccacgt gaagcactac acgaatccca gccaggatgt gactgtgccc 300
tgcccagttc cctcaactcc acctacccca tctccctcaa ctccacctac cccatctccc 360
tcatgctgcc acccccgact gtcactgcac cgaccggccc tcgaggacct gctcttaggt 420
tcagaagcga acctcacgtg cacactgacc ggcctgagag atgcctcagg tgtcaccttc 480
acctggacgc cctcaagtgg gaagagcgct gttcaaggac cacctgagcg tgacctctgt 540
ggctgctaca gcgtgtccag tgtcctgccg ggctgtgccg agccatggaa ccatgggaag 600
accttcactt gcactgctgc ctaccccgag tccaagaccc cgctaaccgc caccctctca 660
aaatccggaa acacattccg gcccgaggtc cacctgctgc cgccgccgtc ggaggagctg 720
gccctgaacg agctggtgac gctgacgtgc ctggcacgcg gcttcagccc caaggatgtg 780
ctggttcgct ggctgcaggg gtcacaggag ctgccccgcg agaagtacct gacttgggca 840
tcccggcagg agcccagcca gggcaccacc accttcgctg tgaccagcat actgcgcgtg 900
gcagccgagg actggaagaa gggggacacc ttctcctgca tggtgggcca cgaggccctg 960
ccgctggcct tcacacagaa gaccatcgac cgcttggcgg gtaaacccac ccatgtcaat 1020
gtgtctgttg tcatggcgga ggtggacggc acctgctact ga 1062

<210> SEQ ID NO 223
<211> LENGTH: 888
<212> TYPE: DNA
<213> ORGANISM: homo sapiens;

<400> SEQUENCE: 223
gcctccacca agggcccatc ggtcttcccc ctggcaccct cctccaagag cacctctggg 60
ggcacagcag ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggagta caagtgcaag gtctccaaca aagccctccc agcccccatc 540
gagaaaacca tctccaaagc caaagggcag ccccgagaac cacaggtgta caccctgccc 600
ccatcccggg atgagctgac caagaaccag gtcagcctga cctgcctggt caaaggcttc 660
tatcccagcg acatcgccgt ggagtgggag agcaatgggc agccggagaa caactacaag 720
accacgcctc ccgtgctgga ctccgacggc tccttcttcc tctacagcaa gctcaccgtg 780
gacaagagca ggtggcagca ggggaacgtc ttctcatgct ccgtgatgca tgaggctctg 840
cacaaccact acacacagaa gagcctctcc ctgtctccgg gtaaatga 888

<210> SEQ ID NO 224
<211> LENGTH: 993
<212> TYPE: DNA
<213> ORGANISM: homo sapiens;

<400> SEQUENCE: 224
gcctccacca agggcccatc ggtcttcccc ctggcaccct cctccaagag cacctctggg 60
ggcacagcag ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720
ctgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacaca 960
cagaagagcc tctccctgtc tccgggtaaa tga 993

<210> SEQ ID NO 225
<211> LENGTH: 1362
<212> TYPE: DNA
<213> ORGANISM: homo sapiens;

<400> SEQUENCE: 225
gggagtgcat ccgccccaac ccttttcccc ctcgtctcct gtgagaattc cccgtcggat 60
acgagcagcg tggccgttgg ctgcctcgca caggacttcc ttcccgactc catcactttc 120
tcctggaaat acaagaacaa ctctgacatc agcagcaccc ggggcttccc atcagtcctg 180
agagggggca agtacgcagc cacctcacag gtgctgctgc cttccaagga cgtcatgcag 240
ggcacagacg aacacgtggt gtgcaaagtc cagcacccca acggcaacaa agaaaagaac 300
gtgcctcttc cagtgattgc cgagctgcct cccaaagtga gcgtcttcgt cccaccccgc 360
gacggcttct tcggcaaccc ccgcaagtcc aagctcatct gccaggccac gggtttcagt 420
ccccggcaga ttcaggtgtc ctggctgcgc gaggggaagc aggtggggtc tggcgtcacc 480
acggaccagg tgcaggctga ggccaaagag tctgggccca cgacctacaa ggtgaccagc 540

```
acactgacca tcaaagagag cgactggctc agccagagca tgttcacctg ccgcgtggat    600
cacaggggcc tgaccttcca gcagaatgcg tcctccatgt gtggccccga tcaagacaca    660
gccatccggg tcttcgccat ccccccatcc tttgccagca tcttcctcac caagtccacc    720
aagttgacct gcctggtcac agacctgacc acctatgaca gcgtgaccat ctcctggacc    780
cgccagaatg gcgaagctgt gaaaacccac accaacatct ccgagagcca ccccaatgcc    840
actttcagcg ccgtgggtga ggccagcatc tgcgaggatg actggaattc cggggagagg    900
ttcacgtgca ccgtgaccca cacagacctg ccctcgccac tgaagcagac catctcccgg    960
cccaaggggg tggccctgca caggcccgat gtctacttgc tgccaccagc ccgggagcag   1020
ctgaacctgc gggagtcggc caccatcacg tgcctggtga cgggcttctc tcccgcggac   1080
gtcttcgtgc agtggatgca gagggggcag cccttgtccc cggagaagta tgtgaccagc   1140
gccccaatgc ctgagcccca ggccccaggc cggtacttcg cccacagcat cctgaccgtg   1200
tccgaagagg aatggaacac gggggagacc tacacctgcg tggtggccca tgaggccctg   1260
cccaacaggg tcaccgagag gaccgtggac aagtccaccg gtaaacccac cctgtacaac   1320
gtgtccctgg tcatgtccga cacagctggc acctgctact ga                      1362
```

<210> SEQ ID NO 226
<211> LENGTH: 1200
<212> TYPE: DNA
<213> ORGANISM: homo sapiens;

<400> SEQUENCE: 226

```
gcctccacca agggcccatc ggtcttcccc ctggcaccct cctccaagag cacctctggg     60
ggcacagcag ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacaca    960
cagaagagcc tctccctgtc tccggagctg caactggagg agagctgtgc ggaggcgcag   1020
gacggggagc tggacgggct gtggacgacc atcaccatct tcatcacact cttcctgtta   1080
agcgtgtgct acagtgccac cgtcaccttc ttcaaggtga agtggatctt ctcctcggtg   1140
gtggacctga agcagaccat catccccgac tacaggaaca tgatcggaca gggggcctag   1200
```

<210> SEQ ID NO 227

<211> LENGTH: 1293
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 227

```
ncacccacca aggctccgga tgtgttcccc atcatatcag ggtgcagaca cccaaaggat     60

aacagccctg tggtcctggc atgcttgata actgggtacc acccaacgtc cgtgactgtc    120

acctggtaca tggggacaca gagccagccc cagagaacct tccctgagat acaaagacgg    180

gacagctact acatgacaag cagccagctc tccacccccc tccagcagtg gcgccaaggc    240

gagtacaaat gcgtggtcca gcacaccgcc agcaagagta agaaggagat cttccgctgg    300

ccagagtctc caaaggcaca ggcctcctca gtgcccactg cacaacccca agcagagggc    360

agcctcgcca aggcaaccac agccccagcc accacccgta acacaggaag aggaggagaa    420

gagaagaaga aggagaagga gaaagaggaa caagaagaga gagagacaaa gacaccagag    480

tgtccgagcc acacccagcc tcttggcgtc tacctgctaa cccctgcagt gcaggacctg    540

tggctccggg acaaagccac cttcacctgc ttcgtggtgg gcagtgacct gaaggatgct    600

cacctgacct gggaggtggc cgggaaggtc cccacagggg gcgtggagga agggctgctg    660

gagcggcaca gcaacggctc ccagagccag cacagccgtc tgaccctgcc caggtccttg    720

tggaacgcgg ggacctccgt cacctgcaca ctgaaccatc ccagcctccc accccagagg    780

ttgatggcgc tgagagaacc cgctgcgcag gcacccgtca agctttccct gaacctgctg    840

gcctcgtctg accctcccga ggcggcctcg tggctcctgt gtgaggtgtc tggcttctcg    900

ccccccaaca tcctcctgat gtggctggag gaccagcgtg aggtgaacac ttctgggttt    960

gcccccgcac gcccccctcc acagcccggg agcaccacgt tctgggcctg gagtgtgctg   1020

cgtgtcccag ccccgcccag ccctcagcca gccacctaca cgtgtgtggt cagccacgag   1080

gactcccgga ctctgctcaa cgccagccgg agcctagaag tcagctacct ggccatgacc   1140

cccctgatcc ctcagagcaa ggatgagaac agcgatgact acacgacctt tgatgatgtg   1200

ggcagcctgt ggaccgccct gtccacgttt gtggccctct tcatcctcac cctcctctac   1260

agcggcattg tcactttcat caaggtgaag tag                                1293
```

<210> SEQ ID NO 228
<211> LENGTH: 984
<212> TYPE: DNA
<213> ORGANISM: homo sapiens;

<400> SEQUENCE: 228

```
gcttccacca agggcccatc ggtcttcccc ctggcgccct gctccaggag cacctccgag     60

agcacagccg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc atcatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540
```

```
cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaggctc accgtggaca agagcaggtg gcaggagggg    900

aatgtcttct catgctccgt gatgcatgag gctctgcaca accactacac acagaagagc    960

ctctccctgt ctctgggtaa atga                                           984
```

<210> SEQ ID NO 229
<211> LENGTH: 228
<212> TYPE: DNA
<213> ORGANISM: homo sapiens;

<400> SEQUENCE: 229

```
tccggcttct tcgtcttcag ccgcctggag gtgaccaggg ccgaatggga gcagaaagat     60

gagttcatct gccgtgcagt ccatgaggca gcaagcccct cacagaccgt ccagcgagcg    120

gtgtctgtaa atcccgagct ggacgtgtgc gtggaggagg ccgagggcga ggcgccgtgg    180

acgtggaccg gcctctgcat cttcgccgca ctcttcctgc tcagcgtg                 228
```

<210> SEQ ID NO 230
<211> LENGTH: 324
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 230

```
ngaactgtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg ttag                                           324
```

<210> SEQ ID NO 231
<211> LENGTH: 321
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 231

```
ngtcagccca aggctgcccc ctcggtcact ctgttcccgc cctcctctga ggagcttcaa     60

gccaacaagg ccacactggt gtgtctcata agtgacttct acccgggagc cgtgacagtg    120

gcctggaagg cagatagcag ccccgtcaag gcgggagtgg agaccaccac accctccaaa    180

caaagcaaca acaagtacgc ggccagcagc tatctgagcc tgacgcctga gcagtggaag    240

tcccacagaa gctacagctg ccaggtcacg catgaaggga gcaccgtgga gaagacagtg    300
```

gcccctacag aatgttcata g 321

<210> SEQ ID NO 232
<211> LENGTH: 321
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 232
ngtcagccca aggccaaccc cactgtcact ctgttcccgc cctcctctga ggagctccaa 60
gccaacaagg ccacactagt gtgtctgatc agtgacttct acccgggagc tgtgacagtg 120
gcctggaagg cagatggcag ccccgtcaag gcgggagtgg agaccaccaa accctccaaa 180
cagagcaaca acaagtacgc ggccagcagc tacctgagcc tgacgcccga gcagtggaag 240
tcccacagaa gctacagctg ccaggtcacg catgaaggga gcaccgtgga gaagacagtg 300
gcccctacag aatgttcata g 321

<210> SEQ ID NO 233
<211> LENGTH: 321
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 233
ngtcagccca aggctgcccc ctcggtcact ctgttcccgc cctcctctga ggagcttcaa 60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tacctgagcc tgacgcctga gcagtggaag 240
tcccacagaa gctacagctg ccaggtcacg catgaaggga gcaccgtgga gaagacagtg 300
gcccctacag aatgttcata g 321

<210> SEQ ID NO 234
<211> LENGTH: 321
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 234
ngtcagccca aggctgcccc ctcggtcact ctgttcccac cctcctctga ggagcttcaa 60
gccaacaagg ccacactggt gtgtctcgta agtgacttct acccgggagc cgtgacagtg 120
gcctggaagg cagatggcag ccccgtcaag gtgggagtgg agaccaccaa accctccaaa 180
caaagcaaca acaagtatgc ggccagcagc tacctgagcc tgacgcccga gcagtggaag 240
tcccacagaa gctacagctg ccgggtcacg catgaaggga gcaccgtgga gaagacagtg 300
gcccctgcag aatgctctta g 321

<210> SEQ ID NO 235
<211> LENGTH: 61
<212> TYPE: DNA
<213> ORGANISM: homo sapiens;

```
<400> SEQUENCE: 235

tactactact actacggtat ggacgtctgg ggccaaggga ccacggtcac cgtctcctca      60

g                                                                     61

<210> SEQ ID NO 236
<211> LENGTH: 20
<212> TYPE: PRT
<213> ORGANISM: homo sapiens;

<400> SEQUENCE: 236

Tyr Tyr Tyr Tyr Tyr Gly Met Asp Val Trp Gly Gln Gly Thr Thr Val
1               5                   10                  15

Thr Val Ser Ser
            20

<210> SEQ ID NO 237
<211> LENGTH: 101
<212> TYPE: DNA
<213> ORGANISM: homo sapiens;

<400> SEQUENCE: 237

ggtttttgtg gggtgaggat ggacattctg ccattgtgat tactactact actacggtat      60

ggacgtctgg ggccaaggga ccacggtcac cgtctcctca g                        101

<210> SEQ ID NO 238
<211> LENGTH: 38
<212> TYPE: DNA
<213> ORGANISM: homo sapiens;

<400> SEQUENCE: 238

ggtttttgtg gggtgaggat ggacattctg ccattgtg                             38

<210> SEQ ID NO 239
<211> LENGTH: 52
<212> TYPE: DNA
<213> ORGANISM: homo sapiens;

<400> SEQUENCE: 239

gctgaatact tccagcactg gggccagggc accctggtca ccgtctcctc ag             52

<210> SEQ ID NO 240
<211> LENGTH: 52
<212> TYPE: DNA
<213> ORGANISM: homo sapiens;

<400> SEQUENCE: 240

tactggtact tcgatctctg gggccgtggc accctggtca ctgtctcctc ag             52

<210> SEQ ID NO 241
<211> LENGTH: 49
<212> TYPE: DNA
<213> ORGANISM: homo sapiens;

<400> SEQUENCE: 241

gatgcttttg atatctgggg ccaagggaca atggtcaccg tctcttcag                 49

<210> SEQ ID NO 242
<211> LENGTH: 46
<212> TYPE: DNA
<213> ORGANISM: homo sapiens;
```

-continued

<400> SEQUENCE: 242
tactttgact actggggcca gggaaccctg gtcaccgtct cctcag 46

<210> SEQ ID NO 243
<211> LENGTH: 49
<212> TYPE: DNA
<213> ORGANISM: homo sapiens;

<400> SEQUENCE: 243
aactggttcg acccctgggg ccagggaacc ctggtcaccg tctcctcag 49

<210> SEQ ID NO 244
<211> LENGTH: 61
<212> TYPE: DNA
<213> ORGANISM: homo sapiens;

<400> SEQUENCE: 244
tactactact actactacat ggacgtctgg ggcaaaggga ccacggtcac cgtctcctca 60
g 61

<210> SEQ ID NO 245
<211> LENGTH: 494
<212> TYPE: DNA
<213> ORGANISM: homo sapiens;

<400> SEQUENCE: 245
gcatcaccca aaaaccacac ccctccttgg gagaatcccc tagatcacag ctcctcacca 60
tggactggac ctggagcatc cttttcttgg tggcagcagc aacaggtaac ggactcccca 120
gtcccagggc tgagagagaa accaggccag tcatgtgaga cttcacccac tcctgtgtcc 180
tctccacagg tgcccactcc caggttcagc tggtgcagtc tggagctgag gtgaagaagc 240
ctggggcctc agtgaaggtc tcctgcaagg cttctggtta cacctttacc agctatggta 300
tcagctgggt gcgacaggcc cctggacaag ggcttgagtg gatgggatgg atcagcgctt 360
acaatggtaa cacaaactat gcacagaagc tccagggcag agtcaccatg accacagaca 420
catccacgag cacagcctac atggagctga ggagcctgag atctgacgac acggccgtgt 480
attactgtgc gaga 494

<210> SEQ ID NO 246
<211> LENGTH: 500
<212> TYPE: DNA
<213> ORGANISM: homo sapiens;

<400> SEQUENCE: 246
gagagcatca cccagcaacc acatctgtcc tctagagaat cccctgagag ctccgttcct 60
caccatggac tggacctgga ggatcctctt cttggtggca gcagccacag gtaagaggct 120
ccctagtccc agtgatgaga aagagattga gtccagtcca gggagatctc atccacttct 180
gtgttctctc cacaggagcc cactcccagg tgcagctggt gcagtctggg gctgaggtga 240
agaagcctgg ggcctcagtg aaggtctcct gcaaggcttc tggatacacc ttcaccggct 300
actatatgca ctgggtgcga caggcccctg gacaagggct tgagtggatg ggatggatca 360
accctaacag tggtggcaca aactatgcac agaagtttca gggcagggtc accatgacca 420
gggacacgtc catcagcaca gcctacatgg agctgagcag gctgagatct gacgacacgg 480
ccgtgtatta ctgtgcgaga 500

<210> SEQ ID NO 247
<211> LENGTH: 496
<212> TYPE: DNA
<213> ORGANISM: homo sapiens;

<400> SEQUENCE: 247
accatcacac aacagccaca tccctcccct acagaagccc ccagagcgca gcacctcacc 60
atggactgca cctggaggat cctcttcttg gtggcagcag ctacaggcaa gagaatcctg 120
agttccaggg ctgatgaggg gactgggtcc agttaagtgg tgtctcatcc actcctctgt 180
cctctccaca ggcacccacg cccaggtcca gctggtacag tctggggctg aggtgaagaa 240
gcctggggcc tcagtgaagg tctcctgcaa ggtttccgga tacaccctca ctgaattatc 300
catgcactgg gtgcgacagg ctcctggaaa agggcttgag tggatgggag gttttgatcc 360
tgaagatggt gaaacaatct acgcacagaa gttccagggc agagtcacca tgaccgagga 420
cacatctaca gacacagcct acatggagct gagcagcctg agatctgagg acacggccgt 480
gtattactgt gcaaca 496

<210> SEQ ID NO 248
<211> LENGTH: 478
<212> TYPE: DNA
<213> ORGANISM: homo sapiens;

<400> SEQUENCE: 248
ccacatccct cctcagaagc ccccagagca caactcctca ccatggactg gacctggagg 60
atcctctttt tggtggcagc agccacaggt aaggggctgc caaatcccag tgaggaggaa 120
gggatcgaag ccagtcaagg gggcttccat ccactcctgt gtcttctcta caggtgtcca 180
ctcccaggtt cagctggtgc agtctggggc tgaggtgaag aagcctgggg cctcagtgaa 240
ggtttcctgc aaggcttctg gatacacctt cactagctat gctatgcatt gggtgcgcca 300
ggcccccgga caaaggcttg agtggatggg atggagcaac gctggcaatg gtaacacaaa 360
atattcacag gagttccagg gcagagtcac cattaccagg gacacatccg cgagcacagc 420
ctacatggag ctgagcagcc tgagatctga ggacatggct gtgtattact gtgcgaga 478

<210> SEQ ID NO 249
<211> LENGTH: 494
<212> TYPE: DNA
<213> ORGANISM: homo sapiens;

<400> SEQUENCE: 249
atcacccaac aaccacatcc ctcctctaga gaatcccctg aaagcacagc tcctcaccat 60
ggactggacc tggagaatcc tcttcttggt ggcagcagcc acaggtaagg ggctcccaag 120
tcccagtgat gaggagggga ttgagtccag tcaaggtggc ttttatccac tcctgtgtcc 180
cctccacaga tgcctactcc cagatgcagc tggtgcagtc tggggctgag gtgaagaaga 240
ctgggtcctc agtgaaggtt tcctgcaagg cttccggata caccttcacc taccgctacc 300
tgcactgggt gcgacaggcc cccggacaag cgcttgagtg gatgggatgg atcacacctt 360
tcaatggtaa caccaactac gcacagaaat tccaggacag agtcaccatt accagggaca 420
ggtctatgag cacagcctac atggagctga gcagcctgag atctgaggac acagccatgt 480
attactgtgc aaga 494

<210> SEQ ID NO 250
<211> LENGTH: 740
<212> TYPE: DNA

<213> ORGANISM: homo sapiens;

<400> SEQUENCE: 250
atctgtgggg acttgttctt cagtgaaagg atcctgtccg caaacagaaa tggagcagga 60
catgcatttc ttcaagcagg attagggctt ggaccatcag catcccactc ctgtgtggca 120
gatgggacat ctatcttctt tctcaacctc gatcaggctt tgaggtatga aataatctgt 180
ctcatgaata tgcaaataac cttagatcta ctgaggtaaa tatggataca tctgggccct 240
gaaagcatca tccaacaacc acatcccttc tctacagaag cctctgagag gaaagttctt 300
caccatggac tggacctgga gggtcttctg cttgctggct gtagctccag gtaaagggcc 360
aactggttcc agggctgagg aagggatttt ttccagttta gaggactgtc attctctact 420
gtgtcctctc cgcaggtgct cactcccagg tgcagctggt gcagtctggg gctgaggtga 480
agaagcctgg ggcctcagtg aaggtttcct gcaaggcatc tggatacacc ttcaccagct 540
actatatgca ctgggtgcga caggcccctg gacaagggct tgagtggatg ggaataatca 600
accctagtgg tggtagcaca agctacgcac agaagttcca gggcagagtc accatgacca 660
gggacacgtc cacgagcaca gtctacatgg agctgagcag cctgagatct gaggacacgg 720
ccgtgtatta ctgtgcgaga 740

<210> SEQ ID NO 251
<211> LENGTH: 497
<212> TYPE: DNA
<213> ORGANISM: homo sapiens;

<400> SEQUENCE: 251
agcatcatcc agaaaccaca tccctccgct agagaagccc ctgacggcac agttcctcac 60
tatggactgg atttggaggg tcctcttctt ggtgggagca gcgacaggca aggagatgcc 120
aagtcccagt gatgaggagg ggattgagtc cagtcaaggt ggctttcatc cactcctgtg 180
ttctctccac aggtgcccac tcccaaatgc agctggtgca gtctgggcct gaggtgaaga 240
agcctgggac ctcagtgaag gtctcctgca aggcttctgg attcaccttt actagctctg 300
ctatgcagtg ggtgcgacag gctcgtggac aacgccttga gtggatagga tggatcgtcg 360
ttggcagtgg taacacaaac tacgcacaga agttccagga aagagtcacc attaccaggg 420
acatgtccac aagcacagcc tacatggagc tgagcagcct gagatccgag gacacggccg 480
tgtattactg tgcggca 497

<210> SEQ ID NO 252
<211> LENGTH: 498
<212> TYPE: DNA
<213> ORGANISM: homo sapiens;

<400> SEQUENCE: 252
agcatcacat aacaaccaca ttcctcctct gaagaagccc ctgggagcac agctcatcac 60
catggactgg acctggaggt tcctctttgt ggtggcagca gctacaggta aggggcttcc 120
tagtcctaag gctgaggaag ggatcctggt ttagttaaag aggattttat tcacccctgt 180
gtcctctcca caggtgtcca gtcccaggtg cagctggtgc agtctggggc tgaggtgaag 240
aagcctgggt cctcggtgaa ggtctcctgc aaggcttctg gaggcacctt cagcagctat 300
gctatcagct gggtgcgaca ggcccctgga caagggcttg agtggatggg agggatcatc 360
cctatctttg gtacagcaaa ctacgcacag aagttccagg gcagagtcac gattaccgcg 420
gacaaatcca cgagcacagc ctacatggag ctgagcagcc tgagatctga ggacacggcc 480
gtgtattact gtgcgaga 498

<210> SEQ ID NO 253
<211> LENGTH: 499
<212> TYPE: DNA
<213> ORGANISM: homo sapiens;

<400> SEQUENCE: 253
gagcatcact caacaaccac atctgtcctc tagagaaaac cctgtgagca cagctcctca 60
ccatggactg gacctggagg atcctcttct tggtggcagc agctacaagt aaggggcttc 120
ctagtctcaa agctgaggaa cggatcctgg ttcagtcaaa gaggatttta ttctctcctg 180
tgttctctcc acaggtgccc actcccaggt gcagctggtg cagtctgggg ctgaggtgaa 240
gaagcctggg gcctcagtga aggtctcctg caaggcttct ggatacacct tcaccagtta 300
tgatatcaac tgggtgcgac aggccactgg acaagggctt gagtggatgg gatggatgaa 360
ccctaacagt ggtaacacag gctatgcaca gaagttccag ggcagagtca ccatgaccag 420
gaacacctcc ataagcacag cctacatgga gctgagcagc ctgagatctg aggacacggc 480
cgtgtattac tgtgcgaga 499

<210> SEQ ID NO 254
<211> LENGTH: 467
<212> TYPE: DNA
<213> ORGANISM: homo sapiens;

<400> SEQUENCE: 254
gctcagtgac tcctgtgccc caccatggac acactttgct acacactcct gctgctgacc 60
accccttcct gtgagtgctg tggtcaggga cttcctcaga agtgaaacat cagttgtctc 120
ctttgtgggc ttcatcttct tatgtcttct ccacaggggt cttgtcccag gtcaccttga 180
aggagtctgg tcctgtgctg gtgaaaccca cagagaccct cacgctgacc tgcaccgtct 240
ctgggttctc actcagcaat gctagaatgg gtgtgagctg gatccgtcag cccccaggga 300
aggccctgga gtggcttgca cacatttttt cgaatgacga aaaatcctac agcacatctc 360
tgaagagcag gctcaccatc tccaaggaca cctccaaaag ccaggtggtc cttaccatga 420
ccaacatgga ccctgtggac acagccacat attactgtgc acggata 467

<210> SEQ ID NO 255
<211> LENGTH: 463
<212> TYPE: DNA
<213> ORGANISM: homo sapiens;

<400> SEQUENCE: 255
agtgactcct gtgccccacc atggacacac tttgctccac gctcctgctg ctgaccatcc 60
cttcatgtga gtgctgtggt cagggactcc ttcacgggtg aaacatcagt tttcttgttt 120
gtgggcttca tcttcttatg ctttctccac aggggtcttg tcccagatca ccttgaagga 180
gtctggtcct acgctggtga aacccacaca gaccctcacg ctgacctgca ccttctctgg 240
gttctcactc agcactagtg gagtgggtgt gggctggatc cgtcagcccc caggaaaggc 300
cctggagtgg cttgcactca tttattggaa tgatgataag cgctacagcc catctctgaa 360
gagcaggctc accatcacca aggacacctc caaaaaccag gtggtcctta caatgaccaa 420
catggaccct gtggacacag ccacatatta ctgtgcacac aga 463

<210> SEQ ID NO 256

<211> LENGTH: 519
<212> TYPE: DNA
<213> ORGANISM: homo sapiens;

<400> SEQUENCE: 256
atctccacca gctccaccct cccctgggtt caaaagacga ggacagggcc tcgctcagtg 60
aatcctgctc tccaccatgg acatactttg ttccacgctc ctgctactga ctgtcccgtc 120
ctgtgagtgc tgtggtcagg tagtacttca gaagcaaaaa atctattctc tcctttgtgg 180
gcttcatctt cttatgtctt ctccacaggg gtcttatccc aggtcacctt gagggagtct 240
ggtcctgcgc tggtgaaacc cacacagacc ctcacactga cctgcacctt ctctgggttc 300
tcactcagca ctagtggaat gtgtgtgagc tggatccgtc agcccccagg gaaggccctg 360
gagtggcttg cactcattga ttgggatgat gataaatact acagcacatc tctgaagacc 420
aggctcacca tctccaagga cacctccaaa aaccaggtgg tccttacaat gaccaacatg 480
gaccctgtgg acacagccac gtattattgt gcacggata 519

<210> SEQ ID NO 257
<211> LENGTH: 568
<212> TYPE: DNA
<213> ORGANISM: homo sapiens;

<400> SEQUENCE: 257
ctccctctgc tgataaaaac cagccgagcc cagaccctgc agctctggga gaagagcccc 60
agccccagaa ttcccaggag tttccattcg gtgatcagca ctgaacacag aggactcacc 120
atggagtttg ggctgagctg ggttttcctt gttgctatta taaaaggtga tttatggaga 180
actagagaca ttgagtggac gtgagtgaga taagcagtga atatatgtgg cagtttctga 240
ctaggttgtc tctgtgtttg caggtgtcca gtgtcaggtg cagctggtgg agtctggggg 300
aggcttggtc aagcctggag ggtccctgag actctcctgt gcagcctctg gattcacctt 360
cagtgactac tacatgagct ggatccgcca ggctccaggg aaggggctgg agtgggtttc 420
atacattagt agtagtggta gtaccatata ctacgcagac tctgtgaagg gccgattcac 480
catctccagg gacaacgcca agaactcact gtatctgcaa atgaacagcc tgagagccga 540
ggacacggcc gtgtattact gtgcgaga 568

<210> SEQ ID NO 258
<211> LENGTH: 531
<212> TYPE: DNA
<213> ORGANISM: homo sapiens;

<400> SEQUENCE: 258
agctctggga gtggagcccc agccttggga ttcccaagtg tttgtattca gtgatcagga 60
ctgaacacac aggactcacc atggagttgg ggctgagctg ggttttcctt gttgctatat 120
tagaaggtga ttcatggaga actagagata ttgagtgtga atgggcatga atgagagaaa 180
cagtgggtat gtgtggcaat ttctgacttt tgtgtctctg tgtttgcagg tgtccagtgt 240
gaggtgcagc tggtggagtc tgggggaggc ttggtacagc ctgggggtc cctgagactc 300 tcctgtgcag cctctggatt caccttcagt agctacgaca tgcactgggt ccgccaagct 360
acaggaaaag gtctggagtg ggtctcagct attggtactg ctggtgacac atactatcca 420
ggctccgtga agggccgatt caccatctcc agagaaaatg ccaagaactc cttgtatctt 480
caaatgaaca gcctgagagc cggggacacg gctgtgtatt actgtgcaag a 531

<210> SEQ ID NO 259
<211> LENGTH: 540
<212> TYPE: DNA
<213> ORGANISM: homo sapiens;

<400> SEQUENCE: 259
agctctggga gaggagcccc agccttggga ttcccaagtg ttttcattca gtgatcagga 60
ctgaacacag aggactcacc atggagtttg ggctgagctg gattttcctt gctgctattt 120
taaaaggtga tttatggaga actagagaga ttaagtgtga gtggacgtga gtgagagaaa 180
cagtggatat gtgtggcagt ttctgatctt agtgtctctg tgtttgcagg tgtccagtgt 240
gaggtgcagc tggtggagtc tgggggaggc ttggtaaagc ctggggggtc ccttagactc 300
tcctgtgcag cctctggatt cactttcagt aacgcctgga tgagctgggt ccgccaggct 360
ccagggaagg ggctggagtg ggttggccgt attaaaagca aaactgatgg tgggacaaca 420
gactacgctg cacccgtgaa aggcagattc accatctcaa gagatgattc aaaaaacacg 480
ctgtatctgc aaatgaacag cctgaaaacc gaggacacag ccgtgtatta ctgtaccaca 540

<210> SEQ ID NO 260
<211> LENGTH: 526
<212> TYPE: DNA
<213> ORGANISM: homo sapiens;

<400> SEQUENCE: 260
agccctggga gagaagcccc agccctggga ttctcaggtg tttctattgg gtcaacagca 60
ataaacaaat taccatggaa tttgggctga gctgggtttt tcttgctggt attttaaaag 120
gtgattcatg gagaactaag gatattgagt gagtggacat gagtgagaga aacagtggat 180
atgtgtggca gtttctgacc agggtgtctc tgtgtttgca ggtgtccagt gtgaggtgca 240
gctggtggag tctgggggag gcttggtaca gcctgggggg tccctgagac tctcctgtgc 300
agcctctgga ttcaccttca gtaacagtga catgaactgg gcccgcaagg ctccaggaaa 360
ggggctggag tgggtatcgg gtgttagttg gaatggcagt aggacgcact atgtggactc 420
cgtgaagcgc cgattcatca tctccagaga caattccagg aactccctgt atctgcaaaa 480
gaacagacgg agagccgagg acatggctgt gtattactgt gtgaga 526

<210> SEQ ID NO 261
<211> LENGTH: 515
<212> TYPE: DNA
<213> ORGANISM: homo sapiens;

<400> SEQUENCE: 261
ccagccctga gattcccacg tgtttccatt cagtgatcag cactgaacac agaggactcg 60
ccatggagtt tgggctgagc tgggttttcc ttgttgctat tttaaaaggt gattcatgga 120
tcaatagaga tgttgagtgt gagtgaacac gagtgagaga aacagtggat ttgtgtggca 180
gtttctgacc aggtgtctct gtgtttgcag gtgtccagtg tgaggtgcag ctggtggagt 240
ctgggggagg tgtggtacgg cctggggggt ccctgagact ctcctgtgca gcctctggat 300
tcacctttga tgattatggc atgagctggg tccgccaagc tccagggaag gggctggagt 360
gggtctctgg tattaattgg aatggtggta gcacaggtta tgcagactct gtgaagggcc 420
gattcaccat ctccagagac aacgccaaga actccctgta tctgcaaatg aacagtctga 480
gagccgagga cacggccttg tatcactgtg cgaga 515

<210> SEQ ID NO 262

<211> LENGTH: 531
<212> TYPE: DNA
<213> ORGANISM: homo sapiens;

<400> SEQUENCE: 262
agctctgaga gaggagcctt agccctggat tccaaggcct atccacttgg tgatcagcac 60
tgagcaccga ggattcacca tggaactggg gctccgctgg gttttccttg ttgctatttt 120
agaaggtgaa tcatggaaaa gtagagagat ttagtgtgtg tggatatgag tgagagaaac 180
ggtggatgtg tgtgacagtt tctgaccaat gtctctctgt ttgcaggtgt ccagtgtgag 240
gtgcagctgg tggagtctgg gggaggcctg gtcaagcctg gggggtccct gagactctcc 300
tgtgcagcct ctggattcac cttcagtagc tatagcatga actgggtccg ccaggctcca 360
gggaaggggc tggagtgggt ctcatccatt agtagtagta gtagttacat atactacgca 420
gactcagtga agggccgatt caccatctcc agagacaacg ccaagaactc actgtatctg 480
caaatgaaca gcctgagagc cgaggacacg gctgtgtatt actgtgcgag a 531

<210> SEQ ID NO 263
<211> LENGTH: 533
<212> TYPE: DNA
<213> ORGANISM: homo sapiens;

<400> SEQUENCE: 263
agctctgaga gaggagccca gccctgggat tttcaggtgt tttcatttgg tgatcaggac 60
tgaacagaga gaactcacca tggagtttgg gctgagctgg ctttttcttg tggctatttt 120
aaaaggtaat tcatggagaa atagaaaaat tgagtgtgaa tggataagag tgagagaaac 180
agtggatacg tgtggcagtt tctgaccagg gtttcttttt gtttgcaggt gtccagtgtg 240
aggtgcagct gttggagtct gggggaggct tggtacagcc tggggggtcc ctgagactct 300
cctgtgcagc ctctggattc acctttagca gctatgccat gagctgggtc cgccaggctc 360
cagggaaggg gctggagtgg gtctcagcta ttagtggtag tggtggtagc acatactacg 420
cagactccgt gaagggccgg ttcaccatct ccagagacaa ttccaagaac acgctgtatc 480
tgcaaatgaa cagcctgaga gccgaggaca cggccgtata ttactgtgcg aaa 533

<210> SEQ ID NO 264
<211> LENGTH: 532
<212> TYPE: DNA
<213> ORGANISM: homo sapiens;

<400> SEQUENCE: 264
cagctctggg agaggagccc agcactagaa gtcggcggtg tttccattcg gtgatcagca 60
ctgaacacag aggactcacc atggagtttg ggctgagctg ggttttcctc gttgctcttt 120
taagaggtga ttcatggaga aatagagaga ctgagtgtga gtgaacatga gtgagaaaaa 180
ctggatttgt gtggcatttt ctgataacgg tgtccttctg tttgcaggtg tccagtgtca 240
ggtgcagctg gtggagtctg ggggaggcgt ggtccagcct gggaggtccc tgagactctc 300
ctgtgcagcc tctggattca ccttcagtag ctatggcatg cactgggtcc gccaggctcc 360
aggcaagggg ctggagtggg tggcagttat atcatatgat ggaagtaata aatactatgc 420
agactccgtg aagggccgat tcaccatctc cagagacaat tccaagaaca cgctgtatct 480
gcaaatgaac agcctgagag ctgaggacac ggctgtgtat tactgtgcga ga 532

<210> SEQ ID NO 265
<211> LENGTH: 532

<212> TYPE: DNA
<213> ORGANISM: homo sapiens;

<400> SEQUENCE: 265
cagctctggg agaggagccc agcactagaa gtcggcggtg tttccattcg gtgatcagca 60
ctgaacacag aggactcacc atggagtttg ggctgagctg ggttttcctc gttgctcttt 120
taagaggtga ttcatggaga aatagagaga ctgagtgtga gtgaacatga gtgagaaaaa 180
ctggatttgt gtggcatttt ctgataacgg tgtccttctg tttgcaggtg tccagtgtca 240
ggtgcagctg gtggagtctg ggggaggcgt ggtccagcct gggaggtccc tgagactctc 300
ctgtgcagcg tctggattca ccttcagtag ctatggcatg cactgggtcc gccaggctcc 360
aggcaagggg ctggagtggg tggcagttat atggtatgat ggaagtaata aatactatgc 420
agactccgtg aagggccgat tcaccatctc cagagacaat tccaagaaca cgctgtatct 480
gcaaatgaac agcctgagag ccgaggacac ggctgtgtat tactgtgcga ga 532

<210> SEQ ID NO 266
<211> LENGTH: 467
<212> TYPE: DNA
<213> ORGANISM: homo sapiens;

<400> SEQUENCE: 266
aacaaacaaa ttaccatgga atttgggctg agctgggttt ttcttgctgc tattttaaaa 60
ggtgattcat gaagaactaa ggatattgag tgagtggaca tgagtgagag aaacagtgga 120
tttgtgtggc agtttctgac cagggtgtct ctgtgtttgc aggtgtccag tgtgaggtgc 180
agctggtgga gtctgggggga ggcttggtac agcctggggg atccctgaga ctctcctgtg 240
cagcctctgg attcaccttc agtaacagtg acatgaactg ggtccatcag gctccaggaa 300
aggggctgga gtgggtatcg ggtgttagtt ggaatggcag taggacgcac tatgcagact 360
ctgtgaaggg ccgattcatc atctccagag acaattccag gaacaccctg tatctgcaaa 420
cgaatagcct gagggccgag gacacggctg tgtattactg tgtgaga 467

<210> SEQ ID NO 267
<211> LENGTH: 529
<212> TYPE: DNA
<213> ORGANISM: homo sapiens;

<400> SEQUENCE: 267
ctctgggagt ggagccccag ccttgggatt cccaggtgtt tcccttcagt gatcaggact 60
gaacacacac aactcatcat gcagtttgtg ctgagctggg ttttccttgt tggtatttta 120
aaaggtgatt catggagaac tacagatgtt gagtgtgagt ggacatgagt gagcaaaaca 180
gtgggtttgt gtggcagttt ctgaccttgg tgtctctgtg tttgcaggtg tccagtgtga 240
ggtgcagctg gtggagtctg ggggaggctt ggtacagcct agggggtccc tgagactctc 300
ctgtgcagcc tctggattca ccgtcagtag caatgagatg agctggatcc gccaggctcc 360
agggaagggg ctggagtggg tctcatccat tagtggtggt agcacatact acgcagactc 420
caggaagggc agattcacca tctccagaga caattccaag aacacgctgt atcttcaaat 480
gaacaacctg agagctgagg gcacggccgt gtattactgt gccagatat 529

<210> SEQ ID NO 268
<211> LENGTH: 537
<212> TYPE: DNA
<213> ORGANISM: homo sapiens;

<400> SEQUENCE: 268
agctctggga gaggagcccc agccctgaga ttcccaggtg tttccattcg gtgatcagca 60
ctgaacacag agaacgcacc atggagtttg gactgagctg ggttttcctt gttgctattt 120
taaaaggtga ttcatggata aatagagatg ttgagtgtga gtgaacatga gtgagagaaa 180
cagtggatat gtgtggcagt gtctgaccag ggtgtctctg tgtttgcagg tgtccagtgt 240
gaagtgcagc tggtggagtc tgggggagtc gtggtacagc ctggggggtc cctgagactc 300
tcctgtgcag cctctggatt cacctttgat gattatacca tgcactgggt ccgtcaagct 360
ccggggaagg gtctggagtg ggtctctctt attagttggg atggtggtag cacatactat 420
gcagactctg tgaagggccg attcaccatc tccagagaca acagcaaaaa ctccctgtat 480
ctgcaaatga acagtctgag aactgaggac accgccttgt attactgtgc aaaagat 537

<210> SEQ ID NO 269
<211> LENGTH: 533
<212> TYPE: DNA
<213> ORGANISM: homo sapiens;

<400> SEQUENCE: 269
agctctcaga gaggtgcctt agccctggat tccaaggcat ttccacttgg tgatcagcac 60
tgaacacaga ggactcacca tggagttggg gctgtgctgg gttttccttg ttgctatttt 120
agaaggtgat tcatggaaaa ctagagagat ttagtgtgtg tggatatgag tgagagaaac 180
agtggatatg tgtggcagtt tctgaccttg gtgtctcttt gtttgcaggt gtccagtgtg 240
aggtgcagct ggtggagtct gggggaggct tggtacagcc tggggggtcc ctgagactct 300
cctgtgcagc ctctggattc accttcagta gctatagcat gaactgggtc cgccaggctc 360
cagggaaggg gctggagtgg gtttcataca ttagtagtag tagtagtacc atatactacg 420
cagactctgt gaagggccga ttcaccatct ccagagacaa tgccaagaac tcactgtatc 480
tgcaaatgaa cagcctgaga gacgaggaca cggctgtgta ttactgtgcg aga 533

<210> SEQ ID NO 270
<211> LENGTH: 540
<212> TYPE: DNA
<213> ORGANISM: homo sapiens;

<400> SEQUENCE: 270
agctctggga gaggagcccc agccgtgaga ttcccaggag tttccacttg gtgatcagca 60
ctgaacacag accaccaacc atggagtttg ggcttagctg ggttttcctt gttgctattt 120
taaaaggtaa ttcatggtgt actagagata ctgagtgtga ggggacatga gtggtagaaa 180
cagtggatat gtgtggcagt ttctgacctt ggtgtttctg tgtttgcagg tgtccaatgt 240
gaggtgcagc tggtggagtc tgggggaggc ttggtacagc cagggcggtc cctgagactc 300
tcctgtacag cttctggatt cacctttggt gattatgcta tgagctggtt ccgccaggct 360
ccagggaagg ggctggagtg ggtaggtttc attagaagca aagcttatgg tgggacaaca 420
gaatacgccg cgtctgtgaa aggcagattc accatctcaa gagatgattc caaaagcatc 480
gcctatctgc aaatgaacag cctgaaaacc gaggacacag ccgtgtatta ctgtactaga 540

<210> SEQ ID NO 271
<211> LENGTH: 670
<212> TYPE: DNA
<213> ORGANISM: homo sapiens;

<400> SEQUENCE: 271

```
aataccaatc tcccccagga cacttcatct gcacggagcc cggcctctcc tcagatgtcc     60

caccccagag cttgctatat agtcggggac atccaaatag ggccctccct ctgctgatga    120

aaaccagccc agctgaccct gcagctctgg gagaggagcc cagcactggg attccgaggt    180

gtttccattc ggtgatcagc actgaacaca gaggactcac catggagttt tggctgagct    240

gggttttcct tgttgctatt ttaaaaggtg attcatggag aactagagat attgagtgtg    300

agtgaacacg agtgagagaa acagtggata tgtgtggcag tttctaacca atgtctctgt    360

gtttgcaggt gtccagtgtg aggtgcagct ggtggagtct ggaggaggct tgatccagcc    420

tggggggtcc ctgagactct cctgtgcagc ctctgggttc accgtcagta gcaactacat    480

gagctgggtc cgccaggctc cagggaaggg gctggagtgg gtctcagtta tttatagcgg    540

tggtagcaca tactacgcag actccgtgaa gggccgattc accatctcca gagacaattc    600

caagaacacg ctgtatcttc aaatgaacag cctgagagcc gaggacacgg ccgtgtatta    660

ctgtgcgaga                                                           670
```

<210> SEQ ID NO 272
<211> LENGTH: 534
<212> TYPE: DNA
<213> ORGANISM: homo sapiens;

<400> SEQUENCE: 272

```
agctctggga gaggagcccc cgccctggga ttcccaggtg ttttcatttg gtgatcagca     60

ctgaacacag aagagtcatg atggagtttg ggctgagctg ggttttcctt gttgctattt    120

ttaaaggtga ttcatgagga aatagagata ttgagtgtga gtggacatga gtgagagaaa    180

cagtggattt gtgtggcagt ttctgacctt ggtgtctctg tgtttgcagg tgtccagtgt    240

gaggtgcagc tggtggagtc tggggaaggc ttggtccagc ctggggggtc cctgagactc    300

tcctgtgcag cctctggatt caccttcagt agctatgcta tgcactgggt ccgccaggct    360

ccagggaagg gactggaata tgtttcagct attagtagta atgggggtag cacatattat    420

gcagactctg tgaagggcag attcaccatc tccagagaca attccaagaa cacgctgtat    480

cttcaaatgg gcagcctgag agctgaggac atggctgtgt attactgtgc gaga          534
```

<210> SEQ ID NO 273
<211> LENGTH: 528
<212> TYPE: DNA
<213> ORGANISM: homo sapiens;

<400> SEQUENCE: 273

```
agctctggga gaggagccca gcactgggat tccgaggtgt ttccattcag tgatctgcac     60

tgaacacaga ggactcgcca tggagtttgg gctgagctgg gttttccttg ttgctatttt    120

aaaaggtgat tcatggagaa ctagagatat tgagtgtgag tgaacacgag tgagagaaac    180

agtggatatg tgtggcagtt tctaaccaat gtctctgtgt ttgcaggtgt ccagtgtgag    240

gtgcagctgg tggagtctgg aggaggcttg atccagcctg gggggtccct gagactctcc    300

tgtgcagcct ctgggttcac cgtcagtagc aactacatga gctgggtccg ccaggctcca    360

gggaaggggc tggagtgggt ctcagttatt tatagctgtg gtagcacata ctacgcagac    420

tccgtgaagg gccgattcac catctccaga gacaattcca agaacacgct gtatcttcaa    480

atgaacagcc tgagagctga ggacacggct gtgtattact gtgcgaga                 528
```

<210> SEQ ID NO 274

<211> LENGTH: 533
<212> TYPE: DNA
<213> ORGANISM: homo sapiens;

<400> SEQUENCE: 274
aggtctcaga gaggagcctt agccctggac tccaaggcct ttccacttgg tgatcagcac 60
tgagcacaga ggactcacca tggaattggg gctgagctgg gttttccttg ttgctatttt 120
agaaggtgat tcatggaaaa ctaggaagat tgagtgtgtg tggatatgag tgtgagaaac 180
agtggatttg tgtggcagtt tctgaccttg gtgtctcttt gtttgcaggt gtccagtgtg 240
aggtgcagct ggtggagtct gggggaggct tggtccagcc tggggggtcc ctgagactct 300
cctgtgcagc ctctggattc acctttagta gctattggat gagctgggtc cgccaggctc 360
cagggaaggg gctggagtgg gtggccaaca taaagcaaga tggaagtgag aaatactatg 420
tggactctgt gaagggccga ttcaccatct ccagagacaa cgccaagaac tcactgtatc 480
tgcaaatgaa cagcctgaga gccgaggaca cggctgtgta ttactgtgcg aga 533

<210> SEQ ID NO 275
<211> LENGTH: 540
<212> TYPE: DNA
<213> ORGANISM: homo sapiens;

<400> SEQUENCE: 275
agctctgaga gcggagcccc agccccagaa ttcccaggtg ttttcatttg gtgatcagca 60
ctgaacacag aggactcacc atggagtttg ggctgagctg ggttttcctt gttgttattt 120
tacaaggtga tttatggaga actagagatg ttaagtgtga gtggacgtga gtgagagaaa 180
cagtggattt gtgtgacagt ttctgaccag ggtgtctctg tgtttgcagg tgtccagtgt 240
gaggtgcagc tggtggagtc tgggggaggc ttggtccagc ctggagggtc cctgagactc 300
tcctgtgcag cctctggatt caccttcagt gaccactaca tggactgggt ccgccaggct 360
ccagggaagg ggctggagtg ggttggccgt actagaaaca aagctaacag ttacaccaca 420
gaatacgccg cgtctgtgaa aggcagattc accatctcaa gagatgattc aaagaactca 480
ctgtatctgc aaatgaacag cctgaaaacc gaggacacgg ccgtgtatta ctgtgctaga 540

<210> SEQ ID NO 276
<211> LENGTH: 540
<212> TYPE: DNA
<213> ORGANISM: homo sapiens;

<400> SEQUENCE: 276
agctctggga gaggagctcc agccttggga ttcccagctg tctccactcg gtgatcggca 60
ctgaatacag gagactcacc atggagtttg ggctgagctg ggttttcctt gttgctattt 120
taaaaggtga ttcatgggga actagagata ctgagtgtga gtggacatga gtgagagaaa 180
cagtggacgt gtgtggcact ttctgaccag ggtgtctctg tgtttgcagg tgtccagtgt 240
gaggtgcagc tggtggagtc cgggggaggc ttggtccagc ctggggggtc cctgaaactc 300
tcctgtgcag cctctgggtt caccttcagt ggctctgcta tgcactgggt ccgccaggct 360
tccgggaaag ggctggagtg ggttggccgt attagaagca aagctaacag ttacgcgaca 420
gcatatgctg cgtcggtgaa aggcaggttc accatctcca gagatgattc aaagaacacg 480
gcgtatctgc aaatgaacag cctgaaaacc gaggacacgg ccgtgtatta ctgtactaga 540

<210> SEQ ID NO 277
<211> LENGTH: 690

<212> TYPE: DNA
<213> ORGANISM: homo sapiens;

<400> SEQUENCE: 277
aatttctcaa atcccattgt tgtcacccat cttcctcagg acactttcat ctgccctggg 60
tcctgctctt tcttcaggtg tctcacccca gagcttgata tatagtagga gacatgcaaa 120
tagggccctc actctgctga agaaaaccag ccctgcagct ctgggagagg agccccagcc 180
ctgggattcc cagctgtttc tgcttgctga tcaggactgc acacagagaa ctcaccatgg 240
agtttgggct gagctgggtt ttccttgttg ctattttaaa aggtgattca tggagaactg 300
gagatatgga gtgtgaatgg acatgagtga gataagcagt ggatgtgtgt ggcagtttct 360
gaccagggtg tctctgtgtt tgcaggtgtc cagtgtgagg tgcagctggt ggagtccggg 420
ggaggcttag ttcagcctgg ggggtccctg agactctcct gtgcagcctc tggattcacc 480
ttcagtagct actggatgca ctgggtccgc caagctccag ggaaggggct ggtgtgggtc 540
tcacgtatta atagtgatgg gagtagcaca agctacgcgg actccgtgaa gggccgattc 600
accatctcca gagacaacgc caagaacacg ctgtatctgc aaatgaacag tctgagagcc 660
gaggacacgg ctgtgtatta ctgtgcaaga 690

<210> SEQ ID NO 278
<211> LENGTH: 525
<212> TYPE: DNA
<213> ORGANISM: homo sapiens;

<400> SEQUENCE: 278
agctctggga gaggagcccc agccctgaga ttcccaggtg tttccattca gtgatcagca 60
ctgaacacag aggactcacc atggagttgg gactgagctg gattttcctt ttggctattt 120
taaaaggtga ttcatggaga aatagagaga ttgagtgtga gtggacatga gtggatttgt 180
gtggcagttt ctgaccttgg tgtctctgtg tttgcaggtg tccagtgtga agtgcagctg 240
gtggagtctg gggaggctt ggtacagcct ggcaggtccc tgagactctc ctgtgcagcc 300
tctggattca cctttgatga ttatgccatg cactgggtcc ggcaagctcc agggaagggc 360
ctggagtggg tctcaggtat tagttggaat agtggtagca taggctatgc ggactctgtg 420
aagggccgat tcaccatctc cagagacaac gccaagaact ccctgtatct gcaaatgaac 480
agtctgagag ctgaggacac ggccttgtat tactgtgcaa aagat 525

<210> SEQ ID NO 279
<211> LENGTH: 505
<212> TYPE: DNA
<213> ORGANISM: homo sapiens;

<400> SEQUENCE: 279
atttccttaa attcagggtc ctgctcacat gggaaatact ttctgagagt cctggacctc 60
ctgtgcaaga acatgaaaca cctgtggttc ttcctcctgc tggtggcagc tcccagatgt 120
gagtgtctca aggctgcaga catggagata tgggaggtgc ctctgagccc agggctcact 180
gtgggtctct ctgttcacag tggtcctgtc ccaggtgcag ctgcaggagt cgggcccagg 240
actggtgaag ccttcggaca ccctgtccct cacctgcgct gtctctggtt actccatcag 300
cagtagtaac tggtggggct ggatccggca gcccccaggg aagggactgg agtggattgg 360
gtacatctat tatagtggga gcacctacta caacccgtcc ctcaagagtc gagtcaccat 420
gtcagtagac acgtccaaga accagttctc cctgaagctg agctctgtga ccgccgtgga 480

-continued cacggccgtg tattactgtg cgaga 505

<210> SEQ ID NO 280
<211> LENGTH: 508
<212> TYPE: DNA
<213> ORGANISM: homo sapiens;

<400> SEQUENCE: 280
atttccttaa attcagggtc ctgctcacat gggaaatact ttctgagagt cctggacctc 60
ctgtgcaaga acatgaaaca cctgtggttc ttcctcctgc tggtggcagc tcccagatgt 120
gagtgtctca aggctgcaga catggagata tgggaggtgc ctctgatccc agggctcact 180
gtgtgtctct ctgttcacag gggtcctgcc ccaggtgcag ctgcaggagt cgggcccagg 240
actggtgaag ccttcacaga ccctgtccct cacctgtact gtctctggtg gctccatcag 300
cagtggtggt tactactgga gctggatccg ccagcaccca gggaagggcc tggagtggat 360
tgggtacatc tattacagtg ggagcaccta ctacaacccg tccctcaaga gtcgagttac 420
catatcagta gacacgtcta agaaccagtt ctccctgaag ctgagctctg tgactgccgc 480
ggacacggcc gtgtattact gtgcgaga 508

<210> SEQ ID NO 281
<211> LENGTH: 483
<212> TYPE: DNA
<213> ORGANISM: homo sapiens;

<400> SEQUENCE: 281
cagctcacat gggaagtgct ttctgagagt catggacctc ctgcacaaga acatgaaaca 60
cctgtggttc ttcctcctcc tggtggcagc tcccagatgt gagtgtctca ggaatgcgga 120
tatgaagata tgagatgctg cctctgatcc cagggctcac tgtgggtttc tctgttcaca 180
ggggtcctgt cccaggtgca gctacagcag tggggcgcag gactgttgaa gccttcggag 240
accctgtccc tcacctgcgc tgtctatggt gggtccttca gtggttacta ctggagctgg 300
atccgccagc ccccagggaa ggggctggag tggattgggg aaatcaatca tagtggaagc 360
accaactaca acccgtccct caagagtcga gtcaccatat cagtagacac gtccaagaac 420
cagttctccc tgaagctgag ctctgtgacc gccgcggaca cggctgtgta ttactgtgcg 480
aga 483

<210> SEQ ID NO 282
<211> LENGTH: 508
<212> TYPE: DNA
<213> ORGANISM: homo sapiens;

<400> SEQUENCE: 282
atttccttaa attcaggtcc aactcataag ggaaatgctt tctgagagtc atggatctca 60
tgtgcaagaa aatgaagcac ctgtggttct tcctcctgct ggtggcggct cccagatgtg 120
agtgtttcta ggatgcagac atggagatat gggaggctgc ctctgatccc agggctcact 180
gtgggttttt ctgttcacag gggtcctgtc ccagctgcag ctgcaggagt cgggcccagg 240
actggtgaag ccttcggaga ccctgtccct cacctgcact gtctctggtg gctccatcag 300
cagtagtagt tactactggg gctggatccg ccagccccca gggaaggggc tggagtggat 360
tgggagtatc tattatagtg ggagcaccta ctacaacccg tccctcaaga gtcgagtcac 420
catatccgta gacacgtcca agaaccagtt ctccctgaag ctgagctctg tgaccgccgc 480
agacacggct gtgtattact gtgcgaga 508

<210> SEQ ID NO 283
<211> LENGTH: 494
<212> TYPE: DNA
<213> ORGANISM: homo sapiens;

<400> SEQUENCE: 283
aaattcaggg tccagctcac atgggaaata ctttctgaga ctcatggacc tcctgcacaa 60
gaacatgaaa cacctgtggt tcttcctcct gctggtggca gctcccagat gtgagtgtct 120
caaggctgca gacatgggga tatgggaggt gcctctgatc ccagggctca ctgtgggtct 180
ctctgttcac aggggtcctg tcccaggtgc agctgcagga gtcgggccca ggactggtga 240
agccttcgga gaccctgtcc ctcacctgca ctgtctctgg tggctccatc agtagttact 300
actggagctg gatccggcag cccgccggga agggactgga gtggattggg cgtatctata 360
ccagtgggag caccaactac aacccctccc tcaagagtcg agtcaccatg tcagtagaca 420
cgtccaagaa ccagttctcc ctgaagctga gctctgtgac cgccgcggac acggccgtgt 480
attactgtgc gaga 494

<210> SEQ ID NO 284
<211> LENGTH: 2025
<212> TYPE: DNA
<213> ORGANISM: homo sapiens;

<400> SEQUENCE: 284
ttttcacctc tccatacaaa ggcaccaccc acatgcaaat cctcacttaa gcacccacag 60
gaaaccacca cacatttcct taaattcagg ttccagctca catgggaaat actttctgag 120
agtcctggac ctcctgtgca agaacatgaa acatctgtgg ttcttccttc tcctggtggc 180
agctcccaga tgtgagtatc tcagggatcc agacatgggg atatgggagg tgcctctgat 240
cccagggctc actgtgggtc tctctgttca caggggtcct gtcccaggtg cagctgcagg 300
agtcgggccc aggactggtg aagccttcgg agaccctgtc cctcacctgc actgtctctg 360
gtggctccat cagtagttac tactggagct ggatccggca gcccccaggg aagggactgg 420
agtggattgg gtatatctat tacagtggga gcaccaacta caacccctcc ctcaagagtc 480
gagtcaccat atcagtagac acgtccaaga accagttctc cctgaagctg agctctgtga 540
ccgctgcgga cacggccgtg tattactgtg cgagagacac agtgagggga ggtgagtgtg 600
agcccagaca aaaacctccg tgcagggagg cggaggggac cggcgcaggt gctgctcagc 660
gccagcaggg ggcgcgcggg gcccacagag caggaggccc ggtcaggagc aggtgcaggg 720
agggcggggc ttcctcatct gctcagtggt ctccctcctc gccagcacct cagctgtccc 780
caggggtcct ctttctttat tatctgtggt tctgcttcct cacattcttg tgccaagaaa 840
gaaatgagga agacaaattt tcgtctgtag ttgaagtttc accaattact aggaactttc 900
ctagaagttc ctgcatggcc cattatagct tacagattaa atatatatca agcttctcat 960
ctcttgattt gtgtcatcaa ctgaattgtg ccctctttga aattcatatg cagaaacctt 1020
aaattcaatt gatgtatatt ggaattttaa tgaaataatt aaggttaaat gtggtcataa 1080
gtgtaagact ctaattcaac agacgtgtcg tctttataag aagaggaaga gacaccagag 1140
acctctcact tttcacgtgc aggcagagaa gaggccatgt ggagacgtaa tgcactagaa 1200
ggtggcccag tgcaagccag gaagaagcct caccaagaac caaccctgcc agaacattga 1260
tcttcaacat tcagactgca gaattttaag aaaatcaata tttgttgttt aagccaccca 1320
ctcctgttgt cttcttatga agatccagac agactaatac cacataactc tgttagcgct 1380
gtcccctgga tgcagaatca gcccgctggg gctgggcaca tctctcagat ttccacataa 1440
agtaggcaaa aaatagtagt tctgatataa aaatttgtca tgtccctgtt ggccaatttc 1500
tgggcaaggt cttttaaaga agccctgggg gctttgtcac aaaagttgcc ttttatcatt 1560
tattaggaca taactgatga acaatgagta ccagttggat ggagactgac cactgaccat 1620
cttctgctgt ctcctaagta tgccacagaa aaccacacca acattactct atgtcttcaa 1680
ctttctaaat ttgcactgat tggtatttaa ggcaggccca gcgttgaata actcctttag 1740
tttttgcttc tctgggaaag gtcttatcta tcctggcctt ggtcttcaag tttcagcaat 1800
tctgggaagc caaggacgcc tctatctcct cctccatgct ctgcaactca cctgagaaca 1860
gctttctcat tggaatgtct tctgtttaag gaataagagt ccctgtttca ggcttgggtg 1920
cctgagtaca cctactggat ccagcccagg attggagaaa ctttccagaa cacatcacct 1980
gagaaatgac cagtcacact gttacacttt cacaatttcc gcttc 2025

<210> SEQ ID NO 285
<211> LENGTH: 537
<212> TYPE: DNA
<213> ORGANISM: homo sapiens;

<400> SEQUENCE: 285
acttaagcac ccacaggaaa ccaccacaca tttccttaaa ttcaggttcc agctcacatg 60
ggaaatactt tctgagagtc ctggacctcc tgtgcaagaa catgaaacac ctgtggttct 120
tcctcctcct ggtggcagct cccagatgtg agtgtctcag ggatccagac atgggggtat 180
gggaggtgcc tctgatccca gggctcactg tgggtctctc tgttcacagg ggtcctgtcc 240
caggtgcagc tgcaggagtc gggcccagga ctggtgaagc cttcggagac cctgtccctc 300
acctgcactg tctctggtgg ctccgtcagc agtggtggtt actactggag ctggatccgg 360
cagcccccag ggaagggact ggagtggatt gggtatatct attacagtgg gagcaccaac 420
tacaacccct ccctcaagag tcgagtcacc atatcagtag acacgtccaa gaaccagttc 480
tccctgaagc tgagctctgt gaccgctgcg gacacggccg tgtattactg tgcgaga 537

<210> SEQ ID NO 286
<211> LENGTH: 493
<212> TYPE: DNA
<213> ORGANISM: homo sapiens;

<400> SEQUENCE: 286
tgagtctccc tcactgccca gctgggatct cagggcttca ttttctgtcc tccaccatca 60
tggggtcaac cgccatcctc gccctcctcc tggctgttct ccaaggtcag tcctgccgag 120
ggcttgaggt cacagaggag aacgggtgga aaggagcccc tgattcaaat tttgtgtctc 180
ccccacagga gtctgtgccg aggtgcagct ggtgcagtct ggagcagagg tgaaaaagcc 240
cggggagtct ctgaagatct cctgtaaggg ttctggatac agctttacca gctactggat 300
cggctgggtg cgccagatgc ccgggaaagg cctggagtgg atggggatca tctatcctgg 360
tgactctgat accagataca gcccgtcctt ccaaggccag gtcaccatct cagccgacaa 420
gtccatcagc accgcctacc tgcagtggag cagcctgaag gcctcggaca ccgccatgta 480
ttactgtgcg aga 493

<210> SEQ ID NO 287
<211> LENGTH: 498

<212> TYPE: DNA
<213> ORGANISM: homo sapiens;

<400> SEQUENCE: 287
gcagagcctg ctgaattctg gctgaccagg gcagtcacca gagctccaga caatgtctgt 60
ctccttcctc atcttcctgc ccgtgctggg cctcccatgg ggtcagtgtc agggagatgc 120
cgtattcaca gcagcattca cagactgagg ggtgtttcac tttgctgttt ccttttgtct 180
ccaggtgtcc tgtcacaggt acagctgcag cagtcaggtc caggactggt gaagccctcg 240
cagaccctct cactcacctg tgccatctcc ggggacagtg tctctagcaa cagtgctgct 300
tggaactgga tcaggcagtc cccatcgaga ggccttgagt ggctgggaag gacatactac 360
aggtccaagt ggtataatga ttatgcagta tctgtgaaaa gtcgaataac catcaaccca 420
gacacatcca agaaccagtt ctccctgcag ctgaactctg tgactcccga ggacacggct 480
gtgtattact gtgcaaga 498

<210> SEQ ID NO 288
<211> LENGTH: 489
<212> TYPE: DNA
<213> ORGANISM: homo sapiens;

<400> SEQUENCE: 288
acccaacaac aacatccctc cttgggagaa tcccctagag cacagctcct caccatggac 60
tggacctgga gcatcctctt cttggtggca gcagcaacag gtaaggggct ccccagtctc 120
ggggttgagg cagaaaccag gccactcaag tgaggcttta cccacccctg tgtcctctcc 180
acaggtacct actcccaggt gcagctggtg cagtctggcc atgaggtgaa gcagcctggg 240
gcctcagtga aggtctcctg caaggcttct ggttacagtt tcaccaccta tggtatgaat 300
tgggtgccac aggcccctgg acaagggctt gagtggatgg gatggttcaa cacctacact 360
gggaacccaa catatgccca gggcttcaca ggacggtttg tcttctccat ggacacctct 420
gccagcacag catacctgca gatcagcagc ctaaaggctg aggacatggc catgtattac 480
tgtgcgaga 489

<210> SEQ ID NO 289
<211> LENGTH: 38
<212> TYPE: DNA
<213> ORGANISM: homo sapiens;

<400> SEQUENCE: 289
gtacactttt ggccagggga ccaagctgga gatcaaac 38

<210> SEQ ID NO 290
<211> LENGTH: 38
<212> TYPE: DNA
<213> ORGANISM: homo sapiens;

<400> SEQUENCE: 290
attcactttc ggccctggga ccaaagtgga tatcaaac 38

<210> SEQ ID NO 291
<211> LENGTH: 37
<212> TYPE: DNA
<213> ORGANISM: homo sapiens;

<400> SEQUENCE: 291
ctcactttcg gcggagggac caaggtggag atcaaac 37

<210> SEQ ID NO 292
<211> LENGTH: 38
<212> TYPE: DNA
<213> ORGANISM: homo sapiens;

<400> SEQUENCE: 292
gatcaccttc ggccaaggga cacgactgga gattaaac 38

<210> SEQ ID NO 293
<211> LENGTH: 503
<212> TYPE: DNA
<213> ORGANISM: homo sapiens;

<400> SEQUENCE: 293
aggaatcaga cccagtcagg acacagcatg gacatgagag tcctcgctca gctcctgggg 60
ctcctgctgc tctgtttccc aggtaaggat ggagaacact agcagtttac tcagcccagg 120
gtgctcagta ctgctttact attcagggaa attctcttac aacatgatta attgtgtgga 180
catttgtttt tatgtttcca atctcaggtg ccagatgtga catccagatg acccagtctc 240
catcctcact gtctgcatct gtaggagaca gagtcaccat cacttgtcgg gcgagtcagg 300
gcattagcaa ttatttagcc tggtttcagc agaaaccagg gaaagcccct aagtccctga 360
tctatgctgc atccagtttg caaagtgggg tcccatcaaa gttcagcggc agtggatctg 420
ggacagattt cactctcacc atcagcagcc tgcagcctga agattttgca acttattact 480
gccaacagta taatagttac cct 503

<210> SEQ ID NO 294
<211> LENGTH: 503
<212> TYPE: DNA
<213> ORGANISM: homo sapiens;

<400> SEQUENCE: 294
aggaatcagt cccactcagg acacagcatg gacatgaggg tccccgctca gctcctgggg 60
ctcctgctgc tctggttccc aggtaaggat ggagaacact agcagtttac tcagcccaga 120
gtgctcagta ctgctttact gttcagggaa attctcttac aacatgatta attgtgtgga 180
catttgtttt tatgtttcca atctcaggtg ccaggtgtga catccagatg acccagtctc 240
catcctccct gtctgcatct gtaggagaca gagtcaccat cacttgccgg gcaagtcagg 300
gcattagaaa tgatttaggc tggtatcagc agaaaccagg gaaagcccct aagcgcctga 360
tctatgctgc atccagtttg caaagtgggg tcccatcaag gttcagcggc agtggatctg 420
ggacagaatt cactctcaca atcagcagcc tgcagcctga agattttgca acttattact 480
gtctacagca taatagttac cct 503

<210> SEQ ID NO 295
<211> LENGTH: 657
<212> TYPE: DNA
<213> ORGANISM: homo sapiens;

<400> SEQUENCE: 295
gggacacctg gggacactga gctggtgctg agttactgag atgagccagc tctgcagctg 60
tgcccagcct gccccatccc ctgctcattt gcatgttccc agagcacaac ctcctgccct 120
gaagccttat taataggctg gtcacacttt gtgcaggagt cagacccagt caggacacag 180
catggacatg agggtccccg ctcagctcct ggggctcctg ctgctctggc tcccaggtaa 240
ggaaggagaa cactaggaat ttactcagcc cagtgtgctc agtactgcct ggttattcag 300
ggaagtcttc ctataatatg atcaatagta tgaatatttg tgtttctatt tccaatctca 360
ggtgccaaat gtgacatcca gatgacccag tctccttcca ccctgtctgc atctgtagga 420
gacagagtca ccatcacttg ccgggccagt cagagtatta gtagctggtt ggcctggtat 480
cagcagaaac cagggaaagc ccctaagctc ctgatctata aggcgtctag tttagaaagt 540
ggggtcccat caaggttcag cggcagtgga tctgggacag aattcactct caccatcagc 600
agcctgcagc ctgatgattt tgcaacttat tactgccaac agtataatag ttattct 657

<210> SEQ ID NO 296
<211> LENGTH: 506
<212> TYPE: DNA
<213> ORGANISM: homo sapiens;

<400> SEQUENCE: 296
gcaggagtca gacccactca ggacacagca tggacatgag ggtccccgct cagctcctgg 60
ggctcctgct gctctggctc ccaggtaagg atggagaaca ctggcagttt actcagccca 120
gggtgctcag cacagcctgg ctattcaggg aaattctctt actacatgat taattgtgtg 180
gaccatttgt ttttgtgttt ccaatctcag gtgccagatg tgccatccag atgacccagt 240
ctccatcctc cctgtctgca tctgtaggag acagagtcac catcacttgc cgggcaagtc 300
agggcattag aaatgattta ggctggtatc agcagaaacc agggaaagcc cctaagctcc 360
tgatctatgc tgcatccagt ttacaaagtg gggtcccatc aaggttcagc ggcagtggat 420
ctggcacaga tttcactctc accatcagca gcctgcagcc tgaagatttt gcaacttatt 480
actgtctaca agattacaat taccct 506

<210> SEQ ID NO 297
<211> LENGTH: 523
<212> TYPE: DNA
<213> ORGANISM: homo sapiens;

<400> SEQUENCE: 297
aggctggaca cacttcatgc aggagtcaga ccctgtcagg acacagcata gacatgaggg 60
tccccgctca gctcctgggg ctcctgctgc tctggctccc aggtaaggaa ggagaacact 120
aggaatttac tcagcccagt gtgcttggta cagcctggcc cttcagggaa gttctcttac 180
aacatgatta attgtatgga catttgtttt tatgtttcca atctcaggtg ccagatgtgc 240
catccggatg acccagtctc catcctcatt ctctgcatct acaggagaca gagtcaccat 300
cacttgtcgg gcgagtcagg gtattagcag ttatttagcc tggtatcagc aaaaaccagg 360
gaaagcccct aagctcctga tctatgctgc atccactttg caaagtgggg tcccatcaag 420
gttcagcggc agtggatctg ggacagattt cactctcacc atcagctgcc tgcagtctga 480
agattttgca acttattact gtcaacagta ttatagttac cct 523

<210> SEQ ID NO 298
<211> LENGTH: 534
<212> TYPE: DNA
<213> ORGANISM: homo sapiens;

<400> SEQUENCE: 298
agacttctta ataggctggt cacacctgtg caggagtcag tcccagtcag gacacagcat 60
ggacatgagg gtccccgctc agctcctggg gctcctgctg ctctggctcc caggtaagga 120
aggagaacac taggaattta ctcagcccag tgtgttccgt acagcctggc tcttgaggga 180

| | | |
|---|---|---|
| agttctctta caacatgatt aattctatgg acatttgtgt ttatatttcc aatctcaggt | 240 | |
| gccagatgtg acatccagtt gacccagtct ccatccttcc tgtctgcatc tgtaggagac | 300 | |
| agagtcacca tcacttgccg ggccagtcag ggcattagca gttatttagc ctggtatcag | 360 | |
| caaaaaccag ggaaagcccc taagctcctg atctatgctg catccacttt gcaaagtggg | 420 | |
| gtcccatcaa ggttcagcgg cagtggatct gggacagaat tcactctcac aatcagcagc | 480 | |
| ctgcagcctg aagattttgc aacttattac tgtcaacagc ttaatagtta ccct | 534 | |

<210> SEQ ID NO 299
<211> LENGTH: 656
<212> TYPE: DNA
<213> ORGANISM: homo sapiens;

<400> SEQUENCE: 299

| | | |
|---|---|---|
| gggacacctg gggacactga gctggtgctg agttactgag atgagccagc cctgcagctg | 60 | |
| cgcccagcct gccccatccc ctgctcattt gcatgttccc agagcacagt ctcctgacct | 120 | |
| gaagacttat taacaggctg atcacaccct gtgcaggagt cagacccagt caggacacag | 180 | |
| catggacatg agggtccccg ctcagctcct ggggctcctg ctgctctggt tcccaggtaa | 240 | |
| gaaaggagaa cactaggatt atactcggtc agtgtgctga gtactgcttt actattcagg | 300 | |
| gaacttctct tacagcatga ttaattgtgt ggacatttgt ttttatgttt ccaatctcag | 360 | |
| gttccagatg cgacatccag atgacccagt ctccatcttc tgtgtctgca tctgtaggag | 420 | |
| acagagtcac catcacttgt cgggcgagtc agggtattag cagctggtta gcctggtatc | 480 | |
| agcagaaacc agggaaagcc cctaagctcc tgatctatgc tgcatccagt ttgcaaagtg | 540 | |
| gggtcccatc aaggttcagc ggcagtggat ctgggacaga tttcactctc actatcagca | 600 | |
| gcctgcagcc tgaagatttt gcaacttact attgtcaaca ggctaacagt ttccct | 656 | |

<210> SEQ ID NO 300
<211> LENGTH: 503
<212> TYPE: DNA
<213> ORGANISM: homo sapiens;

<400> SEQUENCE: 300

| | | |
|---|---|---|
| aggaatcaga cccagtcagg acacagcatg gacatgaggg tcctcgctca gctcctgggg | 60 | |
| ctcctgctgc tctgtttccc aggtaaggat ggagaacact agcagtttac tcagcccagg | 120 | |
| gtgctcagta ctgctttact attcagggaa attctcttac aacatgatta attgtgtgga | 180 | |
| catttgttt tatgtttcca atctcaggtg ccagatgtga catccagatg acccagtctc | 240 | |
| catcctcact gtctgcatct gtaggagaca gagtcaccat cacttgtcgg gcgagtcagg | 300 | |
| gtattagcag ctggttagcc tggtatcagc agaaaccaga gaaagcccct aagtccctga | 360 | |
| tctatgctgc atccagtttg caaagtgggg tcccatcaag gttcagcggc agtggatctg | 420 | |
| ggacagattt cactctcacc atcagcagcc tgcagcctga agattttgca acttattact | 480 | |
| gccaacagta taatagttac cct | 503 | |

<210> SEQ ID NO 301
<211> LENGTH: 657
<212> TYPE: DNA
<213> ORGANISM: homo sapiens;

<400> SEQUENCE: 301

| | | |
|---|---|---|
| gggacacctg gggacactga gctgctgctg agttactgag atgagccagc cctgcagctg | 60 | |
| cgcccagcct gccccatccc ctgctcattt gcatgttccc agagcatagc ctcctgccct | 120 | |

gaagccttat taataggctg gacacacttc atggaggaat cagtcccact caggacacag 180
catggacatg agggtccctg ctcagctcct ggggctcctg ctgctctggt tcccaggtaa 240
ggatggagaa cactaacagt ttactcagcc cagagtgctc agtactgctt tactgttcag 300
ggaaattctc ttacaacatg attaattgtg tggacatttg tttttatgtt tccaatctca 360
ggtgccagat gtaacatcca gatgacccag tctccatctg ccatgtctgc atctgtagga 420
gacagagtca ccatcacttg tcgggcgagg cagggcatta gcaattattt agcctggttt 480
cagcagaaac cagggaaagt ccctaagcac ctgatctatg ctgcatccag tttgcaaagt 540
ggggtcccat caaggttcag cggcagtgga tctgggacag aattcactct cacaatcagc 600
agcctgcagc ctgaagattt tgcaacttat tactgtctac agcataatag ttaccct 657

<210> SEQ ID NO 302
<211> LENGTH: 487
<212> TYPE: DNA
<213> ORGANISM: homo sapiens;

<400> SEQUENCE: 302
agtcccagtc aggacacagc atggacatga gggtccccgc tcagctcctg gggctcctgc 60
tgctctggct cccaggtaag gaaggagaac actaggaatt ttcttagccc actgtgctct 120
ggcacttctg ggaagttctc ttataccatg attcatggtg tggatatttg tttttatgtt 180
tccaatctca ggtgtcagat ttgacatcca gatgatccag tctccatctt tcctgtctgc 240
atctgtagga gacagagtca gtatcatttg ctgggcaagt gagggcatta gcagtaattt 300
agcctggtat ctgcagaaac cagggaaatc ccctaagctc ttcctctatg atgcaaaaga 360
tttgcaccct ggggtctcat cgaggttcag tggcagggga tctgggacgg atttcactct 420
caccatcatc agcctgaagc ctgaagattt tgcagcttat tactgtaaac aggacttcag 480
ttaccct 487

<210> SEQ ID NO 303
<211> LENGTH: 657
<212> TYPE: DNA
<213> ORGANISM: homo sapiens;

<400> SEQUENCE: 303
gggacacctg gggacactga gctggtgctg agttactgag atgaaccagc cctgcagctg 60
tgcccagcct gccttgcccc ctgctaattt gcatgttccc agagcacatc ctcctaccct 120
gaagacttat taatgcgctg gtcacacttc atgcaggagt cagacccagt caggacacag 180
catggacatg agggtgcccg ctcagcgcct ggggctcctg ctgctctggt tcccaggtaa 240
ggaaggagaa ccctagcagt ttactcagcc cagtgtgttc cgtacagcct ggctcttgag 300
ggaagttctc ttacaacatg attaattgta tggacatttg tgtttatatt tccaatctca 360
ggtgccagat gtgccatccg gatgacccag tctccattct ccctgtctgc atctgtagga 420
gacagagtca ccatcacttg ctgggccagt cagggcatta gcagttattt agcctggtat 480
cagcaaaaac cagcaaaagc ccctaagctc ttcatctatt atgcatccag tttgcaaagt 540
ggggtcccat caaggttcag cggcagtgga tctgggacgg attacactct caccatcagc 600
agcctgcagc ctgaagattt tgcaacttat tactgtcaac agtattatag taccccct 657

<210> SEQ ID NO 304
<211> LENGTH: 656
<212> TYPE: DNA

<213> ORGANISM: homo sapiens;

<400> SEQUENCE: 304
gggacacctg gggacactga gctggtgctg agttactgag atgagccagc tctgcagctg 60
tgcccagtca gccccatccc ctgctcattt gcatgttccc agagcacaac ctcctgcact 120
gaagccttat taataggctg gccacacttc atgcaggagt cagacccagt caggacacag 180
catggacatg agggtccccg ctcagctcct ggggctcctg ctgctctggc tcccaggtaa 240
ggaaggagaa cactatgaat ttactcagcc aatgtgctca gtacagcctg gcccttcagg 300
gaaattctct tactacatga ttaattgtat ggatatttgt ttttatgttt ccaatctcag 360
gtgccagatg tgtcatctgg atgacccagt ctccatcctt actctctgca tctacaggag 420
acagagtcac catcagttgt cggatgagtc agggcattag cagttattta gcctggtatc 480
agcaaaaacc agggaaagcc cctgagctcc tgatctatgc tgcatccact ttgcaaagtg 540
gggtcccatc aaggttcagt ggcagtggat ctgggacaga tttcactctc accatcagtt 600
gcctgcagtc tgaagatttt gcaacttatt actgtcaaca gtattatagt ttccct 656

<210> SEQ ID NO 305
<211> LENGTH: 833
<212> TYPE: DNA
<213> ORGANISM: homo sapiens;

<400> SEQUENCE: 305
aattaggact cctcaggtca ccttctcaca atgaggctcc ttgctcagct tctggggctg 60
ctaatgctct gggtccctgg tgaggacaga agagagatga gggaggagaa tggggtggga 120
gggtgaactc tgggggcccc attgcctccc atgtgtgttc tgtcctcatg ttagatgtgt 180
acgtcttgta ctccaggatg gggcttgtaa cttttatatc tgcgtgagta aggcatgtga 240
ggtttagatc tgtaagaatg aggaagattc cagaaggaac aaagaccagt gctccggtga 300
agactctaac agagaaagag ggaatggtag aggaaacttc tagcactcaa agcactctgc 360
tgtgctttga aaatatgttt ttattttgaa attatatatt actagggtct gaatcaaatt 420
ataaaaattg atttagcctg aaataaataa cagaagaaaa attattttaa aattgtgctt 480
aaagtttcta cataaccttg cacttctctc tcattatttc aggatccagt ggggatattg 540
tgatgaccca gactccactc tcctcacctg tcacccttgg acagccggcc tccatctcct 600
gcaggtctag tcaaagcctc gtacacagtg atggaaacac ctacttgagt tggcttcagc 660
agaggccagg ccagcctcca agactcctaa tttataagat ttctaaccgg ttctctgggg 720
tcccagacag attcagtggc agtggggcag ggacagattt cacactgaaa atcagcaggg 780
tggaagctga ggatgtcggg gtttattact gcatgcaagc tacacaattt cct 833

<210> SEQ ID NO 306
<211> LENGTH: 816
<212> TYPE: DNA
<213> ORGANISM: homo sapiens;

<400> SEQUENCE: 306
gatcaggact cctcagttca ccttctcaca atgaggctcc ctgctcagct cctggggctg 60
ctaatgctct gggtcccagg taagggtaga agggagatga gggaggagaa tggcatggaa 120
cggtgagttc tggggcccca ctgcctctaa caacagtgat ctctgggggt ctcactacac 180
tcctatgtgt gttcctttcc tgtattggac atgcacatgt tgtcctccag agtggggcat 240
gtgatgatca gatctgtgag agtgaggaag attcaagcag aaacaaggat ctgtgctctg 300

```
gggaagactg acacagaaag gggatggtgt ggggtcttct ggagacccct ttgagccttg    360

gatcccttga gttccatttt gaaactgtgt atttttgaaa tatgaacaaa tacatatata    420

gcctgaaata aacaacaaat caaaatttat gaaaattaca cataaacttt atacataacc    480

ttgctcttct ttctatttat ttcaggatcc agtggggatg ttgtgatgac tcagtctcca    540

ctctccctgc ccgtcaccct tggacagccg gcctccatct cctgcaggtc tagtcaaagc    600

ctcgtataca gtgatggaaa cacctacttg aattggtttc agcagaggcc aggccaatct    660

ccaaggcgcc taatttataa ggtttctaac cgggactctg ggtcccagaa cagattcagc    720

ggcagtgggt caggcactga tttcacactg aaaatcagca gggtggaggc tgaggatgtt    780

ggggtttatt actgcatgca aggtacacac tggcct                              816
```

<210> SEQ ID NO 307
<211> LENGTH: 833
<212> TYPE: DNA
<213> ORGANISM: homo sapiens;

<400> SEQUENCE: 307

```
aattaggact cctcaggtca ccttctcaca atgaggctcc ttgctcagct tctggggctg     60

ctaatgctct gggtccctgg tgaggacaga agagagatga gggaggagaa tggggtggga    120

gggtgaactc tgggggcccc attgcctccc atgtgtgttc tgtcctcatg ttagatgtgt    180

acgtcttgta ctccaggatg ggcttgtaa cttttatatc tgcgtgagta aggcatgtga    240

ggtttagatc tgtaagaatg aggaagattc cagaaggaac aaagaccagt gctccggtga    300

agactctaac agagaaagag ggaatggtag aggaaacttc tagcactcaa agcactctgc    360

tgtgctttga aaatatgttt ttattttgaa attatatatt actagggtct gaatcaaatt    420

ataaaaattg atttagcctg aaataaataa cagaagaaaa attattttaa aattgtgctt    480

aaagtttcta cataaccttg cacttctctc tcattatttc aggatccagt ggggatattg    540

tgatgaccca gactccactc tcctcgcctg tcacccttgg acagccggcc tccatctcct    600

tcaggtctag tcaaagcctc gtacacagtg atggaaacac ctacttgagt tggcttcagc    660

agaggccagg ccagcctcca agactcctaa tttataaggt ttctaaccgg ttctctgggg    720

tcccagacag attcagtggc agtggggcag ggacagattt cacactgaaa atcagcaggg    780

tggaagctga ggatgtcggg gtttattact gcacgcaagc tacacaattt cct           833
```

<210> SEQ ID NO 308
<211> LENGTH: 781
<212> TYPE: DNA
<213> ORGANISM: homo sapiens;

<400> SEQUENCE: 308

```
gatcaggact cctcagttca ccttctcact atgaggctcc ctgctcagct cttggggctg     60

ctaatgctct gggtccctgg taaggacaga aggagatgag ggaggagaat ggggtgggaa    120

ggtaagcctg gggaccccac tgccttccat gtgtgttctg ccctgcccat gtgttagatg    180

tacaggtctt gttctccagg atggggaatg tgaggtttaa atctgtgaga gtgaggacga    240

ttcaaaaaga agcaaggacc tgtgtgctct ggtgaatatc gtcacacaga gaaagggagg    300

tggtgtaggt gacttctaga atccccttg cagcttgcaa atttggaata tgtttagtgt     360

ataaatacaa acaacaaaaa attatatagc ctgaaataaa aaatgaaaat ttatgataaa    420

tgacacatga tatttgtaca tatccttcca cttctttcta tctattttag gatccagtgc    480
```

agagattgtg atgacccaga ctccactctc cttgtctatc acccctggag agcaggcctc 540
catgtcctgc aggtctagtc agagcctcct gcatagtgat ggatacacct atttgtattg 600
gtttctgcag aaagccaggc cagtctccac gctcctgatc tatgaagttt ccaaccggtt 660
ctctggagtg ccagataggt tcagtggcag cgggtcaggg acagatttca cactgaaaat 720
cagccgggtg gaggctgagg attttggagt ttattactgc atgcaagatg cacaagatcc 780
t 781

<210> SEQ ID NO 309
<211> LENGTH: 758
<212> TYPE: DNA
<213> ORGANISM: homo sapiens;

<400> SEQUENCE: 309
gatcaggact tctcagttca tcttctcacc atgaggctcc ctgctcagct cctggggctg 60
ctaatgctct ggatacctgg taaggatgga aggagatgag ggaggaggag ggggtgggaa 120
gctgagctct ggcggcccca ctgattcccg tgtttattct aaccatgtgt taaaggaata 180
tggcctatgc tccagggaga ggaattcata ttttgccctg atgatgattt gaaaactcct 240
aaaagcagtg ctctgaataa tatcttgaga aatgaaagaa ctcttgtgcc tatttaataa 300
agggttcatt taaagagttt gtttttatga tatgaataca aatttgtaaa aataaaagat 360
tagccataaa tcaataccat aaggcaaatc tcaaaagttg ttcattatgc tttcacataa 420
ccttgcactt ctctctcata atttcaggat ccagtgcaga tattgtgatg acccagactc 480
cactctctct gtccgtcacc cctggacagc cggcctccat ctcctgcaag tctagtcaga 540
gcctcctgca tagtgatgga aagacctatt tgtattggta cctgcagaag ccaggccagc 600
ctccacagct cctgatctat gaagtttcca accggttctc tggagtgcca gataggttca 660
gtggcagcgg gtcagggaca gatttcacac tgaaaatcag ccgggtggag gctgaggatg 720
ttggggttta ttactgcatg caaagtatac agcttcct 758

<210> SEQ ID NO 310
<211> LENGTH: 821
<212> TYPE: DNA
<213> ORGANISM: homo sapiens;

<400> SEQUENCE: 310
tgactgatca ggactcctca gttcaccttc tcacaatgag gctccctgct cagctcctgg 60
ggctgctaat gctctgggtc ccaggtaagg gtagaaggga gatgagggag gagaatggca 120
tggaacggtg agttctgggg ccccactgcc tctaacaaca gtgatctctg ggggtctcac 180
tacactccta tgtgtgttcc tttcctgtat tggacatgca catgttgtcc tccagaatgg 240
ggcatgtgat gatcagatct gtgagagtca ggaagattca agaagaaaca aggatctgtg 300
ctctggggaa gactgacaca gaaaggggat ggtgtggggt cttctggaga ccccttttgag 360 ccttggatcc cttgagttcc attttgaaac tgtatatttt tgaaatatga acaaatacat 420
atatagcctg agataaacaa caaatcaaaa tttatgaaaa ttacacataa actttataca 480
taaccttgct cttctttcta tttatttcag gatccagtgg ggatgttgtg atgactcagt 540
ctccactctc cctgcccgtc acccttggac agccggcctc catctcctgc aggtctagtc 600
aaagcctcgt atacagtgat ggaaacacct acttgaattg gtttcagcag aggccaggcc 660
aatctccaag gcgcctaatt tataaggttt ctaactggga ctctggggtc ccagacagat 720
tcagcggcag tgggtcaggc actgatttca cactgaaaat cagcagggtg gaggctgagg 780
atgttggggt ttattactgc atgcaaggta cacactggcc t 821

<210> SEQ ID NO 311
<211> LENGTH: 561
<212> TYPE: DNA
<213> ORGANISM: homo sapiens;

<400> SEQUENCE: 311
gtcagagccc tggggaggaa ctgctcagtt aggacccaga gggaaccatg gaagccccag 60
ctcagcttct cttcctcctg ctactctggc tcccaggtga ggggaacatg aggtggtttt 120
gcacattagt gaaaactctt gccacctctg ctcagcaaga aatataatta aaattcaaag 180
tatatcaaca attttggctc tactcaaaga cagttggttt gatcttgatt acatgagtgc 240
atttctgttt tatttccaat ttcagatacc accggagaaa ttgtgttgac acagtctcca 300
gccaccctgt ctttgtctcc aggggaaaga gccaccctct cctgcagggc cagtcagagt 360
gttagcagct acttagcctg gtaccaacag aaacctggcc aggctcccag gctcctcatc 420
tatgatgcat ccaacagggc cactggcatc ccagccaggt tcagtggcag tgggtctggg 480
acagacttca ctctcaccat cagcagccta gagcctgaag attttgcagt ttattactgt 540
cagcagcgta gcaactggcc t 561

<210> SEQ ID NO 312
<211> LENGTH: 587
<212> TYPE: DNA
<213> ORGANISM: homo sapiens;

<400> SEQUENCE: 312
cctgggtcag agctctggag aagagctgct cagttaggac ccagagggaa ccatggaaac 60
cccagcgcag cttctcttcc tcctgctact ctggctccca ggtgagggga acatgggatg 120
gttttgcatg tcagtgaaaa ccctctcaag tcctgttacc tggcaactct gctcagtcaa 180
tacaataatt aaagctcaat ataaagcaat aattctggct cttctgggaa gacaatgggt 240
ttgatttaga ttacatgggt gacttttctg ttttatttcc aatctcagat accaccggag 300
aaattgtgtt gacgcagtct ccaggcaccc tgtctttgtc tccaggggaa agagccaccc 360
tctcctgcag ggccagtcag agtgttagca gcagctactt agcctggtac cagcagaaac 420
ctggccaggc tcccaggctc ctcatctatg gtgcatccag cagggccact ggcatcccag 480
acaggttcag tggcagtggg tctgggacag acttcactct caccatcagc agactggagc 540
ctgaagattt tgcagtgtat tactgtcagc agtatggtag ctcacct 587

<210> SEQ ID NO 313
<211> LENGTH: 614
<212> TYPE: DNA
<213> ORGANISM: homo sapiens;

<400> SEQUENCE: 313
gcatgtccct cccagctgcc ctaccttcca gagcccatat caatgcctgg gtcagagccc 60
tgggaaggaa ctgctcagtt aggacccaga cggaaccatg gaagccccag ctcagcttct 120
cttcctcctg ctactctggc tcccaggtga ggggaacatg aggtggtttt gcacatcagt 180
gaaaactcct gccacctctg ctcagcaaga aatataatta aaattcaatg tagatcaaca 240
attttggctc tactcaaaga cagctggttt gatctagatt acatgagtgc atttctgttt 300
tatttccaat cttggatacc accagagaaa ttgtaatgac acagtctcca cccaccctgt 360
ctttgtctcc aggggaaaga gtcaccctct cctgcagggc cagtcagagt gttagcagca 420
gctacttaac ctggtatcag cagaaacctg gccaggcgcc caggctcctc atctatggtg 480
catccaccag ggccactagc atcccagcca ggttcagtgg cagtgggtct gggacagact 540
tcactctcac catcagcagc ctgcagcctg aagattttgc agtttattac tgtcagcagg 600
attataactt acct 614

<210> SEQ ID NO 314
<211> LENGTH: 611
<212> TYPE: DNA
<213> ORGANISM: homo sapiens;

<400> SEQUENCE: 314
gcatgtccct cccagctgcc ctaccttcca gagcccatat caatgcctgg gtcagagctc 60
tggggaggaa ctgctcagtt aggacccaga cggaaccatg gaagccccag cgcagcttct 120
cttcctcctg ctactctggc tcccaggtga ggggaatatg aggtgtcttt gcacatcagt 180
gaaaactcct gccacctctg ctcagcaaga aatataatta aaattcaaaa tagatcaaca 240
attttggctc tactcaaaga cagtgggttt gattttgatt acatgagtgc atttctgttt 300
tatttccaat ttcagatacc accggagaaa ttgtgttgac acagtctcca gccaccctgt 360
ctttgtctcc aggggaaaga gccaccctct cctgcagggc cagtcagggt gttagcagct 420
acttagcctg gtaccagcag aaacctggcc aggctcccag gctcctcatc tatgatgcat 480
ccaacagggc cactggcatc ccagccaggt tcagtggcag tgggcctggg acagacttca 540
ctctcaccat cagcagccta gagcctgaag attttgcagt ttattactgt cagcagcgta 600
gcaactggca t 611

<210> SEQ ID NO 315
<211> LENGTH: 563
<212> TYPE: DNA
<213> ORGANISM: homo sapiens;

<400> SEQUENCE: 315
gggtcagagc tctggggagg aactgctcag ttaggaccca gacggaacca tggaagcccc 60
agcgcagctt ctcttcctcc tgctactctg gctcccaggt gaggggaata tgaggtggtt 120
ttgcacatca gtgaaaactc ctgccacctc tgctcagcaa gaaatataat taaaattcaa 180
tgtagatcaa caattttggc tctacttaaa gacagtgggt ttgattttga ttacatgagt 240
gcatttctgt tttatttcca atttcagata ccactggaga aatagtgatg acgcagtctc 300
cagccaccct gtctgtgtct ccaggggaaa gagccaccct ctcctgcagg gccagtcaga 360
gtgttagcag caacttagcc tggtaccagc agaaacctgg ccaggctccc aggctcctca 420
tctatggtgc atccaccagg gccactggca tcccagccag gttcagtggc agtgggtctg 480
ggacagagtt cactctcacc atcagcagcc tgcagtctga agattttgca gtttattact 540
gtcagcagta taataactgg cct 563

<210> SEQ ID NO 316
<211> LENGTH: 632
<212> TYPE: DNA
<213> ORGANISM: homo sapiens;

<400> SEQUENCE: 316
gcatgtccct cccagccgcc ctgcagtcca gagcccatat caatgcctgg gtcagagctc 60
tggggaggaa ctgctcagtt aggacccaga gggaaccatg gaaaccccag cgcagcttct 120

```
cttcctcctg ctactctggc tcccaggtga ggggaacatg ggatggtttt gcatgtcagt    180

gaaaaccctc tcaagtcctg ttacctggca actctgctga atcaatacaa taattaaagc    240

tcaatataaa gcaataattc tggctcttct gggaagacag tgggtttgat ttagattaca    300

tgggtgactt ttctatttta tttccaatct cagataccac cggagaaatt gtgttgacgc    360

agtctccagc caccctgtct ttgtctccag gggaaagagc caccctctcc tgcggggcca    420

gtcagagtgt tagcagcagc tacttagcct ggtaccagca gaaacctggc ctggcgccca    480

ggctcctcat ctatgatgca tccagcaggg ccactggcat cccagacagg ttcagtggca    540

gtgggtctgg gacagacttc actctcacca tcagcagact ggagcctgaa gattttgcag    600

tgtattactg tcagcagtat ggtagctcac ct                                  632
```

<210> SEQ ID NO 317
<211> LENGTH: 757
<212> TYPE: DNA
<213> ORGANISM: homo sapiens;

<400> SEQUENCE: 317

```
tttggctctt gatttacatt gggtactttc acaacccact gctcatgaaa tttgcttttg     60

tactcactgg ttgtttttgc ataggcccct ccaggccacg accagctgtt tggattttat    120

aaacgggccg tttgcattgt gaactgagct acaacaggca ggcaggggca gcaagatggt    180

gttgcagacc caggtcttca tttctctgtt gctctggatc tctggtgagg aattaaaaag    240

tgccacagtc ttttcagagt aatatctgtg tagaaataaa aaaaattaag atatagttgg    300

aaataatgac tatttccaat atggatccaa ttatctgctg acttataata ctactagaaa    360

gcaaatttaa atgacatatt tcaattatat ctgagacagc gtgtataagt ttatgtataa    420

tcattgtcca ttactgacta caggtgccta cggggacatc gtgatgaccc agtctccaga    480

ctccctggct gtgtctctgg gcgagagggc caccatcaac tgcaagtcca gccagagtgt    540

tttatacagc tccaacaata agaactactt agcttggtac cagcagaaac caggacagcc    600

tcctaagctg ctcatttact gggcatctac ccgggaatcc ggggtccctg accgattcag    660

tggcagcggg tctgggacag atttcactct caccatcagc agcctgcagg ctgaagatgt    720

ggcagtttat tactgtcagc aatattatag tactcct                             757
```

<210> SEQ ID NO 318
<211> LENGTH: 553
<212> TYPE: DNA
<213> ORGANISM: homo sapiens;

<400> SEQUENCE: 318

```
ataaaatctg tgctgtcaaa ctgattagga actgactacc acctgcaggt cagggccaag     60

gttatggggt cccaggttca cctcctcagc ttcctcctcc tttggatctc tggtaagaga    120

aacacttcct ctcctctgtg ccaccaagtc ccctgcatat ccacaaaaat aatatatttt    180

cataaggaat tgattttcct cattctctgc aaatatgatg catttgattt atgtttttta    240

ctttgctcca taatcagata ccagggcaga aacgacactc acgcagtctc cagcattcat    300

gtcagcgact ccaggagaca aagtcaacat ctcctgcaaa gccagccaag acattgatga    360

tgatatgaac tggtaccaac agaaaccagg agaagctgct attttcatta ttcaagaagc    420

tactactctc gttcctggaa tcccacctcg attcagtggc agcgggtatg gaacagattt    480

taccctcaca attaataaca tagaatctga ggatgctgca tattacttct gtctacaaca    540
```

tgataatttc cct 553

<210> SEQ ID NO 319
<211> LENGTH: 616
<212> TYPE: DNA
<213> ORGANISM: homo sapiens;

<400> SEQUENCE: 319
atcttaaaag aggttctttc tctgggatgt ggcatgagca aaactgacaa gtcaaggcag 60
gaagatgttg ccatcacaac tcattgggtt tctgctgctc tgggttccag gtgagaatat 120
ttccacaaac ctaggcggag atattctttc aatctgtaat ttctttcatt ggggactctg 180
caataggtga tttttggctt gattttaaaa tcctaatttt aaaaatgtaa tgcatattct 240
ttcttcatgt ctagcaagat taaaggtgat tttcatacac agatatttat gttgtactga 300
tgtttgctgt atattttcag cctccagggg tgaaattgtg ctgactcagt ctccagactt 360
tcagtctgtg actccaaagg agaaagtcac catcacctgc cgggccagtc agagcattgg 420
tagtagctta cactggtacc agcagaaacc agatcagtct ccaaagctcc tcatcaagta 480
tgcttcccag tccttctcag gggtcccctc gaggttcagt ggcagtggat ctgggacaga 540
tttcaccctc accatcaata gcctggaagc tgaagatgct gcaacgtatt actgtcatca 600
gagtagtagt ttacct 616

<210> SEQ ID NO 320
<211> LENGTH: 619
<212> TYPE: DNA
<213> ORGANISM: homo sapiens;

<400> SEQUENCE: 320
ggtatcttaa aagaggttct ttctctggga tgtggcatga gcaaaactga caagtcaagg 60
caggaagatg tcgccatcac aactcattgg gtttctgctg ctctgggttc caggtgagaa 120
tatttccaca aacctaggcg gagatattct ttcaatctgt aatttctttc attggggact 180
ctgcaatagg tgatttttgg cttgatttta aaatcctaat tttaaaaatg taatgcatat 240
tctttcttca tgtctagcaa gattaaaggt gattttcata cacagatatt tatgttgtac 300
tgatgtttgc tgtatatttt cagcctccag gggtgaaatt gtgctgactc agtctccaga 360
ctttcagtct gtgactccaa aggagaaagt caccatcacc tgccgggcca gtcagagcat 420
tggtagtagc ttacactggt accagcagaa accagatcag tctccaaagc tcctcatcaa 480
gtatgcttcc cagtccatct caggggtccc ctcgaggttc agtggcagtg gatctgggac 540
agatttcacc ctcaccatca atagcctgga agctgaagat gctgcagcgt attactgtca 600
tcagagtagt agtttacct 619

<210> SEQ ID NO 321
<211> LENGTH: 577
<212> TYPE: DNA
<213> ORGANISM: homo sapiens;

<400> SEQUENCE: 321
agcaaaactg aagtcaaaac actgagatgg tgtccccgtt gcaattcctg cggcttctgc 60
tcctctgggt tccaggtgag aatatttaga aaaagctaaa actaattctt tgaaccatta 120
attttcttaa ttaggaacct ggcaccatat ggaacttggc ttgtttttaa atgtgatttt 180
tttttaagta atgcgtattc tttcatcttg tgctactaga ttagtggtga tttcattaag 240
cagatgctta tattgtgcta atgtttgctg tatggtttca gcctccaggg gtgatgttgt 300
gatgacacag tctccagctt tcctctctgt gactccaggg gagaaagtca ccatcacctg 360
ccaggccagt gaaggcattg gcaactactt atactggtac cagcagaaac cagatcaagc 420
cccaaagctc ctcatcaagt atgcttccca gtccatctca ggggtcccct cgaggttcag 480
tggcagtgga tctgggacag atttcacctt taccatcagt agcctggaag ctgaagatgc 540
tgcaacatat tactgtcagc agggcaataa gcaccct 577

<210> SEQ ID NO 322
<211> LENGTH: 127
<212> TYPE: DNA
<213> ORGANISM: homo sapiens;

<400> SEQUENCE: 322
cccagcaggc tcctgctcca gcccagcccc cagagagcag accccaggtg ctggccccgg 60
gggttttggt ctgagcctca gtcactgtgt tatgtcttcg gaactgggac caaggtcacc 120
gtcctag 127

<210> SEQ ID NO 323
<211> LENGTH: 175
<212> TYPE: DNA
<213> ORGANISM: homo sapiens;

<400> SEQUENCE: 323
gtgtgggggc catgtggact ccctcatgag cagatgccac cagggccact ggccccagct 60
tcctccttca cagctgcagt gggggctggg gctggggcat cccagggagg gtttttgtat 120
gagcctgtgt cacagtgtgt ggtattcggc ggagggacca agctgaccgt cctag 175

<210> SEQ ID NO 324
<211> LENGTH: 176
<212> TYPE: DNA
<213> ORGANISM: homo sapiens;

<400> SEQUENCE: 324
gtgtgggggc catgtggact ccctcatgag cagatgccac caggaccact ggccccagct 60
tcctccttca cagctgcagt gggggctggg gctaggggca tcccagggag ggtttttgta 120
tgagcctgtg tcacagtgtt gggtgttcgg cggagggacc aagctgaccg tcctag 176

<210> SEQ ID NO 325
<211> LENGTH: 72
<212> TYPE: DNA
<213> ORGANISM: homo sapiens;

<400> SEQUENCE: 325
cagagagggt ttttgtatga gcctgtgtca cagcactggg tgtttggtga ggggacggag 60
ctgaccgtcc ta 72

<210> SEQ ID NO 326
<211> LENGTH: 70
<212> TYPE: DNA
<213> ORGANISM: homo sapiens;

<400> SEQUENCE: 326
ggagggtttg tgtgcagggt tatatcacag tgtaatgtgt tcggcagtgg caccaaggtg 60
accgtcctcg 70

<210> SEQ ID NO 327

<211> LENGTH: 46
<212> TYPE: DNA
<213> ORGANISM: homo sapiens;

<400> SEQUENCE: 327
tcactgtgtg ctgtgttcgg aggaggcacc cagctgaccg ccctcg 46

<210> SEQ ID NO 328
<211> LENGTH: 477
<212> TYPE: DNA
<213> ORGANISM: homo sapiens;

<400> SEQUENCE: 328
gggaatctgc accatgccct gggctctgct cctcctgacc ctcctcactc actctgcagg 60
tgagagtgga ccttacccag ggatctgcac ccacctctgc tccagcttct ccactccctg 120
gctcagtgga ctctgatcct gctctcacat tcctttctgt cccctctaca gtgtcagtgg 180
tccaggcagg gctgactcag ccaccctcgg tgtccaaggg cttgagacag accgccacac 240
tcacctgcac tgggaacagc aacattgttg gcaaccaagg agcagcttgg ctgcagcagc 300
accagggcca ccctcccaaa ctcctatcct acaggaataa caaccggccc tcagggatct 360
cagagagatt ctctgcatcc aggtcaggaa acacagcctc cctgaccatt actggactcc 420
agcctgagga cgaggctgac tattactgct cagcattgga cagcagcctc agtgctc 477

<210> SEQ ID NO 329
<211> LENGTH: 544
<212> TYPE: DNA
<213> ORGANISM: homo sapiens;

<400> SEQUENCE: 329
gctgtgtcca ctatggccct gactcctctc ctcctcctgc tcctctctca ctgcacaggt 60
agggacaggg ctcagagccc agggtggtcc ccagcctgat ctgtccctca tggctcagat 120
ccctcagcag ctgcgccctg accctgctcc tcactgtgct gtgtctgtgt ctgcaggttc 180
cctctcccgg cccgtgctga ctcagccgcc ctctctgtct gcatccccgg gagcaacagc 240
cagactcccc tgcaccctga gcagtgacct cagtgttggt ggtaaaaaca tgttctggta 300
ccagcagaag ccagggagct ctcccaggtt attcctgtat cactactcag actcagacaa 360
gcagctggga cctggggtcc ccagtcgagt ctctggctcc aaggagacct caagtaacac 420
agcgtttttg ctcatctctg ggctccagcc tgaggacgag gccgattatt actgccaggt 480
gtacgaaagt agtgctaatc acagtgagac agatgaggaa gtcggacaaa aaccaaggtt 540
ttaa 544

<210> SEQ ID NO 330
<211> LENGTH: 507
<212> TYPE: DNA
<213> ORGANISM: homo sapiens;

<400> SEQUENCE: 330
gctgcgggta gagaagacag gactcaggac aatctccagc atggcctggt cccctctctt 60
cctcaccctc atcactcact gtgcaggtga caggatgggg accaagagag aggccctggg 120
aagcccatgc gaccctgctt tctcctcttg tctccttttg tctcttgtca atcaccatgt 180
ctgtgtctct ctcacttcca gggtcctggg cccagtctgt gctgactcag ccaccctcgg 240
tgtctgaagc cccccaggcag agggtcacca tctcctgttc tggaagcagc tccaacatcg 300
gaaataatgc tgtaaactgg taccagcagc tcccaggaaa ggctcccaaa ctcctcatct 360
attatgatga tctgctgccc tcaggggtct ctgaccgatt ctctggctcc aagtctggca 420
cctcagcctc cctggccatc agtgggctcc agtctgagga tgaggctgat tattactgtg 480
cagcatggga tgacagcctg aatggtc 507

<210> SEQ ID NO 331
<211> LENGTH: 517
<212> TYPE: DNA
<213> ORGANISM: homo sapiens;

<400> SEQUENCE: 331
gctctgcttc agctgtgggc acaagaggca gcactcagga caatctccag catggcctgg 60
tctcctctcc tcctcactct cctcgctcac tgcacaggtg actggataca ggtccagggg 120
aggggccctg ggaagcctat ggattcttgc tttctcctgt tgtctctaga agccgaataa 180
tgatgcctgt gtctctccca cttccagggt cctgggccca gtctgtgctg acgcagccgc 240
cctcagtgtc tggggcccca gggcagaggg tcaccatctc ctgcactggg agcagctcca 300
acatcggggc aggttatgat gtacactggt accagcagct tccaggaaca gcccccaaac 360
tcctcatcta tggtaacagc aatcggccct caggggtccc tgaccgattc tctggctcca 420
agtctggcac ctcagcctcc ctggccatca ctgggctcca ggctgaggat gaggctgatt 480
attactgcca gtcctatgac agcagcctga gtggttc 517

<210> SEQ ID NO 332
<211> LENGTH: 581
<212> TYPE: DNA
<213> ORGANISM: homo sapiens;

<400> SEQUENCE: 332
ctgatttgca tggatggact ctccccctct cagagtatga agagagggag agatctgggg 60
gaagctcagc ttcagctgtg ggtagagaag acaggactca ggacaatctc cagcatggcc 120
agcttccctc tcctcctcac cctcctcact cactgtgcag gtgacaggat ggggaccaag 180
aaaggggccc tgggaagccc atggggccct gctttctcct cttgtctcct tttgtctctt 240
gtcaatcacc atgtctgtgt ctctctcact tccagggtcc tgggcccagt ctgtgctgac 300
tcagccaccc tcagcgtctg ggacccccgg gcagagggtc accatctctt gttctggaag 360
cagctccaac atcggaagta atactgtaaa ctggtaccag cagctcccag gaacggcccc 420
caaactcctc atctatagta ataatcagcg gccctcaggg gtccctgacc gattctctgg 480
ctccaagtct ggcacctcag cctccctggc catcagtggg ctccagtctg aggatgaggc 540
tgattattac tgtgcagcat gggatgacag cctgaatggt c 581

<210> SEQ ID NO 333
<211> LENGTH: 522
<212> TYPE: DNA
<213> ORGANISM: homo sapiens;

<400> SEQUENCE: 333
ggggaagctc agcttcagct gtggtagaga agacaggatt caggacaatc tccagcatgg 60
ccggcttccc tctcctcctc accctcctca ctcactgtgc aggtgacagg atggggacca 120
agagaggggc cctgggaagc ccatggggcc ctgctttctc ctcttgtctc ctttcgtctc 180
ttgtcaatca ccatgtctgt gtctctctca cttccagggt cctgggccca gtctgtgctg 240
actcagccac cctcagcgtc tgggaccccc gggcagaggg tcaccatctc ttgttctgga 300
agcagctcca acatcggaag taattatgta tactggtacc agcagctccc aggaacggcc 360
cccaaactcc tcatctatag taataatcag cggccctcag ggtccctga ccgattctct 420 ggctccaagt ctggcacctc agcctccctg gccatcagtg ggctccggtc cgaggatgag 480
gctgattatt actgtgcagc atgggatgac agcctgagtg gt 522

<210> SEQ ID NO 334
<211> LENGTH: 515
<212> TYPE: DNA
<213> ORGANISM: homo sapiens;

<400> SEQUENCE: 334
gctctgcttc agctgtgggc acaggaggca gcactcagga caatctccag catggcctgg 60
tcttctctcc tcctcactct cctcgctcac tgcacaggtg actggatgca gatcgagggg 120
agggtccctg ggaagcctat ggattcttgc tttctcctct tgtctctaga agcagaatca 180
tgatgcctgt gtctctccca cttccagggt cctgggccca gtctgtgctg acgcagccgc 240
cctcagtgtc tggggcccca gggcagaggg tcaccatctc ctgcactggg agcagctcca 300
acattggggc gggttatgtt gtacattggt accagcagct tccaggaaca gcccccaaac 360
tcctcatcta tggtaacagc aatcggccct caggggtccc tgaccaattc tctggctcca 420
agtctggcac ctcagcctcc ctggccatca ctggactcca gtctgaggat gaggctgatt 480
attactgcaa agcatgggat aacagcctga atgct 515

<210> SEQ ID NO 335
<211> LENGTH: 509
<212> TYPE: DNA
<213> ORGANISM: homo sapiens;

<400> SEQUENCE: 335
tgagcgcaga aggcaggact cgggacaatc ttcatcatga cctgctcccc tctcctcctc 60
acccttctca ttcactgcac aggtgcccag acacagggtc aggggagggg tccaggaagc 120
ccatgaggcc ctgctttctc cttctctctc tagaccaaga atcaccgtgt ctgtgtctct 180
cctgcttcca gggtcctggg cccagtctgt gttgacgcag ccgccctcag tgtctgcggc 240
cccaggacag aaggtcacca tctcctgctc tggaagcagc tccaacattg ggaataatta 300
tgtatcctgg taccagcagc tcccaggaac agcccccaaa ctcctcattt atgacaataa 360
taagcgaccc tcagggattc ctgaccgatt ctctggctcc aagtctggca cgtcagccac 420
cctgggcatc accggactcc agactgggga cgaggccgat tattactgcg gaacatggga 480
tagcagcctg agtgctggca cagtgctcc 509

<210> SEQ ID NO 336
<211> LENGTH: 517
<212> TYPE: DNA
<213> ORGANISM: homo sapiens;

<400> SEQUENCE: 336
tgctggggtc tcaggaggca gcactctcgg gacgtctcca ccatggcctg ggctctgctc 60
ctcctcagcc tcctcactca gggcacaggt gacacctcca gggaaagggt cacaggggtc 120
tctgggctga tccttggtct cctgctcctc aggctcacct gggcccagca ctgactcact 180
agagtgtgtt tctccctctt tccaggatcc tgggctcagt ctgccctgac tcagcctcgc 240
tcagtgtccg ggtctcctgg acagtcagtc accatctcct gcactggaac cagcagtgat 300
gttggtggtt ataactatgt ctcctggtac caacagcacc caggcaaagc ccccaaactc 360
atgatttatg atgtcagtaa gcggccctca ggggtccctg atcgcttctc tggctccaag 420
tctggcaaca cggcctccct gaccatctct gggctccagg ctgaggatga ggctgattat 480
tactgctgct catatgcagg cagctacact ttccaca 517

<210> SEQ ID NO 337
<211> LENGTH: 519
<212> TYPE: DNA
<213> ORGANISM: homo sapiens;

<400> SEQUENCE: 337
gctggggtct caggaggcag cgctctcagg acatctccac catggcctgg gctctgctgc 60
tcctcaccct cctcactcag ggcacaggtg acgcctccag ggaaggggct tcagggacct 120
ctgggctgat ccttggtctc ctgctcctca ggctcaccgg ggcccagcac tgactcactg 180
gcatgtgttt ctccctcttt ccagggtcct gggcccagtc tgccctgact cagcctgcct 240
ccgtgtctgg gtctcctgga cagtcgatca ccatctcctg cactggaacc agcagtgacg 300
ttggtggtta taactatgtc tcctggtacc aacagcaccc aggcaaagcc cccaaactca 360
tgatttatga ggtcagtaat cggccctcag gggtttctaa tcgcttctct ggctccaagt 420
ctggcaacac ggcctccctg accatctctg ggctccaggc tgaggacgag gctgattatt 480
actgcagctc atatacaagc agcagcactc tccacagtg 519

<210> SEQ ID NO 338
<211> LENGTH: 490
<212> TYPE: DNA
<213> ORGANISM: homo sapiens;

<400> SEQUENCE: 338
gaatatctcc accatggcct gggctctgct cctcctcacc ctcctcactc agggcacagg 60
tgaggcctcc agggaagggg cttcggggac ctctgggctg atccttaact cctgctcctc 120
aggctcacct gggcccagca ctgacttact aaaatgtgtt tcttcctttt tccaggatcc 180
tgggctcagt ctgccctgac tcagcctccc tccgtgtccg ggtctcctgg acagtcagtc 240
accatctcct gcactggaac cagcagtgac gttggtagtt ataaccgtgt ctcctggtac 300
cagcagcccc caggcacagc ccccaaactc atgatttatg aggtcagtaa tcggccctca 360
ggggtccctg atcgcttctc tgggtccaag tctggcaaca cggcctccct gaccatctct 420
gggctccagg ctgaggacga ggctgattat tactgcagct tatatacaag cagcagcact 480
ttccacagag 490

<210> SEQ ID NO 339
<211> LENGTH: 619
<212> TYPE: DNA
<213> ORGANISM: homo sapiens;

<400> SEQUENCE: 339
tctctgagcc caggcccacg tgagggtggg gtgaggagag gagcccagga tgctgatttt 60
catggaggcc ccgccctcct ctgaggcaaa ggggataaga cagggctggg gcagggccag 120
tgctggggtc acaagaggca gcgctctcgg gacgtctcca ccatggcctg ggctctgctg 180
ctcctcactc tcctcactca ggacacaggt gacgcctcca gggaaggggt cttggggacc 240
tctgggctga tccttggtct cctgctcctc aggctcaccg ggcccagca ctgactcact 300 ggcatgtgtt tctccctctt tccagggtcc tgggcccagt ctgccctgac tcagcctgcc 360
tccgtgtctg ggtctcctgg acagtcgatc accatctcct gcactggaac cagcagtgat 420
gttgggagtt ataaccttgt ctcctggtac caacagcacc caggcaaagc ccccaaactc 480
atgatttatg agggcagtaa gcggccctca ggggtttcta atcgcttctc tggctccaag 540
tctggcaaca cggcctccct gacaatctct gggctccagg ctgaggacga ggctgattat 600
tactgctgct catatgcag 619

<210> SEQ ID NO 340
<211> LENGTH: 520
<212> TYPE: DNA
<213> ORGANISM: homo sapiens;

<400> SEQUENCE: 340
ggctagaggc aggcccggtg ctggggtctc aaggcagcgc tctcgggaca tctccaccat 60
ggcctgggct ctgctcctcc tcaccctcct cactcagggc acaggtgaca cctccaggga 120
aatggccttg ggacctctg agctaatgct tggtcttctg ctcctgctcc tcagggtcac 180
tggacccagt actgacccag tagagtgtgt ttctccctct ttccagggtc ctgggcccaa 240
tctgccctga ctcagcctcc ttttgtgtcc ggggctcctg gacagtcggt caccatctcc 300
tgcactggaa ccagcagtga cgttggggat tatgatcatg tcttctggta ccaaaagcgt 360
ctcagcacta cctccagact cctgatttac aatgtcaata ctcggccttc agggatctct 420
gacctcttct caggctccaa gtctggcaac atggcttccc tgaccatctc tgggctcaag 480
tccgaggttg aggctaatta tcactgcagc ttatattcaa 520

<210> SEQ ID NO 341
<211> LENGTH: 635
<212> TYPE: DNA
<213> ORGANISM: homo sapiens;

<400> SEQUENCE: 341
tctctaagcc caggcccaag tgagggtggg gtgagaagag gagctcagga tgcagatttg 60
catggaggtc ccgcccttct ctgaggcaga gggataagac agggctgggg gcaggcccag 120
tgctggggtc tcaggaggca gcgctctcag gacgtcacca ccatggcctg ggctctgctc 180
ctcctcaccc tcctcactca gggcacaggt gatgcctcca gggaaggggc cacagggacc 240
tctgggctga tccttggtct cctgctcctc aggctcacct gggcccagca ctgactcact 300
agactgtgtt tctccctttc cagggtcctg ggcccagtct gccctgactc agcctccctc 360
cgcgtccggg tctcctggac agtcagtcac catctcctgc actggaacca gcagtgacgt 420
tggtggttat aactatgtct cctggtacca acagcaccca ggcaaagccc ccaaactcat 480
gatttatgag gtcagtaagc ggccctcagg ggtccctgat cgcttctctg gctccaagtc 540
tggcaacacg gcctccctga ccgtctctgg gctccaggct gaggatgagg ctgattatta 600
ctgcagctca tatgcaggca gcaacaattt ccaca 635

<210> SEQ ID NO 342
<211> LENGTH: 691
<212> TYPE: DNA
<213> ORGANISM: homo sapiens;

<400> SEQUENCE: 342
aagaacctgc ccagcctggg cctcaggaag cagcatcgga ggtgcctcag ccatggcatg 60
gatccctctc ttcctcggcg tccttgctta ctgcacaggt gctgccccta gggtcctagc 120
cactggtcca gtcccagggc tctgggtcca gcctggccct gactctgagc tcagcagggc 180

```
ccccgcctgt ggtgggcagg atgctcatga ccctgctgca ggtggatggg ctcggcgggg    240

ctgaaatccc cccacacagt gctcatgtgc tcacactgcc ttagggctct ttcatccctg    300

gatctgtgtc caggccaggc acgtgggaag atttacttgg agttcagctc ctcagtttca    360

agccttttct ctcccgtttt ctctcctgta ggatccgtgg cctcctatga gctgactcag    420

ccaccctcag tgtccgtgtc cccaggacag acagccagca tcacctgctc tggagataaa    480

ttgggggata aatatgcttg ctggtatcag cagaagccag gccagtcccc tgtgctggtc    540

atctatcaag atagcaagcg gccctcaggg atccctgagc gattctctgg ctccaactct    600

gggaacacag ccactctgac catcagcggg acccaggcta tggatgaggc tgactattac    660

tgtcaggcgt gggacagcag cactgcacac a                                   691
```

<210> SEQ ID NO 343
<211> LENGTH: 539
<212> TYPE: DNA
<213> ORGANISM: homo sapiens;

<400> SEQUENCE: 343

```
gtgggctcag gaggcagagc tctgggaatc tcaccatggc ctggacccct ctcctgctcc     60

ccctcctcac tttctgcaca ggtgcttctc ccaggccctg ccccaggctc agtgcccata    120

gaccccaagt tggccctgcc ctgaaccctg tgcaaagccc agacacagtc ttagggtagg    180

acccctggga atgggctctt gatcttcaag ccccctctcc tgttttcctt gcagtctctg    240

aggcctccta tgagctgaca cagccaccct cggtgtcagt gtccccagga caaacggcca    300

ggatcacctg ctctggagat gcattgccaa aaaaatatgc ttattggtac cagcagaagt    360

caggccaggc ccctgtgctg gtcatctatg aggacagcaa acgaccctcc gggatccctg    420

agagattctc tggctccagc tcagggacaa tggccacctt gactatcagt ggggcccagg    480

tggaggatga agctgactac tactgttact caacagacag cagtggtaat catagcaca     539
```

<210> SEQ ID NO 344
<211> LENGTH: 763
<212> TYPE: DNA
<213> ORGANISM: homo sapiens;

<400> SEQUENCE: 344

```
gcctcagcca tggcctggac ccctctcctc ctcagcctcc tcgctcactg cacaggtgct     60

ctgcccaggg tatcaccaac ctgcccatcc ccagggctct gggtccagtg tggccatgac    120

tatgagctca ggagggccct gcctgtggtg ggcaggatgc tcatgaccct gctgcagggt    180

gagggactgg cggagctgaa gtcccctcaa actctgctca gaggcttgtg agagcctgag    240

gggctgcacc tgccaggaga gagtactggg ttttcagttc aaaggctcca tgcagaggga    300

aagtccatgg gccactgggg ctagggctga ttgcagggga taccctgagg gttcacagac    360

tctctgaagc ttttccagga cagcagggca ggggatttca tacggatctt ttacctaaaa    420

gccatcctct ccttttttttt tttttttaat ctttgcaggc tctgcgacct cctatgagct    480

gactcagcca cactcagtgt cagtggccac agcacagatg gccaggatca cctgtggggg    540

aaacaacatt ggaagtaaag ctgtgcactg gtaccagcaa aagccaggcc aggaccctgt    600

gctggtcatc tatagcgata gcaaccggcc ctcagggatc cctgagcgat tctctggctc    660

caacccaggg aacaccgcca ccctaaccat cagcaggatc gaggctgggg atgaggctga    720

ctattactgt caggtgtggg acagtagtag tgatcatccc acg                      763
```

<210> SEQ ID NO 345
<211> LENGTH: 529
<212> TYPE: DNA
<213> ORGANISM: homo sapiens;

<400> SEQUENCE: 345
tctgtgggtc caggaggcac agctctggga atctcaccat ggcctggatc cctctcctgc 60
tccccctcct cactctctgc acaggtgctg accccaggcc cttccccagg ctcagtcccc 120
acagattcca agttgagcct gacctgaatc ctgagcaaag cccagacaca gcctctgggt 180
gggactcctg gaaatgggtc ctttgtcttc aagccccctc tcttgttctt ccttgcaggc 240
tctgaggcct cctatgagct gacacagcca ccctcggtgt cagtgtccct aggacagatg 300
gccaggatca cctgctctgg agaagcattg ccaaaaaaat atgcttattg gtaccagcag 360
aagccaggcc agttccctgt gctggtgata tataaagaca gcgagaggcc ctcagggatc 420
cctgagcgat tctctggctc cagctcaggg acaatagtca cattgaccat cagtggagtc 480
caggcagaag acgaggctga ctattactgt ctatcagcag acagcagtg 529

<210> SEQ ID NO 346
<211> LENGTH: 523
<212> TYPE: DNA
<213> ORGANISM: homo sapiens;

<400> SEQUENCE: 346
agctgtgggc tcagaagcag agttctgggg tgtctccacc atggcctgga cccctctctg 60
gctcactctc ctcactcttt gcataggtgc tgcctcccag ggctcaaccc catattatca 120
tgctagctgt gccaacctgg ccctgagctt cggctcaaca cagggagtag tgtagggtgt 180
gggactctag gcgtgaaacc cttatcctca cctcttctgt cctcttttgc aggttctgtg 240
gtttcttctg agctgactca ggaccctgct gtgtctgtgg ccttgggaca gacagtcagg 300
atcacatgcc aaggagacag cctcagaagc tattatgcaa gctggtacca gcagaagcca 360
ggacaggccc ctgtacttgt catctatggt aaaaacaacc ggccctcagg gatcccagac 420
cgattctctg gctccagctc aggaaacaca gcttccttga ccatcactgg ggctcaggcg 480
gaagatgagg ctgactatta ctgtaactcc cgggacagca gtg 523

<210> SEQ ID NO 347
<211> LENGTH: 1515
<212> TYPE: DNA
<213> ORGANISM: homo sapiens;

<400> SEQUENCE: 347
gcacagagga gctgtgccct ggaatggggc ctgtacctgt ccaaggcttg tgccgtcccc 60
tgtgggagat gagaagcgtc cctgcattgg gctcttgggg acccgtcttg gacatgagtg 120
agaatgaaga gggtccctgc attgggctct ggcatgtgac tttaaatgga tttaggcctg 180
taccagacat ctcatgtctg acataaaata tttacaatca ggacattact agagaagcag 240
aaaaaagcta accacctccc tcctgagcca ggatggaatg aaggagggga ctgtggaccc 300
cagataattc ccctgtcacc actgtgactc taacaacctc ttaaatcacg gccaacatct 360
atcccatagg aaggtcttta tatcccctag aaaatacaga ggaagtcagc tctgagcttt 420
tccacgacca acccagccaa ggagcaaggc tgggcacaac ctgggtaaag atgtgagccc 480
agaccatggg accagtgggt gaaggaaaat cgcatgggct gagggggtgg gtaagcaggg 540
gccagccctc ctctctctgt ttcctttggg gctgagtcct tctctggaaa ccacagatct 600
cctccagcag cagcctctga ctctgctgat ttgcatcatg ggccgctctc tccagcaagg 660
ggataagaga ggcctgggag gaacctgctc agtctgggcc taaggaagca gcactggtgg 720
tgcctcagcc atggcctgga ccgttctcct cctcggcctc ctctctcact gcacaggtga 780
tccccccagg gtctcaccaa cctgcccagc ccaagggttc tgggtccagc gtgtccttga 840
ttctgagctc aggagggccc ttcctgtggt gggcaggatg ctcatgaccc tgctgcaggg 900
tgggaggctg gtggggctga actcccccca aactgtgctc aaaggcttgt gagagcctga 960
gggactgcac ctgccaggag agagtagtga gttttcagtt caaagtctcc atacaacagg 1020
aaagtcatgg gccactgggg ctggggctga ttgcagggga taccctgagg gttcacagac 1080
tctctggagc ttgtctggga cagcagggca agggatttca taagaagcat ctttcacctg 1140
caagccaacc tctctcttat ttatttattt atttatttat ttatttattt atttattttt 1200
atctttgcag gctctgtgac ctcctatgtg ctgactcagc caccctcggt gtcagtggcc 1260
ccaggacaga cggccaggat tacctgtggg ggaaacaaca ttggaagtaa aagtgtgcac 1320
tggtaccagc agaagccagg ccaggcccct gtgctggtcg tctatgatga tagcgaccgg 1380
ccctcaggga tccctgagcg attctctggc tccaactctg ggaacacggc caccctgacc 1440
atcagcaggg tcgaagccgg ggatgaggcc gactattact gtcaggtgtg ggatagtagt 1500
agtgatcatc ccacg 1515

<210> SEQ ID NO 348
<211> LENGTH: 558
<212> TYPE: DNA
<213> ORGANISM: homo sapiens;

<400> SEQUENCE: 348
aagagaggcc tgggaagccc agctgtgctg tgggctcagg aggcagagct gtgggtgtct 60
caccatggca tgggccacac tcctgctccc actcctcaac ctctacacag gtgctgcccc 120
cagaccctgc cccaggctca gccctcctaa gcccctggtc ttaccctgaa ccctgagctc 180
agcccaggca tagcctcagg gcgatactac tggaatgggt ttgttatctt caagcccccct 240 ctcttgtcct ctcttgcagg ctctgttgcc tcctatgagc tgacacagct accctcggtg 300
tcagtgtccc caggacagac agccaggatc acctgctctg gagatgtact gggggaaaat 360
tatgctgact ggtaccagca gaagccaggc caggcccctg agttggtgat atacgaagat 420
agtgagcggt accctggaat ccctgaacga ttctctgggt ccacctcagg gaacacgacc 480
accctgacca tcagcagggt cctgaccgaa gacgaggctg actattactg tttgtctggg 540
gatgaggaca atccctca 558

<210> SEQ ID NO 349
<211> LENGTH: 546
<212> TYPE: DNA
<213> ORGANISM: homo sapiens;

<400> SEQUENCE: 349
gctgtgctgt gggtccagga ggcagaactc tgggtgtctc accatggcct ggatccctct 60
acttctcccc ctcttcactc tctgcacagg tgctgtcccc aggccctgct ccaggccctg 120
ctccagtctt attccccaca gatcccaagt tgagcctgcc ctgaatcccg agcaaagccc 180
agacgcagcc tctgggtgcg actcctggga atgggtcctt tgtcttcaag ccccctctct 240
tgttcttcct tgcaggctct gaggcctcct atgagctgac acagccaccc tcggtgtcag 300

```
tgtccccagg acagacggcc aggatcacct gctctggaga tgcattgcca aagcaatatg    360

cttattggta ccagcagaag ccaggccagg cccctgtgct ggtgatatat aaagacagtg    420

agaggccctc agggatccct gagcgattct ctggctccag ctcagggaca acagtcacgt    480

tgaccatcag tggagtccag gcagaagatg aggctgacta ttactgtcaa tcagcagaca    540

gcagtg                                                               546
```

<210> SEQ ID NO 350
<211> LENGTH: 519
<212> TYPE: DNA
<213> ORGANISM: homo sapiens;

<400> SEQUENCE: 350

```
gctgtaggct caggaggcag agctctgaat gtctcaccat ggcctggatc cctctcctgc     60

tccccctcct cattctctgc acaggtgctg cccctaggct cagtctccac agaccccaag    120

ttgagcctga cctgaatcct gagcaaagcc ctgccactgc ctctgggggg gattcctggc    180

aatgcgtcct ttgtcctcaa gccccctctc ctgtcttttc ttgcagtctc tgtggcctcc    240

tatgagctga cacagccatc ctcagtgtca gtgtctccgg gacagacagc caggatcacc    300

tgctcaggag atgtactggc aaaaaaatat gctcggtggt tccagcagaa gccaggccag    360

gcccctgtgc tggtgattta taaagacagt gagcggccct cagggatccc tgagcgattc    420

tccggctcca gctcagggac cacagtcacc ttgaccatca gcggggccca ggttgaggat    480

gaggctgact attactgtta ctctgcggct gacaacaat                           519
```

<210> SEQ ID NO 351
<211> LENGTH: 504
<212> TYPE: DNA
<213> ORGANISM: homo sapiens;

<400> SEQUENCE: 351

```
gctgtggact cagaggcaga gctctggggc atttccatta tggcctggac ccctcccctg     60

ctcgtcctca ctctctgcac aggtgctgcc tcccagggct cagcccccag tgggatcaag    120

atcagcctgg ccctgacctt caactcaaca tagggagtga tgcagggtgt ggggttctgg    180

gaatgaggcc ctcatcctca gactcacctc tcctgtcctc tcttgtgggc tccgttattt    240

cctctgggcc aactcaggtg cctgcagtgt ctgtggcctt gggacaaatg gccaggatca    300

cctgccaggg agacagcatg gaaggctctt atgaacactg gtaccagcag aagccaggcc    360

aggcccccgt gctggtcatc tatgatagca gtgaccggcc ctcaaggatc cctgagcgat    420

tctctggctc caaatcaggc aacacaacca ccctgaccat cactggggcc caggctgagg    480

atgaggctga ttattactat cagt                                           504
```

<210> SEQ ID NO 352
<211> LENGTH: 747
<212> TYPE: DNA
<213> ORGANISM: homo sapiens;

<400> SEQUENCE: 352

```
cttgactctg ctgatttgca tcacaggctg ctctcttcag caaggggata agagagggct     60

ggaaggaacc tgcccagcct gggcctcagg aagcagcatc gggggtgccg cagccatggc    120

ctggaccgct ctccttctga gcctccttgc tcactttaca ggtgctgccc ccagtgtccc    180

agccacctac ccagctccaa ggctctgggt ccagcctggc ctgacagtga tctcagcagg    240

gccctgcctg tggtgtgcag gatgctcatg atcctgctgc agggggaggg gctgctggag    300
```

gtgaaatccc cccacactgt tcttctgtgc tcatggtccc ctgaggacac ttctattcct 360
gaaactcagg ccaggcaggt gggaaggcat tgttgggttg agcctctcag tttcaagtct 420
attctattct ctcccctttt cttgcaggtt ctgtggcctc ctatgagctg actcagccac 480
tctcagtgtc agtggccctg ggacagacgg ccaggattac ctgtggggga aacaacattg 540
gaagtaaaaa tgtgcactgg taccagcaga agccaggcca ggcccctgtg ctggtcatct 600
atagggatag caaccggccc tctgggatcc ctgagcgatt ctctggctcc aactcgggga 660
acacggccac cctgaccatc agcagagccc aagccgggga tgaggctgac tattactgtc 720
aggtgtggga cagcagcact gcacaca 747

<210> SEQ ID NO 353
<211> LENGTH: 529
<212> TYPE: DNA
<213> ORGANISM: homo sapiens;

<400> SEQUENCE: 353
ctcgaataga gctcttggaa gtccctccaa ccatggcctg ggtctccttc tacctactgc 60
ccttcatttt ctccacaggt cagaacatcc cagggaattc agggaaatgt tttcactgct 120
attttcccat gagcaccagt cctcaggggc attctttcca gttcttctgt gcattcagca 180
tcattcatga cattctgttt acaggtctct gtgctctgcc tgtgctgact cagcccccgt 240
ctgcatctgc cttgctggga gcctcgatca agctcacctg caccctaagc agtgagcaca 300
gcacctacac catcgaatgg tatcaacaga gaccagggag gtccccccag tatataatga 360
aggttaagag tgatggcagc cacagcaagg gggacgggat ccccgatcgc ttcatgggct 420
ccagttctgg ggctgaccgc tacctcacct tctccaacct ccagtctgac gatgaggctg 480
agtatcactg tggagagagc cacacgattg atggccaagt cggttgagc 529

<210> SEQ ID NO 354
<211> LENGTH: 483
<212> TYPE: DNA
<213> ORGANISM: homo sapiens;

<400> SEQUENCE: 354
atggcctgga ccccactcct cctcctcttc cctctcctcc tccactgcac aggtcaggag 60
gaccctcagc atcctcatgc cccagctcac tgacaccatc tcccaaactc ataccagaaa 120
tgttgtttgc tcttgtcctt ccttcaggcc ataatgagcg tctctgtttt cagggtctct 180
ctcccagcct gtgctgactc aatcatcctc tgcctctgct tccctgggat cctcggtcaa 240
gctcacctgc actctgagca gtgggcacag tagctacatc atcgcatggc atcagcagca 300
gccagggaag gcccctcggt acttgatgaa gcttgaaggt agtggaagct acaacaaggg 360
gagcggagtt cctgatcgct tctcaggctc cagctctggg gctgaccgct acctcaccat 420
ctccaacctc cagtttgagg atgaggctga ttattactgt gagacctggg acagtaacac 480
tca 483

<210> SEQ ID NO 355
<211> LENGTH: 539
<212> TYPE: DNA
<213> ORGANISM: homo sapiens;

<400> SEQUENCE: 355
agggtgggta agaaatacct gcaactgtca gcctcagcag agctctgggg agtctgcacc 60

-continued

```
atggcttgga ccccactcct cttcctcacc ctcctcctcc actgcacagg tcaggatggc    120

cctcagcacc ctgacctcca gctcactgat accacctccc aaacttatgc caggaatgtc    180

cttccctctt ttcttgactc cagccggtaa tgggtgtctg tgttttcagg gtctctctcc    240

cagcttgtgc tgactcaatc gccctctgcc tctgcctccc tgggagcctc ggtcaagctc    300

acctgcactc tgagcagtgg gcacagcagc tacgccatcg catggcatca gcagcagcca    360

gagaagggcc ctcggtactt gatgaagctt aacagtgatg gcagccacag caaggggggac    420

gggatccctg atcgcttctc aggctccagc tctggggctg agcgctacct caccatctcc    480

agcctccagt ctgaggatga ggctgactat tactgtcaga cctggggcac tggcattca     539
```

<210> SEQ ID NO 356
<211> LENGTH: 496
<212> TYPE: DNA
<213> ORGANISM: homo sapiens;

<400> SEQUENCE: 356

```
ccaccatggc ctggactcct cttcttctct tgctcctctc tcactgcaca ggtagggaca     60

ggcctcagag atcagggcca gccacccaac ctgattctgg ctcttctggt aaagatccct    120

gaaaaacctc accctgaacc ctgcccatca accatgagtg tctgtgtttg caggttccct    180

ctcccagcct gtgctgactc agccaccttc ctcctccgca tctcctggag aatccgccag    240

actcacctgc accttgccca gtgacatcaa tgttggtagc tacaacatat actggtacca    300

gcagaagcca gggagccctc ccaggtatct cctgtactac tactcagact cagataaggg    360

ccagggctct ggagtcccca gccgcttctc tggatccaaa gatgcttcag ccaatacagg    420

gattttactc atctccgggc tccagtctga ggatgaggct gactattact gtatgatttg    480

gccaagcaat gcttct                                                    496
```

<210> SEQ ID NO 357
<211> LENGTH: 520
<212> TYPE: DNA
<213> ORGANISM: homo sapiens;

<400> SEQUENCE: 357

```
actgcggggg taagaggttg tgtccaccat ggcctggact cctctcctcc tcctgttcct     60

ctctcactgc acaggtagga atagacttca gagaccaggg tcagccaccc agcctgattc    120

tgactcttct ggcaaagatc cctgaaaaac tttaccctgg tttctgcctt agcacccatt    180

aatgtctgtg tttccaggtt ccctctcgca ggctgtgctg actcagccgt cttccctctc    240

tgcatctcct ggagcatcag ccagtctcac ctgcaccttg cgcagtggca tcaatgttgg    300

tacctacagg atatactggt accagcagaa gccagggagt cctccccagt atctcctgag    360

gtacaaatca gactcagata agcagcaggg ctctggagtc cccagccgct tctctggatc    420

caaagatgct tcggccaatg cagggatttt actcatctct gggctccagt ctgaggatga    480

ggctgactat tactgtatga tttggcacag cagcgcttct                          520
```

<210> SEQ ID NO 358
<211> LENGTH: 493
<212> TYPE: DNA
<213> ORGANISM: homo sapiens;

<400> SEQUENCE: 358

```
atggcctgga atcctctcct cctcctgttc ctctctcact gcacaggtag gaaaaggcct     60

cagagaccag ggtcagccac acagcctgat tctgactctt gtgtcaaaga tcactaaaaa    120
```

aaatattacc ttggtttctg tcttaaagcc tatatatgcc tgtgttccag gttccctctc 180
gcagcctgtg ctgactcagc caacttccct ctcagcatct cctggagcat cagccagact 240
cacctgcacc ttgcgcagtg gcatcaatct tggtagctac aggatattct ggtaccagca 300
gaagccagag agccctcccc ggtatctcct gagctactac tcagactcaa gtaagcatca 360
gggctctgga gtccccagcc gcttctctgg atccaaagat gcttcgagca atgcagggat 420
tttagtcatc tctgggctcc agtctgagga tgaggctgac tattactgta tgatttggca 480
cagcagtgct tct 493

<210> SEQ ID NO 359
<211> LENGTH: 500
<212> TYPE: DNA
<213> ORGANISM: homo sapiens;

<400> SEQUENCE: 359
ccaccatggc ctggactctt ctccttctcg tgctcctctc tcactgcaca ggtagggaaa 60
gtccttataa actgagtctc agtgtccaac ctacaccatc ccctgtggct cagacctaca 120
agaagcttta ccctgggaac tgccttatca cccatgatgt ctgtgttttc aggttccctc 180
tcccagcctg tgctgactca gccatcttcc cattctgcat cttctggagc atcagtcaga 240
ctcacctgca tgctgagcag tggcttcagt gttggggact tctggataag gtggtaccaa 300
caaaagccag ggaaccctcc ccggtatctc ctgtactacc actcagactc caataagggc 360
caaggctctg gagttcccag ccgcttctct ggatccaacg atgcatcagc caatgcaggg 420
attctgcgta tctctgggct ccagcctgag gatgaggctg actattactg tggtacatgg 480
cacagcaact ctaagactca 500

<210> SEQ ID NO 360
<211> LENGTH: 574
<212> TYPE: DNA
<213> ORGANISM: homo sapiens;

<400> SEQUENCE: 360
tctgaggata cgcgtgacag ataagaaggg ctggtgggat cagtcctggt ggtagctcag 60
gaagcagagc ctggagcatc tccactatgg cctgggctcc actacttctc accctcctcg 120
ctcactgcac aggtggctgc ctgcaaggaa ttcagggagc gttcctggat gtcacctggg 180
ctgatgatct gttcctcctg cctgggaacc agtcttcatc tctcccgact gatctctgtg 240
ttgctctctt cttgcaggtt cttgggccaa ttttatgctg actcagcccc actctgtgtc 300
ggagtctccg gggaagacgg taaccatctc ctgcacccgc agcagtggca gcattgccag 360
caactatgtg cagtggtacc agcagcgccc gggcagttcc cccaccactg tgatctatga 420
ggataaccaa agaccctctg ggtccctgga tcggttctct ggctccatcg acagctcctc 480
caactctgcc tccctcacca tctctggact gaagactgag gacgaggctg actactactg 540
tcagtcttat gatagcagca atcacacagt gctc 574

<210> SEQ ID NO 361
<211> LENGTH: 472
<212> TYPE: DNA
<213> ORGANISM: homo sapiens;

<400> SEQUENCE: 361
tctggcgcca ggggtccctt ccaatatcag caccatggcc tggactcctc tctttctgtt 60

-continued

```
cctcctcact tgctgcccag gttaagagag atttcaaata ccagcctttg gagggatcct    120

tctgtctgcc cttctaattt ctaacatgtg tctgtttttt gtttcagggt ccaattctca    180

gactgtggtg actcaggagc cctcactgac tgtgtcccca ggagggacag tcactctcac    240

ctgtgcttcc agcactggag cagtcaccag tggttactat ccaaactggt tccagcagaa    300

acctggacaa gcacccaggg cactgattta tagtacaagc aacaaacact cctggacccc    360

tgcccggttc tcaggctccc tccttggggg caaagctgcc ctgacactgt caggtgtgca    420

gcctgaggac gaggctgagt attactgcct gctctactat ggtggtgctc ag            472
```

```
<210> SEQ ID NO 362
<211> LENGTH: 473
<212> TYPE: DNA
<213> ORGANISM: homo sapiens;

<400> SEQUENCE: 362

tctggcacca ggggtccctt ccaatatcag caccatggcc tggactcctc tctttctgtt     60

cctcctcact tgctgcccag gttaagagag atttcaaata ccagcctttg gagggatccc    120

tttttctccc tttctaattc ctaatatatg tctgtttttt ttgtttcagg gtccaattcc    180

caggctgtgg tgactcagga gccctcactg actgtgtccc caggagggac agtcactctc    240

acctgtggct ccagcactgg agctgtcacc agtggtcatt atccctactg gttccagcag    300

aagcctggcc aagcccccag gacactgatt tatgatacaa gcaacaaaca ctcctggaca    360

cctgcccggt tctcaggctc cctccttggg ggcaaagctg ccctgaccct tttgggtgcg    420

cagcctgagg atgaggctga gtattactgc ttgctctcct atagtggtgc tcg           473
```

```
<210> SEQ ID NO 363
<211> LENGTH: 513
<212> TYPE: DNA
<213> ORGANISM: homo sapiens;

<400> SEQUENCE: 363

gaggaaaaca aaccccagct gggaagcctg agaacactta gccttcatga gtgtccccac     60

catggcctgg atgatgcttc tcctcggact ccttgcttat ggatcaggtc aggggaaggg    120

actctatccc tgggggacca cagaaaacag ggtccaggtt actctcatcc tcatgatcat    180

aactgtgtct ctcctgttcg ttttaggagt ggattctcag actgtggtga cccaggagcc    240

atcgttctca gtgtcccctg gagggacagt cacactcact tgtggcttga gctctggctc    300

agtctctact agttactacc ccagctggta ccagcagacc ccaggccagg ctccacgcac    360

gctcatctac agcacaaaca ctcgctcttc tggggtccct gatcgcttct ctggctccat    420

ccttgggaac aaagctgccc tcaccatcac gggggcccag gcagatgatg aatctgatta    480

ttactgtgtg ctgtatatgg gtagtggcat ttc                                 513
```

```
<210> SEQ ID NO 364
<211> LENGTH: 546
<212> TYPE: DNA
<213> ORGANISM: homo sapiens;

<400> SEQUENCE: 364

gagagactga agaacccagc attgcagcag ctccaccatg gcctgggctc ctctgctcct     60

caccctcctc agtctcctca caggtcaggg tgggcagtgg gctgggcccc caaagggacc    120

cccacctccc agcctccatc tccccatccc tgctcttcct cctccaacag ctcatcagcc    180

acccaccaac aggagccctc atgggtgtct gtgtttccag ggtccctctc ccagcctgtg    240
```

ctgactcagc caccttctgc atcagcctcc ctgggagcct cggtcacact cacctgcacc 300
ctgagcagcg gctacagtaa ttataaagtg gactggtacc agcagagacc agggaagggc 360
ccccggtttg tgatgcgagt gggcactggt gggattgtgg gatccaaggg ggatggcatc 420
cctgatcgct tctcagtctt gggctcaggc ctgaatcggt acctgaccat caagaacatc 480
caggaagaag atgagagtga ctaccactgt ggggcagacc atggcagtgg gagcaacttc 540
gtgtaa 546

<210> SEQ ID NO 365
<211> LENGTH: 6729
<212> TYPE: DNA
<213> ORGANISM: homo sapiens;

<400> SEQUENCE: 365
gcctccacca agggcccatc ggtcttcccc ctggcaccct cctccaagag cacctctggg 60
ggcacagcag ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttggtgag 300
aggccagcac agggagggag ggtgtctgct ggaagccagg ctcagcgctc ctgcctggac 360
gcatcccggc tatgcagccc cagtccaggg cagcaaggca ggccccgtct gcctcttcac 420
ccggaggcct ctgcccgccc cactcatgct cagggagagg gtcttctggc tttttcccca 480
ggctctgggc aggcacaggc taggtgcccc taacccaggc cctgcacaca aaggggcagg 540
tgctgggctc agacctgcca agagccatat ccgggaggac cctgcccctg acctaagccc 600
accccaaagg ccaaactctc cactccctca gctcggacac cttctctcct cccagattcc 660
agtaactccc aatcttctct ctgcagagcc caaatcttgt gacaaaactc acacatgccc 720
accgtgccca ggtaagccag cccaggcctc gccctccagc tcaaggcggg acaggtgccc 780
tagagtagcc tgcatccagg gacaggcccc agccgggtgc tgacacgtcc acctccatct 840
cttcctcagc acctgaactc ctggggggac cgtcagtctt cctcttcccc ccaaaaccca 900
aggacaccct catgatctcc cggacccctg aggtcacatg cgtggtggtg gacgtgagcc 960
acgaagaccc tgaggtcaag ttcaactggt acgtggacgg cgtggaggtg cataatgcca 1020
agacaaagcc gcgggaggag cagtacaaca gcacgtaccg tgtggtcagc gtcctcaccg 1080
tcctgcacca ggactggctg aatggcaagg agtacaagtg caaggtctcc aacaaagccc 1140
tcccagcccc catcgagaaa accatctcca aagccaaagg tgggacccgt ggggtgcgag 1200
ggccacatgg acagaggccg gctcggccca ccctctgccc tgagagtgac cgctgtacca 1260
acctctgtcc ctacagggca gccccgagaa ccacaggtgt acaccctgcc cccatcccgg 1320
gatgagctga ccaagaacca ggtcagcctg acctgcctgg tcaaaggctt ctatcccagc 1380
gacatcgccg tggagtggga gagcaatggg cagccggaga acaactacaa gaccacgcct 1440
cccgtgctgg actccgacgg ctccttcttc ctctacagca agctcaccgt ggacaagagc 1500
aggtggcagc aggggaacgt cttctcatgc tccgtgatgc atgaggctct gcacaaccac 1560
tacacacaga agagcctctc cctgtctccg ggtaaatgag tgccacggcc ggcaagcccc 1620
cgctccccag gctctcgggg tcgcgcgagg atgcttggca cgtaccccgt gtacatactt 1680
cccaggcacc cagcatggaa ataaagcacc cagcgcttcc ctgggcccct gcgagactgt 1740

-continued

```
gatggttctt tccacgggtc aggccgagtc tgaggcctga gtggcatgag ggaggcagag   1800
tgggtcccac tgtccccaca ctggcccagg ctgtgcaggt gtgcctgggc cgcctagggt   1860
ggggctcagc caggggctgc cctcggcagg gtgggggatt tgccagcgtg gccctccctc   1920
cagcagcagc tgccctgggc tgggccacga gaagccctag gagcccctgg ggacagacac   1980
acagcccctg cctctgtagg agactgtcct gttctgtgag cgccctgtcc tccgacccgc   2040
atgcccactc gggggcatgc ctagtccatg tgcgtaggga caggccctcc ctcacccatc   2100
tacccccacg gcactaaccc ctggcagccc tgcccagcct cgcacccgca tggggacaca   2160
accgactccg gggacatgca ctctcgggcc ctgtggagag actggtccag atgcccacac   2220
acacactcag cccagacccg ttcaacaaac cccgcactga ggttggccgg ccacacggcc   2280
accacacaca cacgtgcacg cctcacacac ggagcctcac ccgggcgaac cgcacagcac   2340
ccagaccaga gcaaggtcct cgcacacgtg aacactcctc ggacacaggc ccccacgagc   2400
cccacgcggc acctcaaggc ccacgagccg ctcggcagct tctccacatg ctgacctgct   2460
cagacaaacc cagccctcct ctcacaaggt gcccctgcag ccgccacaca cacacagggg   2520
atcacacacc acgtcacgtc cctggccctg gcccacttcc cagtgccgcc cttccctgca   2580
gctggggtca catgaggtgt gggcttcacc atcctcctgc cctctgggcc tcagggaggg   2640
acacgggaga cggggagcgg gtcctgctga gggccaggtc gctatctagg gccgggtgtc   2700
tggctgagcc ccggggccaa agctggtgcc cagggcgggc agctgtgggg agctgacctc   2760
aggacattgt tggcccatcc cggccgggcc ctacatcctg ggtcctgcca cagagggaat   2820
cacccccaga ggcccaagcc caggggggaca cagcactgac cacccccttc ctgtccagag   2880
ctgcaactgg aggagagctg tgcggaggcg caggacgggg agctggacgg gctgtggacg   2940
accatcacca tcttcatcac actcttcctg ttaagcgtgt gctacagtgc caccgtcacc   3000
ttcttcaagg tcggccgcac gttgtcccca gctgtccttg acattgtccc ccatgctgtc   3060
acaaactgtc tctgacactg tcccacaggc tgtccccacc tgtccctgac gctgtccccc   3120
atgctctcac aaactgtccc tgacattgtc cccaatgctg cccccacctg tccaacagtg   3180
tcccccaggc tctccccaca tgtccccgac actgtccccc atgctgtccc catctgtccc   3240
caacactgtc ccccaccctg tcccccttttg tccccaacac tgtcccccac agtttccacc   3300
tgtccctgac actgtccccc atgctttccc cacctgtccc tgacaccatc ccccactctg   3360
tcccctatag ttcctggccc tgtcccccac gctgtcccct acagtacctg gcactgtccc   3420
ccatgctgtc ccctcctgta tgaaaccctg tcccacatgc tgtccccacc tgtccgtgac   3480
aatatccccc acactgtccc cacctgtccc cgacactctc ctccacgttg ttcttaccta   3540
aacccgacac tttcctccat gctgtcccca cccatctccg acactgtacc ccacgttgtc   3600
cccacctgtc ctcaacactg tcccccatgc tgtccccacc tgtccccaac actctcctcc   3660
atgctgtccc cacctgtccc tgatattgtc ccccatgcag tctccacctg tccccaatgc   3720
tgtcccccag gctgtaccta ccagtacaac actgtccccc atgctgtccc cacctgtccc   3780
tgacactgtc ccccacgctg tcccctcctg tccccgacac tgtcccccac actgtcccca   3840
cctgtcccca acactatcct ccatgctgtc ccctcctgtc cccacctgtc ccctacactg   3900
tcccccatgc tgtccccacc agtccccaaa actttcctcc acactgtccc cacctgtccc   3960
caacactgtc ccccacgcta tccccccctgt ccccgacaat gtccccactg tttcctcctg   4020
ttccctccta tccctgacac tgtccgccat gctgtcccca cctgtccctg acactgtctc   4080
ccactctgtc ccctataatc cctgacactg tcccccacgc cgtcccctcc cgtatgcacc   4140
```

```
actgtccccc aagctgtccc cacctgtcct caacacagtc ccccatgctg tccccacctg   4200
tccccaacac tctcctccat gtccccacct gtccctgata ttgtccccca tgcagtcccc   4260
acctgtcccc gatgctgtcc cccgggctgt acctaccagt ccaacactgt cccccacact   4320
ctccccacct gtccctgata ctgtccccca tgctgtcccc acctgtcccg gacactgttc   4380
tccacgctct cccctcctgt ccctgacact gtcccccaca ctgtccccac ctgtccccaa   4440
cactatcctc catcctgtcc caacctgtct cctacactgt cccccatgct gtccccacca   4500
gtccccaaca ctgtcctcca tgctgtcccc catgtcccca acactgtccc ccatgctatc   4560
tcccctgtcc ctgacaatgt ccccactgtt tcctgtcccc tcctatccct gacactgtcc   4620
cccatgctgt ccccacctgt cccccacatg gtctccaccg gtccctgaca ctgtctccca   4680
ctctgtcccc tataatccct gacactgtcc cccacaccgt cccctcctgt atgcaccact   4740
gtcccccatg ctgtccccac ctgtccctga tgctgtcctc cacacagtcc ccacctctcc   4800
ctgacactgt ccccatctct ccccaacact ctcctccatg ctgtccttaa ctgtccccaa   4860
cactcttcca cactctgtct ccacctgtcc ctgacactgt cccccacact gtcctcacct   4920
gtgtctgaca ctgtccccca cgctgtcccc acctgtccct gacgctgtct tctgtgctgt   4980
ccacatgctg ttggtgccct ggctctgctc tctatcacca agcctcagag caggcagtgg   5040
tgaggccatg gcacctgggt ggcatgaggg gccggatggg cctcaggggc agggctgtgg   5100
cctgcgtgga ctgacgggtg ggtgggcctt gggggcagag aggtggcctc agtgccctga   5160
ggggtgggtg gggctcgggg gcagggctgt ggcctcgctc acccctgtgc tgtgccttgc   5220
ctacaggtga agtggatctt ctcctcggtg gtggacctga agcagaccat catccccgac   5280
tacaggaaca tgatcggaca gggggcctag ggccaccctc tgcggggtgt ccagggccgc   5340
ccagacccca cacaccagcc atgggccatg ctcagccacc acccaggcca cacctgcccc   5400
cgacctcacc gccctcaacc ccatgactct ctggcctcgc agttgccctc tgaccctgac   5460
acacctgaca cgcccccctt ccagaccctg tgcatagcag gtctacccca gacctccgct   5520
gcttggtgca tgcagggcac tgggggccag gtgtcccctc agcaggacgt ccttgccctc   5580
cggaccacaa ggtgctcaca caaaaggagg cagtgaccgg tatcccaggc ccccacccag   5640
gcaggacctc gccctggagc caaccccgtc cacgccagcc tcctgaacac aggcgtggtt   5700
tccagatggt gagtgggagc gtcagccgcc aaggtaggga agccacagca ccatcaggcc   5760
ctgttgggga ggcttccgag agctgcgaag gctcactcag acggccttcc tcccagcccg   5820
cagccagcca gcctccattc cgggcactcc cgtgaactcc tgacatgagg aatgaggttg   5880
ttctgatttc aagcaaagaa cgctgctctc tggctcctgg gaacagtctc agtgccagca   5940
ccaccccttg gctgcctgcc cacactgctg gattctcggg tggaactgga cccgcaggga   6000
cagccagccc cagagtccgc actggggaga gaaggggcca ggcccaggac actgccacct   6060
cccacccact ccagtccacc gagatcactc agagaagagc ctgggccatg tggccgctgc   6120
aggagcccca cagtgcaagg gtgaggatag cccaaggaag ggctgggcat ctgcccagac   6180
aggcctccca gagaaggctg gtgaccaggt cccaggcggg caagactcag ccttggtggg   6240
gcctgaggac agaggaggcc caggagcatc ggggagagag gtggagggac accgggagag   6300
ccaggagcgt ggacacagcc agaactcatc acagaggctg gcgtccagcc ccgggtcacg   6360
tgcagcagga acaagcagcc actctggggg caccaggtgg agaggcaaga cgacaaagag   6420
ggtgcccgtg ttcttgcgaa agcagggctg ctggccacga gtgctggaca gaggccccca   6480
```

-continued cgctctgctg cccccatcac gccgttccgt gactgtcacg cagaatctgc agacaggaag 6540
ggagactcga gcgggagtgc ggccagcgcc tgcctcggcc gtcagggagg actcctgggc 6600
tcactcgaag gaggtgccac catttcagct ttggtagctt ttcttcttct tttaaatttt 6660
ctaaagctca ttaattgtct ttgatgtttc ttttgtgatg acaataaaat atcctttttta 6720 agtcttgta 6729

<210> SEQ ID NO 366
<211> LENGTH: 888
<212> TYPE: DNA
<213> ORGANISM: homo sapiens;

<400> SEQUENCE: 366
gcctccacca agggcccatc ggtcttcccc ctggcaccct cctccaagag cacctctggg 60
ggcacagcag ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggagta caagtgcaag gtctccaaca aagccctccc agcccccatc 540
gagaaaacca tctccaaagc caaagggcag ccccgagaac cacaggtgta caccctgccc 600
ccatcccggg atgagctgac caagaaccag gtcagcctga cctgcctggt caaaggcttc 660
tatcccagcg acatcgccgt ggagtgggag agcaatgggc agccggagaa caactacaag 720
accacgcctc ccgtgctgga ctccgacggc tccttcttcc tctacagcaa gctcaccgtg 780
gacaagagca ggtggcagca ggggaacgtc ttctcatgct ccgtgatgca tgaggctctg 840
cacaaccact acacacagaa gagcctctcc ctgtctccgg gtaaatga 888

<210> SEQ ID NO 367
<211> LENGTH: 993
<212> TYPE: DNA
<213> ORGANISM: homo sapiens;

<400> SEQUENCE: 367
gcctccacca agggcccatc ggtcttcccc ctggcaccct cctccaagag cacctctggg 60
ggcacagcag ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720

```
ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacaca    960

cagaagagcc tctccctgtc tccgggtaaa tga                                 993
```

<210> SEQ ID NO 368
<211> LENGTH: 1200
<212> TYPE: DNA
<213> ORGANISM: homo sapiens;

<400> SEQUENCE: 368

```
gcctccacca agggcccatc ggtcttcccc ctggcaccct cctccaagag cacctctggg     60

ggcacagcag ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacaca    960

cagaagagcc tctccctgtc tccggagctg caactggagg agagctgtgc ggaggcgcag   1020

gacggggagc tggacgggct gtggacgacc atcaccatct tcatcacact cttcctgtta   1080

agcgtgtgct acagtgccac cgtcaccttc ttcaaggtga agtggatctt ctcctcggtg   1140

gtggacctga agcagaccat catccccgac tacaggaaca tgatcggaca gggggcctag   1200
```

<210> SEQ ID NO 369
<211> LENGTH: 1739
<212> TYPE: DNA
<213> ORGANISM: homo sapiens;

<400> SEQUENCE: 369

```
gcctccacca agggcccatc ggtcttcccc ctggcgccct gctccaggag cacctccgag     60

agcacagcgg ccctgggctg cctggtcaag gactacttcc ccgaaccggt gacggtgtcg    120

tggaactcag gcgctctgac cagcggcgtg cacaccttcc cggctgtcct acagtcctca    180

ggactctact ccctcagcag cgtggtgacc gtgccctcca gcaacttcgg cacccagacc    240

tacacctgca acgtagatca caagcccagc aacaccaagg tggacaagac agttggtgag    300

aggccagctc agggagggag ggtgtctgct ggaagccagg ctcagccctc ctgcctggac    360
```

-continued

```
gcaccccggc tgtgcagccc cagcccaggg cagcaaggca ggccccatct gtctcctcac    420
ccggaggcct ctgcccgccc cactcatgct cagggagagg gtcttctggc tttttccacc    480
aggctccagg caggcacagg ctgggtgccc ctaccccagg cccttcacac acaggggcag    540
gtgcttggct cagacctgcc aaaagccata tccgggagga ccctgcccct gacctaagcc    600
gaccccaaag gccaaactgt ccactccctc agctcggaca ccttctctcc tcccagatcc    660
gagtaactcc caatcttctc tctgcagagc gcaaatgttg tgtcgagtgc ccaccgtgcc    720
caggtaagcc agcccaggcc tcgccctcca gctcaaggcg ggacaggtgc cctagagtag    780
cctgcatcca gggacagacc ccagctgggt gctgacacgt ccacctccat ctcttcctca    840
gcaccacctg tggcaggacc gtcagtcttc ctcttccccc caaaacccaa ggacaccctc    900
atgatctccc ggacccctga ggtcacgtgc gtggtggtgg acgtgagcca cgaagacccc    960
gaggtccagt tcaactggta cgtggacggc gtggaggtgc ataatgccaa gacaaagcca   1020
cgggaggagc agttcaacag cacgttccgt gtggtcagcg tcctcaccgt cgtgcaccag   1080
gactggctga acggcaagga gtacaagtgc aaggtctcca acaaaggcct cccagccccc   1140
atcgagaaaa ccatctccaa aaccaaaggt gggacccgcg gggtatgagg gccacatgga   1200
cagaggccgg ctcggcccac cctctgccct gggagtgacc gctgtgccaa cctctgtccc   1260
tacagggcag ccccgagaac cacaggtgta caccctgccc ccatcccggg aggagatgac   1320
caagaaccag gtcagcctga cctgcctggt caaaggcttc taccccagcg acatctccgt   1380
ggagtgggag agcaatgggc agccggagaa caactacaag accacacctc ccatgctgga   1440
ctccgacggc tccttcttcc tctacagcaa gctcaccgtg gacaagagca ggtggcagca   1500
ggggaacgtc ttctcatgct ccgtgatgca tgaggctctg cacaaccact acacacagaa   1560
gagcctctcc ctgtctccgg gtaaatgagt gccacggccg gcaagccccc gctccccagg   1620
ctctcggggt cgcgcgagga tgcttggcac gtaccccgtc tacatacttc ccgggcaccc   1680
agcatggaaa taaagcaccc agcgctgccc tgggcccctg cgagactgtg atggttctt    1739
```

<210> SEQ ID NO 370
<211> LENGTH: 981
<212> TYPE: DNA
<213> ORGANISM: homo sapiens;

<400> SEQUENCE: 370

```
gcctccacca agggcccatc ggtcttcccc ctggcgccct gctccaggag cacctccgag     60
agcacagcgg ccctgggctg cctggtcaag gactacttcc ccgaaccggt gacggtgtcg    120
tggaactcag gcgctctgac cagcggcgtg cacaccttcc cggctgtcct acagtcctca    180
ggactctact ccctcagcag cgtggtgacc gtgccctcca gcaacttcgg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt cgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatctc cgtggagtgg    780
```

gagagcaatg ggcagccgga gaacaactac aagaccacac ctcccatgct ggactccgac 840
ggctccttct tcctctacag caagctcacc gtggacaaga gcaggtggca gcaggggaac 900
gtcttctcat gctccgtgat gcatgaggct ctgcacaacc actacacaca gaagagcctc 960
tccctgtctc cgggtaaatg a 981

<210> SEQ ID NO 371
<211> LENGTH: 981
<212> TYPE: DNA
<213> ORGANISM: homo sapiens;

<400> SEQUENCE: 371
gcctccacca agggcccatc ggtcttcccc ctggcgccct gctccaggag cacctccgag 60
agcacagcgg ccctgggctg cctggtcaag gactacttcc ccgaaccggt gacggtgtcg 120
tggaactcag gcgctctgac cagcggcgtg cacaccttcc cggctgtcct acagtcctca 180
ggactctact ccctcagcag cgtggtgacc gtgacctcca gcaacttcgg cacccagacc 240
tacacctgca acgtagatca caagcccagc aacaccaagg tggacaagac agttgagcgc 300
aaatgttgtg tcgagtgccc accgtgccca gcaccacctg tggcaggacc gtcagtcttc 360
ctcttccccc caaaacccaa ggacaccctc atgatctccc ggacccctga ggtcacgtgc 420
gtggtggtgg acgtgagcca cgaagacccc gaggtccagt tcaactggta cgtggacggc 480
atggaggtgc ataatgccaa gacaaagcca cgggaggagc agttcaacag cacgttccgt 540
gtggtcagcg tcctcaccgt cgtgcaccag gactggctga acggcaagga gtacaagtgc 600
aaggtctcca acaaaggcct cccagccccc atcgagaaaa ccatctccaa aaccaaaggg 660
cagccccgag aaccacaggt gtacaccctg cccccatccc gggaggagat gaccaagaac 720
caggtcagcc tgacctgcct ggtcaaaggc ttctacccca gcgacatctc cgtggagtgg 780
gagagcaatg ggcagccgga gaacaactac aagaccacac ctcccatgct ggactccgac 840
ggctccttct tcctctacag caagctcacc gtggacaaga gcaggtggca gcaggggaac 900
gtcttctcat gctccgtgat gcatgaggct ctgcacaacc actacacaca gaagagcctc 960
tccctgtctc cgggtaaatg a 981

<210> SEQ ID NO 372
<211> LENGTH: 1739
<212> TYPE: DNA
<213> ORGANISM: homo sapiens;

<400> SEQUENCE: 372
gcctccacca agggcccatc ggtcttcccc ctggcgccct gctccaggag cacctccgag 60
agcacagcgg ccctgggctg cctggtcaag gactacttcc ccgaaccggt gacggtgtcg 120
tggaactcag gcgctctgac cagcggcgtg cacaccttcc cggctgtcct acagtcctca 180
ggactctact ccctcagcag cgtggtgacc gtgacctcca gcaacttcgg cacccagacc 240
tacacctgca acgtagatca caagcccagc aacaccaagg tggacaagac agttggtgag 300
aggccagctc agggagggag ggtgtctgct ggaagccagg ctcagccctc ctgcctggac 360
gcaccccggc tgtgcagccc cagcccaggg cagcaaggca ggccccatct gtctcctcac 420
ccggaggcct ctgcccgccc cactcatgct cagggagagg gtcttctggc tttttccacc 480
aggctccagg caggcacagg ctgggtgccc ctaccccagg cccttcacac acaggggcag 540
gtgcttggct cagacctgcc aaaagccata tccgggagga ccctgcccct gacctaagcc 600
gaccccaaag gccaaactgt ccactccctc agctcggaca ccttctctcc tcccagatcc 660
gagtaactcc caatcttctc tctgcagagc gcaaatgttg tgtcgagtgc ccaccgtgcc 720
caggtaagcc agcccaggcc tcgccctcca gctcaaggcg ggacaggtgc cctagagtag 780
cctgcatcca gggacagacc ccagctgggt gctgacacgt ccacctccat ctcttcctca 840
gcaccacctg tggcaggacc gtcagtcttc ctcttccccc caaaacccaa ggacaccctc 900
atgatctccc ggacccctga ggtcacgtgc gtggtggtgg acgtgagcca cgaagacccc 960
gaggtccagt tcaactggta cgtggacggc atggaggtgc ataatgccaa gacaaagcca 1020
cgggaggagc agttcaacag cacgttccgt gtggtcagcg tcctcaccgt cgtgcaccag 1080
gactggctga acggcaagga gtacaagtgc aaggtctcca acaaaggcct cccagccccc 1140
atcgagaaaa ccatctccaa aaccaaaggt gggacccgcg gggtatgagg gccacatgga 1200
cagaggccgg ctcggcccac cctctgccct gggagtgacc gctgtgccaa cctctgtccc 1260
tacagggcag ccccgagaac cacaggtgta caccctgccc ccatcccggg aggagatgac 1320
caagaaccag gtcagcctga cctgcctggt caaaggcttc taccccagcg acatctccgt 1380
ggagtgggag agcaatgggc agccggagaa caactacaag accacacctc ccatgctgga 1440
ctccgacggc tccttcttcc tctacagcaa gctcaccgtg gacaagagca ggtggcagca 1500
ggggaacgtc ttctcatgct ccgtgatgca tgaggctctg cacaaccact acacacagaa 1560
gagcctctcc ctgtctccgg gtaaatgagt gccacggccg gcaagccccc gctccccagg 1620
ctctcggggt cgcgcgagga tgcttggcac gtaccccgtc tacatacttc ccgggcaccc 1680
agcatggaaa taaagcaccc agcgctgccc tgggcccctg cgagactgtg atggttctt 1739

<210> SEQ ID NO 373
<211> LENGTH: 2304
<212> TYPE: DNA
<213> ORGANISM: homo sapiens;

<400> SEQUENCE: 373
cttccaccaa gggcccatcg gtcttccccc tggcgccctg ctccaggagc acctctgggg 60
gcacagcggc cctgggctgc ctggtcaagg actacttccc agaaccggtg acggtgtcgt 120
ggaactcagg cgccctgacc agcggcgtgc acaccttccc ggctgtccta cagtcctcag 180
gactctactc cctcagcagc gtggtgaccg tgccctccag cagcttgggc acccagacct 240
acacctgcaa cgtgaatcac aagcccagca acaccaaggt ggacaagaga gttggtgaga 300
ggccagcgca gggagggagg gtgtctgctg gaagccaggc tcagccctcc tgcctggacg 360
catcccggct gtgcagtccc agcccagggc accaaggcag gccccgtctg actcctcacc 420
cggaggcctc tgcccgcccc actcatgctc agggagaggg tcttctggct ttttccacca 480
ggctccgggc aggcacaggc tggatgcccc taccccaggc ccttcacaca caggggcagg 540
tgctgcgctc agagctgcca agagccatat ccaggaggac cctgcccctg acctaagccc 600
accccaaagg ccaaactctc tactcactca gctcagatac cttctctctt cccagatctg 660
agtaactccc aatcttctct ctgcagagct caaaacccca cttggtgaca caactcacac 720
atgcccacgg tgcccaggta agccagccca ggcctcgccc tccagctcaa ggcgggacaa 780
gagccctaga gtggcctgag tccagggaca ggccccagca gggtgctgac gcatccacct 840
ccatcccaga tccccgtaac tcccaatctt ctctctgcag agcccaaatc ttgtgacaca 900
cctcccccgt gcccacggtg cccaggtaag ccagcccagg cctcgccctc cagctcaagg 960
caggacaaga gccctagagt ggcctgagtc cagggacagg ccccagcagg gtgctgacgc 1020
gtccacctcc atcccagatc cccgtaactc ccaatcttct ctctgcagag cccaaatctt 1080
gtgacacacc tcccccatgc ccacggtgcc caggtaagcc agcccaggcc tcgccctcca 1140
gctcaaggcg ggacaagagc cctagagtgg cctgagtcca gggacaggcc ccagcagggt 1200
gctgacgcat ccacctccat cccagatccc cgtaactccc aatcttctct ctgcagagcc 1260
caaatcttgt gacacacctc ccccgtgccc aaggtgccca ggtaagccag cccaggcctc 1320
gccctccagc tcaaggcagg acaggtgccc tagagtggcc tgcatccagg gacaggtccc 1380
agtcgggtgc tgacacatct gcctccatct cttcctcagc acctgaactc ctgggaggac 1440
cgtcagtctt cctcttcccc ccaaaaccca aggataccct tatgatttcc cggacccctg 1500
aggtcacgtg cgtggtggtg gacgtgagcc acgaagaccc cgaggtccag ttcaagtggt 1560
acgtggacgg cgtggaggtg cataatgcca agacaaagcc gcgggaggag cagtacaaca 1620
gcacgttccg tgtggtcagc gtcctcaccg tcctgcacca ggactggctg aacggcaagg 1680
agtacaagtg caaggtctcc aacaaagccc tcccagcccc catcgagaaa accatctcca 1740
aaaccaaagg tgggacccgc ggggtatgag ggccacatgg acagaggcca gcttgaccca 1800
ccctctgccc tgggagtgac cgctgtgcca acctctgtcc ctacaggaca gccccgagaa 1860
ccacaggtgt acaccctgcc cccatcccgg gaggagatga ccaagaacca ggtcagcctg 1920
acctgcctgg tcaaaggctt ctaccccagc gacatcgccg tggagtggga gagcagcggg 1980
cagccggaga acaactacaa caccacgcct cccatgctgg actccgacgg ctccttcttc 2040
ctctacagca agctcaccgt ggacaagagc aggtggcagc aggggaacat cttctcatgc 2100
tccgtgatgc atgaggctct gcacaaccgc ttcacgcaga agagcctctc cctgtctccg 2160
ggtaaatgag tgcgacggcc ggcaagcccc cgctccccgg gctctcgggg tcgcgcgagg 2220
atgcttggca cgtaccccgt gtacatactt cccgggcacc cagcatggaa ataaagcacc 2280
cagcgctgcc ctgggcccct gcga 2304

<210> SEQ ID NO 374
<211> LENGTH: 1134
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 374
ncttccacca agggcccatc ggtcttcccc ctggcgccct gctccaggag cacctctggg 60
ggcacagcgg ccctgggctg cctggtcaag gactacttcc cagaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacacctgca acgtgaatca caagcccagc aacaccaagg tggacaagag agttgagctc 300
aaaaccccac ttggtgacac aactcacaca tgcccacggt gcccagagcc caaatcttgt 360
gacacacctc ccccgtgccc acggtgccca gagcccaaat cttgtgacac acctccccca 420
tgcccacggt gcccagagcc caaatcttgt gacacacctc ccccgtgccc aaggtgccca 480
gcacctgaac tcctgggagg accgtcagtc ttcctcttcc ccccaaaacc caaggatacc 540
cttatgattt cccggacccc tgaggtcacg tgcgtggtgg tggacgtgag ccacgaagac 600
cccgaggtcc agttcaagtg gtacgtggac ggcgtggagg tgcataatgc caagacaaag 660
ccgcgggagg agcagtacaa cagcacgttc cgtgtggtca gcgtcctcac cgtcctgcac 720
caggactggc tgaacggcaa ggagtacaag tgcaaggtct ccaacaaagc cctcccagcc 780
cccatcgaga aaaccatctc caaaaccaaa ggacagcccc gagaaccaca ggtgtacacc 840
ctgcccccat cccgggagga gatgaccaag aaccaggtca gcctgacctg cctggtcaaa 900
ggcttctacc ccagcgacat cgccgtggag tgggagagca gcgggcagcc ggagaacaac 960
tacaacacca cgcctcccat gctggactcc gacggctcct tcttcctcta cagcaagctc 1020
accgtggaca agagcaggtg gcagcagggg aacatcttct catgctccgt gatgcatgag 1080
gctctgcaca accgcttcac gcagaagagc ctctccctgt ctccgggtaa atga 1134

<210> SEQ ID NO 375
<211> LENGTH: 1134
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 375
ncttccacca agggcccatc ggtcttcccc ctggcgccct gctccaggag cacctctggg 60
ggcacagcgg ccctgggctg cctggtcaag gactacttcc cagaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacacctgca acgtgaatca caagcccagc aacaccaagg tggacaagag agttgagctc 300
aaaaccccac ttggtgacac aactcacaca tgcccacggt gcccagagcc caaatcttgt 360
gacacacctc ccccgtgccc acggtgccca gagcccaaat cttgtgacac acctccccca 420
tgcccacggt gcccagagcc caaatcttgt gacacacctc ccccgtgccc aaggtgccca 480
gcacctgaac tcctgggagg accgtcagtc ttcctcttcc ccccaaaacc caaggatacc 540
cttatgattt cccggacccc tgaggtcacg tgcgtggtgg tggacgtgag ccacgaagac 600
cccgaggtcc agttcaagtg gtacgtggac ggcgtggagg tgcataatgc caagacaaag 660
ctgcgggagg agcagtacaa cagcacgttc cgtgtggtca gcgtcctcac cgtcctgcac 720
caggactggc tgaacggcaa ggagtacaag tgcaaggtct ccaacaaagc cctcccagcc 780
cccatcgaga aaaccatctc caaaaccaaa ggacagcccc gagaaccaca ggtgtacacc 840
ctgcccccat cccgggagga gatgaccaag aaccaggtca gcctgacctg cctggtcaaa 900
ggcttctacc ccagcgacat cgccgtggag tgggagagca gcgggcagcc ggagaacaac 960
tacaacacca cgcctcccat gctggactcc gacggctcct tcttcctcta cagcaagctc 1020
accgtggaca agagcaggtg gcagcagggg aacatcttct catgctccgt gatgcatgag 1080
gctctgcaca accgctacac gcagaagagc ctctccctgt ctccgggtaa atga 1134

<210> SEQ ID NO 376
<211> LENGTH: 2304
<212> TYPE: DNA
<213> ORGANISM: homo sapiens;

<400> SEQUENCE: 376
cttccaccaa gggcccatcg gtcttccccc tggcgccctg ctccaggagc acctctgggg 60
gcacagcggc cctgggctgc ctggtcaagg actacttccc agaaccggtg acggtgtcgt 120
ggaactcagg cgccctgacc agcggcgtgc acaccttccc ggctgtccta cagtcctcag 180

```
gactctactc cctcagcagc gtggtgaccg tgccctccag cagcttgggc acccagacct    240
acacctgcaa cgtgaatcac aagcccagca acaccaaggt ggacaagaga gttggtgaga    300
ggccagcgca gggagggagg gtgtctgctg gaagccaggc tcagccctcc tgcctggacg    360
catcccggct gtgcagtccc agcccagggc accaaggcag gccccgtctg actcctcacc    420
cggaggcctc tgcccgcccc actcatgctc agggagaggg tcttctggct ttttccacca    480
ggctccgggc aggcacaggc tggatgcccc taccccaggc ccttcacaca caggggcagg    540
tgctgcgctc agagctgcca agagccatat ccaggaggac cctgcccctg acctaagccc    600
accccaaagg ccaaactctc tactcactca gctcagatac cttctctctt cccagatctg    660
agtaactccc aatcttctct ctgcagagct caaaacccca cttggtgaca caactcacac    720
atgcccacgg tgcccaggta agccagccca ggcctcgccc tccagctcaa ggcgggacaa    780
gagccctaga gtggcctgag tccagggaca ggccccagca gggtgctgac gcatccacct    840
ccatcccaga tccccgtaac tcccaatctt ctctctgcag agcccaaatc ttgtgacaca    900
cctcccccgt gcccacggtg cccaggtaag ccagcccagg cctcgccctc cagctcaagg    960
caggacaaga gccctagagt ggcctgagtc cagggacagg ccccagcagg gtgctgacgc   1020
gtccacctcc atcccagatc cccgtaactc ccaatcttct ctctgcagag cccaaatctt   1080
gtgacacacc tcccccatgc ccacggtgcc caggtaagcc agcccaggcc tcgccctcca   1140
gctcaaggcg ggacaagagc cctagagtgg cctgagtcca gggacaggcc ccagcagggt   1200
gctgacgcat ccacctccat cccagatccc cgtaactccc aatcttctct ctgcagagcc   1260
caaatcttgt gacacacctc ccccgtgccc aaggtgccca ggtaagccag cccaggcctc   1320
gccctccagc tcaaggcagg acaggtgccc tagagtggcc tgcatccagg gacaggtccc   1380
agtcgggtgc tgacacatct gcctccatct cttcctcagc acctgaactc ctgggaggac   1440
cgtcagtctt cctcttcccc ccaaaaccca aggataccct tatgatttcc cggacccctg   1500
aggtcacgtg cgtggtggtg gacgtgagcc acgaagaccc cgaggtccag ttcaagtggt   1560
acgtggacgg cgtggaggtg cataatgcca agacaaagct gcgggaggag cagtacaaca   1620
gcacgttccg tgtggtcagc gtcctcaccg tcctgcacca ggactggctg aacggcaagg   1680
agtacaagtg caaggtctcc aacaaagccc tcccagcccc catcgagaaa accatctcca   1740
aaaccaaagg tgggacccgc ggggtatgag ggccacatgg acagaggcca gcttgaccca   1800
ccctctgccc tgggagtgac cgctgtgcca acctctgtcc ctacaggaca gccccgagaa   1860
ccacaggtgt acaccctgcc cccatcccgg gaggagatga ccaagaacca ggtcagcctg   1920
acctgcctgg tcaaaggctt ctaccccagc gacatcgccg tggagtggga gagcagcggg   1980
cagccggaga acaactacaa caccacgcct cccatgctgg actccgacgg ctccttcttc   2040
ctctacagca agctcaccgt ggacaagagc aggtggcagc aggggaacat cttctcatgc   2100
tccgtgatgc atgaggctct gcacaaccgc tacacgcaga agagcctctc cctgtctccg   2160
ggtaaatgag tgcgacggcc ggcaagcccc cgctccccgg gctctcgggg tcgcgcgagg   2220
atgcttggca cgtaccccgt gtacatactt cccgggcacc cagcatggaa ataaagcacc   2280
cagcgctgcc ctgggcccct gcga                                          2304
```

<210> SEQ ID NO 377
<211> LENGTH: 1134
<212> TYPE: DNA
<213> ORGANISM: homo sapiens;
<220> FEATURE:

<221> NAME/KEY: misc_feature
<222> LOCATION: (1)..(1)
<223> OTHER INFORMATION: n is a, c, g, or t

<400> SEQUENCE: 377
ncttccacca agggcccatc ggtcttcccc ctggcgccct gctccaggag cacctctggg 60
ggcacagcgg ccctgggctg cctggtcaag gactacttcc cagaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacacctgca acgtgaatca caagcccagc aacaccaagg tggacaagag agttgagctc 300
aaaaccccac ttggtgacac aactcacaca tgcccacggt gcccagagcc caaatcttgt 360
gacacacctc ccccgtgccc acggtgccca gagcccaaat cttgtgacac acctccccca 420
tgcccacggt gcccagagcc caaatcttgt gacacacctc ccccgtgccc aaggtgccca 480
gcacctgaac tcctgggagg accgtcagtc ttcctcttcc ccccaaaacc caaggatacc 540
cttatgattt cccggacccc tgaggtcacg tgcgtggtgg tggacgtgag ccacgaagac 600
cccgaggtcc agttcaagtg gtacgtggac ggcgtggagg tgcataatgc caagacaaag 660
ccgcgggagg agcagttcaa cagcacgttc cgtgtggtca gcgtcctcac cgtcctgcac 720
caggactggc tgaacggcaa ggagtacaag tgcaaggtct ccaacaaagc cctcccagcc 780
cccatcgaga aaaccatctc caaaaccaaa ggacagcccc gagaaccaca ggtgtacacc 840
ctgcccccat cccgggagga gatgaccaag aaccaggtca gcctgacctg cctggtcaaa 900
ggcttctacc ccagcgacat cgccgtggag tgggagagca gcgggcagcc ggagaacaac 960
tacaacacca cgcctcccat gctggactcc gacggctcct tcttcctcta cagcaagctc 1020
accgtggaca agagcaggtg gcagcagggg aacatcttct catgctccgt gatgcatgag 1080
gctctgcaca accgcttcac gcagaagagc ctctccctgt ctccgggtaa atga 1134

<210> SEQ ID NO 378
<211> LENGTH: 2304
<212> TYPE: DNA
<213> ORGANISM: homo sapiens;

<400> SEQUENCE: 378
cttccaccaa gggcccatcg gtcttccccc tggcgccctg ctccaggagc acctctgggg 60
gcacagcggc cctgggctgc ctggtcaagg actacttccc agaaccggtg acggtgtcgt 120
ggaactcagg cgccctgacc agcggcgtgc acaccttccc ggctgtccta cagtcctcag 180
gactctactc cctcagcagc gtggtgaccg tgccctccag cagcttgggc acccagacct 240
acacctgcaa cgtgaatcac aagcccagca acaccaaggt ggacaagaga gttggtgaga 300
ggccagcgca gggagggagg gtgtctgctg gaagccaggc tcagccctcc tgcctggacg 360
catcccggct gtgcagtccc agcccagggc accaaggcag gccccgtctg actcctcacc 420
cggaggcctc tgcccgcccc actcatgctc agggagaggg tcttctggct ttttccacca 480
ggctccgggc aggcacaggc tggatgcccc taccccaggc ccttcacaca caggggcagg 540
tgctgcgctc agagctgcca agagccatat ccaggaggac cctgcccctg acctaagccc 600
accccaaagg ccaaactctc tactcactca gctcagatac cttctctctt cccagatctg 660
agtaactccc aatcttctct ctgcagagct caaaacccca cttggtgaca caactcacac 720
atgcccacgg tgcccaggta agccagccca ggcctcgccc tccagctcaa ggcgggacaa 780
gagccctaga gtggcctgag tccagggaca ggccccagca gggtgctgac gcatccacct 840

```
ccatcccaga tccccgtaac tcccaatctt ctctctgcag agcccaaatc ttgtgacaca    900

cctccccogt gcccacggtg cccaggtaag ccagcccagg cctcgccctc cagctcaagg    960

caggacaaga gccctagagt ggcctgagtc cagggacagg ccccagcagg gtgctgacgc   1020

gtccacctcc atcccagatc cccgtaactc ccaatcttct ctctgcagag cccaaatctt   1080

gtgacacacc tcccccatgc ccacggtgcc caggtaagcc agcccaggcc tcgccctcca   1140

gctcaaggcg ggacaagagc cctagagtgg cctgagtcca gggacaggcc ccagcagggt   1200

gctgacgcat ccacctccat cccagatccc cgtaactccc aatcttctct ctgcagagcc   1260

caaatcttgt gacacacctc ccccgtgccc aaggtgccca ggtaagccag cccaggcctc   1320

gccctccagc tcaaggcagg acaggtgccc tagagtggcc tgcatccagg gacaggtccc   1380

agtcgggtgc tgacacatct gcctccatct cttcctcagc acctgaactc ctgggaggac   1440

cgtcagtctt cctcttcccc ccaaaaccca aggataccct tatgatttcc cggacccctg   1500

aggtcacgtg cgtggtggtg gacgtgagcc acgaagaccc cgaggtccag ttcaagtggt   1560

acgtggacgg cgtggaggtg cataatgcca agacaaagcc gcgggaggag cagttcaaca   1620

gcacgttccg tgtggtcagc gtcctcaccg tcctgcacca ggactggctg aacggcaagg   1680

agtacaagtg caaggtctcc aacaaagccc tcccagcccc catcgagaaa accatctcca   1740

aaaccaaagg tgggacccgc ggggtatgag ggccacatgg acagaggcca gcttgaccca   1800

ccctctgccc tgggagtgac cgctgtgcca acctctgtcc ctacaggaca gccccgagaa   1860

ccacaggtgt acaccctgcc cccatcccgg gaggagatga ccaagaacca ggtcagcctg   1920

acctgcctgg tcaaaggctt ctaccccagc gacatcgccg tggagtggga gagcagcggg   1980

cagccggaga acaactacaa caccacgcct cccatgctgg actccgacgg ctccttcttc   2040

ctctacagca agctcaccgt ggacaagagc aggtggcagc aggggaacat cttctcatgc   2100

tccgtgatgc atgaggctct gcacaaccgc ttcacgcaga agagcctctc cctgtctccg   2160

ggtaaatgag tgcgacggcc ggcaagcccc cgctccccgg gctctcgggg tcgcgcgagg   2220

atgcttggca cgtaccccgt gtacatactt cccgggcacc cagcatggaa ataaagcacc   2280

cagcgctgcc ctgggcccct gcga                                          2304
```

```
<210> SEQ ID NO 379
<211> LENGTH: 1717
<212> TYPE: DNA
<213> ORGANISM: homo sapiens;

<400> SEQUENCE: 379

gcttccacca agggcccatc ggtcttcccc ctggcgccct gctccaggag cacctccgag     60

agcacagccg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttggtgag    300

aggccagcac agggagggag ggtgtctgct ggaagccagg ctcagccctc ctgcctggac    360

gcaccccggc tgtgcagccc cagcccaggg cagcaaggca ggccccatct gtctcctcac    420

ccggaggcct ctgaccaccc cactcatgct cagggagagg gtcttctgga tttttccacc    480

aggctccggg cagccacagg ctggatgccc ctaccccagg ccctgcgcat acaggggcag    540

gtgctgcgct cagacctgcc aagagccata tccgggagga ccctgcccct gacctaagcc    600
```

-continued

```
caccccaaag gccaaactct ccactccctc agctcagaca ccttctctcc tcccagatct    660

gagtaactcc caatcttctc tctgcagagt ccaaatatgg tcccccatgc ccatcatgcc    720

caggtaagcc aacccaggcc tcgccctcca gctcaaggcg ggacaggtgc cctagagtag    780

cctgcatcca gggacaggcc ccagccgggt gctgacgcat ccacctccat ctcttcctca    840

gcacctgagt tcctgggggg accatcagtc ttcctgttcc ccccaaaacc caaggacact    900

ctcatgatct cccggacccc tgaggtcacg tgcgtggtgg tggacgtgag ccaggaagac    960

cccgaggtcc agttcaactg gtacgtggat ggcgtggagg tgcataatgc caagacaaag   1020

ccgcgggagg agcagttcaa cagcacgtac cgtgtggtca gcgtcctcac cgtcctgcac   1080

caggactggc tgaacggcaa ggagtacaag tgcaaggtct ccaacaaagg cctcccgtcc   1140

tccatcgaga aaaccatctc caaagccaaa ggtgggaccc acggggtgcg agggccacat   1200

ggacagaggt cagctcggcc caccctctgc cctgggagtg accgctgtgc caacctctgt   1260

ccctacaggg cagccccgag agccacaggt gtacaccctg cccccatccc aggaggagat   1320

gaccaagaac caggtcagcc tgacctgcct ggtcaaaggc ttctacccca gcgacatcgc   1380

cgtggagtgg gagagcaatg ggcagccgga gaacaactac aagaccacgc ctcccgtgct   1440

ggactccgac ggctccttct tcctctacag caggctcacc gtggacaaga gcaggtggca   1500

ggaggggaat gtcttctcat gctccgtgat gcatgaggct ctgcacaacc actacacaca   1560

gaagagcctc tccctgtctc tgggtaaatg agtgccaggg ccggcaagcc cccgctcccc   1620

gggctctcgg ggtcgcgcga ggatgcttgg cacgtacccc gtgtacatac ttcccgggcg   1680

cccagcatgg aaataaagca cccagcgctg ccctggg                            1717


<210> SEQ ID NO 380
<211> LENGTH: 984
<212> TYPE: DNA
<213> ORGANISM: homo sapiens;

<400> SEQUENCE: 380

gcttccacca agggcccatc ggtcttcccc ctggcgccct gctccaggag cacctccgag     60

agcacagccg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc atcatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaggctc accgtggaca agagcaggtg gcaggagggg    900

aatgtcttct catgctccgt gatgcatgag gctctgcaca accactacac acagaagagc    960

ctctccctgt ctctgggtaa atga                                           984
```

<210> SEQ ID NO 381
<211> LENGTH: 984
<212> TYPE: DNA
<213> ORGANISM: homo sapiens;

<400> SEQUENCE: 381
gcttccacca agggcccatc ggtcttcccc ctggcgccct gctccaggag cacctccgag 60
agcacagccg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacgaagacc 240
tacacctgca acgtagatca caagcccagc aacaccaagg tggacaagag agttgagtcc 300
aaatatggtc ccccatgccc atcatgccca gcacctgagt tcctgggggg accatcagtc 360
ttcctgttcc ccccaaaacc caaggacact ctcatgatct cccggacccc tgaggtcacg 420
tgcgtggtgg tggacgtgag ccaggaagac cccgaggtcc agttcaactg gtacgtggat 480
ggcgtggagg tgcataatgc caagacaaag ccgcgggagg agcagttcaa cagcacgtac 540
cgtgtggtca gcgtcctcac cgtcgtgcac caggactggc tgaacggcaa ggagtacaag 600
tgcaaggtct ccaacaaagg cctcccgtcc tccatcgaga aaaccatctc caaagccaaa 660
gggcagcccc gagagccaca ggtgtacacc ctgcccccat cccaggagga gatgaccaag 720
aaccaggtca gcctgacctg cctggtcaaa ggcttctacc ccagcgacat cgccgtggag 780
tgggagagca atgggcagcc ggagaacaac tacaagacca cgcctcccgt gctggactcc 840
gacggctcct tcttcctcta cagcaggctc accgtggaca agagcaggtg gcaggagggg 900
aatgtcttct catgctccgt gatgcatgag gctctgcaca accactacac acagaagagc 960
ctctccctgt ctctgggtaa atga 984

<210> SEQ ID NO 382
<211> LENGTH: 1717
<212> TYPE: DNA
<213> ORGANISM: homo sapiens;

<400> SEQUENCE: 382
gcttccacca agggcccatc ggtcttcccc ctggcgccct gctccaggag cacctccgag 60
agcacagccg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacgaagacc 240
tacacctgca acgtagatca caagcccagc aacaccaagg tggacaagag agttggtgag 300
aggccagcac agggagggag ggtgtctgct ggaagccagg ctcagccctc ctgcctggac 360
gcaccccggc tgtgcagccc cagcccaggg cagcaaggca ggccccatct gtctcctcac 420
ccggaggcct ctgaccaccc cactcatgct cagggagagg gtcttctgga tttttccacc 480
aggctccggg cagccacagg ctggatgccc ctaccccagg ccctgcgcat acaggggcag 540
gtgctgcgct cagacctgcc aagagccata tccgggagga ccctgcccct gacctaagcc 600
caccccaaag gccaaactct ccactccctc agctcagaca ccttctctcc tcccagatct 660
gagtaactcc caatcttctc tctgcagagt ccaaatatgg tcccccatgc ccatcatgcc 720
caggtaagcc aacccaggcc tcgccctcca gctcaaggcg ggacaggtgc cctagagtag 780
cctgcatcca gggacaggcc ccagccgggt gctgacgcat ccacctccat ctcttcctca 840

```
gcacctgagt tcctgggggg accatcagtc ttcctgttcc ccccaaaacc caaggacact    900
ctcatgatct cccggacccc tgaggtcacg tgcgtggtgg tggacgtgag ccaggaagac    960
cccgaggtcc agttcaactg gtacgtggat ggcgtggagg tgcataatgc caagacaaag   1020
ccgcgggagg agcagttcaa cagcacgtac cgtgtggtca gcgtcctcac cgtcgtgcac   1080
caggactggc tgaacggcaa ggagtacaag tgcaaggtct ccaacaaagg cctcccgtcc   1140
tccatcgaga aaaccatctc caaagccaaa ggtgggaccc acggggtgcg agggccacat   1200
ggacagaggt cagctcggcc caccctctgc cctgggagtg accgctgtgc caacctctgt   1260
ccctacaggg cagccccgag agccacaggt gtacaccctg cccccatccc aggaggagat   1320
gaccaagaac caggtcagcc tgacctgcct ggtcaaaggc ttctacccca gcgacatcgc   1380
cgtggagtgg gagagcaatg ggcagccgga gaacaactac aagaccacgc ctcccgtgct   1440
ggactccgac ggctccttct tcctctacag caggctcacc gtggacaaga gcaggtggca   1500
ggaggggaat gtcttctcat gctccgtgat gcatgaggct ctgcacaacc actacacaca   1560
gaagagcctc tccctgtctc tgggtaaatg agtgccaggg ccggcaagcc cccgctcccc   1620
gggctctcgg ggtcgcgcga ggatgcttgg cacgtacccc gtgtacatac ttcccgggcg   1680
cccagcatgg aaataaagca cccagcgctg ccctggg                            1717
```

```
<210> SEQ ID NO 383
<211> LENGTH: 1546
<212> TYPE: DNA
<213> ORGANISM: homo sapiens;

<400> SEQUENCE: 383

gcatccccga ccagccccaa ggtcttcccg ctgagcctct gcagcaccca gccagatggg     60
aacgtggtca tcgcctgcct ggtccagggc ttcttccccc aggagccact cagtgtgacc    120
tggagcgaaa gcggacaggg cgtgaccgcc agaaacttcc cacccagcca ggatgcctcc    180
ggggacctgt acaccacgag cagccagctg accctgccgg ccacacagtg cctagccggc    240
aagtccgtga catgccacgt gaagcactac acgaatccca gccaggatgt gactgtgccc    300
tgcccaggtc agagggcagg ctggggagtg gggcggggcc accccgtcgt gccctgacac    360
tgcgcctgca cccgtgttcc ccacagggag ccgccccttc actcacacca gagtggaccg    420
cgggccgagc cccaggaggt ggtggtggac aggccaggag gggcgaggcg ggggcatggg    480
gaagtatgtg ctgaccagct caggccatct ctccactcca gttccctcaa ctccacctac    540
cccatctccc tcaactccac ctaccccatc tccctcatgc tgccaccccc gactgtcact    600
gcaccgaccg gccctcgagg acctgctctt aggttcagaa gcgaacctca cgtgcacact    660
gaccggcctg agagatgcct caggtgtcac cttcacctgg acgccctcaa gtgggaagag    720
cgctgttcaa ggaccacctg agcgtgacct ctgtggctgc tacagcgtgt ccagtgtcct    780
gccgggctgt gccgagccat ggaaccatgg gaagaccttc acttgcactg ctgcctaccc    840
cgagtccaag accccgctaa ccgccaccct ctcaaaatcc ggtgggtcca gaccctgctc    900
ggggccctgc tcagtgctct ggtttgcaaa gcatattcct ggcctgcctc ctccctccca    960
atcctgggct ccagtgctca tgccaagtac agagggaaac tgaggcaggc tgaggggcca   1020
ggacacagcc cagggtgccc accagagcag aggggctctc tcatcccctg cccagccccc   1080
tgacctggct ctctaccctc caggaaacac attccggccc gaggtccacc tgctgccgcc   1140
gccgtcggag gagctggccc tgaacgagct ggtgacgctg acgtgcctgg cacgcggctt   1200
cagccccaag gatgtgctgg ttcgctggct gcaggggtca caggagctgc cccgcgagaa   1260
```

```
gtacctgact tgggcatccc ggcaggagcc cagccagggc accaccacct tcgctgtgac   1320

cagcatactg cgcgtggcag ccgaggactg gaagaagggg gacaccttct cctgcatggt   1380

gggccacgag gccctgccgc tggccttcac acagaagacc atcgaccgct tggcgggtaa   1440

acccacccat gtcaatgtgt ctgttgtcat ggcggaggtg gacggcacct gctactgagc   1500

cgcccgcctg tccccacccc tgaataaact ccatgctccc ccaagc                  1546
```

<210> SEQ ID NO 384
<211> LENGTH: 1062
<212> TYPE: DNA
<213> ORGANISM: homo sapiens;

<400> SEQUENCE: 384

```
gcatccccga ccagccccaa ggtcttcccg ctgagcctct gcagcaccca gccagatggg     60

aacgtggtca tcgcctgcct ggtccagggc ttcttccccc aggagccact cagtgtgacc    120

tggagcgaaa gcggacaggg cgtgaccgcc agaaacttcc cacccagcca ggatgcctcc    180

ggggacctgt acaccacgag cagccagctg accctgccgg ccacacagtg cctagccggc    240

aagtccgtga catgccacgt gaagcactac acgaatccca gccaggatgt gactgtgccc    300

tgcccagttc cctcaactcc acctacccca tctccctcaa ctccacctac cccatctccc    360

tcatgctgcc acccccgact gtcactgcac cgaccggccc tcgaggacct gctcttaggt    420

tcagaagcga acctcacgtg cacactgacc ggcctgagag atgcctcagg tgtcaccttc    480

acctggacgc cctcaagtgg gaagagcgct gttcaaggac cacctgagcg tgacctctgt    540

ggctgctaca gcgtgtccag tgtcctgccg ggctgtgccg agccatggaa ccatgggaag    600

accttcactt gcactgctgc ctaccccgag tccaagaccc cgctaaccgc caccctctca    660

aaatccggaa acacattccg gcccgaggtc cacctgctgc cgccgccgtc ggaggagctg    720

gccctgaacg agctggtgac gctgacgtgc ctggcacgcg gcttcagccc caaggatgtg    780

ctggttcgct ggctgcaggg gtcacaggag ctgccccgcg agaagtacct gacttgggca    840

tcccggcagg agcccagcca gggcaccacc accttcgctg tgaccagcat actgcgcgtg    900

gcagccgagg actggaagaa gggggacacc ttctcctgca tggtgggcca cgaggccctg    960

ccgctggcct tcacacagaa gaccatcgac cgcttggcgg gtaaacccac ccatgtcaat   1020

gtgtctgttg tcatggcgga ggtggacggc acctgctact ga                      1062
```

<210> SEQ ID NO 385
<211> LENGTH: 1546
<212> TYPE: DNA
<213> ORGANISM: homo sapiens;

<400> SEQUENCE: 385

```
gcatccccga ccagccccaa ggtcttcccg ctgagcctct gcagcaccca gccagatggg     60

aacgtggtca tcgcctgcct ggtccagggc ttcttccccc aggagccact cagtgtgacc    120

tggagcgaaa gcggacaggg cgtgaccgcc agaaacttcc cacccagcca ggatgcctcc    180

ggggacctgt acaccacgag cagccagctg accctgccgg ccacacagtg cctagccggc    240

aagtccgtga catgccacgt gaagcactac acgaatccca gccaggatgt gactgtgccc    300

tgcccaggtc agagggcagg ctggggagtg gggcggggcc accccgtcgt gccctgacac    360

tgcgcctgca cccgtgttcc ccacagggag ccgccccttc actcacacca gagtggaccg    420

cgggccgagc cccaggaggt ggtggtggac aggccaggag gggcgaggcg ggggcatggg    480
```

-continued

```
gaagtatgtg ctgaccagct caggccatct ctccactcca gttccctcaa ctccacctac    540
cccatctccc tcaactccac ctaccccatc tccctcatgc tgccaccccc gactgtcact    600
gcaccgaccg gccctcgagg acctgctctt aggttcagaa gcgaacctca cgtgcacact    660
gaccggcctg agagatgcct caggtgtcac cttcacctgg acgccctcaa gtgggaagag    720
cgctgttcaa ggaccacctg accgtgacct ctgtggctgc tacagcgtgt ccagtgtcct    780
gccgggctgt gccgagccat ggaaccatgg gaagaccttc acttgcactg ctgcctaccc    840
cgagtccaag accccgctaa ccgccaccct ctcaaaatcc ggtgggtcca gaccctgctc    900
ggggccctgc tcagtgctct ggtttgcaaa gcatattcct ggcctgcctc ctccctccca    960
atcctgggct ccagtgctca tgccaagtac agagggaaac tgaggcaggc tgaggggcca   1020
ggacacagcc cagggtgccc accagagcag aggggctctc tcatcccctg cccagccccc   1080
tgacctggct ctctaccctc caggaaacac attccggccc gaggtccacc tgctgccgcc   1140
gccgtcggag gagctggccc tgaacgagct ggtgacgctg acgtgcctgg cacgcggctt   1200
cagccccaag gatgtgctgg ttcgctggct gcaggggtca caggagctgc cccgcgagaa   1260
gtacctgact tgggcatccc ggcaggagcc cagccagggc accaccacct tcgctgtgac   1320
cagcatactg cgcgtggcag ccgaggactg gaagaagggg gacaccttct cctgcatggt   1380
gggccacgag gccctgccgc tggccttcac acagaagacc atcgaccgct tggcgggtaa   1440
acccacccat gtcaatgtgt ctgttgtcat ggcggaggtg gacggcacct gctactgagc   1500
cgcccgcctg tccccacccc tgaataaact ccatgctccc ccaagc                  1546
```

<210> SEQ ID NO 386
<211> LENGTH: 1062
<212> TYPE: DNA
<213> ORGANISM: homo sapiens;

<400> SEQUENCE: 386

```
gcatccccga ccagccccaa ggtcttcccg ctgagcctct gcagcaccca gccagatggg     60
aacgtggtca tcgcctgcct ggtccagggc ttcttccccc aggagccact cagtgtgacc    120
tggagcgaaa gcggacaggg cgtgaccgcc agaaacttcc cacccagcca ggatgcctcc    180
ggggacctgt acaccacgag cagccagctg accctgccgg ccacacagtg cctagccggc    240
aagtccgtga catgccacgt gaagcactac acgaatccca gccaggatgt gactgtgccc    300
tgcccagttc cctcaactcc acctacccca tctccctcaa ctccacctac cccatctccc    360
tcatgctgcc acccccgact gtcactgcac cgaccggccc tcgaggacct gctcttaggt    420
tcagaagcga acctcacgtg cacactgacc ggcctgagag atgcctcagg tgtcaccttc    480
acctggacgc cctcaagtgg gaagagcgct gttcaaggac cacctgaccg tgacctctgt    540
ggctgctaca gcgtgtccag tgtcctgccg ggctgtgccg agccatggaa ccatgggaag    600
accttcactt gcactgctgc ctaccccgag tccaagaccc cgctaaccgc caccctctca    660
aaatccggaa acacattccg gcccgaggtc cacctgctgc cgccgccgtc ggaggagctg    720
gccctgaacg agctggtgac gctgacgtgc ctggcacgcg gcttcagccc caaggatgtg    780
ctggttcgct ggctgcaggg gtcacaggag ctgccccgcg agaagtacct gacttgggca    840
tcccggcagg agcccagcca gggcaccacc accttcgctg tgaccagcat actgcgcgtg    900
gcagccgagg actggaagaa gggggacacc ttctcctgca tggtgggcca cgaggccctg    960
ccgctggcct tcacacagaa gaccatcgac cgcttggcgg gtaaacccac ccatgtcaat   1020
gtgtctgttg tcatggcgga ggtggacggc acctgctact ga                      1062
```

<210> SEQ ID NO 387
<211> LENGTH: 1507
<212> TYPE: DNA
<213> ORGANISM: homo sapiens;

<400> SEQUENCE: 387
gcatccccga ccagccccaa ggtcttcccg ctgagcctcg acagcacccc ccaagatggg 60
aacgtggtcg tcgcatgcct ggtccagggc ttcttccccc aggagccact cagtgtgacc 120
tggagcgaaa gcggacagaa cgtgaccgcc agaaacttcc cacctagcca ggatgcctcc 180
ggggacctgt acaccacgag cagccagctg accctgccgg ccacacagtg cccagacggc 240
aagtccgtga catgccacgt gaagcactac acgaattcca gccaggatgt gactgtgccc 300
tgccgaggtc agagggcagg ctggggagtg gggcggggcc accccgtcct gccctgacac 360
tgcgcctgca cccgtgttcc ccacagggag ccgccccttc actcacacca gagtggaccg 420
cgggccgagc cccaggaggt ggtggtggac aggccaggag gggcgaggcg ggggcacggg 480
gaagggcgtt ctgaccagct caggccatct ctccactcca gttcccccac ctcccccatg 540
ctgccacccc cgactgtcgc tgcaccgacc ggccctcgag gacctgctct taggttcaga 600
agcgaacctc acgtgcacac tgaccggcct gagagatgcc tctggtgcca ccttcacctg 660
gacgccctca agtgggaaga gcgctgttca aggaccacct gagcgtgacc tctgtggctg 720
ctacagcgtg tccagtgtcc tgcctggctg tgcccagcca tggaaccatg ggagaccttt 780
cacctgcact gctgcccacc ccgagttgaa gaccccacta accgccaaca tcacaaaatc 840
cggtgggtcc agaccctgct cggggccctg ctcagtgctc tggtttgcaa agcatattcc 900
cggcctgcct cctccctccc aatcctgggc tccagtgctc atgccaagta cagagggaaa 960
ctgaggcagg ctgaggggcc aggacacagc ccagggtgcc caccagagca gaggggctct 1020
ctcatcccct gcccagcccc ctgacctggc tctctaccct ccaggaaaca cattccggcc 1080
cgaggtccac ctgctgccgc cgccgtcgga ggagctggcc ctgaacgagc tggtgacgct 1140
gacgtgcctg gcacgtggct tcagccccaa ggatgtgctg gttcgctggc tgcaggggtc 1200
acaggagctg ccccgcgaga agtacctgac ttgggcatcc cggcaggagc ccagccaggg 1260
caccaccacc tacgctgtaa ccagcatact gcgcgtggca gctgaggact ggaagaaggg 1320
ggagaccttc tcctgcatgg tgggccacga ggccctgccg ctggccttca cacagaagac 1380
catcgaccgc atggcgggta aacccaccca catcaatgtg tctgttgtca tggcggaggc 1440
ggatggcacc tgctactgag ccgcccgcct gtccccaccc ctgaataaac tccatgctcc 1500
cccaagc 1507

<210> SEQ ID NO 388
<211> LENGTH: 1023
<212> TYPE: DNA
<213> ORGANISM: homo sapiens;

<400> SEQUENCE: 388
gcatccccga ccagccccaa ggtcttcccg ctgagcctcg acagcacccc ccaagatggg 60
aacgtggtcg tcgcatgcct ggtccagggc ttcttccccc aggagccact cagtgtgacc 120
tggagcgaaa gcggacagaa cgtgaccgcc agaaacttcc cacctagcca ggatgcctcc 180
ggggacctgt acaccacgag cagccagctg accctgccgg ccacacagtg cccagacggc 240
aagtccgtga catgccacgt gaagcactac acgaattcca gccaggatgt gactgtgccc 300

-continued

```
tgccgagttc ccccacctcc cccatgctgc cacccccgac tgtcgctgca ccgaccggcc    360

ctcgaggacc tgctcttagg ttcagaagcg aacctcacgt gcacactgac cggcctgaga    420

gatgcctctg gtgccacctt cacctggacg ccctcaagtg ggaagagcgc tgttcaagga    480

ccacctgagc gtgacctctg tggctgctac agcgtgtcca gtgtcctgcc tggctgtgcc    540

cagccatgga accatgggga gaccttcacc tgcactgctg cccaccccga gttgaagacc    600

ccactaaccg ccaacatcac aaaatccgga aacacattcc ggcccgaggt ccacctgctg    660

ccgccgccgt cggaggagct ggccctgaac gagctggtga cgctgacgtg cctggcacgt    720

ggcttcagcc ccaaggatgt gctggttcgc tggctgcagg ggtcacagga gctgccccgc    780

gagaagtacc tgacttgggc atcccggcag gagcccagcc agggcaccac cacctacgct    840

gtaaccagca tactgcgcgt ggcagctgag gactggaaga agggggagac cttctcctgc    900

atggtgggcc acgaggccct gccgctggcc ttcacacaga agaccatcga ccgcatggcg    960

ggtaaaccca cccacatcaa tgtgtctgtt gtcatggcgg aggcggatgg cacctgctac   1020

tga                                                                 1023
```

```
<210> SEQ ID NO 389
<211> LENGTH: 1507
<212> TYPE: DNA
<213> ORGANISM: homo sapiens;

<400> SEQUENCE: 389

gcatccccga ccagccccaa ggtcttcccg ctgagcctcg acagcacccc ccaagatggg     60

aacgtggtcg tcgcatgcct ggtccagggc ttcttccccc aggagccact cagtgtgacc    120

tggagcgaaa gcggacagaa cgtgaccgcc agaaacttcc cacctagcca ggatgcctcc    180

ggggacctgt acaccacgag cagccagctg accctgccgg ccacacagtg cccagacggc    240

aagtccgtga catgccacgt gaagcactac acgaatccca gccaggatgt gactgtgccc    300

tgcccaggtc agagggcagg ctggggagtg gggcggggcc accccgtcct gccctgacac    360

tgcgcctgca cccgtgttcc ccacagggag ccgccccttc actcacacca gagtggaccg    420

cgggccgagc cccaggaggt ggtggtggac aggccaggag gggcgaggcg ggggcacggg    480

gaagggcgtt ctgaccagct caggccatct ctccactcca gttcccccac ctcccccatg    540

ctgccacccc cgactgtcgc tgcaccgacc ggccctcgag gacctgctct taggttcaga    600

agcgaacctc acgtgcacac tgaccggcct gagagatgcc tctggtgcca ccttcacctg    660

gacgccctca agtgggaaga gcgctgttca aggaccacct gagcgtgacc tctgtggctg    720

ctacagcgtg tccagtgtcc tgcctggctg tgcccagcca tggaaccatg ggagaccttt    780

cacctgcact gctgcccacc ccgagttgaa gaccccacta accgccaaca tcacaaaatc    840

cggtgggtcc agaccctgct cggggccctg ctcagtgctc tggtttgcaa agcatattcc    900

cggcctgcct cctccctccc aatcctgggc tccagtgctc atgccaagta cagagggaaa    960

ctgaggcagg ctgaggggcc aggacacagc ccagggtgcc caccagagca gaggggctct   1020

ctcatcccct gcccagcccc ctgacctggc tctctaccct ccaggaaaca cattccggcc   1080

cgaggtccac ctgctgccgc cgccgtcgga ggagctggcc ctgaacgagc tggtgacgct   1140

gacgtgcctg gcacgtggct tcagccccaa ggatgtgctg gttcgctggc tgcaggggtc   1200

acaggagctg ccccgcgaga agtacctgac ttgggcatcc cggcaggagc ccagccaggg   1260

caccaccacc ttcgctgtaa ccagcatact gcgcgtggca gctgaggact ggaagaaggg   1320

ggacaccttc tcctgcatgg tgggccacga ggccctgccg ctggccttca cacagaagac   1380
```

catcgaccgc atggcgggta aacccaccca catcaatgtg tctgttgtca tggcggaggt 1440
ggatggcacc tgctactgag ccgcccgcct gtccccaccc ctgaataaac tccatgctcc 1500
cccaagc 1507

<210> SEQ ID NO 390
<211> LENGTH: 1022
<212> TYPE: DNA
<213> ORGANISM: homo sapiens;

<400> SEQUENCE: 390
gcatccccga ccagccccaa ggtcttcccg ctgagcctcg acagcacccc ccaagatggg 60
aacgtggtcg tcgcatgcct ggtccagggc ttcttccccc aggagccact cagtgtgacc 120
tggagcgaaa gcggacagaa cgtgaccgcc agaaacttcc cacctagcca ggatgcctcc 180
ggggacctgt acaccacgag cagccagctg accctgccgg ccacacagtg cccagacggc 240
aagtccgtga catgccacgt gaagcactac acgaatccca gccaggatgt gactgtgccc 300
tgccagttcc cccacctccc ccatgctgcc acccccgact gtcgctgcac cgaccggccc 360
tcgaggacct gctcttaggt tcagaagcga acctcacgtg cacactgacc ggcctgagag 420
atgcctctgg tgccaccttc acctggacgc cctcaagtgg gaagagcgct gttcaaggac 480
cacctgagcg tgacctctgt ggctgctaca gcgtgtccag tgtcctgcct ggctgtgccc 540
agccatggaa ccatggggag accttcacct gcactgctgc ccaccccgag ttgaagaccc 600
cactaaccgc caacatcaca aaatccggaa acacattccg gcccgaggtc cacctgctgc 660
cgccgccgtc ggaggagctg gccctgaacg agctggtgac gctgacgtgc ctggcacgtg 720
gcttcagccc caaggatgtg ctggttcgct ggctgcaggg gtcacaggag ctgccccgcg 780
agaagtacct gacttgggca tcccggcagg agcccagcca gggcaccacc accttcgctg 840
taaccagcat actgcgcgtg gcagctgagg actggaagaa gggggacacc ttctcctgca 900
tggtgggcca cgaggccctg ccgctggcct tcacacagaa gaccatcgac cgcatggcgg 960
gtaaacccac ccacatcaat gtgtctgttg tcatggcgga ggtggatggc acctgctact 1020
ga 1022

<210> SEQ ID NO 391
<211> LENGTH: 1507
<212> TYPE: DNA
<213> ORGANISM: homo sapiens;

<400> SEQUENCE: 391
gcatccccga ccagccccaa ggtcttcccg ctgagcctcg acagcacccc ccaagatggg 60
aacgtggtcg tcgcatgcct ggtccagggc ttcttccccc aggagccact cagtgtgacc 120
tggagcgaaa gcggacagaa cgtgaccgcc agaaacttcc cacctagcca ggatgcctcc 180
ggggacctgt acaccacgag cagccagctg accctgccgg ccacacagtg cccagacggc 240
aagtccgtga catgccacgt gaagcactac acgaatccca gccaggatgt gactgtgccc 300
tgcccaggtc agagggcagg ctggggagtg ggcggggcc accccgtcct gccctgacac 360
tgcgcctgca cccgtgttcc ccacagggag ccgccccttc actcacacca gagtggaccg 420
cgggccgagc cccaggaggt ggtggtggac aggccaggag gggcgaggcg gggcacggg 480 gaagggcgtt ctgaccagct caggccatct ctccactcca gttcccccac ctcccccatg 540
ctgccacccc cgactgtcgc tgcaccgacc ggccctcgag gacctgctct taggttcaga 600
agcgaacctc acgtgcacac tgaccggcct gagagatgcc tctggtgcca ccttcacctg 660
gacgccctca agtgggaaga gcgctgttca aggaccacct gagcgtgacc tctgtggctg 720
ctacagcgtg tccagtgtcc tgcctggctg tgcccagcca tggaaccatg ggagaccttt 780
cacctgcact gctgcccacc ccgagttgaa gaccccacta accgccaaca tcacaaaatc 840
cggtgggtcc agaccctgct cggggccctg ctcagtgctc tggtttgcaa agcatattcc 900
cggcctgcct cctccctccc aatcctgggc tccagtgctc atgccaagta cagagggaaa 960
ctgaggcagg ctgaggggcc aggacacagc ccagggtgcc caccagagca gaggggctct 1020
ctcatcccct gcccagcccc ctgacctggc tctctaccct ccaggaaaca cattccggcc 1080
cgaggtccac ctgctgccgc cgccgtcgga ggagctggcc ctgaacgagc tggtgacgct 1140
gacgtgcctg gcacgtggct tcagccccaa ggatgtgctg gttcgctggc tgcaggggtc 1200
acaggagctg ccccgcgaga agtacctgac ttgggcatcc cggcaggagc ccagccaggg 1260
caccaccacc tacgctgtaa ccagcatact gcgcgtggca gctgaggact ggaagaaggg 1320
ggagaccttc tcctgcatgg tgggccacga ggccctgccg ctggccttca cacagaagac 1380
catcgaccgc atggcgggta aacccaccca catcaatgtg tctgttgtca tggcggaggc 1440
ggatggcacc tgctactgag ccgcccgcct gtccccaccc ctgaataaac tccatgctcc 1500
cccaagc 1507

<210> SEQ ID NO 392
<211> LENGTH: 1022
<212> TYPE: DNA
<213> ORGANISM: homo sapiens;

<400> SEQUENCE: 392
gcatccccga ccagccccaa ggtcttcccg ctgagcctcg acagcacccc ccaagatggg 60
aacgtggtcg tcgcatgcct ggtccagggc ttcttccccc aggagccact cagtgtgacc 120
tggagcgaaa gcggacagaa cgtgaccgcc agaaacttcc cacctagcca ggatgcctcc 180
ggggacctgt acaccacgag cagccagctg accctgccgg ccacacagtg cccagacggc 240
aagtccgtga catgccacgt gaagcactac acgaatccca gccaggatgt gactgtgccc 300
tgccagttcc cccacctccc ccatgctgcc acccccgact gtcgctgcac cgaccggccc 360
tcgaggacct gctcttaggt tcagaagcga acctcacgtg cacactgacc ggcctgagag 420
atgcctctgg tgccaccttc acctggacgc cctcaagtgg gaagagcgct gttcaaggac 480
cacctgagcg tgacctctgt ggctgctaca gcgtgtccag tgtcctgcct ggctgtgccc 540
agccatggaa ccatggggag accttcacct gcactgctgc ccaccccgag ttgaagaccc 600
cactaaccgc caacatcaca aaatccggaa acacattccg gcccgaggtc cacctgctgc 660
cgccgccgtc ggaggagctg gccctgaacg agctggtgac gctgacgtgc ctggcacgtg 720
gcttcagccc caaggatgtg ctggttcgct ggctgcaggg gtcacaggag ctgccccgcg 780
agaagtacct gacttgggca tcccggcagg agcccagcca gggcaccacc acctacgctg 840
taaccagcat actgcgcgtg gcagctgagg actggaagaa gggggagacc ttctcctgca 900
tggtgggcca cgaggccctg ccgctggcct tcacacagaa gaccatcgac cgcatggcgg 960
gtaaacccac ccacatcaat gtgtctgttg tcatggcgga ggcggatggc acctgctact 1020
ga 1022

<210> SEQ ID NO 393
<211> LENGTH: 8912

<212> TYPE: DNA
<213> ORGANISM: homo sapiens;

<400> SEQUENCE: 393
cacccaccaa ggctccggat gtgttcccca tcatatcagg gtgcagacac ccaaaggata 60
acagccctgt ggtcctggca tgcttgataa ctgggtacca cccaacgtcc gtgactgtca 120
cctggtacat ggggacacag agccagcccc agagaacctt ccctgagata caaagacggg 180
acagctacta catgacaagc agccagctct ccacccccct ccagcagtgg cgccaaggcg 240
agtacaaatg cgtggtccag cacaccgcca gcaagagtaa gaaggagatc ttccgctggc 300
caggtaggtc gcaccggaga tcacccagaa gggcccccca ggacccccag caccttccac 360
tcagggcctg accacaaaga cagaagcaag ggctgggctg tgaggcaacc cccacctccc 420
cctcagagca cgttcctccc ccttcaccct gtatccaccc ctccggaccc tccccatctc 480
agtccctccg ctccctctct ctgaggccca tctcccaata cccagatcac tttccttcca 540
gacccttccc tcagtgtgca cggaggcagc ttgcccagca aaggtgactg tctagtgggc 600
ttcccacagc caagctccca ccccatgctg cggcccttcc cttcttcctg cttggctgcc 660
tgtgcccccc acctgcctgt ccacaaccca gcctctggta catccatgcc ctctgccctc 720
agcctcacct gcacttttcc ttggatttca gagtctccaa aggcacaggc ctcctcagtg 780
cccactgcac aaccccaagc agagggcagc ctcgccaagg caaccacagc cccagccacc 840
acccgtaaca caggtgagaa gccccttccc tgcacactcc acccccaccc acctgctcat 900
tcctcagccg cctcctccag gcagcccttc ataactcctt gtctgagtct ccaagtcaca 960
ctttggtaag gagagggaca ctgaacggac ctctaacaaa cacctactgc cagccagccc 1020
cagtctgggg gccagcagat gccaaacagc cagcagactc ccagagcaga cctgggccgg 1080
ctccctggcc catggaccca gctctgcctc gctgagctga ggcatgggct ctcagcgcag 1140
cctcacatag agccaccctg ccgaggcagt ccggcttgca gactcacagg tcacttgggc 1200
cgcagcagcc cctccccgtg accctcgcct cccgcccgcc ccagcctggc tctctccaag 1260
tgttggatct tggtggccag cctgcttctc accctcaccc tgcctgccac ctcagaatgg 1320
caggggaaag agggccctca ccaagaactt tatctgagga gtctgaggct tgtgactctg 1380
acctgcctga gatgtccatg tggccggggg gacgggttca gtgttcggga gaactcgggt 1440
acgtgcctga ctttctctga gtagggcagg aagctgttag gagaagcagc agtgaggtgg 1500
gctggaccaa caggcagaat gactgtccct cagccaccct ctgggatgtg ggtcaagctc 1560
tgacaaaggc atggcacagc catggtggcc cctgcttgga tgagtggcca cggtgccctc 1620
accctgggcc agaatctgcc tccactctgc aggtgcagaa acacgacatt cccgtctcta 1680
aacacaccta gctcctaggc ttggggtggg cctatcaaat gcagggagat ggacacagca 1740
caagggccag agcttcccat gagaaaggtg agggcagctg ctccctgacc cgggcatctg 1800
cacttgtccc tctccaccct cctcatgggc agtggagact cagcaacaaa acaagttgag 1860
tgcattagca gccagctctg gagccaagtc actcacccca cggccttggc tgctggtgga 1920
ggggccttcc cctgggcagc ctccaagaag acggccaagt gctcttactc agaccacggc 1980
gctgcttcct ggcacctcga tttcccacaa caacatgggg tgcagacagg ctagggcccc 2040
ctgccctggg gcctggacgg catccagtta aagatgaccc ttcacgggcg gtgcctgagg 2100
tgtgctgacc tcagcagcta agccctcagg tctggtctgc actgccccac ctggaggacc 2160
caactgaccc agacacagcc agggttatgg catgaccccg tggacggtga cccacaggcc 2220

-continued

```
agatgcagcc aggggctgtt ttgtgtggcc tagaaatgtc tttacagttg tagtgggatg   2280
gaggaggaag aggaagagag gaggggagag aaaagcaggg aaggggaaaa agaggagttc   2340
aatgcaaccc caaaagccag aacagttttg agctgaaaga acaaggcagg aaacatccca   2400
gtacctgact tcaaaacata ctataaagca gttgtaatca aaacaggatc ataaaaacag   2460
acacacagac ccatggaaca gaaaagcgag cccagaaata aatctacatg cttgcagtcc   2520
attgattttc aacaaaggca ccaggaaaac acaatgggga gaggacagtt tcctcaataa   2580
atagtgctgg ggaaactgga tatccatgtg cagactaatg aaactacaca aaaatcaatt   2640
gaaaacagtc taggccaggc gcggtggctc atgccggtaa tcccagcact ttgggaggcc   2700
gagacaggcg gatcacctga ggtcaggagt tcgagaccag cttggccaac atggcgaaac   2760
ccggtctcca ctaaaaatac aaaaattagc acatggtggc ctacgtctgt tatcccagct   2820
tttcaggagg ctgaggcagg agaatcgctt gaatccggga ggtgaaggtt gcagggagcc   2880
aagattgcgc cactgcattc cagcctgggc aatggagcga gactgtctca aaaaaaaaaa   2940
aaaaaagaaa agaaaacagt ctaaaggttt aactgaacag ataaagctac tagaagaaaa   3000
catagggga aaactccatg acattagtct gagcaacgat ttttggatat gatcccaaaa    3060
gctcaggcag cactagtcac aaaagccaag atacagaacc aacctaagca cccctcagca   3120
gatgcacagg taaagaaaat gtggtacgta tggggcacaa tggaatacga ttcagccttt   3180
aaaaacagtg aaattctgtc attggcaaca atgtagatga acctgaagga cacttatgct   3240
aagtgaaata agccaggcac agaaggagca atactgcatg attgcactta catctggcag   3300
gttaaaaagg caaactctta gaggcagaca gtagagaggt ggtgccaggg agcgggcact   3360
ggtggctggg gagatgttgg tcaaagggca caaaactgca gttgggagga attagttcag   3420
gacatccctt gtacatgggg acagtggtta gtaacaacgg attgtatcct tgaaaaccgc   3480
taagaaaata gtttttaagt gttcttgaca caaaaagtga cacgtatgtg agatactgca   3540
tggtcattag ctggatttag ccattccaca atgtacacat atttcaaaca ttgtgttgta   3600
tatgataaac atgtataatt tttgtcaatt aaaaattttt aggaagagga ggagaagaga   3660
agaagaagga gaaggagaaa gaggaacaag aagagagaga gacaaagaca ccaggttttt   3720
tctgacccct gggctatcaa aacacctatt gcccaataac tagttggccg ttggtgccct   3780
aaactattga agcgattgct gttatgtgga tgggccccgg acacttagaa actcgtgacc   3840
cctgaggacc cccacgagga cagtcagggt ccccccgaac tcagggagca ctgaggaagg   3900
agctcttaga ggcgtggggc ccctcaggcc cctcagaggg ctctgccaca tgggtcaggg   3960
gcaggctgag gggagtccc aggctccatg cccagcctct gtgcctctga ccagggtgtc    4020
ccccacaccg cctcctcccc agtgccctcc actggccaca cctggccaga agctggggag   4080
aggagagcac agtggttaag tcagtccctg cagggagacg gcaccagaaa aacctggcct   4140
gtggatgagt cccggcctgg cagccacaga gcagagagct ctagaagcaa cgaaggcccg   4200
agtctgctca gggaagagcg ggcagcagcc ccagggccgg acagtgacca agagtggcac   4260
cgcccatggc tcaacgggtc tttgcccaca gatcccccag cccctggaga cagggtctgt   4320
gtgcctggcc gtgcaggcag gcaccacact caggggggagg ccactgtgga gctctgtgca   4380
gagccccggg cgggagccta ctgctcccga aggtccggcc acagctgctc tcgtttgctc   4440
tcccctgcag agtgtccgag ccacacccag cctcttggcg tctacctgct aacccctgca   4500
gtgcaggacc tgtggctccg ggacaaagcc accttcacct gcttcgtggt gggcagtgac   4560
ctgaaggatg ctcacctgac ctgggaggtg gccgggaagg tccccacagg gggcgtggag   4620
```

gaagggctgc tggagcggca cagcaacggc tcccagagcc agcacagccg tctgaccctg 4680
cccaggtcct tgtggaacgc ggggacctcc gtcacctgca cactgaacca tcccagcctc 4740
ccaccccaga ggttgatggc gctgagagaa cccggtgagc ctggctccca ggtggggaga 4800
cgagggtgcc cacagcctgc tgacccctac gcctgcccca gggccatgac cccagctggg 4860
ccccagcagc accggtcatc ctccacagga aaggagaagg gaggcaccag caccctggcc 4920
ggccccactt ctctcccagt gcccccgtgg ccagaggctg acagcctccc ccacctcccc 4980
gcagctgcgc aggcacccgt caagctttcc ctgaacctgc tggcctcgtc tgaccctccc 5040
gaggcggcct cgtggctcct gtgtgaggtg tctggcttct cgccccccaa catcctcctg 5100
atgtggctgg aggaccagcg tgaggtgaac acttctgggt ttgcccccgc acgcccccct 5160
ccacagcccg ggagcaccac gttctgggcc tggagtgtgc tgcgtgtccc agccccgccc 5220
agccctcagc cagccaccta cacgtgtgtg gtcagccacg aggactcccg gactctgctc 5280
aacgccagcc ggagcctaga agtcagctgt gagtcacccc caggcccagg gttgggacgg 5340
ggactctgag gggggccata aggagctgga atccatacta ggcaggggtg ggcactgggc 5400
aggggcgggg ctaggctgtc ctgggcacac aggccccttc tcggtgtccg gcaggagcac 5460
agacttccca gtactcctgg gccatggatg tcccagcgtc catccttgct gtccacacca 5520
cgtgctggcc caggctggct ggcacagtgt aagaggtgga tacaacccct cgccgtgccc 5580
tgaggagtgg cggtttcctc ccaagacatt ccccacggct gggtgctggg cacaggcctt 5640
ccctggtgtg accgtgaatg tggtcaccct gaacagctgc cctctctggg gacatctgac 5700
tgtccaagac cacagtcagc acctctggga gccagagggg tctccagaga cccccagatg 5760
tcaggcttgg gctcagtgcc cagcgaaagg tcagccccac acatgcccat aatgggcgcc 5820
cacccagagt gacagccccc agcctcctgc caggcccacc cttttccgcc cccttgaggc 5880
atggcacaca gaccagtgcg cccactgccc gagcatggcc ccagtgggat gtggtggcca 5940
cgaggggctg tacacacagc aggaggctgt ccgccctgct cagggcctgc tgcctatgcc 6000
ccagctgtcc aaccaaggga ggcatggaag ggcccctggt gtaagctgga gccaggcacc 6060
caggcccccg gccaccctgc agagccaagg aaaggaagac acccaagtca acaaggggca 6120
gggctgaggg ctgtcccagg ctcttttggc ccgaggggct gccagcagcc ctgacccggc 6180
atgggccttc cccaaaagcg accctgtgag gtggcctcac agagaacccc ctctgaggac 6240
agtgtctgac cctgcctgcc tcacacagat gggccccaca gcagtgggca acctgggggg 6300
cagcagccca acctgaccct gcagggactg ccccctgcag cagcagctgc ttctcagtcc 6360
cccaacctcc ctgtccccgc cagagggtct tccccgaagc tgcagcccca acccatggct 6420
gcccacctgg aaccgggact ccctgtccac tgccccctcc ccttcggggc cccatctgtg 6480
ctggggccca ggttcggcct acagattccc atcattgcca tggcctcctg accttgccta 6540
tccaccccca accaccggct ccatgctgac cctcccccag gctcccacgc ccagctggcc 6600
ggccatcccc aggcacagac agtctgggat ctcacaggtt agcctggacc atccacctgg 6660
ccagacctgg gagaggctgg aagctgccct gccaccatgc tccagggccc caggttgcag 6720
tactatgggg tgagggtgtg tgtgcacacc tgtgtgtacc taggatatcc gagtgtaccc 6780
ttgtgccccc aagcacaagt ctccctccca ggcagtgagg cccagatggt gcagtggtta 6840
gagctgaggc ttatcccaca gagaaccctg gcgccttggt caaggaagcc cctatgcctt 6900
tcttgcctcg atttcccctc ttgtctgctg agccagcagg ggccacgtcc tgggctgctg 6960

-continued

```
tgaggaggaa gcaagttggt gctaggaggg gctcctgtgt gtgcatgggc gggaggggtg   7020

caggtatctg agcaccccgg tctccacttg agagagcagg gcaggagctc cctgacccac   7080

ccagactaca cacgctgtgt ccacgtgtct cccattatct gtggcagagg atccggcttc   7140

tttctcaatt tccagttctt cacaaagcaa tgcctttgta aaatgcaata agaaatacta   7200

gaaaaatgat atgaacagaa agacacgccg attttttgtt attagatgta acagaccatg   7260

gccccatgaa atgatcccgg accagatccg tccacacccg ccactcagca gctctggccg   7320

agctcacagt acaaccacaa taaactcttg ttgaatgaac tctaggaagt ctgtgacgtg   7380

gctggttctt gtcaatgctt cctgcctgcc cacaggctct tcctcgtgga tggggctgtg   7440

cttgccacgg aagcgcgttt ttcccggcct aggcttgcct tgggccccac tgccgtctcc   7500

agctggagat gaccttctat acacacattt gctcatgaca gacccttgct tagccccctt   7560

ccatggctcc ctcctgctgc tgggataaaa tcaccttgcc tggatatccc ctcctgggcc   7620

cctttccacc ctccttagtc agcaccccca gttcagggca cctgctttcc ccgctgcgga   7680

gaagccactc tctccttgct gcccggctgt gtcttgcctt ccacaccttg tcacagtggc   7740

cacttcctaa ggaaggcctc cctgtgtgca ggtgtgcaga agtgccccag cctcccgtca   7800

cctttgtcac gggagcccaa tccatgagag tctatggttc tgtctgtctg ccccactcag   7860

ggcagcgaca agtccaggcg gggaggacac agtaggcaga gatttgtcga ggggacatat   7920

gagcaagagg gtgaggctgg gagctccctg gagataacca cgcctcctgg gaagactcgc   7980

cgtcatttca gctccacgct gtgcgggggt gggtggaggg gtagcctggc cctcatgacc   8040

agggagcttc tcactcagcc cctgttcctc cccagacctg gccatgaccc ccctgatccc   8100

tcagagcaag gatgagaaca gcgatgacta cacgaccttt gatgatgtgg gcagcctgtg   8160

gaccgccctg tccacgtttg tggccctctt catcctcacc ctcctctaca gcggcattgt   8220

cactttcatc aaggtcaggg gagcggccag gctctcagtg accctcgggg tgggtgtggg   8280

gcaaggtgcc cttccagggg acatgccaga gctggtccag ggatcctgga ccaggcagag   8340

gcagggctga gggagcctgg aggacatgca ggccctctgt ggcctgtgga cactgtcgaa   8400

ggccctcttg accctgtgga taaaggacaa cacccccctcc cctgctcctc tgtctcccct   8460

gcccctccac ccctcaggct tctagccccc tgtctgaccc caggggctgt ctttcaggtg   8520

aagtagcccc agaagagcag gacgccctgt acctgcagag aagggaagca gcctctgtac   8580

ctcatctgtg gctaccagag agcagaaagg acccaccctg gactcttctg tgtgcaggaa   8640

gatgcgccag cccctgcccc cggctcccct ctgtccgcca cagaatccag tcttctagac   8700

caggggggacg ggcacccatc actccgcagg cgaatcagag ccccccctgcc ccggccctaa   8760

cccctgtgcc tccttcccgt gcttccccca gagccagcta cacccctgcc ccggccctaa   8820

cccccatgcc tccttcctgt gcttccccca gagccagcta gtcccacctg cagcccgctg   8880

gcctccccat aaacacgctt tggttcattt ca                                 8912
```

<210> SEQ ID NO 394
<211> LENGTH: 1293
<212> TYPE: DNA
<213> ORGANISM: homo sapiens;
<220> FEATURE:
<221> NAME/KEY: misc_feature
<222> LOCATION: (1)..(1)
<223> OTHER INFORMATION: n is a, c, g, or t

<400> SEQUENCE: 394

```
ncacccacca aggctccgga tgtgttcccc atcatatcag ggtgcagaca cccaaaggat     60
```

```
aacagccctg tggtcctggc atgcttgata actgggtacc acccaacgtc cgtgactgtc    120
acctggtaca tggggacaca gagccagccc cagagaacct tccctgagat acaaagacgg    180
gacagctact acatgacaag cagccagctc tccaccccc tccagcagtg gcgccaaggc    240
gagtacaaat gcgtggtcca gcacaccgcc agcaagagta agaaggagat cttccgctgg    300
ccagagtctc caaaggcaca ggcctcctca gtgcccactg cacaacccca agcagagggc    360
agcctcgcca aggcaaccac agccccagcc accacccgta acacaggaag aggaggagaa    420
gagaagaaga aggagaagga gaaagaggaa caagaagaga gagagacaaa gacaccagag    480
tgtccgagcc acacccagcc tcttggcgtc tacctgctaa cccctgcagt gcaggacctg    540
tggctccggg acaaagccac cttcacctgc ttcgtggtgg gcagtgacct gaaggatgct    600
cacctgacct gggaggtggc cgggaaggtc cccacagggg gcgtggagga agggctgctg    660
gagcggcaca gcaacggctc ccagagccag cacagccgtc tgaccctgcc caggtccttg    720
tggaacgcgg ggacctccgt cacctgcaca ctgaaccatc ccagcctccc accccagagg    780
ttgatggcgc tgagagaacc cgctgcgcag gcacccgtca agctttccct gaacctgctg    840
gcctcgtctg accctcccga ggcggcctcg tggctcctgt gtgaggtgtc tggcttctcg    900
ccccccaaca tcctcctgat gtggctggag gaccagcgtg aggtgaacac ttctgggttt    960
gcccccgcac gcccccctcc acagcccggg agcaccacgt tctgggcctg gagtgtgctg   1020
cgtgtcccag ccccgcccag ccctcagcca gccacctaca cgtgtgtggt cagccacgag   1080
gactcccgga ctctgctcaa cgccagccgg agcctagaag tcagctacct ggccatgacc   1140
cccctgatcc ctcagagcaa ggatgagaac agcgatgact acacgacctt tgatgatgtg   1200
ggcagcctgt ggaccgccct gtccacgttt gtggccctct tcatcctcac cctcctctac   1260
agcggcattg tcactttcat caaggtgaag tag                                1293
```

<210> SEQ ID NO 395
<211> LENGTH: 3842
<212> TYPE: DNA
<213> ORGANISM: homo sapiens;

<400> SEQUENCE: 395

```
gcctccacac agagcccatc cgtcttcccc ttgacccgct gctgcaaaaa cattccctcc     60
aatgccacct ccgtgactct gggctgcctg gccacgggct acttcccgga gccggtgatg    120
gtgacctggg acacaggctc cctcaacggg acaactatga ccttaccagc caccaccctc    180
acgctctctg gtcactatgc caccatcagc ttgctgaccg tctcgggtgc gtgggccaag    240
cagatgttca cctgccgtgt ggcacacact ccatcgtcca cagactgggt cgacaacaaa    300
accttcagcg gtaagagagg gccaagctca gagaccacag ttcccaggag tgccaggctg    360
agggctggca gagtgggcag ggttgaggg ggtgggtggg ctcaaacgtg ggaacaccca    420
gcatgcctgg ggacccgggc caggacgcgg gggcaagagg agggcacaca gagctcagag    480
aggccaacaa ccctcatgac caccagctct cccccagtct gctccaggga cttcaccccg    540
cccaccgtga agatcttaca gtcgtcctgc gacggcggcg ggcacttccc cccgaccatc    600
cagctcctgt gcctcgtctc tgggtacacc ccagggacta tcaacatcac ctggctggag    660
gacgggcagg tcatggacgt ggacttgtcc accgcctcta ccacgcagga gggtgagctg    720
gcctccacac aaagcgagct caccctcagc cagaagcact ggctgtcaga ccgcacctac    780
acctgccagg tcacctatca aggtcacacc tttgaggaca gcaccaagaa gtgtgcaggt    840
```

-continued

```
acgttcccac ctgccctggt ggccgccacg gaggccagag aagaggggcg ggtgggcctc    900
acacagccct ccggtgtacc acagattcca acccgagagg ggtgagcgcc tacctaagcc    960
ggcccagccc gttcgacctg ttcatccgca agtcgcccac gatcacctgt ctggtggtgg   1020
acctggcacc cagcaagggg accgtgaacc tgacctggtc ccgggccagt gggaagcctg   1080
tgaaccactc caccagaaag gaggagaagc agcgcaatgg cacgttaacc gtcacgtcca   1140
ccctgccggt gggcacccga gactggatcg agggggagac ctaccagtgc agggtgaccc   1200
acccccacct gcccagggcc ctcatgcggt ccacgaccaa gaccagcggt gagccatggg   1260
caggccgggg tcgtggggga agggagggag cgagtgagcg gggcccgggc tgaccccacg   1320
tctggccaca ggcccgcgtg ctgccccgga agtctatgcg tttgcgacgc cggagtggcc   1380
ggggagccgg gacaagcgca ccctcgcctg cctgatccag aacttcatgc ctgaggacat   1440
ctcggtgcag tggctgcaca acgaggtgca gctcccggac gcccggcaca gcacgacgca   1500
gccccgcaag accaagggct ccggcttctt cgtcttcagc cgcctggagg tgaccagggc   1560
cgaatgggag cagaaagatg agttcatctg ccgtgcagtc catgaggcag caagcccctc   1620
acagaccgtc cagcgagcgg tgtctgtaaa tcccggtaaa tgacgtactc ctgcctccct   1680
ccctcccagg gctccatcca gctgtgcagt ggggaggact ggccagacct tctgtccact   1740
gttgcaatga ccccaggaag ctacccccaa taaactgtgc ctgctcagag ccccaggtac   1800
acccattctt gggagcgggc agggctgtgg gcaggtgcat cttggcacag aggaatgggc   1860
cccccaggag gggcagtggg aggaggtggg cagggctgag tccccccagg agaggcggtg   1920
ggaggaggtg ggcagggctg aggtgccact catccatctg ccttcgtgtc agggttattt   1980
gtcaaacagc atatctgcag ggactcatca cagctacccc gggccctctc tgcccccact   2040
ctgggtctac cccctccaag gagtccaaag acccagggga ggtcctcagg gaaggggcaa   2100
gggagccccc acagccctct ctcttggggg cttggcttct accccccctgg acaggagccc   2160
ctgcaccccc aggtatagat gggcacacag gcccctccag gtggaaaaac agccctaagt   2220
gaaaccccca cacagacaca cacgacccga cagccctcgc ccaagtctgt gccactggcg   2280
ttcgcctctc tgccctgtcc cgccttgccg agtcctggcc ccagcaccgg ggccggtgga   2340
gccgagccca ctcacacccc gcagcctccg ccaccctgcc ctgtgggcac accaggccca   2400
ggtcagcagc caggcccccct ctcctactgc cccccaccgc cccttggtcc atcctgaatc   2460
ggcccccagg ggatcgccag cctcacacac ccagtctcgc ccactcacgc ctcactcaag   2520
gcacagctgt gcacacacta ggccccatag caactccaca gcaccctgta ccaccaccag   2580
ggcgccatag acaccccaca cgtggtcaca cgtggcccac actccgcctc tcacgctgcc   2640
tccagcgagg ctactgccaa gcccttcctc tgagccatac ctgggccgct ggatcccaga   2700
gagaaatgga gaggccctca cgtggtgtcc tccagtccaa ccctccctgt caccctgtca   2760
gcagcagcac cccacagcca aacacaggat ggatgcgtgg gctccatccc ccactcaccc   2820
acaccggaac cccagagcag gctacgtgcc cctcacagac ctcaaaccca catgtgcatc   2880
tgacacccca gatccaaacg ctccccccgg tcatgcacac caagggcaca gcacccacca   2940
aatccacacg gaaacacggg caccgggcac cccatgagca caaagcccct ccatgtctga   3000
agacagtccc tgcacaccgt cacagccata cattcagctt cactctcacg tcccagccca   3060
cctgcaccca gctctgggcc tggagcagca gaaagaggtg tgagggcccg aggcgggacc   3120
tgcacctgct gatgacccgg gaccagcagg cagctcacgg tgttggggaa gggagtggag   3180
ggcacccagg gcaggagcca gagggaccag gctggtgggc ggggccgggc cggggtaggg   3240
```

```
ccaggaggca gctctggaca cccacaggcc tgggctcata gtccacacca ggacagcccc   3300

tcagagcacc catgcagtga gtcccaggtc ttgggagcca ggccgcagag ctcacgcatc   3360

cttccgaggg ccctgagtga ggcggccact gctgtgccga ggggttgggt ccttctctgg   3420

ggagggcgtg gggtctagag aggcggagtg gaggtaacca gaggtcagga gagaagccgt   3480

aaggaacaga gggaaaatgg ggccagagtc ggggcgcagg gacgagaggt caggagtggt   3540

cggcctggct ctgggccgtt gactgactcg ggacctgggt gcccaccctc agggctggct   3600

ggcggctccg cgcagtccca gagggccccg gatagggtgc tctgccactc cggacagcag   3660

cagggactgc cgagagcagc aggaggctct gtcccccacc cccgctgcca ctgtggagcc   3720

gggagggctg actggccagg tcccccagag ctggacgtgt gcgtggagga ggccgagggc   3780

gaggcgccgt ggacgtggac cggcctctgc atcttcgccg cactcttcct gctcagcgtg   3840

ag                                                                  3842
```

<210> SEQ ID NO 396
<211> LENGTH: 1287
<212> TYPE: DNA
<213> ORGANISM: homo sapiens;

<400> SEQUENCE: 396

```
gcctccacac agagcccatc cgtcttcccc ttgacccgct gctgcaaaaa cattccctcc     60

aatgccacct ccgtgactct gggctgcctg gccacgggct acttcccgga gccggtgatg    120

gtgacctggg acacaggctc cctcaacggg acaactatga ccttaccagc caccaccctc    180

acgctctctg gtcactatgc caccatcagc ttgctgaccg tctcgggtgc gtgggccaag    240

cagatgttca cctgccgtgt ggcacacact ccatcgtcca cagactgggt cgacaacaaa    300

accttcagcg tctgctccag ggacttcacc ccgcccaccg tgaagatctt acagtcgtcc    360

tgcgacggcg gcgggcactt ccccccgacc atccagctcc tgtgcctcgt ctctgggtac    420

accccaggga ctatcaacat cacctggctg gaggacgggc aggtcatgga cgtggacttg    480

tccaccgcct ctaccacgca ggagggtgag ctggcctcca cacaaagcga gctcaccctc    540

agccagaagc actggctgtc agaccgcacc tacacctgcc aggtcaccta tcaaggtcac    600

acctttgagg acagcaccaa gaagtgtgca gattccaacc cgagaggggt gagcgcctac    660

ctaagccggc ccagcccgtt cgacctgttc atccgcaagt cgcccacgat cacctgtctg    720

gtggtggacc tggcacccag caaggggacc gtgaacctga cctggtcccg ggccagtggg    780

aagcctgtga accactccac cagaaaggag gagaagcagc gcaatggcac gttaaccgtc    840

acgtccaccc tgccggtggg cacccgagac tggatcgagg gggagaccta ccagtgcagg    900

gtgacccacc cccacctgcc cagggccctc atgcggtcca cgaccaagac cagcggcccg    960

cgtgctgccc cggaagtcta tgcgtttgcg acgccggagt ggccggggag ccgggacaag   1020

cgcaccctcg cctgcctgat ccagaacttc atgcctgagg acatctcggt gcagtggctg   1080

cacaacgagg tgcagctccc ggacgcccgg cacagcacga cgcagccccg caagaccaag   1140

ggctccggct tcttcgtctt cagccgcctg gaggtgacca gggccgaatg ggagcagaaa   1200

gatgagttca tctgccgtgc agtccatgag gcagcaagcc cctcacagac cgtccagcga   1260

gcggtgtctg taaatcccgg taaatga                                       1287
```

<210> SEQ ID NO 397
<211> LENGTH: 30
<212> TYPE: DNA

<213> ORGANISM: homo sapiens;

<400> SEQUENCE: 397
tccggcttct tcgtcttcag ccgcctggag 30

<210> SEQ ID NO 398
<211> LENGTH: 228
<212> TYPE: DNA
<213> ORGANISM: homo sapiens;

<400> SEQUENCE: 398
tccggcttct tcgtcttcag ccgcctggag gtgaccaggg ccgaatggga gcagaaagat 60
gagttcatct gccgtgcagt ccatgaggca gcaagcccct cacagaccgt ccagcgagcg 120
gtgtctgtaa atcccgagct ggacgtgtgc gtggaggagg ccgagggcga ggcgccgtgg 180
acgtggaccg gcctctgcat cttcgccgca ctcttcctgc tcagcgtg 228

<210> SEQ ID NO 399
<211> LENGTH: 1975
<212> TYPE: DNA
<213> ORGANISM: homo sapiens;

<400> SEQUENCE: 399
gggagtgcat ccgccccaac ccttttcccc ctcgtctcct gtgagaattc cccgtcggat 60
acgagcagcg tggccgttgg ctgcctcgca caggacttcc ttcccgactc catcactttc 120
tcctggaaat acaagaacaa ctctgacatc agcagcaccc ggggcttccc atcagtcctg 180
agagggggca agtacgcagc cacctcacag gtgctgctgc cttccaagga cgtcatgcag 240
ggcacagacg aacacgtggt gtgcaaagtc cagcacccca acggcaacaa agaaaagaac 300
gtgcctcttc caggtgaggg ccgggcccag ccaccgggac agagagggag ccgaaggggg 360
cgggagtggc gggcaccggg ctgacacgtg tccctcactg cagtgattgc cgagctgcct 420
cccaaagtga gcgtcttcgt cccaccccgc gacggcttct tcggcaaccc ccgcaagtcc 480
aagctcatct gccaggccac gggtttcagt ccccggcaga ttcaggtgtc ctggctgcgc 540
gaggggaagc aggtggggtc tggcgtcacc acggaccagg tgcaggctga ggccaaagag 600
tctgggccca cgacctacaa ggtgaccagc acactgacca tcaaagagag cgactggctc 660
agccagagca tgttcacctg ccgcgtggat cacaggggcc tgaccttcca gcagaatgcg 720
tcctccatgt gtggccccgg tgagtgacct gtccccaggg gcagcaccca ccgacacaca 780
ggggtccact cgggtctggc attcgccacc ccggatgcag ccatctactc cctgagcctt 840
ggcttcccag agcggccaag ggcaggggct cgggcggcag gacccctggg ctcggcagag 900
gcagttgcta ctctttgggt gggaaccatg cctccgccca catccacacc tgccccacct 960
ctgactccct tctcttgact ccagatcaag acacagccat ccgggtcttc gccatccccc 1020
catcctttgc cagcatcttc ctcaccaagt ccaccaagtt gacctgcctg gtcacagacc 1080
tgaccaccta tgacagcgtg accatctcct ggacccgcca gaatggcgaa gctgtgaaaa 1140
cccacaccaa catctccgag agccacccca atgccacttt cagcgccgtg ggtgaggcca 1200
gcatctgcga ggatgactgg aattccgggg agaggttcac gtgcaccgtg acccacacag 1260
acctgccctc gccactgaag cagaccatct cccggcccaa gggtaggccc cactcttgcc 1320
cctcttcctg cactccctgg gacctccctt ggcctctggg gcatggtgga aagcacccct 1380
cactcccccg ttgtctgggc aactggggaa aaggggactc aaccccagcc cacaggctgg 1440
tccccccact gccccgccct caccaccatc tctgttcaca ggggtggccc tgcacaggcc 1500
cgatgtctac ttgctgccac cagcccggga gcagctgaac ctgcgggagt cggccaccat 1560
cacgtgcctg gtgacgggct tctctcccgc ggacgtcttc gtgcagtgga tgcagagggg 1620
gcagcccttg tccccggaga agtatgtgac cagcgcccca atgcctgagc cccaggcccc 1680
aggccggtac ttcgcccaca gcatcctgac cgtgtccgaa gaggaatgga acacggggga 1740
gacctacacc tgcgtggtgg cccatgaggc cctgcccaac agggtcaccg agaggaccgt 1800
ggacaagtcc accggtaaac ccaccctgta caacgtgtcc ctggtcatgt ccgacacagc 1860
tggcacctgc tactgaccct gctggcctgc ccacaggctc ggggcggctg gccgctctgt 1920
gtgtgcatgc aaactaaccg tgtcaacggg gtgagatgtt gcatcttata aaatt 1975

<210> SEQ ID NO 400
<211> LENGTH: 1362
<212> TYPE: DNA
<213> ORGANISM: homo sapiens;

<400> SEQUENCE: 400
gggagtgcat ccgccccaac ccttttcccc ctcgtctcct gtgagaattc cccgtcggat 60
acgagcagcg tggccgttgg ctgcctcgca caggacttcc ttcccgactc catcactttc 120
tcctggaaat acaagaacaa ctctgacatc agcagcaccc ggggcttccc atcagtcctg 180
agagggggca agtacgcagc cacctcacag gtgctgctgc cttccaagga cgtcatgcag 240
ggcacagacg aacacgtggt gtgcaaagtc cagcacccca acggcaacaa agaaaagaac 300
gtgcctcttc cagtgattgc cgagctgcct cccaaagtga gcgtcttcgt cccaccccgc 360
gacggcttct tcggcaaccc ccgcaagtcc aagctcatct gccaggccac gggtttcagt 420
ccccggcaga ttcaggtgtc ctggctgcgc gaggggaagc aggtggggtc tggcgtcacc 480
acggaccagg tgcaggctga ggccaaagag tctgggccca cgacctacaa ggtgaccagc 540
acactgacca tcaaagagag cgactggctc agccagagca tgttcacctg ccgcgtggat 600
cacaggggcc tgaccttcca gcagaatgcg tcctccatgt gtggccccga tcaagacaca 660
gccatccggg tcttcgccat ccccccatcc tttgccagca tcttcctcac caagtccacc 720
aagttgacct gcctggtcac agacctgacc acctatgaca gcgtgaccat ctcctggacc 780
cgccagaatg gcgaagctgt gaaaacccac accaacatct ccgagagcca ccccaatgcc 840
actttcagcg ccgtgggtga ggccagcatc tgcgaggatg actggaattc cggggagagg 900
ttcacgtgca ccgtgaccca cacagacctg ccctcgccac tgaagcagac catctcccgg 960
cccaaggggg tggccctgca caggcccgat gtctacttgc tgccaccagc ccgggagcag 1020
ctgaacctgc gggagtcggc caccatcacg tgcctggtga cgggcttctc tcccgcggac 1080
gtcttcgtgc agtggatgca gagggggcag cccttgtccc cggagaagta tgtgaccagc 1140
gccccaatgc ctgagcccca ggccccaggc cggtacttcg cccacagcat cctgaccgtg 1200
tccgaagagg aatggaacac gggggagacc tacacctgcg tggtggccca tgaggccctg 1260
cccaacaggg tcaccgagag gaccgtggac aagtccaccg gtaaacccac cctgtacaac 1320
gtgtccctgg tcatgtccga cacagctggc acctgctact ga 1362

<210> SEQ ID NO 401
<211> LENGTH: 1975
<212> TYPE: DNA
<213> ORGANISM: homo sapiens;

<400> SEQUENCE: 401

```
gggagtgcat ccgccccaac ccttttcccc ctcgtctcct gtgagaattc cccgtcggat     60

acgagcagcg tggccgttgg ctgcctcgca caggacttcc ttcccgactc catcactttc    120

tcctggaaat acaagaacaa ctctgacatc agcagcaccc ggggcttccc atcagtcctg    180

agagggggca agtacgcagc cacctcacag gtgctgctgc cttccaagga cgtcatgcag    240

ggcacagacg aacacgtggt gtgcaaagtc cagcacccca acggcaacaa agaaaagaac    300

gtgcctcttc caggtgaggg ccgggcccag ccaccgggac agagagggag ccgaaggggg    360

cgggagtggc gggcaccggg ctgacacgtg tccctcactg cagtgattgc cgagctgcct    420

cccaaagtga gcgtcttcgt cccacccccgc gacggcttct tcggcaaccc ccgcaagtcc   480

aagctcatct gccaggccac gggtttcagt ccccggcaga ttcaggtgtc ctggctgcgc    540

gaggggaagc aggtggggtc tggcgtcacc acggaccagg tgcaggctga ggccaaagag    600

tctgggccca cgacctacaa ggtgaccagc acactgacca tcaaagagag cgactggctc    660

agccagagca tgttcacctg ccgcgtggat cacaggggcc tgaccttcca gcagaatgcg    720

tcctccatgt gtgtccccgg tgagtgacct gtccccaggg gcagcaccca ccgacacaca    780

ggggtccact cgggtctggc attcgccacc ccggatgcag ccatctactc cctgagcctt    840

ggcttcccag agcggccaag ggcaggggct cgggcggcag gacccctggg ctcggcagag    900

gcagttgcta ctctttgggt gggaaccatg cctccgccca catccacacc tgccccacct    960

ctgactccct tctcttgact ccagatcaag acacagccat ccgggtcttc gccatccccc   1020

catcctttgc cagcatcttc ctcaccaagt ccaccaagtt gacctgcctg gtcacagacc   1080

tgaccaccta tgacagcgtg accatctcct ggacccgcca gaatggcgaa gctgtgaaaa   1140

cccacaccaa catctccgag agccacccca atgccacttt cagcgccgtg ggtgaggcca   1200

gcatctgcga ggatgactgg aattccgggg agaggttcac gtgcaccgtg acccacacag   1260

acctgccctc gccactgaag cagaccatct cccggcccaa gggtaggccc cactcttgcc   1320

cctcttcctg cactccctgg gacctccctt ggcctctggg gcatggtgga aagcacccct   1380

cactcccccg ttgtctgggc aactggggaa aaggggactc aaccccagcc cacaggctgg   1440

tccccccact gccccgccct caccaccatc tctgttcaca ggggtggccc tgcacaggcc   1500

cgatgtctac ttgctgccac cagcccggga gcagctgaac ctgcgggagt cggccaccat   1560

cacgtgcctg gtgacgggct tctctcccgc ggacgtcttc gtgcagtgga tgcagagggg   1620

gcagcccttg tccccggaga agtatgtgac cagcgcccca atgcctgagc cccaggcccc   1680

aggccggtac ttcgcccaca gcatcctgac cgtgtccgaa gaggaatgga acacggggga   1740

gacctacacc tgcgtggtgg cccatgaggc cctgcccaac agggtcaccg agaggaccgt   1800

ggacaagtcc accggtaaac ccaccctgta caacgtgtcc ctggtcatgt ccgacacagc   1860

tggcacctgc tactgaccct gctggcctgc ccacaggctc ggggcggctg gccgctctgt   1920

gtgtgcatgc aaactaaccg tgtcaacggg gtgagatgtt gcatcttata aaatt         1975
```

<210> SEQ ID NO 402
<211> LENGTH: 1362
<212> TYPE: DNA
<213> ORGANISM: homo sapiens;

<400> SEQUENCE: 402

```
gggagtgcat ccgccccaac ccttttcccc ctcgtctcct gtgagaattc cccgtcggat     60

acgagcagcg tggccgttgg ctgcctcgca caggacttcc ttcccgactc catcactttc    120

tcctggaaat acaagaacaa ctctgacatc agcagcaccc ggggcttccc atcagtcctg    180
```

agagggggca agtacgcagc cacctcacag gtgctgctgc cttccaagga cgtcatgcag 240
ggcacagacg aacacgtggt gtgcaaagtc cagcacccca acggcaacaa agaaaagaac 300
gtgcctcttc cagtgattgc cgagctgcct cccaaagtga gcgtcttcgt cccaccccgc 360
gacggcttct tcggcaaccc ccgcaagtcc aagctcatct gccaggccac gggtttcagt 420
ccccggcaga ttcaggtgtc ctggctgcgc gaggggaagc aggtggggtc tggcgtcacc 480
acggaccagg tgcaggctga ggccaaagag tctgggccca cgacctacaa ggtgaccagc 540
acactgacca tcaaagagag cgactggctc agccagagca tgttcacctg ccgcgtggat 600
cacaggggcc tgaccttcca gcagaatgcg tcctccatgt gtgtccccga tcaagacaca 660
gccatccggg tcttcgccat ccccccatcc tttgccagca tcttcctcac caagtccacc 720
aagttgacct gcctggtcac agacctgacc acctatgaca gcgtgaccat ctcctggacc 780
cgccagaatg gcgaagctgt gaaaacccac accaacatct ccgagagcca ccccaatgcc 840
actttcagcg ccgtgggtga ggccagcatc tgcgaggatg actggaattc cggggagagg 900
ttcacgtgca ccgtgaccca cacagacctg ccctcgccac tgaagcagac catctcccgg 960
cccaaggggg tggccctgca caggcccgat gtctacttgc tgccaccagc ccgggagcag 1020
ctgaacctgc gggagtcggc caccatcacg tgcctggtga cgggcttctc tcccgcggac 1080
gtcttcgtgc agtggatgca gagggggcag ccccttgtccc cggagaagta tgtgaccagc 1140
gccccaatgc ctgagcccca ggccccaggc cggtacttcg cccacagcat cctgaccgtg 1200
tccgaagagg aatggaacac gggggagacc tacacctgcg tggtggccca tgaggccctg 1260
cccaacaggg tcaccgagag gaccgtggac aagtccaccg gtaaacccac cctgtacaac 1320
gtgtccctgg tcatgtccga cacagctggc acctgctact ga 1362

<210> SEQ ID NO 403
<211> LENGTH: 1975
<212> TYPE: DNA
<213> ORGANISM: homo sapiens;

<400> SEQUENCE: 403
gggagtgcat ccgccccaac ccttttcccc ctcgtctcct gtgagaattc cccgtcggat 60
acgagcagcg tggccgttgg ctgcctcgca caggacttcc ttcccgactc catcactttc 120
tcctggaaat acaagaacaa ctctgacatc agcagcaccc ggggcttccc atcagtcctg 180
agagggggca agtacgcagc cacctcacag gtgctgctgc cttccaagga cgtcatgcag 240
ggcacagacg aacacgtggt gtgcaaagtc cagcacccca acggcaacaa agaaaagaac 300
gtgcctcttc caggtgaggg ccgggcccag ccaccgggac agagagggag ccgaaggggg 360
cgggagtggc gggcaccggg ctgacacgtg tccctcactg cagtgattgc cgagctgcct 420
cccaaagtga gcgtcttcgt cccaccccgc gacggcttct tcggcaaccc ccgcaagtcc 480
aagctcatct gccaggccac gggtttcagt ccccggcaga ttcaggtgtc ctggctgcgc 540
gaggggaagc aggtggggtc tggcgtcacc acggaccagg tgcaggctga ggccaaagag 600
tctgggccca cgacctacaa ggtgaccagc acactgacca tcaaagagag cgactggctc 660
ggccagagca tgttcacctg ccgcgtggat cacaggggcc tgaccttcca gcagaatgcg 720
tcctccatgt gtgtccccgg tgagtgacct gtccccaggg gcagcaccca ccgacacaca 780
ggggtccact cgggtctggc attcgccacc ccggatgcag ccatctactc cctgagcctt 840
ggcttcccag agcggccaag ggcaggggct cgggcggcag gacccctggg ctcggcagag 900

-continued

```
gcagttgcta ctctttgggt gggaaccatg cctccgccca catccacacc tgccccacct    960
ctgactccct tctcttgact ccagatcaag acacagccat ccgggtcttc gccatccccc   1020
catcctttgc cagcatcttc ctcaccaagt ccaccaagtt gacctgcctg gtcacagacc   1080
tgaccaccta tgacagcgtg accatctcct ggacccgcca gaatggcgaa gctgtgaaaa   1140
cccacaccaa catctccgag agccacccca atgccacttt cagcgccgtg ggtgaggcca   1200
gcatctgcga ggatgactgg aattccgggg agaggttcac gtgcaccgtg acccacacag   1260
acctgccctc gccactgaag cagaccatct cccggcccaa gggtaggccc cactcttgcc   1320
cctcttcctg cactccctgg gacctccctt ggcctctggg gcatggtgga aagcacccct   1380
cactcccccg ttgtctgggc aactggggaa aaggggactc aaccccagcc cacaggctgg   1440
tccccccact gccccgccct caccaccatc tctgttcaca ggggtggccc tgcacaggcc   1500
cgatgtctac ttgctgccac cagcccggga gcagctgaac ctgcgggagt cggccaccat   1560
cacgtgcctg gtgacgggct tctctcccgc ggacgtcttc gtgcagtgga tgcagagggg   1620
gcagcccttg tccccggaga agtatgtgac cagcgcccca atgcctgagc cccaggcccc   1680
aggccggtac ttcgcccaca gcatcctgac cgtgtccgaa gaggaatgga acacggggga   1740
gacctacacc tgcgtggtgg cccatgaggc cctgcccaac agggtcaccg agaggaccgt   1800
ggacaagtcc accggtaaac ccaccctgta caacgtgtcc ctggtcatgt ccgacacagc   1860
tggcacctgc tactgaccct gctggcctgc ccacaggctc ggggcggctg gccgctctgt   1920
gtgtgcatgc aaactaaccg tgtcaacggg gtgagatgtt gcatcttata aaatt        1975
```

<210> SEQ ID NO 404
<211> LENGTH: 1362
<212> TYPE: DNA
<213> ORGANISM: homo sapiens;

<400> SEQUENCE: 404

```
gggagtgcat ccgccccaac ccttttcccc ctcgtctcct gtgagaattc cccgtcggat     60
acgagcagcg tggccgttgg ctgcctcgca caggacttcc ttcccgactc catcactttc    120
tcctggaaat acaagaacaa ctctgacatc agcagcaccc ggggcttccc atcagtcctg    180
agagggggca agtacgcagc cacctcacag gtgctgctgc cttccaagga cgtcatgcag    240
ggcacagacg aacacgtggt gtgcaaagtc cagcacccca acggcaacaa agaaaagaac    300
gtgcctcttc cagtgattgc cgagctgcct cccaaagtga gcgtcttcgt cccaccccgc    360
gacggcttct tcggcaaccc ccgcaagtcc aagctcatct gccaggccac gggtttcagt    420
ccccggcaga ttcaggtgtc ctggctgcgc gaggggaagc aggtggggtc tggcgtcacc    480
acggaccagg tgcaggctga ggccaaagag tctgggccca cgacctacaa ggtgaccagc    540
acactgacca tcaaagagag cgactggctc ggccagagca tgttcacctg ccgcgtggat    600
cacaggggcc tgaccttcca gcagaatgcg tcctccatgt gtgtccccga tcaagacaca    660
gccatccggg tcttcgccat ccccccatcc tttgccagca tcttcctcac caagtccacc    720
aagttgacct gcctggtcac agacctgacc acctatgaca gcgtgaccat ctcctggacc    780
cgccagaatg gcgaagctgt gaaaacccac accaacatct ccgagagcca ccccaatgcc    840
actttcagcg ccgtgggtga ggccagcatc tgcgaggatg actggaattc cggggagagg    900
ttcacgtgca ccgtgaccca cacagacctg ccctcgccac tgaagcagac catctcccgg    960
cccaaggggg tggccctgca caggcccgat gtctacttgc tgccaccagc ccgggagcag   1020
ctgaacctgc gggagtcggc caccatcacg tgcctggtga cgggcttctc tcccgcggac   1080
```

gtcttcgtgc agtggatgca gagggggcag cccttgtccc cggagaagta tgtgaccagc 1140
gccccaatgc ctgagcccca ggccccaggc cggtacttcg cccacagcat cctgaccgtg 1200
tccgaagagg aatggaacac gggggagacc tacacctgcg tggtggccca tgaggccctg 1260
cccaacaggg tcaccgagag gaccgtggac aagtccaccg gtaaacccac cctgtacaac 1320
gtgtccctgg tcatgtccga cacagctggc acctgctact ga 1362

<210> SEQ ID NO 405
<211> LENGTH: 11
<212> TYPE: DNA
<213> ORGANISM: homo sapiens;

<400> SEQUENCE: 405
ctaactgggg a 11

<210> SEQ ID NO 406
<211> LENGTH: 31
<212> TYPE: DNA
<213> ORGANISM: homo sapiens;

<400> SEQUENCE: 406
aggatattgt agtggtggta gctgctactc c 31

<210> SEQ ID NO 407
<211> LENGTH: 37
<212> TYPE: DNA
<213> ORGANISM: homo sapiens;

<400> SEQUENCE: 407
gtattatgat tacgtttggg ggagttatcg ttatacc 37

<210> SEQ ID NO 408
<211> LENGTH: 18
<212> TYPE: DNA
<213> ORGANISM: homo sapiens;

<400> SEQUENCE: 408
gagtatagca gctcgtcc 18

<210> SEQ ID NO 409
<211> LENGTH: 20
<212> TYPE: DNA
<213> ORGANISM: homo sapiens;

<400> SEQUENCE: 409
gtggatacag ctatggttac 20

<210> SEQ ID NO 410
<211> LENGTH: 31
<212> TYPE: DNA
<213> ORGANISM: homo sapiens;

<400> SEQUENCE: 410
aggatattgt agtagtacca gctgctatgc c 31

<210> SEQ ID NO 411
<211> LENGTH: 16
<212> TYPE: DNA
<213> ORGANISM: homo sapiens;

<400> SEQUENCE: 411
tgactacagt aactac 16

<210> SEQ ID NO 412
<211> LENGTH: 23
<212> TYPE: DNA
<213> ORGANISM: homo sapiens;

<400> SEQUENCE: 412
gtggatatag tggctacgat tac 23

<210> SEQ ID NO 413
<211> LENGTH: 31
<212> TYPE: DNA
<213> ORGANISM: homo sapiens;

<400> SEQUENCE: 413
gtattacgat ttttggagtg gttattatac c 31

<210> SEQ ID NO 414
<211> LENGTH: 31
<212> TYPE: DNA
<213> ORGANISM: homo sapiens;

<400> SEQUENCE: 414
aggatattgt actaatggtg tatgctatac c 31

<210> SEQ ID NO 415
<211> LENGTH: 16
<212> TYPE: DNA
<213> ORGANISM: homo sapiens;

<400> SEQUENCE: 415
tgactacagt aactac 16

<210> SEQ ID NO 416
<211> LENGTH: 19
<212> TYPE: DNA
<213> ORGANISM: homo sapiens;

<400> SEQUENCE: 416
tgactacggt ggtaactcc 19

<210> SEQ ID NO 417
<211> LENGTH: 17
<212> TYPE: DNA
<213> ORGANISM: homo sapiens;

<400> SEQUENCE: 417
ggtataaccg gaaccac 17

<210> SEQ ID NO 418
<211> LENGTH: 31
<212> TYPE: DNA
<213> ORGANISM: homo sapiens;

<400> SEQUENCE: 418
gtattactat ggttcgggga gttattataa c 31

<210> SEQ ID NO 419
<211> LENGTH: 20
<212> TYPE: DNA
<213> ORGANISM: homo sapiens;

<400> SEQUENCE: 419
ggtatagtgg gagctactac 20

<210> SEQ ID NO 420
<211> LENGTH: 31
<212> TYPE: DNA
<213> ORGANISM: homo sapiens;

<400> SEQUENCE: 420
gtattacgat attttgactg gttattataa c 31

<210> SEQ ID NO 421
<211> LENGTH: 17
<212> TYPE: DNA
<213> ORGANISM: homo sapiens;

<400> SEQUENCE: 421
ggtacaactg gaacgac 17

<210> SEQ ID NO 422
<211> LENGTH: 18
<212> TYPE: DNA
<213> ORGANISM: homo sapiens;

<400> SEQUENCE: 422
gggtatagca gcggctac 18

<210> SEQ ID NO 423
<211> LENGTH: 20
<212> TYPE: DNA
<213> ORGANISM: homo sapiens;

<400> SEQUENCE: 423
gtagagatgg ctacaattac 20

<210> SEQ ID NO 424
<211> LENGTH: 28
<212> TYPE: DNA
<213> ORGANISM: homo sapiens;

<400> SEQUENCE: 424
agcatattgt ggtggtgact gctattcc 28

<210> SEQ ID NO 425
<211> LENGTH: 17
<212> TYPE: DNA
<213> ORGANISM: homo sapiens;

<400> SEQUENCE: 425
ggtataactg gaacgac 17

<210> SEQ ID NO 426
<211> LENGTH: 21
<212> TYPE: DNA
<213> ORGANISM: homo sapiens;

<400> SEQUENCE: 426
gggtatagca gcagctggta c 21

<210> SEQ ID NO 427
<211> LENGTH: 16
<212> TYPE: DNA
<213> ORGANISM: homo sapiens;

<400> SEQUENCE: 427
tgactacggt gactac 16

<210> SEQ ID NO 428
<211> LENGTH: 31
<212> TYPE: DNA
<213> ORGANISM: homo sapiens;

<400> SEQUENCE: 428
gtattactat gatagtagtg gttattacta c 31

<210> SEQ ID NO 429
<211> LENGTH: 20
<212> TYPE: DNA
<213> ORGANISM: homo sapiens;

<400> SEQUENCE: 429
gtggatacag ctatggttac 20

<210> SEQ ID NO 430
<211> LENGTH: 21
<212> TYPE: DNA
<213> ORGANISM: homo sapiens;

<400> SEQUENCE: 430
gggtatagca gtggctggta c 21

<210> SEQ ID NO 431
<211> LENGTH: 17
<212> TYPE: DNA
<213> ORGANISM: homo sapiens;

<400> SEQUENCE: 431
ggtataactg gaactac 17

<210> SEQ ID NO 432
<211> LENGTH: 6
<212> TYPE: PRT
<213> ORGANISM: Oryctolagus cuniculus;

<400> SEQUENCE: 432

Tyr Tyr Gly Met Asp Leu
1 5

<210> SEQ ID NO 433
<211> LENGTH: 20
<212> TYPE: DNA
<213> ORGANISM: Oryctolagus cuniculus;

<400> SEQUENCE: 433
attactacgg catggacctc 20

<210> SEQ ID NO 434
<211> LENGTH: 6
<212> TYPE: PRT
<213> ORGANISM: Ovis aries;

<400> SEQUENCE: 434

Tyr Tyr Gly Val Asp Val
1 5

<210> SEQ ID NO 435
<211> LENGTH: 20

<212> TYPE: DNA
<213> ORGANISM: Ovis aries;

<400> SEQUENCE: 435
attactacgg tgtagatgtc 20

<210> SEQ ID NO 436
<211> LENGTH: 6
<212> TYPE: PRT
<213> ORGANISM: Bos taurus;

<400> SEQUENCE: 436

Tyr Tyr Gly Val Asp Val
1 5

<210> SEQ ID NO 437
<211> LENGTH: 20
<212> TYPE: DNA
<213> ORGANISM: Bos taurus;

<400> SEQUENCE: 437
attactacgg tgtagatgtc 20

<210> SEQ ID NO 438
<211> LENGTH: 6
<212> TYPE: PRT
<213> ORGANISM: Canis familiaris;

<400> SEQUENCE: 438

Tyr Tyr Gly Met Asp Tyr
1 5

<210> SEQ ID NO 439
<211> LENGTH: 20
<212> TYPE: DNA
<213> ORGANISM: Canis familiaris;

<400> SEQUENCE: 439
attactatgg tatggactac 20

<210> SEQ ID NO 440
<211> LENGTH: 9
<212> TYPE: PRT
<213> ORGANISM: homo sapiens;

<400> SEQUENCE: 440

Tyr Tyr Tyr Tyr Tyr Gly Met Asp Val
1 5

<210> SEQ ID NO 441
<211> LENGTH: 29
<212> TYPE: DNA
<213> ORGANISM: homo sapiens;

<400> SEQUENCE: 441
attactacta ctactacggt atggacgtc 29

<210> SEQ ID NO 442
<211> LENGTH: 57
<212> TYPE: DNA
<213> ORGANISM: Homo sapiens

<400> SEQUENCE: 442
atgggctggt cctgcatcat cctgtttctg gtggccaccg ccaccggcgt gcacagc 57

<210> SEQ ID NO 443
<211> LENGTH: 19
<212> TYPE: PRT
<213> ORGANISM: Homo sapiens

<400> SEQUENCE: 443

Met Gly Trp Ser Cys Ile Ile Leu Phe Leu Val Ala Thr Ala Thr Gly
1 5 10 15

Val His Ser

<210> SEQ ID NO 444
<211> LENGTH: 21
<212> TYPE: DNA
<213> ORGANISM: Artificial Sequence
<220> FEATURE:
<223> OTHER INFORMATION: Primer

<400> SEQUENCE: 444
aggccagcag agggttccat g 21

<210> SEQ ID NO 445
<211> LENGTH: 22
<212> TYPE: DNA
<213> ORGANISM: Artificial Sequence
<220> FEATURE:
<223> OTHER INFORMATION: Primer

<400> SEQUENCE: 445
ggctcccaga tcctcaaggc ac 22

<210> SEQ ID NO 446
<211> LENGTH: 62
<212> TYPE: DNA
<213> ORGANISM: Homo sapiens

<400> SEQUENCE: 446
attactacta ctactacggt atggacgtct ggggccaagg gaccacggtc accgtctcct 60
ca 62

<210> SEQ ID NO 447
<211> LENGTH: 63
<212> TYPE: DNA
<213> ORGANISM: Homo sapiens

<400> SEQUENCE: 447
attactacta ctactacggt atggacgtct ggggccaagg gaccacggtc accgtctcct 60
cag 63

<210> SEQ ID NO 448
<211> LENGTH: 20
<212> TYPE: PRT
<213> ORGANISM: Homo sapiens

<400> SEQUENCE: 448

Tyr Tyr Tyr Tyr Tyr Tyr Met Asp Val Trp Gly Lys Gly Thr Thr Val
1 5 10 15

Thr Val Ser Ser
20

<210> SEQ ID NO 449
<211> LENGTH: 62

<212> TYPE: DNA
<213> ORGANISM: Homo sapiens

<400> SEQUENCE: 449
attactacta ctactactac atggacgtct ggggcaaagg gaccacggtc accgtctcct 60
ca 62

<210> SEQ ID NO 450
<211> LENGTH: 20
<212> TYPE: PRT
<213> ORGANISM: Homo sapiens

<400> SEQUENCE: 450

Tyr Tyr Tyr Tyr Tyr Tyr Met Asp Val Trp Gly Lys Gly Thr Thr Val
1 5 10 15

Thr Val Ser Ser
20

<210> SEQ ID NO 451
<211> LENGTH: 62
<212> TYPE: DNA
<213> ORGANISM: Homo sapiens

<400> SEQUENCE: 451
attactacta ctactactac atggacgtct ggggcaaagg gaccacggtc accgtctcct 60
ca 62

<210> SEQ ID NO 452
<211> LENGTH: 20
<212> TYPE: PRT
<213> ORGANISM: Homo sapiens

<400> SEQUENCE: 452

Tyr Tyr Tyr Tyr Tyr Tyr Met Asp Val Trp Gly Lys Gly Thr Thr Val
1 5 10 15

Thr Val Ser Ser
20

<210> SEQ ID NO 453
<211> LENGTH: 63
<212> TYPE: DNA
<213> ORGANISM: Homo sapiens

<400> SEQUENCE: 453
attactacta ctactactac atggacgtct ggggcaaagg gaccacggtc accgtctcct 60
cag 63

<210> SEQ ID NO 454
<211> LENGTH: 20
<212> TYPE: PRT
<213> ORGANISM: Homo sapiens

<400> SEQUENCE: 454

Tyr Tyr Tyr Tyr Tyr Gly Met Asp Val Trp Gly Lys Gly Thr Thr Val
1 5 10 15

Thr Val Ser Ser
20

<210> SEQ ID NO 455
<211> LENGTH: 63
<212> TYPE: DNA

<213> ORGANISM: Homo sapiens

<400> SEQUENCE: 455
attactacta ctactacggt atggacgtct ggggcaaagg gaccacggtc accgtctcct 60
cag 63

<210> SEQ ID NO 456
<211> LENGTH: 98
<212> TYPE: PRT
<213> ORGANISM: Homo sapiens

<400> SEQUENCE: 456

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 457
<211> LENGTH: 296
<212> TYPE: DNA
<213> ORGANISM: Homo sapiens

<400> SEQUENCE: 457
caggtccagc tggtgcaatc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 458
<211> LENGTH: 274
<212> TYPE: DNA
<213> ORGANISM: Homo sapiens

<400> SEQUENCE: 458
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgatgac acgg 274

<210> SEQ ID NO 459
<211> LENGTH: 296
<212> TYPE: DNA
<213> ORGANISM: Homo sapiens

<400> SEQUENCE: 459
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 460
<211> LENGTH: 294
<212> TYPE: DNA
<213> ORGANISM: Homo sapiens

<400> SEQUENCE: 460
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accacggacg aatccacgag cacagcctac 240
atggagctga gcagcctgag atctgaggac acggccgtgt attactgtgc gaga 294

<210> SEQ ID NO 461
<211> LENGTH: 296
<212> TYPE: DNA
<213> ORGANISM: Homo sapiens

<400> SEQUENCE: 461
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 462
<211> LENGTH: 233
<212> TYPE: DNA
<213> ORGANISM: Homo sapiens

<400> SEQUENCE: 462
agaagcctgg gtcctcggtg aaggtctcct gcaaggcttc tggaggcacc ttcagcagct 60
atgctatcag ctgggtgcga caggcccctg gacaagggct tgagtggatg ggaaggatca 120
tccctatctt tggtacagca aactacgcac agaagttcca gggcagagtc acgattaccg 180
cggacgaatc cacgagcaca gcctacatgg agctgagcag cctgagatct gag 233

<210> SEQ ID NO 463
<211> LENGTH: 296
<212> TYPE: DNA
<213> ORGANISM: Homo sapiens

<400> SEQUENCE: 463
caggtccagc tggtgcaatc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaagg atcatcccta tccttggtac agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 464
<211> LENGTH: 296
<212> TYPE: DNA
<213> ORGANISM: Homo sapiens

<400> SEQUENCE: 464
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 465
<211> LENGTH: 296
<212> TYPE: DNA
<213> ORGANISM: Homo sapiens

<400> SEQUENCE: 465
caggtccagc tggtgcagtc tggggctgag gtgaagaagc ctgggtcctc agtgaaggtc 60
tcctgcaagg cttctggagg caccttcagc agctatgcta tcagctgggt gcgacaggcc 120
cctggacaag ggcttgagtg gatgggaggg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 466
<211> LENGTH: 296
<212> TYPE: DNA
<213> ORGANISM: Homo sapiens

<400> SEQUENCE: 466
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaagg atcatcccta tccttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 467
<211> LENGTH: 296
<212> TYPE: DNA
<213> ORGANISM: Homo sapiens

<400> SEQUENCE: 467
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 468
<211> LENGTH: 296
<212> TYPE: DNA
<213> ORGANISM: Homo sapiens

<400> SEQUENCE: 468
caggtccagc tggtgcagtc tggggctgag gtgaagaagc ctgggtcctc agtgaaggtc 60
tcctacaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 469
<211> LENGTH: 98
<212> TYPE: PRT
<213> ORGANISM: Homo sapiens

<400> SEQUENCE: 469

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Thr Ile Ser Trp Val Arg Gln Ala Pro Gly Gln Gly Leu Glu Trp Met
35 40 45

Gly Arg Ile Ile Pro Ile Leu Gly Ile Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 470
<211> LENGTH: 91
<212> TYPE: PRT
<213> ORGANISM: Homo sapiens

<400> SEQUENCE: 470

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Asp Asp Thr
85 90

<210> SEQ ID NO 471
<211> LENGTH: 98
<212> TYPE: PRT
<213> ORGANISM: Homo sapiens

<400> SEQUENCE: 471

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr

```
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg


<210> SEQ ID NO 472
<211> LENGTH: 98
<212> TYPE: PRT
<213> ORGANISM: Homo sapiens

<400> SEQUENCE: 472

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg


<210> SEQ ID NO 473
<211> LENGTH: 98
<212> TYPE: PRT
<213> ORGANISM: Homo sapiens

<400> SEQUENCE: 473

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg


<210> SEQ ID NO 474
<211> LENGTH: 77
<212> TYPE: PRT
<213> ORGANISM: Homo sapiens

<400> SEQUENCE: 474
```

Lys Pro Gly Ser Ser Val Lys Val Ser Cys Lys Ala Ser Gly Gly Thr
1 5 10 15

Phe Ser Ser Tyr Ala Ile Ser Trp Val Arg Gln Ala Pro Gly Gln Gly
20 25 30

Leu Glu Trp Met Gly Arg Ile Ile Pro Ile Phe Gly Thr Ala Asn Tyr
35 40 45

Ala Gln Lys Phe Gln Gly Arg Val Thr Ile Thr Ala Asp Glu Ser Thr
50 55 60

Ser Thr Ala Tyr Met Glu Leu Ser Ser Leu Arg Ser Glu
65 70 75

<210> SEQ ID NO 475
<211> LENGTH: 98
<212> TYPE: PRT
<213> ORGANISM: Homo sapiens

<400> SEQUENCE: 475

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Thr Ile Ser Trp Val Arg Gln Ala Pro Gly Gln Gly Leu Glu Trp Met
35 40 45

Gly Arg Ile Ile Pro Ile Leu Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 476
<211> LENGTH: 98
<212> TYPE: PRT
<213> ORGANISM: Homo sapiens

<400> SEQUENCE: 476

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Ile Ile Pro Ile Leu Gly Ile Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 477
<211> LENGTH: 98
<212> TYPE: PRT
<213> ORGANISM: Homo sapiens

<400> SEQUENCE: 477

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Leu Gly Ile Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 478
<211> LENGTH: 98
<212> TYPE: PRT
<213> ORGANISM: Homo sapiens

<400> SEQUENCE: 478

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Ile Ile Pro Ile Leu Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 479
<211> LENGTH: 6
<212> TYPE: PRT
<213> ORGANISM: Homo sapiens
<220> FEATURE:
<221> NAME/KEY: Motif in human JH6
<222> LOCATION: (4)..(4)
<223> OTHER INFORMATION: X can be any natural amino acid
<220> FEATURE:
<221> NAME/KEY: Motif in human JH6
<222> LOCATION: (6)..(6)
<223> OTHER INFORMATION: X can be any natural amino acid

<400> SEQUENCE: 479

Tyr Tyr Gly Xaa Asp Xaa
1 5

<210> SEQ ID NO 480
<211> LENGTH: 57
<212> TYPE: DNA
<213> ORGANISM: Artificial Sequence
<220> FEATURE:
<223> OTHER INFORMATION: Encodes leader sequence for antibody heavy chain

<400> SEQUENCE: 480

-continued

```
atgggctggt cctgcatcat cctgtttctg gtggccaccg ccaccggcgt gcacagc        57


<210> SEQ ID NO 481
<211> LENGTH: 19
<212> TYPE: PRT
<213> ORGANISM: Artificial Sequence
<220> FEATURE:
<223> OTHER INFORMATION: Leader sequence for antibody heavy chain

<400> SEQUENCE: 481

Met Gly Trp Ser Cys Ile Ile Leu Phe Leu Val Ala Thr Ala Thr Gly
1               5                   10                  15

Val His Ser
```

ANTIBODIES, VARIABLE DOMAINS AND CHAINS TAILORED FOR HUMAN USE

CROSS REFERENCE

This application is a divisional of U.S. application Ser. No. 13/875,892 filed May 2, 2013, the entire contents of which are hereby incorporated by reference.

FIELD OF THE INVENTION

The present invention relates to the provision of antibody therapeutics and prophylactics that are tailored specifically for human use.

The present invention provides libraries, vertebrates and cells, such as transgenic mice or rats or transgenic mouse or rat cells. Furthermore, the invention relates to methods of using the vertebrates to isolate antibodies or nucleotide sequences encoding antibodies. Antibodies, heavy chains, polypeptides, nucleotide sequences, pharmaceutical compositions and uses are also provided by the invention.

BACKGROUND

The state of the art provides non-human vertebrates (eg, mice and rats) and cells comprising transgenic immunoglobulin loci, such loci comprising human variable (V), diversity (D) and/or joining (J) segments, and optionally human constant regions. Alternatively, endogenous constant regions of the host vertebrate (eg, mouse or rat constant regions) are provided in the transgenic loci. Methods of constructing such transgenic vertebrates and use of these to generate antibodies and nucleic acids thereof following antigen immunisation are known in the art, eg, see U.S. Pat. No. 7,501,552 (Medarex), U.S. Pat. No. 5,939,598 (Abgenix), U.S. Pat. No. 6,130,364 (Abgenix), WO02/066630 (Regeneron), WO2011004192 (Genome Research Limited), WO2009076464, WO2009143472 and WO2010039900 (Ablexis), the disclosures of which are explicitly incorporated herein. Such transgenic loci in the art include varying amounts of the human V(D) J repertoire. Existing transgenic immunoglobulin loci are based on a single human DNA source. The potential diversity of human antibody variable regions in non-human vertebrates bearing such transgenic loci is thus confined.

The inventors considered that it would be desirable to tailor the genomes of these transgenic non-human vertebrates (and thus antibody and antibody chain products of these) to address the variability—and commonality—in the natural antibody gene usage of humans. The inventors wanted to do this in order to better address human use of antibody-based therapeutic and prophylactic drugs.

It would be desirable also to provide for novel and potentially expanded repertoire and diversity of human variable regions in transgenic immunoglobulin loci and non-human vertebrates harbouring these, as well as in antibodies produced following immunisation of such animals.

SUMMARY OF THE INVENTION

The present invention has been developed from extensive bioinformatics analysis of natural antibody gene segment distributions across a myriad of different human populations and across more than two thousand samples from human individuals. The inventors have undertaken this huge task to more thoroughly understand and design non-human vertebrate systems and resultant antibodies to better address human medical therapeutics as a whole, as well as to enable rational design to address specific ethnic populations of humans. Using such rational design, the inventors have constructed transgenic non-human vertebrates and isolated antibodies; antibody chains and cells expressing these in a way that yields products that utilise gene segments that have been purposely included on the basis of the human bioinformatics analysis. The examples illustrate worked experiments where the inventors isolated many cells and antibodies to this effect.

The invention also relates to synthetically-extended & ethnically-diverse superhuman immunoglobulin gene repertoires. The present invention thus provides for novel and potentially expanded synthetic immunoglobulin diversities, thus providing a pool of diversity from which human antibody therapeutic leads can be selected. This expanded pool is useful when seeking to find antibodies with desirable characteristics, such as relatively high affinity to target antigen without the need for further affinity maturation (eg, using laborious in vitro techniques such as phage or ribosome display); or improved biophysical characteristics, or to address targets and new epitopes that have previously been difficult to address with antibodies are not reached by prior antibody binding sites.

The invention also provides for diversity that is potentially biased towards variable gene usage common to members of a specific human population, which is useful for generating antibodies for treating and/or preventing diseases or conditions within such population. This ability to bias the antibody repertoire allows one to tailor antibody therapeutics with the aim of more effectively treating and/or preventing disease or medical conditions in specific human populations.

The present inventors realised the possibility of providing immunoglobulin gene segments from disparate sources in transgenic loci, in order to provide for novel and potentially-expanded antibody diversities from which antibody therapeutics (and antibody tool reagents) could be generated. This—opens up the potential of transgenic human-mouse/rat technologies to the possibility of interrogating different and possibly larger antibody sequence-spaces than has hitherto been possible.

In rationally designing transgenic antibody loci, as well as antibodies and antibody chains, the inventors also realised that a relatively long HCDR3 length (at least 20 amino acids) is often desirable to address epitopes. For example, naturally-occurring antibodies have been isolated from humans infected with infectious disease pathogens, such antibodies having a long HCDR3 length. Neutralising antibodies have been found in this respect. A long HCDR3 length would be desirable to address other antigens (eg, receptor clefts or enzyme active sites), not just limited to infectious disease pathogens, and thus the inventors realised the general desirability of the possibility of engineering transgenic loci to be able to produce long HCDR3 antibodies and heavy chains. The inventors, through laborious execution of bioinformatics on in excess of 2000 human DNA samples via the 1000 Genomes project together with rational sequence choices, identified that the inclusion of the specific human gene segment variant JH6*02 is desirable for producing long HCDR3 antibodies and chains.

Additional rational design and bioinformatics has led the inventors to realise that specific human constant region variants are conserved across many diverse human populations. The inventors realised that this opens up the possibility of making a choice to humanise antibodies, chains and variable domains by using such specific constant regions in products, rather than arbitrarily choosing the human constant region (or a synthetic version of a human constant region). This aspect of the invention also enables one to tailor antibody-based drugs to specific human ethnic populations, thereby more closely matching drug to patient (and thus disease setting) than has hitherto been performed. It can be a problem in the state of the art that antibodies are humanised with an arbitrary choice of human constant region (presumably derived from one (often unknown) ethnic population or non-naturally occurring) that does not function as well in patients of a different human ethnic population. This is important, since the constant region has the major role in providing antibody effector functions, eg, for antibody recycling, cellular and complement recruitment and for cell killing.

To this end, in a first configuration of the invention, there is provided

First Configuration

A non-human vertebrate or vertebrate cell (optionally an ES cell or antibody-producing cell) comprising a genome having a superhuman immunoglobulin heavy chain human VH and/or D and/or J gene repertoire.

A non-human vertebrate or vertebrate cell (optionally an ES cell or antibody-producing cell) comprising a genome having a superhuman immunoglobulin light chain human VL gene repertoire; optionally wherein the vertebrate or cell is according to the first configuration.

A non-human vertebrate or vertebrate cell (optionally an ES cell or antibody-producing cell) whose genome comprises a transgenic immunoglobulin locus (eg, a heavy chain locus or a light chain locus), said locus comprising immunoglobulin gene segments according to the first and second human immunoglobulin gene segments (optionally V segments) as mentioned below operably connected upstream of an immunoglobulin constant region; optionally wherein the genome is homozygous for said transgenic immunoglobulin locus;

optionally wherein the immunoglobulin locus comprises more than the natural human complement of functional V gene segments; and/or optionally wherein the immunoglobulin locus comprises more than the natural human complement of functional gene segments; and/or optionally wherein the immunoglobulin locus comprises more than the natural human complement of functional J gene segments.

A transgenic non-human vertebrate (eg, a mouse or rat) or vertebrate cell (optionally an ES cell or antibody-producing cell) whose genome comprises a transgenic immunoglobulin locus comprising a plurality of human immunoglobulin gene segments operably connected upstream of a non-human vertebrate constant region for the production of a repertoire of chimaeric antibodies, or chimaeric light or heavy chains, having a non-human vertebrate constant region and a human variable region; wherein the transgenic locus comprises one or more human immunoglobulin V gene segments, one or more human J gene segments and optionally one or more human D gene segments, a first (optionally a V segment) of said gene segments and a second (optionally a V segment) of said gene segments being different and derived from the genomes of first and second human individuals respectively, wherein the individuals are different; and optionally not related; optionally wherein the immunoglobulin locus comprises more than the natural human complement of functional V gene segments; and/or optionally wherein the immunoglobulin locus comprises more than the natural human complement of functional D gene segments; and/or optionally wherein the immunoglobulin locus comprises more than the natural human complement of functional J gene segments.

A transgenic non-human vertebrate (eg, a mouse or rat) or vertebrate cell (optionally an ES cell or antibody-producing cell) whose genome comprises first and second transgenic immunoglobulin loci, each locus comprising a plurality of human immunoglobulin gene segments operably connected upstream of a non-human vertebrate constant region for the production of a repertoire of chimaeric antibodies, or chimaeric light or heavy chains, having a non-human vertebrate constant region and a human variable region;

wherein (i) the first transgenic locus comprises one or more human immunoglobulin V gene segments, one or more human J gene segments and optionally one or more human D gene segments, (ii) the second transgenic locus comprises one or more human immunoglobulin V gene segments, one or more human J gene segments and optionally one or more human D gene segments; and (iii) wherein a first (optionally a V) gene segment of said first locus and a second (optionally a V) gene segment of said second gene locus are different and derived from the genomes of first and second human individuals respectively, wherein the individuals are different; and optionally not related;

optionally wherein the first and second loci are on different chromosomes (optionally chromosomes with the same chromosome number) in said genome;

optionally wherein each immunoglobulin locus comprises more than the natural human complement of functional V gene segments; and/or optionally wherein each immunoglobulin locus comprises more than the natural human complement of functional D gene segments; and/or optionally wherein each immunoglobulin locus comprises more than the natural human complement of functional J gene segments.

A method of constructing a cell (eg, an ES cell) according to the invention, the method comprising (a) identifying functional V and J (and optionally D) gene segments of the genome sequence of a (or said) first human individual;

(b) identifying one or more functional V and/or D and/or J gene segments of the genome sequence of a (or said) second human individual, wherein these additional gene segments are not found in the genome sequence of the first individual;

(c) and constructing a transgenic immunoglobulin locus in the cell, wherein the gene segments of (a) and (b) are provided in the locus operably connected upstream of a constant region.

In one embodiment, the gene segment(s) in step (b) are identified from an immunoglobulin gene database selected from the 1000 Genomes, Ensembl, Genbank and IMGT databases.

Throughout this text, Genbank is a reference to Genbank release number 185.0 or 191.0; the 1000 Genomes database is Phase 1, release v3, 16 Mar. 2012; the Ensembl database is assembly GRCh37.p8 (Oct. 4, 2012); the IMGT database is available at www.imgt.org.

In one embodiment, the first and second human individuals are members of first and second ethnic populations respectively, wherein the populations are different, optionally wherein the human immunoglobulin gene segment derived from the genome sequence of the second individual is low-frequency (optionally rare) within the second ethnic population.

This configuration of the invention also provides a method of making a transgenic non-human vertebrate (eg, a mouse or rat), the method comprising (a) constructing an ES cell (eg, a mouse C57BL/6N, C57BL/6J, 129S5 or 129Sv strain ES cell) by carrying out the method above;

(b) injecting the ES cell into a donor non-human vertebrate blastocyst (eg, a mouse C57BL/6N, C57BL/6J, 129S5 or 129Sv strain blastocyst);

(c) implanting the blastocyst into a foster non-human vertebrate mother (eg, a C57BL/6N, C57BL/6J, 129S5 or 129Sv strain mouse); and (d) obtaining a child from said mother, wherein the child genome comprises a transgenic immunoglobulin locus.

In one embodiment, the invention provides a method of isolating an antibody that binds a predetermined antigen (eg, a bacterial or viral pathogen antigen), the method comprising immunising a non-human vertebrate according to the invention.

Second Configuration

A library of antibody-producing transgenic cells whose genomes collectively encode a repertoire of antibodies, wherein (a) a first transgenic cell expresses a first antibody having a chain encoded by a first immunoglobulin gene, the gene comprising a first variable domain nucleotide sequence produced following recombination of a first human unrearranged immunoglobulin gene segment;

(b) a second transgenic cell expresses a second antibody having a chain encoded by a second immunoglobulin gene, the second gene comprising a second variable domain nucleotide sequence produced following recombination of a second human unrearranged immunoglobulin gene segment, the first and second antibodies being non-identical;

(c) the first and second gene segments are different and derived from the genome sequences of first and second human individuals respectively, wherein the individuals are different; and optionally not related;

(d) wherein the cells are non-human vertebrate (eg, mouse or rat) cells.

In one embodiment, the first and second human individuals are members of first and second ethnic populations respectively, wherein the populations are different; optionally wherein the ethnic populations are selected from those identified in the 1000 Genomes database.

In another embodiment, the second human immunoglobulin gene segment is a polymorphic variant of the first human immunoglobulin gene segment; optionally wherein the second gene segment is selected from the group consisting of a gene segment in any of Tables 1 to 7 and 9 to 14 below (eg, selected from Table 13 or Table 14), eg, the second gene segment is a polymorphic variant of VH1-69.

Third Configuration an Isolated Antibody Having (a) a heavy chain encoded by a nucleotide sequence produced following recombination in a transgenic non-human vertebrate cell of an unrearranged human immunoglobulin V gene segment with a human D and human J segment, optionally with affinity maturation in said cell, wherein one of the gene segments is derived from the genome of an individual from a first human ethnic population; and the other two gene segments are derived from the genome of an individual from a second, different, human ethnic population, and wherein the antibody comprises heavy chain constant regions of said non-human vertebrate (eg, rodent, mouse or rat heavy chain constant regions); and/or (b) a light chain encoded by a nucleotide sequence produced following recombination in a transgenic non-human vertebrate cell of an unrearranged human immunoglobulin V gene segment with a human J segment, optionally with affinity maturation in said cell, wherein one of the gene segments is derived from the genome of an individual from a first human ethnic population (optionally the same as the first population in (a)); and the other gene segment is derived from the genome of an individual from a second, different, human ethnic population (optionally the same as the second population in (a)), and wherein the antibody comprises light chain constant regions of said non-human vertebrate (eg, rodent; mouse or rat heavy light constant regions);

(c) Optionally wherein each variable domain of the antibody is a human variable domain.

(d) Optionally wherein the heavy chain constant regions are gamma-type constant regions.

The invention also provides an isolated nucleotide sequence encoding the antibody, optionally wherein the sequence is provided in an antibody expression vector, optionally in a host cell.

The invention also provides a method of producing a human antibody, the method comprising replacing the non-human vertebrate constant regions of the antibody of the third configuration with human antibody constant regions.

The invention also provides a pharmaceutical composition comprising an antibody according to the third configuration, or an antibody produced according to the method above and a diluent, excipient or carrier; optionally wherein the composition is provided in a container connected to an IV needle or syringe or in an IV bag.

The invention also provides an antibody-producing cell that expresses the second antibody recited in any one of the configurations.

In an alternative configuration, the invention contemplates the combination of nucleotide sequences of first and second immunoglobulin gene segments (eg, two or more polymorphic variants of a particular human germline VH or VL gene segment) to provide a synthetic gene segment. Such synthetic gene segment is used, in one embodiment, to build a transgenic immunoglobulin locus, wherein the synthetic gene segment is provided in combination with one or more human variable and J regions (and optionally one or more human D regions) operably connected upstream of a constant region. When provided in the genome of a non-human vertebrate or cell (eg, mouse or rat cell, eg, ES cell), the invention provides for superhuman gene segment diversity. The sequences to be combined can be selected from gene segments that have been observed to be commonly used in human antibodies raised against a particular antigen (eg, a flu antigen, such as haemaglutinin). By combining the sequences, the synthetic gene segment may recombine in vivo to produce an antibody that is well suited to the treatment and/or prevention of a disease or condition (eg, influenza) mediated by said antigen.

Fourth Configuration

A non-human vertebrate (optionally a mouse or a rat) or vertebrate cell whose genome comprises an immunoglobulin heavy chain locus comprising human gene segment JH6*02, one or more VH gene segments and one or more D gene segments upstream of a constant region; wherein the gene segments in the heavy chain locus are operably linked to the constant region thereof so that the mouse is capable of producing an antibody heavy chain produced by recombination of the human JH6*02 with a D segment and a VH segment.

A non-human vertebrate cell (optionally a mouse cell or a rat cell) whose genome comprises an immunoglobulin heavy chain locus comprising human gene segment JH6*02, one or more VH gene segments and one or more D gene segments upstream of a constant region; wherein the gene segments in the heavy chain locus are operably linked to the constant region thereof for producing (eg, in a subsequent progeny cell) an antibody heavy chain produced by recombination of the human JH6*02 with a D segment and a VH segment.

A heavy chain (eg, comprised by an antibody) isolated from a vertebrate of the invention wherein the heavy chain comprises a HCDR3 of at least 20 amino acids.

A method for producing a heavy chain, VH domain or an antibody specific to a target antigen, the method comprising immunizing a non-human vertebrate according to the invention with the antigen and isolating the heavy chain, VH domain or an antibody specific to a target antigen or a cell producing the heavy chain, VH domain or an antibody, wherein the heavy chain, VH domain or an antibody comprises a HCDR3 that is derived from the recombination of human JH6*02 with a VH gene segment and a D gene segment.

A heavy chain, VH domain or an antibody produced by the method.

A B-cell or hybridoma expressing a heavy chain VH domain that is identical to the VH domain of the heavy chain.

A nucleic acid encoding the VH domain of the heavy chain of claim 22, 23 or 28, or encoding the heavy chain.

A vector (eg, a CHO cell or HEK293 cell vector) comprising the nucleic acid; optionally wherein the vector is in a host cell (eg, a CHO cell or HEK293 cell).

A pharmaceutical composition comprising the antibody, heavy chain or VH domain (eg, comprised by an antibody), together with a pharmaceutically-acceptable excipient, diluent or a medicament (eg, a further antigen-specific variable domain, heavy chain or antibody).

The antibody, heavy chain or VH domain (eg, comprised by an antibody) as above for use in medicine.

The use of an antibody, heavy chain or VH domain (eg, comprised by an antibody) as above in the manufacture of a medicament for treating and/or preventing a medical condition in a human.

Fifth Configuration

A method of producing an antibody heavy chain, the method comprising (a) providing an antigen-specific heavy chain variable domain; and (b) combining the variable domain with a human heavy chain constant region to produce an antibody heavy chain comprising (in N- to C-terminal direction) the variable domain and the constant region;

wherein the human heavy chain constant region is an IGHG1ref, IGHG2ref, IGHG2a, IGHG3ref, IGHG3a, IGHG3b, IGHG4ref or IGHG4a constant region.

An antibody comprising a human heavy chain, the heavy chain comprising a variable domain that is specific for an antigen and a constant region that is an IGHG1ref, IGHG2ref, IGHG2a, IGHG3ref, IGHG3a, IGHG3b, IGHG4ref or IGHG4a constant region. Optionally, the variable domain comprises mouse-pattern AID somatic mutations.

A polypeptide comprising (in N- to C-terminal direction) a leader sequence; a human variable domain that is specific for an antigen and a human constant region that is an IGHG1ref, IGHG2ref, IGHG2a, IGHG3ref, IGHG3a, IGHG3b, IGHG4ref or IGHG4a constant region wherein (i) the leader sequence is not the native human variable domain leader sequence; and/or (ii) the variable domain comprises mouse AID-pattern somatic mutations and/or mouse Terminal deoxynucleotidyl transferase (TdT)-pattern junctional mutations.

A nucleotide sequence encoding (in 5' to 3' direction) a leader sequence and a human antibody heavy chain, the heavy chain comprising a variable domain that is specific for an antigen and a constant region that is an IGHG1ref, IGHG2ref, IGHG2a, IGHG3ref, IGHG3a, IGHG3b, IGHG4ref or IGHG4a constant region; and the leader sequence being operable for expression of the heavy chain and wherein the leader sequence is not the native human variable domain leader sequence.

A nucleotide sequence encoding (in 5' to 3' direction) a promoter and a human antibody heavy chain, the heavy chain comprising a variable domain that is specific for an antigen and a constant region that is an IGHG1ref; IGHG2ref, IGHG2a, IGHG3ref, IGHG3a, IGHG3b, IGHG4ref or IGHG4a constant region; and the promoter being operable for expression of the heavy chain and wherein the promoter is not the native human promoter.

A vector (eg, a CHO cell or HEK293 cell vector) comprising a IGHG1ref, IGHG2ref, IGHG2a, IGHG3ref, IGHG3a, IGHG3b, IGHG4ref or IGHG4a constant region nucleotide sequence that is 3' of a cloning site for the insertion of a human antibody heavy chain variable domain nucleotide sequence, such that upon insertion of such a variable domain sequence the vector comprises (in 5' to 3' direction) a promoter, a leader sequence, the variable domain sequence and the constant region sequence so that the vector is capable of expressing a human antibody heavy chain when present in a host cell.

Sixth Configuration

A non-human vertebrate (eg, a mouse or rat) or a non-human vertebrate cell (eg, an ES cell or a B-cell) having a genome comprising at least 3 human variable region gene segments of the same type (eg, at least 3 human VH6-1 gene segments, at least 3 human JH6 gene segments, at least 3 human VK1-39 gene segments, at least 3 human D2-2 gene segments or at least 3 human JK1 gene segments), wherein at least two of the human gene segments are variants that are not identical to each other.

A non-human vertebrate (eg, a mouse or rat) or a non-human vertebrate cell (eg, an ES cell or a B-cell) having a genome comprising at least 2 different non-endogenous variable region gene segments of the same type (eg, at least 2 human VH6-1 gene segments, at least 3 human JH6 gene segments, at least 2 human VK1-39 gene segments, at least 2 human D2-2 gene segments or at least 2 human JK1 gene segments) cis at the same Ig locus.

A non-human vertebrate (eg, a mouse or rat) or a non-human vertebrate cell (eg, an ES cell or a B-cell) having a genome comprising at least 2 different human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments) trans at the same Ig locus; and optionally a third human gene segment of the same type, wherein the third gene segment is cis with one of said 2 different gene segments.

A population of non-human vertebrates (eg, mice or rats) comprising a repertoire of human variable region gene segments; wherein the plurality comprises at least 2 human variable region gene segments of the same type (eg, at least 2 human VH6-1 gene segments, at least 2 human JH6 gene segments, at least 2 human VK1-39 gene segments, at feast 2 human D2-2 gene segments or at least 2 human JK1 gene segments), a first of said different gene segments is provided in the genome of a first vertebrate of the population, and a second of said different gene segments being provided in the genome of a second vertebrate of the population, wherein the genome of the first vertebrate does not comprise the second gene segment.

A non-human vertebrate (eg, a mouse or rat) or a non-human vertebrate cell (eg, an ES cell or a B-cell) having a genome comprising at least 2 different non-endogenous variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein the gene segments are derived from the genome sequence of different human individuals that are not genetically related over at least 3 generations.

A method of enhancing the human immunoglobulin gene diversity of a non-human vertebrate (eg, a mouse or rat), the method comprising providing the vertebrate with a genome comprising at least 3 human variable region gene segments of the same type (eg, at least 3 human VH6-1 gene segments, at least 3 human JH6 gene segments, at least 3 human VK1-39 gene segments, at least 3 human D2-2 gene segments or at least 3 human JK1 gene segments), wherein at least two of the human gene segments are variants that are not identical to each other.

A method of enhancing the immunoglobulin gene diversity of a non-human vertebrate (eg, a mouse or rat), the method comprising providing the vertebrate with a genome comprising at least 2 different non-endogenous variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments) cis at the same Ig locus.

A method of enhancing the immunoglobulin gene diversity of a non-human vertebrate (eg, a mouse or rat), the method comprising providing the vertebrate with a genome comprising at least 2 different human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments) trans at the same Ig locus; and optionally a third human gene segment of the same type, wherein the third gene segment is cis with one of said 2 different gene segments.

A method of providing an enhanced human immunoglobulin variable region gene segment repertoire, the method comprising providing a population of non-human vertebrates (eg, a mouse or rat) comprising a repertoire of human variable region gene segments, wherein the method comprises providing at least 2 different human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein a first of said different gene segments is provided in the genome of a first vertebrate of the population, and a second of said different gene segments is provided in the genome of a second vertebrate of the population, wherein the genome of the first vertebrate does not comprise the second gene segment.

A method of enhancing the human immunoglobulin gene diversity of a non-human vertebrate (eg, a mouse or rat), the method comprising providing the vertebrate with a genome comprising at least 2 different non-endogenous variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein the gene segments are derived from the genome sequence of different human individuals that are not genetically related over at least 3 generations.

A method of enhancing the human immunoglobulin gene diversity of a non-human vertebrate (eg, a mouse or rat), the method comprising providing the vertebrate with a genome comprising at least 2 human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein the gene segments are derived from the genome sequence of different human individuals that are not genetically related over at least 3 generations; optionally wherein at least 2 or 3 of said different gene segments are provided at the same Ig locus in said genome.

A non-human vertebrate (eg, a mouse or rat) or a non-human vertebrate cell (eg, an ES cell or a B-cell) having a genome comprising first and second human Ig locus gene segments of the same type (eg, first and second human JH6 gene segments; or first and second IgG2 gene segments; or first and second human Jλ7 gene segments), wherein the first gene segment is a gene segment selected from any one of Tables 1 and 9 to 14 (eg; selected from Table 13 or Table 14) (eg; IGHJ6-a) and the second gene segment is the corresponding reference sequence.

A population of non-human vertebrates (eg, mice or rats) comprising first and second human Ig locus gene segments of the same type (eg, first and second human JH6 gene segments; or first and second IgG2 gene segments; or first and second human Jλ7 gene segments), wherein the first gene segment is a gene segment selected from any one of Tables 1 and 9 to 14 (eg, selected from Table 13 or Table 14) (eg, IGHJ6-a) and the second gene segment is the corresponding reference sequence, wherein the first gene segment is provided in the genome of a first vertebrate of the population; and the second gene segment is provided in the genome of a second vertebrate of the population.

A method of enhancing the human immunoglobulin gene diversity of a non-human vertebrate (eg, a mouse or rat), the method comprising providing the vertebrate with a genome comprising first and second human Ig locus gene segments of the same type (eg, first and second human JH6 gene segments; or first and second IgG2 gene segments; or first and second human Jλ7 gene segments), wherein the first gene segment is a gene segment selected from any one of Tables 1 and 9 to 14 (eg, selected from Table 13 or Table 14) (eg, IGHJ6-a) and the second gene segment is the corresponding reference sequence.

In one aspect of this configuration, the invention relates to human D gene segment variants as described further below.

In one aspect of this configuration, the invention relates to human V gene segment variants as described further below.

In one aspect of this configuration, the invention relates to human J gene segment variants as described further below.

BRIEF DESCRIPTION OF THE FIGURES

FIGS. 5A-5D: Alignment of 13 IGHV1-69 variants showing the variable (V) coding region only. Nucleotides that differ from VH1-69 variant *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

SEQ ID NO: 456 and SEQ ID NO: 18 denote the amino acid sequence and nucleic acid sequence, respectively, displayed for L22582, IGHV1-69*01; hv1051.

SEQ ID NO: 469 and SEQ ID NO: 457 denote the amino acid sequence and nucleic acid sequence, respectively, displayed for Z27506, IGHV1-69*02, yIGH6(YAC7).

SEQ ID NO: 470 and SEQ ID NO: 458 denote the amino acid sequence and nucleic acid sequence, respectively, displayed for X92340, IGHV1-69*03, 57GTA8.

SEQ ID NO: 471 and SEQ ID NO: 459 denote the amino acid sequence and nucleic acid sequence, respectively, displayed for M83132, IGHV1-69*04, hv1263.

SEQ ID NO: 472 and SEQ ID NO: 460 denote the amino acid sequence and nucleic acid sequence, respectively, displayed for K67905, IGHV1-69*05, RR.VH1.2.

SEQ ID NO: 473 and SEQ ID NO: 461 denote the amino acid sequence and nucleic acid sequence, respectively, displayed for L22583, IGHV1-69*06, hv1051K.

SEQ ID NO: 474 and SEQ ID NO: 462 denote the amino acid sequence and nucleic acid sequence, respectively, displayed for 229978, IGHV1-69*07, DA-2.

SEQ ID NO: 475 and SEQ ID NO: 463 denote the amino acid sequence and nucleic acid sequence, respectively, displayed for Z14309; IGHV1-69*08.

SEQ ID NO: 476 and SEQ ID NO: 464 denote the amino acid sequence and nucleic acid sequence, respectively, displayed for Z14307, IGHV1-69*09. SEQ ID NO: 477 and SEQ ID NO: 465 denote the amino acid sequence and nucleic acid sequence, respectively, displayed for Z14300, IGHV1-69*10.

SEQ ID NO: 478 and SEQ ID NO: 466 denote the amino acid sequence and nucleic acid sequence, respectively, displayed for Z14296, IGHV1-69*11.

SEQ ID NO: 467 denotes the nucleic acid sequence displayed for Z14301, IGHV1-69*12.

SEQ ID NO: 468 denotes the nucleic acid sequence displayed for 214214, IGHV1-69*13.

Figure 6:
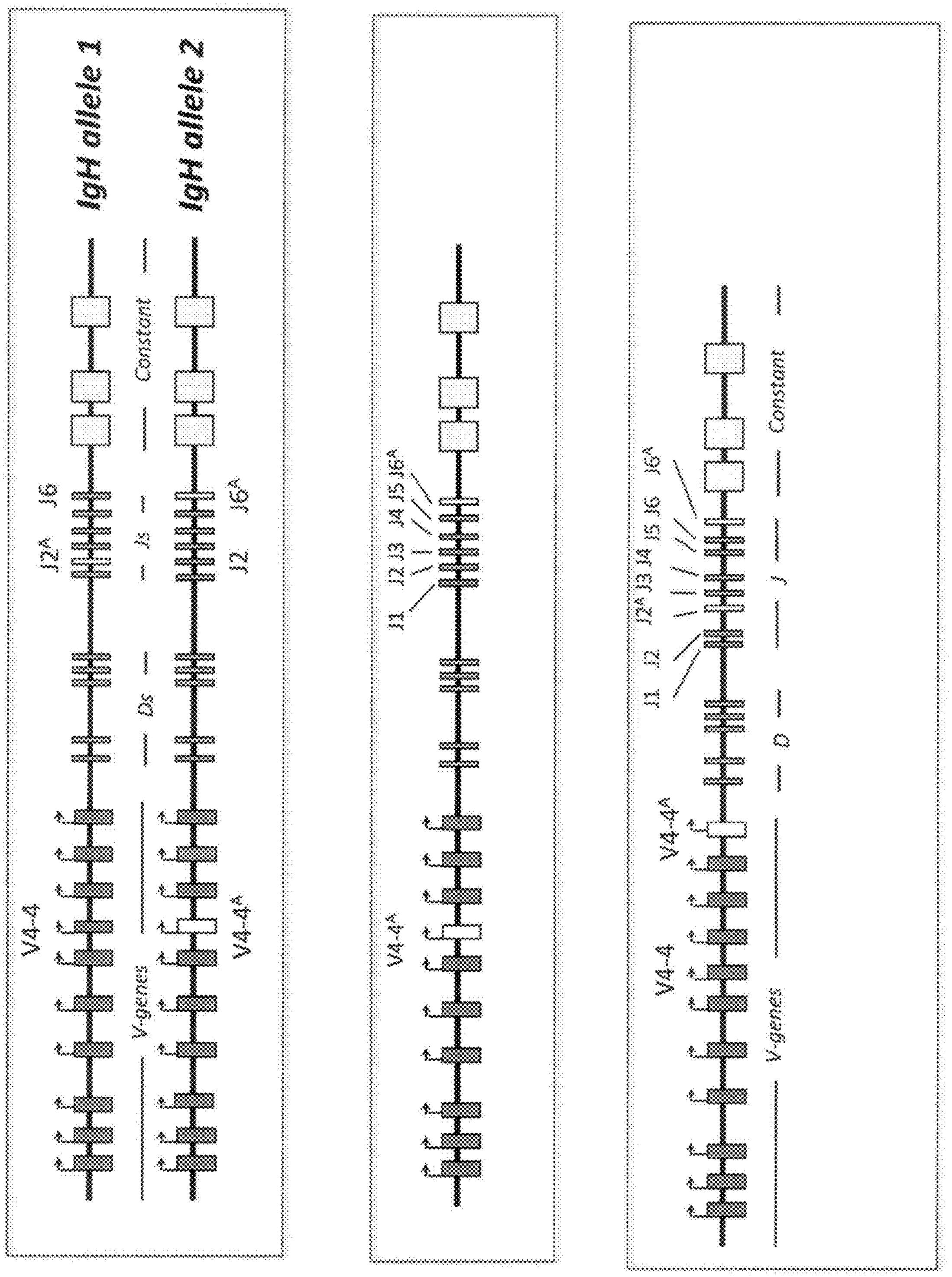

FIG. 6 is a schematic illustrating gene segment diversity and the effect of including variant variants in cis according to the invention:—

(a) Situation in a normal person: Recombination on the same chromosome limits combinations of variants, for instance the antibody gene V4-4 can only be recombined within variant 1 to form for instance for instance V4-4-D-J6 or V4-4-D-J2A. Similarly the variant V4-4A can't be recombined with either J6 or J2A from variant 1 and can only be joined with J-genes from variant 2 to form V4-4A-D-J6A and V4-4A-D-J2. V4-4-J2/J6 complexity=4.

(b) Situation in a transgenic mouse: Only one variant s provided so the genome is limited. V4-4-J6/J2 complexity=2.

(c) Supra mouse of the invention: The variants are added in cis and thus can be recombined in every combination, expanding the repertoire. For instance V4-4 can be combined with J6A, J6, J2A or J2 and similarly V4-4A can be recombined with these same J-genes. The V4-4-J6/J2 complexity=8, which in this simple example is double that of a person and 4× that of a mouse with a single variant.

FIG. 7: Alignment of human JH6*02 variants. Nucleotides that differ from JH6*01 are indicated at the appropriate position whereas identical nucleotides are marked with a dash. Where nucleotide changes result in amino acid differences, the encoded amino acid is shown above. Accession numbers (eg, J00256) are shown to the left of the IMGT variant name. SEQ ID NO: 236 and SEQ ID NO: 99 denote the amino acid sequence and nucleic acid sequence, respectively, displayed for J00256, IGHJ6*01. SEQ ID NO: 446 is the nucleic acid sequence displayed for X86355, IGHJ6*02; for X86357, IGHJ6*02; and for X86358, IGHJ6*02. SEQ ID NO: 447 is the nucleic acid sequence displayed for M63031, IGHJ6*02; for X97051, IGHJ6*02; and for M25625, IGHJ6*02. SEQ ID NO: 448 and SEQ ID NO: 449 denote the amino acid sequence and nucleic acid sequence, respectively, displayed for X86356, IGHJ6*03. SEQ ID NO: 450 and SEQ ID NO: 451 denote the amino acid sequence and nucleic acid sequence, respectively, displayed for X86359, IGHJ6*03. SEQ ID NO: 552 and SEQ ID NO: 553 denote the amino acid sequence and nucleic acid sequence, respectively, displayed for M63030, IGHJ6*03, SEQ ID NO: 454 and SEQ ID NO: 455 denote the amino acid sequence and nucleic acid sequence, respectively, displayed for AJ879487, IGHJ6*04.—

Figure 10:
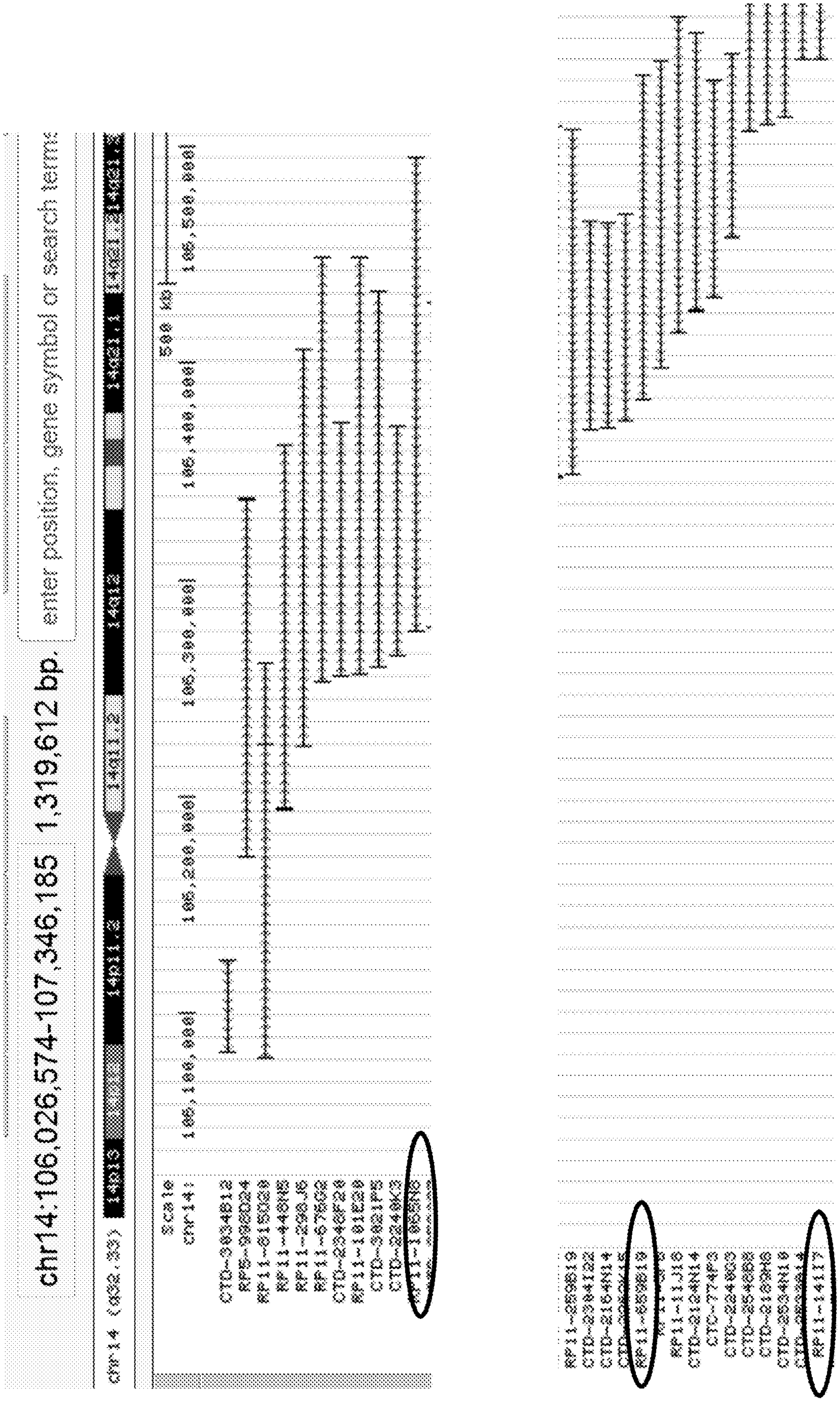

FIG. 8: Alignment of JH sequences from various species. SEQ ID NO: 432 and SEQ ID NO: 433 denote the amino acid sequence and nucleic acid sequence, respectively, displayed for Rabbit JH6. SEQ ID NO: 434 and SEQ ID NO: 435 denote the amino acid sequence and nucleic acid sequence, respectively, displayed for Sheep JH6. SEQ ID NO: 436 and SEQ ID NO: 437 denote the amino acid sequence and nucleic acid sequence, respectively, displayed for Bovine JH6. SEQ ID NO: 438 and SEQ ID NO: 439 denote the amino acid sequence and nucleic acid sequence, respectively, displayed for Dog JH6. SEQ ID NO: 440 and SEQ ID NO: 441 denote the amino acid sequence and nucleic acid sequence, respectively, displayed for Human JH6, FIG. 9: Codon Table FIG. 10: BAC database extract

BRIEF DESCRIPTION OF THE TABLES

Table 1: Human IgH V Polymorphic Variants

Table 2: Human IgH D Polymorphic Variants

Table 3: Human IgH J Polymorphic Variants

Table 4: Human Ig Vk Polymorphic Variants

Table 5: Human Ig VA Polymorphic Variants

Table 6: Human IgH Jλ Polymorphic Variants

Table 7: Human IgH Jλ Polymorphic Variants

Table 8: 1000 Genomes Project Human Populations

Table 9: Immunoglobulin Gene Usage in Human Antibody Responses to Infectious Disease Pathogens Table 10A: Human IgH JH5 Variant Occurrences Table 10B: Non-Synonymous Human IgH JH5 Variants Table 11A: Human IgH JH6 Variant Occurrences Table 11B: Non-Synonymous Human IgH JH6 Variants Table 12A: Human IgH JH2 Variant Occurrences Table 12B: Non-Synonymous Human IgH JH2 Variants Table 13: Variant Frequency Analyses & Human Population Distributions Table 14: Frequent Human Variant Distributions Table 15: Human Gene Segment Usage: Heavy Chain Repertoires From Naive Non-Human Vertebrates Table 16: Human Gene Segment Usage: Heavy Chain Repertoires From Immunised Non-Human Vertebrates Table 17: Human Gene Segment Usage: Heavy Chain Repertoires From Antigen-Specific Hybridomas Table 18: Sequence Correlation Table Table 19: Summary Of Function Correlated With Human Gamma Constant Region Sub-Type Table 20: Gene Segments Prevalent In Few Human Populations Table 21: Genomic and sequence information

DETAILED DESCRIPTION OF THE INVENTION

A suitable source of JH6*02 and other human DNA sequences for use in the invention will be readily apparent to the skilled person. For example, it is possible to collect a DNA sample from a consenting human donor (eg, a cheek swab sample as per the Example herein) from which can be obtained suitable DNA sequences for use in constructing a locus of the invention. Other sources of human DNA are commercially available, as will be known to the skilled person. Alternatively, the skilled person is able to construct gene segment sequence by referring to one or more databases of human Ig gene segment sequences disclosed herein.

An example source for human V, D and J gene segments according to the invention are Bacterial Artificial Chromosomes (RPCI-11 BACs) obtained from Roswell Park Cancer Institute (RPCI)/Invitrogen. See http://bacpac.chori.org/hmale11.htm, which describes the BACs as follows:—

"RPCI-11 Human Male BAC Library

The RPCI-11 Human Male BAC Library (Osoegawa et al., 2001) was constructed using improved cloning techniques (Osoegawa et al., 1998) developed by Kazutoyo Osoegawa. The library was generated by Kazutoyo Osoegawa. Construction was funded by a grant from the National Human Genome Research Institute (NHGRI, NIH) (#1R01RG01165-03). This library was generated according to the new NHGRI/DOE "Guidance on Human Subjects in Large-Scale DNA Sequencing, "Male blood was obtained via a double-blind selection protocol. Male blood DNA was isolated from one randomly chosen donor (out of 10 male donors)".

Osoegawa K, Mammoser A G, Wu C, Frengen E, Zeng C, Catanese J J, de Jong P J; Genome Res. 2001 March; 11(3):483-96; "A bacterial artificial chromosome library for sequencing the complete human genome";

Osoegawa, K., Woon, P. Y., Zhao, B., Frengen, E., Tateno, M., Catanese, J. J, and de Jong, P. J. (1998); "An Improved Approach for Construction of Bacterial Artificial Chromosome Libraries"; Genomics 52, 1-8.

Superhuman immunoglobulin Gene Repertoires

The invention relates to synthetically-extended & ethnically-diverse superhuman immunoglobulin gene repertoires. The human immunoglobulin repertoires are beyond those found in nature (ie, "Superhuman"), for example, they are more diverse than a natural human repertoire or they comprise combinations of human immunoglobulin gene segments from disparate sources in a way that is non-natural. Thus, the repertoires of the invention are "superhuman" immunoglobulin repertoires; and the invention relates to the application of these in transgenic cells and non-human vertebrates for utility in producing chimaeric antibodies (with the possibility of converting these into fully-human, isolated antibodies using recombinant DNA technology). The present invention thus provides for novel and potentially expanded synthetic immunoglobulin diversities, which provides for a pool of diversity from which antibody therapeutic leads (antibody therapeutics and antibody tool reagents) can be selected. This opens up the potential of transgenic human-mouse/rat technologies to the possibility of interrogating different and possibly larger antibody sequence-spaces than has hitherto been possible. To this end, in one embodiment, the invention provides a SUPERHUMAN MOUSE™ (aka SUPRA-MOUSE™) and a SUPERHUMAN RAT™ (aka SUPRA-RAT™)

In developing this thinking, the present inventors have realised the possibility of mining the huge genetics resources now available to the skilled person thanks to efforts such as the HapMap Project, 1000 Genomes Project and sundry other immunoglobulin gene databases (see below for more details). Thus, in some embodiments, the inventors realised the application of these genome sequencing developments in the present invention to generate synthetically-produced and ethnically-diverse artificial immunoglobulin gene repertoires. In one aspect, the inventors realised that such repertoires are useful for the production of antibodies having improved affinity and/or biophysical characteristics, and/or wherein the range of epitope specificities produced by means of such repertoire is novel, provides for antibodies to epitopes that have hitherto been intractable by prior transgenic immunoglobulin loci or difficult to address.

The present invention provides libraries, vertebrates and cells, such as transgenic mice or rats or transgenic mouse or rat cells. Furthermore, the invention relates to methods of using the vertebrates to isolate antibodies or nucleotide sequences encoding antibodies. Antibodies, nucleotide sequences, pharmaceutical compositions and uses are also provided by the invention.

Variation Analysis

The present inventors have realized methods and antibody loci designs that harness the power of genetic variation analysis. The reference human genome provides a foundation for experimental work and genetic analysis of human samples. The reference human is a compilation of the genomes from a small number of individuals and for any one segment of the genome a high quality single reference genome for one of the two chromosomes is available. Because the reference genome was assembled from a series of very large insert clones, the identity of these clones is known. Accordingly, experimental work with human genomic DNA is usually conducted on the clones from which the reference sequence was derived.

Individual humans differ in their sequence and recently several individuals have had their genomes sequenced, for instance James Watson and Craig Venter. Comparison of the genome sequence of these individuals has revealed differences between their sequences and the reference genome in both coding and non-coding parts of the genome, approximately 1 in 1000 bases are different. Some variants will be significant and contribute to differences between individuals. In extreme cases these will result in genetic disease. Variation can be implicated in differing responses to drugs administered to human patients, eg, yielding an undesirable lowering of patient response to treatment.

The 1000-Genomes Project has the objective of identifying the most frequent variations in the human genome. This public domain project involved sequencing the genomes of more than 1000 individuals from diverse ethnic groups, comparing these sequences to the reference and assembling a catalogue of variants. This has enabled the annotation of variants in coding regions, but because this sequence wasn't derived from large clones of DNA, the analysis of the sequence from diploid individuals can't discriminate the distribution of the variation between the maternal and paternally inherited chromosomes. Where more than one variant is identified in a protein coding gene, it is not possible to illuminate the distribution of the pattern of variants in each version of the protein. For example, if two variants are detected in different positions of the same protein in an individual, this could have resulted from one copy with two variants and none in the other or each copy could have just one variant. To illuminate the sequence of real proteins, the 1000-Genome Project has sequenced mother-father-child trios. This allows one to "phase" the sequence variants, in other words identify blocks of sequence that are inherited from one or other parent and deconvolute the variants.

To further understand the variation within the 1000-genome set a tool has been developed that can identify the significant variants (defined as non-synonymous amino acid changes) from a region of DNA from the phased data in the 1000-genome data set. This tool has been made available online www at 0.1000genomes.org/variation-pattern-finder. This tool allows an investigator to download non-synonymous variation delimited between specific coordinates. The downloaded files are configured as individual genotypes, but the data is phased so the haplotype information and the frequencies of specific haplotypes in different populations can be extracted.

The inventors' analysis of the 1000-genome data for the individual human coding segments of the C, V D and J genes from the heavy and light chains reveals that there is significant variation in these segments. Individuals will usually have two different heavy chain alleles and also different light chain alleles at both kappa and lambda loci. The repertoire of antibodies that can be generated from each allele will be different. This variation will contribute to a better or differing immune response to certain antigens.

Humanized mice that have hitherto been generated with immunoglobulin heavy and light chain loci contain just one type of immunoglobulin locus. Even if these mice contain a full human heavy chain locus, the variation will be less than contained in a typical human because only one set of C, V, D and J genes are available, while a typical human would have two sets.

The inventors have devised ways to improve on this limitation when constructing transgenic non-human vertebrates and cells for human antibody and variable region production in vivo.

Mice can be generated with two different loci, each engineered to have a different repertoire of V, D and J segments. This could be in a single mouse or two or more separate mouse strains and would be analogous to or beyond the repertoire found in a normal human. The engineering of such a mouse would go beyond the repertoire described in humanized mice to date which only have one set of alleles.

However, the inventors also realized that this also has limitations, because the different loci would not normally interact to shuffle V, D and J variants between loci. This same limitation is also inherent in a human, thus this system does not utilize the advantage of recombining variants in all combinations.

To go beyond the normal repertoire in humans and take advantage of combinations of C, V, D and J variants the inventors decided, in one embodiment, to provide these on the same chromosome in cis. See FIG. 6. These loci would be characterized by having more than the normal number of J, D or V genes. For example n=6 for the J genes, but including one J6 variant and one J2 variant would increase this to n=8. This could be combined with additional variants for the D and V genes, for example. By detailed analysis of the 1000-Genomes database, the inventors have devised a collection of candidate polymorphic human variant gene segments, eg, JH gene segments (eg, see the examples), that can be built into the design of transgenic heavy and light chain loci in mice for expressing increasingly diverse and new, synthetic repertoires of human variable regions. Moreover, by utilizing naturally-occurring human variant gene segments, as per embodiments of the invention, this addresses compatibility with human patients since the inventors analysis has drawn out candidate variants that are naturally conserved and sometimes very prevalent amongst human ethnic populations. Additionally this enables one to tailor the configurations of the invention to provide for antibody-based drugs that better address specific human ethnic populations.

In an example according to any configuration of the invention, loci (and cells and vertebrates comprising these) are provided in which gene segments from different human populations are used. This is desirable to increase antibody gene diversity to better address more diverse human patients. In an example, the gene segments are from first and second different human populations respectively, and thus the second gene segment is found in the second human population, but not so (or rarely) in the first human population. Rarely means, for example, that the gene segment is found in 5, 4, 3, 2, or 1 or zero individuals in the first population in the 1000 Genomes database. For example, the first gene segment may be shown as present in a first population by reference to Table 13 or 14 herein, the second gene segment may be shown as present in the second population by reference to Table 13 and not in the first population. Optionally, the first gene segment may also be shown as being present in the second population by reference to Table 13 or 14.

In any configuration or aspect of the invention, where a V gene segment is used, this may be used optionally with the native leader sequence. For example, use of genomic DNA (eg, from BACs as in the examples) will mean that the native leader will be used for each V gene segment incorporated into the locus and genomes of the invention. In an alternative, the skilled person may wish to inert a non-native leader sequence together with one or more of the V gene segments. Similarly, in any configuration or aspect of the invention, where a V gene segment is used, this may be used optionally with the native 5' UTR sequence. For example, use of genomic DNA (eg, from BACs as in the examples) will mean that the native 5' UTR sequence will be used for each V gene segment incorporated into the locus and genomes of the invention. In an alternative, the skilled person may wish to exclude the native 5' UTR sequence.

The present invention provides, in a first configuration (a) Superhuman Heavy Chain Gene Repertoires A non-human vertebrate or vertebrate cell (optionally an ES cell or antibody-producing cell) comprising a genome having a superhuman immunoglobulin heavy chain human VH and/or D and/or J gene repertoire.

In one aspect the cell of the invention is an embryonic stem cell. For example, the ES cell is derived from the mouse C57BL/6N, C57BL/6J, 129S5 or 129Sv strain. In one aspect the non-human vertebrate is a rodent, suitably a mouse, and cells of the invention, are rodent cells or ES cells, suitably mouse ES cells. The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a transgenic animal comprised of ES cell-derived tissue and host embryo derived tissue. In one aspect the invention relates to genetically-altered subsequent generation animals, which include animals having a homozygous recombinants for the VDJ and/or VJ regions.

The natural human immunoglobulin gene segment repertoire consists of (see eg, www at .imgt.org):—

VH; total-125; functional-41 DH: total-27; functional-23
JH: total-8; functional-6
Vk: total-77; functional-38 Jk; total-5; functional-5
V lambda: total-75; functional-31
J lambda: total-7; functional-5

In one embodiment, the vertebrate or cell genome comprises a transgenic immunoglobulin heavy chain locus comprising a plurality of human immunoglobulin VH gene segments, one or more human D gene segments and one or more human J gene segments, wherein the plurality of VH gene segments consists of more than the natural human repertoire of functional VH gene segments; optionally wherein the genome is homozygous for said transgenic heavy chain locus.

In one embodiment of the vertebrate or cell, the VH gene repertoire consists of a plurality of VH gene segments derived from the genome sequence of a first human individual, supplemented with one or more different VH gene segments derived from the genome sequence of a second, different human individual. Optionally the D and J segments are derived from the genome sequence of the first human individual. Optionally the VH gene segments from the genome sequence of the second individual are selected from the VH gene segments listed in Table 1, 13 or 14. In this way, the locus provides a superhuman repertoire of D gene segments.

Optionally the individuals are not related. Individuals are "not related" in the context of any configuration or aspect of the invention, for example, if one of the individuals does not appear in a family tree of the other individual in the same generation or going back one, two, three or four generations. Alternatively, are not related, for example, if they do not share a common ancestor in the present generation or going back one, two, three or four generations.

In one embodiment of the vertebrate or cell, the transgenic locus comprises more than 41 functional human VH gene segment species, and thus more than the natural human functional repertoire. Optionally the locus comprises at least 42, 43, 44, 45, 46, 47, 48, 49 or 50 functional human VH gene segment species (eg, wherein the locus comprises the full functional VH repertoire of said first individual supplemented with one or more VH gene segments derived from the genome sequence of the second human individual and optionally with one or more VH gene segments derived from the genome sequence of a third human individual). In this way, the locus provides a superhuman repertoire of VH gene segments that is useful for generating a novel gene and antibody diversity for use in therapeutic and tool antibody selection.

In one embodiment of the vertebrate or cell, the transgenic locus comprises a first VH gene segment derived from the genome sequence of the first individual and a second VH gene segment derived from the genome sequence of the second individual, wherein the second VH gene segment is a polymorphic variant of the first VH gene segment. For example, the VH gene segments are polymorphic variants of VH1-69 as illustrated in the examples below. Optionally the locus comprises a further polymorphic variant of the first VH gene segment (eg, a variant derived from the genome sequence of a third human individual). In this way, the locus provides a superhuman repertoire of VH gene segments.

In one embodiment of the vertebrate or cell, the genome (alternatively or additionally to the superhuman VH diversity) comprises a transgenic immunoglobulin heavy chain locus comprising a plurality of human immunoglobulin VH gene segments, a plurality of human D gene segments and one or more human J gene segments, wherein the plurality of D gene segments consists of more than the natural human repertoire of functional D gene segments. Optionally the genome is homozygous for said transgenic heavy chain locus.

In one embodiment of the vertebrate or cell, the D gene repertoire consists of a plurality of D gene segments derived from the genome sequence of a (or said) first human individual, supplemented with one or more different D gene segments derived from the genome sequence of a (or said) second, different human individual. Optionally the individuals are not related. Optionally the J segments are derived from the genome sequence of the first human individual. Optionally the D gene segments from the genome sequence of the second individual are selected from the D gene segments listed in Table 2, 13 or 14. In this way, the locus provides a superhuman repertoire of D gene segments.

In one embodiment of the vertebrate or cell, the transgenic locus comprises more than 23 functional human D gene segment species; optionally wherein the locus comprises at least 24, 25, 26, 27, 28, 29, 30 or 31 functional human D gene segment species (eg, wherein the locus comprises the full functional D repertoire of said first individual supplemented with one or more D gene segments derived from the genome sequence of the second human individual and optionally with one or more D gene segments derived from the genome sequence of a third human individual). In this way, the locus provides a superhuman repertoire of D gene segments.

In one embodiment of the vertebrate or cell, the transgenic locus comprises a first D gene segment derived from the genome sequence of the first individual and a second D gene segment derived from the genome sequence of the second individual, wherein the second D gene segment is a polymorphic variant of the first gene segment. Optionally the locus comprises a further polymorphic variant of the first D gene segment (eg, a variant derived from the genome sequence of a third human individual). In this way, the locus provides a superhuman repertoire of D gene segments.

In one embodiment of the vertebrate or cell (alternatively or additionally to the superhuman VH and/or JH diversity), the genome comprises a (or said) transgenic immunoglobulin heavy chain locus comprising a plurality of human immunoglobulin VH gene segments, one or more human D gene segments and a plurality of human JH gene segments, wherein the plurality of J gene segments consists of more than the natural human repertoire of functional J gene segments; optionally wherein the genome is homozygous for said transgenic heavy chain locus.

In one embodiment of the vertebrate or cell, the JH gene repertoire consists of a plurality of J gene segments derived from the genome sequence of a (or said) first human individual; supplemented with one or more different J gene segments derived from the genome sequence of a (or said) second, different human individual. Optionally the individuals are not related. Optionally D segments are derived from the genome sequence of the first human individual. Optionally the J gene segments from the genome sequence of the second individual are selected from the J gene segments listed in Table 3 13 or 14. In this way, the locus provides a superhuman repertoire of JH gene segments.

In one embodiment of the vertebrate or cell, the transgenic locus comprises more than 6 functional human JH gene segment segments. Optionally the locus comprises at least 7; 8, 9, 10, 11, 12, 13, 14, 15, or 16 functional human JH gene segments (eg, wherein the locus comprises the full functional JH repertoire of said first individual supplemented with one or more JH gene segments derived from the genome sequence of the second human individual and optionally with one or more JH gene segments derived from the genome sequence of a third human individual). In this way, the locus provides a superhuman repertoire of JH gene segments.

In one embodiment of the vertebrate or cell, the transgenic locus comprises a first JH gene segment derived from the genome sequence of the first individual and a second JH gene segment derived from the genome sequence of the second individual, wherein the second JH gene segment is a polymorphic variant of the first JH gene segment. Optionally the locus comprises a further polymorphic variant of the first JH gene segment (eg, a variant derived from the genome sequence of a third human individual). In this way, the locus provides a superhuman repertoire of JH gene segments.

(b) Superhuman Light Chain Gene Repertoires

The first configuration of the invention also provides:—

A non-human vertebrate or vertebrate cell (optionally an ES cell or antibody-producing cell) comprising a genome having a superhuman immunoglobulin light chain human VL gene repertoire, Optionally the vertebrate or cell comprises a heavy chain transgene according to aspect (a) of the first configuration, Thus, superhuman diversity is provided in both the heavy and light chain immunoglobulin gene segments in the cell and vertebrate. For example, the genome of the cell or vertebrate is homozygous for the heavy and light chain transgenes and endogenous antibody expression is inactivated. Such a vertebrate is useful for immunisation with a predetermined antigen to produce one or more selected antibodies that bind the antigen and have human variable regions resulting from recombination within the superhuman gene segment repertoire. This provides potentially for a novel antibody and gene sequence space from which to select therapeutic, prophylactic and tool antibodies.

In one embodiment of aspect (b) of the first configuration, the vertebrate or cell genome comprises (i) a transgenic immunoglobulin kappa light chain locus comprising a plurality of human immunoglobulin VK gene segments and one or more human J gene segments, wherein the plurality of VK gene segments consists of more than the natural human repertoire of functional VK gene segments; optionally wherein the genome is homozygous for said transgenic kappa light chain locus; and/or (ii) a transgenic immunoglobulin lambda light chain locus comprising a plurality of human immunoglobulin Vλ gene segments and one or more human J gene segments, wherein the plurality of Vλ gene segments consists of more than the natural human repertoire of functional Vλ gene segments; optionally wherein the genome is homozygous for said transgenic lambda light chain locus, In this way, the locus provides a superhuman repertoire of VL gene segments, In one embodiment of the vertebrate or cell, (i) the VK gene repertoire consists of a plurality of VK gene segments derived from the genome sequence of a first human individual, supplemented with one or more VK gene segments derived from the genome sequence of a second, different human individual; optionally wherein the individuals are not related; optionally wherein the J segments are derived from the genome sequence of the first human individual; and optionally wherein the VK gene segments from the genome sequence of the second individual are selected from the VK gene segments listed in Table 4, 13 or 14; and (i) the Vλ gene repertoire consists of a plurality of Vλ gene segments derived from the genome sequence of a first human individual, supplemented with one or more Vλ gene segments derived from the genome sequence of a second, different human individual; optionally wherein the individuals are not related; optionally wherein the J segments are derived from the genome sequence of the first human individual; and optionally wherein the Vλ gene segments from the genome sequence of the second individual are selected from the Vλ gene segments listed in Table 5, 13 or 14.

In this way, the locus provides a superhuman repertoire of VL gene segments.

In one embodiment of the vertebrate or cell, the kappa light transgenic locus comprises more than 38 functional human VK gene segment species; optionally wherein the locus comprises at least 39, 40, 41, 42; 43; 44, 45, 46, 47 or 48 functional human VK gene segment species (eg, wherein the locus comprises the full functional VK repertoire of said first individual supplemented with one or more VK gene segments derived from the genome sequence of the second human individual and optionally with one or more VK gene segments derived from the genome sequence of a third human individual); and the lambda light transgenic locus comprises more than 31 functional human VA gene segment species; optionally wherein the locus comprises at least 32, 33, 34, 35, 36, 37, 38, 39, 40 or 41 functional human Vλ gene segment species (eg, wherein the locus comprises the full functional VA repertoire of said first individual supplemented with one or more Vλ gene segments derived from the genome sequence of the second human individual and optionally with one or more Vλ gene segments derived from the genome sequence of a third human individual).

In this way, the locus provides a superhuman repertoire of VL gene segments.

In one embodiment of the vertebrate or cell, the kappa light transgenic locus comprises a first VK gene segment derived from the genome sequence of the first individual and a second VK gene segment derived from the genome sequence of the second individual, wherein the second VK gene segment is a polymorphic variant of the first VK gene segment; optionally wherein the locus comprises a further polymorphic variant of the first VK gene segment (eg, a variant derived from the genome sequence of a third human individual); and the lambda light transgenic locus comprises a first Vλ gene segment derived from the genome sequence of the first individual and a second Vλ gene segment derived from the genome sequence of the second individual, wherein the second Vλ gene segment is a polymorphic variant of the first Vλ gene segment; optionally wherein the locus comprises a further polymorphic variant of the first Vλ gene segment (eg, a variant derived from the genome sequence of a third human individual).

In this way, the locus provides a superhuman repertoire of VL gene segments.

In one embodiment of the vertebrate or cell; the genome comprises a (or said) transgenic immunoglobulin light chain locus comprising a plurality of human immunoglobulin VL gene segments and a plurality of human JL gene segments, wherein the plurality of J gene segments consists of more than the natural human repertoire of functional J gene segments; optionally wherein the genome is homozygous for said transgenic heavy chain locus.

In one embodiment of the vertebrate or cell, (i) the JK gene repertoire consists of a plurality of JK gene segments derived from the genome sequence of a (or said) first human individual, supplemented with one or more JK gene segments derived from the genome sequence of a (or said) second, different human individual; optionally wherein the individuals are not related; optionally wherein the VK segments are derived from the genome sequence of the first human individual; optionally wherein the JK gene segments from the genome sequence of the second individual are selected from the JK gene segments listed in Table 6, 13 or 14; and (ii) the JK gene repertoire consists of a plurality of Jλ gene segments derived from the genome sequence of a (or said) first human individual, supplemented with one or more Jλ gene segments derived from the genome sequence of a (or said) second, different human individual; optionally wherein the individuals are not related; optionally wherein the VA segments are derived from the genome sequence of the first human individual; optionally wherein the Jλ gene segments from the genome sequence of the second individual are selected from the Jλ gene segments listed in Table 7, 13 or 14.

In this way, the locus provides a superhuman repertoire of JL gene segments. In one embodiment of the vertebrate or cell, (i) the transgenic light chain locus comprises more than 5 functional human JK gene segment species; optionally wherein the locus comprises at least 6, 7, 8; 9, 10, 11, 12, 13, 14 or 15 functional human JK gene segment species (eg, wherein the locus comprises the full functional JK repertoire of said first individual supplemented with one or more JK gene segments derived from the genome sequence of the second human individual and optionally with one or more JK gene segments derived from the genome sequence of a third human individual); and/or (i) the transgenic light chain locus comprises more than 5 functional human Jλ gene segment species; optionally wherein the locus comprises at least 6, 7, 8, 9, 10, 11, 12, 13, 14 or 15 functional human Jλ gene segment species (eg, wherein the locus comprises the full functional Jλ repertoire of said first individual supplemented with one or more Jλ gene segments derived from the genome sequence of the second human individual and optionally with one or more Jλ gene segments derived from the genome sequence of a third human individual).

In this way, the locus provides a superhuman repertoire of JL gene segments.

In one embodiment of the vertebrate or cell, (i) the kappa light transgenic locus comprises a first JK gene segment derived from the genome sequence of the first individual and a second JK gene segment derived from the genome sequence of the second individual, wherein the second JK gene segment is a polymorphic variant of the first JK gene segment; optionally wherein the locus comprises a further polymorphic variant of the first JK gene segment (eg, a variant derived from the genome sequence of a third human individual); and (ii) the lambda light transgenic locus comprises a first Jλ gene segment derived from the genome sequence of the first individual and a second Jλ gene segment derived from the genome sequence of the second individual, wherein the second JK gene segment is a polymorphic variant of the first Jλ gene segment; optionally wherein the locus comprises a further polymorphic variant of the first Jλ gene segment (eg, a variant derived from the genome sequence of a third human In this way, the locus provides a superhuman repertoire of JL gene segments. Further aspects of the first configuration are described below.

The Present Invention Provides, in a Second Configuration

A library of antibody-producing transgenic cells whose genomes collectively encode a repertoire of antibodies, wherein (a) a first transgenic cell expresses a first antibody having a chain (eg, heavy chain) encoded by a first immunoglobulin gene, the gene comprising a first variable domain nucleotide sequence produced following recombination of a first human unrearranged immunoglobulin gene segment (eg, a VH);

(b) a second transgenic cell expresses a second antibody having a chain (eg, a heavy chain) encoded by a second immunoglobulin gene, the second gene comprising a second variable domain nucleotide sequence produced following recombination of a second human unrearranged immunoglobulin gene segment (eg, a VH), the first and second antibodies being non-identical;

(c) the first and second gene segments are different and derived from the genome sequences of first and second human individuals respectively, wherein the individuals are different; and optionally not related;

(d) wherein the cells are non-human vertebrate (eg, mouse or rat) cells (eg, B-cells or hybridomas).

In one embodiment, the library is provided in vitro. In another embodiment, the library is provided in vivo by one or a plurality of transgenic non-human vertebrates. For example, the or each vertebrate is according to any aspect of the first configuration of the invention.

In one embodiment, the library encodes an antibody repertoire of from 10 to 109 antibodies, for example, 10, 20, 30, 40, 50, 100 or 1000 to 108; or 10, 20, 30, 40, 50, 100 or 1000 to 107; or 10, 20, 30, 40, 50, 100 or 1000 to 106: or 10, 20, 30, 40, 50, 100 or 1000 to 105; or 10, 20, 30, 40, 50, 100 or 1000 to 104 antibodies. In an example, library encodes an antibody repertoire of at least 103, 104, 105, 106, 107, 108, 109, or 1010 antibodies.

The first variable domain nucleotide sequence is produced following recombination of the first human unrearranged immunoglobulin gene segment with one or more other immunoglobulin gene segments (for example, human immunoglobulin gene segments). For example, where the first gene segment is a VH, the first variable domain nucleotide sequence (a VH domain) is produced following recombination of the VH with a human D and JH segments in vivo, optionally with somatic hypermutation, in the first transgenic cell or an ancestor thereof. For example, where the first gene segment is a VL, the first variable domain nucleotide sequence (a VL domain) is produced following recombination of the VL with a human JL segment in vivo, optionally with somatic hypermutation, in the first transgenic cell or an ancestor thereof.

The second variable domain nucleotide sequence is produced following recombination of the second human unrearranged immunoglobulin gene segment with one or more other immunoglobulin gene segments (for example, human immunoglobulin gene segments). For example, where the second gene segment is a VH, the second variable domain nucleotide sequence (a VH domain) is produced following recombination of the VH with a human D and JH segments in vivo, optionally with somatic hypermutation, in the second transgenic cell or an ancestor thereof. For example, where the second gene segment is a VL, the second variable domain nucleotide sequence (a VL domain) is produced following recombination of the VL with a human JL segment in vivo, optionally with somatic hypermutation, in the second transgenic cell or an ancestor thereof.

The first and second gene segments are respectively derived from genome sequences of first and second human individuals. In one example, such a gene segment is isolated or cloned from a sample cell taken from said individual using standard molecular biology techniques as known to the skilled person. The sequence of the gene segment may be mutated (eg, by the introduction of up to 5, 6, 7, 8, 9, 10, 11, 12, 13, 14 or 15 nucleotide changes) prior to use in the present invention. In another example, a gene segment is derived by identifying a candidate human immunoglobulin gene segment in a database (see guidance below) and a nucleotide sequence encoding a gene segment for use in the present invention is made by reference (eg, to be identical or a mutant with up to 5, 6, 7, 8, 9, 10, 11, 12, 13, 14 or 15 nucleotide changes to the reference sequence) to the database sequence. The skilled person will be aware of methods of obtaining nucleotide sequences by reference to databases or by obtaining from cellular samples.

In one embodiment of the vertebrate, cell or library of any configuration of the invention, the first and second human individuals are members of first and second ethnic populations respectively, wherein the populations are different. This, therefore, provides for superhuman gene diversity in transgenic loci, cells and vertebrates as per the invention.

Human Populations

Optionally the ethnic populations are selected from those identified in the 1000 Genomes Project of database. In this respect, see Table 8 which provides details of the ethnic populations on which the 1000 Genomes database is based.

N A Rosenberg et al (Science 20 Dec. 2002: vol. 298 no. 5602 2342-2343) studied the genetic structure of human populations of differing geographical ancestry. In total, 52 populations were sampled, these being populations with:

African Ancestry (Mbuti Pygmies, Biaka Pygmies, San peoples, and speakers of Niger-Kordofanian languages (Bantu, Yoruba or Mandenka populations), Eurasian Ancestry (European ancestry (Orcadian, Adygei, Basque, French, Russians, Italians, Sardinian, Tuscan), Middle Eastern ancestry (Mozabite, Bedouin, Druze, Palestinians), Central/South Asian ancestry (Balochl, Brahul, Makrani, Sindhi, Pathan, Burusho, Hazara, Uygur, Kalash)), East Asian Ancestry (Han, Dal, Daur, Hezhen, Lahu, Miao, Orogen, She, Tujia, Tu, Xibo, Yi, Mongola, Naxi, Cambodian, Japanese, Yakut), Oceanic ancestry (Melanesian, Papuan); or Americas Ancestry (Karitiana, Surui, Colombian, Maya, Pima).

The International HapMap Project, Nature, 2003 Dec. 18; 426(6968):789-96, discloses that goal of the HapMap Project: to determine the common patterns of DNA sequence variation in the human genome by determining the genotypes of one million or more sequence variants, their frequencies and the degree of association between them in DNA samples from populations with ancestry from parts of Africa, Asia and Europe. The relevant human populations of differing geographical ancestry include Yoruba, Japanese, Chinese, Northern European and Western European populations. More specifically:—

Utah population with Northern or Western European ancestry (samples collected in 1980 by the Centre d'Etude du Polymorphisme Humain (CEPH)); population with ancestry of Yoruba people from lbadan, Nigeria; population with Japanese ancestry; and population with ancestry of Han Chinese from China.

The authors, citing earlier publications, suggest that ancestral geography is a reasonable basis for sampling human populations.

A suitable sample of human populations from which the populations used in the present invention are selected is as follows:—

(a) European Ancestry (b) Northern European ancestry; Western European ancestry; Toscani ancestry; British ancestry, Finnish ancestry or Iberian ancestry.

(c) More specifically, population of Utah residents with Northern and/or Western European ancestry; Toscani population in Italia; British population in England and/or Scotland; Finnish population in Finland; or Iberian population in Spain.

(a) East Asian Ancestry (b) Japanese ancestry; Chinese ancestry or Vietnamese ancestry.

(c) More specifically, Japanese population in Tokyo, Japan; Han Chinese population in Beijing, China; Chinese Dai population in Xishuangbanna; Kinh population in Ho Chi Minh City, Vietnam; or Chinese population in Denver, Colo., USA.

(a) West African Ancestry (b) Yoruba ancestry; Luhya ancestry; Gambian ancestry; or Malawian ancestry.

(c) More specifically, Yoruba population in Ibadan, Nigeria; Luhya population in Webuye, Kenya; Gambian population in Western Division, The Gambia; or Malawian population in Blantyre, Malawi.

(a) Population of the Americas (b) Native American ancestry; Afro-Caribbean ancestry; Mexican ancestry; Puerto Rican ancestry; Columbian ancestry; or Peruvian ancestry.

(c) More specifically, population of African Ancestry in Southwest US; population of African American in Jackson, Miss.; population of African Caribbean in Barbados; population of Mexican Ancestry in Los Angeles, Calif.; population of Puerto Rican in Puerto Rico; population of Colombian in Medellin, Colombia; or population of Peruvian in Lima, Peru.

(a) South Asian Ancestry (b) Ahom ancestry; Kayadtha ancestry; Reddy ancestry; Maratha; or Punjabi ancestry.

(c) More specifically, Ahom population in the State of Assam, India; Kayadtha population in Calcutta, India; Reddy population in Hyderabad, India; Maratha population in Bombay, India; or Punjabi population in Lahore, Pakistan.

In any configuration of the invention, in one embodiment, each human population is selected from a population marked "(a)" above.

In any configuration of the invention, in another embodiment, each human population is selected from a population marked "(b)" above.

In any configuration of the invention, in another embodiment, each human population is selected from a population marked "(c)" above.

In one embodiment of the library of the vertebrate, cell or library of the invention, the first and second ethnic populations are selected from the group consisting of an ethnic population with European ancestry, an ethnic population with East Asian, an ethnic population with West African ancestry, an ethnic population with Americas ancestry and an ethnic population with South Asian ancestry.

In one embodiment of the library of the vertebrate, cell or library of the invention, the first and second ethnic populations are selected from the group consisting of an ethnic population with Northern European ancestry; or an ethnic population with Western European ancestry; or an ethnic population with Toscani ancestry; or an ethnic population with British ancestry; or an ethnic population with Icelandic ancestry; or an ethnic population with Finnish ancestry; or an ethnic population with Iberian ancestry; or an ethnic population with Japanese ancestry; or an ethnic population with Chinese ancestry; or an ethnic population Vietnamese ancestry; or an ethnic population with Yoruba ancestry; or an ethnic population with Luhya ancestry; or an ethnic population with Gambian ancestry; or an ethnic population with Malawian ancestry; or an ethnic population with Native American ancestry; or an ethnic population with Afro-Caribbean ancestry; or an ethnic population with Mexican ancestry; or an ethnic population with Puerto Rican ancestry; or an ethnic population with Columbian ancestry; or an ethnic population with Peruvian ancestry; or an ethnic population with Ahom ancestry; or an ethnic population with Kayadtha ancestry; or an ethnic population with Reddy ancestry; or an ethnic population with Maratha; or an ethnic population with Punjabi ancestry.

In one embodiment of any configuration of the vertebrate; cell or library of the invention, the human immunoglobulin gene segment derived from the genome sequence of the second individual is low-frequency (optionally rare) within the second ethnic population. Optionally human immunoglobulin gene segment has a Minor Allele Frequency (MAF) (cumulative frequency) of between 0.5%-5%, optionally less than 0.5%, in the second human population, eg, as in the 1000 Genomes database.

In one embodiment of any configuration of the vertebrate, cell or library of the invention, the first variable region nucleotide sequence is produced by recombination of the first human immunoglobulin gene segment with a first J gene segment and optionally a first D gene segment, wherein the first human immunoglobulin gene segment is a V gene segment and the V, D and J segments are derived from the first human population, optionally from the genome of one individual of the first human population.

In one embodiment of the library of the vertebrate, cell or library of the invention, the second variable region nucleotide sequence is produced by recombination of the second human immunoglobulin gene segment with a second J gene segment and optionally a second D gene segment, wherein the second human immunoglobulin gene segment is a V gene segment derived from the second population and the and/or J segments are derived from the first human population, optionally the D and J gene segments being from the genome of one individual of the first human population.

In one embodiment of the library of the vertebrate, cell or library of the invention, all of the D and J segments that have been recombined with the first and second V gene segments are D and J segments derived from the first human population; optionally the D and J gene segments being from the genome of one individual of the first human population.

In one embodiment of the library, the second human immunoglobulin gene segment is a polymorphic variant of the first human immunoglobulin gene segment; optionally wherein the second gene segment is selected from the group consisting of a gene segment in any of Tables 1 to 7 and 9 to 14 (eg, selected from Table 13 or 14).

In one embodiment of the library, the first and second human immunoglobulin gene segments are both (i) VH gene segments; (ii) D segments; (iii) J segments (optionally both JH segments, both JK segments or both J^ segments); (iv) constant regions (optionally both a gamma constant region, optionally both a C gamma-1 constant region); (v) CH1 regions; (vi) CH2 regions; or (vii) CH3 regions.

The library is, for example, a naive and optionally has a library size of from 10 or 102 to 109 cells. For example, from 10, 20, 30, 40, 50, 100 or 1000 to 108; or 10, 20, 30, 40, 50, 100 or 1000 to 107; or 10, 20, 30, 40, 50, 100 or 1000 to 10s; or 10, 20, 30, 40, 50, 100 or 1000 to 105; or 10, 20, 30, 40, 50, 100 or 1000 to 104 cells.

The library has, for example, been selected against a predetermined antigen and optionally has a library size of from 10 or 102 to 109 cells. For example, from 10, 20, 30, 40, 50, 100 or 1000 to 108; or 10, 20, 30, 40, 50, 100 or 1000 to 107; or 10, 20, 30, 40, 50, 100 or 1000 to 10s; or 10, 20, 30, 40, 50, 100 or 1000 to 105; or 10, 20, 30, 40, 50, 100 or 1000 to 104 cells.

In one embodiment of the library of the invention, said first and second cells are progeny of first and second ancestor non-human vertebrate cells respectively, wherein the first ancestor cell comprises a genome comprising said first human immunoglobulin gene segment; and the second ancestor cell comprises a genome comprising said second human immunoglobulin gene segment.

The invention further provides a library of antibody-producing transgenic cells whose genomes collectively encode a repertoire of antibodies, wherein the library comprises the first and second ancestor cells described above.

The invention further provides a library of hybridoma cells produced by fusion of the library of the invention (eg, a B-cell library) with fusion partner cells and optionally has a library size of from 10 or 102 to 109 cells. For example, from 10, 20, 30, 40, 50, 100 or 1000 to 108; or 10, 20, 30, 40, 50, 100 or 1000 to 107; or 10, 20, 30, 40, 50, 100 or 1000 to 10s; or 10, 20, 30, 40, 50, 100 or 1000 to 105; or 10, 20, 30, 40, 50, 100 or 1000 to 104 cells. Production of hybridomas is well known to the skilled person. Examples of fusion partners are SP2/0-g14 (obtainable from ECACC), P3XS3-Ag8.S53 (obtainable from LGC Standards; CRL-1580), NS1 and NS0 cells. PEG fusion or electrofusion can be carried out, as is conventional.

The Invention Provides, in a Third Configuration:—

An isolated antibody having (a) a heavy chain encoded by a nucleotide sequence produced following recombination in a transgenic non-human vertebrate cell of an unrearranged human immunoglobulin V gene segment with a human D and human J segment, optionally with affinity maturation in said cell, wherein one of the gene segments (eg, VH) is derived from the genome of an individual from a first human ethnic population; and the other two gene segments (eg, and JH) are derived from the genome of an individual from a second (eg, a second and third respectively), different, human ethnic population, and wherein the antibody comprises heavy chain constant regions (eg, C gamma) of said non-human vertebrate (eg, rodent, mouse or rat heavy chain constant regions); and/or (b) a light chain encoded by a nucleotide sequence produced following recombination in a transgenic non-human vertebrate cell of an unrearranged human immunoglobulin V gene segment with a human J segment, optionally with affinity maturation in said cell, wherein one of the gene segments (eg, VL) is derived from the genome of an individual from a first human ethnic population (optionally the same as the first population in (a)); and the other gene segment (eg, JL) is derived from the genome of an individual from a second, different, human ethnic population (optionally the same as the second population in (a)), and wherein the antibody comprises light chain constant regions of said non-human vertebrate (eg, rodent, mouse or rat heavy light constant regions);

(c) Optionally wherein each variable domain of the antibody is a human variable domain.

(d) Optionally wherein the heavy chain constant regions are mu- or gamma-type constant regions.

The invention also provides an isolated nucleotide sequence encoding the antibody of the third configuration, optionally wherein the sequence is provided in an antibody expression vector, optionally in a host cell. Suitable vectors are mammalian expression vectors (eg, CHO cell vectors or HEK293 cell vectors), yeast vectors (eg, a vector for expression in *Picchia pastoris*, or a bacterial expression vector, eg, a vector for *E. coli* expression.

The invention also provides a method of producing a human antibody, the method comprising replacing the non-human vertebrate constant regions of the antibody of the third configuration with human antibody constant regions (eg, a C variant disclosed in table 13 or 18). The skilled person will be aware of standard molecular biology techniques to do this. For example, see Harlow, E. & Lane, D. 1998, 5th edition, Antibodies: A Laboratory Manual, Cold Spring Harbor Lab. Press, Plainview, N.Y.; and Pasqualini and Arap, Proceedings of the National Academy of Sciences (2004) 101:257-259 for standard immunisation. Joining of the variable regions of an antibody to a human constant region can be effected by techniques readily available in the art, such as using conventional recombinant DNA and RNA technology as will be apparent to the skilled person. See e.g. Sambrook, J and Russell, D. (2001, 3'd edition) Molecular Cloning: A Laboratory Manual (Cold Spring Harbor Lab. Press, Plainview, N.Y.).

In one embodiment, the method comprises further making a mutant or derivative of the antibody.

The invention also provides a pharmaceutical composition comprising an antibody according to the third configuration, or a human antibody of the invention and a diluent, excipient or carrier; optionally wherein the composition is provided in a container connected to an IV needle or syringe or in an IV bag.

The invention also provides an antibody-producing cell (eg, a mammalian cell, eg, CHO or HEK293; a yeast cell, eg, *P pastoris*; a bacterial cell, eg, *E coli*; a B-cell; or a hybridoma) that expresses the second antibody of the third configuration or the isolated antibody of the invention.

The First Configuration of the Invention Also Provides:—

A non-human vertebrate or vertebrate cell (optionally an ES cell or antibody-producing cell) whose genome comprises a transgenic immunoglobulin locus (eg, a heavy chain locus or a light chain locus), said locus comprising immunoglobulin gene segments according to the first and second human immunoglobulin gene segments (optionally V segments) described above in connection with the third configuration. The gene segments are operably connected upstream of an immunoglobulin constant region; optionally wherein the genome is homozygous for said transgenic immunoglobulin locus.

Optionally the immunoglobulin locus comprises more than the natural human complement of functional V gene segments; and/or Optionally wherein the immunoglobulin locus comprises more than the natural human complement of functional D gene segments; and/or Optionally wherein the immunoglobulin locus comprises more than the natural human complement of functional J gene segments.

In this way, a superhuman immunoglobulin gene repertoire is provided in a transgenic non-human vertebrate or vertebrate cell according to the invention.

The First Configuration Also Provides:—

A transgenic non-human vertebrate (eg, a mouse or rat) or vertebrate cell (optionally an ES cell or antibody-producing cell) whose genome comprises a transgenic immunoglobulin locus comprising a plurality of human immunoglobulin gene segments operably connected upstream of a non-human vertebrate constant region for the production of a repertoire of chimaeric antibodies, or chimaeric light or heavy chains, having a non-human vertebrate constant region and a human variable region; wherein the transgenic locus comprises one or more human immunoglobulin V gene segments, one or more human J gene segments and optionally one or more human D gene segments, a first (optionally a V segment) of said gene segments and a second (optionally a V segment) of said gene segments being different and derived from the genomes of first and second human individuals respectively, wherein the individuals are different; and optionally not related;

optionally wherein the immunoglobulin locus comprises more than the natural human complement of functional V gene segments; and/or optionally wherein the immunoglobulin locus comprises more than the natural human complement of functional D gene segments; and/or optionally wherein the immunoglobulin locus comprises more than the natural human complement of functional J gene segments.

In this way, a superhuman immunoglobulin gene repertoire is provided in a transgenic non-human vertebrate or vertebrate cell according to the invention.

The First Configuration Also Provides:—

A transgenic non-human vertebrate (eg, a mouse or rat) or vertebrate cell (optionally an ES cell or antibody-producing cell) whose genome comprises first and second transgenic immunoglobulin loci, each locus comprising a plurality of human immunoglobulin gene segments operably connected upstream of a non-human vertebrate constant region for the production of a repertoire of chimaeric antibodies, or chimaeric light or heavy chains, having a non-human vertebrate constant region and a human variable region;

wherein (i) the first transgenic locus comprises one or more human immunoglobulin V gene segments, one or more human J gene segments and optionally one or more human D gene segments, (ii) the second transgenic locus comprises one or more human immunoglobulin V gene segments, one or more human J gene segments and optionally one or more human D gene segments; and (iii) wherein a first (optionally a V) gene segment of said first locus and a second (optionally a V) gene segment of said second gene locus are different and derived from the genomes of first and second human individuals respectively, wherein the individuals are different; and optionally not related;

optionally wherein the first and second loci are on different chromosomes (optionally chromosomes with the same chromosome number) in said genome;

optionally wherein each immunoglobulin locus comprises more than the natural human complement of functional V gene segments; and/or optionally wherein each immunoglobulin locus comprises more than the natural human complement of functional D gene segments; and/or optionally wherein each immunoglobulin locus comprises more than the natural human complement of functional J gene segments.

In this way, a superhuman immunoglobulin gene repertoire is provided in a transgenic non-human vertebrate or vertebrate cell according to the invention.

In these embodiments of the first configuration, the immunoglobulin gene segments are optionally as described for the third configuration.

In these embodiments of the first configuration, the genome optionally comprises a third immunoglobulin gene segment (optionally a V segment), the third gene segment being derived from a human individual that is different from the individual from which the first (and optionally also the second) gene segment is derived; optionally wherein the first, second and third gene segments are polymorphic variants of a human immunoglobulin gene segment (eg, VH1-69—see the examples for further description).

In these embodiments of the first configuration, the genome of the vertebrate or cell is optionally homozygous for the first, second and optional third gene segment, wherein a copy of the first, second and optional third gene segments are provided together on the same chromosome operably connected upstream of a common non-human vertebrate constant region.

For example; each first, second and optional third gene segment is a V gene segment.

In one example, the library of the invention is provided by a collection of non-human vertebrates (optionally a collection of rodents, mice or rats); optionally, wherein a first member of said collection produces said first antibody but not said second antibody, and a second member of the collection produces said second antibody (but optionally not said first antibody). It is therefore contemplated to make non-human vertebrates where different human genomes have been used as a source for building the transgenic loci in the vertebrates. For example, a first vertebrate comprises a transgenic heavy chain locus having gene segments only from a first (and optionally a second) human population or individual; a second vertebrate comprises a transgenic heavy chain locus having gene segments only from a third (and optionally a fourth) human population or individual; and optionally third and more vertebrates can be built similarly based on unique or overlapping human population genomes. However, when provided as a mixed population of transgenic vertebrates, the mixed population provides a collective pool of human immunoglobulin genes that is greater than found in a natural human repertoire. This is useful to extend the antibody and gene sequence space beyond those possible with prior transgenic mice and rats bearing human immunoglobulin loci. As explained above, these have been based on a single human genome.

In one embodiment, the collection of non-human vertebrates bear human immunoglobulin genes confined to human populations that are together grouped under the same population genus "(a)" mentioned above. This provides for a gene repertoire that is biased to producing human antibody variable regions prevalent in the population genus (a) and thus useful for generating antibody therapeutics/prophylactics for members of said population. Alternatively, where gene segments from different human populations are provided in a single transgene according to the invention (not necessarily in a collection of vertebrates), the different human populations are for example together grouped under the same population genus "(a)" mentioned above.

The invention also provides a repertoire of antibodies expressed from a library of cells according to the invention.

In the non-human vertebrate or cell of any configuration of the invention, the constant region of the transgenic locus is, in one example, an endogenous constant region of said vertebrate (eg, endogenous mouse or rat constant region, eg, from the same strain of mouse or rat as the non-human vertebrate itself).

The invention also provides a method of constructing a cell (eg, an ES cell) according to the invention, the method comprising (a) identifying functional V and J (and optionally D) gene segments of the genome sequence of a (or said) first human individual;

(b) identifying one or more functional V and/or D and/or J gene segments of the genome sequence of a (or said) second human individual, wherein these additional gene segments are not found in the genome sequence of the first individual;

(c) and constructing a transgenic immunoglobulin locus in the cell, wherein the gene segments of (a) and (b) are provided in the locus operably connected upstream of a constant region.

Optionally the cell comprises a heavy chain locus constructed according to steps (a) to (c) and/or a light chain locus (kappa and/or lambda loci) constructed according to steps (a) to (c).

Optionally the cell is homozygous for the or each transgenic locus; optionally wherein antibody expression from loci endogenous to said cell has been inactivated. This is useful for confining the functional antibody gene repertoire, and thus antibody production, to antibodies bearing human variable regions.

Optionally the gene segment(s) in step (b) are identified from an immunoglobulin gene database selected from the 1000 Genomes, Ensembl, Genbank and IMGT databases.

Optionally the first and second human individuals are members of first and second ethnic populations respectively, wherein the populations are different, optionally wherein the human immunoglobulin gene segment derived from the genome sequence of the second individual is low-frequency (optionally rare) within the second ethnic population.

The invention also provides a method of making a transgenic non-human vertebrate (eg, a mouse or rat), the method comprising (a) constructing an ES cell (eg, a mouse C57BL/6N, C57BL/6J, 129S5 or 129Sv strain ES cell) by carrying out the method above;

(b) injecting the ES cell into a donor non-human vertebrate blastocyst (eg, a mouse C57BL/6N, C57BL/6J, 129S5 or 129Sv strain blastocyst);

(c) implanting the blastocyst into a foster non-human vertebrate mother (eg, a C57BL/6N, C57BL/6J, 129S5 or 129Sv strain mouse); and (d) obtaining a child from said mother, wherein the child genome comprises a transgenic immunoglobulin locus.

The invention provides a transgenic non-human vertebrate (eg, a mouse or rat) made by the method or a progeny thereof. The invention also provides a population of such non-human vertebrates.

Microinjection of ES cells into blastocysts and generation of transgenic mice therafter are conventional practices in the state of the art, and the skilled person is aware of techniques useful to effect this. C57BL/6N, C57BL/6J, 129S5 or 129Sv mouse strains and ES cells are readily and publicly available.

The invention also provides a method of isolating an antibody that binds a predetermined antigen (eg, a bacterial or viral pathogen antigen), the method comprising (a) providing a vertebrate (optionally a mouse or rat) according to the invention;

(b) immunising (eg, using a standard prime-boost method) said vertebrate with said antigen (optionally wherein the antigen is an antigen of an infectious disease pathogen);

(c) removing B lymphocytes from the vertebrate and selecting one or more B lymphocytes expressing antibodies that bind to the antigen;

(d) optionally immortalising said selected B lymphocytes or progeny thereof; optionally by producing hybridomas therefrom; and (e) isolating an antibody (eg, and IgG-type antibody) expressed by the B lymphocytes; and (f) optionally producing a derivative or variant of the antibody.

This method optionally further comprises after step (e) the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

Bioinformatics Analysis & Selection of Immunoglobulin Gene Segments

See also the discussion on variation analysis above.

The skilled person will know of sources of human antibody gene sequences, such as IMGT (www at .imgt.org), GenBank (www at .ncbi.nlm.nih.gov/genbank) Bioinformatics tools for database manipulation are also readily available and known to the skilled person, eg, as publicly available from the 1000 Genomes Project/EBI (www at .1000genomes.org)

As a source of antibody gene segment sequences, the skilled person will also be aware of the following available databases and resources (including updates thereof):—

1.1. The Kabat Database (G. Johnson and T. T, Wu, 2002; _at www at .kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment; sequence subgroup classification, and the generation of variability plots. See also Kabat, E. A., Wu; T. T., Perry, H., Gottesman, K., and Foeller, C. (1991) Sequences of Proteins of Immunological Interest, 5th ed., NIH Publication No. 91-3242, Bethesda, Md., which is incorporated herein by reference, in particular with reference to human gene segments for use in the present invention.

1.2. KabatMan (A. C. R. Martin, 2002; at www at_.bioinf.org.uk/abs/simkab.html). This is a web interface to make simple queries to the Kabat sequence database.

1.3. IMGT, the International ImMunoGeneTics Information System®; M.-P. Lefranc; 2002; at imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms; specificities, and two-dimensional (2D) and three-dimensional (3D) structures. IMGT includes three sequence databases (IMGTILIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

1.4. V-BASE (I. M. Tomlinson, 2002; at www at_.mrccpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Muller) that allows the assignment of rearranged antibody V genes to their closest germline gene segments, 1.5. Antibodies—Structure and Sequence (A. C. R. Martin, 2002; at www at .bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

1.6. AAAAA—AHo's Amazing Atlas of Antibody Anatomy (A. Honegger, 2001; at www at .unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

1.7. WAM—Web Antibody Modeling (N. Whitelegg and A. R. Rees, 2001; at antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

1.8. Mike's Immunoglobulin Structure/Function Page (M. R. Clark, 2001; at www at path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

1.9. The Antibody Resource Page (The Antibody Resource Page, 2000; at www at .antibodyresource.com). This site describes itself as the "complete guide to antibody research and suppliers." Links to amino acid sequencing tools, nucleotide antibody sequencing tools, and hybridoma/cell-culture databases are provided.

1.9. Humanization bYDesign Saldanha, 2000; at people-.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, Methods in Molecular Biology™, Human Press. Also at at www at .blogsua.com/pdf/antibody-engineering-methods-and-protocolsantibody-engineering-methods-and-protocols.pdf.

As a source of genomic sequence variation data, the skilled person will also be aware of the following available databases and resources (including updates thereof):—

1. HapMap (The International HapMap Consortium, 2003; at hapmap.ncbi.nlm.nih.gov/index.html.en). The HapMap Project is an international project that aims to compare the genetic sequences of different individuals to identify chromosomal regions containing shared genetic variants. The HapMap www site provides tools to identify chromosomal regions and the variant therein, with options to drill down to population level frequency data.

2. 1000 Genomes (The 1000 Genomes Project Consortium 2010; at www at 0.1000genomes.org/). This resource provides complete genomic sequence for 2500 unidentified individuals from one of 25 distinct population groups, with the aim of identifying genomic variants of >1%. The site provides the ability to interrogate data utilizing online tools (e.g. 'Variation Pattern Finder') and to download variant data for individual population groups.

3. Japanese SNP Database (H. Haga et al. 2002; at snp.ims.u-tokyo.ac.jp/index.html). Based on a study identifying 190,562 human genetic variants this site catalogues genomic variants with useful features for searching and summarizing data.

It is possible to identify variants in immunoglobulin genes classed as low-frequency or rare variants that segregate with specific human ethnic populations. For the purpose of this analysis, a low-frequency immunoglobulin gene segment is classed as one with 'Minor Allele Frequency' (MAF) (cumulative frequency) of between 0.5%-5%, rare variants are those classed as having a MAF of less than 0.5% in a particular human population.

The following bioinformatics protocol is envisaged to identify human immunoglobulin gene segments for use in the present invention:

(a) Identify one or more genomic regions containing gene segments of interest ('target genomic regions') and calculate the genomic coordinates, using coordinates that match the sequence assembly build used by either the 1000 Genomes project or International HapMap project (or another selected human gene database of choice).

(b) Identify genomic variants mapped to the genomic regions previously identified in (a). Retrieve variant frequencies for variants for each super population and preferably sub-population where such data is available. Tools readily available on the HapMap WWW site and the VWC tools for the 1000Genomes Project are useful for this step.

(c) Filter list of genomic variants from target genomic regions to contain only variants classed as either 'Non-synonymous' single nucleotide polymorphisms (SNPs) or genomic 'insertions or defections' (indels). Filter further to include those that are present in exonic sequences only.

(d) Correlate population frequency data for each of the identified variants for each of the super populations (for example 'European Ancestry', 'East Asian ancestry', 'West African ancestry', 'Americas', and 'South Asian ancestry') to identify those variants that segregate with less than two super-populations. Further correlate all identified variants with each of the sub-populations (for example, 'European ancestry' super-population might be subdivided into groups such as 'CEU—Utah residents with Northern or Western European ancestry', 'TSI Toscani in Italia' and 'British from England and Scotland') and produce a second score for rarity of variants in within a super-population.

(e) Collect one or more gene segments that show segregation to specific sub-populations for construction of synthetic loci according to the invention.

In one embodiment throughout the present text, "germline" refers to the canonical germline gene segment sequence.

By detailed analysis of the 1000 Genomes database, the inventors have devised a collection of candidate polymorphic antibody gene segment variants, eg, human variant JH gene segments (eg, see Example 4), that can be built into the design of transgenic heavy chain loci in mice for expressing increasingly diverse and new, synthetic repertoires of human variable regions. To this end, the invention provides the following embodiments.

The Present Invention Provides in a Fourth Configuration—

Selection of Human JH6*02 Variant

Transgenic IqH Loci, Non-Human Vertebrates, Cells & Antibodies Based on Human JH6*02

Figure 1:
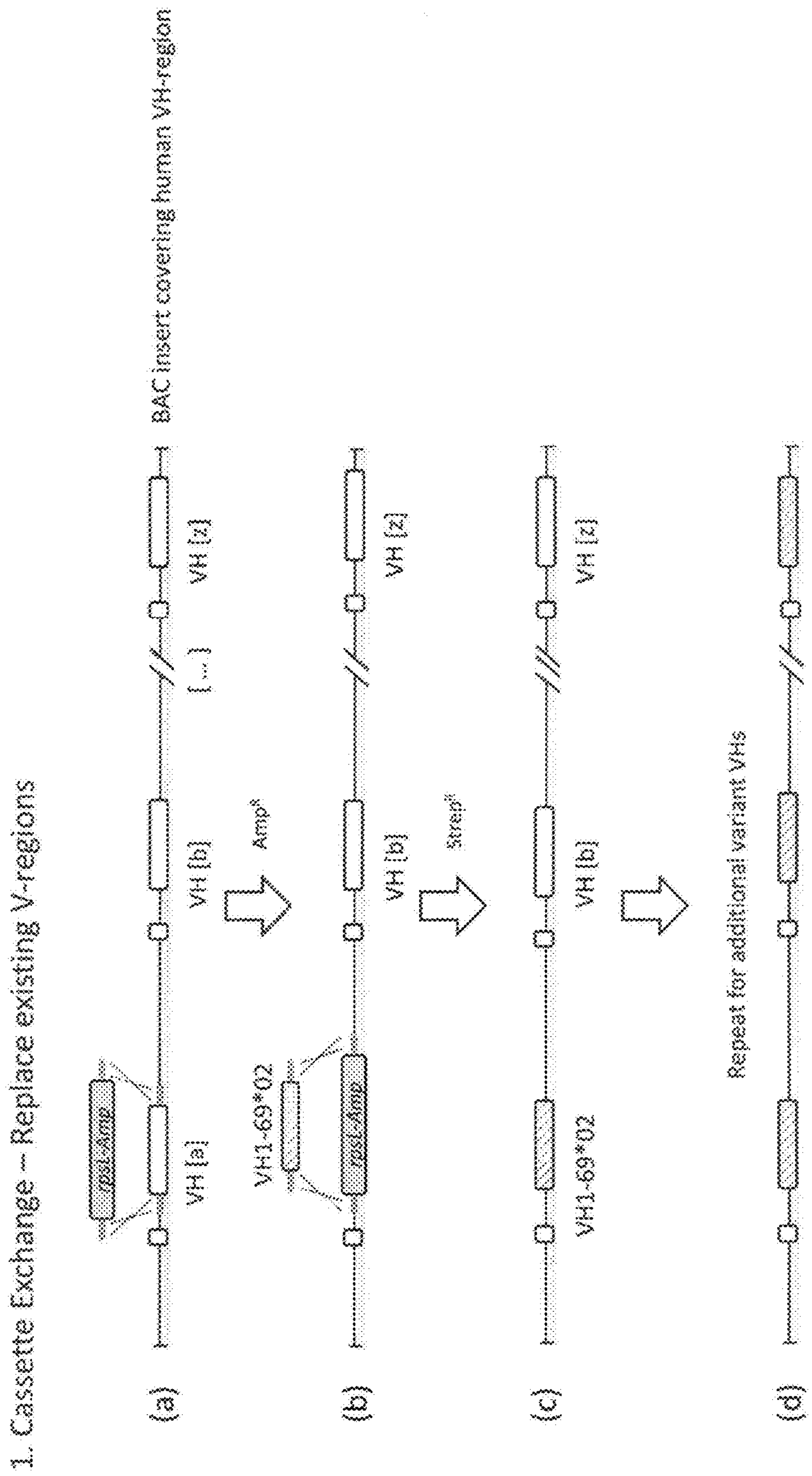
FIGS. 1 to 3: Schematic illustrating a protocol for producing recombineered BAC vectors to add V gene segments into a mouse genome.

As explained above, in designing transgenic Ig heavy chain loci the present inventors have considered the huge amount of data available from the 1000 Genomes project (see www at .1000genomes.org) that analyses gene distributions amongst many human populations; and in particular data on Ig gene segments. The inventors were also aware of human gene segments disclosed in the IMGT database (see www at .imgt.org) and in Ensembl (see www at .ensemble.org"). The inventors needed to make choices about which human gene segments to include amongst the large number of human gene segments presented in these databases and the other sources of human Ig gene segment information known in the art, including those other databases disclosed herein. When choosing human JH gene segments, the inventors were aware that human JH6 encodes a relatively long amino acid sequence, and thus the inventors thought it desirable to include this for increasing the chances of producing IgH chains with relatively long HCDR3 regions. Antibodies with long HCDR3 (at least 20 amino acids according to IMGT nomenclature) have been shown to neutralise a variety of pathogens effectively including HIV; Influenza virus, malaria and Africa trypanosomes. Reference is also made to naturally-occurring Camelid (eg, llama or camel) heavy chain-only antibodies which bear long HCDR3s for reaching relatively inaccessible epitopes (see, eg, EP0937140). Long HCDR3s can form unique stable subdomains with extended loop structure that towers above the antibody surface to confer fine specificity. In some cases, the long HCDR3 itself is sufficient for epitope binding and neutralization (Liu, L et al; Journal of Virology. 2011. 85: 8467-8476, incorporated herein by reference). The unique structure of the long HCDR3 allows it to bind to cognate epitopes within inaccessible structure or extensive glycosylation on a pathogen surface. In human peripheral blood, there is around 3.5% of naive B antibodies or 1.9% of memory B IgG antibodies containing the HCDR3s with lengths of more than 24 amino acids (PLoS One. 2012; 7(5):e36750. Epub 2012 May 9; "Human peripheral blood antibodies with long HCDR3s are established primarily at original recombination using a limited subset of germline genes"; Briney B S e al, incorporated herein by reference) (FIG. 1). The usage analysis indicates that these antibodies have the preference to use human JH6 with human D2-2, D3-3 or D2-15 (Brinley, B S et al, FIGS. 2-5). See also PLoS One, 2011 Mar. 30; 6(3):e16857; Comparison of antibody repertoires produced by HIV-1 infection; other chronic and acute infections, and systemic autoimmune disease"; Breden F et al, incorporated herein by reference. Around 20% of all HCDR3 of antibodies use JH6. However, in those antibodies with HCDR3 of more than 24 amino acids, 70% use JH6 (Brinley, B S et al, FIG. 2).

There is a need in the art for genetically modified non-human vertebrates and cells that can make antibodies and heavy chains that have long human HCDR3s, as well as antibodies; chains and VH domains that can be selected from such vertebrates and cells wherein these can address target epitopes better accessed by long HCDR3s.

The inventors, therefore, chose in this configuration of the invention to include a human JH6 gene segment as a mandatory human gene segment in their IgH locus design. Several different naturally-occurring human JH6 variants are known (eg, JH6*01 to *04 as well as others; IMGT nomenclature). The inventors considered this when deciding upon which human JH6 variant should be included in the transgenic IgH locus design. An alignment of some human JH6 variants is shown in FIG. 7 (from www, at "imgt.org"; dashes indicate identical nucleotides; nucleotide changes versus the *01 variant are shown by underlined nucleotides and corresponding amino acid changes are shown by underlined amino acids; Genbank accession numbers (release 185.0) are shown prefixed by J, X, M or A). The inventors used sequencing of human genomic DNA samples, inspection of public IgH DNA databases as well as informed choices on the basis of variant sequences as means to arrive at a rational choice of which JH6 variant to use.

The 1000 Genomes database uses human JH6*03 as the reference sequence; which would be a possible choice for the skilled person wishing to construct a transgenic IgH locus. The inventors noticed (eg, FIG. 7 herein) that position 6 in JH6*03 is a tyrosine (Y) encoded by a TAC codon, whereas some other naturally-occurring human variants have a glycine (G) encoded by a GGT codon (the glycine being present as a YYG motif, forming part of a larger YYGXDX (SEQ ID NO:479) motif). To understand the potential significance of this, the inventors carried out analysis of JH sequences from other vertebrate species. The inventors surprisingly noticed that YYG and YYGXDX (SEQ ID NO:479) motifs are conserved across many vertebrate species (see FIGS. 7 & 8). This suggested to the inventors, therefore, that preservation of this motif might be desirable, which could guide the choice of JH6 variant for use in the present invention.

Another pointer arose when the inventors considered the TAC codon versus the GGT codon encoding Y or G respectively. The inventors considered the impact of these nucleotide sequences on the action of activation-induced cytidine deaminase (AID). The inventors knew that activation-induced cytidine deaminase (AID) is believed to initiate Ig somatic hypermutation (SHM) in a multi-step mechanism and they addressed this activity when rationally designing the locus. AID catalyses the deamination of C to U in DNA, generating mutations at C bases. Cytidines located within hotspot motifs are preferentially deaminated. Certain motifs are hotspots for AID activity (DGYW, WRC, WRCY, WRCH, RGYW, AGY, TAC, WGCW, wherein W=A or T, Y=C or T, D=A, G or T, H=A or C or T, and R=A or G). The presence of a TAC codon encoding Y at position 6 in JH6*03 creates AID mutation hotspots (the cytidine being the substrate of AID), these hotspots being the underlined motifs in the previous sentence. The inventors considered the impact of this and in doing so they considered possible mutants created by AID activity at the cytidine. Reference is made to FIG. 9. The inventors noticed that a mutation at the third base of the TAC codon would yield 3 possible outcomes: Y, stop or stop. Thus, out of the three stop codons possible in the genetic code (the other being encoded by TGA—see FIG. 9), two of them would be provided by mutation of the cytidine in the TAC codon encoding position 6 in JH6*03. The inventors, therefore, considered that this might increase the chances of non-productive IgH variable region production in transgenic loci based on JH6*03. Moreover, the inventors noticed that provision of a GGT codon instead (as per the other human JH6 variants) seemed preferable since mutation of the third base would never yield a stop codon (see FIG. 9), and furthermore would retain coding, and thus conservation, of glycine at position 6, which the inventors also noticed was is in the YYG and YYGXDX (SEQ ID NO:479) motifs conserved across species.

Having decided against using JH6*03, the inventors needed to make a choice from other possible human variants. The MDV motif is at the C-terminus of HCDR3 based on human JH6, the adjacent framework 4 (FW4) starting with the WGQ motif (with reference to the sequence shown encoded by JH6*01; FIG. 7). In making their choices for locus design, the inventors wished to maximise conservation of this HCDR3/FW4 junction in product IgH chains and antibodies including these. The inventors believed this to be desirable for heavy chain variable domain functionality and conformation. The inventors thought that this might in some cases be desirable to minimise immunogenicity (suitable for human pharmaceutical use). Consistent with these considerations, the inventors wanted to make a choice that would minimise mutation around the HCDR3/FW4 junction as a result of SHM in vivo to conserve junction configuration. See Rogozin & Diaz; "Cutting Edge: DGYW/WRCH Is a Better Predictor of Mutability at G:C Bases in Ig Hypermutation Than the Widely Accepted RGYW/WRCY Motif and Probably Reflects a Two-Step Activation-Induced Cytidine Deaminase-Triggered Process"; Journal of Immunology; Mar. 15, 2004 vol. 172 no. 6 3382-3384. An example of a DGYW motif is GGCA. The inventors had this in mind when analysing the variant sequences.

With these considerations in mind; the inventors decided specifically to use human JH6*02 as the mandatory human JH6 for their IgH locus design. JH6*01 was rejected as the mandatory JH6 gene segment since the nucleotide sequence GGG CAA (encoding G and Q) contains a GGCA motif which is an AID recognition hotspot. The inventors realised that JH6*04 also contains such a motif due to the presence of the sequence GGC AAA encoding G and K (positions 11 and 12 respectively). The inventors also realised that the *02 variant has a C instead of a G that is in the *01 variant, the C desirably being a synonymous change (ie, not changing the encoded amino acid sequence around the CDR3/FW4 junction) and also this does not provide a GGCA AID hotspot motif. The inventors, therefore, decided that the mandatory JH6 should have this C base and this too pointed them to using the human JH6*02 variant.

In one example of any configuration of the invention herein, the only JH6 species included in the locus or genome is human JH6*02.

The inventors obtained 9 anonymised DNA samples from cheek swabs of 9 consenting human adults. Sequencing was performed on IgH locus DNA to confirm natural JH6 variant usage. It was found that the genome of all 9 humans contained a JH6*02 variant gene segment. In 7 out of the 9 humans, the genome was homozygous for JH6*02 (ie, each chromosome 14 had JH6*02 as its JH6 gene segment in the IgH locus). The inventors also inspected the publicly-available sequence information from the genomes of well-known scientists Craig Venter and Jim Watson. Both of these genomes contain JH6*02 too. This indicated to the inventors that this variant is common in humans.

So, the inventors made a choice of human JH6*02 on the basis of (i) Containing the YYG and YYGXDX (SEQ ID NO:479) motifs that is conserved across several vertebrate species;

(ii) Provision of one less TAC codon (an AID hotspot that risks stop codons) and a choice instead of a codon that preserves the YYG and YYGXDX (SEQ ID NO:79) motifs;

(iii) Avoidance of a GGCA AID hotspot in the region of the HCDR3/FW4 junction; and (iv) Common occurrence (and thus conservation and acceptability) in humans of the JH6*02 variant.

This rationale was tested by the inventors in laboratory examples, in order to see if human JH6*02 could desirably participate in antibody gene segment recombination and heavy chain production in a foreign (non-human vertebrate) setting, and moreover to assess if long HCDR3s based on human JH6*02 could be produced in vivo (in naive and immunised settings) in such non-human systems. It was noted that in some non-human settings, such as a mouse, the YYG and YYGXDX (SEQ ID NO:479) motifs are not conserved, and thus the inventors decided that it was important to test whether or not JH6*02 (having the YYG and YYGXDX (SEQ ID NO:479) motifs) could function properly in such a foreign setting to participate in VDJ recombination and selection against antigen.

Thus, as explained further in the examples, the inventors constructed transgenic JH6*02-containing IgH loci in ES cells; generated transgenic non-human vertebrates from the ES cells (both naive and immunised with a range of different target antigen types), isolated antibodies and heavy chain sequences based on JH6*02 as well as B-cells expressing these and made hybridomas expressing antigen-specific antibodies that are based on the chosen JH6*02 variant. The inventors found that the JH6*02 variant was extensively used and could contribute to the production of HCDR3 of at least 20 amino acids in many different heavy chains (including antigen-specific heavy chains). The chosen variant was preferably used over other JH gene segments in all settings (naive, immunised and antigen-specific) for the production of HCDR3 of at least 20 amino acids.

Thus, the present invention provides an IgH locus including human JH6*02 (IMGT nomenclature) as a mandatory JH gene segment. In one embodiment, the locus comprises non-human vertebrate (eg, mouse or rat) constant region gene segments downstream (ie, 3' of) the human JH6*02; and one or more VH gene segments (eg, a plurality of human VH gene segments) and one or more D gene segments (eg, a plurality of human D gene segments) upstream of (ie, 5' of) the human JH6*02. For example; the locus is comprised by a vector (eg, a DNA vector, eg, a yeast artificial chromosome (YAC), BAC or PAC). Such a vector (eg; YAC) can be introduced into a non-human vertebrate (eg, mouse or rat) cell using standard techniques (eg, pronuclear injection) so that the locus is integrated into the cell genome for expression of IgH chains comprising at least one chain whose variable domain is a product of the recombination of human JH6*02 with a VH and a D gene segment.

In another example, the locus (eg, with a completely human, rat or mouse constant region, or a human/mouse chimaeric constant region) can be provided in the genome of a non-human vertebrate (eg, mouse or rat) cell. For example, the cell is an ES cell or an antibody-producing cell (eg, an isolated B-cell, an iFS cell or a hybridoma).

In another example, the invention provides a non-human vertebrate (eg, a mouse or a rat) comprising an IgH locus of the invention which comprises a human JH6*02 gene segment, wherein the locus can express an IgH chain whose variable domain is a product of the recombination of human JH6*02 with a VH and a D gene segment. As shown in the examples, the inventors have successfully produced such mice which produce such IgH chains with VH domains based on human JH6*02. The inventors isolated and sequenced IgH chains from the mice before (naive) and after (immunised) exposure to a range of target antigens and confirmed by comparison to IMGT IgH gene segment sequences that the isolated chains (and antibodies containing these) were produced based on JH6*02. Such chains were found in naive mice, as well as in antigen-specific antibodies from immunised mice. B-cells were isolated from immunised mice, wherein the B-cells express antibodies based on JH6*02 and hybridomas were generated from the B-cells, the hybridomas expressing antigen-specific antibodies based on JH6*02. The inventors, therefore; provided the locus, vertebrate, cell and hybridoma of the invention based on the use of human JH6*02 and showed that antibodies based on JH6*02 and B-cells expressing these can be successfully produced and isolated following immunisation of the vertebrates, corresponding hybridomas being a good source of antibodies whose VH domains are based on JH6*02, eg for administration to a patient, eg, for human medicine. Furthermore, it was found possible to produce and isolated antigen-specific antibodies whose VH domains are based on JH6*02 and which had a relatively long HCDR3 (eg, 20 amino acids).

Thus, the present invention provides embodiments as in the following clauses:—

1. non-human vertebrate (optionally a mouse or a rat) or vertebrate cell whose genome comprises an immunoglobulin heavy chain locus comprising human gene segment JH6*02, one or more VH gene segments and one or more D gene segments upstream of a constant region; wherein the gene segments in the heavy chain locus are operably linked to the constant region thereof so that the mouse is capable of producing an antibody heavy chain produced by recombination of the human JH6*02 with a D segment and a VH segment.

In another example; the invention provides

A non-human vertebrate (optionally a mouse or a rat) or vertebrate cell whose genome comprises an immunoglobulin heavy chain locus comprising one, more or all of human IGHV gene segments selected from V3-21, V3-13, V3-7, V6-1, V1-8, V1-2, V7-4-1, V1-3, V1-18, V4-4, V3-9, V3-23, V3-11 and V3-20 (eg, one, more or all of V3-21*03; V3-13-01, V3-7-01, V6-1*01, V1-8*01, V1-2*02; V7-4-1-01, V1-3-01, V1-18*01, V4-4*01, V3-9*01 and V3-23*04). These segments were found in naive repertoires to be productive to produce HCDR3s of at least 20 amino acids in length. In an embodiment, the locus comprises a human JH6, eg; JH6*02.

The invention also provides a HCDR3, VH domain, antibody heavy chain or antibody having a HCDR3 size of at least 20 amino acids. Optionally, the HCDR3 or VH domain (or VH domain of the heavy chain or antibody) comprises mouse AID-pattern somatic hypermutations and/or mouse dTd-pattern mutations. This can be provided, for example, wherein VH domain is produced in a mouse comprising mouse AID and/or mouse TdT (eg, endogenous AID or TdT). See also Annu. Rev. Biochem. 2007. 76:1-22; Javier M. Di Noia and Michael S. Neuberger; "Molecular Mechanisms of Antibody Somatic Hypermutation" (in particular FIG. 1 and associated discussion on AID hotspots in mouse); and Curr Opin Immunol. 1995 April; 7(2):248-54, "Somatic hypermutation", Neuberger M S and Milstein C (in particular; discussion on hotspots in mouse); the disclosures of which are incorporated herein by reference.

These segments were found in naive repertoires to be productive in recombination with human JH6*02 to produce HCDR3s of at least 20 amino acids in length.

In an example, the vertebrate is naive. In another embodiment, the vertebrate instead is immunised with a target antigen.

In an example; the vertebrate or cell mentioned below is capable of so producing an antibody heavy chain upon immunisation with a target antigen. In an example, the vertebrate is an immunised vertebrate that produces antibody heavy chains specific for a target antigen and wherein the variable domains of the heavy chains are the product of recombination between a VH, D and JH6*02. For example, the D is selected from human D3-3, 02-15, D3-9; D4-17; D3-10; D2-2; 05-24; D6-19; D3-22; D6-13; D5-12; D1-26; D1-20; 05-18; D3-16; 02-21; D1-14; D7-27; D1-1; D6-25; D2-14 and D4-23 (eg, selected from D3-9*01; D4-17*01; D3-10*01; D2-2-02; D5-24*01; D6-19-01; D3-22*01; D6-13*01; D5-12*01; D1-26*01; D1-20*01; D5-18*01; D3-16*02; D2-21*02; D1-14*01; D7-27*02; D1-1*01; D6-25*01; D2-15*01; and D4-23*01). For example, the D is human D3-9 or D3-10. In an example, the HCDR3 length is at least 20 amino acids (eg; 20; 21, 23 or 24).

In an example of the vertebrate or cell, the genome comprises additional human JH gene segments (eg, JH2, 3, 4 and 5 gene segments).

In an example of the vertebrate or cell, the genome comprises an immunoglobulin light chain locus comprising one or more human V gene segments and one or more human J gene segments upstream of a constant region (eg, a human or a mouse lambda or kappa constant region).

For rearrangement and expression of heavy chains, the locus comprises control elements, such as an Eˆ and Sˆ between the J gene segment(s) and the constant region as is known by the skilled person. In one example, a mouse Eˆ and Sˆ is included in the heavy chain locus between the JH6*02 and the constant region (ie, in 5' to 3' order the locus comprises the JH6*02, Eˆ and Sˆ and constant region). In an example, the Eˆ and Sˆ are Eˆ and Sˆ of a mouse 129-derivedgenome (eg, a 129Sv-derived genome, eg, 129Sv/EV (such as 129S7Sv/Ev (such as from AB2.1 or AB2.2 cells obtainable from Baylor College of Medicine, Tex., USA) or 129S6Sv/Ev))); in another example, the Eˆ and Sˆ are Eˆ and Sˆ of a mouse C57BL/6-derived genome. In this respect, the locus can be constructed in the IgH locus of the genome of a cell selected from AB2.1, AB2.2, VGF1, CJ7 and FH14. VGF1 cells were established and described in Auerbach W, Dunmore J H, Fairchild-Huntress V, et al; Establishment and chimera analysis of 129/SvEv- and C57BL/6-derived mouse embryonic stem cell lines. Biotechniques 2000; 29:1024-8, 30, 32, incorporated herein by reference.

Additionally or alternatively, the constant region (or at least a Cˆ or Cˆ and gamma constant regions thereof) is a constant region (or Cˆ or Cˆ and gamma constant regions thereof) is of a genome described in the paragraph immediately above.

A suitable source of JH6*02 and other human DNA sequences will be readily apparent to the skilled person. For example, it is possible to collect a DNA sample from a consenting human donor (eg, a cheek swab sample as per the Example herein) from which can be obtained suitable DNA sequences for use in constructing a locus of the invention. Other sources of human DNA are commercially available, as will be known to the skilled person. Alternatively, the skilled person is able to construct gene segment sequence by referring to one or more databases of human Ig gene segment sequences disclosed herein.

2. The vertebrate of clause 1, wherein the vertebrate has been immunised with a target antigen and wherein the variable domain of the heavy chain is the product of recombination between a VH, D and JH6*02 and wherein the HCDR3 length is at least 20 amino acids (eg, 20, 21, 23 or 24).

Optionally, the immunised vertebrate produces an antibody heavy chain specific for a target antigen and wherein the variable domain of the heavy chain is the product of recombination between a VH, D and JH6*02 and wherein the HCDR3 length is at least 20 amino acids (eg, 20, 21, 23 or 24).

3. A non-human vertebrate cell (optionally a mouse cell or a rat cell) whose genome comprises an immunoglobulin heavy chain locus comprising human gene segment JH6*02, one or more VH gene segments and one or more D gene segments upstream of a constant region; wherein the gene segments in the heavy chain locus are operably linked to the constant region thereof for producing (eg, in a subsequent progeny cell) an antibody heavy chain produced by recombination of the human JH6*02 with a D segment and a VH segment.

4. The cell of clause 3, which is an ES cell capable of differentiation into a progeny antibody-producing cell that expresses said heavy chain.

5. The vertebrate or cell of any preceding clause, wherein the heavy chain locus comprises a human JH6*02 recombination signal sequence (RSS) operably connected 5' to the JH6*02 gene segment.

For example, the native RSS-JH6*02 sequence can be used to advantageously maintain the natural pairing between RSS and thesis JH gene segment. In this respect, the following sequence is used:—

```
                                      (SEQ ID NO: 238)
ggtttttgtggggtgaggatggacattctgccattgtgattactactact

actacggtatggacgtctggggccaagggaccacggtcaccg tctcctc

ag
```

RSSs have a common architecture: 9mer (eg, first underlined sequence above) followed by a 22 bp spacer and then a 7mer (eg, second underlined sequence above). Spacers are 23 bp+/−1 normally, while the 9 and 7mer are more conserved.

6. The vertebrate or cell of clause 5, wherein the RSS is SEQ ID NO: 238 or a sequence having an identical 9mer and 7mer sequence flanking a sequence that is at least 70% identical to the 22mer sequence of SEQ ID NO: 238.

7. The vertebrate or cell of clause 6, wherein the RSS and JH6*02 are provided as SEQ ID NO: 237.

8. The vertebrate or cell of any preceding clause, wherein the JH6*02 is the only JH6-type gene segment in the genome, 9. The vertebrate or cell of any preceding clause, wherein the JH6*02 is the closest JH gene segment to the constant region in the locus.

10. The vertebrate or cell of any preceding clause, wherein the locus comprises one, more or all human D gene segments D3-9; D4-17; D3-10; D2-2; D5-24; D6-19; D3-22; D6-13; D5-12; D1-26; D1-20; D5-18; D3-16; D2-21; D1-14; D7-27; D1-1; D6-25; D2-14; and D4-23.

For example, the locus comprises one, more or all of human D gene segments D3-9*01; D4-17*01; D3-10*01; D2-2*02; D5-24*01; D6-19*01; D3-22*01; D6-13*01; 05-12*01; D1-26*01; D1-20*01; D5-18*01; D3-16*02; D2-21*02; D1-14*01; D7-27*02; D1-1*01; D6-25*01; D2-15*01; and D4-23*01.

11. The vertebrate or cell of clause 10, wherein the locus comprises one, more or all human D gene segments D3-9, D3-10, D6-19, D4-17, D6-13, D3-22, D2-2, D2-25 and D3-3.

These D segments were found to be productive in recombination with human JH6*02 to produce HCDR3s of at least 20 amino acids in length.

In an example, the locus comprises one, more or all human D gene segments D3-9, D3-10, D6-19, D4-17, D6-13 and D3-22 (for example one, more or all of D3-9*01, D3-10*01, D6-19*01, D4-17'101, D6-13*01 and D3-22*01). These D segments were found in naive repertoires to be productive in recombination with human JH6*02 to produce HCDR3s of at least 20 amino acids in length.

In an example, the locus comprises one, more or all human D gene segments D3-10, D6-19 and D1-26 (for example, one, more or all of D3-10*01, D6-19*01 and D1-26*01), These D segments were found in immunised repertoires to be productive in recombination with human JH6*02 to produce HCDR3s of at least 20 amino acids in length.

In an example, the locus comprises one, more or all human D gene segments D3-9 and D3-10 (for example, one, more or all of D3-9*01 and D3-10*01). These D segments were found in antigen-specific repertoires to be productive in recombination with human JH6*02 to produce HCDR3s of at least 20 amino acids in length.

12. The vertebrate or cell of any preceding clause, wherein the locus comprises a plurality of human D gene segments and the JH6*02 is in human germline configuration with respect to the 3'-most human D gene segment (or all of the human D segments comprised by the locus).

In an example, the 3'-most D gene segment is D7-27. In an example, the locus comprises all of human D gene segments from D1-1 to D7-27 as present in a germline human IgH locus (eg, as shown in the IMGT database).

Alternatively or additionally, the JH6*02 is in human germline configuration with respect to one, more or all of the Eμ Sμ and constant region (eg, Cu)

13. The vertebrate or cell of any preceding clause, wherein the locus comprises one, more or all of IGHV gene segments selected from V3-21, V3-13, V3-7, V6-1, V1-8, V1-2, V7-4-1, V1-3, V1-18, V4-4, V3-9, V3-23, V3-11 and V3-20.

In an example, the locus comprises one, more or all human IGHV gene segments V3-21, V3-13, V3-7, V6-1, V1-8, V1-2, V7-4-1, V1-3, V1-18, V4-4, V3-9, V3-23 (for example, one, more or all of V3-21*03, V3-13*01, V3-7*01, V6-1*01, V1-8*01, V1-2*02, V7-4-1*01 V1-3*01, V1-18*01, V4-4*01, V3-9*01 and V3-23*04). These segments were found in naive repertoires to be productive in recombination with human JH6*02 to produce HCDR3s of at least 20 amino acids in length.

In an example, the locus comprises one, more or all human IGHV gene segments V3-7, V3-11 and V4-4 (for example, one, more or all of V3-7*01, V3-11*01 and V4-4*02). These segments were found in immunised repertoires to be productive in recombination with human JH6*02 to produce HCDR3s of at least 20 amino acids in length.

In an example, the locus comprises one, more or all human IGHV gene segments V4-4, V1-8, V3-9, V3-11 and V3-20 (for example, one, more or all of V4-4*02, V1-8*01, V3-9*01, V3-11*01 and V3-20 (eg, *d01), These segments were found in antigen-specific repertoires to be productive in recombination with human JH6*02 to produce HCDR3s of at least 20 amino acids in length.

14. The vertebrate or cell of any preceding clause, wherein the locus comprises one, more or all of human D3-9*01, D3-10*01, D6-19*01, D6-13*01, D1-26*01, IGHV1-8*01, IGHV4-61*01, IGHV6-1*01, IGHV4-4*02, IGHV1-3*01, IGHV3-66*03, IGHV3-7*01 and IGHV3-9*01.

These are gene segments that very frequently combine with JH6*02 to produce productive heavy chains and antibodies.

For example, the locus comprises one, more or all of human IGHV1-8*01, D3-9*01 and D3-10*01, These gene segments were productive with JH6*02 to produce HCDR3s of at least 20 amino acids in more than 10 antibodies.

15. An antibody-producing cell (eg, a B-cell) that is a progeny of the cell of any one of clauses 3 to 14, wherein the antibody-producing cell comprises a heavy chain locus comprising a rearranged variable region produced by recombination of human JH6*02 with a D segment and a VH segment (eg, JH6*02 with human VH3-11 (eg, VH3-11*01) and D3-9; VH3-20 (eg, VH3-20*01) and D3-10; VH4-4 (eg, VH4-4*02) and D3-10; VH3-9 (eg, VH3-9*01) and D3-10: or VH1-8 (eg, VH1-8*01) and D310).

Such a variable region would be the product of in vivo somatic hypermutation in a non-human vertebrate or cell of the invention.

16. The cell of clause 15, which is a B-cell or hybridoma that expresses a target antigen-specific antibody comprising a heavy chain that comprises a rearranged variable region produced by recombination of human JH6*02 with a D segment and a VH segment (eg, JH6*02 with human VH3-11 (eg, VH3-11*01) and D3-9; VH3-20 (eg, VH3-20*01) and D3-10; VH4-4 (eg, VH4-4*02) and D3-10; VH3-9 (eg, VH3-9*01) and D3-10; or VH1-8 (eg, VH1-8*01) and D310).

Such a variable region would be the product of in vivo somatic hypermutation in a non-human vertebrate or cell of the invention 17. The vertebrate or cell of any preceding clause, wherein the antibody heavy chain specifically binds a target antigen.

18. The vertebrate or cell of any preceding clause, wherein the antibody heavy chain has a HCDR3 length of at least 20 amino acids.

Optionally, the HCDR3 length is at least 21; 22, 23, 24, 25; 26, 27, 28; 29 or 30 amino acids. Additionally, in one example the length is no more than 35, 34, 33, 32 or 31 amino acids. For example, the HCDR3 length is 20, 21, 22, 23 or 24 amino acids.

19. The vertebrate or cell of any preceding clause, wherein the antibody heavy chain is a product of the recombination of JH6*02 with a human VH gene segment recited in clause 13 or 14 and/or a D gene segment recited in clause 10, 11 or 14.

20. The vertebrate or cell of any preceding clause, wherein all endogenous non-human vertebrate heavy chain variable region gene segments have been inactivated in the genome (Eg, by gene segment deletion or inversion).

21. The vertebrate or cell of any preceding clause, wherein the genome is homozygous for said heavy chain locus.

22. A heavy chain (eg, comprised by an antibody) isolated from a vertebrate of any one of clauses 1, 2, 5 to 14 and 17 to 21 wherein the heavy chain comprises a HCDR3 of at least 20 amino acids.

23. The heavy chain of clause 22, wherein the HCDR3 is the product of recombination of human JH6*02 with a human VH gene segment recited in clause 13 or 14 and/or a D gene segment recited in clause 10, 11 or 14.

In an example, the heavy chain is chimaeric where the C region is non-human. In an example, the heavy chain is human where the C region is human.

24. A heavy chain (eg, comprised by an antibody) whose VH variable domain is identical to the VH variable domain of the heavy chain of clause 22 or 23, and which comprises a human constant region or a human-mouse chimaeric constant region (eg, CH1 is human and the other constant domains are mouse).

25. The heavy chain of clause 22, 23 or 24, whose VH variable domain is specific for a target antigen.

26. A method for producing a heavy chain, VH domain or an antibody specific to a target antigen, the method comprising immunizing a non-human vertebrate according to any one of clauses 1, 2, 5 to 14 and 17 to 21 with the antigen and isolating the heavy chain, VH domain or an antibody specific to a target antigen or a cell producing the heavy chain, VH domain or an antibody, wherein the heavy chain, VH domain or an antibody comprises a HCDR3 that is derived from the recombination of human JH6*02 with a VH gene segment and a D gene segment.

27. A method for producing a human heavy chain or antibody comprising carrying out the method of clause 26, wherein the constant region of the locus is a non-human vertebrate (eg, mouse or rat) constant region, and then replacing the non-human constant region of the isolated heavy chain or antibody with a human constant region (eg, by engineering of the nucleic acid encoding the antibody).

28. A heavy chain, VH domain or an antibody produced by the method of clause 26 or 27. Optionally the HCDR3 length is at least 20 amino acids as herein described.

29. A B-cell or hybridoma expressing a heavy chain VH domain that is identical to the VH domain of the heavy chain of clause 22, 23 or 28.

30. A nucleic acid encoding the VH domain of the heavy chain of clause 22, 23 or 28, or encoding the heavy chain of clause 22, 23, 24, 25 or 28.

31. A vector (eg, a CHO cell or HEK293 cell vector) comprising the nucleic acid of clause 30; optionally wherein the vector is in a host cell (eg, a CHO cell or HEK293 cell).

32. A pharmaceutical composition comprising the antibody, heavy chain or VH domain (eg, comprised by an antibody) of any one of clauses 22 to 25 and 28, together with a pharmaceutically-acceptable excipient, diluent or a medicament (eg, a further antigen-specific variable domain, heavy chain or antibody).

33. The antibody, heavy chain or VH domain (eg, comprised by an antibody) of any one of clauses 22 to 25 and 28 for use in medicine (eg, human medicine).

For example, the locus comprises the following human VH gene segments

IGHV6-1
IGHV3-7
IGHV1-8
IGHV3-9
IGHV3-11
IGHV3-13
IGHV1-18
IGHV3-30
IGHV4-31
IGHV4-39 IGHV4-59

Optionally also (i) and/or (ii)

(i)
IGHV1-2 IGHV2-5 and IGHV3-21
(ii)
IGHV1-2 IGHV2-5 IGHV3-21 IGHV1-24

For example, the locus comprises the following human VH gene segment variants

IGHV6-1*01
IGHV3-7*01
IGHV1-8*01
IGHV3-9*01
IGHV3-11*01
IGHV3-13*01
IGHV1-18*01
IGHV3-30*18
IGHV4-31*03
IGHV4-39*01 and
IGHV4-59*01:

Optionally also (iii) or (iv)

(ii)
IGHV1-2*04 IGHV2-5*10 and IGHV3-21*03
(iv)
IGHV1-2*02 IGHV2-5*01 IGHV3-21*01 and IGHV1-24*01

For example, the locus comprises the following human JH gene segment variants

IGHJ2*01 IGHJ3*02
IGHJ4*02 IGHJ5*02 and IGHJ6*02

For example, the locus comprises the following human D gene segments

IGHD1-1
IGHD2-2
IGHD3-9
IGHD3-10
IGHD5-12
IGHD6-13
IGHD1-14
IGHD2-15
IGHD3-16
IGHD4-17
IGHD6-19
IGHD2-21
IGHD5-24
IGHD1-26 and
IGHD7-27 and optionally also (v) or (vi)

(v)
IGHD3-3
(vi)
IGHD3-3
IGHD4-4
IGHD5-5
IGHD6-6
IGHD1-7
IGHD2-8 and
IGHD2-8

The Present Invention Provides in a Fifth Configuration—Constant Regions Tailored to Human Use & Antibody Humanisation Additional rational design and bioinformatics has led the inventors to realise that specific human constant region variants are conserved across many diverse human populations. The inventors realised that this opens up the possibility of making a choice to humanise antibodies, chains and variable domains by using such specific constant regions in products, rather than arbitrarily choosing the human constant region (or a synthetic version of a human constant region), This aspect of the invention also enables one to tailor antibody-based drugs to specific human ethnic populations, thereby more closely matching drug to patient (and thus disease setting) than has hitherto been performed. It can be a problem in the state of the art that antibodies are humanised with an arbitrary choice of human constant region (presumably derived from one (often unknown) ethnic population or non-naturally occurring) that does not function as well in patients of a different human ethnic population. This is important, since the constant region has the major role in providing antibody effector functions, eg, for antibody recycling, cellular and complement recruitment and for cell killing.

As discussed further in WO2011066501, human IgG sub-types IgG1, IgG2, gG3 and IgG4 exhibit differential capacity to recruit immune functions, such as antibody-dependent cellular cytotoxicity (ADCC, e.g., IgG1 and IgG3), antibody-dependent cellular phagocytosis (ADCP, e.g., IgG1, IgG2, IgG3 and IgG4), and complement dependent cytotoxicity (CDC, e.g., IgG1, IgG3). Sub-type-specific engagement of such immune functions is based on selectivity for Fc receptors on distinct immune cells and the ability to bind C1q and activate the assembly of a membrane attack complex (MAC).

Among the various types, relative affinity for FcY receptors (e.g., FcYRI, FcYRIIa/b/c, FcYRIIIa/b) is high for IgG1 and IgG3, however, there is minimal affinity for IgG2 (restricted to the FcYRIIa 131H polymorphism), and IgG4 only has measurable affinity for FcYRI. Using comparative sequence analysis and co-crystal structures, the key contact residues for receptor binding have been mapped to the amino acid residues spanning the lower hinge and CH2 region. Using standard protein engineering techniques, some success in enhancing or reducing the affinity of an antibody preparation for Fc receptors and the C1q component of complement has been achieved.

Among the isotypes, IgG2 is least capable of binding the family of Fc receptors. Using IgG2 as the starting point, efforts have been made to find a mutant with diminished effector functions but which retains FcRn binding, prolonged stability, and low immunogenicity. Improved mutants of this nature may provide improved antibody therapeutics with retained safety. Human IgG1 therapeutic antibodies that bind to cell surface targets are able to engage effector cells that may mediate cell lysis of the target cell by antibody-dependent cellular cytotoxicity (ADCC) or complement dependent cytotoxicity (CDC). These mechanisms occur through interaction of the CH2 region of the antibody Fc domain to FcyR receptors on immune effector cells or with C1 q, the first component of the complement cascade. Table 19 shows the activities of different human gamma sub-types. The skilled person may choose accordingly to promote or dampen-down activity depending upon the disease setting in humans of interest. For example, use of a human gamma-1 constant region is desirable when one wishes to isolated totally human heavy chains and antibodies that have relatively high complement activation activity by the classical pathway and FcYR1 recognition in human patients. See also Mol Immunol. 2003 December; 40(9): 585-93; "Differential binding to human Fcgamma RIIa and Fcgamma RIIb receptors by human IgG wild type and mutant antibodies"; Armour K L et al, which is incorporated herein by reference.

IgG2 constant regions are well suited to producing antibodies and heavy chains according to the invention for binding to cytokines or soluble targets in humans, since IgG2 is essentially FcYRI,III-silent, FcYRIIa-active and has little Complement activity.

IgG1 constant regions have wide utility for human therapeutics, since IgG1 antibodies and heavy chains are FcYRI, II,III-active and have complement activity. This can be enhanced by using a human gamma-1 constant region that has been activated by engineering as is known in the art.

The work of the inventors has therefore identified a collection of human constant region of different isotypes from which an informed choice can be made when humanising chimaeric antibody chains (or conjugating V domains, such as dAbs or Camelid VHH, to constant regions). The collection was identified on the basis of bioinformatics analysis of the 1000 Genomes database, the inventors selecting constant region variants that are frequently occurring across several human ethnic populations, as well as those that appear with relatively high frequency within individual populations (as assessed by the number of individuals whose genomes comprise the variant). By sorting through the myriad possible sequences on this basis, the inventors have provided a collection of human constant region variants that are naturally-occurring and which can be used when rationally designing antibodies, heavy chains and other antibody-based formats that bear a human constant region. In particular, this is useful when humanising chimaeric heavy chains to produce totally human chains in which both the variable and constant regions are human. This is useful for compatibility with human patients receiving antibody-based drugs.

To this end, the invention provides the following aspects:—

1. method of producing an antibody heavy chain, the method comprising (a) providing an antigen-specific heavy chain variable domain (eg, VH (such as a human VH or dAb) or VHH or a humanised heavy chain variable domain); and (b) combining the variable domain with a human heavy chain constant region to produce an antibody heavy chain comprising (in N- to C-terminal direction) the variable domain and the constant region;

wherein the human heavy chain constant region is an IGHAref, IGHA1a, IGHA2a, IGHA2b, IGHG1ref, IGHG2ref, IGHG2a, IGHG3ref, IGHG3a, IGHG3b, IGHG4ref, IGHG4a, IGHDref, IGHEref, IGHAref, IGHMa or IGHMb constant region.

Step (b) can be carried out, eg, using recombinant DNA technology using the corresponding nucleotide sequences.

For the constant region according to any aspect of this configuration, either genomic DNA or equivalent (ie, having introns and exons and optionally also 5' UTR sequences, eg, with native or a non-native leader sequence) can be used for the constant region. For example, any of the "GENOMIC" sequences disclosed as SEQ ID NO: 365 onwards herein. Alternatively, an intronless sequence can be used, for example any of the "CDS" sequences disclosed as SEQ ID NO: 365 onwards herein (eg, with native or a non-native leader sequence).

Optionally for any aspect of this configuration of the invention, the human heavy chain constant region is an IGHAref constant region.

Optionally for any aspect of this configuration of the invention, the human heavy chain constant region is an IGHA1a constant region.

Optionally for any aspect of this configuration of the invention, the human heavy chain constant region is an IGHA2a constant region.

Optionally for any aspect of this configuration of the invention, the human heavy chain constant region is an IGHA2b constant region.

Optionally for any aspect of this configuration of the invention, the human heavy chain constant region is IGHG1ref constant region.

Optionally for any aspect of this configuration of the invention, the human heavy chain constant region is an IGHG2ref constant region.

Optionally for any aspect of this configuration of the invention, the human heavy chain constant region is an IGHG2a constant region.

Optionally for any aspect of this configuration of the invention, the human heavy chain constant region is an IGHG3ref constant region, Optionally for any aspect of this configuration of the invention, the human heavy chain constant region is an IGHG3a constant region.

Optionally for any aspect of this configuration of the invention, the human heavy chain constant region is an IGHG3b constant region.

Optionally for any aspect of this configuration of the invention, the human heavy chain constant region is an IGHG4ref constant region.

Optionally for any aspect of this configuration of the invention, the human heavy chain constant region is an IGHG4a constant region.

Optionally for any aspect of this configuration of the invention, the human heavy chain constant region is an IGHEref constant region, Optionally for any aspect of this configuration of the invention, the human heavy chain constant region is an IGHEref constant region.

Optionally for any aspect of this configuration of the invention, the human heavy chain constant region is an IGHMref constant region.

Optionally for any aspect of this configuration of the invention, the human heavy chain constant region is an IGHMa constant region.

Optionally for any aspect of this configuration of the invention, the human heavy chain constant region is an IGHMb constant region.

Optionally, a derivative (eg, a mutant or conjugate) of the heavy chain or an antibody containing the heavy chain is produced. For example, a toxic payload can be conjugated (eg, for oncology applications). For example, one or more mutations can be introduced, as is known in the art, to inactivate or enhance Fc effector function.

2. The method of aspect 1, wherein the variable domain is a human variable domain.

A human variable domain is, for example, the product of recombination in a transgenic non-human vertebrate of human VH, and JH gene segments; Alternatively, the variable domain is identified using in vitro display technology from a human VH library, eg, using phage display, ribosome display or yeast display, as is known in the art.

In another embodiment, the variable domain is a humanised variable domain, eg, comprising human frameworks with non-human (eg, mouse or rat) CDRs). Humanisation technology is conventional in the art, and will be readily known to the skilled person.

3. The method of any preceding aspect, wherein the variable domain has previously been selected from a non-human vertebrate that has been immunised with the antigen.

For example, the vertebrate (such as a mouse or rat) genome comprises a chimaeric heavy chain locus comprising a human variable region (human V, and JH gene segments) operably connected upstream of a non-human vertebrate constant region so that the locus is able to rearrange for the expression of heavy chains comprising human variable domains and non-human vertebrate constant regions.

In alternative embodiments, the variable domain is selected using an in vitro technology such as phage display, ribosome display or yeast display. In this case the variable domain may be displayed with or without an constant region, provided that it is later combined with a human constant region as per the invention.

4. The method of any preceding aspect, comprising providing an expression vector (Eg, a mammalian expression vector, such as a CHO or HEK293 vector) comprising a nucleotide sequence encoding the constant region; inserting a nucleotide sequence encoding the variable domain into the vector 5' of the constant region sequence; inserting the vector into a host cell and expressing the heavy chain by the host cell; the method further comprising isolating a heavy chain (eg, as part of an antibody) comprising the variable domain and the human constant region.

The vector comprises regulatory elements sufficient to effect expression of the heavy chain when the vector is harboured by a host cell, eg, a CHO or HEK293 cell.

5. The method of any preceding aspect; further comprising obtaining a nucleotide sequence encoding the heavy chain.

6. An antibody comprising a human heavy chain, the heavy chain comprising a variable domain that is specific for an antigen and a constant region that is an IGHAref, IGHA1a, IGHA2a, IGHA2b, IGHG1ref, IGHG2ref, IGHG2a, IGHG3ref, IGHG3a, IGHG3b, IGHG4ref, IGHG4a, IGHDref, IGHEref, IGHMref, IGHMa or IGHMb constant region.

7. A polypeptide comprising (in N- to C-terminal direction) a leader sequence, a human variable domain that is specific for an antigen and a human constant region that is an IGHAref, IGHA1a, IGHA2a, IGHA2b, IGHG1ref, IGHG2ref, IGHG2a, IGHG3ref, IGHG3a, IGHG3b, IGHG4ref, IGHG4a, IGHDref, IGHEref, IGHMref, IGHMa or IGHMb constant region; wherein (i) the leader sequence is not the native human variable domain leader sequence (eg, the leader sequence is another human leader sequence or a non-human leader sequence); and/or (ii) the variable domain comprises mouse AID-pattern somatic mutations or mouse terminal deoxynucleotidyl transferase (TdT)-pattern junctional mutations.

8. A nucleotide sequence encoding (in 5' to 3' direction) a leader sequence and a human antibody heavy chain; the heavy chain comprising a variable domain that is specific for an antigen and a constant region that is an IGHAref, IGHA1a, IGHA2a, IGHA2b, IGHG1ref, IGHG2ref, IGHG2a, IGHG3ref, IGHG3a, IGHG3b, IGHG4ref, IGHG4a, IGHDref, IGHEref, IGHMref, IGHMa or IGHMb constant region; and the leader sequence being operable for expression (eg, in a mammalian CHO or HEK293 cell) of the heavy chain and wherein the leader sequence is not the native human variable domain leader sequence (eg, the leader sequence is another human leader sequence or a non-human leader sequence).

In an example, the leader sequence is (SEQ ID NO: 480)
ATGGGCTGGTCCTGCATCATCCTGTTTCTGGTGGCCACCGCCACCGGCG

TGCACAGC

Which translates to (SEQ ID NO: 481)
MGWSCIILFLVATATGVHS

9. A nucleotide sequence encoding (in 5' to 3' direction) a promoter and a human antibody heavy chain, the heavy chain comprising a variable domain that is specific for an antigen and a constant region that is an IGHAref, IGHA1a, IGHA2a, IGHA2b, IGHG1ref, IGHG2ref, IGHG2a, IGHG3ref, IGHG3a, IGHG3b, IGHG4ref, IGHG4a, IGHDref, IGHEref, IGHMref, IGHMa or IGHMb constant region; and the promoter being operable for expression (eg, in a mammalian CHO or HEK293 cell) of the heavy chain and wherein the promoter is not the native human promoter.

In one embodiment, the promoter sequence is a human IGK 3-15 promoter.

10. The antibody, polypeptide or nucleotide sequence of any one of aspects 6 to 9, wherein the variable domain comprises mouse AID-pattern somatic mutations and/or mouse terminal deoxynucleotidyl transferase (TdT)-pattern junctional mutations.

For example, one way, in any aspect of this configuration of the invention, to provide mouse AID-pattern somatic mutations and/or mouse terminal deoxynucleotidyl transferase (TdT)-pattern junctional mutations is to select a variable domain from a non-human vertebrate or cell. For example, a vertebrate or cell as disclosed herein.

11. A vector (eg, a CHO cell or HEK293 cell vector) comprising the nucleic acid of aspect 8, 9 or 10; optionally wherein the vector is in a host cell (eg, a CHO cell or HEK293 cell).

12. A pharmaceutical composition comprising the antibody or polypeptide of any one of aspects 6, 7 and 10, together with a pharmaceutically-acceptable excipient, diluent or a medicament (eg, a further antigen-specific variable domain, antibody chain or antibody).

13. The antibody or polypeptide of any one of aspects 6, 7 and 10 for use in treating and/or preventing a medical condition in a human patient.

14. Use of the antibody or polypeptide of any one of aspects 6, 7 and 10 for the manufacture of a medicament for treating and/or preventing a medical condition in a human patient.

15, The antibody, polypeptide or use of aspect 13 or 14, wherein the human is a member of a human population selected from population numbers 1-14, wherein the populations are numbered as follows (population labels being according to 1000 Genomes Project nomenclature)

1=ASW;
2=CEU;
3=CHB;
4=CHS;
5=CLM;
6=FIN;
7=GBR;
8=IBS;
9=JPT;
10=LWK;
11=MXL;
12=PUR;
13=TSI;
14=YRI.

16. The antibody, polypeptide or use of aspect 15, wherein the constant region is a (i) IGHA1a constant region and the human population is selected from any population number 1-14;

(ii) IGHA2a constant region and the human population is selected from any population number 1-14;

(iii) IGHA2b constant region and the human population is selected from any population number 1-14;

(iv) IGHG2a constant region and the human population is selected from any population number 1-9 and 11-13;

(v) IGHG3a constant region and the human population is selected from any population number 1-14;

(vi) IGHG3b constant region and the human population is selected from any population number 1-8 and 11-13, (vii) IGHG4a constant region and the human population is selected from any population number 1-9 and 11-13;

(viii) IGHMa constant region and the human population is selected from any population number 1-14; or (ix) IGHMb constant region and the human population is selected from any population number 1-14;

Wherein the populations are numbered as follows (population labels being according to 1000 Genomes Project nomenclature)

1=ASW;
2=CEU;
3=CHB,
4=CHS,
5=CLM;
6=FIN;
7=GBR;
8=IBS;
9=JPT;
10=LWK;
11=MXL;
12=PUR;
13=TSI;
14=YRI.

17. A vector (eg, a CHO cell or HEK293 cell vector) comprising a IGHG1ref, IGHG2ref, IGHG2a, IGHG3ref, IGHG3a, IGHG3b, IGHG4ref or IGHG4a constant region nucleotide sequence that is 3' of a cloning site for the insertion of a human antibody heavy chain variable domain nucleotide sequence, such that upon insertion of such a variable domain sequence the vector comprises (in 5' to 3' direction) a promoter, a leader sequence, the variable domain sequence and the constant region sequence so that the vector is capable of expressing a human antibody heavy chain when present in a host cell.

The Present Invention Provides in a Sixth Configuration—

Multiple Variants in the Same Genome Cis or Trans

The inventors' analysis has revealed groupings of naturally-occurring human antibody gene segment variants as set out in Table 13 and Table 14. This revealed the possibility of producing transgenic genomes in non-human vertebrates and cells wherein the genomes contain more than the natural human complement of specific human gene segments. In one example, this can be achieved by providing more than the natural human complement of a specific gene segment type on one or both of the respective Ig locus (eg, one or both chromosomes harbouring IgH in a mouse genome or mouse cell genome).

To this end, this configuration of the invention provides the following (as set out in numbered paragraphs):—

1. A non-human vertebrate (eg, a mouse or rat) or a non-human vertebrate cell (eg, an ES cell or a B-cell) having a genome comprising at least 3 human variable region gene segments of the same type (eg, at least 3 human VH6-1 gene segments, at least 3 human JH6 gene segments, at least 3 human VK1-39 gene segments, at least 3 human D2-2 gene segments or at least 3 human JK1 gene segments), wherein at least two of the human gene segments are variants that are not identical to each other.

For example, the genome comprises a variable region that comprises V, D and J gene segments (for the variable region of a heavy chain locus) or V and J gene segments (for the variable region of a light chain locus) upstream of a constant region for expression of heavy or light chains respectively.

In an alternative, the skilled person can choose to provide more than the wild type human complement of a specific gene segment type by providing several copies of one variant type of the human gene segment. Thus, there is provided A non-human vertebrate (eg, a mouse or rat) or a non-human vertebrate cell (eg, an ES cell or a B-cell) having a genome comprising at least 3 human variable region gene segments of the same type (eg, at least 3 human VH6-1 gene segments, at least 3 human JH6 gene segments, at least 3 human VK1-39 gene segments, at least 3 human D2-2 gene segments or at least 3 human JK1 gene segments), wherein the human gene segments are identical variants.

For example, the genome comprises a variable region that comprises V, D and J gene segments (for the variable region of a heavy chain locus) or V and J gene segments (for the variable region of a light chain locus) upstream of a constant region for expression of heavy or light chains respectively.

2. A non-human vertebrate (eg, a mouse or rat) or a non-human vertebrate cell (eg, an ES cell or a B-cell) having a genome comprising at least 2 different non-endogenous variable region gene segments of the same type (eg, at least 2 human VH6-1 gene segments, at least 3 human JH6 gene segments, at least 2 human VK1-39 gene segments, at least 2 human D2-2 gene segments or at least 2 human JK1 gene segments) cis at the same Ig locus.

In an alternative, the skilled person can choose to provide more than the wild type human complement of a specific gene segment type by providing several copies of one variant type of the human gene segment. Thus, there is provided A non-human vertebrate (eg, a mouse or rat) or a non-human vertebrate cell (eg, an ES cell or a B-cell) having a genome comprising at least 2 non-endogenous variable region gene segments of the same variant type (eg, at least 2 human JH6*02 gene segments) cis at the same Ig locus.

3. A non-human vertebrate (eg, a mouse or rat) or a non-human vertebrate cell (eg, an ES cell or a B-cell) having a genome comprising at least 2 different human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments) trans at the same Ig locus; and optionally a third human gene segment of the same type, wherein the third gene segment is cis with one of said 2 different gene segments.

In an alternative, the skilled person can choose to provide more than the wild type human complement of a specific gene segment type by providing several copies of one variant type of the human gene segment. Thus, there is provided A non-human vertebrate (eg, a mouse or rat) or a non-human vertebrate cell (eg, an ES cell or a B-cell) having a genome comprising at least 2 different human variable region gene segments of the same variant type (eg, at least 2 human JH6*02 gene segments) trans at the same Ig locus; and optionally a third human gene segment of the same variant type, wherein the third gene segment is cis with one of said 2 different gene segments.

4. A population of non-human vertebrates (eg, mice or rats) comprising a repertoire of human variable region gene segments, wherein the plurality comprises at least 2 human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), a first of said different gene segments is provided in the genome of a first vertebrate of the population, and a second of said different gene segments being provided in the genome of a second vertebrate of the population, wherein the genome of the first vertebrate does not comprise the second gene segment.

5. A non-human vertebrate (eg, a mouse or rat) or a non-human vertebrate cell (eg, an ES cell or a B-cell) having a genome comprising at least 2 different non-endogenous variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein the gene segments are derived from the genome sequence of different human individuals that are not genetically related over at least 3 generations.

6. A method of enhancing the human immunoglobulin gene diversity of a non-human vertebrate (eg, a mouse or rat), the method comprising providing the vertebrate with a genome comprising at least 3 human variable region gene segments of the same type (eg, at least 3 human VH6-1 gene segments, at least 3 human JH6 gene segments, at least 3 human VK1-39 gene segments, at least 3 human D2-2 gene segments or at least 3 human JK1 gene segments), wherein at least two of the human gene segments are variants that are not identical to each other.

7. A method of enhancing the immunoglobulin gene diversity of a non-human vertebrate (eg, a mouse or rat), the method comprising providing the vertebrate with a genome comprising at least 2 different non-endogenous variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments) cis at the same Ig locus.

8. A method of enhancing the immunoglobulin gene diversity of a non-human vertebrate (eg, a mouse or rat), the method comprising providing the vertebrate with a genome comprising at least 2 different human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments) trans at the same Ig locus: and optionally a third human gene segment of the same type, wherein the third gene segment is cis with one of said 2 different gene segments.

9. A method of providing an enhanced human immunoglobulin variable region gene segment repertoire, the method comprising providing a population of non-human vertebrates (eg, a mouse or rat) comprising a repertoire of human variable region gene segments, wherein the method comprises providing at least 2 different human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein a first of said different gene segments is provided in the genome of a first vertebrate of the population, and a second of said different gene segments is provided in the genome of a second vertebrate of the population, wherein the genome of the first vertebrate does not comprise the second gene segment.

10. A method of enhancing the human immunoglobulin gene diversity of a non-human vertebrate (eg, a mouse or rat), the method comprising providing the vertebrate with a genome comprising at least 2 different non-endogenous variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein the gene segments are derived from the genome sequence of different human individuals that are not genetically related over at least 3 generations.

11. The vertebrate, cell or method of any preceding paragraph, wherein at least 2 or 3 of said different gene segments are provided cis at the same Ig locus in said genome.

12. The vertebrate, cell or method of any preceding paragraph, wherein the gene segments are derived from the genome sequence of different human individuals that are not genetically related over at least 3 generations.

13. The vertebrate, cell or method of any preceding paragraph, wherein the gene segments are derived from the genome sequence of two or more different human individuals; optionally wherein the different human individuals are from different human populations.

14. The vertebrate, cell or method of paragraph 13, wherein the individuals are not genetically related.

15. A method of enhancing the human immunoglobulin gene diversity of a non-human vertebrate (eg, a mouse or rat), the method comprising providing the vertebrate with a genome comprising at least 2 human variable region gene segments of the same type (eg, at least 2 human VH6-1 gene segments, at least 2 human JH6 gene segments, at least 2 human VK1-39 gene segments, at least 2 human D2-2 gene segments or at least 2 human JK1 gene segments), wherein the gene segments are derived from the genome sequence of different human individuals that are not genetically related over at least 3 generations; optionally wherein at least 2 or 3 of said different gene segments are provided at the same Ig locus in said genome.

16. The method of paragraph 15, wherein the different human individuals are from different human populations.

17. The method of paragraph 15, wherein the individuals are not genetically related.

18. The vertebrate, cell or method of preceding paragraph, wherein at least one of the different segments is a synthetic mutant of a human germline gene segment.

19. The vertebrate, cell or method of any preceding paragraph, wherein each of said gene segments occurs in 10 or more different human populations.

20. The vertebrate, cell or method of preceding paragraph, wherein each of said gene segments has a human frequency of 5% or greater (eg, 10, 20; 25; 30; 35, 40, 45, 50, 55, 60, 65, 70, 75, 80, 85, 90, or 95% or greater).

In this respect, the skilled person can be guided by the information provided in Table 14. Frequency can, for example, be cumulative frequency in the 1000 Genomes database.

21. The vertebrate, cell or method of paragraph 20, wherein each of said gene segments occurs in 10 or more different human populations.

22. The vertebrate, cell or method of any preceding paragraph, wherein each of said gene segments occurs in the 1000 Genomes database in more than 50 individuals.

23. The vertebrate, cell or method of preceding paragraph, wherein each of said gene segments (i) has a human frequency of 5% or greater (eg, 10, 20, 25, 30, 35, 40, 45, 50, 55, 60, 65, 70, 75, 80, 85, 90, or 95% or greater); and (ii) occurs in 10 or more different human populations.

In this respect, the skilled person can be guided by the information provided in Table 14.

Frequency can, for example, be cumulative frequency in the 1000 Genomes database.

24. A non-human vertebrate (eg, a mouse or rat) or a non-human vertebrate cell (eg, an ES cell or a B-cell) having a genome comprising first and second human Ig locus gene segments of the same type (eg, first and second human JH6 gene segments; or first and second IgG2 gene segments; or first and second human Jλ7 gene segments), wherein the first gene segment is a gene segment selected from Table 14 (eg, IGHJ6-a) and the second gene segment is the corresponding reference sequence (eg, IGHJ6 ref; SEQ ID NO: 244).

Table 14 lists commonly-occurring natural human variants. It can be seen that these occur across many human populations and thus usefully have wide applicability for human antibody-based drugs.

For example, the gene segments are provided as targeted insertions into an endogenous non-human vertebrate Ig locus. Alternatively, random integration (eg, using YACs) as is know in the art can be performed.

For example, the genome comprises a variable region that comprises V, D and J gene segments (for the variable region of a heavy chain locus) or V and J gene segments (for the variable region of a light chain locus) upstream of a constant region for expression of heavy or light chains respectively.

In another embodiment, the invention enables the skilled person to select two or more different naturally-occurring human gene segment variants for combination into the genome of a non-human vertebrate or cell. A reference sequence need not be included. It may be desirable to use one or more rare gene segments to increase diversity of the repertoire. Additionally or alternatively, it may be desirable to include a mixture of frequent and rare variants of the same type to provide repertoire diversity. The variants may be chosen additionally or alternatively to tailor the gene segment inclusion to one or more specific human populations as indicated by the information provided in Table 13 or Table 14.

Thus, the invention provides

A non-human vertebrate (eg, a mouse or rat) or a non-human vertebrate cell (eg, an ES cell or a B-cell) having a genome comprising first and second human Ig locus gene segments of the same type (eg, first and second human JH6 gene segments; or first and second IgG2 gene segments; or first and second human Jλ7 gene segments), wherein the gene segments are gene segments selected from Table 13 or Table 14; and optionally wherein one or more of the gene segments appears in Table 14 (eg, IGHJ6-a) or is a reference sequence (eg, IGHJ6 ref; SEQ ID NO: 244).

25. The vertebrate or cell of paragraph 24, wherein the genome comprises a third human gene segment of said type, the third gene segment being different from the first and second gene segments.

26. The vertebrate or cell of paragraph 24 or 25, wherein the first and second gene segments are cis on the same chromosome; and optionally the third gene segment is also cis on said chromosome.

27. The vertebrate or cell of paragraph 26, wherein the gene segments are targeted insertions into an endogenous non-human Ig locus.

For example, the gene segments are heavy chain gene segments and the non-human locus is an IgH locus. For example, the gene segments are light chain (kappa or lambda) gene segments and the non-human locus is an IgL locus.

28. The vertebrate or cell of paragraph 24 or 25, wherein the first and second gene segments are trans on different chromosomes.

Thus, the chromosomes are the same type (eg, both mouse chromosome 6 or rat chromosome 4).

29. The vertebrate or cell of any one of paragraphs 24 to 28, wherein the first gene segment is a gene segment selected from any one of Tables 1 to 7 and 9 to 14 (eg, selected from Table 13 or 14) and the second gene segment is the corresponding reference sequence.

30. A population of non-human vertebrates (eg, mice or rats) comprising first and second human Ig locus gene segments of the same type (eg, first and second human JH6 gene segments; or first and second IgG2 gene segments; or first and second human Jλ7 gene segments), wherein the first gene segment is a gene segment selected from any one of Tables 1 to 7 and 9 to 14 (eg, Table 13 or 14) (eg, IGHJ6-a) and the second gene segment is the corresponding reference sequence (eg, SEQ ID NO: 7), wherein the first gene segment is provided in the genome of a first vertebrate of the population, and the second gene segment is provided in the genome of a second vertebrate of the population.

31. The population of paragraph 30, wherein the genome of the first vertebrate does not comprise the second gene segment.

32. The population of paragraph 30 or 31, wherein the population comprises a third human gene segment of said type, the third gene segment being different from the first and second gene segments and optionally wherein the first and third gene segments are present in the genome of the first vertebrate.

33. The population of paragraph 30, 31 or 32, wherein the gene segments are targeted insertions into an endogenous non-human Ig locus in the respective genome.

For example, the gene segments are heavy chain gene segments and the non-human locus is an IgH locus. For example, the gene segments are light chain (kappa or lambda) gene segments and the non-human locus is an IgL locus.

34. The population of any one of paragraphs 30 to 33, wherein the first gene segment is a gene segment selected from any one of Tables 1 to 7 and 9 to 14 (eg, Table 13 or 14) and the second gene segment is the corresponding reference sequence.

35. A method of enhancing the human immunoglobulin gene diversity of a non-human vertebrate (eg, a mouse or rat), the method comprising providing the vertebrate with a genome comprising first and second human Ig locus gene segments of the same type (eg, first and second human JH6 gene segments; or first and second IgG2 gene segments; or first and second human Jλ7 gene segments), wherein the first gene segment is a gene segment selected from any one of Tables 1 to 7 and 9 to 14 (eg, Table 13 or 14) (eg, IGHJ6-a) and the second gene segment is the corresponding reference sequence (eg, SEQ ID NO: 7), 36. A method of providing an enhanced human immunogolobulin gene segment repertoire, the method comprising providing a population according to any one of paragraphs 30 to 33.

Variants Prevalent in Few Populations

In another aspect, it is of note that certain human gene segment variants may appear relatively frequently in one or a small number of populations, but is not found prevalently across many different human populations. There is thinking that specific germline gene segment repertoires have evolved in individual human ethnic populations due to iterative exposure to antigens (eg, disease pathogen antigens) to which the population is often exposed. Repeated exposure and mutation may have lead to the evolution of gene segment variants that can provide an effective response to the antigen (pathogen) in the population, and this may explain the conservation of the gene segments in those populations (as opposed to other human ethnic populations that may not have frequently encountered the antigen). With this in mind, the inventors identified gene segment variants from their analysis that are relatively prevalent in a small number of human populations, and not across many populations. The inventors realized that inclusion of one or more of such gene segments in the configurations of the invention (eg, in transgenic Ig loci, vertebrates and cells) would be useful for producing antibodies, Ig chains and variable domains that can address antigens (eg, disease-causing antigens or pathogens) to which the small number of human populations may become exposed. Such products would be useful for treating and/or preventing disease or medical conditions in members of such a population. This aspect could also be useful for addressing infectious disease pathogens that may have been common in the small number of populations, but which in the future or relatively recently in evolution has become a more prevalent disease-causing pathogen in other human populations (ie, those not listed in Table 13 against the gene segment variant(s) in question). To this end, from the 1000 Genomes database the inventors have identified the gene segment variants listed in Table 20.

Thus, according to any configuration or aspect described herein, one, more or all of the gene segments used in the present invention can be a gene segment listed in Table 20A, 20B, 20C or 20D.

Multiple JH Gene Segment Variants

A specific application of this configuration is the provision of multiple human JH gene segments as follows.

A non-human vertebrate (eg, a mouse or rat) or a non-human vertebrate cell (eg, an ES cell or a B-cell) having a genome comprising at least 3 human JH gene segments of the same type (JH1, JH2, JH3, JH4, JH5 or JH6), wherein at least two of the human JH gene segments are variants that are not identical to each other.

In an example, any cell of the invention is an isolated cell. An "isolated" cell is one that has been identified, separated and/or recovered from a component of its production environment (eg, naturally or recombinantly). Preferably, the isolated cell is free of association with all other components from its production environment, eg, so that the cell can produce an antibody to an FDA-approvable or approved standard. Contaminant components of its production environment, such as that resulting from recombinant transfected cells, are materials that would typically interfere with research, diagnostic or therapeutic uses for the resultant antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Ordinarily, however, an isolated cell will be prepared by at least one purification step.

A non-human vertebrate (eg, a mouse or rat) or a non-human vertebrate cell (eg, an ES cell or a B-cell) having a genome comprising at least 2 different non-endogenous JH gene segments (eg, human gene segments) of the same type (JH1, JH2, JH3, JH4, JH5 or JH6) cis at the same Ig (eg, IgH, eg, endogenous IgH, eg, mouse or rat IgH) locus. In an example, the genome comprises a human VH, D and JH repertoire comprising said different JH gene segments. Optionally the non-endogenous JH gene segments are non-mouse or non-rat, eg, human JH gene segments. In an example one or more or all of the non-endogenous gene segments are synthetic.

A non-human vertebrate (eg, a mouse or rat) or a non-human vertebrate cell (eg, an ES cell or a B-cell) having a genome comprising at least 2 different human JH gene segments of the same type (JH1, JH2, JH3, JH4, JH5 or JH6) trans at the same Ig (eg, IgH, eg, endogenous IgH, eg, mouse or rat IgH) locus; and optionally a third human JH gene segments of the same type, wherein the third JH is cis with one of said 2 different JH gene segments.

A population of non-human vertebrates (eg, mice or rats) comprising a repertoire of human JH gene segments, wherein the plurality comprises at least 2 different human JH gene segments of the same type (JH1, JH2, JH3, JH4, JH5 or JH6), a first of said different JH gene segments is provided in the genome of a first vertebrate of the population, and a second of said different JH gene segments being provided in the genome of a second vertebrate of the population; wherein the genome of the first vertebrate does not comprise the second JH gene segment.

A non-human vertebrate (eg, a mouse or rat) or a non-human vertebrate cell (eg, an ES cell or a B-cell) having a genome comprising at least 2 different non-endogenous (eg, human) JH gene segments of the same type (JH1; JH2, JH3, JH4, JH5 or JH6), wherein the JH gene segments are derived from the genome sequence of different human individuals that are not genetically related over at least 3 generations (eg, 3, 4, 5 or 6 generations). Optionally the non-endogenous JH gene segments are human JH gene segments. In an example one or more or all of the non-endogenous gene segments are synthetic.

A method of enhancing the human immunoglobulin gene diversity of a non-human vertebrate (eg, a mouse or rat), the method comprising providing the vertebrate with a genome comprising at least 3 human JH gene segments of the same type (JH1, JH2, JH3, JH4; JH5 or JH6); wherein at least two of the human JH gene segments are variants that are not identical to each other.

A method of enhancing the immunoglobulin gene diversity of a non-human vertebrate (eg, a mouse or rat), the method comprising providing the vertebrate with a genome comprising at least 2 different non-endogenous (eg, human) JH gene segments of the same type (JH1, JH2, JH3, JH4; JH5 or JH6) cis at the same Ig (eg; IgH, eg, endogenous IgH, eg, mouse or rat IgH) locus). Optionally the non-endogenous JH gene segments are non-mouse or non-rat, eg, human JH gene segments. In an example one or more or all of the non-endogenous gene segments are synthetic.

A method of enhancing the immunoglobulin gene diversity of a non-human vertebrate (eg, a mouse or rat), the method comprising providing the vertebrate with a genome comprising at least 2 different human JH gene segments of the same type (JH1, JH2, JH3, JH4, JH5 or JH6) trans at the same Ig (eg, IgH, eg; endogenous IgH, eg, mouse or rat IgH) locus; and optionally a third human JH gene segments of the same type; wherein the third JH is cis with one of said 2 different JH gene segments.

A method of providing an enhanced human immunoglobulin JH gene segment repertoire; the method comprising providing a population of non-human vertebrates (eg, a mouse or rat) comprising a repertoire of human JH gene segments, wherein the method comprises providing at least 2 different human JH gene segments of the same type (JH1, JH2; JH3, JH4, JH5 or JH6), wherein a first of said different JH gene segments is provided in the genome of a first vertebrate of the population; and a second of said different JH gene segments is provided in the genome of a second vertebrate of the population, wherein the genome of the first vertebrate does not comprise the second JH gene segment.

A method of enhancing the human immunoglobulin gene diversity of a non-human vertebrate (eg, a mouse or rat), the method comprising providing the vertebrate with a genome comprising at least 2 different non-endogenous (eg, human) JH gene segments of the same type (JH1, JH2, JH3, JH4, JH5 or JH6), wherein the JH gene segments are derived from the genome sequence of different human individuals that are not genetically related over at least 3 generations (eg, 3, 4, 5, or 6 generations). Optionally the non-endogenous JH gene segments are human JH gene segments. In an example one or more or all of the non-endogenous gene segments are synthetic.

In an example of the vertebrate or cell or the method of the invention at least 2 or 3 of said different gene segments are provided cis at the same Ig locus in said genome.

In an example of the vertebrate or cell or the method of the invention the JH gene segments are derived from the genome sequence of different human individuals that are not genetically related over at least 3 generations (eg, 3, 4, 5, or 6 generations).

In an example of the vertebrate or cell or the method of the invention the JH gene segments are derived from the genome sequence of two or more different human individuals; optionally wherein the different human individuals are from different human populations.

In an example of the vertebrate or cell or the method of the invention the individuals are not genetically related (eg, going back 3, 4, 5; or 6 generations).

In an example of the vertebrate or cell or the method of the invention at least one of the different JH segments is a synthetic mutant of a human germline JH gene segment.

The invention also provides a method of enhancing the human immunoglobulin gene diversity of a non-human vertebrate (eg, a mouse or rat), the method comprising providing the vertebrate with a genome comprising at least 2 human JH gene segments of the same type (JH1, JH2, JH3, JH4, JH5 or JH6), wherein the JH gene segments are derived from the genome sequence of different human individuals that are not genetically related over at least 3 generations (eg, 3, 4, 5, or 6 generations); optionally wherein at least 2 or 3 of said different gene segments are provided at the same IgH locus in said genome.

In an example of the vertebrate or cell or the method of this embodiment of the invention the genome comprises a substantially complete functional repertoire of human JH gene segment types supplemented with one, two or more human JH gene segments, wherein said substantially complete functional repertoire and the supplementary JH gene segments are not found together in the germline genome of a human individual.

In an example of the population of the invention, the population comprises a substantially complete functional repertoire of human JH gene segment types supplemented with one, two or more human JH gene segments, wherein said substantially complete functional repertoire and the supplementary JH gene segments are not found together in the germline genome of a human individual.

A non-human vertebrate (eg, a mouse or rat) or a non-human cell (eg, an ES cell or a B-cell) having a genome comprising a substantially complete functional repertoire of human JH gene segment types supplemented with one, two or more human JH gene segments, wherein said substantially complete functional repertoire and the supplementary JH gene segments are not found together in the germline genome of a human individual.

A population of non-human vertebrates (eg, mice or rats) comprising a substantially complete functional repertoire of human JH gene segment types supplemented with one, two or more human JH gene segments, wherein said substantially complete functional repertoire and the supplementary JH gene segments are not found together in the germline genome of a human individual.

In an example of the vertebrate or the population; at least one of said JH gene segments is SEQ ID NO: 1, 2, 3 or 4. For example, at least one of said JH gene segments is SEQ ID NO: 1 and at least one, two or more of said supplementary JH gene segments is a variant according to any example above. For example, at least one of said JH gene segments is SEQ ID NO: 2 and at least one; two or more of said supplementary JH gene segments is a variant according to any one of the examples above. For example; at least one of said JH gene segments is SEQ ID NO: 2 and at least one, two or more of said supplementary JH gene segments is a variant according to any one of the examples above.

In an embodiment, the non-human vertebrate or vertebrate cell of the invention comprises a genome that comprises VH, D and JH gene repertoires comprising human gene segments, the JH gene repertoire (eg, a human JH gene segment repertoire) comprising a plurality of JH1 gene segments provided by at least 2 different JH1 gene segments in cis at the same Ig locus in said genome;

a plurality of JH2 gene segments provided by at least 2 different JH2 gene segments in cis at the same Ig locus in said genome;

a plurality of JH3 gene segments provided by at least 2 different JH3 gene segments in cis at the same Ig locus in said genome;

a plurality of JH4 gene segments provided by at least 2 different JH4 gene segments in cis at the same Ig locus in said genome;

a plurality of JH5 gene segments provided by at least 2 different JH5 gene segments in cis at the same Ig locus in said genome; and/or a plurality of JH6 gene segments provided by at least 2 different JH6 gene segments in cis at the same Ig locus in said genome;

optionally wherein the JH gene segments are derived from the genome sequence of two or more different human individuals.

Optionally said at least 2 different JH gene segments are human gene segments or synthetic gene segments derived from human gene segments.

Optionally, the Ig locus is a IgH locus, eg, an endogenous locus, eg, a mouse or rat IgH locus.

In an embodiment, the non-human vertebrate or vertebrate cell of the invention comprises a genome that comprises VH, D and JH gene repertoires comprising human gene segments, the JH gene repertoire (eg, a human JH gene segment repertoire) comprising a plurality of JH1 gene segments provided by at least different JH1 gene segments; a plurality of JH2 gene segments provided by at least 3 different JH2 gene segments; a plurality of JH3 gene segments provided by at least 3 different JH3 gene segments; a plurality of JH4 gene segments provided by at least 3 different JH4 gene segments; a plurality of JH5 gene segments provided by at least 3 different JH5 gene segments; and/or a plurality of JH6 gene segments provided by at least 3 different JH6 gene segments; optionally wherein the JH gene segments are derived from the genome sequence of two or three different human individuals;

optionally wherein at least 2 or 3 of said different gene segments are provided in cis at the same Ig locus in said genome.

Optionally said at least 3 different JH gene segments are human gene segments or synthetic gene segments derived from human gene segments.

Optionally, the Ig locus is a IgH locus, eg, an endogenous locus, eg, a mouse or rat IgH locus.

Optionally in the vertebrate or cell the different human individuals are from different human populations.

Optionally in the vertebrate or cell the individuals are not genetically related (eg, Going back 3, 4, 5 or 6generations).

Optionally in the vertebrate or cell at least one of the different JH segments is a synthetic mutant of a human germline JH gene segment.

In an embodiment of a non-human vertebrate or vertebrate cell (optionally an ES cell or B-cell) according to the invention, the vertebrate or cell genome comprises human VH, D and JH gene repertoires, the JH gene repertoire (eg, a human JH gene repertoire) comprising a plurality of JH1 gene segments provided by at least 2 different human JH1 gene segments, optionally in cis at the same Ig locus in said genome;

a plurality of JH2 gene segments provided by at least 2 different human JH2 gene segments, optionally in cis at the same Ig locus in said genome;

a plurality of JH3 gene segments provided by at least 2 different human JH3 gene segments, optionally in cis at the same Ig locus in said genome;

a plurality of JH4 gene segments provided by at least 2 different human JH4 gene segments, optionally in cis at the same Ig locus in said genome;

a plurality of JH5 gene segments provided by at least 2 different human JH5 gene segments, optionally in cis at the same Ig locus in said genome; and/or a plurality of JH6 gene segments provided by at least 2 different human JH6 gene segments, optionally in cis at the same Ig locus in said genome;

wherein the JH gene segments are derived from the genome sequence of different human individuals that are not genetically related over at least 3 generations (eg, 3, 4, 5 or 6 generations).

Optionally said at least 2 different JH gene segments are human gene segments or synthetic gene segments derived from human gene segments.

Optionally, the Ig locus is a IgH locus, eg, an endogenous locus, eg, a mouse or rat IgH locus. Optionally in the vertebrate or cell the human individuals are from different human populations.

JH5

An embodiment provides a vertebrate, cell or population of the invention whose genome comprises a plurality of JH5 gene segments, wherein the plurality comprises a human JH5 gene variant of SEQ ID NO: 1, wherein the variant comprises a nucleotide mutation at one or more positions corresponding to positions 106,330,024
106,330,027
106,330,032
106,330,041
106,330,44
106,330,45
106,330,62
106,330,63
106,330,65
106,330,66
106,330,67
106,330,68 and
106,330,071 on human chromosome 14.

In the vertebrate, cell or population optionally the plurality comprises a human JH5 gene variant of SEQ ID NO: 1, wherein the variant comprises a guanine at a position corresponding to position 106,330,067 on human chromosome 14; and optionally no further mutation from the sequence of SEQ ID NO: 1.

Optionally the variant comprises additionally a mutation at a position corresponding to (i) position 106,330,071 on human chromosome 14 (optionally the additional mutation being a guanine); (ii) position 106,330,066 on human chromosome 14 (optionally the additional mutation being a guanine); and/or (iii) position 106,330,068 on human chromosome 14 (optionally the additional mutation being a thymine).

Optionally the plurality comprises a human JH5 gene variant of SEQ ID NO: 1, wherein the variant comprises a guanine at a position corresponding to position 106,330,071 on human chromosome 14; and optionally no further mutation from the sequence of SEQ ID NO: 1.

Optionally the variant comprises additionally a mutation at a position corresponding to (i) position 106,330,063 on human chromosome 14 (optionally the additional mutation being an adenine); and/or (ii) position 106,330,067 on human chromosome 14 (optionally the additional mutation being a guanine).

Optionally the plurality comprises a human JH5 gene variant of SEQ ID NO: 1, wherein the variant comprises a cytosine at a position corresponding to position 106,330,045 on human chromosome 14; and optionally no further mutation from the sequence of SEQ ID NO: 1.

Optionally the plurality comprises a human JH5 gene variant of SEQ ID NO: 1, wherein the variant comprises an adenine at a position corresponding to position 106,330,044 on human chromosome 14; and optionally no further mutation from the sequence of SEQ ID NO: 1.

Optionally the variant comprises additionally a mutation at a position corresponding to (i) position 106.330.66 on human chromosome 14 (optionally the additional mutation being a guanine); and/or (ii) position 106,330,068 on human chromosome 14 (optionally the additional mutation being a thymine).

Optionally the plurality comprises a human JH5 gene variant of SEQ ID NO: 1, wherein the variant comprises a guanine at a position corresponding to position 106,330,066 on human chromosome 14; and optionally no further mutation from the sequence of SEQ ID NO: 1.

Optionally the variant comprises additionally a mutation at a position corresponding to (i) position 106,330.67 on human chromosome 14 (optionally the additional mutation being a guanine); and/or (ii) position 106,330,068 on human chromosome 14 (optionally the additional mutation being a thymine).

Optionally the plurality comprises a human JH5 gene variant of SEQ ID NO: 1, wherein the variant comprises a thymine at a position corresponding to position 106,330,068 on human chromosome 14; and optionally no further mutation from the sequence of SEQ ID NO: 1.

Optionally the variant comprises additionally a mutation at a position corresponding to (i) position 106,330,067 on human chromosome 14 (optionally the additional mutation being a guanine); and/or (ii) position 106,330,066 on human chromosome 14 (optionally the additional mutation being a guanine).

Optionally the plurality comprises a human JH5 gene variant of SEQ ID NO: 1, wherein the variant comprises a cytosine at a position corresponding to position 106, 330, 027 on human chromosome 14; and optionally no further mutation from the sequence of SEQ ID NO: 1, Optionally the plurality comprises a human JH5 gene variant of SEQ ID NO: 1, wherein the variant comprises an adenine at a position corresponding to position 106,330,024 on human chromosome 14; and optionally no further mutation from the sequence of SEQ ID NO: 1.

Optionally the plurality comprises a human JH5 gene variant of SEQ ID NO: 1, wherein the variant comprises a thymine at a position corresponding to position 106,330,032 on human chromosome 14; and optionally no further mutation from the sequence of SEQ ID NO: 1.

Optionally the plurality comprises a human JH5 gene variant of SEQ ID NO: 1, wherein the variant comprises a thymine at a position corresponding to position 106,330,041 on human chromosome 14; and optionally no further mutation from the sequence of SEQ ID NO: 1.

Optionally the plurality comprises a human JH5 gene variant of SEQ ID NO: 1, wherein the variant comprises an adenine or thymine at a position corresponding to position 106,330,063 on human chromosome 14; and optionally no further mutation from the sequence of SEQ ID NO: 1.

Optionally the variant comprises additionally a mutation at a position corresponding to position 106,330,071 on human chromosome 14 (optionally the additional mutation being a guanine).

Optionally the plurality comprises a human JH5 gene variant of SEQ ID NO: 1, wherein the variant comprises a cytosine at a position corresponding to position 106,330,062 on human chromosome 14; and optionally no further mutation from the sequence of SEQ ID NO: 1.

Optionally the genome comprises SEQ ID NO:1; optionally in cis at the same Ig locus as one, two or more of the variants.

JH6

An embodiment provides a vertebrate, cell or population of the invention whose genome comprises a plurality of JH6 gene segments, wherein the plurality comprises a human JH6 gene variant of SEQ ID NO: 2, wherein the variant comprises a nucleotide mutation at one or more positions corresponding to positions 106,329,411
106,329,413
106,329,414
106,329,417
106,329,419
106,329,426
106,329,434
106,329,435, and
106,329,468
on human chromosome 14.

Optionally the genome of the vertebrate, cell or population comprises a plurality of JH6 gene segments, wherein the plurality comprises a human JH6 gene variant of SEQ ID NO: 2, wherein the variant comprises a guanine at a position corresponding to position 106,329,435 on human chromosome 14; and optionally no further mutation from the sequence of SEQ ID NO: 2.

Optionally the variant comprises additionally a mutation at a position corresponding to (i) position 106,329,468 on human chromosome 14 (optionally the additional mutation being a guanine); (ii) position 106,329,419 on human chromosome 14 (optionally the additional mutation being an adenine); (iii) position 106,329,434 on human chromosome 14 (optionally the additional mutation being a cytosine) and/or position 106,329,414 on human chromosome 14 (optionally the additional mutation being a guanine); (iv) position 106,329,426 on human chromosome 14 (optionally the additional mutation being an adenine); (v) position 106,329,413 on human chromosome 14 (optionally the additional mutation being an adenine); (vi) position 106,329,417 on human chromosome 14 (optionally the additional mutation being a thymine); (vii) position 106,329,411 on human chromosome 14 (optionally the additional mutation being a thymine); (viii) position 106,329,451 on human chromosome 14 (optionally the additional mutation being an adenine); (ix) position 106,329,452 on human chromosome 14 (optionally the additional mutation being a cytosine); and/or (x) position 106,329,453 on human chromosome 14 (optionally the additional mutation being a cytosine).

Optionally the variant comprises additionally mutations at positions corresponding to position 106.329.451 on human chromosome 14, the additional mutation being an adenine; position 106.329.452 on human chromosome 14, the additional mutation being a cytosine; and position 106.329.453 on human chromosome 14, the additional mutation being a cytosine.

The vertebrate, cell or population optionally comprises a plurality of JH6 gene segments, wherein the plurality comprises a human JH6 gene variant of SEQ ID NO: 2, wherein the variant comprises a guanine at a position corresponding to position 106; 329,468 on human chromosome 14; and optionally no further mutation from the sequence of SEQ ID NO: 2.

Optionally the variant comprises additionally a mutation at a position corresponding to position 106,329,435 on human chromosome 14 (optionally the additional mutation being a guanine).

Optionally the vertebrate, cell or population comprises a plurality of JH6 gene segments, wherein the plurality comprises a human JH6 gene variant of SEQ ID NO: 2, wherein the variant comprises a thymine at a position corresponding to position 106,329,417 on human chromosome 14; and optionally no further mutation from the sequence of SEQ ID NO: 2.

Optionally the variant comprises additionally a mutation at a position corresponding to position 106,329,435 on human chromosome 14 (optionally the additional mutation being a guanine).

Optionally the vertebrate, cell or population comprises a plurality of JH6 gene segments, wherein the plurality comprises a human JH6 gene variant of SEQ ID NO: 2; wherein the variant comprises a cytosine at a position corresponding to position 106,329; 434 on human chromosome 14; and optionally no further mutation from the sequence of SEQ ID NO: 2.

Optionally the variant comprises additionally a mutation at a position corresponding to (i) position 106,329,414 on human chromosome 14 (optionally the additional mutation being a guanine); and/or (ii) position 106,329,435 on human chromosome 14 (optionally the additional mutation being a guanine).

Optionally the vertebrate, cell or population comprises a plurality of JH6 gene segments, wherein the plurality comprises a human JH6 gene variant of SEQ ID NO: 2, wherein the variant comprises a thymine at a position corresponding to position 106; 329,411 on human chromosome 14; and optionally no further mutation from the sequence of SEQ ID NO: 2.

Optionally the variant comprises additionally a mutation at a position corresponding to position 106,329,435 on human chromosome 14 (optionally the additional mutation being a guanine).

Optionally the vertebrate, cell or population comprises a plurality of JH6 gene segments, wherein the plurality comprises a human JH6 gene variant that is an antisense sequence of a variant described above.

Optionally the genome comprises SEQ ID NO:2; optionally cis at the same Ig locus as one, two or more of the JH6 variants.

JH2

An embodiment provides a vertebrate, cell or population of the invention whose genome comprises a plurality of JH2 gene segments, wherein the plurality comprises a human JH2 gene variant of SEQ ID NO: 3, wherein the variant comprises a nucleotide mutation at one or more positions corresponding to positions 106,331,455
106,331,453, and
106,331,409
on human chromosome 14.

Optionally the vertebrate, cell or population comprises said plurality of JH2 gene segments, wherein the plurality comprises a human JH2 gene variant of SEQ ID NO: 3, wherein the variant comprises a guanine at a position corresponding to position 106,331,455 on human chromosome 14; and optionally no further mutation from the sequence of SEQ ID NO: 3.

Optionally the variant comprises additionally a mutation at a position corresponding to (i) position 106,331,453 on human chromosome 14 (optionally the additional mutation being an adenine); and/or (ii) position 106,331,409 on human chromosome 14 (optionally the additional mutation being an adenine); (iii) position 106,329,434 on human chromosome 14 (optionally the additional mutation being an adenine).

Optionally the vertebrate, cell or population comprises a plurality of JH2 gene segments, wherein the plurality comprises a human JH2 gene variant of SEQ ID NO: 3, wherein the variant comprises an adenine at a position corresponding to position 106; 331,453 on human chromosome 14; and optionally no further mutation from the sequence of SEQ ID NO: 3.

Optionally the variant comprises additionally a mutation at a position corresponding to position 106,331,409 on human chromosome 14 (optionally the additional mutation being an adenine).

Optionally the vertebrate, cell or population comprises a plurality of JH2 gene segments, wherein the plurality comprises a human JH2 gene variant of SEQ ID NO: 3; wherein the variant comprises an adenine at a position corresponding to position 106,331; 409 on human chromosome 14; and optionally no further mutation from the sequence of SEQ ID NO: 3.

Optionally the vertebrate, cell or population comprises a plurality of JH2 gene segments, wherein the plurality comprises a human JH2 gene variant that is an antisense sequence of a variant described above.

Optionally the genome comprises SEQ ID NO:3; optionally cis at the same Ig locus as one, two or more of the JH2 variants.

Optionally the vertebrate, cell or population genome comprises two or more different JH gene segments selected from SEQ ID NOs: 1 to 3 and variants described above; optionally wherein said JH gene segments are cis at the same immunoglobulin Ig locus.

Multiple Human D Gene Segment Variants

A specific application of this configuration is the provision of multiple human D gene segments as follows (as set out in numbered clauses, starting at clause number 154).

154. A non-human vertebrate (eg, a mouse or rat) or a non-human vertebrate cell (eg, an ES cell or a B-cell) having a genome comprising at least 3 human D gene segments of the same type (eg, D2-2 gene segments), wherein at least two of the human D gene segments are variants that are not identical to each other (eg, D2-2ref and D2-2a).

In an example of any aspect of the sixth configuration of the invention (V, D, J or C), one or more or all of the variants are naturally-occurring human gene segments.

In an example of any aspect of the sixth configuration of the invention (V, D, J or C), one or more of the variants may be a synthetic variant of a human gene segment.

155. A non-human vertebrate (eg, a mouse or rat) or a non-human vertebrate cell (eg, an ES cell or a B-cell) having a genome comprising at least 2 different non-endogenous D gene segments of the same type (eg, D2-2ref and D2-2a) cis at the same Ig locus.

156. A non-human vertebrate (eg, a mouse or rat) or a non-human vertebrate cell (eg, an ES cell or a B-cell) having a genome comprising at least 2 different human D gene segments of the same type (eg, D2-2ref and D2-2a) trans at the same Ig locus; and optionally a third human D gene segment (eg, (eg, D2-2ref, D2-2a or D2-2b) of the same type, wherein the third D is cis with one of said 2 different D gene segments.

157. A population of non-human vertebrates (eg, mice or rats) comprising a repertoire of human D gene segments, wherein the plurality comprises at least 2 different human D gene segments of the same type (eg, D2-2 gene segments), a first of said different D gene segments (eg, D2-2ref) is provided in the genome of a first vertebrate of the population; and a second of said different D gene segment (eg, D2-2a) being provided in the genome of a second vertebrate of the population; wherein the genome of the first vertebrate does not comprise the second D gene segment.

158. A non-human vertebrate (eg, a mouse or rat) or a non-human vertebrate cell (eg, an ES cell or a B-cell) having a genome comprising at least 2 different non-endogenous D gene segments of the same type (eg, human D2-2 gene segments), wherein the D gene segments are derived from the genome sequence of different human individuals that are not genetically related over at least 3 generations.

159. A method of enhancing the human immunoglobulin gene diversity of a non-human vertebrate (eg, a mouse or rat); the method comprising providing the vertebrate with a genome comprising at least 3 human D gene segments of the same type (eg, D2-2 gene segments), wherein at least two of the human D gene segments are variants that are not identical to each other (eg, D2-2ref and D2-2a).

160. A method of enhancing the immunoglobulin gene diversity of a non-human vertebrate (eg; a mouse or rat), the method comprising providing the vertebrate with a genome comprising at least 2 different non-endogenous D gene segments of the same type (eg, human D2-2 gene segments) cis at the same Ig locus.

161. A method of enhancing the immunoglobulin gene diversity of a non-human vertebrate (eg, a mouse or rat), the method comprising providing the vertebrate with a genome comprising at least 2 different human D gene segments of the same type (eg, D2-2ref and D2-2a) trans at the same Ig locus; and optionally a third human gene segment (eg, D2-2ref, D2-2a or D2-2b) of the same type, wherein the third D is cis with one of said 2 different D gene segments.

162. A method of providing an enhanced human immunoglobulin D gene segment repertoire, the method comprising providing a population of non-human vertebrates (eg, a mouse or rat) comprising a repertoire of human D gene segments, wherein the method comprises providing at least 2 different human D gene segments of the same type (eg, D2-2ref and D2-2a), wherein a first of said different D gene segments is provided in the genome of a first vertebrate of the population, and a second of said different D gene segments is provided in the genome of a second vertebrate of the population, wherein the genome of the first vertebrate does not comprise the second D gene segment.

163. A method of enhancing the human immunoglobulin gene diversity of a non-human vertebrate (eg, a mouse or rat), the method comprising providing the vertebrate with a genome comprising at least 2 different non-endogenous D gene segments of the same type (eg, D2-2ref and D2-2a), wherein the D gene segments are derived from the genome sequence of different human individuals that are not genetically related over at least 3 generations.

164. The vertebrate or cell of clause 154, 156 or 158, or the method of clause 159, 161 or 163, wherein at least 2 or 3 of said different gene segments are provided cis at the same Ig locus in said genome.

165. The vertebrate or cell of clause 154, 155 or 156, or the method of any one of clauses 159 to 162 and 164, wherein the D gene segments are derived from the genome sequence of different human individuals that are not genetically related over at least 3 generations.

166. The vertebrate or cell of any one of clauses 154 to 157, or the method of any one of clauses 159 to 162 and 165, wherein the D gene segments are derived from the genome sequence of two or more different human individuals; optionally wherein the different human individuals are from different human populations.

167. The vertebrate; cell or method of clause 166, wherein the individuals are not genetically related.

168. The vertebrate, cell or method of any one of clauses 154 to 167, wherein at least one of the different D segments is a synthetic mutant of a human germline gene segment.

169. A method of enhancing the human immunoglobulin gene diversity of a non-human vertebrate (eg, a mouse or rat), the method comprising providing the vertebrate with a genome comprising at least 2 human D gene segments of the same type (eg, D2-2ref and D2-2a), wherein the D gene segments are derived from the genome sequence of different human individuals that are not genetically related over at least 3 generations; optionally wherein at least 2 or 3 of said different gene segments are provided at the same IgH locus in said genome.

170. The vertebrate or cell of any one of clauses 154 to 158 and 164 to 168, wherein the genome comprises a substantially complete functional repertoire of human D gene segment types supplemented with one, two or more variant human D gene segments, wherein said substantially complete functional repertoire and the supplementary D gene segments are not found together in the germline genome of a human individual.

171. The population of clause 157, wherein the population comprises a substantially complete functional repertoire of human D gene segment types supplemented with one, two or more variant human D gene segments, wherein said substantially complete functional repertoire and the supplementary D gene segments are not found together in the germline genome of a human individual.

172. A non-human vertebrate (eg, a mouse or rat) or a non-human cell (eg, an ES cell or a B-cell) having a genome comprising a substantially complete functional repertoire of human D gene segment types supplemented with one, two or more variant human D gene segments, wherein said substantially complete functional repertoire and the supplementary D gene segments are not found together in the germline genome of a human individual.

173. A population of non-human vertebrates (eg, mice or rats) comprising a substantially complete functional repertoire of human JH gene segment types supplemented with one, two or more variant human D gene segments, wherein said substantially complete functional repertoire and the supplementary D gene segments are not found together in the germline genome of a human individual.

174. The vertebrate or cell of clause 172 or the population of clause 173, comprising first and second D gene segments selected from D2-2ref and D2-2a; or D2-21ref and D2-21a; or D3-10refand D3-10a: or D3-16refand D3-16a; or D2-8ref and D2-8a; or D3-3ref and D3-3a; or D4-23ref and D4-23a; or D6-13refand D6-13a; or D3-9ref and D3-9a; or D4-4ref and D4-4a; or D7-27ref and D7-27a;

Optionally wherein the first and/or second D gene segment is present in two or more copies.

For example, there are provided two or three copies of the first gene segment, optionally with one, two or three copies of the second gene segment. Copies can be arranged in cis or trans.

175. The vertebrate, cell or population of clause 174, comprising human gene segments D2-2ref and D2-2a; and D3-3ref and D3-3a; and optionally also D2-15.

In an example, the vertebrate; cell or population comprises one or more D segments selected from human D3-3, D2-15, D3-9; D4-17; D3-10, D2-2; D5-24; D6-19; D3-22; D6-13; D5-12; D1-26; D1-20; D5-18; D3-16; D2-21; D1-14; D7-27; D1-1, D6-25; 02-14 and D4-23 (eg, selected from D3-9*01; D4-17*01; D3-10*01; D2-2*02; D5-24*01; D6-19*01; D3-22*01; D6-13*01; D5-12*01; D1-26*01; D1-20*01; D5-18*01; D3-16*02; D2-21*02; D1-14*01; D7-27*02; D1-1*01; D6-25*01; D2-15*01; and D4-23*01), together with the reference sequence(s) of said selected segment(s). These were found in variable domains having a HCDR3 length of at least 20 amino acids (see examples herein).

176. A non-human vertebrate or vertebrate cell according to clause 155; comprising a genome that comprises VH, D and JH gene repertoires comprising human gene segments, the D gene repertoire comprising one or more of a plurality of D2-2 gene segments provided by at least 2 different D2-2 gene segments in cis at the same Ig locus in said genome;

a plurality of D2-21 gene segments provided by at least 2 different D2-21 gene segments in cis at the same Ig locus in said genome;

a plurality of D3-10 gene segments provided by at least 2 different D3-10 gene segments in cis at the same Ig locus in said genome;

a plurality of D3-16 gene segments provided by at east 2 different D3-16 gene segments in cis at the same Ig locus in said genome;

a plurality of D2-8 gene segments provided by at least 2 different D2-8 gene segments in cis at the same Ig locus in said genome;

a plurality of D3-3 gene segments provided by at least 2 different D3-3 gene segments in cis at the same Ig locus in said genome;

a plurality of D4-23 gene segments provided by at least 2 different D4-23 gene segments in cis at the same Ig locus in said genome;

a plurality of D6-13 gene segments provided by at least 2 different D6-13 gene segments in cis at the same Ig locus in said genome;

a plurality of D3-9 gene segments provided by at least 2 different D3-9 gene segments in cis at the same Ig locus in said genome;

a plurality of D4-4 gene segments provided by at least 2 different D4-4 gene segments in cis at the same Ig locus in said genome; and a plurality of D7-27 gene segments provided by at least 2 different D7-27 gene segments in cis at the same Ig locus in said genome;

optionally wherein the D gene segments are derived from the genome sequence of two or more different human individuals.

177. A non-human vertebrate or vertebrate cell according to clause 155, comprising a genome that comprises VH, D and JH gene repertoires comprising human gene segments, the D gene repertoire comprising one or more of a plurality of D2-2 gene segments provided by at least 2 different D2-2 gene segments in trans in said genome;

a plurality of D2-21 gene segments provided by at least 2 different D2-21 gene segments in trans in said genome;

a plurality of D3-10 gene segments provided by at least 2 different D3-10 gene segments in trans in said genome;

a plurality of D3-16 gene segments provided by at least 2 different D3-16 gene segments in trans in said genome;

a plurality of D2-8 gene segments provided by at least 2 different D2-8 gene segments in trans in said genome;

a plurality of D3-3 gene segments provided by at least 2 different D3-3 gene segments in trans in said genome;

a plurality of D4-23 gene segments provided by at east 2 differentD4-23 gene segments in trans in said genome;

a plurality of D6-13 gene segments provided by at least 2 different D6-13 gene segments in trans in said genome;

a plurality of D3-9 gene segments provided by at least 2 different D3-9 gene segments in trans in said genome;

a plurality of D4-4 gene segments provided by at least 2 different D4-4 gene segments in trans in said genome; and a plurality of D7-27 gene segments provided by at least 2 different D7-27 gene segments in trans in said genome;

optionally wherein the D gene segments are derived from the genome sequence of two or more different human individuals.

178. A non-human vertebrate or vertebrate cell (optionally an ES cell or B-cell), according to clause 154, comprising a genome that comprises VH, D and JH gene repertoires comprising human gene segments, the D gene repertoire comprising one or more of a plurality of D2-2 gene segments provided by at least 3 different D2-2 gene segments; a plurality of D2-21 gene segments provided by at least 3 different D2-21 gene segments; a plurality of D3-10 gene segments provided by at least 3 different D3-10 gene segments; a plurality of D3-16 gene segments provided by at least 3 different D3-16 gene segments; a plurality of D2-8 gene segments provided by at least 3 different D2-8 gene segments; a plurality of D3-3 gene segments provided by at least 3 different D3-3 gene segments; a plurality of D4-23 gene segments provided by at least 3 different D4-23 gene segments; a plurality of D6-13 gene segments provided by at least 3 different 06-13 gene segments; a plurality of D3-9 gene segments provided by at least 3 different D3-9 gene segments; a plurality of D4-4 gene segments provided by at least 3 different D4-4 gene segments; and a plurality of D7-27 gene segments provided by at least 3 different D7-27 gene segments;

optionally wherein the D gene segments are derived from the genome sequence of two or three different human individuals;

optionally wherein at least 2 or 3 of said different gene segments are provided in cis at the same Ig locus in said genome.

179. The vertebrate or cell of clause 176, 177 or 178, wherein the different human individuals are from different human populations.

180. The vertebrate or cell of any one of clauses 176 to 179, wherein the individuals are not genetically related.

181. The vertebrate or cell of any one of clauses 176 to 180, wherein at least one of the different D segments is a synthetic mutant of a human germline D gene segment.

182. A non-human vertebrate or vertebrate cell (optionally an ES cell or B-cell) according to clause 158, comprising a genome comprising human VH, D and JH gene repertoires, the D gene repertoire comprising of one or more of a plurality of D2-2 gene segments provided by at least 2 different D2-2 gene; optionally in cis in said genome;

a plurality of D2-21 gene segments provided by at least 2 different D2-21 gene; optionally in cis in said genome;

a plurality of D3-10 gene segments provided by at least 2 differentD3-10 gene; optionally in cis in said genome;

a plurality of D3-16 gene segments provided by at least 2 different D3-16 gene; optionally in cis in said genome;

a plurality of D2-8 gene segments provided by at least 2 different D2-8 gene; optionally in cis in said genome;

a plurality of D3-3 gene segments provided by at least 2 different D3-3 gene; optionally in cis in said genome;

a plurality of D4-23 gene segments provided by at east 2 different D4-23 gene; optionally in cis in said genome;

a plurality of D6-13 gene segments provided by at least 2 different D6-13 gene; optionally in cis in said genome;

a plurality of D3-9 gene segments provided by at least 2 different D3-9 gene; optionally in cis in said genome;

a plurality of D4-4 gene segments provided by at least 2 different D4-4 gene; optionally in cis in said genome; and a plurality of D7-27 gene segments provided by at least 2 differentD7-27 gene; optionally in cis in said genome;

wherein the D gene segments are derived from the genome sequence of different human individuals that are not genetically related over at least 3 generations.

183. The vertebrate or cell of clause 182, wherein the human individuals are from different human populations.

184. The vertebrate, cell or population of any one of clauses 154 to 183, wherein one or more of the D gene segments is a variant of a human germline D gene segment, wherein the variant gene segment encodes an amino acid sequence that differs by 1, 2 or 3 amino acids from the corresponding amino acid sequence encoded by the human germline D gene segment, provided in that said amino acid sequence encoded by the variant does not include a stop codon when said corresponding amino acid sequence does not include a stop codon.

Optionally, the variant and germline D gene segments encode the respective amino acid sequences in reading frame 2 (IMGT numbering). See Briney et al 2012, 185. The vertebrate, cell or population of clause 184, wherein said corresponding amino acid sequence encoded by the human germline D gene segment is a hydrophilic or hydrophobic sequence (according to J Mol Biol, 1997 Jul. 25; 270(4):587-97; Corbett S J et al; Table 2).

186. The vertebrate, cell or population of clause 184 or 185, comprising said variant and said germline human D gene segments; optionally wherein the variant and germline human D gene segments are cis on the same chromosome.

187. The vertebrate, cell or population of any one of clauses 184 to 186, wherein germline human D gene segment is a D2, D3, D5 or D6 family gene segment; optionally a D2-2, D2-15, D3-3, D3-9, D3-10, D3-22, D5-5, D5-18, D6-6; D6-13, 06-19 gene segment.

These D segments are usable in all three reading frames.

Optionally a variant of 1, 2, 3, 4, 5, 6, 7, 8, 9, 10 or all of these human germline D gene segments is used.

188. The vertebrate, cell or population of any one of clauses 154 to 187, comprising a plurality of D2-2 gene segments, wherein the plurality comprises D2-2 gene segments that vary from each other at one or more nucleotide positions corresponding to positions 106,382,687 and 106,382,711 on human chromosome 14.

189. The vertebrate, cell or population of clause 188, wherein the plurality comprises a human D2-2 gene segment ((optionally two copies and/or in homozygous state) comprising a thymine at a position corresponding to position 106,382,687 on human chromosome 14; and optionally no further mutation from the sequence of D2-2ref.

190. The vertebrate, cell or population of clause 188 or 189, wherein the plurality comprises a human D2-2 gene segment comprising a cytosine at a position corresponding to position 106,382,687 on human chromosome 14; and optionally no further mutation from the sequence of D2-2a.

191. The vertebrate, cell or population of any one of clauses 188 to 190, wherein the plurality comprises a human D2-2 gene segment comprising an adenine at a position corresponding to position 106,382,711 on human chromosome 14; and optionally no further mutation from the sequence of D2-2b.

192. The vertebrate, cell or population of any one of clauses 188 to 191, wherein the plurality comprises a human D2-2 gene segment comprising an thymine at a position corresponding to position 106,382; 711 on human chromosome 14; and optionally no further mutation from the sequence of D2-2ref, 193. The vertebrate, cell or population of any one of clauses 154 to 192, comprising a plurality of D7-27 gene segments, wherein the plurality comprises D7-27 gene segments that vary from each other at a nucleotide position corresponding to position 106,331,767 on human chromosome 14.

194. The vertebrate, cell or population of clause 193, wherein the plurality comprises a human D7-27 gene segment (optionally two copies and/or in homozygous state) comprising a cytosine at a position corresponding to position 106,331,767 on human chromosome 14; and optionally no further mutation from the sequence of D7-27ref.

195. The vertebrate, cell or population of clause 193 or 194, wherein the plurality comprises a human D7-27 gene segment comprising a guanine at a position corresponding to position 106,331,767 on human chromosome 14; and optionally no further mutation from the sequence of 07-27a.

196. The vertebrate, cell or population of any one of clauses 154 to 195, comprising a plurality of D4-23 gene segments, wherein the plurality comprises D4-23 gene segments that vary from each other at a nucleotide position corresponding to position 106,350,740 on human chromosome 14.

197. The vertebrate, cell or population of clause 196, wherein the plurality comprises a human D4-23 gene segment (optionally two copies and/or in homozygous state) comprising an adenine at a position corresponding to position 106,350,740 on human chromosome 14; and optionally no further mutation from the sequence of D4-23ref.

198. The vertebrate, cell or population of clause 196 or 197, wherein the plurality comprises a human D4-23 gene segment (optionally two copies and/or in homozygous state) comprising an guanine at a position corresponding to position 106,350,740 on human chromosome 14; and optionally no further mutation from the sequence of D4-23a.

199. The vertebrate, cell or population of any one of clauses 154 to 197, comprising a plurality of D2-21 gene segments, wherein the plurality comprises D2-21 gene segments that vary from each other at a nucleotide position corresponding to position 106,354,418 on human chromosome 14.

200. The vertebrate, cell or population of clause 199, wherein the plurality comprises a human D2-21 gene segment (optionally two copies and/or in homozygous state) comprising an adenine at a position corresponding to position 106,354,418 on human chromosome 14; and optionally no further mutation from the sequence of D2-21ref.

201. The vertebrate, cell or population of clause 199 or 200, wherein the plurality comprises a human D2-21 gene segment (optionally two copies and/or in homozygous state) comprising a guanine at a position corresponding to position 106,354,418 on human chromosome 14; and optionally no further mutation from the sequence of D2-21a.

202. The vertebrate, cell or population of any one of clauses 154 to 201, comprising a plurality of D3-16 gene segments, wherein the plurality comprises D3-16 gene segments that vary from each other at a nucleotide position corresponding to position 106,354,418 on human chromosome 14.

203. The vertebrate, cell or population of clause 202, wherein the plurality comprises a human D3-16 gene segment (optionally two copies and/or in homozygous state) comprising a thymine at a position corresponding to position 106,361,515 on human chromosome 14; and optionally no further mutation from the sequence of D3-16ref.

204. The vertebrate, cell or population of clause 202 or 203, wherein the plurality comprises a human D3-16 gene segment (optionally two copies and/or in homozygous state) comprising a cytosine at a position corresponding to position 106,361,515 on human chromosome 14; and optionally no further mutation from the sequence of D3-16a, 205. The vertebrate, cell or population of any one of clauses 154 to 204, comprising a plurality of D6-13 gene segments, wherein the plurality comprises 06-13 gene segments that vary from each other at a nucleotide position corresponding to position 106,367,013 on human chromosome 14.

206. The vertebrate, cell or population of clause 205, wherein the plurality comprises a human D6-13 gene segment (optionally two copies and/or in homozygous state) comprising a thymine at a position corresponding to position 106; 367,013 on human chromosome 14; and optionally no further mutation from the sequence of D6-13ref.

207. The vertebrate, cell or population of clause 205 or 206, wherein the plurality comprises a human D6-13 gene segment (optionally two copies and/or in homozygous state) comprising a cytosine at a position corresponding to position 106,367; 013 on human chromosome 14; and optionally no further mutation from the sequence of D6-13a.

208. The vertebrate, cell or population of any one of clauses 154 to 207, comprising a plurality of D3-10 gene segments, wherein the plurality comprises D3-10 gene segments that vary from each other at one or more nucleotide positions corresponding to positions 106.370.370 and 106.370.371 on human chromosome 14.

209. The vertebrate, cell or population of clause 208, wherein the plurality comprises a human D3-10 gene segment (optionally two copies and/or in homozygous state) comprising a thymine at a position corresponding to position 106,370; 370 on human chromosome 14; and optionally no further mutation from the sequence of D3-10ref.

210. The vertebrate, cell or population of clause 208 or 209, wherein the plurality comprises a human D3-10 gene segment (optionally two copies and/or in homozygous state) comprising a cytosine at a position corresponding to position 106; 370,370 on human chromosome 14; and optionally no further mutation from the sequence of D3-10a.

211. The vertebrate, cell or population of clause 208, 209 or 210 wherein the plurality comprises a human D3-10 gene segment (optionally two copies and/or in homozygous state) comprising an adenine at a position corresponding to position 106,370,371 on human chromosome 14; and optionally no further mutation from the sequence of D3-10ref.

212. The vertebrate, cell or population of any one of clauses 208 to 211, wherein the plurality comprises a human D3-10 gene segment (optionally two copies and/or in homozygous state) comprising a guanine at a position corresponding to position 106,370,371 on human chromosome 14; and optionally no further mutation from the sequence of D3-10b.

213 The vertebrate, cell or population of any one of clauses 154 to 212, comprising a plurality of D3-9 gene segments, wherein the plurality comprises D3-9 gene segments that vary from each other at a nucleotide position corresponding to position 106,370,567 on human chromosome 14.

214. The vertebrate, cell or population of clause 213, wherein the plurality comprises a human D3-9 gene segment (optionally two copies and/or in homozygous state) comprising an adenine at a position corresponding to position 106,370,567 on human chromosome 14; and optionally no further mutation from the sequence of D3-9ref.

215. The vertebrate, cell or population of clause 213 or 214, wherein the plurality comprises a human D3-9 gene segment (optionally two copies and/or in homozygous state) comprising a thymine at a position corresponding to position 106,370,567 on human chromosome 14; and optionally no further mutation from the sequence of D3-9a.

216. The vertebrate, cell or population of any one of clauses 154 to 215, comprising a plurality of D2-8 gene segments, wherein the plurality comprises D2-8 gene segments that vary from each other at one or more nucleotide positions corresponding to positions 106,373,085; 106,373,086 and 106,373,089 on human chromosome 14.

217. The vertebrate, cell or population of clause 216, wherein the plurality comprises a human D2-8 gene segment (optionally two copies and/or in homozygous state) comprising a cytosine at a position corresponding to position 106,373,085 on human chromosome 14.

218. The vertebrate, cell or population of clause 216 or 217, wherein the plurality comprises a human D2-8 gene segment (optionally two copies and/or in homozygous state) comprising a thymine at a position corresponding to position 106,373,085 on human chromosome 14; and optionally no further mutation from the sequence of D2-8b.

219. The vertebrate, cell or population of clause 216, 217 or 218 wherein the plurality comprises a human D2-8 gene segment (optionally two copies and/or in homozygous state) comprising a cytosine at a position corresponding to position 106,373,086 on human chromosome 14; and optionally no further mutation from the sequence of D2-8ref.

220. The vertebrate, cell or population of any one of clauses 216 to 219, wherein the plurality comprises a human D2-8 gene segment comprising a thymine at a position corresponding to position 106,373,086 on human chromosome 14; and optionally no further mutation from the sequence of D2-8ref, 221. The vertebrate, cell or population of any one of clauses 154 to 220, comprising a plurality of D4-4 gene segments, wherein the plurality comprises D4-4 gene segments that vary from each other at one or more nucleotide positions corresponding to positions 106,379,086; and 106,379,089 on human chromosome 14.

222. The vertebrate, cell or population of clause 221, wherein the plurality comprises a D4-4 gene segment (optionally two copies and/or in homozygous state) comprising a cytosine at a position corresponding to position 106,379,086 on human chromosome 14; and optionally no further mutation from the sequence of D4-4ref.

223. The vertebrate, cell or population of clause 221 or 222, wherein the plurality comprises a human D4-4 gene segment (optionally two copies and/or in homozygous state) comprising a thymine at a position corresponding to position 106,379,086 on human chromosome 14; and optionally no further mutation from the sequence of D4-4a.

224. The vertebrate, cell or population of clause 221, 222 or 223 wherein the plurality comprises a human D4-4 gene segment (optionally two copies and/or in homozygous state) comprising a cytosine at a position corresponding to position 106,379,089 on human chromosome 14; and optionally no further mutation from the sequence of D4-4ref or a cytosine at a position corresponding to position 106,379,086 on human chromosome 14.

225. The vertebrate, cell or population of any one of clauses 221 to 224, wherein the plurality comprises a human D4-4 gene segment (optionally two copies and/or in homozygous state) comprising a thymine at a position corresponding to position 106,373,089 on human chromosome 14; and optionally no further mutation from the sequence of D4-4a.

226. The vertebrate, cell or population of any one of clauses 154 to 225, comprising a plurality of D3-3 gene segments, wherein the plurality comprises D3-3 gene segments that vary from each other at one or more nucleotide positions corresponding to positions 106,380,241; and 106,380,246 on human chromosome 14.

227. The vertebrate, cell or population of clause 226, wherein the plurality comprises a D3-3 gene segment (optionally two copies and/or in homozygous state) comprising a thymine at a position corresponding to position 106,380,241 on human chromosome 14; and optionally no further mutation from the sequence of D3-3ref.

228. The vertebrate, cell or population of clause 226 or 227, wherein the plurality comprises a human D3-3 gene segment (optionally two copies and/or in homozygous state) comprising a cytosine at a position corresponding to position 106,380,241 on human chromosome 14; and optionally no further mutation from the sequence of D3-3a.

229. The vertebrate, cell or population of clause 226, 227 or 228 wherein the plurality comprises a human D3-3 gene segment (optionally two copies and/or in homozygous state) comprising an adenine at a position corresponding to position 106,380,246 on human chromosome 14; and optionally no further mutation from the sequence of D3-3ref.

230. The vertebrate, cell or population of any one of clauses 226 to 229, wherein the plurality comprises a human D3-3 gene segment (optionally two copies and/or in homozygous state) comprising a thymine at a position corresponding to position 106,380,246 on human chromosome 14; and optionally no further mutation from the sequence of D3-3a.

Multiple Human JL Gene Segment Variants

A specific application of this configuration is the provision of multiple human JL gene segments (JK and/or Jλ) as follows (as set out in numbered paragraphs, starting at paragraph number 80).

80. A non-human vertebrate (eg, a mouse or rat) or a non-human vertebrate cell (eg, an ES cell or a B-cell) having a genome comprising at least 3 human JL gene segments of the same type (eg, JK1), wherein at least two of the human JL gene segments are variants that are not identical to each other.

81. A non-human vertebrate (eg, a mouse or rat) or a non-human vertebrate cell (eg, an ES cell or a B-cell) having a genome comprising at least 2 different non-endogenous JL gene segments of the same type (eg, JK1) cis at the same Ig locus.

82. A non-human vertebrate (eg, a mouse or rat) or a non-human vertebrate cell (eg, an ES cell or a B-cell) having a genome comprising at least 2 different human JL gene segments of the same type (eg, JK1) trans at the same Ig locus; and optionally a third human JL gene segment of the same type, wherein the third JL is cis with one of said 2 different JL gene segments.

83. A population of non-human vertebrates (eg, mice or rats) comprising a repertoire of human JL gene segments, wherein the plurality comprises at least 2 different human JL gene segments of the same type (eg, JK1), a first of said different JL gene segments is provided in the genome of a first vertebrate of the population, and a second of said different JL gene segments being provided in the genome of a second vertebrate of the population, wherein the genome of the first vertebrate does not comprise the second JL gene segment.

84. A non-human vertebrate (eg, a mouse or rat) or a non-human vertebrate cell (eg, an ES cell or a B-cell) having a genome comprising at least 2 different non-endogenous JL gene segments of the same type (eg, JK1), wherein the JL gene segments are derived from the genome sequence of different human individuals that are not genetically related over at least 3 generations.

85. A method of enhancing the human immunoglobulin gene diversity of a non-human vertebrate (eg, a mouse or rat), the method comprising providing the vertebrate with a genome comprising at least 3 human JL gene segments of the same type (eg, JK1), wherein at least two of the human JL gene segments are variants that are not identical to each other.

86. A method of enhancing the immunoglobulin gene diversity of a non-human vertebrate (eg, a mouse or rat), the method comprising providing the vertebrate with a genome comprising at least 2 different non-endogenous JL gene segments of the same type (eg, JK1) cis at the same Ig locus.

87. A method of enhancing the immunoglobulin gene diversity of a non-human vertebrate (eg, a mouse or rat), the method comprising providing the vertebrate with a genome comprising at least 2 different human JL gene segments of the same type (eg, JK1) trans at the same Ig locus; and optionally a third human JL gene segment of the same type, wherein the third JL is cis with one of said 2 different JL gene segments.

88. A method of providing an enhanced human immunoglobulin JL gene segment repertoire, the method comprising providing a population of non-human vertebrates (eg, a mouse or rat) comprising a repertoire of human JL gene segments, wherein the method comprises providing at least 2 different human JL gene segments of the same type (eg, JK1), wherein a first of said different JLgene segments is provided in the genome of a first vertebrate of the population, and a second of said different JL gene segments is provided in the genome of a second vertebrate of the population, wherein the genome of the first vertebrate does not comprise the second JL gene segment.

89. A method of enhancing the human immunoglobulin gene diversity of a non-human vertebrate (eg, a mouse or rat), the method comprising providing the vertebrate with a genome comprising at least 2 different non-endogenous JL gene segments of the same type (eg, JK1), wherein the JL gene segments are derived from the genome sequence of different human individuals that are not genetically related over at least 3 generations.

90. The vertebrate or cell of paragraph 80, 82 or 84, or the method of paragraph 85, 82 or 89, wherein at least 2 or 3 of said different gene segments are provided cis at the same Ig locus in said genome.

The vertebrate or cell of paragraph 80, 81 or 82, or the method of paragraph 85, 86 or 87, wherein the JL gene segments are derived from the genome sequence of different human individuals that are not genetically related over at least 3 generations.

92. The vertebrate or cell of paragraph 80, 81 or 82, or the method of paragraph 85, 86 or 87, wherein the JL gene segments are derived from the genome sequence of two or more different human individuals; optionally wherein the different human individuals are from different human populations.

93. The vertebrate, cell or method of paragraph 92, wherein the individuals are not genetically related.

94. The vertebrate, cell or method of any one of paragraphs 80 to 93, wherein at least one of the different JL segments is a synthetic mutant of a human germline JL gene segment.

95. A method of enhancing the human immunoglobulin gene diversity of a non-human vertebrate (eg, a mouse or rat), the method comprising providing the vertebrate with a genome comprising at least 2 human JL gene segments of the same type (eg, JK1), wherein the JL gene segments are derived from the genome sequence of different human individuals that are not genetically related over at least 3 generations; optionally wherein at least 2 or 3 of said different gene segments are provided at the same IgL locus in said genome.

96. The vertebrate or cell of any one of paragraphs paragraph 80 to 82 and 84, wherein the genome comprises a substantially complete functional repertoire of human JK and/or Jλ gene segment types supplemented with one, two or more human JK and/or Jλ gene segments respectively, wherein said substantially complete functional repertoire and the supplementary gene segments are not found together in the germline genome of a human individual.

97. The population of paragraph 83, wherein the population comprises a substantially complete functional repertoire of human JL gene segment types supplemented with one, two or more human JK and/or Jλ gene segments respectively, wherein said substantially complete functional repertoire and the supplementary gene segments are not found together in the germline genome of a human individual.

98. A non-human vertebrate (eg, a mouse or rat) or a non-human cell (eg, an ES cell or a B-cell) having a genome comprising a substantially complete functional repertoire of human JK and/or Jλ gene segment types supplemented with one, two or more human JK and/or Jλ gene segments respectively, wherein said substantially complete functional repertoire and the supplementary gene segments are not found together in the germline genome of a human individual.

99. A population of non-human vertebrates (eg, mice or rats) comprising a substantially complete functional repertoire of human JK and/or Jλ gene segment types supplemented with one, two or more human JK and/or Jλ gene segments respectively, wherein said substantially complete functional repertoire and the supplementary gene segments are not found together in the germline genome of a human individual.

100. A non-human vertebrate or vertebrate cell according to paragraph 81, comprising a genome that comprises VL and JL gene repertoires comprising human gene segments, the JL gene repertoire comprising a plurality of human JK1 gene segments provided by at least 2 different human JK1 gene segments in cis at the same Ig locus in said genome;

a plurality of human JK2 gene segments provided by at least 2 different human JK1 gene segments in cis at the same Ig locus in said genome;

a plurality of human JK3 gene segments provided by at least 2 different human JK1 gene segments in cis at the same Ig locus in said genome;

a plurality of human JK4 gene segments provided by at least 2 different human JK1 gene segments in cis at the same Ig locus in said genome;

a plurality of human JK5 gene segments provided by at least 2 different human JK1 gene segments in cis at the same Ig locus in said genome;

a plurality of human Jλ1 gene segments provided by at least 2 different human Jλ1 gene segments in cis at the same Ig locus in said genome;

a plurality of human Jλ2 gene segments provided by at least 2 different human Jλ 2 gene segments in cis at the same Ig locus in said genome;

a plurality of human Jλ3 gene segments provided by at least 2 different human Jλ 3 gene segments in cis at the same Ig locus in said genome;

a plurality of human Jλ 4 gene segments provided by at least 2 different human Jλ 4 gene segments in cis at the same Ig locus in said genome;

a plurality of human Jλ 5 gene segments provided by at least 2 different human Jλ 5 gene segments in cis at the same Ig locus in said genome;

a plurality of human Jλ 6 gene segments provided by at least 2 different human Jλ 6 gene segments in cis at the same Ig locus in said genome; or a plurality of human Jλ 7 gene segments provided by at least 2 different human Jλ 7 gene segments in cis at the same Ig locus in said genome;

optionally wherein the JL gene segments are derived from the genome sequence of two or more different human individuals.

101. A non-human vertebrate or vertebrate cell (optionally an ES cell or B-cell), according to paragraph 80, comprising a genome that comprises VL and JL gene repertoires comprising human gene segments, the JL gene repertoire comprising a plurality of human JK1 gene segments provided by at least 3 (eg, 3, 4, 5, 6, or 7) different human JK1 gene segments;

a plurality of human JK2 gene segments provided by at least 3 (eg, 3, 4, 5; 6; or 7) different human JK1 gene segments;

a plurality of human JK3 gene segments provided by at least 3 (eg, 3, 4, 5, 6, or 7) different human JK1 gene segments;

a plurality of human JK4 gene segments provided by at least 3 (eg, 3, 4, 5, 6, or 7) different human JK1 gene segments;

a plurality of human JK5 gene segments provided by at least 3 (eg, 3, 4, 5, 6, or 7) different human JK1 gene segments;

a plurality of human Jλ 1 gene segments provided by at least 3 (eg, 3, 4, 5, 6, or 7) different human Jλ 1 gene segments;

a plurality of human Jλ 2 gene segments provided by at least 3 (eg, 3, 4, 5, 6, or 7) different human Jλ 2 gene segments;

a plurality of human Jλ 3 gene segments provided by at least 3 (eg, 3, 4, 5, 6, or 7) different human Jλ 3 gene segments;

a plurality of human Jλ 4 gene segments provided by at least 3 (eg, 3, 4, 5, 6, or 7) different human Jλ 4 gene segments;

a plurality of human Jλ 5 gene segments provided by at least 3 (eg, 3, 4, 5, 6, or 7) different human Jλ 5 gene segments;

a plurality of human Jλ 6 gene segments provided by at least 3 (eg, 3, 4, 5, 6, or 7) different human Jλ 6 gene segments; or a plurality of human Jλ 7 gene segments provided by at least 3 (eg, 3, 4, 5, 6, or 7) different human Jλ 7 gene segments;

optionally wherein the JL gene segments are derived from the genome sequence of two or three different human individuals;

optionally wherein at least 2 or 3 of said different gene segments are provided in cis at the same Ig locus in said genome.

102. The vertebrate or cell of paragraph 104 or 105, wherein the different human individuals are from different human populations.

103. The vertebrate or cell of any one of paragraphs 104 to 106, wherein the individuals are not genetically related.

104. The vertebrate or cell of any one of paragraphs 104 to 107, wherein at least one of the different JL segments is a synthetic mutant of a human germline JL gene segment.

105. A non-human vertebrate or vertebrate cell (optionally an ES cell or B-cell) according to paragraph 84, comprising a genome comprising human VL and JL gene repertoires, the JL gene repertoire comprising a plurality of human JK1 gene segments provided by at least 2 different human JK1 gene segments, optionally in cis at the same Ig locus in said genome;

a plurality of human JK2 gene segments provided by at least 2 different human JK1 gene segments, optionally in cis at the same Ig locus in said genome;

a plurality of human JK3 gene segments provided by at least 2 different human JK1 gene segments, optionally in cis at the same Ig locus in said genome;

a plurality of human JK4 gene segments provided by at least 2 different human JK1 gene segments, optionally in cis at the same Ig locus in said genome;

a plurality of human JK5 gene segments provided by at least 2 different human JK1 gene segments, optionally in cis at the same Ig locus in said genome;

a plurality of human Jλ 1 gene segments provided by at least 2 different human Jλ 1 gene segments, optionally in cis at the same Ig locus in said genome;

a plurality of human Jλ 2 gene segments provided by at least 2 different human Jλ 2 gene segments, optionally in cis at the same Ig locus in said genome;

a plurality of human Jλ 3 gene segments provided by at least 2 different human Jλ 3 gene segments, optionally in cis at the same Ig locus in said genome;

a plurality of human Jλ 4 gene segments provided by at least 2 different human Jλ 4 gene segments, optionally in cis at the same Ig locus in said genome;

a plurality of human Jλ 5 gene segments provided by at least 2 different human Jλ 5 gene segments, optionally in cis at the same Ig locus in said genome;

a plurality of human Jλ 6 gene segments provided by at least 2 different human Jλ 6 gene segments, optionally in cis at the same Ig locus in said genome; or a plurality of human Jλ 7 gene segments provided by at least 2 different human Jλ 7 gene segments, optionally in cis at the same Ig locus in said genome;

wherein the JL gene segments are derived from the genome sequence of different human individuals that are not genetically related over at least 3 generations.

106. The vertebrate or cell of paragraph 109, wherein the human individuals are from different human populations.

The skilled person will realise that standard molecular biology techniques can be used to provide vectors comprising synthetic combinations of immunoglobulin gene segments (eg, V; D and/or J) for use in the invention, such that the vectors can be used to build a transgenic immunoglobulin locus (eg, using homologous recombination and/or recombinase mediated cassette exchange as known in the art, eg, see U.S. Pat. No. 7,501,552 (Medarex), U.S. Pat. No. 5,939,598 (Abgenix), U.S. Pat. No. 6,130,364 (Abgenix), WO02/066630 (Regeneron), WO2011004192 (Genome Research Limited), WO2009076464, WO2009143472 and WO2010039900 (Ablexis), the disclosures of which are explicitly incorporated herein. For example, such synthetic combinations of gene segments can be made using standard recombineering techniques in *E coli* to construct BAC vectors harbouring the synthetic combination prior to insertion in embryonic stem cells using homologous recombination or RMCE (eg, using cre/lox site-specific recombination). Details of recombineering can be found at www at .genebridges.com and in EP1034260 and EP1204740 the disclosures of which are explicitly incorporated herein.

In one embodiment, it is useful to bias the immune response of the vertebrate (and thus resultant lead antibodies) to a predetermined gene segment, eg, one known to be commonly used in natural human immune responses to antigens, such as antigens of infectious disease pathogens. For example, VH1-69 is commonly used to produce antibodies in humans against Influenza virus; it is possible, therefore, to include two or more polymorphic DNA versions of the VH segment VH1-69 in the locus of the invention. The examples below illustrate how such a transgenic locus can be constructed in which diversity is extended by extending the VH1-69 gene segment repertoire based on naturally-occurring VH1-69 polymorphic variants.

In one embodiment in any configuration of the invention, the genome has been modified to prevent or reduce the expression of fully-endogenous antibody. Examples of suitable techniques for doing this can be found in PCT/GB2010/051122, U.S. Pat. Nos. 7,501,552, 6,673,986, 6,130,364, WO2009/076464, EP1399559 and U.S. Pat. No. 6,586,251, the disclosures of which are incorporated herein by reference. In one embodiment, the non-human vertebrate VDJ region of the endogenous heavy chain immunoglobulin locus, and optionally VJ region of the endogenous light chain immunoglobulin loci (lambda and/or kappa loci), have been inactivated. For example, all or part of the non-human vertebrate VDJ region is inactivated by inversion in the endogenous heavy chain immunoglobulin locus of the mammal, optionally with the inverted region being moved upstream or downstream of the endogenous Ig locus (see, eg, WO2011004192, the disclosure of which is incorporated herein by reference). For example, all or part of the non-human vertebrate VJ region is inactivated by inversion in the endogenous kappa chain immunoglobulin locus of the mammal, optionally with the inverted region being moved upstream or downstream of the endogenous Ig locus. For example, all or part of the non-human vertebrate VJ region is inactivated by inversion in the endogenous lambda chain immunoglobulin locus of the mammal, optionally with the inverted region being moved upstream or downstream of the endogenous Ig locus. In one embodiment the endogenous heavy chain locus is inactivated in this way as is one or both of the endogenous kappa and lambda loci.

Additionally or alternatively, the vertebrate has been generated in a genetic background which prevents the production of mature host B and T lymphocytes, optionally a RAG-1-deficient and/or RAG-2 deficient background. See U.S. Pat. No. 5,859,301 for techniques of generating RAG-1 deficient animals.

Thus, in one embodiment of any configuration or aspect of the invention herein, endogenous heavy and light chain expression has been inactivated.

In one embodiment each said locus constant region is a heavy chain endogenous non-human vertebrate (optionally host mouse or rat) constant region.

In one embodiment each said locus constant region is a light chain endogenous non-human vertebrate (optionally host mouse or rat) constant region.

The invention provides a monoclonal or polyclonal antibody composition prepared by immunisation of at least one vertebrate (eg, mouse or rat) according to the invention, optionally wherein the antigen is an antigen of an infectious disease pathogen (eg, a bacterial or viral pathogen antigen), optionally wherein the same antigen is used to immunise all the vertebrates; optionally wherein the antibody or antibodies are IgG-type (eg, IgG1).

The invention also provides a monoclonal or polyclonal antibody mixture produced by the method of the invention or a derivative antibody or mixture thereof, eg, where one or more constant region has been changed (eg, replaced with a different constant region such as a human constant region; or mutated to enhance or ablate Fc effector function). In an aspect of the invention, the monoclonal or polyclonal antibody mixture is provided for therapy and/or prophylaxis of a disease or condition in a human, eg, for the treatment and/or prevention of an infectious disease, wherein optionally wherein each antibody binds an antigen of an infectious disease pathogen, preferably the same antigen.

In an aspect of the invention, there is provided the use of an isolated, monoclonal or polyclonal antibody according to the invention, or a mutant or derivative antibody thereof in the manufacture of a medicament for the treatment and/or prevention of a disease or condition in a human, eg, an infectious disease, optionally wherein the infectious disease is a disease caused by a bacterial or viral pathogen.

An example of a mutant antibody is one that bears up to 15 or 10 amino acid mutations in its variable regions relative to an isolated antibody (eg, IgG-type, such as IgG1-type, antibody) obtainable or obtained by the method of the invention. An example of a derivative is one that has been modified to replace a constant region with a different constant region such as a human constant region; or mutated to enhance or ablate Fc effector function.

Examples of infectious diseases are diseases caused or mediated by a bacterial or viral pathogen. For example, the infectious disease is selected from the group consisting of a disease caused by a pathogen selected from the group consisting of *Haemophilus* influenza, *E coli*, *Neisseria meningitidis*, a herpes family virus, cytomegalovirus (CMV), HIV and influenza virus.

Tailoring V(D)J Incorporation into Immuno Globin Loci for the Generation of Antibodies Against Infectious Disease The inventors realised that it would be desirable to provide for vertebrates, cells, methods etc for the production of therapeutic and/or prophylactic antibodies based on natural human immune responses to antigens, such as antigens of infectious disease pathogens. In this respect, the literature observes frequently used immunoglobulin gene segments to raise anti-infective responses in humans (Table 9).

In the various configurations, aspects, embodiments and examples above, the invention provides the skilled addressee with the possibility of choosing immunoglobulin gene segments in a way that tailors or biases the repertoire for application to generating antibodies to treat and/or prevent infectious diseases. The inventors have categorised the following groups of gene segments for use in the invention according to the desired application of resultant antibodies.

List A:

Immunoglobulin Gene Segments for Antibodies that Bind an Antigen Expressed by a Pathogen (a) a VL gene segment selected from the group consisting of a VλII gene family member, VλVII 4A, VλII 2.1, VλVII 4A, a Vλ1 gene family member, a 3gene family member, IGLV1S2, Vλ3-cML70, Ialh2, Ialv1, Ia3h3, Kv325, a VKI gene family member, KI-15A (KL012), V°II family member, a V°III family member, a VKI gene family member, KI-15A (KL012), V°II A2 (optionally the A2a variant), VK A27 (Humkv325) and a gene segment at least 80% identical thereto.

(b) a Vλ gene segment selected from a VλII gene family member, VλVII 4A, VλII 2.1, VλVII 4A, a Vλ1 gene family member, a Vλ3gene family member, IGLV1S2, VA3-cML70, Ialh2, Ialv1, Ia3h3 and a gene segment at least 80% identical thereto.

(c) a VK gene segment selected from Kv325, a VKI gene family member, KI-15A (KL012), V°II family member, a VKIII family member, a VKI gene family member, KI-15A (KL012), V°II A2 (optionally the A2a variant), VK A27 (Humkv325) and a gene segment at least 80% identical thereto.

(d) a VH gene segment a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1 DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto.

(e) a Jλ gene segment selected from Jλ 2, Jλ 3 and a gene segment at least 80% identical thereto.

(f) a D gene segment selected from Dk1, Dxp>>1, Dn4r, D2r and a gene segment at least 80% identical thereto.

List A1:

Immunoglobulin Gene Segments for Antibodies that Bind an Antigen Expressed by a Pathogen (a) a Vλ gene segment selected from a VλII gene family member. VλVII 4AVλII 2.1, VλVII 4A and a gene segment at least 80% identical thereto.

(b) a VK gene segment selected from a VKI gene family member, KI-15A (KL012), V°II family member, a VKIII family member, a VKI gene family member, KI-15A (KL012), V°II A2 (optionally the A2a variant), VK A27 (Humkv325) and a gene segment at least 80% identical thereto.

(c) a VH gene segment a VH3 gene family member (optionally, a VHIIIa or VHIIIb family member), VHIII 9.1 (VH3-15), VHIII VH26 (VH3-23), VH3-21, LSG6.1, LSG12.1, DP77 (V3-21), VH H11 and a gene segment at least 80% identical thereto.

(d) a Jλ gene segment selected from Jλ 2, Jλ 3 and a gene segment at least 80% identical thereto.

(e) a JH gene segment selected from JH2, JH3, JH4 and a gene segment at least 80% identical thereto.

List A1.1:

Immunoglobulin Gene Segments for Antibodies that Bind an Antigen Expressed by H Influenza (a) a Vλgene segment selected from a VλII gene family member, VλVII 4A, VλII 2.1, VλVII 4A and a gene segment at least 80% identical thereto.

(b) a VK gene segment selected from a V°II family member, a VKIII family member, a VKI gene family member, KI-15A (KL012), V°II A2 (optionally the A2a variant), V°A27 (Humkv325) and a gene segment at least 80% identical thereto.

(c) a VH gene segment a VH3 gene family member (optionally, a VHIIIb family member), VHIII 9.1 (VH3-15), VHIII VH26 (VH3-23), VH3-21, LSG6.1, LSG12.1, DP77 (V3-21) and a gene segment at least 80% identical thereto.

(d) a Jλ gene segment selected from Jλ 2, Jλ 3 and a gene segment at least 80% identical thereto.

List A1.2:

Immunoglobulin Gene Segments for Antibodies that Bind an Antigen Expressed by *E Coli* or *Neisseria meningitidis*

(a) a VH gene segment a VH3 gene family member (optionally a VHIIIa or VHIIIb member), VHIII 9.1 (VH3-15), VH H11, VHIII VH26 (VH3-23) a gene segment at least 80% identical thereto, eg, VHIII 9.1 © JH3; or VH H11 JH4; or VHIII VH26 JH2.

(b) a VK gene segment selected from a VKI gene family member, KI-15A (KL012) and a gene segment at least 80% identical thereto.

(c) a Vλ gene segment selected from a VλII gene family member, VλII 2.1 and a gene segment at least 80% identical thereto.

(d) a JH gene segment selected from JH2, JH3, JH4 and a gene segment at least 80% identical thereto.

A2;

Immunoglobulin Gene Segments for Antibodies that Bind an Antigen Expressed by a viral Pathogen (a) a VH gene segment selected from a VHIII gene family member, a VHIV gene family member, VHIII-VH26 (VH3-23), VH1GRR, ha3h2, VHI-ha1c1, VHIII-VH2-1 VH4.18, ha4h3, Hv1051, 71-2, Hv1f10, VH4.11, 71-4, VH251, VH1-69 and a gene segment at least 80% identical thereto.

(b) a Vλ gene segment selected from a VA1 gene family member, a VA3 gene family member, IGLV1S2, Vλ3-cML70, Ialh2, Ialv1, Ia3h3 and a gene segment at least 80% identical thereto.

(c) a Vk gene segment selected from Kv325 and a gene segment at least 80% identical thereto.

(d) a JH gene segment selected from JH3, JH5, JH6 and a gene segment at least 80% identical thereto.

(e) a D gene segment selected from Dk1, Dxp>>1, Dn4r, D2r and a gene segment at least 80% identical thereto.

(f) a Jλ gene segment selected from Jλ 2, Jλ 3 and a gene segment at least 80% identical thereto.

A2.1:

Immunoglobulin Gene Segments for Antibodies that Bind an Antigen Expressed by Herpes Virus Family (Eg, VZV or HSV)

(a) a VH gene segment selected from a VHIII gene family member, a VHIV gene family member, VHIII-VH26 (VH3-23), VH1GRR, ha3h2, VHI-ha1c1, VHIII-VH2-1, VH4.18, ha4h3, and a gene segment at least 80% identical thereto.

(b) a Vλ gene segment selected from a VA1 gene family member, a VA3gene family member, IGLV1S2, VA3-cML70, la h2, Ialv1, Ia3h3 and a gene segment at least 80% identical thereto.

(c) a JH gene segment selected from JH3, JH5, JH6 and a gene segment at least 80% identical thereto.

(d) a 0 gene segment selected from Dk1, Dxp>>1, Dn4r, D2r and a gene segment at least 80% identical thereto.

(e) a Jλ gene segment selected from Jλ 2, Jλ 3 and a gene segment at east 80% identical thereto.

A2.2:

Immunoglobulin Gene Segments for Antibodies that Bind an Antigen Expressed by CMV (a) a VH gene segment selected from Hv1051 and a gene segment at least 80% identical thereto.

(b) a Vk gene segment selected from Kv325 and a gene segment at least 80% identical thereto. A2.3:

Immunoglobulin Gene Segments for Antibodies that Bind an Antigen Expressed by HIV (a) a VH gene segment selected from 71-2, Hv1f10, VH4.11, 71-4, VH251, VH1-69 and a gene segment at least 80% identical thereto.

A2.4:

Immunoglobulin Gene Segments for Antibodies that Bind an Antigen Expressed by Influenza Virus (a) a VH gene segment selected from VH1-69 and a gene segment at least 80% identical thereto.

Thus,

Where one wishes to generate an antibody or antibody mixture to treat and/or prevent an infectious disease, one or more V, D and/or or all J gene segments used in any configuration, aspect, method, example or embodiment of the invention can be selected from List A1. Thus, for example in (a) of the first configuration of the invention, the recited heavy chain V gene segment is selected from the VH gene segments in List A, optionally with a D in that list.

Where one wishes to generate an antibody or antibody mixture to treat and/or prevent an infectious disease caused or mediated by a bacterial pathogen, one or more or all V, D and/or J gene segments used in any configuration, aspect, method, example or embodiment of the invention can be selected from List A1.

Where one wishes to generate an antibody or antibody mixture to treat and/or prevent an infectious disease caused or mediated by a viral pathogen, one or more or all V, D and/or J gene segments used in any configuration, aspect, method, example or embodiment of the invention can be selected from List A2.

Where one wishes to generate an antibody or antibody mixture to treat and/or prevent an infectious disease caused or mediated by H influenza, one or more or all V, D and/or J gene segments used in any configuration, aspect, method, example or embodiment of the invention can be selected from List A1.1.

Where one wishes to generate an antibody or antibody mixture to treat and/or prevent an infectious disease caused or mediated by *E Coli* or *Neisseria meningitidis*, one or more or all V, D and/or J gene segments used in any configuration, aspect, method, example or embodiment of the invention can be selected from List A1.2.

Where one wishes to generate an antibody or antibody mixture to treat and/or prevent an infectious disease caused or mediated by Herpes Virus Family (eg, VZV or HSV), one or more or all V, D and/or J gene segments used in any configuration, aspect, method, example or embodiment of the invention can be selected from List A2.1.

Where one wishes to generate an antibody or antibody mixture to treat and/or prevent an infectious disease caused or mediated by CMV, one or more or all V, and/or J gene segments used in any configuration, aspect, method, example or embodiment of the invention can be selected from List A2.2.

Where one wishes to generate an antibody or antibody mixture to treat and/or prevent an infectious disease caused or mediated by HIV, one or more or all V, D and/or J gene segments used in any configuration, aspect, method, example or embodiment of the invention can be selected from List A2.3.

Where one wishes to generate an antibody or antibody mixture to treat and/or prevent an infectious disease caused or mediated by Influenza Virus, one or more or all V, D and/or J gene segments used in any configuration, aspect, method, example or embodiment of the invention can be selected from List A2.4.

Optionally each VH segment in the locus of the invention is selected from List A1, A2, A1.1, A1.2, A2.1, A2.2, A2.3 or A2.4.

Optionally each VL segment in the locus of the invention is selected from List A1, A2, A1.1, A1.2, A2.1, A2.2, A2.3 or A2.4

Optionally each D segment in the locus of the invention is selected from List A1, A2, A1.1, A1.2, A2.1, A2.2, A2.3 or A2.4.

Optionally each JL segment in the locus of the invention is selected from List A1, A2, A1.1, A1.2, A2.1, A2.2, A2.3 or A2.4.

Antibodies for Therapy & Prophylaxis of Patients of Specific Ancestry

The inventors, having undertaken the extensive Bioinformatics analysis exercise described herein, realised that the output of that analysis has made it possible to identify specific gene segments that are useful to produce antibody- and VH domain-based drugs that are tailored specifically to a patient's ancestry (ie, genotype). That is, antibodies can be selected on the basis that they are made in vivo in a transgenic non-human vertebrate (eg, mouse or rat with transgenic IgH loci) and particularly derived from gene segments that are relatively prevalent in members of the patient's population, ie, from individuals of the same human ancestry. Since variant distributions differ across different populations (see Table 13), this presumably reflects the effects of evolution, adaptation and conservation of useful variant gene types in those populations. Thus, by tailoring the antibody-based drugs according to the invention, it is possible to match the drug to the population gene biases, thus with the aim of making better drugs for that specific population of humans. Better can, for example, mean more efficacious, better neutralising, higher target antigen affinity, less immunogenic, less patient reactions to the drug etc. This can be determined empirically, as is standard in drug research and development processes.

Thus, the invention provides the following embodiments (numbered from clause 345 onwards):—

345. An isolated antibody for administration to a Chinese patient, the antibody comprising a human heavy chain, the heavy chain comprising a variable domain that is specific for an antigen and a constant region, wherein the constant region is a human constant region selected from a constant region (eg, an IGHG constant region) in Table 13 found in a Chinese population and with a cumulative frequency of at least 1 or 5%; and wherein (i) the variable domain is derived from the recombination of said human gene segments in a non-human vertebrate (eg, in a mouse or a rat): and/or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

In another embodiment, the invention provides

An isolated antibody for administration to a Chinese patient, the antibody comprising a human heavy chain, the heavy chain comprising a variable domain that is specific for an antigen and a constant region, wherein the constant region is a human constant region selected from a constant region (eg, an IGHG constant region) present in a Chinese population with a cumulative frequency of at least 5%, and wherein (i) the variable domain is derived from the recombination of said human gene segments in a non-human vertebrate (eg, in a mouse or a rat); and/or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

In an example, the constant region is found in the 1000 Genomes database. In an example, the constant region is found in Table 13.

346. The antibody of clause 345 wherein the constant region is a IGHG1a, IGHG2a, IGHG3a, IGHG3b or IGHG4a constant region.

347. The antibody of clause 345 or 346, wherein the variable domain is derived from the recombination of a human VH gene segment with a human D gene segment and a human JH gene segment, the VH gene segment being selected from a VH in Table 13 found in a Chinese population and with a cumulative frequency of at least 5%.

In another embodiment, the invention provides

The antibody of clause 345 or 346, wherein the variable domain is derived from the recombination of a human VH gene segment with a human D gene segment and a human JH gene segment, the VH gene segment being selected from a VH present in a Chinese population with a cumulative frequency of at least 5%.

In an example, the gene segment is found in the 1000 Genomes database. In an example; the gene segment is found in Table 13.

348. The antibody of clause 345, 346 or 347, wherein the variable domain is derived from the recombination of a human VH gene segment with a human D gene segment and a human JH gene segment, the D gene segment being selected from a D in Table 13 found in a Chinese population and with a cumulative frequency of at least 5%.

In another embodiment, the invention provides

The antibody of clause 345, 346 or 347, wherein the variable domain is derived from the recombination of a human VH gene segment with a human D gene segment and a human JH gene segment, the D gene segment being selected from a D present in a Chinese population with a cumulative frequency of at least 5%.

In an example, the gene segment is found in the 1000 Genomes database. In an example, the gene segment is found in Table 13.

349. The antibody of clause 345, 346, 347 or 348 wherein the variable domain is derived from the recombination of a human VH gene segment with a human D gene segment and a human JH gene segment, the JH gene segment being selected from a JH in Table 13 found in a Chinese population and with a cumulative frequency of at least 5%.

In another embodiment, the invention provides

The antibody of clause 345, 346, 347 or 348 wherein the variable domain is derived from the recombination of a human VH gene segment with a human D gene segment and a human JH gene segment the JH gene segment being selected from a JH present in a Chinese population with a cumulative frequency of at least 5%.

In an example, the gene segment is found in the 1000 Genomes database. In an example, the gene segment is found in Table 13.

350. An isolated VH domain identical to a variable domain as recited in any one of clauses 347 to 349, optionally fused at its C-terminus to a polypeptide (eg, an antibody Fc).

In an embodiment, there is provided an isolated VH domain identical to a variable domain as recited in any one of clauses 347 to 349 which is part of a conjugate, conjugated with a label (eg, for imaging in the patient) or a toxin (eg, a radioactive toxic payload, such as for cancer treatment in the patient) or a half-life-extending moiety (eg, PEG of human serum albumin).

351. A pharmaceutical composition comprising the antibody or variable domain of any one of clauses 345 to 350 together with a pharmaceutically-acceptable excipient, diluent or a medicament (eg, a further antigen-specific variable domain, antibody chain or antibody).

352. An isolated antibody for administration to a Chinese patient, the antibody comprising a human heavy chain, the heavy chain comprising a variable domain that is specific for an antigen and a constant region, wherein the variable domain is derived from the recombination of a human VH gene segment with a human D gene segment and a human JH gene segment, the VH gene segment being selected from a VH in Table 13 found in a Chinese population and with a cumulative frequency of at least 5%; and wherein (i) the variable domain is derived from the recombination of said human gene segments in a non-human vertebrate (eg, in a mouse or a rat); and/or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

In another embodiment, the invention provides

An isolated antibody for administration to a Chinese patient, the antibody comprising a human heavy chain, the heavy chain comprising a variable domain that is specific for an antigen and a constant region, wherein the variable domain is derived from the recombination of a human VH gene segment with a human D gene segment and a human JH gene segment, the VH gene segment being selected from a VH present in a Chinese population with a cumulative frequency of at least 5%; and wherein (i) the variable domain is derived from the recombination of said human gene segments in a non-human vertebrate (eg, in a mouse or a rat); and/or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

353. The antibody of clause 352, wherein the variable domain is derived from the recombination of a human VH gene segment with a human D gene segment and a human JH gene segment, the D gene segment being selected from a D in Table 13 found in a Chinese population and with a cumulative frequency of at least 5%.

In another embodiment; the invention provides

The antibody of clause 352, wherein the variable domain is derived from the recombination of a human VH gene segment with a human D gene segment and a human JH gene segment, the D gene segment being selected from a D present in a Chinese population with a cumulative frequency of at least 5%.

In an example, the gene segment is found in the 1000 Genomes database. In an example, the gene segment is found in Table 13.

354. The antibody of clause 352 or 353, wherein the variable domain is derived from the recombination of a human VH gene segment with a human D gene segment and a human JH gene segment, the JH gene segment being selected from a JH in Table 13 found in a Chinese population and with a cumulative frequency of at least 5%.

In another embodiment; the invention provides

The antibody of clause 352 or 353, wherein the variable domain is derived from the recombination of a human VH gene segment with a human D gene segment and a human JH gene segment, the JH gene segment being selected from a JH present in a Chinese population with a cumulative frequency of at least 5%.

In an example, the gene segment is found in the 1000 Genomes database. In an example, the gene segment is found in Table 13.

355. An isolated VH domain identical to a variable domain as recited in any one of clauses 352 to 354, optionally fused at its C-terminus to a polypeptide (eg, an antibody Fc).

In an embodiment, there is provided a VH domain identical to a variable domain as recited in any one of clauses 352 to 354 which is part of a conjugate, conjugated with a label (eg, for imaging in the patient) or a toxin (eg, a radioactive toxic payload, such as for cancer treatment in the patient) or a half-life-extending moiety (eg, PEG of human serum albumin).

356. A pharmaceutical composition comprising the antibody or variable domain of any one of clauses 352 to 355 together with a pharmaceutically-acceptable excipient, diluent or a medicament (eg, a further antigen-specific variable domain, antibody chain or antibody).

357. An antibody heavy chain or VH domain (eg, provided as part of an antibody) for therapy and/or prophylaxis of a disease or medical condition in a Chinese patient, wherein the heavy chain is a heavy chain produced by the following steps (or is a copy of such a heavy chain):—

(a) Selection of an antigen-specific antibody heavy chain or VH domain from a non-human vertebrate (eg, a mouse or a rat), wherein the heavy chain or VH domain is derived from the recombination of a human VH gene segment with a human D gene segment and a human JH gene segment, the VH gene segment being selected from a VH in Table 13 found in a Chinese population and with a cumulative frequency of at least 5%;

(b) Optional humanisation of the heavy chain by combining the variable domain of the heavy chain with a human constant region; or optional humanisation of the selected VH domain by combining with a human constant region.

In another embodiment, the invention provides

An antibody heavy chain or VH domain (eg, provided as part of an antibody) for therapy and/or prophylaxis of a disease or medical condition in a Chinese patient, wherein the heavy chain is a heavy chain produced by the following steps (or is a copy of such a heavy chain):—

(a) Selection of an antigen-specific antibody heavy chain or VH domain from a non-human vertebrate (eg, a mouse or a rat), wherein the heavy chain or VH domain is derived from the recombination of a human VH gene segment with a human D gene segment and a human JH gene segment, the VH gene segment being selected from a VH present in a Chinese population with a cumulative frequency of at least 5%;

(b) Optional humanisation of the heavy chain by combining the variable domain of the heavy chain with a human constant region; or optional humanisation of the selected VH domain by combining with a human constant region.

In an example, the VH gene segment is found in the 1000 Genomes database. In an example, the gene segment is found in Table 13.

358. The antibody heavy chain or VH domain of clause 357, wherein the human constant region is as recited in clause 345 or 346.

359. An antibody heavy chain or VH domain as recited in clause 357 or 358 for use in a medicament for therapy and/or prophylaxis of a disease or medical condition in a Chinese patient.

360. A method of treating and/or preventing a disease or medical condition in a Chinese patient, the method comprising administering to the patient a therapeutically or prophylactically-effective amount of the antibody heavy chain or VH domain as recited in clause 357 or 358.

361. An isolated antibody for administration to a patient of European, East Asian, West African, South Asian or Americas ancestry, the antibody comprising a human heavy chain, the heavy chain comprising a variable domain that is specific for an antigen and a constant region, wherein the constant region is a human constant region selected from a constant region (eg, an IGHG constant region) in Table 13 found in a population of European, East Asian, West African, South Asian or Americas ancestry respectively and with a cumulative frequency of at least 1 or 5%, and wherein (i) the variable domain is derived from the recombination of said human gene segments in a non-human vertebrate (eg, in a mouse or a rat); or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

In another embodiment, the invention provides

An isolated antibody for administration to a patient of European, East Asian, West African, South Asian or Americas ancestry, the antibody comprising a human heavy chain, the heavy chain comprising a variable domain that is specific for an antigen and a constant region, wherein the constant region is a human constant region selected from a constant region (eg, an IGHG constant region) present in a population of European, East Asian, West African, South Asian or Americas ancestry respectively with a cumulative frequency of at least 1 or and wherein (i) the variable domain is derived from the recombination of said human gene segments in a non-human vertebrate (eg, in a mouse or a rat); or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

In an example, the constant region is found in the 1000 Genomes database. In an example, the constant region is found in Table 13.

362. The antibody of clause 361 wherein the constant region is a IGHG1a, IGHG2a, IGHG3a, IGHG3b or IGHG4a constant region and the patient is of European ancestry.

363. The antibody of clause 361 or 362, wherein the variable domain is derived from the recombination of a human VH gene segment with a human D gene segment and a human JH gene segment, the VH gene segment being selected from a VH in Table 13 found in said population and with a cumulative frequency of at least 1 or 5%.

In another embodiment, the invention provides

The antibody of clause 361 or 362, wherein the variable domain is derived from the recombination of a human VH gene segment with a human D gene segment and a human JH gene segment, the VH gene segment being selected from a VH present in a Chinese population with a cumulative frequency of at least 5%.

In an example, the gene segment is found in the 1000 Genomes database. In an example, the gene segment is found in Table 13.

364. The antibody of clause 361, 362 or 363, wherein the variable domain is derived from the recombination of a human VH gene segment with a human D gene segment and a human JH gene segment, the D gene segment being selected from a D in Table 13 found in said population and with a cumulative frequency of at least 1 or 5%.

In another embodiment, the invention provides

The antibody of clause 361, 362 or 363, wherein the variable domain is derived from the recombination of a human VH gene segment with a human D gene segment and a human JH gene segment, the D gene segment being selected from a D present in a Chinese population with a cumulative frequency of at least 5%.

In an example, the gene segment is found in the 1000 Genomes database. In an example, the gene segment is found in Table 13.

365. The antibody of clause 361, 362, 363 or 364 wherein the variable domain is derived from the recombination of a human VH gene segment with a human D gene segment and a human JH gene segment, the JH gene segment being selected from a JH in Table 13 found in said population and with a cumulative frequency of at least 1 or 5%, In another embodiment, the invention provides The antibody of clause 361, 362, 363 or 364 wherein the variable domain is derived from the recombination of a human VH gene segment with a human D gene segment and a human JH gene segment the JH gene segment being selected from a JH present in a Chinese population with a cumulative frequency of at least 5%.

In an example, the gene segment is found in the 1000 Genomes database. In an example, the gene segment is found in Table 13.

366. An isolated VH domain identical to a variable domain as recited in any one of clauses 363 to 365, optionally fused at its C-terminus to a polypeptide (eg, an antibody Fc).

367. A pharmaceutical composition comprising the antibody or variable domain of any one of clauses 361 to 366 together with a pharmaceutically-acceptable excipient, diluent or a medicament (eg, a further antigen-specific variable domain, antibody chain or antibody).

368. An isolated antibody for administration to a patient of European, East Asian, West African or Americas ancestry, the antibody comprising a human heavy chain, the heavy chain comprising a variable domain that is specific for an antigen and a constant region, wherein the variable domain is derived from the recombination of a human VH gene segment with a human D gene segment and a human JH gene segment, the VH gene segment being selected from a VH in Table 13 found in a population of European, East Asian, West African, South Asian or Americas ancestry respectively and with a cumulative frequency of at least 1 or 5%; and wherein the variable domain is derived from the recombination of said human gene segments in a non-human vertebrate (eg, in a mouse or a rat); or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

In another embodiment the invention provides:—

An isolated antibody for administration to a patient of European, East Asian, West African or Americas ancestry, the antibody comprising a human heavy chain, the heavy chain comprising a variable domain that is specific for an antigen and a constant region, wherein the variable domain is derived from the recombination of a human VH gene segment with a human D gene segment and a human JH gene segment, the VH gene segment being selected from a VH present in a population of European, East Asian, West African, South Asian or Americas ancestry respectively with a cumulative frequency of at least 1 or 5%; and wherein (i) the variable domain is derived from the recombination of said human gene segments in a non-human vertebrate (eg, in a mouse or a rat); or (ii) the variable domain comprises non-human vertebrate (eg, mouse or rat) AID-pattern mutations and non-human vertebrate (eg, mouse or rat) terminal deoxynucleotidyl transferase (TdT)-pattern mutations.

In an example, the VH gene segment is found in the 1000 Genomes database. In an example, the gene segment is found in Table 13.

369. The antibody of clause 368, wherein the variable domain is derived from the recombination of a human VH gene segment with a human D gene segment and a human JH gene segment, the D gene segment being selected from a D in Table 13 found in said population and with a cumulative frequency of at least 1 or 5%.

In another example there is provided

The antibody of clause 368, wherein the variable domain is derived from the recombination of a human VH gene segment with a human D gene segment and a human JH gene segment, the D gene segment being selected from a D present in said population with a cumulative frequency of at least 1 or In an example, the D gene segment is found in the 1000 Genomes database. In an example, the gene segment is found in Table 13.

370. The antibody of clause 368 or 369, wherein the variable domain is derived from the recombination of a human VH gene segment with a human D gene segment and a human JH gene segment, the JH gene segment being selected from a JH in Table 13 found in said population and with a cumulative frequency of at least 1 or 5%.

In another example there is provided

The antibody of clause 368 or 369; wherein the variable domain is derived from the recombination of a human VH gene segment with a human D gene segment and a human JH gene segment; the JH gene segment being selected from a JH present in said population and with a cumulative frequency of at least 1 or 5%.

In an example, the JH gene segment is found in the 1000 Genomes database. In an example, the gene segment is found in Table 13.

371. An isolated VH domain identical to a variable domain as recited in any one of clauses 368 to 370, optionally fused at its C-terminus to a polypeptide (eg, an antibody Fc).

372. A pharmaceutical composition comprising the antibody or variable domain of any one of clauses 368 to 371 together with a pharmaceutically-acceptable excipient; diluent or a medicament (eg, a further antigen-specific variable domain; antibody chain or antibody).

373. An antibody heavy chain or VH domain (eg, provided as part of an antibody) for therapy and/or prophylaxis of a disease or medical condition in a patient of European, East Asian, West African, South Asian or Americas ancestry, wherein the heavy chain is a heavy chain produced by the following steps (or is a copy of such a heavy chain):—

(a) Selection of an antigen-specific antibody heavy chain or VH domain from a non-human vertebrate (eg, a mouse or a rat), wherein the heavy chain or VH domain is derived from the recombination of a human VH gene segment with a human D gene segment and a human JH gene segment, the VH gene segment being selected from a VH in Table 13 found in said population and with a cumulative frequency of at least 1 or 5%;

(b) Optional humanisation of the heavy chain by combining the variable domain of the heavy chain with a human constant region; or optional humanisation of the selected VH domain by combining with a human constant region.

In another embodiment, there is provided:—

An antibody heavy chain or VH domain (eg, provided as part of an antibody) for therapy and/or prophylaxis of a disease or medical condition in a patient of European, East Asian, West African, South Asian or Americas ancestry, wherein the heavy chain is a heavy chain produced by the following steps (or is a copy of such a heavy chain):—

(a) Selection of an antigen-specific antibody heavy chain or VH domain from a non-human vertebrate (eg, a mouse or a rat), wherein the heavy chain or VH domain is derived from the recombination of a human VH gene segment with a human D gene segment and a human JH gene segment, the VH gene segment being selected from a VH present in said population with a cumulative frequency of at least 1 or 5%;

(b) Optional humanisation of the heavy chain by combining the variable domain of the heavy chain with a human constant region; or optional humanisation of the selected VH domain by combining with a human constant region.

In an example, the VH gene segment is found in the 1000 Genomes database. In an example, the gene segment is found in Table 13.

374. The antibody heavy chain or VH domain of clause 373, wherein the human constant region is as recited in clause 361 or 362.

375. An antibody heavy chain or VH domain as recited in clause 373 or 374 for use in a medicament for therapy and/or prophylaxis of a disease or medical condition in a patient of said ancestry.

376. A method of treating and/or preventing a disease or medical condition in a patient of European, East Asian, West African, South Asian or Americas ancestry, the method comprising administering to the patient a therapeutically or prophylactically-effective amount of the antibody heavy chain or VH domain as recited in clause 373 or 374.

In embodiments herein, a Chinese patient can be a Han Chinese patient.

In embodiments herein, a patient of European ancestry can be a patient of Northern or Western European ancestry, Italian ancestry, British or Scottish ancestry, Finnish ancestry or Iberian ancestry.

In embodiments herein, a patient of East Asian ancestry can be a patient of Han Chinese ancestry, Japanese ancestry Chinese Dai ancestry, Vietnamese ancestry or Kinh ancestry.

In embodiments herein, a patient of West African ancestry can be a patient of Yoruba ancestry, Luhya ancestry, Gambian ancestry or Malawian ancestry.

In embodiments herein, a patient of Americas ancestry can be a patient of African American ancestry, African Caribbean ancestry, Mexican ancestry, Puerto Rican ancestry, Colombian ancestry or Peruvian ancestry.

In embodiments herein, a patient of South Asian ancestry can be a patient of Ahom ancestry, Kayadtha ancestry, Reddy ancestry, Maratha ancestry, or Punjabi ancestry.

In an example of any aspect, the cumulative frequency is at least 1, 2, 3, 4, 5, 6, 7, 8, 9, 10, 15, 20, 25, 30, 35, 40, 45, 50, 55, 60, 65, 70, 75, 80, 85, 90 or 95%.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word “a” or “an” when used in conjunction with the term “comprising” in the claims and/or the specification may mean “one,” but it is also consistent with the meaning of “one or more,” “at least one,” and “one or more than one.” The use of the term “or” in the claims is used to mean “and/or” unless explicitly indicated to refer to alternatives only or the alternatives are mutually exclusive, although the disclosure supports a definition that refers to only alternatives and “and/or.” Throughout this application, the term “about” is used to indicate that a value includes the inherent variation of error for the device, the method being employed to determine the value, or the variation that exists among the study subjects.

As used in this specification and claim(s), the words “comprising” (and any form of comprising, such as “comprise” and “comprises”), “having” (and any form of having, such as “have” and “has”), “including” (and any form of including, such as “includes” and “include”) or “containing” (and any form of containing, such as “contains” and “contain”) are inclusive or open-ended and do not exclude additional, unrecited elements or method steps The term “or combinations thereof” as used herein refers to all permutations and combinations of the listed items preceding the term. For example, “A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting prophetic Examples.

EXAMPLES

Example 1

“Recombineered BAC Vectors to add Polymorphic V-regions to the Mouse Genome”

Figure 2:
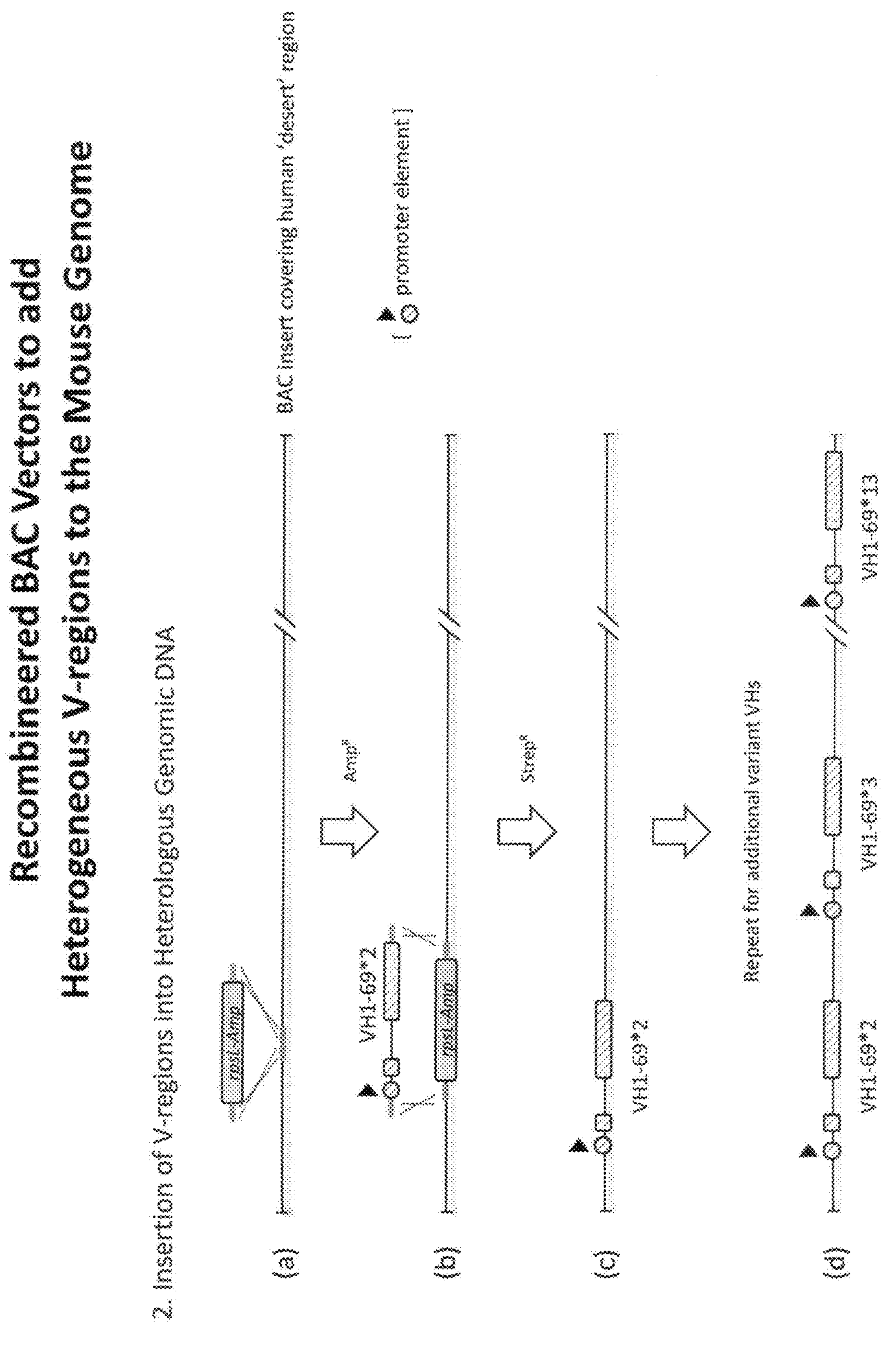
Figure 3:
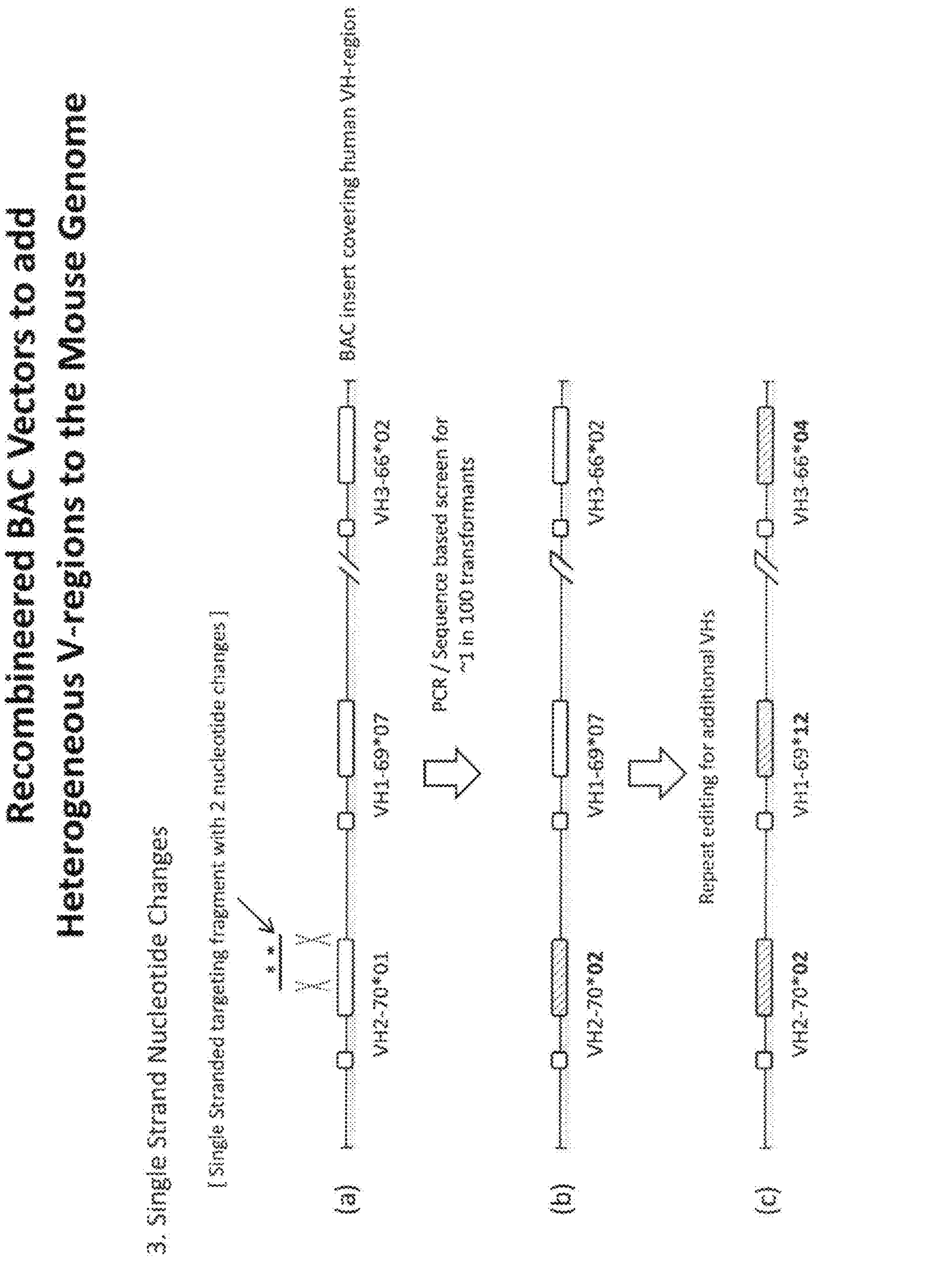

FIG. 1 through 3 depict recombineering methods (see references above) that can be used to introduce polymorphic V-gene regions into genomic DNA. In one embodiment, a genomic fragment from the human heavy chain region is inserted into a bacterial artificial chromosome (BAC) vector by standard techniques. Preferably, such a BAC, which can range in size from 20-kb to 200-kb or more, can be isolated from libraries of BACs by standard techniques including sequence searches of commercially available libraries or by hybridization to bacterial colonies containing BACs to identify those with a BAC of interest.

A BAC is chosen that has several VH gene segments; in FIG. 1, these are generically identified as VH[a] through VH[z] for example. One skilled in the art will readily identify appropriate genomic fragments; for example; an approximately 120-kb fragment from human VH5-78 through VH1-68 which includes 5 endogenous active VH gene segments and 7 VH pseudogenes. Using recombineering techniques, the endogenous VH gene segments can be replaced by polymorphic VH or VL gene segments. In this example, two steps are required. The first step replaces the V-region coding exon of an endogenous VH gene segment with a positive-negative selection operon, in this example, an operon encoding an ampicillin resistance gene (Amp) and a streptomycin-sensitizing ribosomal protein (rpsL). Certain strains of bacteria can be selected for the absence of the rpsL gene by resistance to streptomycin. Short stretches of DNA homologous to sequences flanking the endogenous VH gene exon are placed 5' and 3' of the rpsL-Amp operon. In the presence of appropriate recombination factors per standard recombineering techniques (see references above) recombination between the operon fragment and the BAC will result in replacement of the endogenous VH gene exon with the operon (FIG. 1*a*) which are selected by resistance to ampicillin. The second step uses the same homologous sequences in order to replace the inserted operon with a desired polymorphic VH gene segment. In this example, a human VH1-69 gene is inserted (FIGS. 1*b* and 1*c*). In particular the *02 variant of VH1-69 is used [ref IMGT and FIG. 5]. Successful integrations of the polymorphic VH gene segment are selected in bacteria that become resistant to streptomycin due to the loss of the operon, specifically the rpsL portion.

In this example, the two step process as described can be repeated for each of the endogenous VH gene segments or for as many endogenous gene segments that one wishes to replace with polymorphic V gene segments (FIG. 1*d*), As is apparent, any polymorphic V gene segment can be inserted in this manner and any endogenous V gene segment can act as a target, including pseudogenes. V gene segments in each of the heavy chain and two light chain loci can be replaced using this technique with appropriate genomic fragments available as BAC inserts.

FIG. 2 depicts another method for creating a genomic fragment encoding polymorphic V gene segments. In this example, polymorphic V gene segments are inserted into a region of genomic DNA devoid of other genes, control elements or other functions. Such 'desert' regions can be selected based on sequence analysis and corresponding DNA fragments cloned into BACs or identified in existing BAC libraries. Starting with such a genomic fragment, recombineering techniques can be used to insert polymorphic V gene segments at intervals of, for example, 10-kb. In this example, a 150-kb genomic fragment might accommodate insertion of up to 15 polymorphic V gene segments. Insertion of the segments is a two-step process. The first recombineering step inserts the rpsL-Amp operon at a specific site. Sequences homologous to a specific site are used to flank the operon. These are used by the recombineering system to insert the element specifically into the BAC genomic fragment and positive events are selected by resistance to ampicillin (FIG. 2*a*). The second step replaces the operon in the genomic fragment with a polymorphic V gene segment by a similar recombineering step using the same sequence homology (FIG. 2*b*). In this example, both exons and promoter element of a polymorphic VH gene segment are inserted, resulting in replacement of the rpsL-Amp operon and therefore resistance to streptomycin (FIG. 2*c*).

The two step technique for inserting polymorphic V gene segments into a specific site on the genomic fragment can be repeated multiple times resulting in a BAC genomic fragment with several polymorphic gene segments, including their promoter elements. It is apparent that the examples shown in FIGS. 1 and 2 can be combined wherein the technique for insertion can be used to add extra polymorphic V gene segments to a BAC genomic fragment as depicted in FIG. 1. One might choose to add these extra segments to an IG genomic fragment since such a fragment would be more amenable to proper IG gene expression once inserted into a non-human mammal's genome. It is known that a genomic fragment can have elements such as enhancers or elements that contribute to certain chromatin conformations, both important in wild-type gene expression.

FIG. 3 depicts an additional method to create genomic fragments with polymorphic V gene segments. This method depends upon the efficiency with which short (around 50 to 150 bases, preferably 100 bases) single stranded DNA fragments recombine with a homologous sequence using recombineering (Nat Rev Genet. 2001 October; 2(10):769-79; Recombineering: a powerful new tool for mouse functional genomics; Copeland N G, Jenkins N A, Court D L). The recombinases used in recombineering preferentially bind and use such short single-stranded fragments of DNA as a substrate for initiating homologous recombination. The efficiency can be as high as 10-2, that is, a positive event can be found in approximately 100 randomly picked (not selected) clones resulting from recombineering. A positive event in this example occurring when one or more single nucleotide changes introduced into the single-stranded fragment get transferred to the BAC insert containing V gene segments and surrounding genomic DNA, said nucleotide change or changes occurring at a homologous sequence on the BAC.

Polymorphic V gene segments can differ from endogenous V gene segments by only 1 or 2, or up to 10 or 15 nucleotide changes, for example. An example of such nucleotide polymorphisms are depicted in FIG. 5. Short single stranded regions that encompass the polymorphic nucleotide changes can be chemically synthesized using standard techniques. The resulting single stranded DNA fragments are introduced into bacteria and via recombineering techniques approximately 1 in 100 BAC fragments will have incorporated the polymorphic nucleotides via homologous incorporation of the single stranded fragment (FIG. 3*a*). BACs with the desired nucleotide change can be identified by screening for example several hundred individual clones by polymerase chain reaction (FOR) amplification and sequencing, both by standard techniques. In the example, two nucleotide changes will convert a VH1-69*01 gene segment into a VH1-69*02 gene segment (FIG. 3*b*).

It is clear that this process can be repeated for multiple endogenous V gene segments contained on a single BAC genomic fragment. In addition, the techniques depicted in FIG. 2 can be used to add additional polymorphic V gene segments by insertion into regions between existing V gene segments. As would be evident to one skilled in the art, a combination of these techniques can be used to create numerous variations of both polymorphic and endogenous human V gene segments. And it would be evident that several different genomic fragments with engineered polymorphic V gene segments and endogenous human V gene segments can be combined to create even more variations.

Example 2

"Adding Polymorphic V-regions to the Genome using SRMCE of Modified BACs"

Modified BACs with polymorphic V gene segments created using the methods described in Example 1 can be used to alter the genome of non-human mammals. These alterations can result in an intact IG locus in which normal immunoglobulin region recombination results in VDJ or VJ combinations which includes the human V gene segments. An example of how such an animal can be created is by altering the genome of, for example, mouse embryonic stem (ES) cells using the strategy outlined in FIG. 4.

One technique to integrate modified BACs with polymorphic V gene segments into a genome is sequential recombinase mediated cassette exchange (SRMCE). The technique is described in WO2011004192 (Genome Research Limited), which is incorporated here in its entirety by reference.

Figure 4:
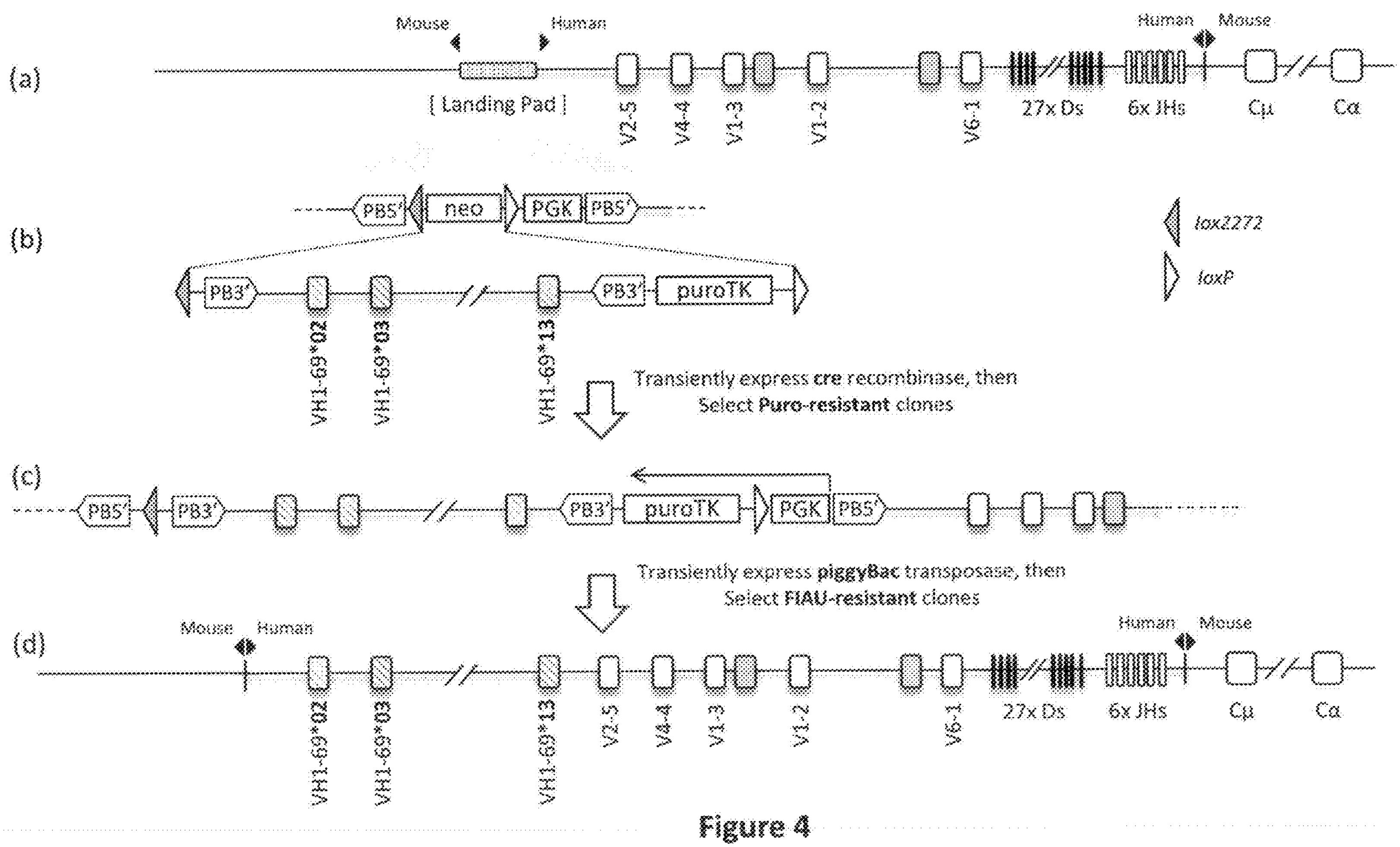
FIG. 4: Schematic illustrating a protocol for adding V gene segments to a mouse genome using sequential recombinase mediated cassette exchange (sRMCE)

SRMCE provides for a locus modified with a 'landing pad' inserted at a specific location. This insertion can either be de novo via homologous recombination or as a consequence of a previous BAC insertion. In this example, the landing pad is inserted in the mouse IGH locus between the most 3' J gene segment and the CA gene segment and a previous BAC insertion via SRMCE techniques have resulted in the addition of 5 human V gene segments and 2 V region pseudogenes. The landing pad has elements as shown in FIG. 4 that will allow the selection of correct insertion of a second targeting BAC fragment. The specificity of this insertion is provided by cre recombinase-mediated exchange between permissive lox sites. A lox site is permissive for recombination only with a compatible lox site. In this example, the loxP site will only recombine with loxP and lox2272 will only recombine with lox2272. This provides directionality to the insertion of the BAC fragment as depicted in FIGS. 4*b* and 4*c*.

ES cell clones with correct insertions are selected from a pool of clones without insertions or with non-productive insertions by resistance to puromycin. Resistance to puromycin results from the juxtaposition of an active promoter element, PGK, with the puroTK coding region. Correct insertions are verified by standard techniques including FOR of junctions, FOR of internal elements, Southern blotting, comparative genomic hybridization (CGH), sequencing and etc. In the example, correct 10)(2272-10)(2272 and loxP-loxP recombination also results in two intact sets of piggyBac elements that did not exist prior to insertion. An intact piggyBac element is comprised of a set of inverted repeats which are depicted in the figure by "PB5'" and "PB3'". An appropriated oriented set of piggyBac elements are the substrate of piggyBac transposase which can catalyse recombination between the elements, resulting in deletion of intervening sequences as well as both elements. The DNA remaining after a piggyBac transposition is left intact and is lacking any remnant of the piggyBac element. In the example, ES cell clones with successful piggyBac transposition are selected by loss of the active puroTK element which renders the cells resistant to the drug FIAU (FIGS. 4*c* and 4*d*).

The final product of the SRMCE method in this example is a IGH locus with several polymorphic V gene segments inserted along with a set of endogenous unmodified VH gene segments between sequences of the mouse genome on the 5' side and the mouse IGH constant region gene segments on the 3' side. The polymorphic V gene segments are positioned such that they can participate in the recombination events associated with B cell maturation yielding VDJ gene segments. These gene segments can then be transcribed and spliced to the mouse constant region. Translation of these transcripts will result in the production of an antibody heavy chain encoded by the polymorphic V gene segment, a human OH gene segment, a human JH gene segment and a mouse constant heavy chain gene segment.

As is well known to those skilled in the art, an ES cell clone can be used to create a line of genetically modified mice via injection of said cells into a mouse blastocyst embryo, transferring the injected embryo to a suitable recipient and breeding the chimeric offspring that result. The modified gene locus can be propagated through breeding and made either heterozygous or homozygous depending on the genetic cross.

It is evident from the structure of the IGH locus provided in this example and by knowledge of the mechanisms involved in B cell receptor (BCR) and antibody gene rearrangements that a large set of different combinations of polymorphic V gene segments with various OH and JH gene segments will result and these can contribute to a large repertoire of functional antibody genes in a population of B cells in genetically modified animals. In this example, several different human VH1-69 polymorphs are incorporated to provide superhuman VH diversity. This particular VH gene segment is known to be prevalent in antibodies that bind infectious disease pathogens (such as influenza virus) and therefore the antibody repertoire of a mouse with the genetic modification of this example would be expected to produce antibodies with a bias in favour of those that bind infectious disease pathogens. The repertoire, in other words, would have a larger subset of antibodies with superior affinities for pathogen antigens. Examples of such pathogens include influenza virus, hepatitis C virus (HCV) and human immunodeficiency virus-1 (HIV-1) (see also table above).

Example 3

Alignment of 13 VH1-69 Alleles

Building a more diverse antibody repertoire by incorporating additional V gene segment polymorphs requires availability of polymorphic variants of V gene segments. One source of such variants include sequence databases. In this example, 13 distinct variants of the VH1-69 gene segment are provided.

These variant sequences and comparisons are drawn from the "IMmunoGeneTics" IMGT Information System (www at .imgt.com) database. FIG. 5 is a diagram of the alignment of variants *02 through *13 with the *01 variant. The VH1-69'01 nucleotide and amino acid sequence is provided at the top of the figure. Where the remaining variants are identical to the *01 variant sequence a dash is inserted below the sequence. Nucleotide differences are noted alongside the appropriate variant and if the sequence change results in a protein coding change, the amino acid change is indicated above the triplet.

FIG. 5 depicts between 1 and 4 amino acid changes for each variant in comparison to the *01 variant. All of the amino acid changes occur in the part of the heavy chain protein encoding the complementarity determining regions (CDRs). These regions are responsible for antigen specificity and the affinity of the antibody for the antigen. It is evident that providing additional polymorphic CDRs in a repertoire of antibodies will increase the likelihood of there being an antibody with superior binding characteristics for various antigens. In several reports, it has been observed that the VH1-69-encoded variable region of the heavy chain is often found in antibodies that bind influenza virus, HCV and HIV-1 antigens (see table above). Therefore incorporating the polymorphic V gene segments of this example into a transgenic animal model using the methods of Examples 1 and 2 would likely result in an antibody repertoire in said transgenic animal with more antibodies that bind to antigens associated with these and other pathogens. And as is known in the art, a larger repertoire increases the probability of finding monoclonal antibodies using, for example, hybridoma technology, that bind with high affinity and specificity to a desired antigen.

This disclosure therefore describes in these examples a transgenic mouse model which can be immunized with pathogen or other antigens. Plasma B cells from such an immunized mouse can be used to make a hybridoma library that can be screened for production of antibodies that bind the pathogen antigens. This library will be superior to libraries from traditional transgenic mice for finding such antibodies given the addition of polymorphic VH1-69 gene segments to the IGH locus in said transgenic mouse.

These examples are not limiting to the human polymorphic V gene segments that can be chosen or to the methods used to introduce them into an animal model. The method can be used to construct a transgenic locus with immunoglobulin D and/or J segments. The V, D, J segments can be from a plurality of human sources (optionally more than one human ethnic population).

Example 4

Human IgH JH Gene Variants Selected from the 1000 Genomes Database

Data is presented for human JH2, 5 and 6 variants. In Tables 10A, 11A and 12A samples from humans from various populations are listed where the sequence analysis of the inventors has revealed the presence of polymorphisms in one or both IgH JH alleles. The population codes are explained in Table 8 above. The polymorphisms are nucleotide variants from JH2, 5 and 6 reference sequences (SEQ ID NOs: 1, 2 and 3 respectively; see below). All references are sequences taken from the Ensembl database (www at .ensembl.org). The JH5 reference is human IgH J5-001 disclosed in that database. The JH6 reference is human IgH J6-001 disclosed in that database. The JH2 reference is human IgH J2-001 disclosed in that database.

The reference nucleotide and encoded amino acid sequences are shown on the next page. Alignments with encoded amino acid sequences are also provided, including the corresponding position numbers on human chromosome 14.

Variant Frequencies are shown in Tables 10A, 11A and 12A and these relate to the frequency of the variants in the 1000 Genomes Database (release current at October 2011).

Tables 10B, 11B and 12B show the non-synonymous nucleotide polymorphisms in the human JH variants, as sorted by the present inventors from the 1000 Genomes database. Position numbers corresponding to nucleotide positions on human chromosome 14 are shown for variant positions (chromosome 14 being the chromosome bearing the IgH locus in humans). Thus, for example, the first entry in Table 11B is "14; 106330027:A1C" which refers to a position in a variant JH5 sequence wherein the position corresponds to position 106,330,027 on human chromosome 14, such position being A (adenine) in the reference sequence. The "C" indicates that the present inventors observed a mutation to cytosine at this position in the variants found in the 1000 Genomes database. This change leads to a change at the amino acid level of the encoded sequence (i.e., a "non-synonymous" change), in this case a change from a serine (found in the reference) to an alanine in the variant.

Example 5

Human Antibody Gene Segment Variant Identification & Population Analysis

The genomic coding region coordinates for each target gene for variant analysis were identified from the Ensembl WWW site (www at .ensembl.org) using coordinates from the GRCh.p8 Human Genome assembly (www at .ncbi.nlm.nih.gov/projects/genome/assembly/grc). Using the collected gene location coordinates; variant data was extracted from the public ftp site of the 1000 Genomes Project using the Perl 'Variant Pattern Finder' (VPF—www at .1000genomes.org/variation-pattern-finder-api-documentation).

Data extracted by VPF was post processed using software to extract all non-synonymous (NSS) variants with their associated genotype calls. Genotypes calls were assembled to form unique haplotypes, representing groups of NSS variants associated with 1000 Genome population groups and frequency of occurrence within those populations.

The output of the analysis results in tables such as in Table 13. The main body of the table describes each haplotype in turn giving a unique ID for that gene (in the range a-z,aa-zz), the population frequencies and occurrence in individuals and unique population groups; one or more subsequent columns describe the DNA base calls at each location that form the haplotype giving both the base from the reference sequence or the variant base call.

Table 13 was constructed in this manner. The table can be read as follows:

The first four columns (left to right) consist of (1) the haplotype ID letter ('ref' indicates reference—the DNA base call at each genomic location from the GRCh37 Human Reference Assembly) (2) the observed cumulative frequency of the haplotype among the different populations (3) the number of individuals in which a specific haplotype was observed (4) the number of unique population groups that the identified individuals belong to (the actual population group identifiers are displayed as a string of ID's in the most right hand column for each haplotype. For example haplotype 'a' has a population ID string of '3,4,9,13').

The populations are numbered as follows (population labels being according to 1000 Genomes Project nomenclature)

1=ASW;
2=CFU;
3=CHB;
4=CHS;
5=CLM;
6=FIN;
7=GBR;
8=IBS;
9=JPT;

10=LWK;
11=MXL;
12=PUR;
13=TSI;
14=YRI.

Subsequent columns detail a single point variant and have the following format (top to bottom) (1) the human genomic location of the variant (format [chromosome number]; [location] e.g. 14:106204113'); (2) The identifier for the point variant as defined in DbSNP (www at .ncbi.nlm.nih.gov/projects/SNP/); (3) One or additional rows show the amino acid change as result of the variant for a specific transcript (denoted by the Ensembl transcript ID in the most right-hand column for each row), the format is the amino acid in the reference sequence followed by '->' and the amino acid caused by the substitution of the variant in the reference sequence (e.g. 'Gly→Arg' means a that the translated reference sequence would result in a glycine at that location, whereas the substitution of the identified variant would result in translated protein containing arginine) using the IUPAC three letter amino acid codes (at pac.iupac.org/publications/pac/pdf/1972/pdf/3104x0639.pdf). Subsequent rows (one per haplotype) show the DNA base at each location, bases matching the reference sequence are shown in black on white back ground, bases varying from the reference are shown as white text on a black background.

The most right-hand column contains the Ensembl transcript ID's (e.g. 'ENST00000390542') for each of the gene transcript and relates to the amino acid changes to the left of this column. Because the transcripts are differing lengths each variant position may or may not have an associated amino acid change at the that position.

Example 6

Transgenic Mice, B-Cells, Hybridomas, Antibodies & Heavy Chains Based on Human JH6*02

A functional human gene segment repertoire (from VH2-26 to JH6, see the MGT database for the structure of the human IgH locus; at www at .imgt.org/IMGTrepertoire/index.php?section=LocusGenes&repertoire=locus&species=human&group=IGK) was sectored by the inventors to produce two different transgenic heavy chain alleles (denoted S2F and S3F) and corresponding mice. The transgenic alleles were expressed in the mice and the heavy chain repertoires were assessed at the RNA transcript level. Deep sequence analysis was carried out using Bioinformatics methods to assess V, D and JH gene usage, including in variable domain sequences having a HCDR3 length of at least 20 amino acids. Endogenous, mouse variable region gene segments were inactivated by inversion (as per the method described in WO2011004192, this disclosure being incorporated herein by reference).

Sequencing of Human Donor DNA Samples: Identification of Conserved JH6*02 Variant DNA samples from 9 anonymised consenting human donors were obtained by taking cheek swabs.

The samples were processed and the DNA Samples were extracted follow the protocol of QIAamp DNA Mini Kit (Cat. No. 51304, Qiagen).

FOR reactions were set up to amplify the JH6 region and FOR products were sequenced (PCR Oligos sequence: Fwd. 5'-AGGCCAGCAGAGGGTTCCATG-3' (SEQ ID NO: 444), Rev. 5-GGCTCCCAGATCCTCAAGGCAC-3' (SEQ ID NO: 445)).

Sequence analysis was carried out by comparing to the JH6 reference sequence from IMGT annotated database (at www at .imgt.org/), and this identified that all 9 donor genomes contained the human JH6*02 variant, with this variant being in the homozygous state in 7 out of the 9 donors. The inventors also consulted the genomic sequences publicly available for Jim Watson and Craig Venter at Ensembl human genome database [at www at .ensembl.org/]. These too contained the human JH6*02 variant. This confirmed to the inventors that human JH6*02 is a common, conserved variant in humans, and thus a good candidate for construction of a transgenic IgH locus as per the invention Identification of Suitable Human DNA Sequence BACs A series of human bacterial artificial chromosome (BAC) clones were identified from Ensemble (at www at .ensembl.org/index.html) or UCSC (at genome.ucsc.edu/) human database searches based on gene name (IGH) or location (chromosome 14: 106026574-107346185). Seven human RP11 BAC clones (see an extract of the UCSC database in FIG. 10, identified BACs being circled) were selected, RP11-1065N8 BAC carrying human JH6*02. In total, the following BACs were identified as sources of human IgH locus DNA: RP11-1065N8, RP11-659319 RP11-14117, RP-112H5, RP11-101G24, RP11-12F16 and RP11-47P23.

With a similar approach, different BAC clones (eg, different RP11 clone IDs or different sources from RP11) or genetically engineered BACs can be selected for insertion into the mouse IGH locus to provide different sets of human repertoires in the transgenic mouse.

Construction of Transgenic IgH Loci

Insertion of human heavy gene segments from a 1st IGH BAC (RP11-1065N8) into the IGH locus of mouse AB2.1 ES cells (Baylor College of Medicine) was performed to create a heavy chain allele denoted the S1 allele. The inserted human sequence corresponds to the sequence of human chromosome 14 from position 106494908 to position 106328951 and comprises functional heavy gene segments VH2-5, VH7-4-1, VH4-4, VH1-3, VH1-2, VH6-1, D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, 01-26, D7-27, JH1, JH2, JH3, JH4, JH5 and JH6 (in 5' to 3' order), wherein the JH6 was chosen to be the human JH6*02 variant. The insertion was made between positions 114666435 and 114666436 on mouse chromosome 12, which is upstream of the mouse C^ region. The mouse VH, D and J H gene segments were retained in the locus, immediately upstream of (5' of) the inserted human heavy chain DNA.

A second allele, S2 was constructed in which more human functional VH gene segments were inserted upstream (5') of the 5'-most VH inserted in the S1 allele by the sequential insertion of human DNA from a second BAC (BAC2). The inserted human sequence from BAC2 corresponds to the sequence of human chromosome 14 from position 106601551 to position 106494909 and comprises functional heavy chain gene segments VH3-13, VH3-11, VH3-9, VH1-8, VH3-7. The mouse VH, D and JH gene segments were retained in the locus, immediately upstream of (5' of) the inserted human heavy chain DNA. In a subsequent step, these were inverted to inactivate them, thereby producing S2F mice in which only the human heavy chain variable region gene segments are active.

A third allele, S3 was constructed in which more human functional VH gene segments were inserted upstream (5') of the 5'-most VH inserted in the S2 allele by the sequential insertion of human DNA from a third BAC (BAC3). The inserted sequence corresponds to the sequence of human chromosome 14 from position 106759988 to position 106609301, and comprises functional heavy chain gene segments, VH2-26, VH1-24, VH3-23, VH3-21, VH3-20, VH1-18, and VH3-15. The mouse VH, D and JH gene segments were retained in the locus, immediately upstream of (5' of) the inserted human heavy chain DNA. In a subsequent step, these were inverted to inactivate them, thereby producing S3F mice in which only the human heavy chain variable region gene segments are active.

Mice bearing either the S2F or S3F insertion into an endogenous heavy chain locus were generated from the ES cells using standard procedures. The other endogenous heavy chain locus was inactivated in the mice by insertion of an inactivating sequence comprising neon into the mouse JH-C^ intron (to produce the "HA" allele).

Immunisation Procedure

Transgenic mice of the S2F or S3F genotype were primed with 20-40 ug recombinant proteins obtained commercially or produced in house with Antigen 1 (OVA (Sigma A7641); Antigen 2 (a human infectious disease pathogen antigen) and Antigen 3 (a human antigen) via the ip route in complete Freunds adjuvant (Sigma F 5881) and 10 ug/animal CpG (CpG oligo; Invivogen, San Diego, Calif., USA) and then boosted twice in about two weekly intervals with about half the amount of antigen in incomplete Freunds adjuvant (Sigma F 5506) and 10 ug/animal CpG. Final boosts were administered two weeks later iv without any adjuvant and contained 5-10 ug protein in PBS.

Hybridoma Fusion Procedure

Spleens were taken 3 days after the final boost and splenocytes were treated with CpG (25 µm final concentration) for and left until the following day. Cells were then fused with SP0/2 Ag14 myeloma cells (HPA Cultures Cat No 85072401) using a BTX ECM2001 electrofusion instrument. Fused cells were left to recover for 20 minutes then seeded in a T75 flask until next morning. Then the cells were spun down and plated out by dilution series on 96-well culture plates and left for about 10 days before screening. Media was changed 1-3 times during this period.

Screening

Culture supernatants of the hybridoma wells above were screened using homogenious time resolved fluorescence assay (htrf) using Europium cryptate labelled anti-mouse IgG (Cisbio anti-mouse Ig Europium Cryptate) and a biotin tagged target antigen with a commercially available streptavidin conjucated donor (Cisbio: streptaviding conjugated D2) or by IgG-specific 384 well ELISA. Positive wells identified by htrf were scaled to 24-well plates or immediately counterscreened using an IgG-specific detection ELISA method. Positives identified by primary ELISA screen were immediately expanded to 24-well plates. Once cultures were expanded to 24-well stage and reached confluency, supernatants were re-tested using htrf or IgG-specific ELISA to confirm binding to target antigen. Supernatant of such confirmed cultures were then also analysed by surface plasmon resonance using a BioRad ProteOn XPR36 instrument. For this, antibody expressed in the hybridoma cultures was captured on a biosensor GLM chip (BioRad 176-512) which had an anti-mouse lgG (GE Healthcare BR-1008-38)) covalently coupled the biosensor chip surface. The antigen was then used as the analyte and passed over the captured hybridoma antibody surface. For Antigen 2 and Antigen 3, concentrations of 256 nM, 64 nM, 16 nM, 4 nM and 1 nM were typically used, for Antigen 1, concentrations of 1028 nM, 256 nM, 64 nM, 16 nM and 4 nM were typically used, binding curves were double referenced using a OnM injection (i.e. buffer alone). Kinetics and overall affinities were determined using the 1:1 model inherent to the BioRad ProteOn XPR36 analysis software.

Any clones with confirmed binding activity were used for preparing total RNA and followed by FOR to recover the heavy chain variable region sequences. Standard 5'-RACE was carried out to analyse RNA transcripts from the transgenic heavy chain loci in the S2F and S3F mice. Additionally, deep sequence analysis of almost 2000 sequences produced by the mice was carried out.

Bionformatics Analysis

Sequences for analysis were obtained from two different methods:

The first is from RNA extracted from the spleen: first cDNA strand was synthesized using an oligo based on the Cmu region of the mouse IGH locus as a FOR template. FOR was performed using this oligo with an oligo dT-anchor primer. Then FOR product was cloned into pDrive vector (Qiagen) and then sequenced.

The second is from hybridomas generated through electro-fusion: total RNA was extracted from hybridoma lines of interest using standard Trizol methods and frozen at −80° C. for long term storage. cDNA was generated from 100 ng total RNA using standard Superscript III reverse transcriptase and a gene-specific reverse primer binding to all mouse IgG isotypes for heavy chain and a mouse kappa constant region primer for the light chain amplification. 2-3 µl of cDNA were then used as template in a PCR reaction using Pfu DNA polymerase and a panel of degenerate forward primers annealing to the leader sequence of the human immunoglobulin variable domain as well as one mouse pan-IgG reverse primer. PCR products were run out of a 1% agarose gel and bands of approximately 350-450 base pairs extracted and purified. DNA was then sequenced.

The sequences from the first method can either be from IgM from Naive mice or IgG from immunised mice. The samples from the second method are all from IgG from immunised mice, and specific to the immunising antigen. Almost 2000 sequences were analysed.

The sequences were obtained as a pair of forward and reverse reads. These were first trimmed to remove low-quality base calls from the ends of the reads (trimmed from both ends until a 19 nucleotide window had an average quality score of 25 or more). The reads were combined together by taking the reverse complement of the reverse read, and aligning it against the forward read. The alignment scoring was 5 for a match, −4 for a mismatch, a gap open penalty of 10 and a gap extension penalty of 1. A consensus sequence was then produced by stepping through the alignment and comparing bases. When there was a disagreement the base with the highest quality value from sequencing was used.

The BLAST© (Basic Local Alignment Search Tool) (Camacho C., Coulouris G., Avagyan V., Ma N., Papadopoulos J., Bealer K., & Madden T. L. (2008) "BLAST©: architecture and applications." BMC Bioinformatics 10:421 at www at .ncbi.nlm.nih.gov/pubmed/20003500) program 'blastn' was then used to find the germline J and V segments used in each sequence. A wordsize of 30 was used for V matching, and 15 for J matching. The database searched against was constructed from the NGS sequencing of the BACs which were used to generate the Kymouse.

If a sequence matched both a V and a J segment, the sequence between the two was then compared to a database of germline D segments in the mouse using 'blastn' with a wordsize of 4 and the options 'blastn-short' and 'ungapped'. This was used to assign a D segment, if possible. The CDR3 was identified by searching for the conserved "TAT- TACTGT" sequence in the V segment, and the "CTGGGG" in the J segment. If these motifs were not found, then up to 4 mismatches were allowed. The IMGT definition of CDR3 was used, so the CDR3 length is calculated from after the "TGT" in the V to before the "TGG" in the J. Sequences with an out of frame junction (those which do not have a CDR3 nucleotide length divisible by 3) or which contained a stop codon ("TAA", "TAG" or "TGA") were excluded.

The identity of the matching V, J and D segments as well as the CDR3 length from this assignment were then saved as a table for downstream analysis. The ratio of IGHJ6*02 used increased from the naive to immunised mice, as well as being enriched in the sub-population of sequences with a long HCDR3 (defined as consisting of 20 or more amino acids):

| | | | All HCDR3 > 20 | | |
|---|---|---|---|---|---|
| | JH6*02% | Total Count | JH6*02% | Total Count | % HCDR3 > 20 |
| Naive | 22.31% | 1340 | 91.11% | 45 | 3.36% |
| Immunised | 37.50% | 256 | 66.67% | 9 | 3.52% |
| Hybridoma | 36.13% | 119 | 63.64% | 11 | 9.24% |

This shows that the JH6*02 gene segment is selected for by immunisation, as the proportion of JH6*02 usage increases after immunisation. JH6*02 is also used in the majority of antibodies with a long HCDR3 length, which is desirable for targets which are specifically bound by long HCDR3 length antibodies.

SEQ ID NO: 1 (JH5 Reference)

| | | | | |
|---|---|---|---|---|
| T<br>G<br>A | T<br>G<br>G | G<br>T<br>A | A<br>C<br>G | C<br>C<br>G |
| C<br>C<br>A | A<br>T<br>G | A<br>T<br>T | G<br>G<br>C | C<br>G |
| T<br>G | G<br>A | G<br>C | G<br>C | G<br>A |
| A<br>G | C<br>T | C<br>G | C<br>G | C<br>C |

JH5 Alignment
(top line = SEQ ID NO: 1, Middle line = SEQ ID NO: 5, Bottom line = SEQ ID NO: 6)

| | | | | |
|---|---|---|---|---|
| IgH J5-001 | 106,330,072 | 106,330,071 | | |
| | T<br>A | T<br>A<br>N | G<br>C | A<br>T |
| 106,330,066 | 106,330,067 | 106,330,066 | 106,330,065 | |
| C<br>G<br>W | C<br>G | A<br>T | A<br>T<br>F | G<br>C |
| 106,330,063 | 106,330,062 | | | |
| C<br>G | T<br>A<br>D | G<br>C | G<br>C | G<br>C<br>P |
| G<br>C | A<br>T | C<br>G<br>W | C<br>G | C<br>G |
| C<br>G<br>G | G<br>C | G<br>C | T<br>A<br>Q | C<br>G |
| | | | 106,330,045 | 106,330,044 |
| C<br>G | C<br>G<br>G | T<br>A | T<br>A | G<br>C<br>T |
| | | 106,330,041 | | |
| G<br>C | G<br>C | A<br>T<br>L | C<br>G | C<br>G |

-continued

| | | | | |
|---|---|---|---|---|
| A<br>T<br>V | G<br>C | T<br>A | G<br>C<br>T | G<br>C |
| | 106,330,032 | | | |
| C<br>G | A<br>T<br>V | G<br>C | A<br>T | G<br>C<br>S |
| | 106,330,027 | | | 106,330,024 |
| G<br>C | A<br>T | G<br>C<br>S | T<br>A | C<br>G |

SEQ ID NO: 2 (JH6 Reference)

| | | | | |
|---|---|---|---|---|
| A<br>C<br>G<br>C | T<br>C<br>G | G<br>T<br>T | A<br>G<br>G | T<br>C<br>C |
| G<br>A<br>C | A<br>G<br>A | T<br>A<br>G | G<br>C<br>T | A<br>C<br>G |
| T<br>C<br>G | G<br>C<br>C | A<br>G<br>A | T<br>T<br>G | G<br>T<br>A |
| A<br>T<br>G | T<br>C<br>G | G<br>C<br>A | T<br>C<br>G | A<br>T<br>T |

JH6 Alignment:
(top line = SEQ ID NO: 2, Middle line = SEQ ID NO: 7, Bottom line = SEQ ID NO: 8)

| | | | | |
|---|---|---|---|---|
| IgH J6-001 | 106,329,466 | | | |
| | A<br>T | T<br>A<br>Y | G<br>C | A<br>T |
| T<br>A<br>Y | G<br>C | A<br>T | T<br>A<br>Y | G<br>C |
| A<br>T | T<br>A<br>Y | G<br>C | A<br>T | T<br>A<br>Y |
| | 106,329,453 | 106,329,452 | 106,329,451 | |
| G<br>C | A<br>T | T<br>A<br>Y | G<br>C | T<br>A |
| A<br>T<br>M | C<br>G | C<br>G | T<br>A<br>D | G<br>C |
| C<br>G | A<br>T<br>V | G<br>C | A<br>T | C<br>G<br>W |
| | | | | 106,329,435 |
| C<br>G | C<br>G | C<br>G<br>G | G<br>C | T<br>A |
| | | | 106,329,436 | |
| | | | T<br>A<br>K | T<br>A |

-continued

| | | | | |
|---|---|---|---|---|
| C<br>G | C<br>G<br>G | C<br>G | T<br>A | G<br>C<br>T |
| | 106,329,426 | | | |
| G<br>C | T<br>A | G<br>C<br>T | C<br>G | C<br>T |
| | | | 106,329,419 | |
| A<br>T<br>V | G<br>C | T<br>A | G<br>C<br>T | G<br>C |
| 160,329,417 | | | 106,329,414 | 160,329,413 |
| C<br>G | A<br>T<br>V | G<br>C | A<br>T | G<br>C<br>S |
| G<br>C | 106,329,411<br>A<br>T | G<br>C<br>S | T<br>A | 106,329,408<br>C<br>G |
| SEQ ID NO: 3 (JH2 Reference) | | | | |
| A<br>C<br>G | T<br>C<br>A | G<br>C<br>C | A<br>G<br>A | C<br>G<br>G |
| C<br>C<br>A | A<br>A<br>G | T<br>C<br>G | G<br>C<br>A | A<br>G<br>G |
| A<br>T<br>T | G<br>G<br>C | C<br>G | T<br>G | A<br>A |
| G<br>C | A<br>C | G<br>A | A<br>G | C<br>T |
| JH2 Alignment:<br>(top line = SEQ ID NO: 3, Middle line = SEQ ID NO: 9, Bottom line = SEQ ID NO: 10) | | | | |
| IgH J5-001 | 106,331,460 | | | |
| | A<br>T | T<br>A<br>Y | G<br>C | A<br>T |
| | 106,331,455 | | 106,331,453 | |
| C<br>G<br>W | C<br>G | A<br>T | T<br>A<br>Y | G<br>C |
| A<br>T | A<br>T<br>F | G<br>C | C<br>G | T<br>A<br>D |
| A<br>T | G<br>C | A<br>T<br>L | G<br>C | A<br>T |
| C<br>G<br>W | C<br>G | C<br>G | C<br>G<br>G | G<br>C |
| G<br>C | C<br>G<br>R | A<br>T | C<br>G | C<br>G<br>G |
| G<br>C | T<br>A | G<br>C<br>T | G<br>C | G<br>C |

-continued

| | | | | |
|---|---|---|---|---|
| A<br>T<br>L | C<br>G | C<br>G | A<br>T<br>V | G<br>C |
| T<br>A | G<br>C<br>T | A<br>T | C<br>G | A<br>T<br>V |
| G<br>C | A<br>T | G<br>C<br>S | G<br>C | A<br>T |
| | | G<br>C<br>S | T<br>A | 106,331,453<br>C<br>G |

Tables

In the tables, the notation is illustrated by the following example

| | | | |
|---|---|---|---|
| IGLV1 40 | G1 40*02 | X53936 | :g9>lc1)>g,L4>VI |

Polymorphic variant IGV lambda VI-40*02 has Genbank Accession No. X53936 and when compared to the *01 variant, the VI-40*02 variant has mutations at positions 9, 10 and 4. For example, at position 9, a "C" appears instead of a "G" that is present in the *01 variant. The "|" is simply a notation separator, and does not indicate any mutation. For example the "g282|" notation indicates no change (ie, position 282 is a g). "del #" means that the residue at that position is absent.

Lengthy table referenced here

US10730930-20200804-T00001

Please refer to the end of the specification for access instructions.

Lengthy table referenced here

US10730930-20200804-T00002

Please refer to the end of the specification for access instructions.

Lengthy table referenced here

US10730930-20200804-T00003

Please refer to the end of the specification for access instructions.

Lengthy table referenced here

US10730930-20200804-T00004

Please refer to the end of the specification for access instructions.

Lengthy table referenced here

US10730930-20200804-T00005

Please refer to the end of the specification for access instructions.

Lengthy table referenced here

US10730930-20200804-T00006

Please refer to the end of the specification for access instructions.

Lengthy table referenced here

US10730930-20200804-T00007

Please refer to the end of the specification for access instructions.

Lengthy table referenced here

US10730930-20200804-T00008

Please refer to the end of the specification for access instructions.

Lengthy table referenced here

US10730930-20200804-T00009

Please refer to the end of the specification for access instructions.

Lengthy table referenced here

US10730930-20200804-T00010

Please refer to the end of the specification for access instructions.

Lengthy table referenced here

US10730930-20200804-T00011

Please refer to the end of the specification for access instructions.

Lengthy table referenced here

US10730930-20200804-T00012

Please refer to the end of the specification for access instructions.

Lengthy table referenced here

US10730930-20200804-T00013

Please refer to the end of the specification for access instructions.

Lengthy table referenced here

US10730930-20200804-T00014

Please refer to the end of the specification for access instructions.

Lengthy table referenced here

US10730930-20200804-T00015

Please refer to the end of the specification for access instructions.

Lengthy table referenced here

US10730930-20200804-T00016

Please refer to the end of the specification for access instructions.

Lengthy table referenced here

US10730930-20200804-T00017

Please refer to the end of the specification for access instructions.

Lengthy table referenced here

US10730930-20200804-T00018

Please refer to the end of the specification for access instructions.

Lengthy table referenced here

US10730930-20200804-T00019

Please refer to the end of the specification for access instructions.

Lengthy table referenced here

US10730930-20200804-T00020

Please refer to the end of the specification for access instructions.

Lengthy table referenced here

US10730930-20200804-T00021

Please refer to the end of the specification for access instructions.

Lengthy table referenced here

US10730930-20200804-T00022

Please refer to the end of the specification for access instructions.

Lengthy table referenced here

US10730930-20200804-T00023

Please refer to the end of the specification for access instructions.

Lengthy table referenced here

US10730930-20200804-T00024

Please refer to the end of the specification for access instructions.

Lengthy table referenced here

US10730930-20200804-T00025

Please refer to the end of the specification for access instructions.

Lengthy table referenced here

US10730930-20200804-T00026

Please refer to the end of the specification for access instructions.

Lengthy table referenced here

US10730930-20200804-T00027

Please refer to the end of the specification for access instructions.

Lengthy table referenced here

US10730930-20200804-T00028

Please refer to the end of the specification for access instructions.

Lengthy table referenced here

US10730930-20200804-T00029

Please refer to the end of the specification for access instructions.

Lengthy table referenced here

US10730930-20200804-T00030

Please refer to the end of the specification for access instructions.

Lengthy table referenced here

US10730930-20200804-T00031

Please refer to the end of the specification for access instructions.

Lengthy table referenced here

US10730930-20200804-T00032

Please refer to the end of the specification for access instructions.

Lengthy table referenced here

US10730930-20200804-T00033

Please refer to the end of the specification for access instructions.

Lengthy table referenced here

US10730930-20200804-T00034

Please refer to the end of the specification for access instructions.

Lengthy table referenced here

US10730930-20200804-T00035

Please refer to the end of the specification for access instructions.

Lengthy table referenced here

US10730930-20200804-T00036

Please refer to the end of the specification for access instructions.

Lengthy table referenced here

US10730930-20200804-T00037

Please refer to the end of the specification for access instructions.

Lengthy table referenced here

US10730930-20200804-T00038

Please refer to the end of the specification for access instructions.

Lengthy table referenced here

US10730930-20200804-T00039

Please refer to the end of the specification for access instructions.

Lengthy table referenced here

US10730930-20200804-T00040

Please refer to the end of the specification for access instructions.

Lengthy table referenced here

US10730930-20200804-T00041

Please refer to the end of the specification for access instructions.

Lengthy table referenced here

US10730930-20200804-T00042

Please refer to the end of the specification for access instructions.

Lengthy table referenced here

US10730930-20200804-T00043

Please refer to the end of the specification for access instructions.

Lengthy table referenced here

US10730930-20200804-T00044

Please refer to the end of the specification for access instructions.

Lengthy table referenced here

US10730930-20200804-T00045

Please refer to the end of the specification for access instructions.

Lengthy table referenced here

US10730930-20200804-T00046

Please refer to the end of the specification for access instructions.

Lengthy table referenced here

US10730930-20200804-T00047

Please refer to the end of the specification for access instructions.

Lengthy table referenced here

US10730930-20200804-T00048

Please refer to the end of the specification for access instructions.

Lengthy table referenced here

US10730930-20200804-T00049

Please refer to the end of the specification for access instructions.

Lengthy table referenced here

US10730930-20200804-T00050

Please refer to the end of the specification for access instructions.

Lengthy table referenced here

US10730930-20200804-T00051

Please refer to the end of the specification for access instructions.

Lengthy table referenced here

US10730930-20200804-T00052

Please refer to the end of the specification for access instructions.

Lengthy table referenced here

US10730930-20200804-T00053

Please refer to the end of the specification for access instructions.

Lengthy table referenced here

US10730930-20200804-T00054

Please refer to the end of the specification for access instructions.

Lengthy table referenced here

US10730930-20200804-T00055

Please refer to the end of the specification for access instructions.

Lengthy table referenced here

US10730930-20200804-T00056

Please refer to the end of the specification for access instructions.

Lengthy table referenced here

US10730930-20200804-T00057

Please refer to the end of the specification for access instructions.

Lengthy table referenced here

US10730930-20200804-T00058

Please refer to the end of the specification for access instructions.

Lengthy table referenced here

US10730930-20200804-T00059

Please refer to the end of the specification for access instructions.

Lengthy table referenced here

US10730930-20200804-T00060

Please refer to the end of the specification for access instructions.

Lengthy table referenced here

US10730930-20200804-T00061

Please refer to the end of the specification for access instructions.

Lengthy table referenced here

US10730930-20200804-T00062

Please refer to the end of the specification for access instructions.

Lengthy table referenced here

US10730930-20200804-T00063

Please refer to the end of the specification for access instructions.

Lengthy table referenced here

US10730930-20200804-T00064

Please refer to the end of the specification for access instructions.

Lengthy table referenced here

US10730930-20200804-T00065

Please refer to the end of the specification for access instructions.

Lengthy table referenced here

US10730930-20200804-T00066

Please refer to the end of the specification for access instructions.

Lengthy table referenced here

US10730930-20200804-T00067

Please refer to the end of the specification for access instructions.

Lengthy table referenced here

US10730930-20200804-T00068

Please refer to the end of the specification for access instructions.

Lengthy table referenced here

US10730930-20200804-T00069

Please refer to the end of the specification for access instructions.

Lengthy table referenced here

US10730930-20200804-T00070

Please refer to the end of the specification for access instructions.

Lengthy table referenced here

US10730930-20200804-T00071

Please refer to the end of the specification for access instructions.

Lengthy table referenced here

US10730930-20200804-T00072

Please refer to the end of the specification for access instructions.

Lengthy table referenced here

US10730930-20200804-T00073

Please refer to the end of the specification for access instructions.

Lengthy table referenced here

US10730930-20200804-T00074

Please refer to the end of the specification for access instructions.

Lengthy table referenced here

US10730930-20200804-T00075

Please refer to the end of the specification for access instructions.

Lengthy table referenced here

US10730930-20200804-T00076

Please refer to the end of the specification for access instructions.

Lengthy table referenced here

US10730930-20200804-T00077

Please refer to the end of the specification for access instructions.

Lengthy table referenced here

US10730930-20200804-T00078

Please refer to the end of the specification for access instructions.

Lengthy table referenced here

US10730930-20200804-T00079

Please refer to the end of the specification for access instructions.

Lengthy table referenced here

US10730930-20200804-T00080

Please refer to the end of the specification for access instructions.

Lengthy table referenced here

US10730930-20200804-T00081

Please refer to the end of the specification for access instructions.

Lengthy table referenced here

US10730930-20200804-T00082

Please refer to the end of the specification for access instructions.

Lengthy table referenced here
US10730930-20200804-T00083
Please refer to the end of the specification for access instructions.

Lengthy table referenced here
US10730930-20200804-T00084
Please refer to the end of the specification for access instructions.

Lengthy table referenced here
US10730930-20200804-T00085
Please refer to the end of the specification for access instructions.

Lengthy table referenced here
US10730930-20200804-T00086
Please refer to the end of the specification for access instructions.

Lengthy table referenced here
US10730930-20200804-T00087
Please refer to the end of the specification for access instructions.

Lengthy table referenced here
US10730930-20200804-T00088
Please refer to the end of the specification for access instructions.

Lengthy table referenced here
US10730930-20200804-T00089
Please refer to the end of the specification for access instructions.

Lengthy table referenced here
US10730930-20200804-T00090
Please refer to the end of the specification for access instructions.

Lengthy table referenced here
US10730930-20200804-T00091
Please refer to the end of the specification for access instructions.

Lengthy table referenced here
US10730930-20200804-T00092
Please refer to the end of the specification for access instructions.

Lengthy table referenced here
US10730930-20200804-T00093
Please refer to the end of the specification for access instructions.

Lengthy table referenced here
US10730930-20200804-T00094
Please refer to the end of the specification for access instructions.

Lengthy table referenced here
US10730930-20200804-T00095
Please refer to the end of the specification for access instructions.

Lengthy table referenced here
US10730930-20200804-T00096
Please refer to the end of the specification for access instructions.

Lengthy table referenced here
US10730930-20200804-T00097
Please refer to the end of the specification for access instructions.

Lengthy table referenced here
US10730930-20200804-T00098
Please refer to the end of the specification for access instructions.

Lengthy table referenced here
US10730930-20200804-T00099
Please refer to the end of the specification for access instructions.

Lengthy table referenced here
US10730930-20200804-T00100
Please refer to the end of the specification for access instructions.

Lengthy table referenced here

US10730930-20200804-T00101

Please refer to the end of the specification for access instructions.

Lengthy table referenced here

US10730930-20200804-T00102

Please refer to the end of the specification for access instructions.

Lengthy table referenced here

US10730930-20200804-T00103

Please refer to the end of the specification for access instructions.

Lengthy table referenced here

US10730930-20200804-T00104

Please refer to the end of the specification for access instructions.

Lengthy table referenced here

US10730930-20200804-T00105

Please refer to the end of the specification for access instructions.

Lengthy table referenced here

US10730930-20200804-T00106

Please refer to the end of the specification for access instructions.

Lengthy table referenced here

US10730930-20200804-T00107

Please refer to the end of the specification for access instructions.

Lengthy table referenced here

US10730930-20200804-T00108

Please refer to the end of the specification for access instructions.

Lengthy table referenced here

US10730930-20200804-T00109

Please refer to the end of the specification for access instructions.

Lengthy table referenced here

US10730930-20200804-T00110

Please refer to the end of the specification for access instructions.

Lengthy table referenced here

US10730930-20200804-T00111

Please refer to the end of the specification for access instructions.

Lengthy table referenced here

US10730930-20200804-T00112

Please refer to the end of the specification for access instructions.

Lengthy table referenced here

US10730930-20200804-T00113

Please refer to the end of the specification for access instructions.

Lengthy table referenced here

US10730930-20200804-T00114

Please refer to the end of the specification for access instructions.

Lengthy table referenced here

US10730930-20200804-T00115

Please refer to the end of the specification for access instructions.

Lengthy table referenced here

US10730930-20200804-T00116

Please refer to the end of the specification for access instructions.

Lengthy table referenced here

US10730930-20200804-T00117

Please refer to the end of the specification for access instructions.

Lengthy table referenced here

US10730930-20200804-T00118

Please refer to the end of the specification for access instructions.

Lengthy table referenced here

US10730930-20200804-T00119

Please refer to the end of the specification for access instructions.

Lengthy table referenced here

US10730930-20200804-T00120

Please refer to the end of the specification for access instructions.

Lengthy table referenced here

US10730930-20200804-T00121

Please refer to the end of the specification for access instructions.

Lengthy table referenced here

US10730930-20200804-T00122

Please refer to the end of the specification for access instructions.

Lengthy table referenced here

US10730930-20200804-T00123

Please refer to the end of the specification for access instructions.

Lengthy table referenced here

US10730930-20200804-T00124

Please refer to the end of the specification for access instructions.

Lengthy table referenced here

US10730930-20200804-T00125

Please refer to the end of the specification for access instructions.

Lengthy table referenced here

US10730930-20200804-T00126

Please refer to the end of the specification for access instructions.

Lengthy table referenced here

US10730930-20200804-T00127

Please refer to the end of the specification for access instructions.

Lengthy table referenced here

US10730930-20200804-T00128

Please refer to the end of the specification for access instructions.

Lengthy table referenced here

US10730930-20200804-T00129

Please refer to the end of the specification for access instructions.

Lengthy table referenced here

US10730930-20200804-T00130

Please refer to the end of the specification for access instructions.

Lengthy table referenced here

US10730930-20200804-T00131

Please refer to the end of the specification for access instructions.

Lengthy table referenced here

US10730930-20200804-T00132

Please refer to the end of the specification for access instructions.

Lengthy table referenced here

US10730930-20200804-T00133

Please refer to the end of the specification for access instructions.

Lengthy table referenced here

US10730930-20200804-T00134

Please refer to the end of the specification for access instructions.

Lengthy table referenced here

US10730930-20200804-T00135

Please refer to the end of the specification for access instructions.

Lengthy table referenced here

US10730930-20200804-T00136

Please refer to the end of the specification for access instructions.

Lengthy table referenced here

US10730930-20200804-T00137

Please refer to the end of the specification for access instructions.

Lengthy table referenced here

US10730930-20200804-T00138

Please refer to the end of the specification for access instructions.

Lengthy table referenced here

US10730930-20200804-T00139

Please refer to the end of the specification for access instructions.

Lengthy table referenced here

US10730930-20200804-T00140

Please refer to the end of the specification for access instructions.

Lengthy table referenced here

US10730930-20200804-T00141

Please refer to the end of the specification for access instructions.

Lengthy table referenced here

US10730930-20200804-T00142

Please refer to the end of the specification for access instructions.

Lengthy table referenced here

US10730930-20200804-T00143

Please refer to the end of the specification for access instructions.

Lengthy table referenced here

US10730930-20200804-T00144

Please refer to the end of the specification for access instructions.

Lengthy table referenced here

US10730930-20200804-T00145

Please refer to the end of the specification for access instructions.

Lengthy table referenced here

US10730930-20200804-T00146

Please refer to the end of the specification for access instructions.

Lengthy table referenced here

US10730930-20200804-T00147

Please refer to the end of the specification for access instructions.

Lengthy table referenced here

US10730930-20200804-T00148

Please refer to the end of the specification for access instructions.

Lengthy table referenced here

US10730930-20200804-T00149

Please refer to the end of the specification for access instructions.

Lengthy table referenced here

US10730930-20200804-T00150

Please refer to the end of the specification for access instructions.

Lengthy table referenced here

US10730930-20200804-T00151

Please refer to the end of the specification for access instructions.

Lengthy table referenced here

US10730930-20200804-T00152

Please refer to the end of the specification for access instructions.

Lengthy table referenced here

US10730930-20200804-T00153

Please refer to the end of the specification for access instructions.

Lengthy table referenced here

US10730930-20200804-T00154

Please refer to the end of the specification for access instructions.

Lengthy table referenced here

US10730930-20200804-T00155

Please refer to the end of the specification for access instructions.

Lengthy table referenced here

US10730930-20200804-T00156

Please refer to the end of the specification for access instructions.

Lengthy table referenced here

US10730930-20200804-T00157

Please refer to the end of the specification for access instructions.

Lengthy table referenced here

US10730930-20200804-T00158

Please refer to the end of the specification for access instructions.

Lengthy table referenced here

US10730930-20200804-T00159

Please refer to the end of the specification for access instructions.

Lengthy table referenced here

US10730930-20200804-T00160

Please refer to the end of the specification for access instructions.

Lengthy table referenced here

US10730930-20200804-T00161

Please refer to the end of the specification for access instructions.

Lengthy table referenced here

US10730930-20200804-T00162

Please refer to the end of the specification for access instructions.

Lengthy table referenced here

US10730930-20200804-T00163

Please refer to the end of the specification for access instructions.

Lengthy table referenced here

US10730930-20200804-T00164

Please refer to the end of the specification for access instructions.

Lengthy table referenced here

US10730930-20200804-T00165

Please refer to the end of the specification for access instructions.

Lengthy table referenced here

US10730930-20200804-T00166

Please refer to the end of the specification for access instructions.

Lengthy table referenced here

US10730930-20200804-T00167

Please refer to the end of the specification for access instructions.

Lengthy table referenced here

US10730930-20200804-T00168

Please refer to the end of the specification for access instructions.

Lengthy table referenced here

US10730930-20200804-T00169

Please refer to the end of the specification for access instructions.

Lengthy table referenced here

US10730930-20200804-T00170

Please refer to the end of the specification for access instructions.

Lengthy table referenced here

US10730930-20200804-T00171

Please refer to the end of the specification for access instructions.

Lengthy table referenced here

US10730930-20200804-T00172

Please refer to the end of the specification for access instructions.

Lengthy table referenced here

US10730930-20200804-T00173

Please refer to the end of the specification for access instructions.

Lengthy table referenced here

US10730930-20200804-T00174

Please refer to the end of the specification for access instructions.

Lengthy table referenced here

US10730930-20200804-T00175

Please refer to the end of the specification for access instructions.

Lengthy table referenced here

US10730930-20200804-T00176

Please refer to the end of the specification for access instructions.

Lengthy table referenced here

US10730930-20200804-T00177

Please refer to the end of the specification for access instructions.

Lengthy table referenced here

US10730930-20200804-T00178

Please refer to the end of the specification for access instructions.

Lengthy table referenced here

US10730930-20200804-T00179

Please refer to the end of the specification for access instructions.

Lengthy table referenced here

US10730930-20200804-T00180

Please refer to the end of the specification for access instructions.

Lengthy table referenced here

US10730930-20200804-T00181

Please refer to the end of the specification for access instructions.

Lengthy table referenced here

US10730930-20200804-T00182

Please refer to the end of the specification for access instructions.

Lengthy table referenced here

US10730930-20200804-T00183

Please refer to the end of the specification for access instructions.

Lengthy table referenced here

US10730930-20200804-T00184

Please refer to the end of the specification for access instructions.

Lengthy table referenced here

US10730930-20200804-T00185

Please refer to the end of the specification for access instructions.

Lengthy table referenced here

US10730930-20200804-T00186

Please refer to the end of the specification for access instructions.

Lengthy table referenced here

US10730930-20200804-T00187

Please refer to the end of the specification for access instructions.

Lengthy table referenced here

US10730930-20200804-T00188

Please refer to the end of the specification for access instructions.

Lengthy table referenced here

US10730930-20200804-T00189

Please refer to the end of the specification for access instructions.

Lengthy table referenced here

US10730930-20200804-T00190

Please refer to the end of the specification for access instructions.

Lengthy table referenced here

US10730930-20200804-T00191

Please refer to the end of the specification for access instructions.

Lengthy table referenced here

US10730930-20200804-T00192

Please refer to the end of the specification for access instructions.

Lengthy table referenced here

US10730930-20200804-T00193

Please refer to the end of the specification for access instructions.

Lengthy table referenced here

US10730930-20200804-T00194

Please refer to the end of the specification for access instructions.

Lengthy table referenced here

US10730930-20200804-T00195

Please refer to the end of the specification for access instructions.

Lengthy table referenced here

US10730930-20200804-T00196

Please refer to the end of the specification for access instructions.

Lengthy table referenced here

US10730930-20200804-T00197

Please refer to the end of the specification for access instructions.

Lengthy table referenced here

US10730930-20200804-T00198

Please refer to the end of the specification for access instructions.

Lengthy table referenced here

US10730930-20200804-T00199

Please refer to the end of the specification for access instructions.

Lengthy table referenced here

US10730930-20200804-T00200

Please refer to the end of the specification for access instructions.

Lengthy table referenced here

US10730930-20200804-T00201

Please refer to the end of the specification for access instructions.

Lengthy table referenced here

US10730930-20200804-T00202

Please refer to the end of the specification for access instructions.

Lengthy table referenced here

US10730930-20200804-T00203

Please refer to the end of the specification for access instructions.

Lengthy table referenced here

US10730930-20200804-T00204

Please refer to the end of the specification for access instructions.

Lengthy table referenced here

US10730930-20200804-T00205

Please refer to the end of the specification for access instructions.

Lengthy table referenced here

US10730930-20200804-T00206

Please refer to the end of the specification for access instructions.

Lengthy table referenced here

US10730930-20200804-T00207

Please refer to the end of the specification for access instructions.

Lengthy table referenced here

US10730930-20200804-T00208

Please refer to the end of the specification for access instructions.

Lengthy table referenced here

US10730930-20200804-T00209

Please refer to the end of the specification for access instructions.

Lengthy table referenced here

US10730930-20200804-T00210

Please refer to the end of the specification for access instructions.

Lengthy table referenced here

US10730930-20200804-T00211

Please refer to the end of the specification for access instructions.

Lengthy table referenced here

US10730930-20200804-T00212

Please refer to the end of the specification for access instructions.

Lengthy table referenced here

US10730930-20200804-T00213

Please refer to the end of the specification for access instructions.

Lengthy table referenced here

US10730930-20200804-T00214

Please refer to the end of the specification for access instructions.

Lengthy table referenced here

US10730930-20200804-T00215

Please refer to the end of the specification for access instructions.

Lengthy table referenced here

US10730930-20200804-T00216

Please refer to the end of the specification for access instructions.

Lengthy table referenced here

US10730930-20200804-T00217

Please refer to the end of the specification for access instructions.

Lengthy table referenced here

US10730930-20200804-T00218

Please refer to the end of the specification for access instructions.

Lengthy table referenced here

US10730930-20200804-T00219

Please refer to the end of the specification for access instructions.

Lengthy table referenced here

US10730930-20200804-T00220

Please refer to the end of the specification for access instructions.

Lengthy table referenced here

US10730930-20200804-T00221

Please refer to the end of the specification for access instructions.

Lengthy table referenced here

US10730930-20200804-T00222

Please refer to the end of the specification for access instructions.

Lengthy table referenced here

US10730930-20200804-T00223

Please refer to the end of the specification for access instructions.

Lengthy table referenced here

US10730930-20200804-T00224

Please refer to the end of the specification for access instructions.

Lengthy table referenced here

US10730930-20200804-T00225

Please refer to the end of the specification for access instructions.

Lengthy table referenced here

US10730930-20200804-T00226

Please refer to the end of the specification for access instructions.

Lengthy table referenced here

US10730930-20200804-T00227

Please refer to the end of the specification for access instructions.

Lengthy table referenced here

US10730930-20200804-T00228

Please refer to the end of the specification for access instructions.

Lengthy table referenced here

US10730930-20200804-T00229

Please refer to the end of the specification for access instructions.

Lengthy table referenced here

US10730930-20200804-T00230

Please refer to the end of the specification for access instructions.

Lengthy table referenced here

US10730930-20200804-T00231

Please refer to the end of the specification for access instructions.

Lengthy table referenced here

US10730930-20200804-T00232

Please refer to the end of the specification for access instructions.

Lengthy table referenced here

US10730930-20200804-T00233

Please refer to the end of the specification for access instructions.

Lengthy table referenced here

US10730930-20200804-T00234

Please refer to the end of the specification for access instructions.

Lengthy table referenced here

US10730930-20200804-T00235

Please refer to the end of the specification for access instructions.

Lengthy table referenced here

US10730930-20200804-T00236

Please refer to the end of the specification for access instructions.

Lengthy table referenced here

US10730930-20200804-T00237

Please refer to the end of the specification for access instructions.

Lengthy table referenced here

US10730930-20200804-T00238

Please refer to the end of the specification for access instructions.

Lengthy table referenced here

US10730930-20200804-T00239

Please refer to the end of the specification for access instructions.

Lengthy table referenced here

US10730930-20200804-T00240

Please refer to the end of the specification for access instructions.

Lengthy table referenced here

US10730930-20200804-T00241

Please refer to the end of the specification for access instructions.

Lengthy table referenced here

US10730930-20200804-T00242

Please refer to the end of the specification for access instructions.

Lengthy table referenced here

US10730930-20200804-T00243

Please refer to the end of the specification for access instructions.

Lengthy table referenced here

US10730930-20200804-T00244

Please refer to the end of the specification for access instructions.

REFERENCES

1. Nat Biotechnol. 2005 September; 23(9):1117-25; Human antibodies from transgenic animals; Lonberg N.
2. J Clin Invest. 1992 March; 89(3):729-38: immunoglobulin light chain variable region gene sequences for human antibodies to *Haemophilus influenzae* type b capsular polysaccharide are dominated by a limited number of V kappa and V lambda segments and VJ combinations; Adderson E E, Shackelford P G. Insel R A, Quinn A, Wilson PM, Carroll WL.
3. J Immunol. 1993 Oct. 15; 151(8):4352-61; Clonal characterization of the human IgG antibody repertoire to *Haemophilus influenzae* type b polysaccharide. V. In vivo expression of individual antibody clones is dependent on Ig CH haplotypes and the categories of antigen; Chung G H, Scott M G, Kim K H, Kearney J, Siber G R, Ambrosino D M, Nahm M H,
4. J Imrnunol. 1998 Dec. 1; 161(11):6068-73; Decreased frequency of rearrangement due to the synergistic effect of nucleotide changes in the heptamer and nonamer of the recombination signal sequence of the V kappa gene A2b, which is associated with increased susceptibility of Navajos to *Haemophilus influenzae* type b disease; Nadel B, Tang A, Lugo G, Love V, Escuro G, Feeney A J.
5. J Clin Invest. 1996 May 15:97(10):2277-82; A defective Vkappa A2 allele in Navajos which may play a role in increased susceptibility to *Haemnophilus influenzae* type b disease; Feeney A J, Atkinson M J, Cowan M J, Escuro G, Lugo G.
6. Infect Imrmun. 1994 September; 62(9):3873-80; Variable region sequences of a protective human monoclonal antibody specific for the *Haemophilus influenzae* type b capsular polysaccharide; Lucas A H, Larrick J W, Reason D C.
7. J Clin Invest. 1993 June; 91(6):2734-43; Restricted immunoglobulin VH usage and VDJ combinations in the human response to *Haemophilus influenzae* type b capsular polysaccharide. Nucleotide sequences of monospecific anti-*Haemophilus* antibodies and polyspecific antibodies cross-reacting with self antigens; Adderson EE, Shackelford PG, Quinn A, Wilson P M, Cunningham M W, Insel R A, Carroll WL.
8. J Clin Invest. 1993 March; 91(3):788-96; Variable region expression in the antibody responses of infants vaccinated with *Haemophilus influenzae* type b polysaccharide-protein conjugates. Description of a new lambda light chain-associated idiotype and the relation between idiotype expression, avidity, and vaccine formulation. The Collaborative Vaccine Study Group; Granoff D M, Shackelford P G, Holmes S J, Lucas A H.
9. Infect immun. 1994 May; 62(5):1776-86; Variable region sequences and idiotypic expression of a protective human immunoglobulin M antibody to capsular polysaccharides of *Neisseria meningitidis* group B and *Escherichia coli* KI; Azmi F H, Lucas A H, Raff H V, Granoff D M.
10. J Clin Invest. 1992 December; 90(6):2197-208; Sequence analyses of three immunoglobulin G anti-virus antibodies reveal their utilization of autoantibody-related immunoglobulin Vh genes, but not V lambda genes; Huang D F, Olee T, Masuho Y, Matsumoto Y, Carson D A, Chen P P.
11. Science. 2011 Aug. 12; 333(6044):834-5, Biochemistry. Catching a moving target, Wang TT, Palese P
12. Science. 2009 Apr. 10; 324(5924):246-51. Epub 2009 Feb. 26; Antibody recognition of a highly conserved influenza virus epitope; Ekiert D C, Bhabha G, Eisliger M A, Friesen R H, Jongeneelen M, Throsby M, Goudsmit J, Wilson I A.
13. PLoS One. 2008; 3(12):e3942. Epub 2008 Dec. 16; Heterosubtypic neutralizing monoclonal antibodies cross-protective against H5N1 and H1N1 recovered from human IgM© memory B cells; Throsby M, van den Brink E, Jongeneelen M, Poon L L, Alard P, Cornelissen L, Bakker A, Cox F, van Deventer E, Guan Y, Cinatl J, ter Meulen J, Lasters i, Carsetti R, Peiris M, de Kruif J, Goudsmit J.
14. Nat Struct Mol Biol. 2009 March; 16(3):265-73. Epub 2009 Feb. 22,Structural and functional bases for broad-spectrum neutralization of avian and human influenza A viruses, Sui J, Hwang W C, Perez S, Wei G, Aird D, Chen L M, Santelli E, Stec B, Cadwell G, Ali M, Wan H, Murakami A, Yammanuru A, Han T, Cox N J, Bankston L A, Donis R O, Liddington R C, Marasco W A.
15. Science. 2011 Aug. 12; 333(6044):843-50. Epub 2011 Jul. 7, A highly conserved neutralizing epitope on group 2 influenza A viruses, Ekiert D C, Friesen R H, Bhabha G, Kwaks T, Jongeneelen M, Yu W, Ophorst C, Cox F, Korse H J, Brandenburg B, Vogels R, Brakenhoff J P, Kompier R, Koldijk M H, Cornelissen L A, Poon L L, Peiris M, Koudstaal W, Wilson I A, Goudsmit J.

LENGTHY TABLES

The patent contains a lengthy table section. A copy of the table is available in electronic form from the USPTO web site (http://seqdata.uspto.gov/?pageRequest=docDetail&DocID=US10730930B2). An electronic copy of the table will also be available from the USPTO upon request and payment of the fee set forth in 37 CFR 1.19(b)(3).

The invention claimed is:

1. A method for producing an antibody heavy chain, VH domain or an antibody specific to a target antigen, wherein the heavy chain, VH domain or antibody comprises an HCDR3 that is at least 20 amino acids in length and is derived from the recombination of human JH6*02 with a human VH gene segment and a human D gene segment, the method comprising expressing the heavy chain, VH domain or antibody from a cell, wherein the cell comprises nucleic acid encoding the heavy chain, VH domain or antibody, wherein the heavy chain, VH domain or antibody is of a transgenic non-human vertebrate contacted with the target antigen, the transgenic non-human vertebrate being a mouse, wherein the transgenic non-human vertebrate has a genome comprising an immunoglobulin heavy chain locus comprising unrearranged human gene segment JH6*02, one or more human VH gene segments and a plurality of human D gene segments upstream of a constant region, wherein the plurality of human D gene segments comprises D3-9, D3-10, D6-19, D4-17, D6-13, D3-22 and D1-26, wherein the gene segments in the heavy chain locus are operably linked to the constant region thereof so that the vertebrate is capable of producing an antibody heavy chain produced by recombination of the human JH6*02 with a human D segment and a human VH segment, wherein the JH6*02 gene segment comprises the following nucleotide sequence: ATTACTA CTACTACTAC GGTATGGACG TCTGGGGCCA AGGGACCACG GTCACCGTCT CCTCAG, wherein the JH6*02 is the only JH6-type gene segment in the genome, wherein the JH6*02 is the closest JH gene segment to the constant region in the locus, wherein the JH6*02 is in human germline configuration with respect to the 3'-most human D gene segment, and wherein the transgenic non-human vertebrate produces an antibody heavy chain specific for the target antigen wherein the variable domain of the heavy chain is the product of recombination between a human VH, D and JH6*02 and wherein the HCDR3 length is at least 20 amino acids.

2. The method of claim 1, wherein the constant region of the locus is a mouse constant region.

3. The method of claim 2, comprising producing a heavy chain or antibody in which said mouse constant region is replaced with a human constant region.

4. The method of claim 1, wherein the plurality of human D gene segments further comprises one, more or all human D gene segments D2-2; D5-24; D5-12; D1-20; D5-18; D3-16; D2-21; D1-14; D7-27; D1-1; D6-25 and D4-23.

5. The method of claim 1, wherein the plurality of human D gene segments further comprises one, more or all human D gene segments D2-2, D2-25 and D3-3.

6. The method of claim 1, wherein all endogenous transgenic non-human vertebrate heavy chain variable region gene segments have been inactivated in the genome and/or wherein the genome is homozygous for said heavy chain locus.

7. The method of claim 1, wherein the mouse comprises functional heavy gene segments VH2-5, VH7-4-1, VH4-4, VH1-3, VH1-2, VH6-1, DI-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, JH1, JH2, JH3, JH4, JH5 and JH6, in 5' to 3' order, wherein the JH6 is the human JH6*02 variant, wherein the insertion of human DNA is made between positions 114666435 and 114666436 on mouse chromosome 12;

wherein human functional heavy chain gene segments VH3-13, VH3-11, VH3-9, VH1-8, VH3-7 are inserted upstream of VH2-5;

wherein the mouse VH, D and JH gene segments are retained in the locus, immediately upstream of (5' of) the inserted human heavy chain DNA;

and wherein the mouse VH, D and J segments are inverted to inactivate them, thereby producing mice in which only the human heavy chain variable region gene segments are active.

8. The method of claim 7 additionally comprising VH2-26, VH1-24, VH3-23, VH3-21, VH3-20, VH1-18, and VH 3-15 inserted upstream (5') of the 5'-most VH.

9. The method of claim 1, wherein (i) the target antigen is an antigen of an infectious disease pathogen;

(ii) the target antigen is a receptor, and the antibody heavy chain specifically binds a receptor cleft; or (iii) the target antigen is an enzyme, and the antibody heavy chain specifically binds the enzyme active site.

10. The method of claim 9, wherein the target antigen is a bacterial or viral pathogen antigen.

11. The method of claim 1, further comprising isolating the heavy chain, antibody or VH domain expressed by the cell.

12. The method of claim 11, further comprising providing a composition comprising (i) said antibody or an antibody comprising said heavy chain or said VH domain, and (ii) a pharmaceutically acceptable carrier or excipient.

13. The method according to claim 1, wherein the mouse comprises a mouse Eμ and Sμ in the heavy chain locus between the JH6*02 and the constant region.

14. The method according to claim 13 wherein the Eμ and Sμ are Eμ and Sμ of a mouse 129-derived genome or of a mouse C57BL/6 -derived genome.

15. A method for producing an antibody heavy chain, VH domain or an antibody specific to a target antigen, wherein the heavy chain, VH domain or antibody comprises an HCDR3 that is at least 20 amino acids in length and is derived from the recombination of human JH6*02 with a human VH gene segment and a human D gene segment, the method comprising expressing the heavy chain, VH domain or antibody from a cell, wherein the cell comprises nucleic acid encoding the heavy chain, VH domain or antibody, wherein the heavy chain, VH domain or antibody is of a transgenic mouse, wherein the transgenic mouse has a genome comprising an immunoglobulin heavy chain locus comprising unrearranged human gene segment JH6*02, one or more human VH gene segments and a plurality of human D gene segments upstream of a constant region, wherein said one or more human VH gene segments is selected from the group consisting of V3-21, V3-13, V3-7, V6-1, V1-8, V1-2, V7-4-1, V1-3, V1-18, V4-4, V3-9, V3-23, V3-11, V3-20, IGHV1-8*01, IGHV4-61*01, IGHV6-1*01, IGHV4-4*02, IGHV1-3*01, IGHV3-66*03, IGHV3-7*01 and IGHV3-9*01 wherein the plurality of human D gene segments includes a human D gene segment selected from the group consisting of D3-9*01, D3-10*01, D6-19*01, D6-13*01 and D1-26*01.

* * * * *